(12) United States Patent
Takeda et al.

(10) Patent No.: US 7,977,087 B2
(45) Date of Patent: Jul. 12, 2011

(54) DETECTION INSTRUMENT WITH THE USE OF POLYNUCLEOTIDES MAPPED ON BARLEY CHROMOSOME

(75) Inventors: Kazuyoshi Takeda, Kurashiki (JP); Kazuhiro Sato, Kurashiki (JP)

(73) Assignee: Japan Science and Technology Agency, Saitama (JP)

( * ) Notice: Subject to any disclaimer, the term of this patent is extended or adjusted under 35 U.S.C. 154(b) by 956 days.

(21) Appl. No.: 11/547,284

(22) PCT Filed: Mar. 31, 2005

(86) PCT No.: PCT/JP2005/006825
§ 371 (c)(1),
(2), (4) Date: Jul. 26, 2007

(87) PCT Pub. No.: WO2005/095603
PCT Pub. Date: Oct. 13, 2005

(65) Prior Publication Data
US 2009/0186402 A1    Jul. 23, 2009

(30) Foreign Application Priority Data

| | | |
|---|---|---|
| Mar. 31, 2004 | (JP) | 2004-101618 |
| Mar. 31, 2004 | (JP) | 2004-101626 |
| Mar. 31, 2004 | (JP) | 2004-101641 |
| Mar. 31, 2004 | (JP) | 2004-101646 |
| Mar. 31, 2004 | (JP) | 2004-101662 |
| Mar. 31, 2004 | (JP) | 2004-101675 |
| Mar. 31, 2004 | (JP) | 2004-101682 |
| Nov. 26, 2004 | (JP) | 2004-341944 |
| Nov. 26, 2004 | (JP) | 2004-342018 |
| Nov. 26, 2004 | (JP) | 2004-342097 |
| Nov. 26, 2004 | (JP) | 2004-342261 |
| Nov. 26, 2004 | (JP) | 2004-342406 |
| Nov. 26, 2004 | (JP) | 2004-342458 |
| Nov. 26, 2004 | (JP) | 2004-342598 |

(51) Int. Cl.
*C12M 1/00* (2006.01)
*C12M 3/00* (2006.01)
*C12Q 1/68* (2006.01)
*C12N 15/29* (2006.01)

(52) U.S. Cl. ...... 435/287.2; 435/6; 435/285.1; 536/23.6

(58) Field of Classification Search .................. None
See application file for complete search history.

(56) References Cited

U.S. PATENT DOCUMENTS

2009/0241220 A1*  9/2009  Abad et al. .......... 800/278

FOREIGN PATENT DOCUMENTS

| | | |
|---|---|---|
| EP | 1 026 258 A2 | 8/2000 |
| EP | 1 466973 A1 | 10/2004 |
| JP | 2000-228999 A | 8/2000 |
| JP | 2001-17181 A | 1/2001 |
| JP | 2002-524044 A * | 8/2002 |
| JP | 2002-291474 A | 10/2002 |
| JP | 2003-111593 A | 4/2003 |
| JP | 2003-144173 A | 5/2003 |
| JP | 2003-180362 | 7/2003 |
| JP | 2003-245075 | 9/2003 |
| JP | 2003-259898 | 9/2003 |
| JP | 2003-289885 A | 10/2003 |
| JP | 2004-065251 | 3/2004 |
| WO | WO 00/08160 | 2/2000 |
| WO | 03/057877 A1 | 7/2003 |
| WO | WO 2004/066719 A1 | 8/2004 |

OTHER PUBLICATIONS

K. Sato et al., "Single Nucleotide Polymorphisms Found in Barley ESTs"; Breeding Research, vol. 3, separate vol. 2, pp. 114, 2001.
Damian Jacoud et al., "Diversity Arrays: a Solid State Technology . . . ", Nucleic Acids Research, vol. 29, No. 4 e25, pp. 1-7, 2001.
Magnus Jobs et al., "DASH-2: Flexible, Low-Cost, and High-Throughput SNP . . . ", Genome Research, www.genome.org, pp. 916-924, May 2003.
Hajime Matsuzaki et al., "Parallel Genotyping of Over 10,000 SNPs . . . ", Genome Research, www.genome.org, pp. 414-425, May 2004.
International Search Report of PCT/JP2005/006825, mailed Jul. 26, 2005.
Vladimir et al; "Discovery and assay of single-nucleotide polymorphisms in barley (*Hordeum vulgare*)", Plant Molecular Biology 2002, vol. 48, pp. 529-536.
Raja et al; "Generation and comparison of EST-derived SSRs and SNPs in barley (*Hordeum vulgare* L.)", Hereditas 2001, vol. 135, pp. 145-151.
Yuzo Minobe, Risa Monna, Zi-Xuan Wang; "The breeding based on genome-wide selection: Rice breeding technology in the era of the post-genomic sequence"; Protein, Nucleic Acid, and Enzyme, vol. 48 No. 3(2003), p. 252-256.
A New Resource of Cereal Genomics: 22K Barley GeneChip Comes of Age, Plant Physiology, Mar. 2004, vol. 134, p. 960-968, Close et al.
Office Action mailed Jul. 17, 2007, by the Japanese Patent Office for Japanese Patent Application No. 2006-511892.
Japanese Interrogation for related JP 2006-511892 mailed May 25, 2010 and English translation thereof.

* cited by examiner

*Primary Examiner* — James Martinell
(74) *Attorney, Agent, or Firm* — Nixon & Vanderhye P.C.

(57) ABSTRACT

As the results of mass sequencing of cDNA clones originating in barley varieties "*H. spontaneum*", "Haruna Nijo" and "Akashinriki", a large number of sites showing single nucleotide polymorphisms (SNPs) among the varieties are found out. Because of involving nonsynonymous substitutions and likely relating to phenotypes inherent in respective varieties, these SNPs are usable for various purposes, for example, genetically distinguishing a variety, isolating a gene, producing/selecting a novel transformant and so on.

2 Claims, 3 Drawing Sheets

DETECTION INSTRUMENT WITH THE USE OF POLYNUCLEOTIDES MAPPED ON BARLEY CHROMOSOME

This application is US national phase of International application PCT/JP2005/006825, filed 31 Mar. 2005, which designated the U.S. and claims priority of JP 2004-101626 filed 31 Mar. 2004; JP 2004-101662 filed 31 Mar. 2004; JP 2004-101646 filed 31 Mar. 2004; JP 2004-101641 filed 31 Mar. 2004; JP 2004-101618 filed 31 Mar. 2004; JP 2004-101682 filed 31 Mar. 2004; JP 2004-101675 filed 31 Mar. 2004; JP 2004-342598 filed 26 Nov. 2004; JP 2004-342261 filed 26 Nov. 2004; JP 2004-342018 filed 26 Nov. 2004; JP 2004-341944 filed 26 Nov. 2004; JP 2004-342458 filed 26 Nov. 2004; JP 2004-342406 filed 26 Nov. 2004; and JP 2004-342097 filed 26 Nov. 2004, the entire contents of each of which are hereby incorporated by reference.

TECHNICAL FIELD

The present invention relates to a detection instrument that uses polynucleotides mapped on barley chromosomes. Particularly, the invention relates to a detection instrument for detecting, in Triticeae species, gene expression, gene polymorphism, proteins (polypeptides), and substances that interact with proteins (polypeptides).

BACKGROUND ART

Over the last years, the entire genomes of human and many other model organisms have been sequenced. In many of these organisms, sequencing of the entire genomes has been finished already. There has also been ongoing development in the analysis of transcripts and proteins based on the sequence information of genomes. Specifically, transcriptome analysis and proteome analysis have won the recognition. The transcriptome analysis is used for the analysis of transcripts, whereby the expression of all transcripts in an organism or cells are analyzed both systematically and comprehensively. The proteome analysis is a systematic and comprehensive method of analyzing proteins, in which the properties or expression of all proteins expressed at any given location and any given time in an organism or cells are analyzed.

For the systematic and comprehensive analyses, various array techniques are often used. The array technique refers to a technique using an array, in which biosubstances, such as DNA or various proteins obtained from the organism of interest being analyzed, or synthetic substances (for example, compounds with hydrophobic groups or ion exchange groups) that interact with such biosubstances are immobilized on a support in an orderly manner.

With the array technique, the systematic and comprehensive analysis can be performed efficiently. For example, for the analysis of gene transcription control mechanism, it is required to measure transcription level of genes, which varies according to the state of the cell. For this purpose, use of a DNA micro array, one form of the array technique, allows for systematic measurement of transcription level of several thousand to several ten thousand of genes. Among such DNA micro array techniques, one that has been widely used is the DNA micro array technique developed by Affymetrix. In this technique, oligonucleotides are directly synthesized on a silica substrate using a microfabrication technique employed in the fabrication of semiconductors (see Patent Document 1, for example). Meanwhile, arrays have been developed that are modified to detect single nucleotide polymorphism (SNP) (see Non-Patent Documents 1 and 2, for example).

In order to reduce breeding time, labor, and field area, breeding of Triticeae species nowadays employs a method whereby screening is made using genetic markers as an index. Genetic markers have been used since the advent of DNA markers in the late 1980s, and the study of linkage map has advanced greatly with the use of DNA markers. Today, linkage analysis is performed in many organisms based on their high-density linkage maps. Currently, genetic markers that are strongly linked to target traits are available. By using these genetic markers, breeding can be performed more efficiently. The inventors of the present invention have been actively developing genetic markers in Triticeae species. For example, the inventors have proposed (1) a technique concerning genetic markers that are linked to genes conferring aluminum resistance to barley, and use of such genetic markers (see Patent Publication 2), and (2) a technique concerning novel primer sets that are used to detect barley chromosome nucleic acid markers on a wheat background (see Patent Publication 3), and use of such primer sets.

[Patent Publication 1]
Japanese Laid-Open Patent Publication No. 2000-228999 (published on Aug. 22, 2000)
[Patent Publication 2]
Japanese Laid-Open Patent Publication No. 2002-291474 (published on Oct. 8, 2002)
[Patent Publication 3]
Japanese Laid-Open Patent Publication No. 2003-111593 (published on Apr. 15, 2003)
[Non-Patent Publication 1]
Jobs M, Howell W M, Stromqvist L, Mayr T, Brookes A J. Related Articles, Links. DASH-2: flexible, low-cost, and high-throughput SNP genotyping by dynamic allele-specific hybridization on membrane arrays. Genome Res. 2003 May; 13(5): 916-24.
[Non-Patent Publication 2]
Matsuzaki H, Loi H, Dong S, Tsai Y Y, Fang J, Law J, Di X, Liu W M, Yang G, Liu G, Huang J, Kennedy G C, Ryder T B, Marcus G A, Walsh P S, Shriver M D, Puck J M, Jones K W, Mei R. Links. Parallel Genotyping of Over 10,000 SNPs Using a One-Primer Assay on a High-Density Oligonucleotide Array. Genome Res. 2004 March; 14(3): 414-25.

As described above, genomes of many organisms have been sequenced and many type of arrays have been marketed. However, none of these arrays is usable for the breeding of Triticeae species. Meanwhile, while breeding using genetic markers can greatly improve efficiency as compared with the conventional screening conducted in a field, the genotype of each genetic marker needs to be confirmed individually. In breeding, large numbers of agriculturally desirable traits are screened for and undesirable traits are selected out. If genotypes of these multiple genetic markers were confirmed comprehensively, it would be possible to further improve efficiency of breeding.

The present invention was made in view of the foregoing problems, and an object of the invention is to provide a detection instrument for detecting, in Triticeae species, gene expression, gene polymorphism, proteins (polypeptides), and substances that interact with proteins (polypeptides).

DISCLOSURE OF INVENTION

In order to achieve the foregoing object, the inventors of the present invention designed primers based on the EST sequences independently developed by the inventors. By finding polymorphisms between different varieties in the amplified fragments that had been amplified using the genomic DNA as a template, genetic markers were developed. The genetic markers were mapped on barley chromosomes, and a detailed genetic map was made. Upon further study, the inventors have found that, if polynucleotides with the barley EST sequences or genetic marker sequences were immobilized on a support, it would be possible to realize a gene expression detection instrument or gene polymorphism detection instrument applicable to breeding of Triticeae species. Further, the inventors also found that a protein (polypeptide)-interacting substance detection instrument or protein (polypeptide) detection instrument could be realized when proteins encoded by the EST sequences, or antibodies against such proteins were immobilized on a support. The present invention was accomplished based on these findings.

Specifically, the present invention provides a gene detection instrument for detecting expression or polymorphism of genes existing in a genome of Triticeae species, the gene detection instrument comprising a support on which is immobilized at least one polynucleotide selected from: (a) polynucleotides with partial base sequences of chromosomal DNA of barley, or polynucleotides mutated by substitution, deletion, insertion, and/or addition of one or more bases in the partial base sequences of chromosomal DNA of barley; or (b) polynucleotides with combined partial base sequences of chromosomal DNA of barley, or polynucleotides mutated by substitution, deletion, insertion, and/or addition of one or more bases in the combined partial base sequences of chromosomal DNA of barley.

It is preferable that the polynucleotide immobilized on the support comprise at least one kind of polynucleotide selected from the group consisting of: (1) polynucleotides with the base sequences of SEQ ID NO: 1 through 5780, or polynucleotides mutated by substitution, deletion, insertion, and/or addition of one or more bases in the base sequences of SEQ ID NO: 1 through 5780; (2) a polynucleotide that comprises a part of any one of the polynucleotides set forth in (1); (3) a polynucleotide whose partial sequence comprises all of or part of any one of the polynucleotides set forth in (1); and (4) a polynucleotide whose partial sequence comprises: all of or part of a base sequence of SEQ ID NO: n (where n is an odd number), or its variant base sequence, in the polynucleotides set forth in (1); and all of or part of a base sequence of SEQ ID NO: n+1, or its variant base sequence, in the polynucleotides set forth in (1). Since the polynucleotides include base sequence of barley cDNA, gene expression or gene polymorphism in Triticeae species can be detected with a gene detection instrument in which the polynucleotides are immobilized on a support.

It is preferable that two or more kinds of polynucleotides be immobilized on the support, and that regions on the support in which the polynucleotides are respectively immobilized be arranged in the same order as a chromosomal order of the polynucleotides immobilized on the support. The gene detection instrument may be adapted so that two or more kinds of polynucleotides are immobilized on the support, and that information indicative of a chromosomal order of the polynucleotides immobilized on the support is appended to regions on the support in which the polynucleotides are respectively immobilized. With the immobilizing regions arranged in the chromosomal order or with the information indicative of the chromosomal order, the locations of recombination that has occurred in crossbreeding of Triticeae species can be found with ease. As a result, efficiency of breeding can be improved.

It is preferable that the polynucleotide immobilized on the support comprise cDNA. When the polynucleotide is cDNA, gene expression can be evaluated efficiently through hybridization with polynucleotides in a sample.

According to the present invention, there is provided a gene polymorphism detection instrument for detecting polymorphism of genes existing in a genome of Triticeae species, the gene polymorphism detection instrument comprising a support on which is immobilized at least one polynucleotide selected from: polynucleotides with partial base sequences of chromosomal DNA of barley; or polynucleotides mutated by substitution, deletion, insertion, and/or addition of one or more bases in the partial base sequences of chromosomal DNA of barley.

It is preferable that the polynucleotide immobilized on the support comprise a partial base sequence of at least one of DNA fragments amplified, using genomic DNA of Triticeae species as a template, with a primer set that comprises a combination of any two primers arbitrarily selected from: a plurality of primers designed based on a base sequence of SEQ ID NO: n (where n is an odd number) from among base sequences of SEQ ID NO: 1 through 5780; and a plurality of primers designed based on a base sequence of SEQ ID NO: n+1 from among the base sequences of SEQ ID NO: 1 through 5780. Gene polymorphism in Triticeae species can be detected with the gene polymorphism detection instrument in which a polynucleotide with a polymorphism-containing base sequence of the amplified DNA fragments is immobilized on a support.

It is preferable that two or more kinds of polynucleotides be immobilized on the support, and that regions on the support in which the polynucleotides are respectively immobilized be arranged in the same order as a chromosomal order of the polynucleotides immobilized on the support. The gene polymorphism detection instrument may be adapted so that two or more kinds of polynucleotides are immobilized on the support, and that information indicative of a chromosomal order of the polynucleotides immobilized on the support is appended to regions on the support in which the polynucleotides are respectively immobilized. With the immobilizing regions arranged in the chromosomal order or with the information indicative of the chromosomal order, the locations of recombination that has occurred in crossbreeding of Triticeae species can be found with ease. As a result, efficiency of breeding can be improved.

It is preferable that the polynucleotide immobilized on the support comprise a synthetic oligonucleotide. With an oligonucleotide synthesized to have a sequence suitable for detection of polymorphism, the efficiency of detection can be improved.

According to the present invention, there is provided a polypeptide-interacting substance detection instrument for detecting a substance which interacts with a polypeptide that comprises a protein, or part of a protein, encoded by a gene present in the genome of Triticeae species, the polypeptide-interacting substance detection instrument comprising a support on which is immobilized at least one of polypeptides encoded by: (a) polynucleotides with partial base sequences of chromosomal DNA of barley, or polynucleotides mutated by substitution, deletion, insertion, and/or addition of one or more bases in the partial base sequences of chromosomal DNA of barley; or (b) polynucleotides with combined partial base sequences of chromosomal DNA of barley, or polynucleotides mutated by substitution, deletion, insertion, and/ or addition of one or more bases in the combined partial base sequences of chromosomal DNA of barley.

It is preferable that the polypeptide immobilized on the support be encoded by a polynucleotide selected from the group consisting of: (1) polynucleotides with the base sequences of SEQ ID NO: 1 through 5780, or polynucleotides mutated by substitution, deletion, insertion, and/or addition of one or more bases in the base sequences of SEQ ID NO: 1 through 5780; (2) a polynucleotide that comprises a part of any one of the polynucleotides set forth in (1); (3) a polynucleotide whose partial sequence comprises all of or part of any one of the polynucleotides set forth in (1); and (4) a polynucleotide whose partial sequence comprises: all of or part of a base sequence of SEQ ID NO: n (where n is an odd number), or its variant base sequence, in the polynucleotides set forth in (1); and all of or part of a base sequence of SEQ ID NO: n+1, or its variant base sequence, in the polynucleotides set forth in (1). Substances that interact with proteins of Triticeae species can be detected with the polypeptide-interacting substance detection instrument in which the polypeptides are immobilized on a support.

It is preferable that two or more kinds of polypeptides are immobilized on the support, and that regions on the support in which the polypeptides are respectively immobilized are arranged in the same order as a chromosomal order of the polynucleotides respectively encoding the polypeptides immobilized on the support. The polypeptide-interacting substance detection instrument may be adapted so that two or more kinds of polypeptides are immobilized on the support, and that information indicative of a chromosomal order of the polynucleotides respectively encoding the polypeptides immobilized on the support is appended to regions on the support in which the polypeptides are respectively immobilized. With the immobilizing regions arranged in the chromosomal order or with the information indicative of the chromosomal order, the locations of recombination that has occurred in crossbreeding of Triticeae species can be found with ease. As a result, efficiency of breeding can be improved.

According to the present invention, there is provided a polypeptide detection instrument for detecting a polypeptide that comprises a protein, or part of a protein, encoded by a gene present in a genome of Triticeae species, the polypeptide detection instrument comprising a support on which is immobilized at least one of antibodies against polypeptides encoded by: (a) polynucleotides with partial base sequences of chromosomal DNA of barley, or polynucleotides mutated by substitution, deletion, insertion, and/or addition of one or more bases in the partial base sequences of chromosomal DNA of barley; or (b) polynucleotides with combined partial base sequences of chromosomal DNA of barley, or polynucleotides mutated by substitution, deletion, insertion, and/or addition of one or more bases in the combined partial base sequences of chromosomal DNA of barley.

It is preferable that the polynucleotide encoding the polypeptide used for production of the antibody immobilized on the support comprise at least one kind of polynucleotide selected from the group consisting of: (1) polynucleotides with the base sequences of SEQ ID NO: 1 through 5780, or polynucleotides mutated by substitution, deletion, insertion, and/or addition of one or more bases in the base sequences of SEQ ID NO: 1 through 5780; (2) a polynucleotide that comprises a part of any one of the polynucleotides set forth in (1); (3) a polynucleotide whose partial sequence comprises all of or part of any one of the polynucleotides set forth in (1); and (4) a polynucleotide whose partial sequence comprises: all of or part of a base sequence of SEQ ID NO: n (where n is an odd number), or its variant base sequence, in the polynucleotides set forth in (1); and all of or part of a base sequence of SEQ ID NO: n+1, or its variant base sequence, in the polynucleotides set forth in (1). Substances that interact with proteins of Triticeae species can be detected with the polypeptide-interacting substance detection instrument in which the antibodies are immobilized on a support.

It is preferable that two or more kinds of antibodies be immobilized on the support, and that regions on the support in which the antibodies are respectively immobilized be arranged in the same order as a chromosomal order of the polynucleotides respectively encoding polypeptides used for production of the antibodies immobilized on the support. The polypeptide detection instrument may be adapted so that two or more kinds of antibodies are immobilized on the support, and that information indicative of a chromosomal order of the polynucleotides respectively encoding polypeptides used for preparation of the antibodies immobilized on the support is appended to regions on the support in which the antibodies are respectively immobilized. With the immobilizing regions arranged in the chromosomal order or with the information indicative of the chromosomal order, the locations of recombination that has occurred in crossbreeding of Triticeae species can be found with ease. As a result, efficiency of breeding can be improved.

According to the present invention, there are provided polynucleotides usable for an instrument for detecting expression or polymorphism of genes present in the genome of Triticeae species, the polynucleotides comprising: base sequences of SEQ ID NO: 1 through 5780; or base sequences of SEQ ID NO: 1 through 5780, with substitution, deletion, insertion, and/or addition of one or more bases. Further, according to the present invention, there are provided polynucleotides whose partial sequence comprises polynucleotides usable for an instrument for detecting polymorphism of genes present in the genome of Triticeae species, the polynucleotides comprising DNA fragments amplified, using genomic DNA of Triticeae species as a template, with a primer set that comprises a combination of any two primers arbitrarily selected from: a plurality of primers designed based on a base sequence of SEQ ID NO: n (where n is an odd number) from among base sequences of SEQ ID NO: 1 through 5780; and a plurality of primers designed based on a base sequence of SEQ ID NO: n+1 from among the base sequences of SEQ ID NO: 1 through 5780.

The foregoing polynucleotides are suitable as the polynucleotides immobilized on a support of a gene detection instrument and a gene polymorphism detection instrument according to the present invention.

Additional objects, features, and strengths of the present invention will be made clear by the description below. Further, the advantages of the present invention will be evident from the following explanation in reference to the drawings.

BEST MODE FOR CARRYING OUT THE INVENTION

Figure 1:
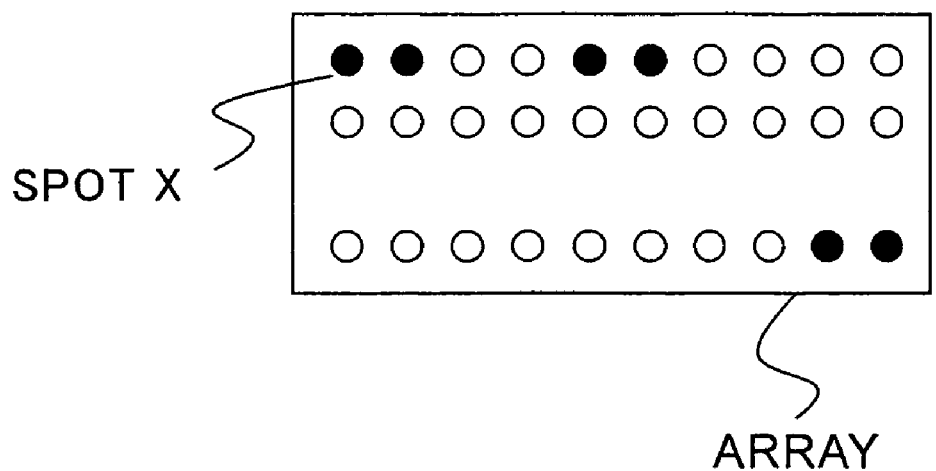
FIG. 1(a) is a plan view of an array as one example of a detection instrument according to the present invention, schematically illustrating expression of genes conferring certain characteristics.
FIG. 1(b) is a plan view of an array as one example of a detection instrument according to the present invention, schematically illustrating expression of genes conferring characteristics different from the characteristics represented in FIG. 1(a).
Figure 1:
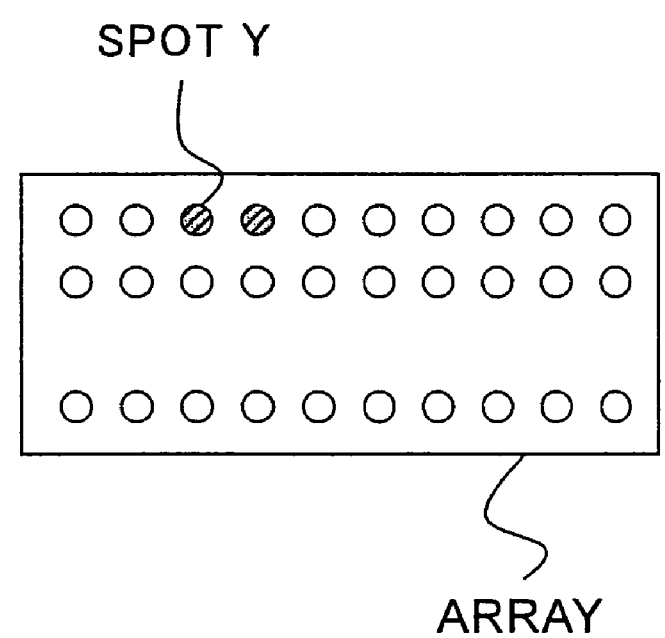

The following will describe one embodiment of the present invention. It should be appreciated that the invention is not limited in any way by the following description.

(1) Gene Detection Instrument according to the Present Invention

A gene detection instrument according to the present invention is an instrument for detecting expression or polymorphism of genes in the genomes of Triticeae species. The organisms to which a gene detection instrument of the invention is applicable may be any Triticeae species, among which barley, wheat, and rye are preferable. As will be described later, a gene detection instrument according to the present invention includes a support on which polynucleotides constituting part of barley chromosomal (1H, 2H, 3H, 4H, 5H, 6H, and 7H) DNA are immobilized. The polynucleotides immobilized on the support may solely be polynucleotides that constitute part of the barley chromosomal DNA, or other polynucleotides may additionally be immobilized on the support. Such additional polynucleotides are not particularly limited as long as they can detect expression or polymorphism of genes in the genomes of Triticeae species. For example, the additional polynucleotides may be those with the base sequences originating in non-barley organisms, or those with arbitrary base sequences that have been artificially synthesized.

In the case where the polynucleotides are immobilized in more than one region of the support, the polynucleotides immobilized in these regions may have non-overlapping base sequences or partially overlapping base sequences. Alternatively, polynucleotides with the same base sequence may be immobilized in these different regions of the support. In the case where the polynucleotides have overlapping base sequences, the polynucleotides may have partially overlapping base sequences, or the base sequence of one of the polynucleotides may be a partial sequence of the other polynucleotide.

Further, the polynucleotide immobilized in each region is not necessarily required to be of the same kind. More than one kind of polynucleotide may be immobilized in each region.

The support is not particularly limited as long as it can immobilize polynucleotides, and it may have any shape and may be made of any material. Examples of a support material generally include: inorganic materials such as glass and silicon wafer; natural polymers such as paper; synthetic polymers such as nitrocellulose and nylon; and gels using synthetic polymers or natural polymers. The shape of the support is not particularly limited as long as it provides enough area to support the polynucleotides. Generally, those with a two-dimensional plane, for example, such as a substrate with little or no flexibility, a flexible membrane, or a flexible substrate with intermediate flexibility can be preferably used. The thickness of the substrate or membrane is not particularly limited either, and it can be suitably set according to the material or use of the substrate or membrane. Various types of beads may be used as supports.

[Polynucleotides Immobilized on a Support of the Gene Detection Instrument]

In a gene detection instrument according to the present invention, at least one polynucleotide from the following polynucleotides (a) or (b) is immobilized on a support.

(a) Polynucleotides with base sequences constituting part of barley chromosomal DNA, or variants thereof with the substitution, deletion, insertion, and/or addition of one or more bases.

(b) Polynucleotides with a combination of base sequences constituting part of barley chromosomal DNA, or variants thereof with the substitution, deletion, insertion, and/or addition of one or more bases.

As used herein, a polynucleotide with a base sequence constituting part of barley chromosomal DNA is not particularly limited as long as it is a polynucleotide with a base sequence constituting part of the entire base sequences of chromosomal DNA of barley 1H, 2H, 3H, 4H, 5H, 6H, and 7H chromosomes. Further, a polynucleotide with a combination of base sequences constituting part of barley chromosomal DNA refers to a polynucleotide in which a base sequence constituting part of the entire base sequences of chromosomal DNA of barley 1H, 2H, 3H, 4H, 5H, 6H, and 7H chromosomes is joined to non-continuous base sequences constituting other parts of the chromosomes. For example, base sequences from two different parts of the chromosomes may constitute the polynucleotide, or three or more base sequences may join together to form the polynucleotide. Specifically, for example, cDNA with a plurality of exons from a protein-coding gene on barley chromosomal DNA can be regarded as a polynucleotide with a combination of base sequences constituting part of barley chromosomal DNA. However, the polynucleotide is not just limited to this specific example.

A variant with the substitution, deletion, insertion, and/or addition of one or more bases in the polynucleotide with a base sequence, or a combination of base sequences, constituting part of barley chromosomal DNA may be a polynucleotide that has been mutated on purpose, or a polynucleotide that exists in nature. For example, think of a base sequence of chromosomal DNA in a specific variety of barley. Comparing this base sequence with those of other varieties, no sequence is completely identical. Rather, these sequences are variants with the substitution, deletion, insertion, and/or addition of one or more bases.

Polynucleotides immobilized on a support of a gene detection instrument according to the present invention are preferably polynucleotides with the base sequences of SEQ ID NO: 1 through 5780, or variants with the substitution, deletion, insertion, and/or addition of one or more bases in the polynucleotides with the base sequences of SEQ ID NO: 1 through 5780. (Such polynucleotides and variants will be referred to as polynucleotides or the like with the base sequences of SEQ ID NO: 1 through 5780.)

The base sequences of SEQ ID NO: 1 through 5780 are base sequences of the barley EST (expressed sequence tag) independently developed by the inventors. The inventors have previously confirmed that a polynucleotide with the base sequences of SEQ ID NO: 1 through 770, a polynucleotide with the base sequences of SEQ ID NO: 771 through 1754, a polynucleotide with the base sequences of SEQ ID NO: 1755 through 2642, a polynucleotide with the base sequences of SEQ ID NO: 2643 through 3324, a polynucleotide with the base sequences of SEQ ID NO: 3325 through 4320, a polynucleotide with the base sequences of SEQ ID NO: 4321 through 4962, and a polynucleotide with the base sequences of SEQ ID NO: 4963 through 5780 are mapped on 1H, 2H, 3H, 4H, 5H, 6H, and 7H chromosomes, respectively.

The following briefly describes the inventors' EST and mapping. The inventors prepared mRNA from leaves of several different varieties of barley, and constructed cDNA libraries according to a conventional method. Plasmids with the cDNA were used as templates, and the base sequences in portions of the plasmids on the both ends of the inserts were used as primers. The base sequence that was read by a single sequence analysis on either end was adjusted, and a vector sequence was removed therefrom to obtain the barley EST sequence. Currently, about 140,000 EST sequences are available from the database of the inventors.

These EST sequences were divided into groups of about 10,000 genes based on homology of sequences at the 3' end. Using primer design software Primer 3, a primer set was designed for each EST, starting from the EST with the longest sequence. These primer sets were used to check for polymorphism in the hybrids of the mapped populations: malting barley Haruna Nijo and wild type barley H602. More specifically, first, the fragment lengths yielded by agarose gel electrophoresis were checked for polymorphism. If there were no difference in fragment length, the amplified fragments of the parents were aligned by direct sequencing. If the base sequences of the parents had differences to be recognized by restriction enzyme, the amplified fragments were digested with restriction enzyme and subjected to agarose gel electrophoresis to detect differences in fragment length. Then, using MAPMAKER/EXP, a linkage analysis was performed using the marker polymorphism information, together with the markers with known chromosomal locations. In this way, a genetic map based on the EST sequences was constructed.

It follows from this that the base sequences of SEQ ID NO: 1 through 5780 are partial sequences of barley cDNA. Thus, if polynucleotides with the base sequences of SEQ ID NO: 1 through 5780 were immobilized on the support, gene expression can be detected through hybridization with mRNA (probe based on mRNA) in a sample. Variants with the substitution, deletion, insertion, and/or addition of one or more bases in the base sequences of SEQ ID NO: 1 through 5780 may be polynucleotides that have been mutated on purpose, or polynucleotides that exist in nature.

A polynucleotide immobilized on a support of a gene detection instrument according to the present invention may be a part of the polynucleotides or the like with the base sequences of SEQ ID NO: 1 through 5780. Since the base sequence of such partial polynucleotide is a partial base sequence of barley cDNA, it can still be used to detect gene expression.

Further, a polynucleotide immobilized on a support of a gene detection instrument according to the present invention may be a polynucleotide whose partial sequence comprises all of or part of the base sequences of SEQ ID NO: 1 through 5780. The remaining base sequences of the polynucleotide are not limited. For example, since the base sequences of SEQ ID NO: 1 through 5780 are partial sequences of barley cDNA, these base sequences do not have the sequences on either end as originally found in the full length cDNA. Thus, a polynucleotide whose partial sequence comprises all of or part of the base sequences of SEQ ID NO: 1 through 5780, and which additionally includes the cDNA sequences on the both ends or one end as originally found in the full length cDNA can be regarded as a polynucleotide whose partial sequence comprises all of or part of the base sequences of SEQ ID NO: 1 through 5780. Further, vectors such as plasmids and BACs (bacterial artificial chromosomes) that have incorporated all of or part of the polynucleotides or the like with the base sequences of SEQ ID NO: 1 through 5780, and polynucleotides in which the partial sequence is ligated to arbitrary base sequences can also be regarded as polynucleotides whose partial sequence comprises all of or part of the base sequences of SEQ ID NO: 1 through 5780. Such polynucleotides at least include all of or part of the polynucleotides or the like with the base sequences of SEQ ID NO: 1 through 5780, i.e., part of barley cDNA, and are therefore capable of detecting gene expression.

Further, polynucleotides immobilized on a support of a gene detection instrument according to the present invention may be polynucleotides or the like whose partial sequences comprise all of or part of the base sequence, or a variant thereof, of SEQ ID NO: n (where n is an odd number), and all of or part of the base sequence, or a variant thereof, of SEQ ID NO: n+1, from among the base sequences of SEQ ID NO: 1 through 5780. As described above, the base sequences of SEQ ID NO: 1 through 5780 are EST sequences of barley, and comprise sequences that can be read by sequencing the cloned cDNA from the both ends only once. In other words, the base sequences of SEQ ID NO: n (where n is an odd number) and SEQ ID NO: n+1 among the base sequences of SEQ ID NO: 1 through 5780 are base sequences that are read from the both ends of the cDNA of the same clone. As such, these base sequences can realize a full length cDNA base sequence, which corresponds to all of or part of the full length cDNA. Thus, polynucleotides or the like whose partial sequences comprise all of or part of the base sequence, or a variant thereof, of SEQ ID NO: n (where n is an odd number), and all of or part of the base sequence, or a variant thereof, of SEQ ID NO: n+1, from among the base sequences of SEQ ID NO: 1 through 5780 can be regarded as polynucleotides with full length cDNA that comprises the base sequences of SEQ ID NO: n (where n is an odd number) and SEQ ID NO: n+1, or polynucleotides that comprise part of the full length cDNA. Further, the foregoing polynucleotides may be polynucleotides in which vector sequences or arbitrary base sequences for example are ligated to the both ends or one end of the full length cDNA or polynucleotides that comprise part of the full length cDNA. Further, the foregoing polynucleotides may be variants that have a base substitution or other mutations in sequences other than the base sequences of SEQ ID NO: 1 through 5780, i.e., a middle section of the total cDNA unspecified by SEQ ID NO: n (where n is an odd number) and SEQ ID NO: n+1. Such polynucleotides include the full length or part of barley cDNA, and are therefore capable of detecting gene expression.

The polynucleotide immobilized on a support is preferably cDNA. In this case, cDNA is not limited to full length cDNA. Rather, it may be a polynucleotide that comprises part of cDNA. Further, the polynucleotide may include other base sequences, for example, such as vector sequences, as long as it includes cDNA. Further, the polynucleotide may be a synthetic oligonucleotide that is produced by artificially synthesizing part of the cDNA base sequences.

In the case where a gene detection instrument according to the present invention is used for detection of gene expression, the substance to be detected in a sample is mRNA (probe based on mRNA). Therefore, for strong hybridization, it is preferable that the polynucleotide immobilized on a support be full length cDNA. The polynucleotide immobilized on a support may include any number of bases as long as it can detect gene expression. For example, in the case where only one polynucleotide is immobilized in each region, a polynucleotide with at least 50 bases is considered to be sufficient for detection of gene expression. When more than one polynucleotide (oligonucleotide) is immobilized in each region as in the Affymetrix system, a polynucleotide with about 25 bases is sufficient.

[Gene Detection Instrument with the Polynucleotides Immobilized in Regions that are Arranged in the Chromosomal Order]

As described above, the base sequences of SEQ ID NO: 1 through 5780 are base sequences of barley EST mapped on barley chromosomes. Further, the base sequences of SEQ ID NO: n (where n is an odd number) and SEQ ID NO: n+1 are base sequences that are read from the both ends of cDNA of the same clone, wherein n represents a base sequence on the 5' end, and n+1 represents a base sequence on the 3' end.

As used herein, the "chromosomal order" refers to the order from an arbitrary position of a chromosome. The distance by which the order is determined may be a genetic distance based on recombinations in hybrid populations, or a physical distance based on the number of bases or the length of chromosomes observed with a microscope.

As shown in Table 1-1 to Table 1-8, the chromosomal order in barley 1H chromosome (distance from the short arm end of 1H chromosome) has been specified for 385 clones including the base sequences of SEQ ID NO: n (where n is an odd number) and SEQ ID NO: n+1 from among the base sequences of SEQ ID NO: 1 through SEQ ID NO: 770. The chromosomal order in barley 1H chromosome has also been specified for 3 known clones (HVM20, Bmag211, and WMCIE8).

TABLE 1-1

| Order from the short arm end | Clones | SEQ ID NO: (5' end) | SEQ ID NO: (3' end) | Distance from the short arm end (cM) |
|---|---|---|---|---|
| 1 | bah55e06 | 1 | 2 | 0 |
| 2 | bags30b07 | 3 | 4 | 14 |
| 3 | baak21o3 | 5 | 6 | 17.4 |
| 4 | BaAK17D13 | 7 | 8 | 18.5 |
| 4 | basd26l20 | 9 | 10 | 18.5 |
| 4 | bah61p17 | 11 | 12 | 18.5 |
| 7 | BaGS11O06 | 13 | 14 | 19.6 |
| 7 | kr12H0216 | 15 | 16 | 19.6 |
| 7 | BaGS32E23 | 17 | 18 | 19.6 |
| 7 | basd13k20 | 19 | 20 | 19.6 |
| 11 | BaAK24O11 | 21 | 22 | 20.7 |
| 11 | kr26D0507 | 23 | 24 | 20.7 |
| 11 | BaSD2D08 | 25 | 26 | 20.7 |
| 11 | baak41n21 | 27 | 28 | 20.7 |
| 15 | bah11b15 | 29 | 30 | 21.8 |
| 15 | kr24B0903 | 31 | 32 | 21.8 |
| 17 | bast50E0709 | 33 | 34 | 22.9 |
| 18 | baal17o01 | 35 | 36 | 23.5 |
| 19 | baak41a04 | 37 | 38 | 24 |
| 20 | BaH28C07 | 39 | 40 | 24.2 |
| 21 | bags16g18 | 41 | 42 | 24.4 |
| 22 | BaSD3C22 | 43 | 44 | 25.1 |
| 23 | BaGS17B21 | 45 | 46 | 26.7 |
| 23 | basd27b10 | 47 | 48 | 26.7 |
| 25 | bah47d23 | 49 | 50 | 27.2 |
| 26 | BaAK21D02 | 51 | 52 | 27.7 |
| 27 | BaH17D02 | 53 | 54 | 32.1 |
| 28 | baal4f12 | 55 | 56 | 32.7 |
| 29 | BaGS11I03 | 57 | 58 | 33.8 |
| 29 | bah56a03 | 59 | 60 | 33.8 |
| 29 | kr16A0501 | 61 | 62 | 33.8 |
| 29 | bah19f01 | 63 | 64 | 33.8 |
| 33 | BaAK27F07 | 65 | 66 | 37 |
| 34 | bah47f18 | 67 | 68 | 41.1 |
| 34 | bah45l19 | 69 | 70 | 41.1 |
| 36 | BaAK12I12 | 71 | 72 | 44.1 |
| 37 | BaAL6N04 | 73 | 74 | 45.2 |
| 37 | baal16l05 | 75 | 76 | 45.2 |
| 37 | BaSD18O20 | 77 | 78 | 45.2 |
| 37 | BaSD3J13 | 79 | 80 | 45.2 |
| 41 | bah63j19 | 81 | 82 | 49.5 |
| 41 | BaH36O18 | 83 | 84 | 49.5 |
| 43 | BaAK20A06 | 85 | 86 | 50.6 |
| 43 | BaGS8G13 | 87 | 88 | 50.6 |
| 45 | bah25n06 | 89 | 90 | 53.8 |
| 45 | BaAK1P06 | 91 | 92 | 53.8 |
| 47 | BaAK16M07 | 93 | 94 | 55.1 |
| 47 | BaH36M15 | 95 | 96 | 55.1 |
| 49 | BaGS12K12 | 97 | 98 | 62.4 |
| 50 | BaAL39C22 | 99 | 100 | 71.9 |

TABLE 1-2

| Order from the short arm end | Clones | SEQ ID NO: (5' end) | SEQ ID NO: (3' end) | Distance from the short arm end (cM) |
|---|---|---|---|---|
| 50 | kr68B0303 | 101 | 102 | 71.9 |
| 52 | baak24d09 | 103 | 104 | 75.8 |
| 53 | BaGS11J13 | 105 | 106 | 76.9 |
| 54 | baal38l23 | 107 | 108 | 79.5 |
| 54 | BaAL36B15 | 109 | 110 | 79.5 |
| 56 | bast60D0610 | 111 | 112 | 80.6 |
| 56 | kr22D0808 | 113 | 114 | 80.6 |
| 56 | baal19i12 | 115 | 116 | 80.6 |
| 56 | basd23o02 | 117 | 118 | 80.6 |
| 56 | baak1i14 | 119 | 120 | 80.6 |
| 56 | baak24k18 | 121 | 122 | 80.6 |
| 56 | kr18G0814 | 123 | 124 | 80.6 |
| 63 | BaH38H09 | 125 | 126 | 82.3 |
| 64 | BaGS8B13 | 127 | 128 | 85.4 |
| 64 | BaH25J08 | 129 | 130 | 85.4 |
| 66 | baak3d11 | 131 | 132 | 88.6 |
| 67 | baal12p08 | 133 | 134 | 89.7 |
| 67 | bags39j20 | 135 | 136 | 89.7 |
| 67 | bags32m16 | 137 | 138 | 89.7 |
| 70 | kr15A0402 | 139 | 140 | 91.3 |
| 71 | baal3c01 | 141 | 142 | 91.9 |
| 72 | baak41i03 | 143 | 144 | 93.9 |
| 73 | BaGS29M13 | 145 | 146 | 95.7 |
| 74 | basdl7m22 | 147 | 148 | 98 |
| 74 | bags15g01 | 149 | 150 | 98 |
| 74 | BaH24I06 | 151 | 152 | 98 |
| 77 | BaH57E12 | 153 | 154 | 99.1 |
| 78 | BaSD25C22 | 155 | 156 | 99.7 |
| 79 | baal19m17 | 157 | 158 | 101.9 |
| 80 | bah46p14 | 159 | 160 | 102.3 |
| 80 | bags18d19 | 161 | 162 | 102.3 |
| 80 | BaAK34J19 | 163 | 164 | 102.3 |
| 83 | bags6d01 | 165 | 166 | 105.6 |
| 84 | bags3p11 | 167 | 168 | 108.9 |
| 84 | BaAK14J21 | 169 | 170 | 108.9 |
| 84 | baak2m05 | 171 | 172 | 108.9 |
| 87 | baak37g19 | 173 | 174 | 109.4 |
| 88 | BaGS31B11 | 175 | 176 | 109.9 |
| 88 | BaAL35M08 | 177 | 178 | 109.9 |
| 88 | BaSD16G03 | 179 | 180 | 109.9 |
| 88 | BaH58J20 | 181 | 182 | 109.9 |
| 88 | BaGS22B13 | 183 | 184 | 109.9 |
| 88 | BaAK43M01 | 185 | 186 | 109.9 |
| 88 | bah14i07 | 187 | 188 | 109.9 |
| 88 | BaH13F14 | 189 | 190 | 109.9 |
| 88 | baal9i16 | 191 | 192 | 109.9 |
| 88 | basd27b20 | 193 | 194 | 109.9 |
| 88 | BaAK2O24 | 195 | 196 | 109.9 |
| 88 | basd18l16 | 197 | 198 | 109.9 |
| 88 | BaAL19J14 | 199 | 200 | 109.9 |

TABLE 1-3

| Order from the short arm end | Clones | SEQ ID NO: (5' end) | SEQ ID NO: (3' end) | Distance from the short arm end (cM) |
|---|---|---|---|---|
| 88 | bags22i15 | 201 | 202 | 109.9 |
| 102 | baak44a23 | 203 | 204 | 111.5 |
| 102 | BaAK32N04 | 205 | 206 | 111.5 |
| 104 | basd21e22 | 207 | 208 | 112 |
| 104 | BaGS7K03 | 209 | 210 | 112 |
| 104 | baak42e22 | 211 | 212 | 112 |
| 107 | bast21D0808 | 213 | 214 | 113.1 |
| 107 | bast75E0610 | 215 | 216 | 113.1 |
| 107 | baet16A1002 | 217 | 218 | 113.1 |
| 107 | basd17m16 | 219 | 220 | 113.1 |
| 107 | bags17g08 | 221 | 222 | 113.1 |
| 107 | baak21i01 | 223 | 224 | 113.1 |
| 107 | baakl3n06 | 225 | 226 | 113.1 |
| 107 | baak22o23 | 227 | 228 | 113.1 |
| 107 | baet42E0410 | 229 | 230 | 113.1 |
| 116 | BaGS27M04 | 231 | 232 | 114.2 |

TABLE 1-3-continued

| Order from the short arm end | Clones | SEQ ID NO: (5' end) | SEQ ID NO: (3' end) | Distance from the short arm end (cM) |
|---|---|---|---|---|
| 116 | BaH52H18 | 233 | 234 | 114.2 |
| 116 | baak33k20 | 235 | 236 | 114.2 |
| 116 | bags21f16 | 237 | 238 | 114.2 |
| 116 | bags34e05 | 239 | 240 | 114.2 |
| 116 | bags15d20 | 241 | 242 | 114.2 |
| 116 | bags18g10 | 243 | 244 | 114.2 |
| 116 | bags19a02 | 245 | 246 | 114.2 |
| 116 | BaAK17J19 | 247 | 248 | 114.2 |
| 125 | bags35k02 | 249 | 250 | 115.3 |
| 126 | bah35a22 | 251 | 252 | 116.4 |
| 126 | BaGS17H13 | 253 | 254 | 116.4 |
| 126 | bah47n12 | 255 | 256 | 116.4 |
| 126 | baak12p11 | 257 | 258 | 116.4 |
| 126 | baet38B1004 | 259 | 260 | 116.4 |
| 126 | BaGS13K12 | 261 | 262 | 116.4 |
| 126 | BaAL25A05 | 263 | 264 | 116.4 |
| 133 | bah27k23 | 265 | 266 | 117.2 |
| 134 | BaAK24J12 | 267 | 268 | 118.3 |
| 135 | BaSD14M22 | 269 | 270 | 119.8 |
| 135 | bah17l24 | 271 | 272 | 119.8 |
| 137 | baal29i09 | 273 | 274 | 120.5 |
| 137 | bah16d09 | 275 | 276 | 120.5 |
| 137 | bah60d03 | 277 | 278 | 120.5 |
| 137 | bah45i13 | 279 | 280 | 120.5 |
| 137 | bah11h03 | 281 | 282 | 120.5 |
| 137 | bah47h17 | 283 | 284 | 120.5 |
| 143 | bags35d02 | 285 | 286 | 122.7 |
| 143 | bags37e17 | 287 | 288 | 122.7 |
| 143 | baak14c12 | 289 | 290 | 122.7 |
| 143 | baak34c01 | 291 | 292 | 122.7 |
| 143 | BaH35A11 | 293 | 294 | 122.7 |
| 148 | BaAK30M16 | 295 | 296 | 123.8 |
| 148 | BaSD11P04 | 297 | 298 | 123.8 |
| 148 | bah12i09 | 299 | 300 | 123.8 |

TABLE 1-4

| Order from the short arm end | Clones | SEQ ID NO: (5' end) | SEQ ID NO: (3' end) | Distance from the short arm end (cM) |
|---|---|---|---|---|
| 148 | BaAL2G20 | 301 | 302 | 123.8 |
| 152 | bags14j09 | 303 | 304 | 126 |
| 152 | kr26E0610 | 305 | 306 | 126 |
| 152 | bah37f01 | 307 | 308 | 126 |
| 152 | bags29m05 | 309 | 310 | 126 |
| 156 | BaGS17A18 | 311 | 312 | 126.5 |
| 157 | baet34A0501 | 313 | 314 | 127 |
| 157 | BaSD22O13 | 315 | 316 | 127 |
| 157 | bags15a22 | 317 | 318 | 127 |
| 157 | baet21H1016 | 319 | 320 | 127 |
| 157 | BaH30E13 | 321 | 322 | 127 |
| 157 | bags4e23 | 323 | 324 | 127 |
| 157 | baak45b03 | 325 | 326 | 127 |
| 157 | bah12o12 | 327 | 328 | 127 |
| 165 | baak34k14 | 329 | 330 | 127.9 |
| 166 | baal3e14 | 331 | 332 | 131.5 |
| 167 | bags22f12 | 333 | 334 | 136.3 |
| 168 | BaH45P03 | 335 | 336 | 137.2 |
| 168 | basd11d13 | 337 | 338 | 137.2 |
| 168 | Bmag211 | — | — | 137.2 |
| 168 | HVM20 | — | — | 137.2 |
| 168 | basd1j14 | 339 | 340 | 137.2 |
| 173 | bags35b18 | 341 | 342 | 138.3 |
| 173 | baal41i11 | 343 | 344 | 138.3 |
| 175 | bags13e23 | 345 | 346 | 139.4 |
| 176 | bah20d03 | 347 | 348 | 140 |
| 177 | baet19F0212 | 349 | 350 | 140.5 |
| 177 | bags12j05 | 351 | 352 | 140.5 |
| 179 | BaSD24D17 | 353 | 354 | 141.6 |
| 180 | BaGS24K10 | 355 | 356 | 142.1 |
| 181 | baal9e05 | 357 | 358 | 142.6 |
| 181 | BaGS33M23 | 359 | 360 | 142.6 |

TABLE 1-4-continued

| Order from the short arm end | Clones | SEQ ID NO: (5' end) | SEQ ID NO: (3' end) | Distance from the short arm end (cM) |
|---|---|---|---|---|
| 183 | bah46g14 | 361 | 362 | 143.1 |
| 184 | bags33h05 | 363 | 364 | 143.6 |
| 185 | baak24h12 | 365 | 366 | 143.9 |
| 186 | BaH50N19 | 367 | 368 | 144.2 |
| 187 | BaAK31O05 | 369 | 370 | 144.4 |
| 188 | BaGS39L14 | 371 | 372 | 144.7 |
| 189 | BaGS27C22 | 373 | 374 | 146.8 |
| 189 | bags20o24 | 375 | 376 | 146.8 |
| 189 | bags34j05 | 377 | 378 | 146.8 |
| 189 | bah56l03 | 379 | 380 | 146.8 |
| 189 | basd12k03 | 381 | 382 | 146.8 |
| 189 | BaAK39I18 | 383 | 384 | 146.8 |
| 189 | bags21h06 | 385 | 386 | 146.8 |
| 189 | bah56k04 | 387 | 388 | 146.8 |
| 189 | bah60e11 | 389 | 390 | 146.8 |
| 198 | baak22i05 | 391 | 392 | 147.9 |
| 198 | baal5i02 | 393 | 394 | 147.9 |
| 200 | BaAK2E05 | 395 | 396 | 149 |

TABLE 1-5

| Order from the short arm end | Clones | SEQ ID NO: (5' end) | SEQ ID NO: (3' end) | Distance from the short arm end (cM) |
|---|---|---|---|---|
| 201 | baak33g12 | 397 | 398 | 151.2 |
| 201 | bags4e05 | 399 | 400 | 151.2 |
| 203 | bast42C0806 | 401 | 402 | 155.4 |
| 204 | baak26c05 | 403 | 404 | 156.6 |
| 205 | bags19a16 | 405 | 406 | 158.6 |
| 206 | kr11F1212 | 407 | 408 | 159.7 |
| 206 | BaH28K13 | 409 | 410 | 159.7 |
| 206 | baak20d06 | 411 | 412 | 159.7 |
| 206 | BaSD1I24 | 413 | 414 | 159.7 |
| 206 | baak35l20 | 415 | 416 | 159.7 |
| 211 | bah57m07 | 417 | 418 | 161.8 |
| 211 | bah60k11 | 419 | 420 | 161.8 |
| 213 | basd20o09 | 421 | 422 | 162.9 |
| 213 | basd24i22 | 423 | 424 | 162.9 |
| 215 | bags30g20 | 425 | 426 | 164 |
| 216 | bags1m11 | 427 | 428 | 164.6 |
| 217 | bags23g20 | 429 | 430 | 165.1 |
| 218 | BaGS15B05 | 431 | 432 | 166.2 |
| 219 | BaGS24P05 | 433 | 434 | 167.3 |
| 220 | bags10g06 | 435 | 436 | 168.4 |
| 220 | bah32o04 | 437 | 438 | 168.4 |
| 220 | BaGS32P08 | 439 | 440 | 168.4 |
| 223 | bags4e02 | 441 | 442 | 169.5 |
| 223 | bast04H0315 | 443 | 444 | 169.5 |
| 223 | BaGS37L06 | 445 | 446 | 169.5 |
| 226 | basd2b18 | 447 | 448 | 170.6 |
| 227 | bags3h12 | 449 | 450 | 172.1 |
| 228 | bags1e21 | 451 | 452 | 174.6 |
| 228 | BaAK27M21 | 453 | 454 | 174.6 |
| 230 | BaSD18F05 | 455 | 456 | 174.9 |
| 231 | BaH35B05 | 457 | 458 | 175.3 |
| 232 | basd21h11 | 459 | 460 | 176.4 |
| 232 | BaH32E20 | 461 | 462 | 176.4 |
| 234 | BaGS22A20 | 463 | 464 | 177.5 |
| 235 | BaSD14B13 | 465 | 466 | 179 |
| 236 | bags29l04 | 467 | 468 | 182 |
| 236 | bags22g16 | 469 | 470 | 182 |
| 238 | BaAL4B14 | 471 | 472 | 184.2 |
| 238 | bah61h20 | 473 | 474 | 184.2 |
| 240 | bah15p01 | 475 | 476 | 186.4 |
| 240 | baak41p03 | 477 | 478 | 186.4 |
| 242 | BaSD12L06 | 479 | 480 | 187.7 |
| 242 | BaSD23P07 | 481 | 482 | 187.7 |
| 242 | BaGS7J05 | 483 | 484 | 187.7 |
| 245 | bah29b06 | 485 | 486 | 188.3 |
| 245 | BaGS31N17 | 487 | 488 | 188.3 |
| 247 | BaGS13F08 | 489 | 490 | 190.4 |
| 248 | BaAK39G10 | 491 | 492 | 195.7 |

TABLE 1-5-continued

| Order from the short arm end | Clones | SEQ ID NO: (5' end) | SEQ ID NO: (3' end) | Distance from the short arm end (cM) |
|---|---|---|---|---|
| 249 | BaAK39G03 | 493 | 494 | 200 |
| 249 | baak2a18 | 495 | 496 | 200 |

TABLE 1-6

| Order from the short arm end | Clones | SEQ ID NO: (5' end) | SEQ ID NO: (3' end) | Distance from the short arm end (cM) |
|---|---|---|---|---|
| 251 | bags39d12 | 497 | 498 | 201.1 |
| 251 | basd17l04 | 499 | 500 | 201.1 |
| 251 | BaAK20B19 | 501 | 502 | 201.1 |
| 251 | bags15j15 | 503 | 504 | 201.1 |
| 251 | BaAK30F02 | 505 | 506 | 201.1 |
| 256 | BaGS22A21 | 507 | 508 | 202.2 |
| 256 | baet45E0410 | 509 | 510 | 202.2 |
| 256 | BaGS22C14 | 511 | 512 | 202.2 |
| 256 | bah23k12 | 513 | 514 | 202.2 |
| 260 | BaH15O13 | 515 | 516 | 203.2 |
| 260 | kr24F0412 | 517 | 518 | 203.3 |
| 260 | BaGS28O21 | 519 | 520 | 203.3 |
| 260 | BaAL15N19 | 521 | 522 | 203.3 |
| 264 | bags10j15 | 523 | 524 | 207.6 |
| 265 | bags32j03 | 525 | 526 | 209.7 |
| 266 | bags20e14 | 527 | 528 | 211.1 |
| 267 | bags3c15 | 529 | 530 | 214 |
| 268 | basd27n01 | 531 | 532 | 216 |
| 269 | BaGS6M19 | 533 | 534 | 217.1 |
| 270 | baak13e03 | 535 | 536 | 219.2 |
| 271 | BaH15M10 | 537 | 538 | 221.5 |
| 271 | bags14k12 | 539 | 540 | 221.5 |
| 271 | bast61E0509 | 541 | 542 | 221.5 |
| 271 | BaGS31N04 | 543 | 544 | 221.5 |
| 275 | BaAK27D22 | 545 | 546 | 230 |
| 275 | baal5o19 | 547 | 548 | 230 |
| 277 | bah55b18 | 549 | 550 | 231.1 |
| 278 | bah23i02 | 551 | 552 | 232.6 |
| 278 | BaAK15H22 | 553 | 554 | 232.6 |
| 280 | bags32b03 | 555 | 556 | 244.3 |
| 281 | baak30c15 | 557 | 558 | 248.9 |
| 281 | BaGS22A05 | 559 | 560 | 248.9 |
| 281 | bah16m01 | 561 | 562 | 248.9 |
| 284 | bags15e08 | 563 | 564 | 250 |
| 284 | BaGS37D12 | 565 | 566 | 250 |
| 284 | BaAL37N24 | 567 | 568 | 250 |
| 287 | BaH28B09 | 569 | 570 | 251.1 |
| 287 | bah47h08 | 571 | 572 | 251.1 |
| 289 | BaH57N07 | 573 | 574 | 252.2 |
| 290 | baak38o02 | 575 | 576 | 253.5 |
| 290 | baak20f16 | 577 | 578 | 253.5 |
| 292 | baak28n19 | 579 | 580 | 257.4 |
| 292 | bah59j07 | 581 | 582 | 257.4 |
| 292 | bah44j20 | 583 | 584 | 257.4 |
| 292 | BaH47J05 | 585 | 586 | 257.4 |
| 296 | baet39B0303 | 587 | 588 | 260.7 |
| 297 | BaAK27D19 | 589 | 590 | 261.8 |
| 297 | basd25g01 | 591 | 592 | 261.8 |
| 299 | BaAL34K17 | 593 | 594 | 262.9 |
| 299 | basd21i17 | 595 | 596 | 262.9 |

TABLE 1-7

| Order from the short arm end | Clones | SEQ ID NO: (5' end) | SEQ ID NO: (3' end) | Distance from the short arm end (cM) |
|---|---|---|---|---|
| 301 | bags15o12 | 597 | 598 | 264 |
| 301 | baal2j10 | 599 | 600 | 264 |
| 303 | baak44n10 | 601 | 602 | 264.4 |
| 304 | baak21e08 | 603 | 604 | 264.8 |
| 305 | BaGS37F14 | 605 | 606 | 265.2 |

TABLE 1-7-continued

| Order from the short arm end | Clones | SEQ ID NO: (5' end) | SEQ ID NO: (3' end) | Distance from the short arm end (cM) |
|---|---|---|---|---|
| 306 | BaAK41I21 | 607 | 608 | 266.3 |
| 306 | BaGS19C07 | 609 | 610 | 266.3 |
| 308 | BaGS15O08 | 611 | 612 | 268.4 |
| 308 | baak40p22 | 613 | 614 | 268.4 |
| 310 | BaH21K05 | 615 | 616 | 269.5 |
| 310 | baal40n03 | 617 | 618 | 269.5 |
| 312 | bags23b08 | 619 | 620 | 269.9 |
| 313 | BaGS39L18 | 621 | 622 | 270.6 |
| 313 | BaGS25K24 | 623 | 624 | 270.6 |
| 313 | bags1a18 | 625 | 626 | 270.6 |
| 313 | baal15k07 | 627 | 628 | 270.6 |
| 313 | bags14o13 | 629 | 630 | 270.6 |
| 318 | BaH18D15 | 631 | 632 | 271.7 |
| 319 | bastl04F0911 | 633 | 634 | 272.8 |
| 319 | BaGS31E03 | 635 | 636 | 272.8 |
| 321 | BaGS19J21 | 637 | 638 | 273.9 |
| 322 | BaGS39P08 | 639 | 640 | 275 |
| 323 | BaH56B06 | 641 | 642 | 276.1 |
| 324 | baal13m24 | 643 | 644 | 277.2 |
| 324 | bags15h14 | 645 | 646 | 277.2 |
| 324 | bags35j22 | 647 | 648 | 277.2 |
| 324 | baak20h22 | 649 | 650 | 277.2 |
| 328 | baal34b14 | 651 | 652 | 278.3 |
| 328 | bah16j04 | 653 | 654 | 278.3 |
| 328 | BaH54J03 | 655 | 656 | 278.3 |
| 331 | bast58C1206 | 657 | 658 | 280.4 |
| 332 | BaH26M05 | 659 | 660 | 281.5 |
| 332 | bastl20B0404 | 661 | 662 | 281.5 |
| 334 | baak14e23 | 663 | 664 | 288.1 |
| 334 | BaH15P22 | 665 | 666 | 288.1 |
| 334 | BaGS17I22 | 667 | 668 | 288.1 |
| 337 | bags15h01 | 669 | 670 | 292.4 |
| 338 | bags7p13 | 671 | 672 | 294.5 |
| 339 | BaGS29H13 | 673 | 674 | 296.7 |
| 339 | bah47b01 | 675 | 676 | 296.7 |
| 341 | bastl45E1109 | 677 | 678 | 299.9 |
| 341 | bags32m15 | 679 | 680 | 299.9 |
| 341 | basd12c09 | 681 | 682 | 299.9 |
| 344 | baal27m11 | 683 | 684 | 301 |
| 344 | basd12k01 | 685 | 686 | 301 |
| 344 | baak41n15 | 687 | 688 | 301 |
| 344 | bags1b01 | 689 | 690 | 301 |
| 348 | BaH56O11 | 691 | 692 | 302.1 |
| 349 | bah15k16 | 693 | 694 | 303.2 |
| 349 | bags31a22 | 695 | 696 | 303.2 |

TABLE 1-8

| Order from the short arm end | Clones | SEQ ID NO: (5' end) | SEQ ID NO: (3' end) | Distance from the short arm end (cM) |
|---|---|---|---|---|
| 349 | bags21e21 | 697 | 698 | 303.2 |
| 349 | baak32n05 | 699 | 700 | 303.2 |
| 353 | baet02B0503 | 701 | 702 | 304.3 |
| 353 | BaH29L05 | 703 | 704 | 304.3 |
| 355 | baet43H1016 | 705 | 706 | 305.4 |
| 356 | BaGS38N20 | 707 | 708 | 306.5 |
| 356 | BaGS23O09 | 709 | 710 | 306.5 |
| 356 | bastl26B0410 | 711 | 712 | 306.5 |
| 359 | BaH15N14 | 713 | 714 | 309.6 |
| 359 | baak20b06 | 715 | 716 | 309.6 |
| 361 | BaH16I04 | 717 | 718 | 311.7 |
| 362 | bah22p07 | 719 | 720 | 312.8 |
| 363 | baak21j02 | 721 | 722 | 313.9 |
| 363 | bah30o13 | 723 | 724 | 313.9 |
| 363 | bags38f18 | 725 | 726 | 313.9 |
| 363 | bah13o05 | 727 | 728 | 313.9 |
| 363 | baak36b12 | 729 | 730 | 313.9 |
| 363 | bags18o09 | 731 | 732 | 313.9 |
| 363 | BaAK16L10 | 733 | 734 | 313.9 |
| 363 | BaAK38E16 | 735 | 736 | 313.9 |
| 371 | bah13e15 | 737 | 738 | 317.4 |

TABLE 1-8-continued

| Order from the short arm end | Clones | SEQ ID NO: (5' end) | SEQ ID NO: (3' end) | Distance from the short arm end (cM) |
|---|---|---|---|---|
| 372 | bags1f22 | 739 | 740 | 319.8 |
| 373 | bags21o12 | 741 | 742 | 321.4 |
| 374 | BaGS9B14 | 743 | 744 | 324.7 |
| 375 | BaAL1N23 | 745 | 746 | 325.2 |
| 375 | bbak1a17 | 747 | 748 | 325.2 |
| 377 | BaH32B01 | 749 | 750 | 326.3 |
| 377 | BaSD18L13 | 751 | 752 | 326.3 |
| 379 | baak12p07 | 753 | 754 | 328.4 |
| 379 | BaH58A04 | 755 | 756 | 328.4 |
| 381 | bags1p04 | 757 | 758 | 329.1 |
| 381 | BaAL17O03 | 759 | 760 | 329.1 |
| 383 | baal8e17 | 761 | 762 | 332 |
| 384 | BaH50I05 | 763 | 764 | 335.2 |
| 384 | bastl28A0101 | 765 | 766 | 335.2 |
| 386 | BaH39L18 | 767 | 768 | 336.3 |
| 387 | bags18e18 | 769 | 770 | 342.1 |
| 388 | WMCIE8 | — | — | 362.7 |

As shown in Table 2-1 to Table 2-10, the chromosomal order in barley 2H chromosome (distance from the short arm end of 2H chromosome) has been specified for 492 clones including the base sequences of SEQ ID NO: n (where n is an odd number) and SEQ ID NO: n+1 from among the base sequences of SEQ ID NO: 771 through SEQ ID NO: 1754. The chromosomal order in barley 2H chromosome has also been specified for 8 known clones (Bmac134, cMWG682, HVM36, cMWG699, Bmag125, cMWG694, EBmac415, and MWG2076).

TABLE 2-1

| Order from the short arm end | Clones | SEQ ID NO: (5' end) | SEQ ID NO: (3' end) | Distance from the short arm end (cM) |
|---|---|---|---|---|
| 1 | BaGS20L10 | 771 | 772 | 0 |
| 2 | BaSD15P22 | 773 | 774 | 15.4 |
| 2 | bags7b16 | 775 | 776 | 15.4 |
| 4 | BaAK34H02 | 777 | 778 | 20.7 |
| 5 | BaAK22H13 | 779 | 780 | 21.7 |
| 6 | BaGS37P19 | 781 | 782 | 23.2 |
| 7 | BaAL19P17 | 783 | 784 | 24.3 |
| 8 | BaH41L14 | 785 | 786 | 25.2 |
| 9 | BaAK24H17 | 787 | 788 | 26.3 |
| 10 | bast21a0602 | 789 | 790 | 26.4 |
| 10 | BaAL27L20 | 791 | 792 | 26.4 |
| 12 | Bmac134 | — | — | 26.7 |
| 12 | cMWG682 | — | — | 26.7 |
| 12 | bags34p10 | 793 | 794 | 26.7 |
| 12 | basd18b14 | 795 | 796 | 26.7 |
| 16 | bags38p20 | 797 | 798 | 27.8 |
| 17 | BaAK41N22 | 799 | 800 | 28.9 |
| 17 | BaAK21D17 | 801 | 802 | 28.9 |
| 19 | BaAL29B07 | 803 | 804 | 30 |
| 19 | baak20o16 | 805 | 806 | 30 |
| 21 | bast42A0602 | 807 | 808 | 31.1 |
| 21 | BaH36B07 | 809 | 810 | 31.1 |
| 21 | BaAK26L07 | 811 | 812 | 31.1 |
| 21 | baal12a06 | 813 | 814 | 31.1 |
| 25 | BaSD3C20 | 815 | 816 | 33.3 |
| 26 | bastl17G0113 | 817 | 818 | 34.6 |
| 27 | baak11h14 | 819 | 820 | 39.2 |
| 28 | baal12m14 | 821 | 822 | 40.2 |
| 29 | baal33a18 | 823 | 824 | 41.3 |
| 30 | bah28a18 | 825 | 826 | 43.5 |
| 30 | bags39o04 | 827 | 828 | 43.5 |
| 30 | BaH48H04 | 829 | 830 | 43.5 |
| 30 | BaGS6B11 | 831 | 832 | 43.5 |
| 34 | bags4p16 | 833 | 834 | 44.6 |
| 34 | basd24j22 | 835 | 836 | 44.6 |
| 34 | basd16p15 | 837 | 838 | 44.6 |
| 34 | bags15k16 | 839 | 840 | 44.6 |

TABLE 2-1-continued

| Order from the short arm end | Clones | SEQ ID NO: (5' end) | SEQ ID NO: (3' end) | Distance from the short arm end (cM) |
|---|---|---|---|---|
| 34 | bast23D1208 | 841 | 842 | 44.6 |
| 39 | BaAL32B22 | 843 | 844 | 45.3 |
| 39 | BaGS39D07 | 845 | 846 | 45.3 |
| 41 | BaH19L09 | 847 | 848 | 48 |
| 41 | bags38a17 | 849 | 850 | 48 |
| 41 | BaAK39I11 | 851 | 852 | 48 |
| 44 | BaSD3I24 | 853 | 854 | 49.9 |
| 44 | BaH35F01 | 855 | 856 | 49.9 |
| 46 | BaAL30K02 | 857 | 858 | 53.9 |
| 47 | bah13l23 | 859 | 860 | 54.9 |
| 48 | BaAL26H21 | 861 | 862 | 55.7 |
| 49 | BaGS22H22 | 863 | 864 | 56.8 |
| 49 | bags13n11 | 865 | 866 | 56.8 |

TABLE 2-2

| Order from the short arm end | Clones | SEQ ID NO: (5' end) | SEQ ID NO: (3' end) | Distance from the short arm end (cM) |
|---|---|---|---|---|
| 51 | bags1h03 | 867 | 868 | 62 |
| 52 | baak32l16 | 869 | 870 | 63.2 |
| 52 | baal19a12 | 871 | 872 | 63.2 |
| 52 | BaAK45G16 | 873 | 874 | 63.2 |
| 55 | BaGS37N19 | 875 | 876 | 64.3 |
| 56 | baak3f03 | 877 | 878 | 65.4 |
| 57 | bags5c02 | 879 | 880 | 66.4 |
| 58 | BaGS35P07 | 881 | 882 | 67.4 |
| 58 | HVM36 | — | — | 67.4 |
| 60 | bah45e07 | 883 | 884 | 70.5 |
| 61 | BaAK24B09 | 885 | 886 | 71.6 |
| 61 | bags33a11 | 887 | 888 | 71.6 |
| 63 | bah62i11 | 889 | 890 | 72.7 |
| 64 | BaH56A24 | 891 | 892 | 74.9 |
| 65 | BaSD21D14 | 893 | 894 | 77.1 |
| 66 | basd1a17 | 895 | 896 | 78.2 |
| 66 | bah17n24 | 897 | 898 | 78.2 |
| 68 | kr70G0113 | 899 | 900 | 79.3 |
| 68 | basd15f08 | 901 | 902 | 79.3 |
| 68 | BaGS4J04 | 903 | 904 | 79.3 |
| 68 | baak33f06 | 905 | 906 | 79.3 |
| 72 | basd14f16 | 907 | 908 | 79.9 |
| 73 | BaH59K20 | 909 | 910 | 80.4 |
| 73 | baal35h05 | 911 | 912 | 80.4 |
| 73 | BaGS20M01 | 913 | 914 | 80.4 |
| 76 | BaH25N22 | 915 | 916 | 82.6 |
| 77 | baak14a24 | 917 | 918 | 83.7 |
| 77 | baak30d07 | 919 | 920 | 83.7 |
| 79 | bah11n18 | 921 | 922 | 84.8 |
| 79 | kr14C0305 | 923 | 924 | 84.8 |
| 79 | baet18F0911 | 925 | 926 | 84.8 |
| 79 | BaGS4J18 | 927 | 928 | 84.8 |
| 83 | bast74C0705 | 929 | 930 | 85.9 |
| 83 | BaAL4G17 | 931 | 932 | 85.9 |
| 85 | bastl43H0515 | 933 | 934 | 86.2 |
| 85 | BaH58M22 | 935 | 936 | 86.2 |
| 87 | bags10i21 | 937 | 938 | 87 |
| 87 | bah20h16 | 939 | 940 | 87 |
| 87 | BaH17P13 | 941 | 942 | 87 |
| 87 | baak41d10 | 943 | 944 | 87 |
| 91 | BaGS14F01 | 945 | 946 | 88.1 |
| 91 | BaAK16E24 | 947 | 948 | 88.1 |
| 93 | BaSD18F09 | 949 | 950 | 92.4 |
| 93 | baet42A0501 | 951 | 952 | 92.4 |
| 93 | BaAK20L07 | 953 | 954 | 92.4 |
| 96 | baak16e20 | 955 | 956 | 92.9 |
| 97 | BaGS13N14 | 957 | 958 | 93.5 |
| 98 | basd13m14 | 959 | 960 | 94.6 |
| 99 | bags20g23 | 961 | 962 | 95.2 |
| 100 | basd1l17 | 963 | 964 | 95.7 |

TABLE 2-3

| Order from the short arm end | Clones | SEQ ID NO: (5' end) | SEQ ID NO: (3' end) | Distance from the short arm end (cM) |
|---|---|---|---|---|
| 100 | basd26l01 | 965 | 966 | 95.7 |
| 100 | BaAL37J18 | 967 | 968 | 95.7 |
| 103 | bags7i05 | 969 | 970 | 96.8 |
| 103 | bah60m17 | 971 | 972 | 96.8 |
| 105 | bags21l01 | 973 | 974 | 99 |
| 106 | baet31E0109 | 975 | 976 | 101.2 |
| 107 | bags34m12 | 977 | 978 | 102.3 |
| 107 | bah50n02 | 979 | 980 | 102.3 |
| 107 | BaH50M11 | 981 | 982 | 102.3 |
| 107 | bast27E1010 | 983 | 984 | 102.3 |
| 107 | bags23c12 | 985 | 986 | 102.3 |
| 107 | bah51m11 | 987 | 988 | 102.3 |
| 113 | baak20d17 | 989 | 990 | 102.8 |
| 114 | bags23l21 | 991 | 992 | 103.4 |
| 115 | BaH52K04 | 993 | 994 | 104.5 |
| 115 | BaAL37F24 | 995 | 996 | 104.5 |
| 115 | bags23d01 | 997 | 998 | 104.5 |
| 118 | BaSD11K22 | 999 | 1000 | 105 |
| 119 | baal29m02 | 1001 | 1002 | 105.5 |
| 119 | bah17e21 | 1003 | 1004 | 105.5 |
| 119 | bah56j18 | 1005 | 1006 | 105.5 |
| 119 | bags38n06 | 1007 | 1008 | 105.5 |
| 119 | baet44D1208 | 1009 | 1010 | 105.5 |
| 119 | BaAL34O13 | 1011 | 1012 | 105.5 |
| 125 | BaGS4N05 | 1013 | 1014 | 108.7 |
| 125 | BaSD15P20 | 1015 | 1016 | 108.7 |
| 125 | baal13d11 | 1017 | 1018 | 108.7 |
| 125 | bah27g02 | 1019 | 1020 | 108.7 |
| 125 | basd27m10 | 1021 | 1022 | 108.7 |
| 125 | basd23f16 | 1023 | 1024 | 108.7 |
| 125 | bah16i19 | 1025 | 1026 | 108.7 |
| 125 | BaH50I20 | 1027 | 1028 | 108.7 |
| 125 | BaH34M23 | 1029 | 1030 | 108.7 |
| 134 | bah28b24 | 1031 | 1032 | 109.3 |
| 135 | BaH50P13 | 1033 | 1034 | 109.8 |
| 135 | basd11m16 | 1035 | 1036 | 109.8 |
| 137 | bags10p15 | 1037 | 1038 | 110.9 |
| 137 | bags4g01 | 1039 | 1040 | 110.9 |
| 137 | bags10k08 | 1041 | 1042 | 110.9 |
| 137 | bags5e16 | 1043 | 1044 | 110.9 |
| 141 | bags18l02 | 1045 | 1046 | 114.1 |
| 141 | baak44k02 | 1047 | 1048 | 114.1 |
| 141 | bags35a20 | 1049 | 1050 | 114.1 |
| 141 | BaGS26M11 | 1051 | 1052 | 114.1 |
| 141 | basd14h21 | 1053 | 1054 | 114.1 |
| 141 | BaSD13D12 | 1055 | 1056 | 114.1 |
| 147 | bags38k23 | 1057 | 1058 | 114.3 |
| 147 | BaH42E05 | 1059 | 1060 | 114.3 |
| 147 | bastl55A0701 | 1061 | 1062 | 114.3 |
| 147 | bags13g18 | 1063 | 1064 | 114.3 |

TABLE 2-4

| Order from the short arm end | Clones | SEQ ID NO: (5' end) | SEQ ID NO: (3' end) | Distance from the short arm end (cM) |
|---|---|---|---|---|
| 147 | BaH15D23 | 1065 | 1066 | 114.3 |
| 147 | kr28B0604 | 1067 | 1068 | 114.3 |
| 147 | bags10f01 | 1069 | 1070 | 114.3 |
| 154 | BaGS33I07 | 1071 | 1072 | 116.4 |
| 154 | BaSD27B02 | 1073 | 1074 | 116.4 |
| 154 | BaGS30N12 | 1075 | 1076 | 116.4 |
| 154 | basd3h13 | 1077 | 1078 | 116.4 |
| 154 | BaGS37L19 | 1079 | 1080 | 116.4 |
| 159 | bah16g18 | 1081 | 1082 | 117.5 |
| 159 | bags20i15 | 1083 | 1084 | 117.5 |
| 161 | bags35c23 | 1085 | 1086 | 118 |
| 162 | bah56k07 | 1087 | 1088 | 118.5 |
| 162 | bags37d02 | 1089 | 1090 | 118.5 |
| 164 | BaAK19K05 | 1091 | 1092 | 121.6 |
| 164 | bah11i16 | 1093 | 1094 | 121.6 |
| 166 | bags22l23 | 1095 | 1095 | 123.6 |
| 166 | kr33A0901 | 1097 | 1098 | 123.6 |
| 168 | bastl38C0606 | 1099 | 1100 | 125.4 |
| 168 | baak11i13 | 1101 | 1102 | 125.4 |
| 168 | BaH58E19 | 1103 | 1104 | 125.4 |
| 168 | BaGS31G22 | 1105 | 1106 | 125.4 |
| 168 | bah37h01 | 1107 | 1108 | 125.4 |
| 168 | BaAL29P13 | 1109 | 1110 | 125.4 |
| 174 | bags39a22 | 1111 | 1112 | 126 |
| 175 | bah19g10 | 1113 | 1114 | 126.4 |
| 175 | BaAL31A14 | 1115 | 1116 | 126.4 |
| 175 | BaH50G15 | 1117 | 1118 | 126.4 |
| 175 | BaH51M12 | 1119 | 1120 | 126.4 |
| 175 | bags18k22 | 1121 | 1122 | 126.4 |
| 175 | BaGS20N21 | 1123 | 1124 | 126.4 |
| 175 | BaSD17O21 | 1125 | 1126 | 126.4 |
| 175 | BaH37G17 | 1127 | 1128 | 126.4 |
| 183 | bags30l22 | 1129 | 1130 | 128.6 |
| 184 | baak22b17 | 1131 | 1132 | 129.7 |
| 184 | bags20f22 | 1133 | 1134 | 129.7 |
| 186 | bast72G0113 | 1135 | 1136 | 131.8 |
| 186 | BaH30B05 | 1137 | 1138 | 131.8 |
| 186 | BaH60B14 | 1139 | 1140 | 131.8 |
| 186 | BaH17B16 | 1141 | 1142 | 131.8 |
| 190 | basd12n23 | 1143 | 1144 | 133.9 |
| 190 | BaH61A21 | 1145 | 1146 | 133.9 |
| 190 | BaAK19H17 | 1147 | 1148 | 133.9 |
| 190 | bah47l12 | 1149 | 1150 | 133.9 |
| 190 | baak18p11 | 1151 | 1152 | 133.9 |
| 190 | baet29H0715 | 1153 | 1154 | 133.9 |
| 190 | BaH13D11 | 1155 | 1156 | 133.9 |
| 190 | baet39D1107 | 1157 | 1158 | 133.9 |
| 190 | BaH53E15 | 1159 | 1160 | 133.9 |
| 190 | bags32o15 | 1161 | 1162 | 133.9 |
| 190 | bast48A0701 | 1163 | 1164 | 133.9 |

TABLE 2-5

| Order from the short arm end | Clones | SEQ ID NO: (5' end) | SEQ ID NO: (3' end) | Distance from the short arm end (cM) |
|---|---|---|---|---|
| 190 | bast62D0907 | 1165 | 1166 | 133.9 |
| 190 | BaH45P22 | 1167 | 1168 | 133.9 |
| 190 | BaGS32L16 | 1169 | 1170 | 133.9 |
| 190 | BaAK30J05 | 1171 | 1172 | 133.9 |
| 190 | bah52a14 | 1173 | 1174 | 133.9 |
| 190 | bah58i22 | 1175 | 1176 | 133.9 |
| 190 | BaH56L16 | 1177 | 1178 | 133.9 |
| 190 | bah52a21 | 1179 | 1180 | 133.9 |
| 190 | BaSD14G11 | 1181 | 1182 | 133.9 |
| 190 | bags6a03 | 1183 | 1184 | 133.9 |
| 190 | bast72E0109 | 1185 | 1186 | 133.9 |
| 190 | bags21a21 | 1187 | 1188 | 133.9 |
| 190 | BaH58P13 | 1189 | 1190 | 133.9 |
| 214 | bah27n22 | 1191 | 1192 | 134.4 |
| 215 | bags20c13 | 1193 | 1194 | 134.9 |
| 215 | bags30i14 | 1195 | 1196 | 134.9 |
| 215 | BaAK17E11 | 1197 | 1198 | 134.9 |
| 215 | baal1d17 | 1199 | 1200 | 134.9 |
| 215 | bags22f06 | 1201 | 1202 | 134.9 |
| 215 | baal10l01 | 1203 | 1204 | 134.9 |
| 215 | baak26e17 | 1205 | 1206 | 134.9 |
| 215 | bah16a03 | 1207 | 1208 | 134.9 |
| 215 | BaAL11F18 | 1209 | 1210 | 134.9 |
| 215 | BaAK29E10 | 1211 | 1212 | 134.9 |
| 215 | bags32d21 | 1213 | 1214 | 134.9 |
| 215 | bah54j22 | 1215 | 1216 | 134.9 |
| 215 | baak16f14 | 1217 | 1218 | 134.9 |
| 215 | baak44c12 | 1219 | 1220 | 134.9 |
| 215 | bah13f11 | 1221 | 1222 | 134.9 |
| 215 | baal39m19 | 1223 | 1224 | 134.9 |
| 215 | baak4e02 | 1225 | 1226 | 134.9 |
| 215 | baak46f04 | 1227 | 1228 | 134.9 |

TABLE 2-5-continued

| Order from the short arm end | Clones | SEQ ID NO: (5' end) | SEQ ID NO: (3' end) | Distance from the short arm end (cM) |
|---|---|---|---|---|
| 215 | BaAK13N23 | 1229 | 1230 | 134.9 |
| 215 | BaGS20E09 | 1231 | 1232 | 134.9 |
| 215 | baal4f01 | 1233 | 1234 | 134.9 |
| 215 | BaSD19I17 | 1235 | 1236 | 134.9 |
| 215 | baal4l21 | 1237 | 1238 | 134.9 |
| 215 | BaAK19P01 | 1239 | 1240 | 134.9 |
| 215 | BaAK31O14 | 1241 | 1242 | 134.9 |
| 240 | BaH26P22 | 1243 | 1244 | 135.3 |
| 241 | baal13d17 | 1245 | 1246 | 136 |
| 242 | bags22j12 | 1247 | 1248 | 138.3 |
| 242 | bags33p05 | 1249 | 1250 | 138.3 |
| 242 | bags38j07 | 1251 | 1252 | 138.3 |
| 242 | kr59F0311 | 1253 | 1254 | 138.3 |
| 242 | baal13e10 | 1255 | 1256 | 138.3 |
| 242 | bags15d19 | 1257 | 1258 | 138.3 |
| 242 | BaGS5K11 | 1259 | 1260 | 138.3 |
| 242 | BaGS10J14 | 1261 | 1262 | 138.3 |
| 242 | baak41m17 | 1263 | 1264 | 138.3 |

TABLE 2-6

| Order from the short arm end | Clones | SEQ ID NO: (5' end) | SEQ ID NO: (3' end) | Distance from the short arm end (cM) |
|---|---|---|---|---|
| 242 | bah57o03 | 1265 | 1266 | 138.3 |
| 242 | baak41d22 | 1267 | 1268 | 138.3 |
| 242 | bah61c16 | 1269 | 1270 | 138.3 |
| 242 | BaAL7M13 | 1271 | 1272 | 138.3 |
| 242 | BaAK31F11 | 1273 | 1274 | 138.3 |
| 242 | basd22k05 | 1275 | 1276 | 138.3 |
| 242 | basd3p19 | 1277 | 1278 | 138.3 |
| 242 | baak17o09 | 1279 | 1280 | 138.3 |
| 242 | baal33d23 | 1281 | 1282 | 138.3 |
| 242 | BaAK12F04 | 1283 | 1284 | 138.3 |
| 242 | bah53j16 | 1285 | 1286 | 138.3 |
| 262 | BaSD2E24 | 1287 | 1288 | 138.5 |
| 263 | bags39h08 | 1289 | 1290 | 138.7 |
| 264 | BaSD1N02 | 1291 | 1292 | 139.5 |
| 264 | bags20m21 | 1293 | 1294 | 139.5 |
| 264 | baal10h19 | 1295 | 1296 | 139.5 |
| 264 | basd12m11 | 1297 | 1298 | 139.5 |
| 264 | bah29d24 | 1299 | 1300 | 139.5 |
| 264 | BaGS39P09 | 1301 | 1302 | 139.5 |
| 264 | BaGS31F17 | 1303 | 1304 | 139.5 |
| 264 | BaGS23D08 | 1305 | 1306 | 139.5 |
| 264 | bags39d15 | 1307 | 1308 | 139.5 |
| 264 | BaGS34I17 | 1309 | 1310 | 139.5 |
| 274 | BaH32N02 | 1311 | 1312 | 141.6 |
| 274 | BaSD18H19 | 1313 | 1314 | 141.6 |
| 274 | bast63A0101 | 1315 | 1316 | 141.6 |
| 274 | BaH50N04 | 1317 | 1318 | 141.6 |
| 278 | baal4a13 | 1319 | 1320 | 147.5 |
| 278 | baal41l18 | 1321 | 1322 | 147.5 |
| 280 | BaH31A03 | 1323 | 1324 | 152.2 |
| 280 | bastl39A0901 | 1325 | 1326 | 152.2 |
| 280 | baet46D0507 | 1327 | 1328 | 152.2 |
| 283 | baal27e20 | 1329 | 1330 | 153.3 |
| 283 | bags37l16 | 1331 | 1332 | 153.3 |
| 283 | baak34o06 | 1333 | 1334 | 153.3 |
| 286 | BaAL30I11 | 1335 | 1336 | 155.4 |
| 286 | BaH62C15 | 1337 | 1338 | 155.4 |
| 286 | basd12i15 | 1339 | 1340 | 155.4 |
| 286 | BaAK40I03 | 1341 | 1342 | 155.4 |
| 286 | BaAK23E14 | 1343 | 1344 | 155.4 |
| 286 | BaAL21F11 | 1345 | 1346 | 155.4 |
| 286 | BaAK16L19 | 1347 | 1348 | 155.4 |
| 293 | baal27a24 | 1349 | 1350 | 156.5 |
| 294 | kr41H0315 | 1351 | 1352 | 157.6 |
| 294 | BaH62I23 | 1353 | 1354 | 157.6 |
| 296 | bah52i24 | 1355 | 1356 | 158.7 |
| 296 | bastl33A0301 | 1357 | 1358 | 158.7 |
| 296 | BaH28J15 | 1359 | 1360 | 158.7 |

TABLE 2-6-continued

| Order from the short arm end | Clones | SEQ ID NO: (5' end) | SEQ ID NO: (3' end) | Distance from the short arm end (cM) |
|---|---|---|---|---|
| 299 | bastl56A0301 | 1361 | 1362 | 159.8 |
| 299 | baal39a03 | 1363 | 1364 | 159.8 |

TABLE 2-7

| Order from the short arm end | Clones | SEQ ID NO: (5' end) | SEQ ID NO: (3' end) | Distance from the short arm end (cM) |
|---|---|---|---|---|
| 242 | bah57o03 | 1265 | 1266 | 138.3 |
| 242 | baak41d22 | 1267 | 1268 | 138.3 |
| 242 | bah61c16 | 1269 | 1270 | 138.3 |
| 242 | BaAL7M13 | 1271 | 1272 | 138.3 |
| 242 | BaAK31F11 | 1273 | 1274 | 138.3 |
| 242 | basd22k05 | 1275 | 1276 | 138.3 |
| 242 | basd3p19 | 1277 | 1278 | 138.3 |
| 242 | baak17o09 | 1279 | 1280 | 138.3 |
| 242 | baal33d23 | 1281 | 1282 | 138.3 |
| 242 | BaAK12F04 | 1283 | 1284 | 138.3 |
| 242 | bah53j16 | 1285 | 1286 | 138.3 |
| 262 | BaSD2E24 | 1287 | 1288 | 138.5 |
| 263 | bags39h08 | 1289 | 1290 | 138.7 |
| 264 | BaSD1N02 | 1291 | 1292 | 139.5 |
| 264 | bags20m21 | 1293 | 1294 | 139.5 |
| 264 | baal10h19 | 1295 | 1296 | 139.5 |
| 264 | basd12m11 | 1297 | 1298 | 139.5 |
| 264 | bah29d24 | 1299 | 1300 | 139.5 |
| 264 | BaGS39P09 | 1301 | 1302 | 139.5 |
| 264 | BaGS31F17 | 1303 | 1304 | 139.5 |
| 264 | BaGS23D08 | 1305 | 1306 | 139.5 |
| 264 | bags39d15 | 1307 | 1308 | 139.5 |
| 264 | BaGS34I17 | 1309 | 1310 | 139.5 |
| 274 | BaH32N02 | 1311 | 1312 | 141.6 |
| 274 | BaSD18H19 | 1313 | 1314 | 141.6 |
| 274 | bast63A0101 | 1315 | 1316 | 141.6 |
| 274 | BaH50N04 | 1317 | 1318 | 141.6 |
| 278 | baal4a13 | 1319 | 1320 | 147.5 |
| 278 | baal41l18 | 1321 | 1322 | 147.5 |
| 280 | BaH31A03 | 1323 | 1324 | 152.2 |
| 280 | bastl39A0901 | 1325 | 1326 | 152.2 |
| 280 | baet46D0507 | 1327 | 1328 | 152.2 |
| 283 | baal27e20 | 1329 | 1330 | 153.3 |
| 283 | bagsS7l16 | 1331 | 1332 | 153.3 |
| 283 | baak34o06 | 1333 | 1334 | 153.3 |
| 286 | BaAL30I11 | 1335 | 1336 | 155.4 |
| 286 | BaH62C15 | 1337 | 1338 | 155.4 |
| 286 | basd12i15 | 1339 | 1340 | 155.4 |
| 286 | BaAK40I03 | 1341 | 1342 | 155.4 |
| 286 | BaAK23E14 | 1343 | 1344 | 155.4 |
| 286 | BaAL21F11 | 1345 | 1346 | 155.4 |
| 286 | BaAK16L19 | 1347 | 1348 | 155.4 |
| 293 | baal27a24 | 1349 | 1350 | 156.5 |
| 294 | kr41H0315 | 1351 | 1352 | 157.6 |
| 294 | BaH62I23 | 1353 | 1354 | 157.6 |
| 296 | bah52i24 | 1355 | 1356 | 158.7 |
| 296 | bastl33A0301 | 1357 | 1358 | 158.7 |
| 296 | BaH28J15 | 1359 | 1360 | 158.7 |
| 299 | bastl56A0301 | 1361 | 1362 | 159.8 |
| 299 | baal39a03 | 1363 | 1364 | 159.8 |

TABLE 2-8

| Order from the short arm end | Clones | SEQ ID NO: (5' end) | SEQ ID NO: (3' end) | Distance from the short arm end (cM) |
|---|---|---|---|---|
| 345 | kr14F0911 | 1459 | 1460 | 190.8 |
| 352 | BaGS36A04 | 1461 | 1462 | 192.8 |
| 352 | bags13a16 | 1463 | 1464 | 192.8 |
| 354 | bags26e20 | 1465 | 1466 | 196.1 |
| 355 | baet45G1214 | 1467 | 1468 | 197.6 |

TABLE 2-8-continued

| Order from the short arm end | Clones | SEQ ID NO: (5' end) | SEQ ID NO: (3' end) | Distance from the short arm end (cM) |
|---|---|---|---|---|
| 356 | BaAK35F14 | 1469 | 1470 | 202 |
| 357 | BaAK23N21 | 1471 | 1472 | 203.2 |
| 357 | basd13j22 | 1473 | 1474 | 203.2 |
| 359 | BaAK46E10 | 1475 | 1476 | 208.4 |
| 359 | bastl55F0812 | 1477 | 1478 | 208.4 |
| 361 | baak46l06 | 1479 | 1480 | 209.4 |
| 361 | BaAL2D11 | 1481 | 1482 | 209.4 |
| 363 | baak15p17 | 1483 | 1484 | 210.5 |
| 364 | BaGS33J16 | 1485 | 1486 | 211.6 |
| 364 | bags7p21 | 1487 | 1488 | 211.6 |
| 366 | BaAK22E05 | 1489 | 1490 | 212.7 |
| 366 | bah42m05 | 1491 | 1492 | 212.7 |
| 368 | BaAK25L01 | 1493 | 1494 | 213.8 |
| 369 | bags39e24 | 1495 | 1496 | 214.9 |
| 369 | BaH56N24 | 1497 | 1498 | 214.9 |
| 371 | baak44i12 | 1499 | 1500 | 215.4 |
| 372 | bah21j03 | 1501 | 1502 | 215.9 |
| 373 | kr71B0103 | 1503 | 1504 | 217.4 |
| 373 | BaGS16D15 | 1505 | 1506 | 217.4 |
| 375 | baak21p23 | 1507 | 1508 | 217.9 |
| 376 | BaGS6G09 | 1509 | 1510 | 219 |
| 376 | BaSD15M02 | 1511 | 1512 | 219 |
| 376 | basd13f02 | 1513 | 1514 | 219 |
| 376 | BaH19F21 | 1515 | 1516 | 219 |
| 380 | bags20b10 | 1517 | 1518 | 224.5 |
| 380 | bah26j10 | 1519 | 1520 | 224.5 |
| 382 | bast65G0113 | 1521 | 1522 | 225.5 |
| 383 | baak4k13 | 1523 | 1524 | 226.5 |
| 383 | baal19j23 | 1525 | 1526 | 226.5 |
| 383 | bags34h11 | 1527 | 1528 | 226.5 |
| 386 | bags37j03 | 1529 | 1530 | 227.6 |
| 387 | baal15e13 | 1531 | 1532 | 230.5 |
| 387 | BaAL5O10 | 1533 | 1534 | 230.5 |
| 389 | BaGS29J10 | 1535 | 1536 | 234.4 |
| 390 | bah22o08 | 1537 | 1538 | 235.7 |
| 390 | bags6k13 | 1539 | 1540 | 235.7 |
| 392 | bastl43C0705 | 1541 | 1542 | 236.8 |
| 393 | BaAL4D10 | 1543 | 1544 | 237.4 |
| 393 | basd12n12 | 1545 | 1546 | 237.4 |
| 395 | bags23h03 | 1547 | 1548 | 240.3 |
| 395 | bags6l02 | 1549 | 1550 | 240.3 |
| 397 | bast63B0703 | 1551 | 1552 | 243.4 |
| 397 | BaSD13E02 | 1553 | 1554 | 243.4 |
| 399 | BaSD14P15 | 1555 | 1556 | 248.7 |
| 399 | bah13a17 | 1557 | 1558 | 248.7 |

TABLE 2-9

| Order from the short arm end | Clones | SEQ ID NO: (5' end) | SEQ ID NO: (3' end) | Distance from the short arm end (cM) |
|---|---|---|---|---|
| 401 | BaH50L23 | 1559 | 1560 | 250.9 |
| 401 | bags19g04 | 1561 | 1562 | 250.9 |
| 403 | bast73E0210 | 1563 | 1564 | 252 |
| 403 | BaH50O21 | 1565 | 1566 | 252 |
| 403 | basd21g05 | 1567 | 1568 | 252 |
| 406 | bah33p11 | 1569 | 1570 | 253.1 |
| 406 | baal5i19 | 1571 | 1572 | 253.1 |
| 406 | bah16e04 | 1573 | 1574 | 253.1 |
| 406 | baak32p24 | 1575 | 1576 | 253.1 |
| 406 | EBmac415 | — | — | 253.1 |
| 411 | bags38f12 | 1577 | 1578 | 254.2 |
| 411 | basd26p18 | 1579 | 1580 | 254.2 |
| 413 | baak45h16 | 1581 | 1582 | 255.3 |
| 414 | bah28p12 | 1583 | 1584 | 257.5 |
| 415 | bah19a10 | 1585 | 1586 | 258.6 |
| 416 | baak13d11 | 1587 | 1588 | 258.8 |
| 417 | bah49p10 | 1589 | 1590 | 259.1 |
| 417 | baal32n15 | 1591 | 1592 | 259.1 |
| 419 | bast09C0305 | 1593 | 1594 | 260.6 |
| 420 | basd16l09 | 1595 | 1596 | 263.9 |
| 420 | BaAK22H04 | 1597 | 1598 | 263.9 |

TABLE 2-9-continued

| Order from the short arm end | Clones | SEQ ID NO: (5' end) | SEQ ID NO: (3' end) | Distance from the short arm end (cM) |
|---|---|---|---|---|
| 422 | BaGS15J13 | 1599 | 1600 | 265 |
| 422 | kr66G0414 | 1601 | 1602 | 265 |
| 424 | BaSD22C07 | 1603 | 1604 | 266.1 |
| 424 | kr71C1105 | 1605 | 1606 | 266.1 |
| 424 | bags34i11 | 1607 | 1608 | 266.1 |
| 427 | BaH23K17 | 1609 | 1610 | 267.3 |
| 428 | bast39D0107 | 1611 | 1612 | 270.5 |
| 428 | BaH44K24 | 1613 | 1614 | 270.5 |
| 430 | BaGS18N21 | 1615 | 1616 | 273.5 |
| 430 | baak32k15 | 1617 | 1618 | 273.5 |
| 432 | bah61a13 | 1619 | 1620 | 275.7 |
| 432 | bags35n11 | 1621 | 1622 | 275.7 |
| 432 | BaAK24I03 | 1623 | 1624 | 275.7 |
| 435 | baal4h20 | 1625 | 1626 | 277.5 |
| 435 | BaH28N23 | 1627 | 1628 | 277.5 |
| 435 | bags10e13 | 1629 | 1630 | 277.5 |
| 438 | baak27i10 | 1631 | 1632 | 278.5 |
| 438 | bags19d13 | 1633 | 1634 | 278.5 |
| 438 | baak19d04 | 1635 | 1636 | 278.5 |
| 438 | BaAL34O19 | 1637 | 1638 | 278.5 |
| 438 | baal12l02 | 1639 | 1640 | 278.5 |
| 438 | BaAK1P04 | 1641 | 1642 | 278.5 |
| 438 | baak35m13 | 1643 | 1644 | 278.5 |
| 438 | bags35a12 | 1645 | 1646 | 278.5 |
| 446 | bah41n09 | 1647 | 1648 | 279.6 |
| 446 | BaGS23I12 | 1649 | 1650 | 279.6 |
| 448 | BaH16P20 | 1651 | 1652 | 280.4 |
| 448 | BaAK42L17 | 1653 | 1654 | 280.4 |
| 450 | baak36d23 | 1655 | 1656 | 284.2 |

TABLE 2-10

| Order from the short arm end | Clones | SEQ ID NO: (5' end) | SEQ ID NO: (3' end) | Distance from the short arm end (cM) |
|---|---|---|---|---|
| 450 | bast78C1006 | 1657 | 1658 | 284.2 |
| 452 | BaH45O16 | 1659 | 1660 | 285 |
| 453 | bah21h09 | 1661 | 1662 | 286.1 |
| 454 | bah58p22 | 1663 | 1664 | 287.2 |
| 455 | bags20l19 | 1665 | 1666 | 288.8 |
| 456 | bah13i10 | 1667 | 1668 | 290.4 |
| 457 | BaAK36B07 | 1669 | 1670 | 291.5 |
| 458 | baak26b05 | 1671 | 1672 | 295.5 |
| 459 | baal7c15 | 1673 | 1674 | 296.6 |
| 459 | bah63f05 | 1675 | 1676 | 296.6 |
| 461 | bags15j16 | 1677 | 1678 | 297.9 |
| 462 | BaGS6N10 | 1679 | 1680 | 299.2 |
| 462 | bah41e10 | 1681 | 1682 | 299.2 |
| 464 | BaH54D08 | 1683 | 1684 | 299.7 |
| 465 | baak18c01 | 1685 | 1686 | 300.2 |
| 466 | basd21o07 | 1687 | 1688 | 301.3 |
| 467 | bah41b23 | 1689 | 1690 | 301.9 |
| 468 | basd18g15 | 1691 | 1692 | 302.4 |
| 468 | baak43c03 | 1693 | 1694 | 302.4 |
| 468 | bastl30D0408 | 1695 | 1696 | 302.4 |
| 468 | bah17p16 | 1697 | 1698 | 302.4 |
| 472 | baal13f18 | 1699 | 1700 | 303.5 |
| 472 | bags18i22 | 1701 | 1702 | 303.5 |
| 472 | bags9b02 | 1703 | 1704 | 303.5 |
| 475 | bah11e22 | 1705 | 1706 | 323.4 |
| 476 | bah58h09 | 1707 | 1708 | 332.9 |
| 477 | basd16e16 | 1709 | 1710 | 334.9 |
| 478 | BaAK4C12 | 1711 | 1712 | 340 |
| 479 | bags37a05 | 1713 | 1714 | 343.4 |
| 480 | bags9p10 | 1715 | 1716 | 351.7 |
| 481 | baak24m01 | 1717 | 1718 | 352.7 |
| 482 | basd27d09 | 1719 | 1720 | 353.2 |
| 483 | baak34a14 | 1721 | 1722 | 353.7 |
| 483 | baak36a20 | 1723 | 1724 | 353.7 |
| 483 | BaSD17P09 | 1725 | 1726 | 353.7 |
| 486 | bags5m04 | 1727 | 1728 | 354.8 |
| 487 | BaGS5E06 | 1729 | 1730 | 355.9 |

TABLE 2-10-continued

| Order from the short arm end | Clones | SEQ ID NO: (5' end) | SEQ ID NO: (3' end) | Distance from the short arm end (cM) |
|---|---|---|---|---|
| 487 | MWG2076 | — | — | 355.9 |
| 487 | bags15f03 | 1731 | 1732 | 355.9 |
| 487 | bags18j23 | 1733 | 1734 | 355.9 |
| 487 | baal13m04 | 1735 | 1736 | 355.9 |
| 487 | bags9o24 | 1737 | 1738 | 355.9 |
| 493 | kr49E0610 | 1739 | 1740 | 356.4 |
| 494 | bah12h16 | 1741 | 1742 | 356.9 |
| 494 | baak33n16 | 1743 | 1744 | 356.9 |
| 494 | BaGS22E05 | 1745 | 1746 | 356.9 |
| 497 | bah26n01 | 1747 | 1748 | 358 |
| 497 | BaGS39E07 | 1749 | 1750 | 358 |
| 497 | BaH45O03 | 1751 | 1752 | 358 |
| 500 | BaH38A09 | 1753 | 1754 | 360.2 |

As shown in Table 3-1 to Table 3-10, the chromosomal order in barley 3H chromosome (distance from the short arm end of 3H chromosome) has been specified for 444 clones including the base sequences of SEQ ID NO: n (where n is an odd number) and SEQ ID NO: n+1 from among the base sequences of SEQ ID NO: 1755 through SEQ ID NO: 2642. The chromosomal order in barley 3H chromosome has also been specified for 13 known clones (MWG848, HvLTPPB, HVM9, Bmac67, Bmag136, Bmac209, HVM27, HvBRI1, HVM33, HVM60, Bmag225, Bmag13, and HVM62).

TABLE 3-1

| Order from the short arm end | Clones | SEQ ID NO: (5' end) | SEQ ID NO: (3' end) | Distance from the short arm end (cM) |
|---|---|---|---|---|
| 1 | BaAL15P01 | 1755 | 1756 | 0 |
| 2 | BaAK42D06 | 1757 | 1758 | 9.8 |
| 2 | bags12k16 | 1759 | 1760 | 9.8 |
| 2 | BaAL36H19 | 1761 | 1762 | 9.8 |
| 2 | bags1d06 | 1763 | 1764 | 9.8 |
| 6 | bast18A0602 | 1765 | 1766 | 10.9 |
| 6 | basd22i04 | 1767 | 1768 | 10.9 |
| 8 | BaGS31M01 | 1769 | 1770 | 12 |
| 9 | BaH63H24 | 1771 | 1772 | 12.4 |
| 10 | basd15n13 | 1773 | 1774 | 12.8 |
| 11 | MWG848 | — | — | 13.1 |
| 11 | BaAK13C16 | 1775 | 1776 | 13.1 |
| 13 | BaGS32C19 | 1777 | 1778 | 15.3 |
| 13 | baak36f08 | 1779 | 1780 | 15.3 |
| 15 | bastl04C0406 | 1781 | 1782 | 16.4 |
| 15 | bastl42D1107 | 1783 | 1784 | 16.4 |
| 17 | BaGS31B20 | 1785 | 1786 | 17.5 |
| 17 | baak39l17 | 1787 | 1788 | 17.5 |
| 19 | BaAL17J24 | 1789 | 1790 | 20.7 |
| 19 | bah15p03 | 1791 | 1792 | 20.7 |
| 21 | baak20g06 | 1793 | 1794 | 21.8 |
| 21 | baal22c16 | 1795 | 1796 | 21.8 |
| 21 | baak46o05 | 1797 | 1798 | 21.8 |
| 24 | basd15h22 | 1799 | 1800 | 22.9 |
| 25 | BaSD19C07 | 1801 | 1802 | 24 |
| 26 | bags22i13 | 1803 | 1804 | 25.7 |
| 27 | baak39a14 | 1805 | 1806 | 26.8 |
| 28 | bah31e12 | 1807 | 1808 | 27.9 |
| 28 | BaSD15L22 | 1809 | 1810 | 27.9 |
| 30 | BaGS20D21 | 1811 | 1812 | 30.1 |
| 31 | bags39o21 | 1813 | 1814 | 30.7 |
| 31 | basd21j11 | 1815 | 1816 | 30.7 |
| 33 | BaH48C10 | 1817 | 1818 | 32.3 |
| 34 | BaH54J07 | 1819 | 1820 | 33.9 |
| 35 | BaSD19H23 | 1821 | 1822 | 36.1 |
| 35 | baak35n06 | 1823 | 1824 | 36.1 |
| 37 | bags35b22 | 1825 | 1826 | 39.3 |
| 37 | BaAK30H06 | 1827 | 1828 | 39.3 |
| 37 | BaAL15M07 | 1829 | 1830 | 39.3 |
| 40 | BaGS20N02 | 1831 | 1832 | 40.4 |
| 40 | BaAL19L12 | 1833 | 1834 | 40.4 |

TABLE 3-1-continued

| Order from the short arm end | Clones | SEQ ID NO: (5' end) | SEQ ID NO: (3' end) | Distance from the short arm end (cM) |
|---|---|---|---|---|
| 42 | bags25b05 | 1835 | 1836 | 41.5 |
| 42 | HvLTPPB | — | — | 41.5 |
| 42 | baal1h04 | 1837 | 1838 | 41.5 |
| 45 | baet46B0903 | 1839 | 1840 | 42.6 |
| 45 | BaGS19F16 | 1841 | 1842 | 42.6 |
| 45 | baak13g18 | 1843 | 1844 | 42.6 |
| 48 | BaH45N12 | 1845 | 1846 | 47 |
| 49 | bast74H0216 | 1847 | 1848 | 48.1 |
| 50 | bah24l06 | 1849 | 1850 | 50.5 |

TABLE 3-2

| Order from the short arm end | Clones | SEQ ID NO: (5' end) | SEQ ID NO: (3' end) | Distance from the short arm end (cM) |
|---|---|---|---|---|
| 51 | BaAK45C14 | 1851 | 1852 | 53.4 |
| 51 | baal5k12 | 1853 | 1854 | 53.4 |
| 53 | kr63F0111 | 1855 | 1856 | 54.1 |
| 53 | baak13h18 | 1857 | 1858 | 54.1 |
| 53 | baak12j16 | 1859 | 1860 | 54.1 |
| 56 | BaAK28J20 | 1861 | 1862 | 55.2 |
| 56 | BaH27G14 | 1863 | 1864 | 55.2 |
| 56 | BaH49B13 | 1865 | 1866 | 55.2 |
| 59 | BaGS35A09 | 1867 | 1868 | 57.4 |
| 60 | BaGS38L24 | 1869 | 1870 | 58.6 |
| 61 | BaAK43H20 | 1871 | 1872 | 66.5 |
| 61 | bast16A0802 | 1873 | 1874 | 66.5 |
| 61 | basd18k01 | 1875 | 1876 | 66.5 |
| 64 | BaH58D17 | 1877 | 1878 | 67.6 |
| 65 | BaAK30M07 | 1879 | 1880 | 69.2 |
| 65 | bags6a04 | 1881 | 1882 | 69.2 |
| 67 | kr15H0915 | 1883 | 1884 | 69.7 |
| 67 | bags26d01 | 1885 | 1886 | 69.7 |
| 69 | basd14k04 | 1887 | 1888 | 70.8 |
| 69 | BaSD24D11 | 1889 | 1890 | 70.8 |
| 69 | BaH53L10 | 1891 | 1892 | 70.8 |
| 72 | BaH60D22 | 1893 | 1894 | 73 |
| 72 | BaSD1G06 | 1895 | 1896 | 73 |
| 72 | BaAK21L13 | 1897 | 1898 | 73 |
| 72 | bah57m03 | 1899 | 1900 | 73 |
| 76 | baal30b10 | 1901 | 1902 | 74.1 |
| 77 | bah62n16 | 1903 | 1904 | 74.7 |
| 78 | BaGS22F15 | 1905 | 1906 | 75.2 |
| 78 | BaH50J14 | 1907 | 1908 | 75.2 |
| 80 | bah19d23 | 1909 | 1910 | 75.7 |
| 81 | bags38c06 | 1911 | 1912 | 76.2 |
| 81 | BaGS25N05 | 1913 | 1914 | 76.2 |
| 81 | bastl29B0503 | 1915 | 1916 | 76.2 |
| 84 | baak27d01 | 1917 | 1918 | 77.3 |
| 84 | baak43n21 | 1919 | 1920 | 77.3 |
| 86 | BaAL4F05 | 1921 | 1922 | 78.4 |
| 86 | baal4a06 | 1923 | 1924 | 78.4 |
| 88 | bast17D1008 | 1925 | 1926 | 80 |
| 89 | BaGS16B17 | 1927 | 1928 | 81.1 |
| 90 | BaGS27P18 | 1929 | 1930 | 81.7 |
| 90 | BaGS4J14 | 1931 | 1932 | 81.7 |
| 90 | BaAK16B19 | 1933 | 1934 | 81.7 |
| 90 | baal40p07 | 1935 | 1936 | 81.7 |
| 94 | bah49c19 | 1937 | 1938 | 84 |
| 95 | bast58C0406 | 1939 | 1940 | 87.4 |
| 95 | BaAK35M24 | 1941 | 1942 | 87.4 |
| 95 | bags19h13 | 1943 | 1944 | 87.4 |
| 95 | bah57c21 | 1945 | 1946 | 87.4 |
| 99 | BaH53P15 | 1947 | 1948 | 88.5 |
| 99 | BaGS20A10 | 1949 | 1950 | 88.5 |

TABLE 3-3

| Order from the short arm end | Clones | SEQ ID NO: (5' end) | SEQ ID NO: (3' end) | Distance from the short arm end (cM) |
|---|---|---|---|---|
| 99 | bast02D0808 | 1951 | 1952 | 88.5 |
| 99 | bags31c04 | 1953 | 1954 | 88.5 |
| 99 | BaH32J06 | 1955 | 1956 | 88.5 |
| 99 | bah60o22 | 1957 | 1958 | 88.5 |
| 99 | BaH50C16 | 1959 | 1960 | 88.5 |
| 99 | BaH57K23 | 1961 | 1962 | 88.5 |
| 99 | bags21g23 | 1963 | 1964 | 88.5 |
| 99 | HVM9 | — | — | 88.5 |
| 109 | Bmac67 | — | — | 89.6 |
| 109 | baak43e04 | 1965 | 1966 | 89.6 |
| 111 | kr17G1113 | 1967 | 1968 | 92.8 |
| 111 | bags19k19 | 1969 | 1970 | 92.8 |
| 111 | baak38b13 | 1971 | 1972 | 92.8 |
| 111 | baak1d12 | 1973 | 1974 | 92.8 |
| 111 | BaH28M14 | 1975 | 1976 | 92.8 |
| 116 | BaH48I15 | 1977 | 1978 | 93.9 |
| 116 | basd27h23 | 1979 | 1980 | 93.9 |
| 116 | BaAK21A11 | 1981 | 1982 | 93.9 |
| 119 | bast04B0804 | 1983 | 1984 | 94.4 |
| 120 | bah45f13 | 1985 | 1986 | 94.9 |
| 120 | BaAL8J18 | 1987 | 1988 | 94.9 |
| 120 | BaGS9D01 | 1989 | 1990 | 94.9 |
| 120 | baal12d12 | 1991 | 1992 | 94.9 |
| 120 | baal4i06 | 1993 | 1994 | 94.9 |
| 125 | bah26i01 | 1995 | 1996 | 96.5 |
| 125 | BaGS15C17 | 1997 | 1998 | 96.5 |
| 127 | baak1k08 | 1999 | 2000 | 97 |
| 127 | bags9b03 | 2001 | 2002 | 97 |
| 127 | baet42G1214 | 2003 | 2004 | 97 |
| 127 | bah18d12 | 2005 | 2006 | 97 |
| 127 | BaSD14G02 | 2007 | 2008 | 97 |
| 127 | bags22b22 | 2009 | 2010 | 97 |
| 127 | bah13f10 | 2011 | 2012 | 97 |
| 134 | baal36g05 | 2013 | 2014 | 97.5 |
| 135 | bags33j15 | 2015 | 2016 | 98 |
| 135 | BaAL12H04 | 2017 | 2018 | 98 |
| 135 | BaGS16I18 | 2019 | 2020 | 98 |
| 138 | bast61D0707 | 2021 | 2022 | 98.5 |
| 139 | bah11k22 | 2023 | 2024 | 99 |
| 139 | baak32p21 | 2025 | 2026 | 99 |
| 139 | bah63l21 | 2027 | 2028 | 99 |
| 139 | BaGS38D03 | 2029 | 2030 | 99 |
| 143 | BaSD23A04 | 2031 | 2032 | 100.1 |
| 144 | BaSD14C15 | 2033 | 2034 | 101.2 |
| 144 | bast63C0105 | 2035 | 2036 | 101.2 |
| 144 | bast23C1105 | 2037 | 2038 | 101.2 |
| 147 | bags23b01 | 2039 | 2040 | 102.3 |
| 147 | bags29c09 | 2041 | 2042 | 102.3 |
| 147 | bags6b06 | 2043 | 2044 | 102.3 |
| 147 | BaAK27G06 | 2045 | 2046 | 102.3 |

TABLE 3-4

| Order from the short arm end | Clones | SEQ ID NO: (5' end) | SEQ ID NO: (3' end) | Distance from the short arm end (cM) |
|---|---|---|---|---|
| 147 | BaAK39I07 | 2047 | 2048 | 102.3 |
| 147 | BaGS20G21 | 2049 | 2050 | 102.3 |
| 147 | bastl22E0810 | 2051 | 2052 | 102.3 |
| 147 | bah11m03 | 2053 | 2054 | 102.3 |
| 147 | BaAL3C04 | 2055 | 2056 | 102.3 |
| 156 | BaAL19H10 | 2057 | 2058 | 103.4 |
| 156 | bags24n16 | 2059 | 2060 | 103.4 |
| 156 | BaSD24B15 | 2061 | 2062 | 103.4 |
| 156 | bah48n17 | 2063 | 2064 | 103.4 |
| 156 | bags9i05 | 2065 | 2066 | 103.4 |
| 156 | bags1l22 | 2067 | 2068 | 103.4 |
| 156 | bah62p18 | 2069 | 2070 | 103.4 |
| 156 | bah55n21 | 2071 | 2072 | 103.4 |
| 156 | bah44a05 | 2073 | 2074 | 103.4 |
| 156 | bah19c13 | 2075 | 2076 | 103.4 |
| 156 | baal12b04 | 2077 | 2078 | 103.4 |
| 156 | Bmag136 | — | — | 103.4 |
| 156 | Bmac209 | — | — | 103.4 |
| 156 | BaAK28A10 | 2079 | 2080 | 103.4 |
| 156 | kr28B0703 | 2081 | 2082 | 103.4 |
| 156 | bastl50C0606 | 2083 | 2084 | 103.4 |
| 156 | BaGS36B01 | 2085 | 2086 | 103.4 |
| 156 | BaH19A05 | 2087 | 2088 | 103.4 |
| 156 | baal10c06 | 2089 | 2090 | 103.4 |
| 156 | bags19p04 | 2091 | 2092 | 103.4 |
| 176 | BaAK21A17 | 2093 | 2094 | 104.5 |
| 176 | bah20j14 | 2095 | 2096 | 104.5 |
| 176 | BaAK19A03 | 2097 | 2098 | 104.5 |
| 176 | BaGS30E19 | 2099 | 2100 | 104.5 |
| 176 | BaAK28C21 | 2101 | 2102 | 104.5 |
| 176 | bags11o14 | 2103 | 2104 | 104.5 |
| 182 | BaGS13P22 | 2105 | 2106 | 105.6 |
| 182 | kr27A1101 | 2107 | 2108 | 105.6 |
| 182 | HVM27 | — | — | 105.6 |
| 185 | baal12i18 | 2109 | 2110 | 106.7 |
| 186 | BaAL8G07 | 2111 | 2112 | 107.8 |
| 187 | bast58F0412 | 2113 | 2114 | 108.9 |
| 187 | bags3f23 | 2115 | 2116 | 108.9 |
| 189 | baal4m06 | 2117 | 2118 | 109.3 |
| 190 | baal32p23 | 2119 | 2120 | 109.7 |
| 191 | basd23m17 | 2121 | 2122 | 110 |
| 191 | bastl30E0509 | 2123 | 2124 | 110 |
| 191 | bah44b08 | 2125 | 2126 | 110 |
| 191 | BaGS14N10 | 2127 | 2128 | 110 |
| 191 | BaGS32B13 | 2129 | 2130 | 110 |
| 191 | BaH30B03 | 2131 | 2132 | 110 |
| 191 | basd1l23 | 2133 | 2134 | 110 |
| 191 | basd11o06 | 2135 | 2136 | 110 |
| 191 | bah17f24 | 2137 | 2138 | 110 |
| 191 | BaAK26L17 | 2139 | 2140 | 110 |

TABLE 3-5

| Order from the short arm end | Clones | SEQ ID NO: (5' end) | SEQ ID NO: (3' end) | Distance from the short arm end (cM) |
|---|---|---|---|---|
| 191 | bags23f03 | 2141 | 2142 | 110 |
| 191 | bags20o06 | 2143 | 2144 | 110 |
| 203 | bags19n12 | 2145 | 2146 | 111.1 |
| 203 | baal12a09 | 2147 | 2148 | 111.1 |
| 203 | bast14F0612 | 2149 | 2150 | 111.1 |
| 203 | baak13p20 | 2151 | 2152 | 111.1 |
| 207 | BaGS16K13 | 2153 | 2154 | 111.9 |
| 207 | baak22c16 | 2155 | 2156 | 111.9 |
| 209 | baal40m06 | 2157 | 2158 | 115.4 |
| 210 | BaH29I03 | 2159 | 2160 | 116.8 |
| 211 | bah16h01 | 2161 | 2162 | 117.6 |
| 211 | bah57a11 | 2163 | 2164 | 117.6 |
| 211 | BaH41E23 | 2165 | 2166 | 117.6 |
| 211 | baal11c11 | 2167 | 2168 | 117.6 |
| 215 | BaSD14L18 | 2169 | 2170 | 118.1 |
| 216 | bah14d17 | 2171 | 2172 | 118.7 |
| 216 | BaGS1N17 | 2173 | 2174 | 118.7 |
| 216 | bags27h17 | 2175 | 2176 | 118.7 |
| 219 | bah47p22 | 2177 | 2178 | 119.8 |
| 219 | BaH50A16 | 2179 | 2180 | 119.8 |
| 219 | bags7b20 | 2181 | 2182 | 119.8 |
| 219 | bags22a02 | 2183 | 2184 | 119.8 |
| 223 | HvBRI1 | — | — | 120.4 |
| 224 | basd12g02 | 2185 | 2186 | 122.6 |
| 225 | basd15o18 | 2187 | 2188 | 123.1 |
| 226 | baal25d19 | 2189 | 2190 | 125.3 |
| 226 | bast52G0414 | 2191 | 2192 | 125.3 |
| 228 | baal11c20 | 2193 | 2194 | 126.4 |
| 229 | bags37k06 | 2195 | 2196 | 127 |
| 230 | bags6e22 | 2197 | 2198 | 127.5 |
| 230 | basd15a02 | 2199 | 2200 | 127.5 |
| 230 | bags7b06 | 2201 | 2202 | 127.5 |

TABLE 3-5-continued

| Order from the short arm end | Clones | SEQ ID NO: (5' end) | SEQ ID NO: (3' end) | Distance from the short arm end (cM) |
|---|---|---|---|---|
| 230 | bah15k11 | 2203 | 2204 | 127.5 |
| 230 | bast46C0406 | 2205 | 2206 | 127.5 |
| 230 | bastl45E0509 | 2207 | 2208 | 127.5 |
| 236 | baal35p14 | 2209 | 2210 | 128.6 |
| 237 | BaH41G07 | 2211 | 2212 | 129.3 |
| 237 | bast46H1016 | 2213 | 2214 | 129.3 |
| 239 | bah60d12 | 2215 | 2216 | 131.8 |
| 239 | baal39a19 | 2217 | 2218 | 131.8 |
| 241 | baak11n24 | 2219 | 2220 | 132.9 |
| 241 | bastl4E0909 | 2221 | 2222 | 132.9 |
| 241 | baet13G0713 | 2223 | 2224 | 132.9 |
| 244 | HVM33 | — | — | 135.8 |
| 244 | BaSD14L04 | 2225 | 2226 | 135.8 |
| 246 | baak13c05 | 2227 | 2228 | 136 |
| 246 | bastl41G0513 | 2229 | 2230 | 136 |
| 248 | BaGS39M09 | 2231 | 2232 | 137.6 |
| 249 | baal19b12 | 2233 | 2234 | 138.6 |
| 250 | BaAL39B05 | 2235 | 2236 | 144 |

TABLE 3-6

| Order from the short arm end | Clones | SEQ ID NO: (5' end) | SEQ ID NO: (3' end) | Distance from the short arm end (cM) |
|---|---|---|---|---|
| 250 | BaAL1J03 | 2237 | 2238 | 144 |
| 250 | basd11k09 | 2239 | 2240 | 144 |
| 253 | BaGS33N15 | 2241 | 2242 | 146.1 |
| 253 | baet43H0416 | 2243 | 2244 | 146.1 |
| 253 | bah11m06 | 2245 | 2246 | 146.1 |
| 253 | baak31a24 | 2247 | 2248 | 146.1 |
| 253 | bags27h20 | 2249 | 2250 | 146.1 |
| 253 | basd27c09 | 2251 | 2252 | 146.1 |
| 259 | BaAL25O01 | 2253 | 2254 | 146.6 |
| 260 | bags7f08 | 2255 | 2256 | 147.1 |
| 261 | BaGS13O12 | 2257 | 2258 | 148.2 |
| 261 | bags38b06 | 2259 | 2260 | 148.2 |
| 263 | BaAK19J09 | 2261 | 2262 | 149.3 |
| 263 | bags9e16 | 2263 | 2264 | 149.3 |
| 265 | bags20n14 | 2265 | 2266 | 150.4 |
| 265 | bah42o12 | 2267 | 2268 | 150.4 |
| 265 | baak31k16 | 2269 | 2270 | 150.4 |
| 265 | bags4p14 | 2271 | 2272 | 150.4 |
| 265 | bah27a22 | 2273 | 2274 | 150.4 |
| 270 | bags21n02 | 2275 | 2276 | 151.5 |
| 271 | BaH62B09 | 2277 | 2278 | 153.7 |
| 271 | BaGS19J10 | 2279 | 2280 | 153.7 |
| 273 | bags15k18 | 2281 | 2282 | 154.2 |
| 274 | BaAK29G03 | 2283 | 2284 | 154.7 |
| 274 | baak23e11 | 2285 | 2286 | 154.7 |
| 274 | bags31k04 | 2287 | 2288 | 154.7 |
| 274 | bast56C0305 | 2289 | 2290 | 154.7 |
| 278 | basd26c09 | 2291 | 2292 | 159 |
| 278 | BaSD20B11 | 2293 | 2294 | 159 |
| 278 | HVM60 | — | — | 159 |
| 281 | BaH46F11 | 2295 | 2296 | 160.1 |
| 281 | BaH30F03 | 2297 | 2298 | 160.1 |
| 281 | BaSD27G02 | 2299 | 2300 | 160.1 |
| 284 | Bmag225 | — | — | 161.2 |
| 284 | BaAK33I12 | 2301 | 2302 | 161.2 |
| 286 | baak32m10 | 2303 | 2304 | 162.3 |
| 286 | BaAL4L02 | 2305 | 2306 | 162.3 |
| 286 | kr44F0911 | 2307 | 2308 | 162.3 |
| 289 | BaGS37A16 | 2309 | 2310 | 163.5 |
| 290 | bags39p06 | 2311 | 2312 | 163.9 |
| 290 | BaAL12N06 | 2313 | 2314 | 163.9 |
| 292 | bags22p05 | 2315 | 2316 | 165.4 |
| 293 | bags9a03 | 2317 | 2318 | 166.5 |
| 293 | baet24F1212 | 2319 | 2320 | 166.5 |
| 295 | baak29d10 | 2321 | 2322 | 167.6 |
| 295 | bags13i12 | 2323 | 2324 | 167.6 |
| 295 | BaAL16A23 | 2325 | 2326 | 167.6 |
| 298 | bastl16B1204 | 2327 | 2328 | 171.6 |

TABLE 3-6-continued

| Order from the short arm end | Clones | SEQ ID NO: (5' end) | SEQ ID NO: (3' end) | Distance from the short arm end (cM) |
|---|---|---|---|---|
| 298 | bastl29F0711 | 2329 | 2330 | 171.6 |
| 300 | BaGS32M17 | 2331 | 2332 | 172.1 |

TABLE 3-7

| Order from the short arm end | Clones | SEQ ID NO: (5' end) | SEQ ID NO: (3' end) | Distance from the short arm end (cM) |
|---|---|---|---|---|
| 301 | baal15e10 | 2333 | 2334 | 172.5 |
| 301 | basd3g08 | 2335 | 2336 | 172.5 |
| 303 | baal33m18 | 2337 | 2338 | 173.6 |
| 303 | baak24e23 | 2339 | 2340 | 173.6 |
| 303 | baak46j13 | 2341 | 2342 | 173.6 |
| 306 | bah49o05 | 2343 | 2344 | 174.7 |
| 306 | baal15e05 | 2345 | 2346 | 174.7 |
| 306 | BaAK1O08 | 2347 | 2348 | 174.7 |
| 306 | BaGS30P02 | 2349 | 2350 | 174.7 |
| 310 | BaSD15D05 | 2351 | 2352 | 178.9 |
| 311 | BaAL7B16 | 2353 | 2354 | 179.2 |
| 312 | bags38n23 | 2355 | 2356 | 180.3 |
| 313 | baak36a14 | 2357 | 2358 | 181.6 |
| 313 | baak34g01 | 2359 | 2360 | 181.6 |
| 313 | baak12f01 | 2361 | 2362 | 181.6 |
| 316 | BaGS30I18 | 2363 | 2364 | 183.7 |
| 316 | bags35n24 | 2365 | 2366 | 183.7 |
| 316 | bah37j21 | 2367 | 2368 | 183.7 |
| 316 | bah31e13 | 2369 | 2370 | 183.7 |
| 320 | bags22g10 | 2371 | 2372 | 190 |
| 320 | bags22f17 | 2373 | 2374 | 190 |
| 322 | baal30l05 | 2375 | 2376 | 190.9 |
| 322 | bags38o10 | 2377 | 2378 | 190.9 |
| 324 | baak40o04 | 2379 | 2380 | 193.1 |
| 325 | BaH49L21 | 2381 | 2382 | 193.6 |
| 325 | bastl30A0701 | 2383 | 2384 | 193.6 |
| 327 | bags19l03 | 2385 | 2386 | 195.1 |
| 328 | bah18m13 | 2387 | 2388 | 196.6 |
| 329 | baak44p03 | 2389 | 2390 | 198.2 |
| 329 | kr10H0216 | 2391 | 2392 | 198.2 |
| 331 | bags11i04 | 2393 | 2394 | 199.4 |
| 332 | bah52o06 | 2395 | 2396 | 200.5 |
| 333 | bah35c14 | 2397 | 2398 | 200.8 |
| 333 | BaAL30C02 | 2399 | 2400 | 200.8 |
| 335 | bah11i21 | 2401 | 2402 | 201.9 |
| 336 | BaAK36B11 | 2403 | 2404 | 204.1 |
| 337 | BaAK20K23 | 2405 | 2406 | 206 |
| 337 | basd14n22 | 2407 | 2408 | 206 |
| 339 | BaAL25P17 | 2409 | 2410 | 207.6 |
| 339 | BaH49A01 | 2411 | 2412 | 207.6 |
| 341 | basd13p12 | 2413 | 2414 | 209.5 |
| 341 | bags39m17 | 2415 | 2416 | 209.5 |
| 343 | baet44D0707 | 2417 | 2418 | 212.8 |
| 344 | BaH16P10 | 2419 | 2420 | 213.9 |
| 344 | BaAK42J01 | 2421 | 2422 | 213.9 |
| 346 | kr24E0709 | 2423 | 2424 | 215.8 |
| 346 | BaAK38O08 | 2425 | 2426 | 215.8 |
| 348 | BaAL13N01 | 2427 | 2428 | 217.7 |
| 349 | baak12c12 | 2429 | 2430 | 219.8 |
| 350 | BaGS31N06 | 2431 | 2432 | 220.9 |

TABLE 3-8

| Order from the short arm end | Clones | SEQ ID NO: (5' end) | SEQ ID NO: (3' end) | Distance from the short arm end (cM) |
|---|---|---|---|---|
| 351 | baal15f24 | 2433 | 2434 | 221.5 |
| 352 | BaSD18B21 | 2435 | 2436 | 222 |
| 352 | BaSD17G23 | 2437 | 2438 | 222 |
| 354 | baak41k22 | 2439 | 2440 | 223.7 |
| 355 | baak21o03 | 2441 | 2442 | 225.4 |

TABLE 3-8-continued

| Order from the short arm end | Clones | SEQ ID NO: (5' end) | SEQ ID NO: (3' end) | Distance from the short arm end (cM) |
|---|---|---|---|---|
| 356 | BaSD16B18 | 2443 | 2444 | 227 |
| 356 | bast79C1105 | 2445 | 2446 | 227 |
| 358 | BaAK4J17 | 2447 | 2448 | 228.1 |
| 359 | BaAL37H08 | 2449 | 2450 | 228.6 |
| 359 | BaH36L17 | 2451 | 2452 | 228.6 |
| 361 | BaH46A12 | 2453 | 2454 | 229.7 |
| 361 | bags11i15 | 2455 | 2456 | 229.7 |
| 361 | baak20g24 | 2457 | 2458 | 229.7 |
| 364 | baak20h23 | 2459 | 2460 | 230.8 |
| 365 | baak35b18 | 2461 | 2462 | 231.9 |
| 365 | Bmag13 | — | — | 231.9 |
| 365 | baak41o03 | 2463 | 2464 | 231.9 |
| 365 | baet46C0206 | 2465 | 2466 | 231.9 |
| 369 | bags10i20 | 2467 | 2468 | 233 |
| 369 | baal1b16 | 2469 | 2470 | 233 |
| 369 | baal5i05 | 2471 | 2472 | 233 |
| 369 | BaH27B05 | 2473 | 2474 | 233 |
| 369 | bah14a11 | 2475 | 2476 | 233 |
| 369 | basd19k10 | 2477 | 2478 | 233 |
| 369 | bags30n17 | 2479 | 2480 | 233 |
| 369 | bags31e24 | 2481 | 2482 | 233 |
| 369 | BaGS5B16 | 2483 | 2484 | 233 |
| 378 | BaAL5F06 | 2485 | 2486 | 234.1 |
| 378 | bags34a11 | 2487 | 2488 | 234.1 |
| 378 | bags6c16 | 2489 | 2490 | 234.1 |
| 378 | bah42g19 | 2491 | 2492 | 234.1 |
| 378 | BaH47O14 | 2493 | 2494 | 234.1 |
| 383 | BaH12L06 | 2495 | 2496 | 235.2 |
| 383 | basd11a10 | 2497 | 2498 | 235.2 |
| 385 | BaH50I12 | 2499 | 2500 | 237.3 |
| 385 | BaH51A21 | 2501 | 2502 | 237.3 |
| 385 | baak45p02 | 2503 | 2504 | 237.3 |
| 388 | BaSD12P12 | 2505 | 2506 | 241.6 |
| 389 | bags9l16 | 2507 | 2508 | 242.7 |
| 389 | BaSD26O20 | 2509 | 2510 | 242.7 |
| 389 | bags5d10 | 2511 | 2512 | 242.7 |
| 389 | baal0e07 | 2513 | 2514 | 242.7 |
| 393 | baak14e02 | 2515 | 2516 | 243.8 |
| 394 | BaH63F14 | 2517 | 2518 | 244.9 |
| 394 | bah33f19 | 2519 | 2520 | 244.9 |
| 394 | bags19l10 | 2521 | 2522 | 244.9 |
| 397 | BaH56J21 | 2523 | 2524 | 246 |
| 397 | baal40i22 | 2525 | 2526 | 246 |
| 397 | kr42C0105 | 2527 | 2528 | 246 |
| 400 | bags16i19 | 2529 | 2530 | 246.5 |

TABLE 3-9

| Order from the short arm end | Clones | SEQ ID NO: (5' end) | SEQ ID NO: (3' end) | Distance from the short arm end (cM) |
|---|---|---|---|---|
| 400 | BaH54H01 | 2531 | 2532 | 246.5 |
| 402 | kr69E0810 | 2533 | 2534 | 247.8 |
| 403 | bags17j14 | 2535 | 2536 | 250 |
| 404 | bags20e19 | 2537 | 2538 | 253 |
| 405 | bast74C0206 | 2539 | 2540 | 255.1 |
| 405 | BaAK13L10 | 2541 | 2542 | 255.1 |
| 407 | bags20i01 | 2543 | 2544 | 256.2 |
| 407 | basd19n14 | 2545 | 2546 | 256.2 |
| 407 | baak42g21 | 2547 | 2548 | 256.2 |
| 407 | BaAK39A15 | 2549 | 2550 | 256.2 |
| 411 | basd18o21 | 2551 | 2552 | 257.3 |
| 411 | BaAK22K17 | 2553 | 2554 | 257.3 |
| 413 | baal6o24 | 2555 | 2556 | 260.9 |
| 414 | BaH22C09 | 2557 | 2558 | 262.7 |
| 414 | HVM62 | — | — | 262.7 |
| 416 | bags23k14 | 2559 | 2560 | 263.8 |
| 416 | baal24n12 | 2561 | 2562 | 263.8 |
| 418 | BaGS21H17 | 2563 | 2564 | 268.1 |
| 418 | BaSD16I09 | 2565 | 2566 | 268.1 |
| 418 | BaAL13B22 | 2567 | 2568 | 268.1 |
| 421 | bah41l03 | 2569 | 2570 | 270.2 |

TABLE 3-9-continued

| Order from the short arm end | Clones | SEQ ID NO: (5' end) | SEQ ID NO: (3' end) | Distance from the short arm end (cM) |
|---|---|---|---|---|
| 422 | bastl30F0111 | 2571 | 2572 | 272.5 |
| 423 | BaH15L04 | 2573 | 2574 | 275.9 |
| 423 | baak40c12 | 2575 | 2576 | 275.9 |
| 425 | kr23D0408 | 2577 | 2578 | 277 |
| 425 | bah57d15 | 2579 | 2580 | 277 |
| 427 | baak31e03 | 2581 | 2582 | 278.1 |
| 428 | BaAL13O01 | 2583 | 2584 | 281.8 |
| 429 | BaSD26P04 | 2585 | 2586 | 286.3 |
| 430 | bags20f18 | 2587 | 2588 | 287.4 |
| 431 | BaH42J22 | 2589 | 2590 | 288.5 |
| 431 | BaAL3K03 | 2591 | 2592 | 288.5 |
| 431 | kr30B1103 | 2593 | 2594 | 288.5 |
| 434 | baak14i02 | 2595 | 2596 | 289.6 |
| 434 | bags28c17 | 2597 | 2598 | 289.6 |
| 434 | baal4e21 | 2599 | 2600 | 289.6 |
| 434 | BaGS29D05 | 2601 | 2602 | 289.6 |
| 438 | bah54d24 | 2603 | 2604 | 290.7 |
| 439 | basd22g20 | 2605 | 2606 | 291.8 |
| 439 | BaH62H20 | 2607 | 2608 | 291.8 |
| 441 | bags38h17 | 2609 | 2610 | 292.9 |
| 441 | BaAK30B23 | 2611 | 2612 | 292.9 |
| 441 | BaAK24P09 | 2613 | 2614 | 292.9 |
| 441 | baak23i12 | 2615 | 2616 | 292.9 |
| 441 | BaGS22D06 | 2617 | 2618 | 292.9 |
| 441 | BaAL34P18 | 2619 | 2620 | 292.9 |
| 441 | BaAL39F24 | 2621 | 2622 | 292.9 |
| 441 | BaGS4L04 | 2623 | 2624 | 292.9 |
| 441 | bah12e02 | 2625 | 2626 | 292.9 |
| 441 | BaAL15F23 | 2627 | 2628 | 292.9 |

TABLE 3-10

| Order from the short arm end | Clones | SEQ ID NO: (5' end) | SEQ ID NO: (3' end) | Distance from the short arm end (cM) |
|---|---|---|---|---|
| 441 | BaGS25O15 | 2629 | 2630 | 292.9 |
| 441 | BaGS7G14 | 2631 | 2632 | 292.9 |
| 441 | basd24i11 | 2633 | 2634 | 292.9 |
| 454 | baak20l21 | 2635 | 2636 | 294 |
| 455 | bags33m02 | 2637 | 2638 | 295 |
| 455 | BaH48G21 | 2639 | 2640 | 295 |
| 457 | bags27p13 | 2641 | 2642 | 300.4 |

As shown in Table 4-1 to Table 4-7, the chromosomal order in barley 4H chromosome (distance from the short arm end of 4H chromosome) has been specified for 341 clones including the base sequences of SEQ ID NO: n (where n is an odd number) and SEQ ID NO: n+1 from among the base sequences of SEQ ID NO: 2643 through SEQ ID NO: 3324. The chromosomal order in barley 4H chromosome has also been specified for 9 known clones (HVM40, MWG2033, HVM3, MWG058, Bmag353, HVM68, HVM67, sh, and VRN2).

TABLE 4-1

| Order from the short arm end | Clones | SEQ ID NO: (5' end) | SEQ ID NO: (3' end) | Distance from the short arm end (cM) |
|---|---|---|---|---|
| 1 | BaGS10N17 | 2643 | 2644 | 0 |
| 2 | BaAK38K23 | 2645 | 2646 | 1.1 |
| 2 | bah14a22 | 2647 | 2648 | 1.1 |
| 4 | BaAL19O06 | 2649 | 2650 | 2.2 |
| 4 | BaGS32P17 | 2651 | 2652 | 2.2 |
| 6 | bah11j04 | 2653 | 2654 | 3.3 |
| 7 | baak35b06 | 2655 | 2656 | 4.1 |
| 7 | basd21f17 | 2657 | 2658 | 4.1 |
| 9 | BaAK44O11 | 2659 | 2660 | 7 |

TABLE 4-1-continued

| Order from the short arm end | Clones | SEQ ID NO: (5' end) | SEQ ID NO: (3' end) | Distance from the short arm end (cM) |
|---|---|---|---|---|
| 10 | bastl14D0408 | 2661 | 2662 | 8.2 |
| 11 | BaAK42C15 | 2663 | 2664 | 9 |
| 12 | baak40n12 | 2665 | 2666 | 10 |
| 12 | basd2j05 | 2667 | 2668 | 10 |
| 12 | baak46n05 | 2669 | 2670 | 10 |
| 12 | baak24g04 | 2671 | 2672 | 10 |
| 16 | BaAL22H02 | 2673 | 2674 | 11 |
| 17 | bah56g24 | 2675 | 2676 | 16.4 |
| 17 | BaAL2I22 | 2677 | 2678 | 16.4 |
| 19 | bags20c22 | 2679 | 2680 | 17.5 |
| 20 | BaH50O22 | 2681 | 2682 | 18.6 |
| 20 | baak32f06 | 2683 | 2684 | 18.6 |
| 20 | bags35i24 | 2685 | 2686 | 18.6 |
| 20 | BaSD21D13 | 2687 | 2688 | 18.6 |
| 20 | bast46D0408 | 2689 | 2690 | 18.6 |
| 25 | bast55B1204 | 2691 | 2692 | 22.1 |
| 26 | BaGS39M07 | 2693 | 2694 | 24.5 |
| 27 | bags39b15 | 2695 | 2696 | 27.6 |
| 27 | baak37p11 | 2697 | 2698 | 27.6 |
| 27 | bah29o22 | 2699 | 2700 | 27.6 |
| 27 | baak12k14 | 2701 | 2702 | 27.6 |
| 31 | baet31E1010 | 2703 | 2704 | 28.7 |
| 32 | HVM40 | — | — | 29.8 |
| 32 | baal39h14 | 2705 | 2706 | 29.8 |
| 34 | bags14g22 | 2707 | 2708 | 30.9 |
| 35 | baal18m18 | 2709 | 2710 | 32.1 |
| 36 | BaSD24E02 | 2711 | 2712 | 33.2 |
| 36 | BaH50N14 | 2713 | 2714 | 33.2 |
| 36 | kr70A0202 | 2715 | 2716 | 33.2 |
| 39 | baak11d04 | 2717 | 2718 | 34.3 |
| 40 | MWG2033 | — | — | 35.4 |
| 40 | bags20h01 | 2719 | 2720 | 35.4 |
| 42 | BaH39P15 | 2721 | 2722 | 35.9 |
| 43 | BaAK46O20 | 2723 | 2724 | 36.4 |
| 43 | baal33m06 | 2725 | 2726 | 36.4 |
| 43 | bastl50E0309 | 2727 | 2728 | 36.4 |
| 43 | bags20i17 | 2729 | 2730 | 36.4 |
| 47 | BaGS22A07 | 2731 | 2732 | 37.5 |
| 48 | bah41b09 | 2733 | 2734 | 37.7 |
| 49 | kr18G0913 | 2735 | 2736 | 39 |
| 49 | BaGS19O23 | 2737 | 2738 | 39 |

TABLE 4-2

| Order from the short arm end | Clones | SEQ ID NO: (5' end) | SEQ ID NO: (3' end) | Distance from the short arm end (cM) |
|---|---|---|---|---|
| 51 | bags15e12 | 2739 | 2740 | 39.6 |
| 52 | bags29i09 | 2741 | 2742 | 40.1 |
| 52 | baak19m23 | 2743 | 2744 | 40.1 |
| 54 | bags14h12 | 2745 | 2746 | 40.6 |
| 55 | bah32e15 | 2747 | 2748 | 41.2 |
| 55 | bah11l02 | 2749 | 2750 | 41.2 |
| 55 | bags39e16 | 2751 | 2752 | 41.2 |
| 55 | bags10l12 | 2753 | 2754 | 41.2 |
| 59 | BaGS31M13 | 2755 | 2756 | 42.3 |
| 59 | baal32m10 | 2757 | 2758 | 42.3 |
| 59 | basd12b23 | 2759 | 2760 | 42.3 |
| 62 | baal39e15 | 2761 | 2762 | 43.5 |
| 63 | baal16l11 | 2763 | 2764 | 45.8 |
| 64 | BaGS31B01 | 2765 | 2766 | 46.9 |
| 64 | BaSD17F09 | 2767 | 2768 | 46.9 |
| 64 | BaH48L11 | 2769 | 2770 | 46.9 |
| 67 | BaSD14M08 | 2771 | 2772 | 48 |
| 67 | bah56c09 | 2773 | 2774 | 48 |
| 67 | baak17g07 | 2775 | 2776 | 48 |
| 67 | bags20k09 | 2777 | 2778 | 48 |
| 67 | BaSD25B08 | 2779 | 2780 | 48 |
| 67 | bast27E0309 | 2781 | 2782 | 48 |
| 73 | baet20D0107 | 2783 | 2784 | 52.3 |
| 74 | BaAL17L08 | 2785 | 2786 | 56.3 |
| 75 | bah61p18 | 2787 | 2788 | 65.2 |

TABLE 4-2-continued

| Order from the short arm end | Clones | SEQ ID NO: (5' end) | SEQ ID NO: (3' end) | Distance from the short arm end (cM) |
|---|---|---|---|---|
| 75 | bah63d12 | 2789 | 2790 | 65.2 |
| 75 | BaAK26A03 | 2791 | 2792 | 65.2 |
| 78 | baak26n10 | 2793 | 2794 | 67.4 |
| 78 | bast22B0204 | 2795 | 2796 | 67.4 |
| 80 | BaAL3C05 | 2797 | 2798 | 68.5 |
| 80 | BaGS38H14 | 2799 | 2800 | 68.5 |
| 80 | BaAL4D19 | 2801 | 2802 | 68.5 |
| 83 | BaAK20B09 | 2803 | 2804 | 69.6 |
| 83 | BaAK37H01 | 2805 | 2806 | 69.6 |
| 83 | BaGS33P13 | 2807 | 2808 | 69.6 |
| 86 | basd13l12 | 2809 | 2810 | 70.7 |
| 86 | bags11m01 | 2811 | 2812 | 70.7 |
| 88 | BaGS18H09 | 2813 | 2814 | 77.5 |
| 89 | basd3d13 | 2815 | 2816 | 86.5 |
| 89 | baal9m23 | 2817 | 2818 | 86.5 |
| 89 | bags23f08 | 2819 | 2820 | 86.5 |
| 92 | BaGS15L23 | 2821 | 2822 | 87.6 |
| 92 | baak2k13 | 2823 | 2824 | 87.6 |
| 92 | baak17d18 | 2825 | 2826 | 87.6 |
| 92 | bags13a12 | 2827 | 2828 | 87.6 |
| 96 | baak44g22 | 2829 | 2830 | 88.7 |
| 97 | kr34F0212 | 2831 | 2832 | 89.8 |
| 98 | baal16d11 | 2833 | 2834 | 92 |
| 99 | bah22d04 | 2835 | 2836 | 93.1 |
| 99 | bah48m23 | 2837 | 2838 | 93.1 |

TABLE 4-3

| Order from the short arm end | Clones | SEQ ID NO: (5' end) | SEQ ID NO: (3' end) | Distance from the short arm end (cM) |
|---|---|---|---|---|
| 99 | basd15p13 | 2839 | 2840 | 93.1 |
| 99 | BaGS6O07 | 2841 | 2842 | 93.1 |
| 99 | BaH37O10 | 2843 | 2844 | 93.1 |
| 99 | bags21k10 | 2845 | 2846 | 93.1 |
| 99 | bah56n18 | 2847 | 2848 | 93.1 |
| 99 | baal9i11 | 2849 | 2850 | 93.1 |
| 99 | BaAL39N06 | 2851 | 2852 | 93.1 |
| 99 | bags9d05 | 2853 | 2854 | 93.1 |
| 99 | BaAL19I19 | 2855 | 2856 | 93.1 |
| 99 | basd12I11 | 2857 | 2858 | 93.1 |
| 99 | bastl46D1008 | 2859 | 2860 | 93.1 |
| 99 | BaH50H16 | 2861 | 2862 | 93.1 |
| 99 | bags9n05 | 2863 | 2864 | 93.1 |
| 99 | kr61B1103 | 2865 | 2866 | 93.1 |
| 115 | kr27B0103 | 2867 | 2868 | 95.2 |
| 115 | kr33H1115 | 2869 | 2870 | 95.2 |
| 115 | baak30l02 | 2871 | 2872 | 95.2 |
| 115 | bah55a12 | 2873 | 2874 | 95.2 |
| 115 | BaH26K14 | 2875 | 2876 | 95.2 |
| 120 | HVM3 | — | — | 96.3 |
| 120 | BaAK33K19 | 2877 | 2878 | 96.3 |
| 120 | basd18m17 | 2879 | 2880 | 96.3 |
| 120 | BaH50G09 | 2881 | 2882 | 96.3 |
| 120 | BaH53B03 | 2883 | 2884 | 96.3 |
| 120 | BaH54L11 | 2885 | 2886 | 96.3 |
| 120 | basd13i14 | 2887 | 2888 | 96.3 |
| 120 | bah56g09 | 2889 | 2890 | 96.3 |
| 120 | bah41b06 | 2891 | 2892 | 96.3 |
| 120 | bags14d19 | 2893 | 2894 | 96.3 |
| 120 | baal20f05 | 2895 | 2896 | 96.3 |
| 120 | BaH18H12 | 2897 | 2898 | 96.3 |
| 120 | baal9o21 | 2899 | 2900 | 96.3 |
| 120 | bags21a02 | 2901 | 2902 | 96.3 |
| 120 | BaAL3G19 | 2903 | 2904 | 96.3 |
| 120 | baal7a09 | 2905 | 2906 | 96.3 |
| 120 | BaAL29I16 | 2907 | 2906 | 96.3 |
| 137 | bast70B0804 | 2909 | 2910 | 98.4 |
| 137 | bags14n08 | 2911 | 2912 | 98.4 |
| 139 | bastl14F0412 | 2913 | 2914 | 99.5 |
| 139 | BaAK36I12 | 2915 | 2916 | 99.5 |
| 139 | baal3f19 | 2917 | 2916 | 99.5 |

TABLE 4-3-continued

| Order from the short arm end | Clones | SEQ ID NO: (5' end) | SEQ ID NO: (3' end) | Distance from the short arm end (cM) |
|---|---|---|---|---|
| 142 | baal1e10 | 2919 | 2920 | 101.6 |
| 142 | bags6k02 | 2921 | 2922 | 101.6 |
| 142 | kr42H0315 | 2923 | 2924 | 101.6 |
| 145 | bah39p02 | 2925 | 2926 | 102.7 |
| 146 | BaGS9L14 | 2927 | 2928 | 106 |
| 146 | baal35l03 | 2929 | 2930 | 106 |
| 146 | basd12m15 | 2931 | 2932 | 106 |
| 146 | BaAK35P01 | 2933 | 2934 | 106 |
| 146 | basd11d18 | 2935 | 2936 | 106 |

TABLE 4-4

| Order from the short arm end | Clones | SEQ ID NO: (5' end) | SEQ ID NO: (3' end) | Distance from the short arm end (cM) |
|---|---|---|---|---|
| 146 | BaH38E07 | 2937 | 2938 | 106 |
| 146 | BaGS18H13 | 2939 | 2940 | 106 |
| 146 | bags18g16 | 2941 | 2942 | 106 |
| 146 | bags27f21 | 2943 | 2944 | 106 |
| 146 | BaGS7M13 | 2945 | 2946 | 106 |
| 146 | baal39c19 | 2947 | 2948 | 106 |
| 146 | baak46j05 | 2949 | 2950 | 106 |
| 146 | BaAK32D20 | 2951 | 2952 | 106 |
| 146 | MWG058 | — | — | 106 |
| 146 | BaGS18M02 | 2953 | 2954 | 106 |
| 146 | bags9c05 | 2955 | 2956 | 106 |
| 146 | baak46m13 | 2957 | 2958 | 106 |
| 146 | bags35n16 | 2959 | 2960 | 106 |
| 146 | bags39g08 | 2961 | 2962 | 106 |
| 146 | baal33a06 | 2963 | 2964 | 106 |
| 146 | BaSD17F20 | 2965 | 2966 | 106 |
| 146 | bags22i21 | 2967 | 2968 | 106 |
| 168 | bah32g18 | 2969 | 2970 | 107.1 |
| 169 | BaAL37O23 | 2971 | 2972 | 108.2 |
| 169 | bags22p03 | 2973 | 2974 | 108.2 |
| 171 | bags38l18 | 2975 | 2976 | 109.3 |
| 172 | BaGS35C13 | 2977 | 2978 | 112.6 |
| 172 | bah47h04 | 2979 | 2980 | 112.6 |
| 174 | bags30m11 | 2981 | 2982 | 114.7 |
| 174 | BaH22L15 | 2983 | 2984 | 114.7 |
| 176 | bags39e15 | 2985 | 2986 | 115.8 |
| 177 | kr65H0816 | 2987 | 2988 | 116.9 |
| 177 | basd11h11 | 2989 | 2990 | 116.9 |
| 177 | baak2b06 | 2991 | 2992 | 116.9 |
| 177 | Bmag353 | — | — | 116.9 |
| 177 | bags37j11 | 2993 | 2994 | 116.9 |
| 177 | BaAK46L15 | 2995 | 2996 | 116.9 |
| 183 | BaSD14A23 | 2997 | 2998 | 122.3 |
| 183 | bast25C0705 | 2999 | 3000 | 122.3 |
| 185 | bast21B1204 | 3001 | 3002 | 123.3 |
| 186 | bags1l16 | 3003 | 3004 | 129.7 |
| 186 | BaAK21G02 | 3005 | 3006 | 129.7 |
| 188 | bastl26E1109 | 3007 | 3008 | 130.6 |
| 188 | basd13k24 | 3009 | 3010 | 130.6 |
| 188 | BaAL13F02 | 3011 | 3012 | 130.6 |
| 191 | bags13c10 | 3013 | 3014 | 134.7 |
| 191 | bags11o11 | 3015 | 3016 | 134.7 |
| 191 | BaAK36P01 | 3017 | 3018 | 134.7 |
| 194 | bah52d09 | 3019 | 3020 | 135.9 |
| 194 | BaGS26D18 | 3021 | 3022 | 135.9 |
| 196 | baak33c22 | 3023 | 3024 | 137 |
| 196 | basd1d10 | 3025 | 3026 | 137 |
| 196 | baak11c22 | 3027 | 3028 | 137 |
| 196 | bags34l06 | 3029 | 3030 | 137 |
| 196 | baak33j06 | 3031 | 3032 | 137 |

TABLE 4-5

| Order from the short arm end | Clones | SEQ ID NO: (5' end) | SEQ ID NO: (3' end) | Distance from the short arm end (cM) |
|---|---|---|---|---|
| 196 | bags23a11 | 3033 | 3034 | 137 |
| 196 | bags34f02 | 3035 | 3036 | 137 |
| 196 | bags20p21 | 3037 | 3038 | 137 |
| 196 | bah52m01 | 3039 | 3040 | 137 |
| 196 | basd15d07 | 3041 | 3042 | 137 |
| 196 | BaAL20A14 | 3043 | 3044 | 137 |
| 207 | BaGS21B04 | 3045 | 3046 | 137.7 |
| 208 | HVM68 | — | — | 138.1 |
| 209 | BaAL36B07 | 3047 | 3048 | 139.2 |
| 209 | basd11p10 | 3049 | 3050 | 139.2 |
| 209 | BaGS33E17 | 3051 | 3052 | 139.2 |
| 212 | kr67C0206 | 3053 | 3054 | 140.3 |
| 213 | bags15i20 | 3055 | 3056 | 141.4 |
| 214 | BaH15E05 | 3057 | 3058 | 142.5 |
| 215 | BaH58K02 | 3059 | 3060 | 143.6 |
| 216 | basd13d17 | 3061 | 3062 | 146.9 |
| 216 | BaGS17A15 | 3063 | 3064 | 146.9 |
| 216 | BaAK30F13 | 3065 | 3066 | 146.9 |
| 216 | baal17m22 | 3067 | 3068 | 146.9 |
| 216 | baak42f04 | 3069 | 3070 | 146.9 |
| 216 | baal2n22 | 3071 | 3072 | 146.9 |
| 222 | kr30C0705 | 3073 | 3074 | 148 |
| 222 | BaSD19J21 | 3075 | 3076 | 148 |
| 222 | BaH34N22 | 3077 | 3078 | 148 |
| 225 | BaAK2I20 | 3079 | 3080 | 149.1 |
| 225 | BaGS1E22 | 3081 | 3082 | 149.1 |
| 225 | baak34b17 | 3083 | 3084 | 149.1 |
| 228 | BaSD11L18 | 3085 | 3086 | 151.3 |
| 228 | kr32A0202 | 3087 | 3088 | 151.3 |
| 230 | bags27h21 | 3089 | 3090 | 151.9 |
| 231 | bah62d17 | 3091 | 3092 | 152.4 |
| 231 | bah43e22 | 3093 | 3094 | 152.4 |
| 231 | BaAL30I23 | 3095 | 3096 | 152.4 |
| 231 | BaSD13H20 | 3097 | 3098 | 152.4 |
| 231 | BaSD14O04 | 3099 | 3100 | 152.4 |
| 236 | baak34p06 | 3101 | 3102 | 153.5 |
| 237 | bah63b08 | 3103 | 3104 | 156.8 |
| 238 | bastl03F0812 | 3105 | 3106 | 157.9 |
| 239 | basd14m17 | 3107 | 3108 | 159.2 |
| 240 | BaSD2J03 | 3109 | 3110 | 162.2 |
| 241 | bah13b17 | 3111 | 3112 | 171.1 |
| 242 | baal32b23 | 3113 | 3114 | 176.5 |
| 242 | bastl50D1208 | 3115 | 3116 | 176.5 |
| 242 | BaGS9H13 | 3117 | 3118 | 176.5 |
| 242 | baal33e04 | 3119 | 3120 | 176.5 |
| 246 | BaAL40L16 | 3121 | 3122 | 177.6 |
| 247 | bah44n03 | 3123 | 3124 | 178.7 |
| 247 | bags20h05 | 3125 | 3126 | 178.7 |
| 247 | bags20fM5 | 3127 | 3128 | 178.7 |
| 250 | BaGS7E03 | 3129 | 3130 | 179.8 |

TABLE 4-6

| Order from the short arm end | Clones | SEQ ID NO: (5' end) | SEQ ID NO: (3' end) | Distance from the short arm end (cM) |
|---|---|---|---|---|
| 250 | bags9k13 | 3131 | 3132 | 179.8 |
| 252 | bast55E0709 | 3133 | 3134 | 181.1 |
| 253 | bags8a14 | 3135 | 3136 | 184.6 |
| 254 | baak38k04 | 3137 | 3138 | 185.1 |
| 255 | BaH33B15 | 3139 | 3140 | 185.6 |
| 256 | bags29m17 | 3141 | 3142 | 186.7 |
| 257 | BaSD23P08 | 3143 | 3144 | 187.8 |
| 257 | BaH42L12 | 3145 | 3146 | 187.8 |
| 259 | bast79G0313 | 3147 | 3148 | 191 |
| 259 | baet46C0905 | 3149 | 3150 | 191 |
| 259 | baal4o09 | 3151 | 3152 | 191 |
| 259 | bah26e10 | 3153 | 3154 | 191 |
| 263 | BaH32J04 | 3155 | 3156 | 193.1 |
| 264 | bags20l07 | 3157 | 3158 | 194.2 |
| 265 | kr18C0505 | 3159 | 3160 | 195.3 |
| 266 | basd11m24 | 3161 | 3162 | 199.7 |

TABLE 4-6-continued

| Order from the short arm end | Clones | SEQ ID NO: (5' end) | SEQ ID NO: (3' end) | Distance from the short arm end (cM) |
|---|---|---|---|---|
| 266 | basd1i15 | 3163 | 3164 | 199.7 |
| 266 | bah45b02 | 3165 | 3166 | 199.7 |
| 269 | bast40C0206 | 3167 | 3168 | 201.8 |
| 269 | baal40g05 | 3169 | 3170 | 201.8 |
| 269 | bah13i21 | 3171 | 3172 | 201.8 |
| 269 | basd27o20 | 3173 | 3174 | 201.8 |
| 269 | BaAK12L24 | 3175 | 3176 | 201.8 |
| 274 | BaAL12F24 | 3177 | 3178 | 204 |
| 274 | baak45l08 | 3179 | 3180 | 204 |
| 274 | BaAL36N04 | 3181 | 3182 | 204 |
| 274 | baak41d17 | 3183 | 3184 | 204 |
| 274 | kr39E0810 | 3185 | 3186 | 204 |
| 274 | BaGS32G16 | 3187 | 3188 | 204 |
| 274 | BaGS25M06 | 3189 | 3190 | 204 |
| 274 | BaH36F21 | 3191 | 3192 | 204 |
| 274 | BaAK13B12 | 3193 | 3194 | 204 |
| 283 | baal29j18 | 3195 | 3196 | 205.1 |
| 284 | bast63B0604 | 3197 | 3198 | 206.2 |
| 284 | baak11n06 | 3199 | 3200 | 206.2 |
| 286 | kr13F1012 | 3201 | 3202 | 208.4 |
| 287 | bags20k06 | 3203 | 3204 | 209.5 |
| 288 | baak15p20 | 3205 | 3206 | 210.6 |
| 288 | bah18n11 | 3207 | 3208 | 210.6 |
| 290 | BaH23J08 | 3209 | 3210 | 213.9 |
| 291 | baet30B1004 | 3211 | 3212 | 215 |
| 291 | bags34p06 | 3213 | 3214 | 215 |
| 291 | bastl33H0816 | 3215 | 3216 | 215 |
| 294 | BaSD17I17 | 3217 | 3218 | 216.1 |
| 294 | basd19p22 | 3219 | 3220 | 216.1 |
| 294 | bags4e03 | 3221 | 3222 | 216.1 |
| 294 | BaAK36A13 | 3223 | 3224 | 216.1 |
| 294 | bags33i03 | 3225 | 3226 | 216.1 |
| 299 | BaAK14F03 | 3227 | 3228 | 217.2 |
| 300 | BaAK42K19 | 3229 | 3230 | 219.3 |

TABLE 4-7

| Order from the short arm end | Clones | SEQ ID NO: (5' end) | SEQ ID NO: (3' end) | Distance from the short arm end (cM) |
|---|---|---|---|---|
| 300 | bast60A1101 | 3231 | 3232 | 219.3 |
| 302 | bah52l06 | 3233 | 3234 | 220.4 |
| 302 | bah23h10 | 3235 | 3236 | 220.4 |
| 302 | BaGS15O23 | 3237 | 3238 | 220.4 |
| 302 | BaAK20E08 | 3239 | 3240 | 220.4 |
| 306 | kr61A1202 | 3241 | 3242 | 222.6 |
| 307 | bast03F0212 | 3243 | 3244 | 223.7 |
| 307 | bags39m22 | 3245 | 3246 | 223.7 |
| 309 | BaAK30O17 | 3247 | 3248 | 227.3 |
| 310 | baak29a01 | 3249 | 3250 | 232.1 |
| 310 | basd1e04 | 3251 | 3252 | 232.1 |
| 312 | BaGS23K09 | 3253 | 3254 | 233 |
| 313 | BaAL2N04 | 3255 | 3256 | 234.3 |
| 314 | BaH42C12 | 3257 | 3258 | 235.5 |
| 315 | bah39o14 | 3259 | 3260 | 236.1 |
| 316 | bast26A1202 | 3261 | 3262 | 236.6 |
| 317 | BaGS30N15 | 3263 | 3264 | 237.4 |
| 317 | BaAL34D18 | 3265 | 3266 | 237.4 |
| 319 | baak15k23 | 3267 | 3268 | 240.3 |
| 319 | bags37i06 | 3269 | 3270 | 240.3 |
| 319 | BaGS19N09 | 3271 | 3272 | 240.3 |
| 322 | BaSD13H09 | 3273 | 3274 | 241.4 |
| 323 | bags3h19 | 3275 | 3276 | 242.5 |
| 323 | baak28o08 | 3277 | 3278 | 242.5 |
| 325 | BaH15K08 | 3279 | 3280 | 243.6 |
| 325 | HVM67 | — | — | 243.6 |
| 325 | bah17h20 | 3281 | 3282 | 243.6 |
| 325 | BaAL5L13 | 3283 | 3284 | 243.6 |
| 325 | BaGS31P13 | 3285 | 3286 | 243.6 |
| 330 | BaH28A11 | 3287 | 3288 | 247.9 |
| 330 | BaSD25E01 | 3289 | 3290 | 247.9 |
| 330 | sh | — | — | 247.9 |

TABLE 4-7-continued

| Order from the short arm end | Clones | SEQ ID NO: (5' end) | SEQ ID NO: (3' end) | Distance from the short arm end (cM) |
|---|---|---|---|---|
| 333 | baet23F0111 | 3291 | 3292 | 249 |
| 333 | VRN2 | — | — | 249 |
| 333 | bastl41C0806 | 3293 | 3294 | 249 |
| 333 | basd11c04 | 3295 | 3296 | 249 |
| 333 | bags22k17 | 3297 | 3298 | 249 |
| 338 | bastl27A1101 | 3299 | 3300 | 250.2 |
| 338 | bags22a16 | 3301 | 3302 | 250.2 |
| 340 | BaAL5E04 | 3303 | 3304 | 250.3 |
| 341 | baal39f20 | 3305 | 3306 | 250.5 |
| 342 | baak43d13 | 3307 | 3308 | 250.7 |
| 342 | baak41l23 | 3309 | 3310 | 250.7 |
| 344 | baet23B0604 | 3311 | 3312 | 252.3 |
| 345 | BaAK28I08 | 3313 | 3314 | 255.6 |
| 346 | bastl26C1206 | 3315 | 3316 | 258.8 |
| 346 | bah27p20 | 3317 | 3318 | 258.8 |
| 346 | baal12d24 | 3319 | 3320 | 258.8 |
| 346 | bastl41F0511 | 3321 | 3322 | 258.8 |
| 346 | BaGS17E03 | 3323 | 3324 | 258.8 |

As shown in Table 5-1 to Table 5-11, the chromosomal order in barley 5H chromosome (distance from the short arm end of 5H chromosome) has been specified for 498 clones including the base sequences of SEQ ID NO: n (where n is an odd number) and SEQ ID NO: n+1 from among the base sequences of SEQ ID NO: 3325 through SEQ ID NO: 4320. The chromosomal order in barley 5H chromosome has also been specified for 8 known clones (MWG502, Bmac113, HVM30, Bmag223, HvLOX, MWG2077, MWG2249, and HVM6).

TABLE 5-1

| Order from the short arm end | Clones | SEQ ID NO: (5' end) | SEQ ID NO: (3' end) | Distance from the short arm end (cM) |
|---|---|---|---|---|
| 1 | baal10j04 | 3325 | 3326 | 0 |
| 1 | BaAK33J17 | 3327 | 3328 | 0 |
| 1 | BaAL21J19 | 3329 | 3330 | 0 |
| 4 | bast17H0515 | 3331 | 3332 | 0.5 |
| 5 | bags22c02 | 3333 | 3334 | 1 |
| 6 | BaAK35A06 | 3335 | 3336 | 2.2 |
| 7 | BaGS11K08 | 3337 | 3338 | 5.6 |
| 8 | bastl30A0602 | 3339 | 3340 | 6.7 |
| 9 | BaGS39H16 | 3341 | 3342 | 8.8 |
| 9 | MWG502 | — | — | 8.8 |
| 11 | BaAK18M22 | 3343 | 3344 | 9.9 |
| 12 | bast26G0614 | 3345 | 3346 | 11.5 |
| 13 | BaSD22F13 | 3347 | 3348 | 15.9 |
| 14 | BaAK28L16 | 3349 | 3350 | 20.5 |
| 15 | bags35o06 | 3351 | 3352 | 24.9 |
| 16 | bags13d07 | 3353 | 3354 | 25.9 |
| 16 | BaAL24F18 | 3355 | 3356 | 25.9 |
| 16 | bah63l18 | 3357 | 3358 | 25.9 |
| 19 | BaGS9H22 | 3359 | 3360 | 26.4 |
| 20 | BaAK18A05 | 3361 | 3362 | 26.9 |
| 20 | BaH38D03 | 3363 | 3364 | 26.9 |
| 20 | BaH17N17 | 3365 | 3366 | 26.9 |
| 23 | bah18d08 | 3367 | 3368 | 30.1 |
| 24 | bags34a05 | 3369 | 3370 | 31.9 |
| 24 | bags1m23 | 3371 | 3372 | 31.9 |
| 24 | BaH50B05 | 3373 | 3374 | 31.9 |
| 24 | bags1h11 | 3375 | 3376 | 31.9 |
| 28 | BaH47G19 | 3377 | 3378 | 32.4 |
| 29 | BaAK38H10 | 3379 | 3380 | 32.9 |
| 29 | bah47e01 | 3381 | 3382 | 32.9 |
| 29 | bast52E0109 | 3383 | 3384 | 32.9 |
| 32 | bags1o08 | 3385 | 3386 | 34 |
| 32 | BaH31H16 | 3387 | 3388 | 34 |
| 34 | baak32l14 | 3389 | 3390 | 36.1 |
| 34 | BaH50O06 | 3391 | 3392 | 36.1 |
| 34 | BaSD26I01 | 3393 | 3394 | 36.1 |

TABLE 5-1-continued

| Order from the short arm end | Clones | SEQ ID NO: (5' end) | SEQ ID NO: (3' end) | Distance from the short arm end (cM) |
|---|---|---|---|---|
| 37 | bags1h24 | 3395 | 3396 | 38.3 |
| 38 | basd27g16 | 3397 | 3398 | 40.5 |
| 38 | BaGS16G24 | 3399 | 3400 | 40.5 |
| 40 | BaGS34C19 | 3401 | 3402 | 43.7 |
| 40 | bah20k17 | 3403 | 3404 | 43.7 |
| 40 | bah54e13 | 3405 | 3406 | 43.7 |
| 40 | bags35i06 | 3407 | 3408 | 43.7 |
| 40 | bah29g09 | 3409 | 3410 | 43.7 |
| 45 | BaAK29C12 | 3411 | 3412 | 44.8 |
| 46 | bah56c06 | 3413 | 3414 | 48.2 |
| 47 | baal6a09 | 3415 | 3416 | 51.8 |
| 48 | bags6j06 | 3417 | 3418 | 53.1 |
| 49 | BaH30P15 | 3419 | 3420 | 54.2 |
| 50 | baak30k04 | 3421 | 3422 | 55.3 |

TABLE 5-2

| Order from the short arm end | Clones | SEQ ID NO: (5' end) | SEQ ID NO: (3' end) | Distance from the short arm end (cM) |
|---|---|---|---|---|
| 51 | basd25d22 | 3423 | 3424 | 56 |
| 51 | BaGS39M02 | 3425 | 3426 | 56 |
| 53 | baak13n10 | 3427 | 3428 | 58.9 |
| 53 | BaGS18J21 | 3429 | 3430 | 58.9 |
| 53 | BaSD22G22 | 3431 | 3432 | 58.9 |
| 53 | bags18b17 | 3433 | 3434 | 58.9 |
| 53 | bags33j02 | 3435 | 3436 | 58.9 |
| 53 | baak36b16 | 3437 | 3438 | 58.9 |
| 59 | bags37f05 | 3439 | 3440 | 60 |
| 59 | BaAL17L15 | 3441 | 3442 | 60 |
| 61 | BaGS20H12 | 3443 | 3444 | 62.4 |
| 62 | kr65A0802 | 3445 | 3446 | 64 |
| 62 | BaGS13E12 | 3447 | 3448 | 64 |
| 64 | basd3h06 | 3449 | 3450 | 65.2 |
| 65 | basd22j16 | 3451 | 3452 | 66.3 |
| 65 | bah39n18 | 3453 | 3454 | 66.3 |
| 67 | bags20d19 | 3455 | 3456 | 67.4 |
| 67 | BaGS34H19 | 3457 | 3458 | 67.4 |
| 69 | baak42n10 | 3459 | 3460 | 68.5 |
| 69 | BaSD24F03 | 3461 | 3462 | 68.5 |
| 69 | BaGS23N21 | 3463 | 3464 | 68.5 |
| 69 | BaAK45E04 | 3465 | 3466 | 68.5 |
| 69 | bags5n23 | 3467 | 3468 | 68.5 |
| 74 | bast52H1216 | 3469 | 3470 | 69.4 |
| 75 | bags22f23 | 3471 | 3472 | 69.7 |
| 76 | BaH38E02 | 3473 | 3474 | 70.5 |
| 76 | BaH50O07 | 3475 | 3476 | 70.5 |
| 78 | kr07C1006 | 3477 | 3478 | 73.3 |
| 78 | baak26a02 | 3479 | 3480 | 73.3 |
| 78 | BaAK2J22 | 3481 | 3482 | 73.3 |
| 78 | bah45h23 | 3483 | 3484 | 73.3 |
| 82 | bah11h09 | 3485 | 3486 | 74.8 |
| 82 | BaAK46M16 | 3487 | 3488 | 74.8 |
| 84 | bah55m23 | 3489 | 3490 | 75.2 |
| 84 | bah59c05 | 3491 | 3492 | 75.2 |
| 84 | basd11l17 | 3493 | 3494 | 75.2 |
| 84 | bah19e08 | 3495 | 3496 | 75.2 |
| 84 | BaAK21N24 | 3497 | 3498 | 75.2 |
| 84 | BaH50E09 | 3499 | 3500 | 75.2 |
| 84 | BaAK17P18 | 3501 | 3502 | 75.2 |
| 84 | BaAL7A04 | 3503 | 3504 | 75.2 |
| 84 | bast47B0303 | 3505 | 3506 | 75.2 |
| 84 | bah28o17 | 3507 | 3508 | 75.2 |
| 84 | bah37k03 | 3509 | 3510 | 75.2 |
| 84 | bastl38A0501 | 3511 | 3512 | 75.2 |
| 84 | bags23c03 | 3513 | 3514 | 75.2 |
| 84 | basd13j01 | 3515 | 3516 | 75.2 |
| 84 | bags21c02 | 3517 | 3518 | 75.2 |
| 84 | bah28l03 | 3519 | 3520 | 75.2 |
| 84 | BaAK36B17 | 3521 | 3522 | 75.2 |

TABLE 5-3

| Order from the short arm end | Clones | SEQ ID NO: (5' end) | SEQ ID NO: (3' end) | Distance from the short arm end (cM) |
|---|---|---|---|---|
| 84 | bags6k10 | 3523 | 3524 | 75.2 |
| 84 | BaAK32J23 | 3525 | 3526 | 75.2 |
| 84 | bags9k18 | 3527 | 3528 | 75.2 |
| 84 | baal18c19 | 3529 | 3530 | 75.2 |
| 84 | baak27p14 | 3531 | 3532 | 75.2 |
| 84 | BaGS30N21 | 3533 | 3534 | 75.2 |
| 84 | bah55p23 | 3535 | 3536 | 75.2 |
| 84 | bah54p22 | 3537 | 3538 | 75.2 |
| 84 | bags34f05 | 3539 | 3540 | 75.2 |
| 84 | Bmac113 | — | — | 75.2 |
| 84 | bags15i11 | 3541 | 3542 | 75.2 |
| 84 | BaH26I21 | 3543 | 3544 | 75.2 |
| 84 | BaSD20M22 | 3545 | 3546 | 75.2 |
| 114 | bah14a24 | 3547 | 3548 | 75.6 |
| 115 | BaH50J11 | 3549 | 3550 | 76 |
| 116 | bags7a20 | 3551 | 3552 | 76.4 |
| 116 | bah25l12 | 3553 | 3554 | 76.4 |
| 116 | bags6k09 | 3555 | 3556 | 76.4 |
| 116 | BaGS29P21 | 3557 | 3558 | 76.4 |
| 116 | bah58f18 | 3559 | 3560 | 76.4 |
| 116 | bags39i18 | 3561 | 3562 | 76.4 |
| 122 | basd22l21 | 3563 | 3564 | 77.1 |
| 123 | bags4o22 | 3565 | 3566 | 77.5 |
| 124 | kr27E0909 | 3567 | 3568 | 78 |
| 125 | bastl41H0216 | 3569 | 3570 | 78.5 |
| 125 | baak36o17 | 3571 | 3572 | 78.5 |
| 125 | BaH31P15 | 3573 | 3574 | 78.5 |
| 125 | kr07D0208 | 3575 | 3576 | 78.5 |
| 125 | bags9h03 | 3577 | 3578 | 78.5 |
| 130 | BaGS38M11 | 3579 | 3580 | 79.6 |
| 130 | kr26C0705 | 3581 | 3582 | 79.6 |
| 130 | bags3k24 | 3583 | 3584 | 79.6 |
| 130 | bah53e16 | 3585 | 3586 | 79.6 |
| 130 | bags21n10 | 3587 | 3588 | 79.6 |
| 130 | BaGS25E06 | 3589 | 3590 | 79.6 |
| 130 | bah38n03 | 3591 | 3592 | 79.6 |
| 130 | BaAK38G14 | 3593 | 3594 | 79.6 |
| 130 | baal5a06 | 3595 | 3596 | 79.6 |
| 130 | basd26d19 | 3597 | 3598 | 79.6 |
| 140 | BaSD26D07 | 3599 | 3600 | 80.7 |
| 140 | BaH50G14 | 3601 | 3602 | 80.7 |
| 140 | bah21h17 | 3603 | 3604 | 80.7 |
| 140 | bags5d21 | 3605 | 3606 | 80.7 |
| 140 | BaAK34D14 | 3607 | 3608 | 80.7 |
| 140 | baak18a16 | 3609 | 3610 | 80.7 |
| 140 | bags4b01 | 3611 | 3612 | 80.7 |
| 140 | bags38c19 | 3613 | 3614 | 80.7 |
| 140 | BaGS38J23 | 3615 | 3616 | 80.7 |
| 140 | kr42D0208 | 3617 | 3618 | 80.7 |
| 140 | BaH33A16 | 3619 | 3620 | 80.7 |

TABLE 5-4

| Order from the short arm end | Clones | SEQ ID NO: (5' end) | SEQ ID NO: (3' end) | Distance from the short arm end (cM) |
|---|---|---|---|---|
| 140 | bags10e03 | 3621 | 3622 | 80.7 |
| 140 | bags14f17 | 3623 | 3624 | 80.7 |
| 140 | BaAK35N11 | 3625 | 3626 | 80.7 |
| 140 | bags26n10 | 3627 | 3628 | 80.7 |
| 140 | bags37n02 | 3629 | 3630 | 80.7 |
| 140 | baal39l05 | 3631 | 3632 | 80.7 |
| 157 | BaAK26L11 | 3633 | 3634 | 81.3 |
| 158 | BaH57C19 | 3635 | 3636 | 81.7 |
| 158 | bags7a01 | 3637 | 3638 | 81.7 |
| 158 | bah19l15 | 3639 | 3640 | 81.7 |
| 158 | baal4o02 | 3641 | 3642 | 81.7 |
| 158 | bah58a12 | 3643 | 3644 | 81.7 |
| 158 | HVM30 | — | — | 81.7 |
| 158 | bah11b08 | 3645 | 3646 | 81.7 |
| 158 | bags14m15 | 3647 | 3648 | 81.7 |
| 158 | baak1e17 | 3649 | 3650 | 81.7 |

TABLE 5-4-continued

| Order from the short arm end | Clones | SEQ ID NO: (5' end) | SEQ ID NO: (3' end) | Distance from the short arm end (cM) |
|---|---|---|---|---|
| 167 | bags14i11 | 3651 | 3652 | 83.2 |
| 168 | bastl04B1103 | 3653 | 3654 | 87 |
| 169 | bags13g08 | 3655 | 3656 | 94.7 |
| 170 | basd27p03 | 3657 | 3658 | 102.2 |
| 170 | bast38D0707 | 3659 | 3660 | 102.2 |
| 172 | baak35j18 | 3661 | 3662 | 103.7 |
| 172 | baal19k05 | 3663 | 3664 | 103.7 |
| 174 | BaH19C21 | 3665 | 3666 | 104.2 |
| 174 | bah49g10 | 3667 | 3668 | 104.2 |
| 174 | bags14h08 | 3669 | 3670 | 104.2 |
| 174 | bags23g18 | 3671 | 3672 | 104.2 |
| 174 | bags22o22 | 3673 | 3674 | 104.2 |
| 174 | BaAL20A03 | 3675 | 3676 | 104.2 |
| 174 | bags5e24 | 3677 | 3678 | 104.2 |
| 174 | bags5f11 | 3679 | 3680 | 104.2 |
| 174 | BaAK33B10 | 3681 | 3682 | 104.2 |
| 174 | BaSD15J20 | 3683 | 3684 | 104.2 |
| 174 | bags38b22 | 3685 | 3686 | 104.2 |
| 185 | bah39b06 | 3687 | 3688 | 105.3 |
| 185 | bags19j08 | 3689 | 3690 | 105.3 |
| 187 | BaGS1G09 | 3691 | 3692 | 106.4 |
| 188 | bah63j06 | 3693 | 3694 | 107.5 |
| 188 | BaAL39J02 | 3695 | 3696 | 107.5 |
| 188 | BaSD27H14 | 3697 | 3698 | 107.5 |
| 191 | BaH50M01 | 3699 | 3700 | 112 |
| 192 | BaSD24E13 | 3701 | 3702 | 113.3 |
| 193 | baal5j24 | 3703 | 3704 | 116.7 |
| 194 | bah15h18 | 3705 | 3706 | 117.8 |
| 194 | bast62E0610 | 3707 | 3708 | 117.8 |
| 196 | bah28k24 | 3709 | 3710 | 118.9 |
| 196 | bah47c11 | 3711 | 3712 | 118.9 |
| 196 | BaSD26M15 | 3713 | 3714 | 118.9 |
| 196 | bah60o02 | 3715 | 3716 | 118.9 |
| 196 | BaH50G06 | 3717 | 3718 | 118.9 |

TABLE 5-5

| Order from the short arm end | Clones | SEQ ID NO: (5' end) | SEQ ID NO: (3' end) | Distance from the short arm end (cM) |
|---|---|---|---|---|
| 201 | bast15G0913 | 3719 | 3720 | 120 |
| 201 | bah62n12 | 3721 | 3722 | 120 |
| 201 | baal10n23 | 3723 | 3724 | 120 |
| 204 | bags20c12 | 3725 | 3726 | 121.1 |
| 205 | basd16f13 | 3727 | 3728 | 122.2 |
| 206 | baak21h06 | 3729 | 3730 | 124.2 |
| 207 | bags3b05 | 3731 | 3732 | 125.2 |
| 208 | bags22p08 | 3733 | 3734 | 128.3 |
| 208 | BaH23N06 | 3735 | 3736 | 128.3 |
| 208 | bags29c08 | 3737 | 3738 | 128.3 |
| 211 | BaGS11O23 | 3739 | 3740 | 129.4 |
| 211 | baak16a11 | 3741 | 3742 | 129.4 |
| 213 | baak15n22 | 3743 | 3744 | 131.6 |
| 213 | BaAL18J13 | 3745 | 3746 | 131.6 |
| 213 | bah15m02 | 3747 | 3748 | 131.6 |
| 213 | baak38d20 | 3749 | 3750 | 131.6 |
| 213 | BaSD12L21 | 3751 | 3752 | 131.6 |
| 213 | kr68B1103 | 3753 | 3754 | 131.6 |
| 219 | BaAK28L22 | 3755 | 3756 | 133.7 |
| 219 | bags15b10 | 3757 | 3758 | 133.7 |
| 219 | bags20h21 | 3759 | 3760 | 133.7 |
| 219 | BaAK29K06 | 3761 | 3762 | 133.7 |
| 219 | bags21l05 | 3763 | 3764 | 133.7 |
| 219 | bah56j14 | 3765 | 3766 | 133.7 |
| 219 | basd15e02 | 3767 | 3768 | 133.7 |
| 226 | bags3j24 | 3769 | 3770 | 134.8 |
| 226 | bags38m08 | 3771 | 3772 | 134.8 |
| 228 | bah11m18 | 3773 | 3774 | 136.9 |
| 228 | bags35g06 | 3775 | 3776 | 136.9 |
| 228 | bags37b01 | 3777 | 3778 | 136.9 |
| 228 | BaAL19F02 | 3779 | 3780 | 136.9 |
| 232 | BaAL4D09 | 3781 | 3782 | 138 |

TABLE 5-5-continued

| Order from the short arm end | Clones | SEQ ID NO: (5' end) | SEQ ID NO: (3' end) | Distance from the short arm end (cM) |
|---|---|---|---|---|
| 232 | BaAK30H10 | 3783 | 3784 | 138 |
| 234 | bags38b16 | 3785 | 3786 | 142.3 |
| 235 | bags27f15 | 3787 | 3788 | 143.7 |
| 236 | bags10k14 | 3789 | 3790 | 146.6 |
| 236 | bags22f10 | 3791 | 3792 | 146.6 |
| 236 | baak38n21 | 3793 | 3794 | 146.6 |
| 236 | baak30e05 | 3795 | 3796 | 146.6 |
| 236 | bastl04A0101 | 3797 | 3798 | 146.6 |
| 236 | BaAK28P18 | 3799 | 3800 | 146.6 |
| 236 | BaGS34E01 | 3801 | 3802 | 146.6 |
| 236 | BaH54H04 | 3803 | 3804 | 146.6 |
| 236 | bah13o19 | 3805 | 3806 | 146.6 |
| 245 | BaAK29B22 | 3807 | 3808 | 147.7 |
| 245 | BaAK27C16 | 3809 | 3810 | 147.7 |
| 245 | BaGS22H13 | 3811 | 3812 | 147.7 |
| 245 | BaSD27A15 | 3813 | 3814 | 147.7 |
| 249 | BaAK27E07 | 3815 | 3816 | 151 |
| 250 | BaGS9N02 | 3817 | 3818 | 152.1 |

TABLE 5-6

| Order from the short arm end | Clones | SEQ ID NO: (5' end) | SEQ ID NO: (3' end) | Distance from the short arm end (cM) |
|---|---|---|---|---|
| 251 | Bmag223 | — | — | 153.2 |
| 252 | bags28o18 | 3819 | 3820 | 154.3 |
| 253 | baal25b05 | 3821 | 3822 | 155.4 |
| 253 | bastl30A0202 | 3823 | 3824 | 155.4 |
| 253 | bags37d20 | 3825 | 3826 | 155.4 |
| 256 | BaGS22K12 | 3827 | 3828 | 155.8 |
| 257 | BaAK13G12 | 3829 | 3830 | 156.1 |
| 258 | basd2a02 | 3831 | 3832 | 156.5 |
| 258 | BaGS31L06 | 3833 | 3834 | 156.5 |
| 258 | bags17j17 | 3835 | 3836 | 156.5 |
| 258 | baal12j15 | 3837 | 3838 | 156.5 |
| 258 | BaAK19H14 | 3839 | 3840 | 156.5 |
| 263 | BaH34J11 | 3841 | 3842 | 159.8 |
| 263 | BaGS30I11 | 3843 | 3844 | 159.8 |
| 265 | BaH49L06 | 3845 | 3846 | 161 |
| 265 | baal18m24 | 3847 | 3848 | 161 |
| 267 | baak15l06 | 3849 | 3850 | 163.2 |
| 267 | basd18o14 | 3851 | 3852 | 163.2 |
| 269 | bags24p22 | 3853 | 3854 | 164.3 |
| 269 | BaAL37A09 | 3855 | 3856 | 164.3 |
| 269 | bags5l01 | 3857 | 3858 | 164.3 |
| 269 | BaAK12P03 | 3859 | 3860 | 164.3 |
| 273 | baak21f10 | 3861 | 3862 | 164.5 |
| 274 | bastl30E0410 | 3863 | 3864 | 164.7 |
| 274 | kr25C0206 | 3865 | 3866 | 164.7 |
| 276 | baak4j01 | 3867 | 3868 | 166.2 |
| 276 | BaAK27E01 | 3869 | 3870 | 166.2 |
| 278 | bah54n06 | 3871 | 3872 | 167.3 |
| 278 | bags19p05 | 3873 | 3874 | 167.3 |
| 278 | bast22F0311 | 3875 | 3876 | 167.3 |
| 281 | basd1m04 | 3877 | 3878 | 170.6 |
| 282 | bags35i04 | 3879 | 3880 | 171.7 |
| 282 | baak41d01 | 3881 | 3882 | 171.7 |
| 282 | baal19m08 | 3883 | 3884 | 171.7 |
| 282 | baak13j10 | 3885 | 3886 | 171.7 |
| 282 | baak44h11 | 3887 | 3888 | 171.7 |
| 287 | baal19j09 | 3889 | 3890 | 172.2 |
| 288 | baet37C1105 | 3891 | 3892 | 172.7 |
| 288 | baak12d06 | 3893 | 3894 | 172.7 |
| 288 | basd23f10 | 3895 | 3896 | 172.7 |
| 288 | BaH41P07 | 3897 | 3898 | 172.7 |
| 292 | baak1g13 | 3899 | 3900 | 173.8 |
| 293 | basd14b04 | 3901 | 3902 | 174.9 |
| 294 | bags22l14 | 3903 | 3904 | 177.1 |
| 294 | bast26E1210 | 3905 | 3906 | 177.1 |
| 296 | baet25F0911 | 3907 | 3908 | 180 |
| 296 | BaAK32N13 | 3909 | 3910 | 180 |
| 298 | BaSD2C09 | 3911 | 3912 | 180.3 |

TABLE 5-6-continued

| Order from the short arm end | Clones | SEQ ID NO: (5' end) | SEQ ID NO: (3' end) | Distance from the short arm end (cM) |
|---|---|---|---|---|
| 299 | BaGS31P01 | 3913 | 3914 | 180.7 |
| 299 | baak30m11 | 3915 | 3916 | 180.7 |

TABLE 5-7

| Order from the short arm end | Clones | SEQ ID NO: (5' end) | SEQ ID NO: (3' end) | Distance from the short arm end (cM) |
|---|---|---|---|---|
| 301 | BaAK4N16 | 3917 | 3918 | 181.2 |
| 302 | bastl46F1012 | 3919 | 3920 | 181.7 |
| 302 | bags3e06 | 3921 | 3922 | 181.7 |
| 302 | bags31o10 | 3923 | 3924 | 181.7 |
| 305 | bags33j12 | 3925 | 3926 | 182.8 |
| 306 | BaGS30N07 | 3927 | 3928 | 183.8 |
| 307 | BaH37I18 | 3929 | 3930 | 188.1 |
| 307 | baak46p24 | 3931 | 3932 | 188.1 |
| 309 | baak46o19 | 3933 | 3934 | 188.7 |
| 310 | basd3c19 | 3935 | 3936 | 189.2 |
| 310 | bags30f01 | 3937 | 3938 | 189.2 |
| 310 | BaGS20F10 | 3939 | 3940 | 189.2 |
| 313 | BaGS32D08 | 3941 | 3942 | 191.4 |
| 314 | BaAK23M23 | 3943 | 3944 | 193.6 |
| 314 | bah21a16 | 3945 | 3946 | 193.6 |
| 314 | BaAL3M08 | 3947 | 3948 | 193.6 |
| 314 | BaAK21I09 | 3949 | 3950 | 193.6 |
| 314 | baet33A0301 | 3951 | 3952 | 193.6 |
| 319 | baak24k02 | 3953 | 3954 | 195.7 |
| 319 | bah33p03 | 3955 | 3956 | 195.7 |
| 319 | bast75D1208 | 3957 | 3958 | 195.7 |
| 322 | BaSD12K20 | 3959 | 3960 | 196 |
| 323 | bags34f06 | 3961 | 3962 | 196.4 |
| 324 | bags6f09 | 3963 | 3964 | 196.8 |
| 324 | bags7b10 | 3965 | 3966 | 196.8 |
| 326 | BaGS25H01 | 3967 | 3968 | 199 |
| 326 | baak33m08 | 3969 | 3970 | 199 |
| 326 | bags37e01 | 3971 | 3972 | 199 |
| 326 | bags32n20 | 3973 | 3974 | 199 |
| 326 | BaH47A11 | 3975 | 3976 | 199 |
| 326 | BaGS24M06 | 3977 | 3978 | 199 |
| 332 | bags22m23 | 3979 | 3980 | 200.1 |
| 332 | basd18d18 | 3981 | 3982 | 200.1 |
| 332 | bastl06F0212 | 3983 | 3984 | 200.1 |
| 332 | BaH49O16 | 3985 | 3986 | 200.1 |
| 332 | bags39e22 | 3987 | 3988 | 200.1 |
| 332 | BaH38N06 | 3989 | 3990 | 200.1 |
| 332 | BaH56P16 | 3991 | 3992 | 200.1 |
| 339 | BaSD13O13 | 3993 | 3994 | 200.3 |
| 340 | bags19i06 | 3995 | 3996 | 201.4 |
| 340 | bah34f11 | 3997 | 3998 | 201.4 |
| 340 | bags37g04 | 3999 | 4000 | 201.4 |
| 343 | basd11k21 | 4001 | 4002 | 201.7 |
| 344 | HvLOX | — | — | 202.8 |
| 345 | baak43o03 | 4003 | 4004 | 203.6 |
| 345 | BaAL4J21 | 4005 | 4006 | 203.6 |
| 345 | BaH51J22 | 4007 | 4008 | 203.6 |
| 345 | bah58l03 | 4009 | 4010 | 203.6 |
| 345 | BaGS21M18 | 4011 | 4012 | 203.6 |
| 345 | BaGS31K06 | 4013 | 4014 | 203.6 |

TABLE 5-8

| Order from the short arm end | Clones | SEQ ID NO: (5' end) | SEQ ID NO: (3' end) | Distance from the short arm end (cM) |
|---|---|---|---|---|
| 351 | baal4o01*VRN2(sh2) | 4015 | 4016 | 204 |
| 352 | BaAK24H19 | 4017 | 4018 | 204.6 |
| 352 | BaGS17D21 | 4019 | 4020 | 204.6 |
| 352 | bah39o04 | 4021 | 4022 | 204.6 |
| 352 | baak46e06 | 4023 | 4024 | 204.6 |
| 352 | basd13j03 | 4025 | 4026 | 204.6 |
| 357 | bast14H0416 | 4027 | 4028 | 206.8 |
| 357 | BaSD18I03 | 4029 | 4030 | 206.8 |
| 357 | bastl44H1115 | 4031 | 4032 | 206.8 |
| 357 | bast34D0608 | 4033 | 4034 | 206.8 |
| 357 | BaGS30F06 | 4035 | 4036 | 206.8 |
| 357 | bags21k16 | 4037 | 4038 | 206.8 |
| 363 | BaH48G01 | 4039 | 4040 | 207.9 |
| 363 | bags39a24 | 4041 | 4042 | 207.9 |
| 363 | bags15i03 | 4043 | 4044 | 207.9 |
| 363 | bags23f02 | 4045 | 4046 | 207.9 |
| 363 | bastl40E1010 | 4047 | 4048 | 207.9 |
| 368 | bags17p10 | 4049 | 4050 | 211 |
| 369 | BaH57L13 | 4051 | 4052 | 212.6 |
| 369 | bags10e22 | 4053 | 4054 | 212.6 |
| 371 | bags4p07 | 4055 | 4056 | 213.6 |
| 371 | bah63a08 | 4057 | 4058 | 213.6 |
| 373 | baak12f13 | 4059 | 4060 | 214.7 |
| 373 | bah56j15 | 4061 | 4062 | 214.7 |
| 373 | bah15e16 | 4063 | 4064 | 214.7 |
| 373 | BaH50F21 | 4065 | 4066 | 214.7 |
| 373 | basd27o16 | 4067 | 4068 | 214.7 |
| 378 | kr66G0713 | 4069 | 4070 | 216.2 |
| 378 | baak46c17 | 4071 | 4072 | 216.2 |
| 380 | baet19C1206 | 4073 | 4074 | 216.7 |
| 380 | bags34e15 | 4075 | 4076 | 216.7 |
| 380 | baal4d18 | 4077 | 4078 | 216.7 |
| 380 | bah13b13 | 4079 | 4080 | 216.7 |
| 384 | BaGS26G20 | 4081 | 4082 | 217.2 |
| 385 | BaGS28C14 | 4083 | 4084 | 217.7 |
| 385 | kr61G1214 | 4085 | 4086 | 217.7 |
| 385 | bags9g08 | 4087 | 4088 | 217.7 |
| 385 | bags5p01 | 4089 | 4090 | 217.7 |
| 385 | BaAL4D04 | 4091 | 4092 | 217.7 |
| 385 | bah26p09 | 4093 | 4094 | 217.7 |
| 385 | bah11e02 | 4095 | 4096 | 217.7 |
| 385 | MWG2077 | — | — | 217.7 |
| 385 | bast41F0311 | 4097 | 4098 | 217.7 |
| 385 | bastl54D0307 | 4099 | 4100 | 217.7 |
| 395 | BaSD3F21 | 4101 | 4102 | 219.9 |
| 395 | bah56fl8 | 4103 | 4104 | 219.9 |
| 397 | BaH41C21 | 4105 | 4106 | 221 |
| 397 | basd19g21 | 4107 | 4108 | 221 |
| 399 | kr33H0816 | 4109 | 4110 | 223.2 |
| 399 | BaH38F16 | 4111 | 4112 | 223.2 |

TABLE 5-9

| Order from the short arm end | Clones | SEQ ID NO: (5' end) | SEQ ID NO: (3' end) | Distance from the short arm end (cM) |
|---|---|---|---|---|
| 399 | BaGS21P09 | 4113 | 4114 | 223.2 |
| 402 | BaGS36M20 | 4115 | 4116 | 224.2 |
| 403 | bags21m10 | 4117 | 4118 | 228.5 |
| 403 | BaAK14G11 | 4119 | 4120 | 228.5 |
| 405 | BaGS30L20 | 4121 | 4122 | 230.7 |
| 406 | basd21g02 | 4123 | 4124 | 231.8 |
| 406 | bah22m17 | 4125 | 4126 | 231.8 |
| 406 | BaGS9H19 | 4127 | 4128 | 231.8 |
| 409 | bah26m24 | 4129 | 4130 | 232.9 |
| 410 | BaH56D01 | 4131 | 4132 | 234 |
| 411 | bah53i08 | 4133 | 4134 | 237.1 |
| 411 | bags21d10 | 4135 | 4136 | 237.1 |
| 411 | bags9a01 | 4137 | 4138 | 237.1 |
| 414 | baal9m13 | 4139 | 4140 | 238.3 |
| 414 | baak20m05 | 4141 | 4142 | 238.3 |
| 416 | baak21k16 | 4143 | 4144 | 238.6 |
| 417 | bags34d17 | 4145 | 4146 | 239.4 |
| 418 | baal40k24 | 4147 | 4148 | 240.5 |
| 419 | BaGS19O14 | 4149 | 4150 | 243.4 |
| 419 | baak35m03 | 4151 | 4152 | 243.4 |
| 419 | baak33o23 | 4153 | 4154 | 243.4 |

TABLE 5-9-continued

| Order from the short arm end | Clones | SEQ ID NO: (5' end) | SEQ ID NO: (3' end) | Distance from the short arm end (cM) |
|---|---|---|---|---|
| 419 | kr57F1012 | 4155 | 4156 | 243.4 |
| 419 | bah53i05 | 4157 | 4158 | 243.4 |
| 419 | bags22l16 | 4159 | 4160 | 243.4 |
| 419 | baet43C0505 | 4161 | 4162 | 243.4 |
| 419 | BaH33H02 | 4163 | 4164 | 243.4 |
| 419 | bastl22E1010 | 4165 | 4166 | 243.4 |
| 428 | BaH53N24 | 4167 | 4168 | 244.6 |
| 429 | baal8e24 | 4169 | 4170 | 245.9 |
| 429 | BaH62H21 | 4171 | 4172 | 245.9 |
| 431 | BaH42K01 | 4173 | 4174 | 250.7 |
| 432 | basd26p09 | 4175 | 4176 | 252.1 |
| 433 | bags4p18 | 4177 | 4178 | 253.1 |
| 433 | BaH60H14 | 4179 | 4180 | 253.1 |
| 433 | bast70D1107 | 4181 | 4182 | 253.1 |
| 433 | bah26i23 | 4183 | 4184 | 253.1 |
| 437 | baal39g02 | 4185 | 4186 | 253.6 |
| 437 | bags10e02 | 4187 | 4188 | 253.6 |
| 439 | bags22c13 | 4189 | 4190 | 255.1 |
| 439 | bags35n03 | 4191 | 4192 | 255.1 |
| 439 | BaAL16H03 | 4193 | 4194 | 255.1 |
| 442 | BaAL15N07 | 4195 | 4196 | 255.8 |
| 443 | bags18o20 | 4197 | 4198 | 258 |
| 444 | bags37g12 | 4199 | 4200 | 258.4 |
| 445 | bags22l12 | 4201 | 4202 | 259.5 |
| 446 | BaAK44K01 | 4203 | 4204 | 260.6 |
| 446 | BaAK31G07 | 4205 | 4206 | 260.6 |
| 446 | bah53n21 | 4207 | 4208 | 260.6 |
| 449 | BaGS19C02 | 4209 | 4210 | 263.8 |
| 450 | BaH52E20 | 4211 | 4212 | 265.9 |

TABLE 5-10

| Order from the short arm end | Clones | SEQ ID NO: (5' end) | SEQ ID NO: (3' end) | Distance from the short arm end (cM) |
|---|---|---|---|---|
| 450 | BaAL4N05 | 4213 | 4214 | 265.9 |
| 450 | bags7p06 | 4215 | 4216 | 265.9 |
| 453 | bast70C0905 | 4217 | 4218 | 270.9 |
| 453 | BaSD15J01 | 4219 | 4220 | 270.9 |
| 455 | BaH56H18 | 4221 | 4222 | 272.9 |
| 455 | BaGS4N04 | 4223 | 4224 | 272.9 |
| 455 | bags31o13 | 4225 | 4226 | 272.9 |
| 455 | kr29D0107 | 4227 | 4228 | 272.9 |
| 459 | BaAK21A15 | 4229 | 4230 | 274 |
| 459 | bags7h14 | 4231 | 4232 | 274 |
| 459 | basd26b20 | 4233 | 4234 | 274 |
| 459 | baal1g06 | 4235 | 4236 | 274 |
| 459 | bags5n14 | 4237 | 4238 | 274 |
| 464 | BaAK34H17 | 4239 | 4240 | 274.5 |
| 465 | bastl32H0816 | 4241 | 4242 | 275 |
| 465 | basd18m12 | 4243 | 4244 | 275 |
| 465 | baak31p06 | 4245 | 4246 | 275 |
| 465 | bah52i03 | 4247 | 4248 | 275 |
| 469 | BaAK33K05 | 4249 | 4250 | 276.1 |
| 469 | BaAK44J08 | 4251 | 4252 | 276.1 |
| 469 | baak18g16 | 4253 | 4254 | 276.1 |
| 469 | baak11a11 | 4255 | 4256 | 276.1 |
| 473 | BaH25B20 | 4257 | 4258 | 279.3 |
| 473 | bastl12G0113 | 4259 | 4260 | 279.3 |
| 473 | baal9n02 | 4261 | 4262 | 279.3 |
| 473 | bags20f08 | 4263 | 4264 | 279.3 |
| 477 | BaGS9C24 | 4265 | 4266 | 281.5 |
| 477 | BaGS22O02 | 4267 | 4268 | 281.5 |
| 479 | baak13k16 | 4269 | 4270 | 282.6 |
| 479 | MWG2249 | — | — | 282.6 |
| 479 | bah41b17 | 4271 | 4272 | 282.6 |
| 482 | bah63m11 | 4273 | 4274 | 283.7 |
| 482 | BaGS28P07 | 4275 | 4276 | 283.7 |
| 482 | bags1h15 | 4277 | 4278 | 283.7 |
| 482 | kr26H0515 | 4279 | 4280 | 283.7 |
| 482 | bags6n05 | 4281 | 4282 | 283.7 |
| 487 | BaH24P17 | 4283 | 4284 | 284.1 |

TABLE 5-10-continued

| Order from the short arm end | Clones | SEQ ID NO: (5' end) | SEQ ID NO: (3' end) | Distance from the short arm end (cM) |
|---|---|---|---|---|
| 488 | bast03D0408 | 4285 | 4286 | 284.8 |
| 488 | BaAL17G06 | 4287 | 4288 | 284.8 |
| 488 | BaH32G11 | 4289 | 4290 | 284.8 |
| 488 | BaGS4P17 | 4291 | 4292 | 284.8 |
| 488 | baal31o21 | 4293 | 4294 | 284.8 |
| 488 | BaGS36A16 | 4295 | 4296 | 284.8 |
| 488 | bags4d11 | 4297 | 4298 | 284.8 |
| 488 | basd13n18 | 4299 | 4300 | 284.8 |
| 496 | basd0a08 | 4301 | 4302 | 285.2 |
| 497 | BaGS32P24 | 4303 | 4304 | 285.9 |
| 498 | baak12i02 | 4305 | 4306 | 288.2 |
| 498 | kr06H0315 | 4307 | 4308 | 288.2 |
| 498 | BaAL26B09 | 4309 | 4310 | 288.2 |

TABLE 5-11

| Order from the short arm end | Clones | SEQ ID NO: (5' end) | SEQ ID NO: (3' end) | Distance from the short arm end (cM) |
|---|---|---|---|---|
| 498 | kr32C11O5 | 4311 | 4312 | 288.2 |
| 498 | BaH53B15 | 4313 | 4314 | 288.2 |
| 503 | bags13hO4 | 4315 | 4316 | 291.4 |
| 504 | baal15i11 | 4317 | 4318 | 295.7 |
| 505 | bags1m19 | 4319 | 4320 | 307.4 |
| 506 | HVM6 | — | — | 331.7 |

As shown in Table 6-1 to Table 6-7, the chromosomal order in barley 6H chromosome (distance from the short arm end of 6H chromosome) has been specified for 321 clones including the base sequences of SEQ ID NO: n (where n is an odd number) and SEQ ID NO: n+1 from among the base sequences of SEQ ID NO: 4321 through SEQ ID NO: 4962. The chromosomal order in barley 6H chromosome has also been specified for 6 known clones (MWG620, Bmac316, MWG2218, HVM31, Bmac40, and MWG897).

TABLE 6-1

| Order from the short arm end | Clones | SEQ ID NO: (5' end) | SEQ ID NO: (3' end) | Distance from the short arm end (cM) |
|---|---|---|---|---|
| 1 | MWG620 | — | — | 0 |
| 2 | basd14f03 | 4321 | 4322 | 12.1 |
| 2 | BaH30E11 | 4323 | 4324 | 12.1 |
| 4 | BaH59J05 | 4325 | 4326 | 12.6 |
| 5 | BaAL39O22 | 4327 | 4328 | 13.1 |
| 6 | baal16j24 | 4329 | 4330 | 14.2 |
| 7 | BaAL30P12 | 4331 | 4332 | 15.3 |
| 7 | BaGS21H12 | 4333 | 4334 | 15.3 |
| 9 | BaAK15J05 | 4335 | 4336 | 16.4 |
| 9 | BaGS9G15 | 4337 | 4338 | 16.4 |
| 9 | BaAK41J04 | 4339 | 4340 | 16.4 |
| 12 | baak43j24 | 4341 | 4342 | 16.9 |
| 13 | bah26n19 | 4343 | 4344 | 17.4 |
| 13 | Bmac316 | — | — | 17.4 |
| 13 | bags38a05 | 4345 | 4346 | 17.4 |
| 13 | BaH43D06 | 4347 | 4348 | 17.4 |
| 17 | bags9j07 | 4349 | 4350 | 19.6 |
| 17 | baak31p11 | 4351 | 4352 | 19.6 |
| 19 | BaGS17P19 | 4353 | 4354 | 20.7 |
| 20 | baal32j05 | 4355 | 4356 | 23.6 |
| 20 | baal16l16 | 4357 | 4358 | 23.6 |
| 22 | baal6a11 | 4359 | 4360 | 24.4 |
| 22 | bah55p06 | 4361 | 4362 | 24.4 |
| 22 | bags8f03 | 4363 | 4364 | 24.4 |
| 22 | bags3m02 | 4365 | 4366 | 24.4 |
| 22 | BaAL36L08 | 4367 | 4368 | 24.4 |
| 22 | baet19E0309 | 4369 | 4370 | 24.4 |

TABLE 6-1-continued

| Order from the short arm end | Clones | SEQ ID NO: (5' end) | SEQ ID NO: (3' end) | Distance from the short arm end (cM) |
|---|---|---|---|---|
| 22 | BaSD18J06 | 4371 | 4372 | 24.4 |
| 29 | bast48D0307 | 4373 | 4374 | 28.5 |
| 30 | kr55D0707 | 4375 | 4376 | 29.8 |
| 30 | BaAL4B09 | 4377 | 4378 | 29.8 |
| 30 | bags32f21 | 4379 | 4380 | 29.8 |
| 33 | BaGS24F04 | 4381 | 4382 | 31.4 |
| 33 | BaGS10G07 | 4383 | 4384 | 31.4 |
| 35 | BaGS26P07 | 4385 | 4386 | 31.9 |
| 35 | bags12f11 | 4387 | 4388 | 31.9 |
| 35 | MWG2218 | — | — | 31.9 |
| 35 | BaH63O04 | 4389 | 4390 | 31.9 |
| 39 | BaGS26D21 | 4391 | 4392 | 32.3 |
| 40 | bags20o14 | 4393 | 4394 | 33 |
| 41 | baak36d08 | 4395 | 4396 | 34.1 |
| 41 | bast75H0616 | 4397 | 4398 | 34.1 |
| 41 | basd16g17 | 4399 | 4400 | 34.1 |
| 41 | baal4k16 | 4401 | 4402 | 34.1 |
| 41 | bags32b14 | 4403 | 4404 | 34.1 |
| 46 | baal4d01 | 4405 | 4406 | 35.2 |
| 46 | baal7d23 | 4407 | 4408 | 35.2 |
| 46 | BaH62C20 | 4409 | 4410 | 35.2 |
| 49 | BaH21K13 | 4411 | 4412 | 36.3 |
| 49 | BaAK14J02 | 4413 | 4414 | 36.3 |

TABLE 6-2

| Order from the short arm end | Clones | SEQ ID NO: (5' end) | SEQ ID NO: (3' end) | Distance from the short arm end (cM) |
|---|---|---|---|---|
| 51 | bah22c08 | 4415 | 4416 | 38.1 |
| 51 | baak25d07 | 4417 | 4418 | 38.1 |
| 53 | BaAK29M05 | 4419 | 4420 | 40.3 |
| 54 | BaGS31I08 | 4421 | 4422 | 44.7 |
| 54 | bah12n12 | 4423 | 4424 | 44.7 |
| 54 | baal30o06 | 4425 | 4426 | 44.7 |
| 54 | baak13n14 | 4427 | 4428 | 44.7 |
| 54 | bags7a09 | 4429 | 4430 | 44.7 |
| 54 | baak32l04 | 4431 | 4432 | 44.7 |
| 60 | bah31o16 | 4433 | 4434 | 45.8 |
| 60 | BaAL7C19 | 4435 | 4436 | 45.8 |
| 62 | BaAK23F04 | 4437 | 4438 | 46.1 |
| 63 | kr40D0707 | 4439 | 4440 | 46.8 |
| 64 | basd0g08 | 4441 | 4442 | 47.9 |
| 64 | BaAL30H03 | 4443 | 4444 | 47.9 |
| 66 | BaAL21B21 | 4445 | 4446 | 50.9 |
| 66 | BaGS30E05 | 4447 | 4448 | 50.9 |
| 68 | BaAK13G04 | 4449 | 4450 | 52.9 |
| 69 | BaGS27N11 | 4451 | 4452 | 55.8 |
| 70 | BaGS9A04 | 4453 | 4454 | 62.5 |
| 71 | BaAK23M11 | 4455 | 4456 | 68.4 |
| 72 | basd3f22 | 4457 | 4458 | 70.5 |
| 73 | baak41p21 | 4459 | 4460 | 71.6 |
| 73 | BaAK41K07 | 4461 | 4462 | 71.6 |
| 73 | BaH53I11 | 4463 | 4464 | 71.6 |
| 73 | baak26i14 | 4465 | 4466 | 71.6 |
| 73 | BaAL18N03 | 4467 | 4468 | 71.6 |
| 73 | baak40c08 | 4469 | 4470 | 71.6 |
| 73 | bags17l19 | 4471 | 4472 | 71.6 |
| 73 | BaSD25N02 | 4473 | 4474 | 71.6 |
| 81 | BaAK37E04 | 4475 | 4476 | 73.8 |
| 82 | baal33h17 | 4477 | 4478 | 75.4 |
| 83 | bags20d08 | 4479 | 4480 | 77 |
| 84 | BaGS4J01 | 4481 | 4482 | 78.1 |
| 84 | bah48o03 | 4483 | 4484 | 78.1 |
| 84 | bastl31A0901 | 4485 | 4486 | 78.1 |
| 84 | bah20k22 | 4487 | 4488 | 78.1 |
| 84 | BaGS15J17 | 4489 | 4490 | 78.1 |
| 84 | BaAK17I01 | 4491 | 4492 | 78.1 |
| 84 | BaAK30F08 | 4493 | 4494 | 78.1 |
| 84 | bah47a17 | 4495 | 4496 | 78.1 |
| 84 | basd15e10 | 4497 | 4498 | 78.1 |
| 93 | BaH56C11 | 4499 | 4500 | 79.2 |

TABLE 6-2-continued

| Order from the short arm end | Clones | SEQ ID NO: (5' end) | SEQ ID NO: (3' end) | Distance from the short arm end (cM) |
|---|---|---|---|---|
| 93 | BaH18C17 | 4501 | 4502 | 79.2 |
| 93 | BaGS20G24 | 4503 | 4504 | 79.2 |
| 96 | bags19g17 | 4505 | 4506 | 81.5 |
| 97 | BaAK21L02 | 4507 | 4508 | 84.9 |
| 98 | BaH52H21 | 4509 | 4510 | 89.2 |
| 99 | bags9l13 | 4511 | 4512 | 90.2 |
| 99 | BaSD18C12 | 4513 | 4514 | 90.2 |

TABLE 6-3

| Order from the short arm end | Clones | SEQ ID NO: (5' end) | SEQ ID NO: (3' end) | Distance from the short arm end (cM) |
|---|---|---|---|---|
| 101 | baak23k07 | 4515 | 4516 | 91.1 |
| 102 | bags16j16 | 4517 | 4518 | 91.9 |
| 103 | BaSD15O17 | 4519 | 4520 | 93.1 |
| 104 | baak12i20 | 4521 | 4522 | 93.6 |
| 104 | BaAK3M04 | 4523 | 4524 | 93.6 |
| 104 | BaGS4N23 | 4525 | 4526 | 93.6 |
| 104 | baak34k24 | 4527 | 4528 | 93.6 |
| 104 | bah15n23 | 4529 | 4530 | 93.6 |
| 104 | baak45i02 | 4531 | 4532 | 93.6 |
| 104 | basd13i08 | 4533 | 4534 | 93.6 |
| 111 | BaSD17P01 | 4535 | 4536 | 94.7 |
| 111 | HVM31 | — | — | 94.7 |
| 111 | baak13d19 | 4537 | 4538 | 94.7 |
| 111 | baal3h14 | 4539 | 4540 | 94.7 |
| 111 | bags33j18 | 4541 | 4542 | 94.7 |
| 111 | BaH45B01 | 4543 | 4544 | 94.7 |
| 111 | baak21n07 | 4545 | 4546 | 94.7 |
| 111 | BaH36H18 | 4547 | 4548 | 94.7 |
| 119 | BaAL23O14 | 4549 | 4550 | 95.8 |
| 120 | bah53f05 | 4551 | 4552 | 99.1 |
| 121 | baak12d02 | 4553 | 4554 | 100.2 |
| 122 | bags11h12 | 4555 | 4556 | 101.8 |
| 122 | baet01F1212 | 4557 | 4558 | 101.8 |
| 124 | baak17l11 | 4559 | 4560 | 102.3 |
| 124 | basd20e17 | 4561 | 4562 | 102.3 |
| 124 | bah29p24 | 4563 | 4564 | 102.3 |
| 124 | bags30o05 | 4565 | 4566 | 102.3 |
| 124 | kr68D0208 | 4567 | 4568 | 102.3 |
| 124 | bags37l11 | 4569 | 4570 | 102.3 |
| 124 | baal4d14 | 4571 | 4572 | 102.3 |
| 124 | BaH58I23 | 4573 | 4574 | 102.3 |
| 124 | bags39l04 | 4575 | 4576 | 102.3 |
| 124 | baak29i13 | 4577 | 4578 | 102.3 |
| 124 | bags20p18 | 4579 | 4580 | 102.3 |
| 124 | BaAK12J13 | 4581 | 4582 | 102.3 |
| 124 | BaH13K17 | 4583 | 4584 | 102.3 |
| 124 | bah60p09 | 4585 | 4586 | 102.3 |
| 124 | BaH27N11 | 4587 | 4588 | 102.3 |
| 124 | BaGS34D11 | 4589 | 4590 | 102.3 |
| 124 | BaGS39G07 | 4591 | 4592 | 102.3 |
| 124 | bah22o14 | 4593 | 4594 | 102.3 |
| 124 | bah14l20 | 4595 | 4596 | 102.3 |
| 124 | bah42p22 | 4597 | 4598 | 102.3 |
| 124 | BaAK21G03 | 4599 | 4600 | 102.3 |
| 124 | BaAL35D24 | 4601 | 4602 | 102.3 |
| 124 | baak45h14 | 4603 | 4604 | 102.3 |
| 124 | bags28o05 | 4605 | 4606 | 102.3 |
| 124 | BaAK31P07 | 4607 | 4608 | 102.3 |
| 124 | bah36c06 | 4609 | 4610 | 102.3 |
| 124 | BaGS37H24 | 4611 | 4612 | 102.3 |

TABLE 6-4

| Order from the short arm end | Clones | SEQ ID NO: (5' end) | SEQ ID NO: (3' end) | Distance from the short arm end (cM) |
|---|---|---|---|---|
| 124 | bast65B0303 | 4613 | 4614 | 102.3 |
| 124 | BaH51A22 | 4615 | 4616 | 102.3 |
| 153 | BaGS39K23 | 4617 | 4618 | 103.4 |
| 153 | BaSD14O12 | 4619 | 4620 | 103.4 |
| 153 | BaH57F12 | 4621 | 4622 | 103.4 |
| 153 | BaGS32G02 | 4623 | 4624 | 103.4 |
| 153 | BaAL40N06 | 4625 | 4626 | 103.4 |
| 153 | bah11b14 | 4627 | 4628 | 103.4 |
| 153 | bah15j14 | 4629 | 4630 | 103.4 |
| 153 | bast21C1105 | 4631 | 4632 | 103.4 |
| 153 | bags29f03 | 4633 | 4634 | 103.4 |
| 153 | BaAK46B16 | 4635 | 4636 | 103.4 |
| 153 | basd11p22 | 4637 | 4638 | 103.4 |
| 153 | baal16h16 | 4639 | 4640 | 103.4 |
| 165 | BaSD21L07 | 4641 | 4642 | 104.9 |
| 165 | BaH42D07 | 4643 | 4644 | 104.9 |
| 167 | BaGS23K24 | 4645 | 4646 | 106.4 |
| 167 | BaAK24L01 | 4647 | 4648 | 106.4 |
| 167 | BaAL11H22 | 4649 | 4650 | 106.4 |
| 167 | BaAL13O24 | 4651 | 4652 | 106.4 |
| 167 | BaAL6M22 | 4653 | 4654 | 106.4 |
| 167 | BaH56I06 | 4655 | 4656 | 106.4 |
| 167 | BaSD19A18 | 4657 | 4658 | 106.4 |
| 174 | BaSD20P03 | 4659 | 4660 | 108.2 |
| 174 | BaH19B13 | 4661 | 4662 | 108.2 |
| 176 | kr59H0416 | 4663 | 4664 | 110.7 |
| 177 | BaGS14A02 | 4665 | 4666 | 112.2 |
| 177 | BaH34P05 | 4667 | 4668 | 112.2 |
| 177 | bah61o16 | 4669 | 4670 | 112.2 |
| 177 | BaH24N07 | 4671 | 4672 | 112.2 |
| 177 | BaAL20M22 | 4673 | 4674 | 112.2 |
| 177 | BaAL11H20 | 4675 | 4676 | 112.2 |
| 177 | bah54b04 | 4677 | 4678 | 112.2 |
| 177 | BaAK14H23 | 4679 | 4680 | 112.2 |
| 177 | BaSD20M23 | 4681 | 4682 | 112.2 |
| 177 | BaAL15B12 | 4683 | 4684 | 112.2 |
| 177 | baal15d09 | 4685 | 4686 | 112.2 |
| 177 | baak39n20 | 4687 | 4688 | 112.2 |
| 177 | BaH43N16 | 4689 | 4690 | 112.2 |
| 177 | bags39h18 | 4691 | 4692 | 112.2 |
| 177 | BaAL3L23 | 4693 | 4694 | 112.2 |
| 192 | basd22c03 | 4695 | 4696 | 115.6 |
| 193 | bast55G0913 | 4697 | 4698 | 117.9 |
| 193 | kr47F0511 | 4699 | 4700 | 117.9 |
| 195 | bah15l24 | 4701 | 4702 | 118.4 |
| 196 | bast77A0402 | 4703 | 4704 | 118.9 |
| 196 | BaH58F04 | 4705 | 4706 | 118.9 |
| 196 | BaAK30L09 | 4707 | 4708 | 118.9 |
| 196 | kr39G1113 | 4709 | 4710 | 118.9 |
| 196 | baak1c16 | 4711 | 4712 | 118.9 |

TABLE 6-5

| Order from the short arm end | Clones | SEQ ID NO: (5' end) | SEQ ID NO: (3' end) | Distance from the short arm end (cM) |
|---|---|---|---|---|
| 196 | basd20e05 | 4713 | 4714 | 118.9 |
| 196 | BaAK12F18 | 4715 | 4716 | 118.9 |
| 196 | BaH50L11 | 4717 | 4718 | 118.9 |
| 196 | bast50G0814 | 4719 | 4720 | 118.9 |
| 196 | bast70D0107 | 4721 | 4722 | 118.9 |
| 196 | baal17d05 | 4723 | 4724 | 118.9 |
| 196 | baak46g03 | 4725 | 4726 | 118.9 |
| 196 | bah63m17 | 4727 | 4728 | 118.9 |
| 209 | BaH15L15 | 4729 | 4730 | 120 |
| 209 | BaGS19N01 | 4731 | 4732 | 120 |
| 209 | BaAK32P07 | 4733 | 4734 | 120 |
| 212 | bags14l13 | 4735 | 4736 | 121.1 |
| 213 | bags37o24 | 4737 | 4738 | 121.7 |
| 214 | baal5e24 | 4739 | 4740 | 122.8 |
| 215 | BaH46B06 | 4741 | 4742 | 124.5 |
| 215 | bags11a16 | 4743 | 4744 | 124.5 |
| 215 | baal27m03 | 4745 | 4746 | 124.5 |
| 215 | BaAK1C18 | 4747 | 4748 | 124.5 |
| 215 | BaAK38H16 | 4749 | 4750 | 124.5 |
| 215 | BaGS37K02 | 4751 | 4752 | 124.5 |
| 221 | bah28a10 | 4753 | 4754 | 125.6 |
| 221 | bah27c03 | 4755 | 4756 | 125.6 |
| 221 | BaH52B11 | 4757 | 4758 | 125.6 |
| 224 | bah27f05 | 4759 | 4760 | 127.8 |
| 224 | bags37g15 | 4761 | 4762 | 127.8 |
| 224 | bah59c10 | 4763 | 4764 | 127.8 |
| 224 | bags38j06 | 4765 | 4766 | 127.8 |
| 224 | basd14e01 | 4767 | 4768 | 127.8 |
| 224 | BaGS24L06 | 4769 | 4770 | 127.8 |
| 224 | bags17b02 | 4771 | 4772 | 127.8 |
| 224 | BaH54L03 | 4773 | 4774 | 127.8 |
| 224 | BaAK21J17 | 4775 | 4776 | 127.8 |
| 233 | BaGS23G08 | 4777 | 4778 | 128.9 |
| 233 | basd18e06 | 4779 | 4780 | 128.9 |
| 233 | baak19o02 | 4781 | 4782 | 128.9 |
| 233 | basd2o16 | 4783 | 4784 | 128.9 |
| 237 | baak16e08 | 4785 | 4786 | 130 |
| 237 | bags18h01 | 4787 | 4788 | 130 |
| 239 | BaGS4L20 | 4789 | 4790 | 133.4 |
| 240 | BaAL2M19 | 4791 | 4792 | 135.8 |
| 241 | BaH36F15 | 4793 | 4794 | 139.1 |
| 242 | bah58l07 | 4795 | 4796 | 140.2 |
| 243 | baet29C0406 | 4797 | 4798 | 141.3 |
| 243 | BaAK35B04 | 4799 | 4800 | 141.3 |
| 243 | bags34k13 | 4801 | 4802 | 141.3 |
| 246 | baal29i08 | 4803 | 4804 | 142.1 |
| 246 | baak11p10 | 4805 | 4806 | 142.1 |
| 248 | BaH30J08 | 4807 | 4808 | 145.1 |
| 249 | bags4e12 | 4809 | 4810 | 147.3 |
| 250 | bastl05C1206 | 4811 | 4812 | 148.4 |

TABLE 6-6

| Order from the short arm end | Clones | SEQ ID NO: (5' end) | SEQ ID NO: (3' end) | Distance from the short arm end (cM) |
|---|---|---|---|---|
| 250 | bast22G0313 | 4813 | 4814 | 148.4 |
| 252 | basd24b08 | 4815 | 4816 | 149.5 |
| 252 | bastl16C0206 | 4817 | 4818 | 149.5 |
| 252 | bags33n21 | 4819 | 4820 | 149.5 |
| 255 | baak33c11 | 4821 | 4822 | 151.7 |
| 255 | baal13o10 | 4823 | 4824 | 151.7 |
| 257 | BaH36P06 | 4825 | 4826 | 154.9 |
| 258 | basd12l01 | 4827 | 4828 | 157.1 |
| 259 | baet25H0115 | 4829 | 4830 | 158.2 |
| 259 | bags15d14 | 4831 | 4832 | 158.2 |
| 259 | BaGS37E09 | 4833 | 4834 | 158.2 |
| 259 | BaAK29I15 | 4835 | 4836 | 158.2 |
| 259 | BaAK18I01 | 4837 | 4838 | 158.2 |
| 264 | bast62B0404 | 4839 | 4840 | 160.4 |
| 265 | bah25l03 | 4841 | 4842 | 163.9 |
| 266 | BaGS19I11 | 4843 | 4844 | 167.2 |
| 266 | baal1n11 | 4845 | 4846 | 167.2 |
| 268 | baak16l07 | 4847 | 4848 | 167.6 |
| 268 | BaGS18P04 | 4849 | 4850 | 167.6 |
| 270 | bags19e06 | 4851 | 4852 | 168.9 |
| 270 | baak35n07 | 4853 | 4854 | 168.9 |
| 272 | BaAK29K23 | 4855 | 4856 | 173 |
| 272 | baal13c18 | 4857 | 4858 | 173 |
| 272 | bags7d17 | 4859 | 4860 | 173 |
| 275 | bags20j08 | 4861 | 4862 | 174.1 |
| 275 | baal9c20 | 4863 | 4864 | 174.1 |
| 277 | bags20l05 | 4865 | 4866 | 175.2 |
| 278 | bah63k05 | 4867 | 4868 | 176.3 |
| 279 | BaAK14C17 | 4869 | 4870 | 178.5 |
| 280 | Bmac40 | — | — | 179.6 |
| 280 | baal15i23 | 4871 | 4872 | 179.6 |
| 282 | BaAK1N06 | 4873 | 4874 | 181.7 |

TABLE 6-6-continued

| Order from the short arm end | Clones | SEQ ID NO: (5' end) | SEQ ID NO: (3' end) | Distance from the short arm end (cM) |
|---|---|---|---|---|
| 282 | bags38d10 | 4875 | 4876 | 181.7 |
| 282 | BaAK19J15 | 4877 | 4878 | 181.7 |
| 285 | BaH50L14 | 4879 | 4880 | 182.8 |
| 285 | BaGS37E11 | 4881 | 4882 | 182.8 |
| 287 | BaSD27E20 | 4883 | 4884 | 183 |
| 288 | basd17f18 | 4885 | 4886 | 184.1 |
| 289 | baal32m04 | 4887 | 4888 | 188.5 |
| 290 | BaSD12L12 | 4889 | 4890 | 191.7 |
| 291 | BaGS37D24 | 4891 | 4892 | 194 |
| 291 | BaGS9K15 | 4893 | 4894 | 194 |
| 293 | BaGS33L03 | 4895 | 4896 | 196 |
| 293 | BaAK24G10 | 4897 | 4898 | 196 |
| 295 | kr58F0511 | 4899 | 4900 | 196.5 |
| 296 | BaH50F16 | 4901 | 4902 | 197 |
| 296 | basd17d11 | 4903 | 4904 | 197 |
| 298 | BaH37P24 | 4905 | 4906 | 198.1 |
| 298 | bah47l21 | 4907 | 4908 | 198.1 |
| 298 | baet45C1105 | 4909 | 4910 | 198.1 |

TABLE 6-7

| Order from the short arm end | Clones | SEQ ID NO: (5' end) | SEQ ID NO: (3' end) | Distance from the short arm end (cM) |
|---|---|---|---|---|
| 301 | baak39o18 | 4911 | 4912 | 199.2 |
| 301 | bags20p12 | 4913 | 4914 | 199.2 |
| 301 | bags38f23 | 4915 | 4916 | 199.2 |
| 304 | baak14b08 | 4917 | 4918 | 201.4 |
| 304 | bah54n10 | 4919 | 4920 | 201.4 |
| 306 | bags3k09 | 4921 | 4922 | 202.5 |
| 307 | bags34p08 | 4923 | 4924 | 203.6 |
| 308 | baal1e06 | 4925 | 4926 | 204.7 |
| 308 | baak34p14 | 4927 | 4928 | 204.7 |
| 308 | baak14k12 | 4929 | 4930 | 204.7 |
| 308 | BaSD13G17 | 4931 | 4932 | 204.7 |
| 308 | MWG897 | — | — | 204.7 |
| 308 | bags27h05 | 4933 | 4934 | 204.7 |
| 308 | basd15m11 | 4935 | 4936 | 204.7 |
| 308 | BaH28G09 | 4937 | 4938 | 204.7 |
| 308 | bags21b06 | 4939 | 4940 | 204.7 |
| 308 | basd12g17 | 4941 | 4942 | 204.7 |
| 318 | BaH18F07 | 4943 | 4944 | 205 |
| 319 | BaH44A23 | 4945 | 4946 | 205.3 |
| 320 | bags3d07 | 4947 | 4948 | 205.6 |
| 321 | BaAL6A21 | 4949 | 4950 | 205.9 |
| 321 | BaAK24E07 | 4951 | 4952 | 205.9 |
| 321 | BaAL29L09 | 4953 | 4954 | 205.9 |
| 321 | kr66D1107 | 4955 | 4956 | 205.9 |
| 321 | bastl47C0606 | 4957 | 4958 | 205.9 |
| 321 | BaH50M03 | 4959 | 4960 | 205.9 |
| 327 | basd27k17 | 4961 | 4962 | 207.3 |

As shown in Table 7-1 to Table 7-9, the chromosomal order in barley 7H chromosome (distance from the short arm end of 7H chromosome) has been specified for 409 clones including the base sequences of SEQ ID NO: n (where n is an odd number) and SEQ ID NO: n+1 from among the base sequences of SEQ ID NO: 4963 through SEQ ID NO: 5780. The chromosomal order in barley 7H chromosome has also been specified for 16 known clones (HVM4, HVCMA, cMWG704, MWG511, Bmag359, MWG2031, KT3, KT9, MWG975, EBmac764, Bmac0064, Bmag120, Bmac156, HVM49, MWG2062, and HVM5).

TABLE 7-1

| Order from the short arm end | Clones | SEQ ID NO: (5' end) | SEQ ID NO: (3' end) | Distance from the short arm end (cM) |
|---|---|---|---|---|
| 1 | basd2p19 | 4963 | 4964 | 0 |
| 2 | BaAK38B18 | 4965 | 4966 | 4.7 |
| 3 | bah42i06 | 4967 | 4968 | 6.6 |
| 3 | bags6f02 | 4969 | 4970 | 6.6 |
| 5 | BaAK39J07 | 4971 | 4972 | 7.2 |
| 5 | BaAK1L23 | 4973 | 4974 | 7.2 |
| 5 | baak17e10 | 4975 | 4976 | 7.2 |
| 5 | BaH50H08 | 4977 | 4978 | 7.2 |
| 5 | baal17e10 | 4979 | 4980 | 7.2 |
| 5 | BaSD17C05 | 4981 | 4982 | 7.2 |
| 11 | BaGS14P02 | 4983 | 4984 | 8.3 |
| 11 | bastl42H0115 | 4985 | 4986 | 8.3 |
| 11 | BaAK19C08 | 4987 | 4988 | 8.3 |
| 11 | bastl40H1115 | 4989 | 4990 | 8.3 |
| 15 | bags12l21 | 4991 | 4992 | 9.4 |
| 15 | baak12j24 | 4993 | 4994 | 9.4 |
| 15 | bags14d22 | 4995 | 4996 | 9.4 |
| 15 | BaAK21P12 | 4997 | 4998 | 9.4 |
| 15 | baal6b02 | 4999 | 5000 | 9.4 |
| 15 | baak29f13 | 5001 | 5002 | 9.4 |
| 21 | bast79C0406 | 5003 | 5004 | 11.3 |
| 22 | BaH45M08 | 5005 | 5006 | 12.4 |
| 23 | kr28A0301 | 5007 | 5008 | 16.4 |
| 23 | bags19e04 | 5009 | 5010 | 16.4 |
| 25 | BaH28L07 | 5011 | 5012 | 18.6 |
| 26 | baak21m18 | 5013 | 5014 | 20.9 |
| 26 | baak21l22 | 5015 | 5016 | 20.9 |
| 28 | basd15h01 | 5017 | 5018 | 25.2 |
| 28 | BaH19O11 | 5019 | 5020 | 25.2 |
| 28 | BaH59A20 | 5021 | 5022 | 25.2 |
| 31 | bags39l05 | 5023 | 5024 | 27.3 |
| 31 | BaAK31N06 | 5025 | 5026 | 27.3 |
| 33 | BaH58P03 | 5027 | 5028 | 28.4 |
| 34 | bags29c18 | 5029 | 5030 | 29.5 |
| 35 | BaAL4O04 | 5031 | 5032 | 30.6 |
| 35 | bags37n23 | 5033 | 5034 | 30.6 |
| 35 | BaAL39N03 | 5035 | 5036 | 30.6 |
| 38 | BaAK14C23 | 5037 | 5038 | 31.7 |
| 38 | kr61A1101 | 5039 | 5040 | 31.7 |
| 38 | BaH42J17 | 5041 | 5042 | 31.7 |
| 41 | BaH58H08 | 5043 | 5044 | 39.2 |
| 42 | bast78A0202 | 5045 | 5046 | 40.4 |
| 43 | BaGS21E20 | 5047 | 5048 | 42.5 |
| 43 | bags22j18 | 5049 | 5050 | 42.5 |
| 45 | BaGS33H15 | 5051 | 5052 | 45.7 |
| 45 | HVM4 | — | — | 45.7 |
| 47 | BaSD18O16 | 5053 | 5054 | 47.9 |
| 47 | baak22j11 | 5055 | 5056 | 47.9 |
| 49 | BaAK20K04 | 5057 | 5058 | 50.4 |
| 50 | bags29l11 | 5059 | 5060 | 55.2 |

TABLE 7-2

| Order from the short arm end | Clones | SEQ ID NO: (5' end) | SEQ ID NO: (3' end) | Distance from the short arm end (cM) |
|---|---|---|---|---|
| 51 | BaAK17G18 | 5061 | 5062 | 60.3 |
| 52 | baak14o13 | 5063 | 5064 | 61.7 |
| 53 | baal8d17 | 5065 | 5066 | 63.2 |
| 54 | BaAK37P20 | 5067 | 5068 | 64.2 |
| 55 | bags28k04 | 5069 | 5070 | 71.5 |
| 56 | bah34b22 | 5071 | 5072 | 73.8 |
| 57 | BaGS37M03 | 5073 | 5074 | 78.3 |
| 58 | BaGS18C14 | 5075 | 5076 | 79.5 |
| 59 | bast23G0214 | 5077 | 5078 | 80.6 |
| 59 | bah47p02 | 5079 | 5080 | 80.6 |
| 61 | baak42a24 | 5081 | 5082 | 81.7 |
| 61 | baak16f06 | 5083 | 5084 | 81.7 |
| 61 | bah11m12 | 5085 | 5086 | 81.7 |
| 64 | kr66H0216 | 5087 | 5088 | 84.9 |
| 64 | BaGS23D15 | 5089 | 5090 | 84.9 |
| 64 | baal22c17 | 5091 | 5092 | 84.9 |

TABLE 7-2-continued

| Order from the short arm end | Clones | SEQ ID NO: (5' end) | SEQ ID NO: (3' end) | Distance from the short arm end (cM) |
|---|---|---|---|---|
| 67 | baak33d06 | 5093 | 5094 | 86 |
| 67 | bags34l17 | 5095 | 5096 | 86 |
| 67 | BaGS25G03 | 5097 | 5098 | 86 |
| 67 | bah14j16 | 5099 | 5100 | 86 |
| 67 | bah34a23 | 5101 | 5102 | 86 |
| 67 | BaAK21B17 | 5103 | 5104 | 86 |
| 67 | bast42C0406 | 5105 | 5106 | 86 |
| 74 | baak21m13 | 5107 | 5108 | 87.3 |
| 75 | baet45H0115 | 5109 | 5110 | 87.7 |
| 76 | BaH38E01 | 5111 | 5112 | 88.1 |
| 76 | bast03G0313 | 5113 | 5114 | 88.1 |
| 78 | baak38p18 | 5115 | 5116 | 89.5 |
| 79 | basd18g06 | 5117 | 5118 | 90.6 |
| 80 | baak40i22 | 5119 | 5120 | 92 |
| 80 | baal2n12 | 5121 | 5122 | 92 |
| 82 | BaSD3C24 | 5123 | 5124 | 94.1 |
| 83 | BaAK46M07 | 5125 | 5126 | 96.3 |
| 84 | BaGS17N04 | 5127 | 5128 | 99.6 |
| 85 | bags12d09 | 5129 | 5130 | 100.7 |
| 85 | basd20c08 | 5131 | 5132 | 100.7 |
| 87 | bags17i04 | 5133 | 5134 | 101.7 |
| 87 | baak15p03 | 5135 | 5136 | 101.7 |
| 89 | baak24b20 | 5137 | 5138 | 104.9 |
| 89 | baal18g11 | 5139 | 5140 | 104.9 |
| 89 | baal40b06 | 5141 | 5142 | 104.9 |
| 89 | baak40g02 | 5143 | 5144 | 104.9 |
| 93 | baal1m11 | 5145 | 5146 | 106.1 |
| 94 | BaH26B16 | 5147 | 5148 | 107.9 |
| 94 | baal5n08 | 5149 | 5150 | 107.9 |
| 96 | BaSD27F05 | 5151 | 5152 | 109.5 |
| 96 | bags9c08 | 5153 | 5154 | 109.5 |
| 96 | baak3c01 | 5155 | 5156 | 109.5 |
| 99 | basd1j22 | 5157 | 5158 | 110.6 |
| 99 | BaH23N03 | 5159 | 5160 | 110.6 |

TABLE 7-3

| Order from the short arm end | Clones | SEQ ID NO: (5' end) | SEQ ID NO: (3' end) | Distance from the short arm end (cM) |
|---|---|---|---|---|
| 99 | bast46D0808 | 5161 | 5162 | 110.6 |
| 99 | bast22A0802 | 5163 | 5164 | 110.6 |
| 99 | bast34D0808 | 5165 | 5166 | 110.6 |
| 104 | bast48E0509 | 5167 | 5168 | 114.9 |
| 104 | bast26F1012 | 5169 | 5170 | 114.9 |
| 106 | baal30e07 | 5171 | 5172 | 115.5 |
| 107 | bags23n06 | 5173 | 5174 | 116.1 |
| 108 | BaGS18I05 | 5175 | 5176 | 116.6 |
| 109 | BaH52L11 | 5177 | 5178 | 116.8 |
| 110 | baal18b16 | 5179 | 5180 | 117 |
| 111 | bags1a17 | 5181 | 5182 | 118.1 |
| 111 | HVCMA | — | — | 118.1 |
| 111 | bags8o06 | 5183 | 5184 | 118.1 |
| 111 | baak46e14 | 5185 | 5186 | 118.1 |
| 115 | BaGS38N08 | 5187 | 5188 | 118.6 |
| 115 | BaH49P17 | 5189 | 5190 | 118.6 |
| 117 | bah60l22 | 5191 | 5192 | 120.2 |
| 117 | bags21m22 | 5193 | 5194 | 120.2 |
| 117 | BaH54E07 | 5195 | 5196 | 120.2 |
| 120 | BaAK39A20 | 5197 | 5198 | 121.3 |
| 121 | bags21d11 | 5199 | 5200 | 123.5 |
| 122 | kr39H0816 | 5201 | 5202 | 125.6 |
| 123 | baet32B1103 | 5203 | 5204 | 131.1 |
| 124 | BaAK31O16 | 5205 | 5206 | 132.1 |
| 124 | bags39l20 | 5207 | 5208 | 132.1 |
| 124 | BaGS15L12 | 5209 | 5210 | 132.1 |
| 127 | kr67D0208 | 5211 | 5212 | 134.3 |
| 128 | BaAK1H16 | 5213 | 5214 | 135.4 |
| 128 | BaH26F10 | 5215 | 5216 | 135.4 |
| 130 | bags14n02 | 5217 | 5218 | 135.9 |
| 131 | bah36f01 | 5219 | 5220 | 136.4 |
| 132 | bast79F0711 | 5221 | 5222 | 137.5 |

TABLE 7-3-continued

| Order from the short arm end | Clones | SEQ ID NO: (5' end) | SEQ ID NO: (3' end) | Distance from the short arm end (cM) |
|---|---|---|---|---|
| 132 | BaGS29G21 | 5223 | 5224 | 137.5 |
| 134 | bast79D1107 | 5225 | 5226 | 139.6 |
| 134 | BaGS26O20 | 5227 | 5228 | 139.6 |
| 134 | bags11h08 | 5229 | 5230 | 139.6 |
| 134 | bags22h11 | 5231 | 5232 | 139.6 |
| 134 | baet19D0608 | 5233 | 5234 | 139.6 |
| 139 | bags23a14 | 5235 | 5236 | 140.7 |
| 139 | cMWG704 | — | — | 140.7 |
| 139 | bah62d14 | 5237 | 5238 | 140.7 |
| 142 | BaGS37C09 | 5239 | 5240 | 142.6 |
| 142 | bags20a01 | 5241 | 5242 | 142.6 |
| 144 | bah53m11 | 5243 | 5244 | 144.5 |
| 144 | BaGS26L01 | 5245 | 5246 | 144.5 |
| 144 | bags21p23 | 5247 | 5248 | 144.5 |
| 144 | BaAK24B01 | 5249 | 5250 | 144.5 |
| 144 | BaAK13L03 | 5251 | 5252 | 144.5 |
| 149 | MWG511 | — | — | 145.6 |
| 149 | bastl56C0105 | 5253 | 5254 | 145.6 |

TABLE 7-4

| Order from the short arm end | Clones | SEQ ID NO: (5' end) | SEQ ID NO: (3' end) | Distance from the short arm end (cM) |
|---|---|---|---|---|
| 149 | basd20j22 | 5255 | 5256 | 145.6 |
| 149 | bags28d11 | 5257 | 5258 | 145.6 |
| 153 | BaGS4I11 | 5259 | 5260 | 146.7 |
| 153 | BaH52G15 | 5261 | 5262 | 146.7 |
| 153 | baak11d12 | 5263 | 5264 | 146.7 |
| 153 | BaH42A07 | 5265 | 5266 | 146.7 |
| 157 | BaGS38F01 | 5267 | 5268 | 147.2 |
| 158 | BaAK32I05 | 5269 | 5270 | 147.7 |
| 158 | bah60f18 | 5271 | 5272 | 147.7 |
| 160 | baal2n10 | 5273 | 5274 | 148.8 |
| 161 | BaAK14F01 | 5275 | 5276 | 149.9 |
| 161 | bah57o01 | 5277 | 5278 | 149.9 |
| 161 | basd12f05 | 5279 | 5280 | 149.9 |
| 161 | bah58e21 | 5281 | 5282 | 149.9 |
| 161 | bags1d07 | 5283 | 5284 | 149.9 |
| 161 | BaH23J15 | 5285 | 5286 | 149.9 |
| 161 | baak1p09 | 5287 | 5288 | 149.9 |
| 168 | BaAK32C23 | 5289 | 5290 | 151 |
| 168 | baal9e06 | 5291 | 5292 | 151 |
| 168 | baal18g23 | 5293 | 5294 | 151 |
| 168 | bastl47E0309 | 5295 | 5296 | 151 |
| 168 | baak30o08 | 5297 | 5298 | 151 |
| 168 | baet44C0606 | 5299 | 5300 | 151 |
| 174 | bags39g18 | 5301 | 5302 | 152.1 |
| 174 | BaH50P14 | 5303 | 5304 | 152.1 |
| 176 | bags38m06 | 5305 | 5306 | 152.6 |
| 177 | baal33e12 | 5307 | 5308 | 153.2 |
| 177 | bags3i04 | 5309 | 5310 | 153.2 |
| 179 | BaAL1A11 | 5311 | 5312 | 153.7 |
| 179 | BaSD2M23 | 5313 | 5314 | 153.7 |
| 181 | Bmag359 | — | — | 155.3 |
| 181 | BaAK23L23 | 5315 | 5316 | 155.3 |
| 181 | bags7a23 | 5317 | 5318 | 155.3 |
| 181 | bah56l04 | 5319 | 5320 | 155.3 |
| 185 | basd12k23 | 5321 | 5322 | 156.4 |
| 185 | bast22C0105 | 5323 | 5324 | 156.4 |
| 185 | BaGS38H20 | 5325 | 5326 | 156.4 |
| 185 | bah61p21 | 5327 | 5328 | 156.4 |
| 185 | basd11h13 | 5329 | 5330 | 156.4 |
| 185 | BaAL41J12 | 5331 | 5332 | 156.4 |
| 185 | baal0f04 | 5333 | 5334 | 156.4 |
| 185 | kr18E0810 | 5335 | 5336 | 156.4 |
| 185 | BaH15J07 | 5337 | 5338 | 156.4 |
| 185 | BaAL6G08 | 5339 | 5340 | 156.4 |
| 185 | BaGS24F02 | 5341 | 5342 | 156.4 |
| 185 | baal19m12 | 5343 | 5344 | 156.4 |
| 185 | bah34h16 | 5345 | 5346 | 156.4 |
| 185 | baak2e06 | 5347 | 5348 | 156.4 |

TABLE 7-4-continued

| Order from the short arm end | Clones | SEQ ID NO: (5' end) | SEQ ID NO: (3' end) | Distance from the short arm end (cM) |
|---|---|---|---|---|
| 185 | bast10C0406 | 5349 | 5350 | 156.4 |
| 185 | baak12l16 | 5351 | 5352 | 156.4 |

TABLE 7-5

| Order from the short arm end | Clones | SEQ ID NO: (5' end) | SEQ ID NO: (3' end) | Distance from the short arm end (cM) |
|---|---|---|---|---|
| 185 | baak29d01 | 5353 | 5354 | 156.4 |
| 185 | BaAK19N06 | 5355 | 5356 | 156.4 |
| 185 | BaAK4I02 | 5357 | 5358 | 156.4 |
| 185 | BaH49K10 | 5359 | 5360 | 156.4 |
| 185 | baal2o03 | 5361 | 5362 | 156.4 |
| 185 | baak28g14 | 5363 | 5364 | 156.4 |
| 185 | bah62n05 | 5365 | 5366 | 156.4 |
| 185 | bags16e11 | 5367 | 5368 | 156.4 |
| 185 | bags23g13 | 5369 | 5370 | 156.4 |
| 210 | BaSD23C05 | 5371 | 5372 | 157 |
| 211 | BaH19F17 | 5373 | 5374 | 157.4 |
| 211 | BaH15J02 | 5375 | 5376 | 157.4 |
| 211 | baak20d11 | 5377 | 5378 | 157.4 |
| 211 | BaAL6D19 | 5379 | 5380 | 157.4 |
| 211 | baak43e16 | 5381 | 5382 | 157.4 |
| 216 | baak40b02 | 5383 | 5384 | 158.5 |
| 217 | bah62m03 | 5385 | 5386 | 159.6 |
| 218 | BaGS26G17 | 5387 | 5388 | 161.8 |
| 219 | baal6j16 | 5389 | 5390 | 162.9 |
| 219 | bags29b09 | 5391 | 5392 | 162.9 |
| 219 | baal20e03 | 5393 | 5394 | 162.9 |
| 219 | BaGS9L23 | 5395 | 5396 | 162.9 |
| 219 | bah32e22 | 5397 | 5398 | 162.9 |
| 219 | BaAK17O14 | 5399 | 5400 | 162.9 |
| 225 | bah56g23 | 5401 | 5402 | 164 |
| 225 | basd22f14 | 5403 | 5404 | 164 |
| 227 | BaH42O04 | 5405 | 5406 | 164.7 |
| 227 | bast74F0111 | 5407 | 5408 | 164.7 |
| 229 | BaSD21F13 | 5409 | 5410 | 167.3 |
| 230 | BaAK26G13 | 5411 | 5412 | 167.4 |
| 231 | BaAK44D07 | 5413 | 5414 | 168.2 |
| 231 | bast61C0206 | 5415 | 5416 | 168.2 |
| 233 | BaAL29L08 | 5417 | 5418 | 169.4 |
| 233 | BaH34B20 | 5419 | 5420 | 169.4 |
| 233 | baak21a04 | 5421 | 5422 | 169.4 |
| 233 | BaGS37F18 | 5423 | 5424 | 169.4 |
| 233 | baal12h12 | 5425 | 5426 | 169.4 |
| 233 | BaAK42B16 | 5427 | 5428 | 169.4 |
| 233 | BaAK26F12 | 5429 | 5430 | 169.4 |
| 233 | BaH27B21 | 5431 | 5432 | 169.4 |
| 233 | BaGS12B05 | 5433 | 5434 | 169.4 |
| 233 | baal12h24 | 5435 | 5436 | 169.4 |
| 243 | baal35j16 | 5437 | 5438 | 173.5 |
| 243 | BaGS37C07 | 5439 | 5440 | 173.5 |
| 243 | BaAK45D23 | 5441 | 5442 | 173.5 |
| 243 | BaH42G09 | 5443 | 5444 | 173.5 |
| 243 | BaAL40P01 | 5445 | 5446 | 173.5 |
| 243 | kr61A0901 | 5447 | 5448 | 173.5 |
| 249 | baal4d05 | 5449 | 5450 | 174.6 |
| 249 | basd20l03 | 5451 | 5452 | 174.6 |

TABLE 7-6

| Order from the short arm end | Clones | SEQ ID NO: (5' end) | SEQ ID NO: (3' end) | Distance from the short arm end (cM) |
|---|---|---|---|---|
| 249 | baal31b03 | 5453 | 5454 | 174.6 |
| 252 | bags27k21 | 5455 | 5456 | 176.8 |
| 252 | bah55n15 | 5457 | 5458 | 176.8 |
| 254 | BaH44B17 | 5459 | 5460 | 177.9 |
| 254 | BaSD2K11 | 5461 | 5462 | 177.9 |
| 256 | BaAK20B23 | 5463 | 5464 | 180.1 |
| 256 | BaGS23E20 | 5465 | 5466 | 180.1 |
| 256 | bags33i10 | 5467 | 5468 | 180.1 |
| 256 | bags35k06 | 5469 | 5470 | 180.1 |
| 260 | bags22c18 | 5471 | 5472 | 181.2 |
| 260 | MWG2031 | — | — | 181.2 |
| 260 | BaGS22M17 | 5473 | 5474 | 181.2 |
| 263 | baak21j24 | 5475 | 5476 | 184.4 |
| 263 | BaH29D20 | 5477 | 5478 | 184.4 |
| 263 | bah44f20 | 5479 | 5480 | 184.4 |
| 263 | BaAL16O08 | 5481 | 5482 | 184.4 |
| 263 | BaAL27L17 | 5483 | 5484 | 184.4 |
| 263 | sKT3 | — | — | 184.4 |
| 263 | sKT9 | — | — | 184.4 |
| 263 | baet31B1103 | 5485 | 5486 | 184.4 |
| 263 | MWG975 | — | — | 184.4 |
| 272 | BaAL4A11 | 5487 | 5488 | 185.9 |
| 272 | BaGS22I18 | 5489 | 5490 | 185.9 |
| 274 | BaGS24K08 | 5491 | 5492 | 186.4 |
| 274 | bah16c17 | 5493 | 5494 | 186.4 |
| 274 | bah42m04 | 5495 | 5496 | 186.4 |
| 274 | bags28l21 | 5497 | 5498 | 186.4 |
| 274 | basd12f23 | 5499 | 5500 | 186.4 |
| 274 | bah31m22 | 5501 | 5502 | 186.4 |
| 274 | BaAL30C17 | 5503 | 5504 | 186.4 |
| 274 | BaAK40P18 | 5505 | 5506 | 186.4 |
| 274 | baak37n01 | 5507 | 5508 | 186.4 |
| 274 | BaGS24O11 | 5509 | 5510 | 186.4 |
| 274 | BaH27K19 | 5511 | 5512 | 186.4 |
| 274 | BaGS15J07 | 5513 | 5514 | 186.4 |
| 286 | bah19a07 | 5515 | 5516 | 188.9 |
| 287 | BaH50I23 | 5517 | 5518 | 194 |
| 288 | BaH56D06 | 5519 | 5520 | 195 |
| 288 | BaAK39M05 | 5521 | 5522 | 195 |
| 288 | bah11m16 | 5523 | 5524 | 195 |
| 291 | bah49d03 | 5525 | 5526 | 196.1 |
| 291 | bah62l23 | 5527 | 5528 | 196.1 |
| 291 | BaAK38J13 | 5529 | 5530 | 196.1 |
| 291 | BaH37N04 | 5531 | 5532 | 196.1 |
| 291 | basd27c06 | 5533 | 5534 | 196.1 |
| 291 | bah39g10 | 5535 | 5536 | 196.1 |
| 291 | BaSD18P05 | 5537 | 5538 | 196.1 |
| 298 | BaGS20A13 | 5539 | 5540 | 196.6 |
| 299 | bah44n05 | 5541 | 5542 | 197.2 |
| 300 | EBmac764 | — | — | 198.2 |

TABLE 7-7

| Order from the short arm end | Clones | SEQ ID NO: (5' end) | SEQ ID NO: (3' end) | Distance from the short arm end (cM) |
|---|---|---|---|---|
| 301 | BaH27L15 | 5543 | 5544 | 199.3 |
| 301 | BaAK21I02 | 5545 | 5546 | 199.3 |
| 303 | Bmac0064 | — | — | 200.3 |
| 304 | BaH59F07 | 5547 | 5548 | 210.4 |
| 304 | bags9l05 | 5549 | 5550 | 210.4 |
| 306 | BaGS13H12 | 5551 | 5552 | 211.7 |
| 307 | BaAL19B06 | 5553 | 5554 | 212.9 |
| 308 | BaSD15P23 | 5555 | 5556 | 215.1 |
| 309 | bah53j21 | 5557 | 5558 | 217.2 |
| 309 | bah21f16 | 5559 | 5560 | 217.2 |
| 309 | baet39E0309 | 5561 | 5562 | 217.2 |
| 312 | bags5l04 | 5563 | 5564 | 217.7 |
| 313 | bags7g10 | 5565 | 5566 | 218.3 |
| 314 | BaGS9D22 | 5567 | 5568 | 219.5 |
| 315 | kr27H1216 | 5569 | 5570 | 221.2 |
| 315 | BaAK25O11 | 5571 | 5572 | 221.2 |
| 317 | bah18j14 | 5573 | 5574 | 221.7 |
| 317 | bags37k14 | 5575 | 5576 | 221.7 |
| 317 | baak26n19 | 5577 | 5578 | 221.7 |
| 317 | bah42k03 | 5579 | 5580 | 221.7 |
| 317 | BaH36N15 | 5581 | 5582 | 221.7 |

TABLE 7-7-continued

| Order from the short arm end | Clones | SEQ ID NO: (5' end) | SEQ ID NO: (3' end) | Distance from the short arm end (cM) |
|---|---|---|---|---|
| 317 | Bmag120 | — | — | 221.7 |
| 323 | bags12i02 | 5583 | 5584 | 225 |
| 323 | BaAK38E05 | 5585 | 5586 | 225 |
| 325 | baet25B0604 | 5587 | 5588 | 226.1 |
| 325 | BaAK46E21 | 5589 | 5590 | 226.1 |
| 327 | BaGS37J12 | 5591 | 5592 | 229.9 |
| 328 | bast60C0105 | 5593 | 5594 | 231 |
| 328 | baak30b08 | 5595 | 5596 | 231 |
| 328 | BaAL29N13 | 5597 | 5598 | 231 |
| 328 | BaAL24O04 | 5599 | 5600 | 231 |
| 332 | baak20o12 | 5601 | 5602 | 232.1 |
| 332 | basd14k23 | 5603 | 5604 | 232.1 |
| 332 | BaAK23L05 | 5605 | 5606 | 232.1 |
| 332 | BaGS31G02 | 5607 | 5608 | 232.1 |
| 332 | bags33o01 | 5609 | 5610 | 232.1 |
| 332 | basd18g14 | 5611 | 5612 | 232.1 |
| 332 | bah24d24 | 5613 | 5614 | 232.1 |
| 332 | BaGS12F09 | 5615 | 5616 | 232.1 |
| 332 | BaAK33H23 | 5617 | 5618 | 232.1 |
| 332 | bah47p03 | 5619 | 5620 | 232.1 |
| 342 | BaSD14F09 | 5621 | 5622 | 232.3 |
| 343 | bah11k13 | 5623 | 5624 | 232.5 |
| 343 | BaSD22F10 | 5625 | 5626 | 232.5 |
| 345 | bags32a01 | 5627 | 5628 | 234 |
| 346 | bags27o20 | 5629 | 5630 | 235.1 |
| 347 | baak31o10 | 5631 | 5632 | 236.2 |
| 347 | bags10f16 | 5633 | 5634 | 236.2 |
| 347 | baal37j12 | 5635 | 5636 | 236.2 |
| 350 | BaGS9H02 | 5637 | 5638 | 239.5 |

TABLE 7-8

| Order from the short arm end | Clones | SEQ ID NO: (5' end) | SEQ ID NO: (3' end) | Distance from the short arm end (cM) |
|---|---|---|---|---|
| 351 | BaAK40H10 | 5639 | 5640 | 240.3 |
| 352 | bah56m09 | 5641 | 5542 | 240.6 |
| 353 | kr66C0705 | 5643 | 5644 | 240.9 |
| 354 | BaGS33M05 | 5645 | 5646 | 242 |
| 355 | bast60B0204 | 5647 | 5648 | 243.2 |
| 356 | bah56p08 | 5649 | 5650 | 245.4 |
| 357 | baak12e19 | 5651 | 5652 | 246.9 |
| 357 | BaGS1D05 | 5653 | 5654 | 246.9 |
| 359 | BaH29M21 | 5655 | 5656 | 247.6 |
| 359 | bags21c04 | 5657 | 5658 | 247.6 |
| 361 | baak32p09 | 5659 | 5660 | 250.9 |
| 362 | BaAL24B02 | 5661 | 5662 | 254.2 |
| 362 | BaGS34F08 | 5663 | 5664 | 254.2 |
| 364 | bast36D1208 | 5665 | 5666 | 255.3 |
| 364 | kr25B1103 | 5667 | 5668 | 255.3 |
| 366 | kr08D0303 | 5669 | 5670 | 256.4 |
| 367 | baal19g05 | 5671 | 5672 | 257.5 |
| 367 | BaH22B15 | 5673 | 5674 | 257.5 |
| 367 | bags19c10 | 5675 | 5676 | 257.5 |
| 370 | bags29k01 | 5677 | 5678 | 260.7 |
| 370 | bastl54G0414 | 5679 | 5680 | 260.7 |
| 370 | BaGS23J01 | 5681 | 5682 | 260.7 |
| 370 | bags34b15 | 5683 | 5684 | 260.7 |
| 374 | baak46i07 | 5685 | 5686 | 262.9 |
| 375 | BaAL6J13 | 5687 | 5688 | 265 |
| 375 | bah31l17 | 5689 | 5690 | 265 |
| 375 | BaAK32A05 | 5691 | 5692 | 265 |
| 375 | BaGS30N22 | 5693 | 5694 | 265 |
| 379 | BaH54J20 | 5695 | 5696 | 266.4 |
| 380 | BaGS7F20 | 5697 | 5698 | 269.4 |
| 381 | bah63p18 | 5699 | 5700 | 272.8 |
| 382 | bags11p11 | 5701 | 5702 | 274.9 |
| 383 | BaH27L17 | 5703 | 5704 | 277.1 |
| 384 | basd17e11 | 5705 | 5706 | 278.2 |
| 384 | bags15i06 | 5707 | 5708 | 278.2 |
| 384 | BaAK36F09 | 5709 | 5710 | 278.2 |
| 384 | bast57A0101 | 5711 | 5712 | 278.2 |

TABLE 7-8-continued

| Order from the short arm end | Clones | SEQ ID NO: (5' end) | SEQ ID NO: (3' end) | Distance from the short arm end (cM) |
|---|---|---|---|---|
| 388 | baak26h17 | 5713 | 5714 | 280.3 |
| 388 | basd13b15 | 5715 | 5716 | 280.3 |
| 388 | bags9d11 | 5717 | 5718 | 280.3 |
| 391 | BaH20K03 | 5719 | 5720 | 281.4 |
| 391 | BaSD27N21 | 5721 | 5722 | 281.4 |
| 391 | baal13a10 | 5723 | 5724 | 281.4 |
| 394 | kr30F1212 | 5725 | 5726 | 282.5 |
| 394 | bastl45B0903 | 5727 | 5728 | 282.5 |
| 394 | Bmac156 | — | — | 282.5 |
| 394 | bah60k06 | 5729 | 5730 | 282.5 |
| 398 | BaGS32I12 | 5731 | 5732 | 283.6 |
| 398 | BaGS4H02 | 5733 | 5734 | 283.6 |
| 398 | bah44k12 | 5735 | 5736 | 283.6 |

TABLE 7-9

| Order from the short arm end | Clones | SEQ ID NO: (5' end) | SEQ ID NO: (3' end) | Distance from the short arm end (cM) |
|---|---|---|---|---|
| 398 | bags21m21 | 5739 | 5740 | 283.6 |
| 398 | BaSD14J15 | 5741 | 5742 | 283.6 |
| 404 | HVM49 | — | — | 285.7 |
| 404 | basd16e11 | 5743 | 5744 | 285.7 |
| 406 | BaAK21N09 | 5745 | 5746 | 287.9 |
| 407 | baal0e10 | 5747 | 5748 | 289 |
| 408 | baak1g17 | 5749 | 5750 | 290.1 |
| 409 | BaH14K12 | 5751 | 5752 | 291.2 |
| 409 | BaAK31G05 | 5753 | 5754 | 291.2 |
| 411 | MWG2062 | — | — | 291.5 |
| 412 | BaH50G17 | 5755 | 5756 | 292.3 |
| 413 | HVM5 | — | — | 293.4 |
| 413 | bags38n21 | 5757 | 5758 | 293.4 |
| 413 | bastl04B0303 | 5759 | 5760 | 293.4 |
| 413 | baal35f12 | 5761 | 5762 | 293.4 |
| 417 | BaH49M02 | 5763 | 5764 | 293.9 |
| 418 | baak38f04 | 5765 | 5766 | 294.5 |
| 419 | bah29b02 | 5767 | 5768 | 295 |
| 420 | basd15d20 | 5769 | 5770 | 296.1 |
| 421 | kr61C0305 | 5771 | 5772 | 297.1 |
| 421 | BaH23B08 | 5773 | 5774 | 297.1 |
| 423 | kr40H1115 | 5775 | 5776 | 298.6 |
| 424 | bah51g17 | 5777 | 5778 | 301.4 |
| 425 | BaSD22E19 | 5779 | 5780 | 315.4 |

The order on each chromosome can be specified based on the distance from the short arm end or long arm end. In the case where the order on each chromosome was specified by the distance from the short arm end, the polynucleotides mapped on 1H chromosome are first placed based on the distance from the short end, and the polynucleotides mapped on 2H and the subsequent chromosomes (3H to 7H) are placed based on the same reference (distances from the short arm end).

More specifically, in the case where the distance from the short arm end is used as a reference for positioning the polynucleotides with the base sequences of SEQ ID NO: 1 through 5780, the polynucleotides are placed according to the order from the short arm end as shown in Table 1-1 to Table 7-9. For clones that have the same order from the short arm end, the order by which these clones are placed is not particularly limited. Once the precise order of these clones were specified by a future study, these clones will be able to be placed accordingly. Note that, the reference (origin) on the chromosome is not just limited to the short arm end of 1H chromosome. Any position on a chromosome can be used as a reference point.

When using more than one polynucleotide with base sequences from the base sequence of any one of SEQ ID NO:

1 through 5780 for example, the polynucleotides can be placed in order from the 5' end. Further, in the case where a polynucleotide with the base sequence of any one of SEQ ID NO: 1 through 5780 is used together with more than one polynucleotide with base sequences from the base sequence of any one of SEQ ID NO: 1 through 5780 for example, a polynucleotide that is closest to the 5' end is placed first. The same criteria can be used to place other polynucleotides as well.

With the polynucleotides immobilized on a support in the order they are arranged on the chromosomes, the value of a gene detection instrument according to the present invention can be greatly improved in crossbreeding of Triticeae species. More specifically, by using a gene detection instrument according to the present invention for comprehensive investigation of transcripts in hybrids of Triticeae species, the expression level or the presence or absence of polymorphism can be determined for target genes. Further, the location and extent of recombination on chromosomes can be checked to see if unnecessary recombination has occurred. This makes it easy to determine target individuals of screening and thereby improves the efficiency of breeding.

[Gene Detection Instrument with the Polynucleotides Immobilized in Regions Appended with Chromosomal Order Information]

The regions in which the polynucleotides are immobilized (hereinafter, may be referred to as "spots") may be appended with information indicative of the order in which the polynucleotides are arranged on barley chromosomes. The spots may be arranged in any way as long as they are appended with the order information. With the order information added to the spots, the data obtained from the spots can be rearranged in the chromosomal order even when the spots are randomly placed on a support. In this way, a gene detection instrument according to the present invention can improve the efficiency of breeding. Note that, the order information added to the spots can follow the foregoing criteria used to place the polynucleotides.

Adding order information enables the spots to be arranged in an arbitrary order in a gene detection instrument of an array type, in which more than one polynucleotide is immobilized on a support such as a membrane or a glass slide. Further, the chromosomal order information of individual polynucleotides can also be added in a gene detection instrument that employs a collection of beads (bead array) in which the polynucleotide is immobilized on each bead serving as a support.

[Examples of a Gene Detection Instrument According to the Present Invention]

(i) For Detecting Gene Expression

A gene detection instrument according to the present invention can be fabricated according to a conventional gene expression array fabrication method. For example, a cDNA array can be fabricated by preparing a solution of polynucleotide that comprises cDNA (full length or partial), and by spotting it on a support with a spotter or the like. The polynucleotides immobilized on the support may be synthetic oligonucleotides with the base sequences of cDNA. Alternatively, a technique known as the Affymetrix DNA chip technique may be used, in which DNA is synthesized on a substrate.

Various conventional techniques that are designed for detection of gene expression can suitably be used in a gene detecting instrument according to the present invention. For example, cDNA or cRNA prepared from total RNA or mRNA of Triticeae species can be used for the present invention. More specifically, cDNA or cRNA is fluorescent-labeled and hybridized with the polynucleotides immobilized on the support. The expression level of genes can be evaluated by measuring the intensity of hybridization, using the fluorescence as an index. Further, cDNA or cRNA prepared from two kinds of samples may be labeled with fluorescent substances that emit different colors, and hybridized with polynucleotides immobilized on the same support. By measuring the color tone and fluorescent intensity, differences of gene expression can be evaluated.

In breeding of Triticeae species, target individuals can be screened for according to changes in the expression levels of genes that regulate target traits. Further, target individuals can also be screened for according to the expression levels of genes that are linked to target genes.

(ii) For Detecting Gene Polymorphism

Various conventional techniques that are designed for detection of gene polymorphism can suitably be used in a gene detection instrument according to the present invention.

For example, a gene detection instrument according to the present invention can be used to detect fragment length polymorphism such as RFLP (restriction fragment length polymorphism). More specifically, fragment length polymorphism can be detected by immobilizing more than one partial sequence of cDNA of the same clone on the same spot. Here, the hybridization intensity of the spot immobilizing three partial sequences is the strongest in fragments that hybridize with all of the three partial sequences, and is weaker in fragments that hybridize with two partial sequences or only one partial sequence. Thus, fragment length polymorphism can be detected by measuring fluorescence intensity or the like used as an index of hybridization intensity. In the case where fragments hybridize with distinctively different regions in the same spot, fragment length polymorphism can be detected by labeling the two fragments with different fluorescent dyes.

(2) Gene Polymorphism Detection Instrument according to the Present Invention

A gene polymorphism detection instrument according to the present invention is an instrument for detecting polymorphisms of genes in the genomes of Triticeae species. The organisms to which a gene detection instrument of the invention is applicable may be any Triticeae species, among which barley, wheat, and rye are preferable. A gene detection instrument according to the present invention includes a support on which polynucleotides constituting part of barley chromosomal (1H, 2H, 3H, 4H, 5H, 6H, and 7H) DNA are immobilized. The polynucleotides immobilized on the support may solely be polynucleotides that constitute part of barley chromosomal DNA, or other polynucleotides may additionally be immobilized on the support. Such additional polynucleotides are not particularly limited as long as they can detect expression or polymorphism of genes in the genomes of Triticeae species. For example, the additional polynucleotides may be those with the base sequences originating in non-barley organisms, or those with arbitrary base sequences that have been artificially synthesized.

In the case where the polynucleotides are immobilized in more than one region of the support, the polynucleotides immobilized in these regions may have non-overlapping base sequences or partially overlapping base sequences. Alternatively, polynucleotides of the same base sequence may be immobilized in these different regions of the support. In the case where the polynucleotides have overlapping base sequences, the polynucleotides may have partially overlapping base sequences, or the base sequence of one of the polynucleotides may be a partial sequence of the other polynucleotide.

Further, the polynucleotide immobilized in each region is not necessarily required to be of the same kind. More than one kind of polynucleotide may be immobilized in each region.

The support is not particularly limited as long as it can immobilize polynucleotides, and it may have any shape and may be made of any material. Examples of a support material generally include: inorganic materials such as glass and silicon wafer; natural polymers such as paper; synthetic polymers such as nitrocellulose and nylon; and gels using synthetic polymers or natural polymers. The shape of the support is not particularly limited as long as it provides enough area to support the polynucleotides. Generally, those with a two-dimensional plane, for example, such as a substrate with little or no flexibility, a flexible membrane, or a flexible substrate with intermediate flexibility can be preferably used. The thickness of the substrate or membrane is not particularly limited either, and it can be suitably set according to the material or use of the substrate or membrane. Various types of beads may be used as supports.

[Polynucleotides Immobilized on a Support of the Gene Polymorphism Detection Instrument]

In a gene polymorphism detection instrument according to the present invention, at least one polynucleotide from the following polynucleotides is immobilized on a support.

Polynucleotides with base sequences constituting part of barley chromosomal DNA, or variants thereof with the substitution, deletion, insertion, and/or addition of one or more bases.

As used herein, a polynucleotide with a base sequence constituting part of barley chromosomal DNA is not particularly limited as long as it is a polynucleotide with a base sequence constituting part of the entire base sequences of chromosomal DNA of barley 1H, 2H, 3H, 4H, 5H, 6H, and 7H chromosomes.

A variant with the substitution, deletion, insertion, and/or addition of one or more bases in the polynucleotide with a base sequence constituting part of barley chromosomal DNA may be a polynucleotide that has been mutated on purpose, or a polynucleotide that exists in nature. For example, think of a base sequence of chromosomal DNA in a specific variety of barley. Comparing this base sequence with those of other varieties, no sequence is completely identical. Rather, these sequences are variants with the substitution, deletion, insertion, and/or addition of one or more bases.

A polynucleotide immobilized on a support of a gene polymorphism detection instrument according to the present invention is preferably a polynucleotide that constitutes part of the base sequence of at least one DNA fragment that has been amplified with a primer set that comprises two primers arbitrarily selected from a plurality of primers that have been designed based on base sequences of SEQ ID NO: n (where n is an odd number) and SEQ ID NO: n+1 from the base sequences of SEQ ID NO: 1 through 5780, using the genomic DNA of Triticeae species as a template.

The base sequences of SEQ ID NO: 1 through 5780 are base sequences of the barley EST (expressed sequence tag) independently developed by the inventors. The inventors have previously confirmed that a polynucleotide with the base sequences of SEQ ID NO: 1 through 770, a polynucleotide with the base sequences of SEQ ID NO: 771 through 1754, a polynucleotide with the base sequences of SEQ ID NO: 1755 through 2642, a polynucleotide with the base sequences of SEQ ID NO: 2643 through 3324, a polynucleotide with the base sequences of SEQ ID NO: 3325 through 4320, a polynucleotide with the base sequences of SEQ ID NO: 4321 through 4962, and a polynucleotide with the base sequences of SEQ ID NO: 4963 through 5780 are mapped on 1H, 2H, 3H, 4H, 5H, 6H, and 7H chromosomes, respectively.

The primers are not particularly limited as long as they are designed based on the base sequences of SEQ ID NO: 1 through 5780. As such, primer profiles, such as the number of bases and GC content are not particularly limited. Further, as described above, since the base sequence of SEQ ID NO: n (where n is an odd number) and the base sequence of SEQ ID NO: n+1 are base sequences that are read from the both ends of cDNA of the same clone, the primer set with a combination of two primers arbitrarily selected from a plurality of primers that have been designed based on these base sequences flank a specific region of the barley chromosomal DNA. For example, in amplifying DNA with the primer set using the genomic DNA of barley as a template, the base sequences of the amplified fragments will be the same as the base sequences of the cDNA when the primer set is within the same exon. On the other hand, when the primers of the primer set are in different exons, the amplified fragments will include base sequences of the intron portions.

The primers that are designed based on the base sequences of SEQ ID NO: 1 through 5780 may be primers with the base sequences of SEQ ID NO: 5781 through 17340, or primers with the complementary sequences thereof, for example. More specifically, the primers that are designed based on SEQ ID NO: 1 are primers with the base sequences of SEQ ID NO: 5781 and 5782 or the complementary sequences thereof, and the primers that are designed based on SEQ ID NO: 2 are primers with the base sequences of SEQ ID NO: 5783 and 5784 or the complementary sequences thereof. In other words, the SEQ ID NOs for the base sequences of the primers designed based on the individual base sequences of SEQ ID NO: 1 through 5780 are represented by $(2 \times m - 1) + 5780$ and $(2 \times m) + 5780$, where m is the SEQ ID NO of the base sequence used to designed the primer.

As a specific example, amplified DNA fragments can be obtained by PCR that uses the genomic—DNA of barley as a template and is performed with a primer set including a combination of two primers arbitrarily selected from (i) primers that have been designed based on the base sequence of SEQ ID NO: 1 and having the base sequences of SEQ ID NO: 5781 through 5782 or complementary sequences thereof, and (ii) primers that have been designed based on the base sequence of SEQ ID NO: 2 and having the base sequences of SEQ ID NO: 5783 through 5784 or complementary sequences thereof. A means by which amplification is performed is not particularly limited, and PCR and other conventional methods can be used.

The polynucleotides immobilized on a support of a gene polymorphism detection instrument according to the present invention are part of the amplified DNA fragments. When amplification is performed using genomic DNA of different Triticeae species as a template and when polymorphism exists in the amplified fragments, it is preferable that the polynucleotides immobilized on the support include polymorphism-containing portions of the base sequences. The polymorphism may be amplified fragment length polymorphism or single nucleotide polymorphism (SNP), for example.

The inventors of the present invention amplified DNA fragments by using genomic DNA of Triticeae species as a template and with the use of a primer set that included a combination of two primers arbitrarily selected from (i) primers that had been designed based on the base sequence of SEQ ID NO: n (where n is an odd number), and (ii) primers that had been designed based on the base sequence of SEQ ID NO: n+1, from among the base sequences of SEQ ID NO: 1 through 5780. The inventors have found that these DNA fragments could be used as genetic markers for distinguishing different varieties of Triticeae species. That is, the inventors have specified at least 2890 genetic markers.

Specifically, the inventors have found fragment length polymorphism in the DNA fragments that were amplified by PCR that was performed with a primer set that had been designed based on SEQ ID NO: 2 and included a combination of primers with the base sequences of SEQ ID NO: 5783 and 5784, using the genomic DNA of malting barley "Haruna Nijo" (Hordeum vulgare ssp. vulgare variety Harunanijo) and the genomic DNA of wild type barley "H602" (Hordeum vulgare ssp. spontaneum H602) as templates. Further, the inventors have found SNP in the DNA fragments that were amplified by PCR that was performed with a primer set that had been designed based on SEQ ID NO: 4 and included a combination of primers with the base sequences of SEQ ID NO: 5787 and 5788, using the genomic DNA of the foregoing barley varieties as templates. It was found as a result that these DNA fragments with SNPs were CAPS (cleaved amplified polymorphic sequence) markers, which are excised by restriction enzyme in one of the varieties but not in the other varieties.

Table 8-1 through Table 14-9 show kinds of polymorphisms that were found by the inventors between Haruna Nijo and H602. Tables 8-1 through 8-8 show polymorphisms in 1H chromosome, Tables 9-1 through 9-10 in 2H chromosome, Tables 10-1 through 10-9 in 3H chromosome, Tables 11-1 through 11-7 in 4H chromosome, Tables 12-1 through 12-10 in 5H chromosome, Tables 13-1 through 13-7 in 6H chromosome, and Tables 14-1 through 14-9 in 7H chromosome. Corresponding EST sequences of the respective clones are shown in Table 1-1 through Table 7-9. The "Primers Used" are primers that were actually used from among the primers that had been designed based on the EST sequences (SEQ ID NO: n (where n is an odd number) and SEQ ID NO: n+1) corresponding to the respective clones. The primers used for each clone had the base sequences with the SEQ ID NOs shown in the tables. The DNA fragments amplified with these primer sets using the genomic DNA of Haruna Nijo and the genomic DNA of H602 as templates had polymorphisms shown in Table 8-1 through Table 14-9.

The clones are known genetic markers, which have been identified as SSR (simple sequence repeat) marker, STS (sequence tagged site) marker, dCAPS (derived cleaved amplified polymorphic sequence) marker, trait marker, CAPS marker, or size_poly (fragment length polymorphism) marker. SSR is a fragment length polymorphism based on differences in the number of repeats of recurring units of two or three bases of DNA. STS is a sequence site that has been set only for a specific location of DNA. Starting from such a specific sequence site, specific DNA fragments are amplified by PCR or the like, and electrophoresis is run for the amplified products so that polymorphism can be detected based on the presence or absence of bands, or differences in molecular weight. In dCAPS, a mismatch is induced between PCR primers and template DNA, so that polymorphism (the presence or absence of restriction enzyme site) occurs in the PCR products. Trait marker sh is an isolated gene that controls vernalization requirement. Since Haruna Nijo and H602 have polymorphism in the sequence of this gene, it can be used as a marker. CAPS and size_poly will be described later.

TABLE 8-1

| Name | Primers used (SEQ ID NO:) | | marker type |
|---|---|---|---|
| bah55e06 | 5783 | 5784 | size_poly (codominant) |
| bags30b07 | 5787 | 5788 | SNP |
| baak2l03 | 5791 | 5792 | CAPS |
| BaAK17D13 | 5795 | 5796 | SNP |
| basd26l20 | 5799 | 5800 | SNP |
| bah61p17 | 5803 | 5804 | SNP |
| BaGS11O06 | 5807 | 5808 | size_poly (codominant) |
| kr12H0216 | 5811 | 5812 | SNP |
| BaGS32E23 | 5815 | 5816 | CAPS |
| basd13k20 | 5819 | 5820 | CAPS |
| BaAK24O11 | 5823 | 5824 | CAPS |
| kr26D0507 | 5827 | 5828 | SNP |
| BaSD2D08 | 5831 | 5832 | CAPS |
| baak41n21 | 5835 | 5836 | SNP |
| bah11b15 | 5839 | 5840 | CAPS |
| kr24B0903 | 5843 | 5844 | SNP |
| bast50E0709 | 5847 | 5848 | size_poly (codominant) |
| baal17o01 | 5851 | 5852 | SNP |
| baak41a04 | 5855 | 5856 | SNP |
| BaH28C07 | 5859 | 5860 | size_poly (codominant) |
| bags16g18 | 5863 | 5864 | SNP |
| BaSD3C22 | 5867 | 5868 | SNP |
| BaGS17B21 | 5871 | 5872 | CAPS |
| basd27b10 | 5875 | 5876 | SNP |
| bah47d23 | 5879 | 5880 | SNP |
| BaAK21D02 | 5883 | 5884 | CAPS |
| BaH17D02 | 5887 | 5888 | CAPS |
| baal4f12 | 5891 | 5892 | CAPS |
| baGS11I03 | 5895 | 5896 | CAPS |
| bah56a03 | 5899 | 5900 | size_poly (codominant) |
| kr16A0501 | 5903 | 5904 | size_poly (codominant) |
| bah19f01 | 5907 | 5908 | CAPS |
| BaAK27F07 | 5911 | 5912 | CAPS |
| bah47f18 | 5915 | 5916 | size_poly (codominant) |
| bah45l19 | 5919 | 5920 | size_poly (codominant) |
| BaAK12I12 | 5923 | 5924 | SNP |
| BaAL6N04 | 5927 | 5928 | SNP |
| baal16l05 | 5931 | 5932 | CAPS |
| BaSD18O20 | 5935 | 5936 | size_poly (codominant) |
| BaSD3J13 | 5939 | 5940 | SNP |
| bah63j19 | 5943 | 5944 | size_poly (codominant) |
| BaH36O18 | 5947 | 5948 | CAPS |
| BaAK20A06 | 5951 | 5952 | CAPS |
| BaGS8G13 | 5955 | 5956 | CAPS |
| bah25n06 | 5959 | 5960 | CAPS |
| BaAK1P06 | 5963 | 5964 | size_poly (dominant) |
| BaAK16M07 | 5967 | 5968 | SNP |
| BaH36M15 | 5971 | 5972 | SNP |
| BaGS12K12 | 5975 | 5976 | size_poly (dominant) |
| BaAL39C22 | 5979 | 5980 | SNP |
| kr68B0303 | 5983 | 5984 | SNP |

TABLE 8-2

| Name | Primers used (SEQ ID NO:) | | marker type |
|---|---|---|---|
| baak24d09 | 5987 | 5988 | SNP |
| BaGS11J13 | 5991 | 5992 | CAPS |
| baal38l23 | 5995 | 5996 | CAPS |
| BaAL36B15 | 5999 | 6000 | CAPS |
| bast60D0610 | 6003 | 6004 | CAPS |
| kr22D0808 | 6007 | 6008 | CAPS |
| baal19i12 | 6011 | 6012 | SNP |
| basd23o02 | 6015 | 6016 | CAPS |
| baak1j14 | 6019 | 6020 | CAPS |
| baak24k18 | 6023 | 6024 | CAPS |
| kr18G0814 | 6027 | 6028 | SNP |
| BaH38H09 | 6031 | 6032 | CAPS |
| BaGS8B13 | 6035 | 6036 | SNP |
| BaH25J08 | 6039 | 6040 | SNP |
| baak3d11 | 6043 | 6044 | SNP |
| baal12p08 | 6047 | 6048 | SNP |
| bags39i20 | 6051 | 6052 | SNP |
| bags32m16 | 6055 | 6056 | size_poly (codominant) |
| kr15A0402 | 6059 | 6060 | SNP |

TABLE 8-2-continued

| Name | Primers used (SEQ ID NO:) | | marker type |
|---|---|---|---|
| baal3c01 | 6063 | 6064 | SNP |
| baak41i03 | 6067 | 6068 | SNP |
| BaGS29M13 | 6071 | 6072 | SNP |
| basd17m22 | 6075 | 6076 | CAPS |
| bags15g01 | 6079 | 6080 | CAPS |
| BaH24I06 | 6083 | 6084 | SNP |
| BaH57E12 | 6087 | 6088 | CAPS |
| BaSD25C22 | 6091 | 6092 | SNP |
| baal19m17 | 6095 | 6096 | CAPS |
| bah46p14 | 6099 | 6100 | SNP |
| bags18d19 | 6103 | 6104 | SNP |
| BaAK34J19 | 6107 | 6108 | SNP |
| bags6d01 | 6111 | 6112 | CAPS |
| bags3P11 | 6115 | 6116 | CAPS |
| BaAK14J21 | 6119 | 6120 | CAPS |
| baak2m05 | 6123 | 6124 | SNP |
| baak37g19 | 6127 | 6128 | CAPS |
| BaGS31B11 | 6131 | 6132 | SNP |
| BaAL35M08 | 6135 | 6136 | SNP |
| BaSD16G03 | 6139 | 6140 | CAPS |
| BaH58J20 | 6143 | 6144 | SNP |
| BaGS22B13 | 6147 | 6148 | SNP |
| BaAK43M01 | 6151 | 6152 | SNP |
| bah14i07 | 6155 | 6156 | SNP |
| BaH13F14 | 6159 | 6160 | CAPS |
| baal9i16 | 6163 | 6164 | CAPS |
| basd27b20 | 6167 | 6168 | CAPS |
| BaAK2O24 | 6171 | 6172 | SNP |
| basd18l16 | 6175 | 6176 | CAPS |
| BaAL19J14 | 6179 | 6180 | CAPS |
| bags22j15 | 6183 | 6164 | SNP |
| baak44a23 | 6187 | 6188 | SNP |

TABLE 8-3

| Name | Primers used (SEQ ID NO:) | | marker type |
|---|---|---|---|
| BaAK32N04 | 6191 | 6192 | SNP |
| basd21e22 | 6195 | 6196 | SNP |
| BaGS7K03 | 6199 | 6200 | size_poly (codominant) |
| baak42e22 | 6203 | 6204 | SNP |
| bast21D0808 | 6207 | 6208 | size_poly (codominant) |
| bast75E0610 | 6211 | 6212 | SNP |
| baet16A1002 | 6215 | 6216 | SNP |
| basd17m16 | 6219 | 6220 | CAPS |
| bags17g08 | 6223 | 6224 | size_poly (codominant) |
| baak21i01 | 6227 | 6228 | SNP |
| baak13n06 | 6231 | 6232 | CAPS |
| baak22o23 | 6235 | 6236 | SNP |
| baet42E0410 | 6239 | 6240 | size_poly (codominant) |
| BaGS27M04 | 6243 | 6244 | CAPS |
| BaH52H18 | 6247 | 6248 | SNP |
| baak33k20 | 6251 | 6252 | SNP |
| bags21f6 | 6255 | 6256 | SNP |
| bags34e05 | 6259 | 6260 | SNP |
| bags15d20 | 6263 | 6264 | CAPS |
| bags18g10 | 6267 | 6268 | size_poly (codominant) |
| bags19a02 | 6271 | 6272 | SNP |
| BaAK17J19 | 6275 | 6276 | size_poly (codominant) |
| bags35k02 | 6279 | 6280 | SNP |
| bah35a22 | 6283 | 6284 | SNP |
| BaGS17H13 | 6287 | 6288 | SNP |
| bah47n12 | 6291 | 6292 | SNP |
| baak12p11 | 6295 | 6296 | SNP |
| baet38B1004 | 6299 | 6300 | SNP |
| BaGS13K12 | 6303 | 6304 | SNP |
| BaAL25A05 | 6307 | 6308 | SNP |
| bah27k23 | 6311 | 6312 | size_poly (codominant) |
| BaAK24J12 | 6315 | 6316 | SNP |
| BaSD14M22 | 6319 | 6320 | SNP |
| bah17l24 | 6323 | 6324 | SNP |
| baal29j09 | 6327 | 6328 | SNP |
| bah16d09 | 6331 | 6332 | SNP |
| bah60d03 | 6335 | 6336 | SNP |
| bah45i13 | 6339 | 6340 | SNP |

TABLE 8-3-continued

| Name | Primers used (SEQ ID NO:) | | marker type |
|---|---|---|---|
| bah11h03 | 6343 | 6344 | SNP |
| bah47h17 | 6347 | 6348 | SNP |
| bags35d02 | 6351 | 6352 | SNP |
| bags37e17 | 6355 | 6356 | CAPS |
| baak14c12 | 6359 | 6360 | SNP |
| baak34c01 | 6363 | 6364 | SNP |
| BaH35A11 | 6367 | 6368 | SNP |
| BaAK30M16 | 6371 | 6372 | SNP |
| BaSD11P04 | 6375 | 6376 | CAPS |
| bah12j09 | 6379 | 6380 | CAPS |
| BaAL2G20 | 6383 | 6384 | SNP |
| bags14j09 | 6387 | 6388 | CAPS |
| kr26E0610 | 6391 | 6392 | CAPS |

TABLE 8-4

| Name | Primers used (SEQ ID NO:) | | marker type |
|---|---|---|---|
| bah37f01 | 6395 | 6396 | CAPS |
| bags29m05 | 6399 | 6400 | SNP |
| BaGS17A18 | 6403 | 6404 | CAPS |
| baet34A0501 | 6407 | 6408 | SNP |
| BaSD22O13 | 6411 | 6412 | CAPS |
| bags15a22 | 6415 | 6416 | CAPS |
| baet21H1016 | 6419 | 6420 | CAPS |
| BaH30E13 | 6423 | 6424 | SNP |
| bags4e23 | 6427 | 6428 | SNP |
| baak45b03 | 6431 | 6432 | SNP |
| bah12o12 | 6435 | 6436 | SNP |
| baak34k14 | 6439 | 6440 | CAPS |
| baal3e14 | 6443 | 6444 | SNP |
| bags22fl2 | 6447 | 6448 | CAPS |
| BaH45P03 | 6451 | 6452 | CAPS |
| basd11d13 | 6455 | 6456 | CAPS |
| Bmag211 | — | — | SSR |
| HVM20 | — | — | SSR |
| basd1j14 | 6459 | 6460 | SNP |
| bags35b18 | 6463 | 6464 | SNP |
| baal41i11 | 6467 | 6468 | SNP |
| bags13e23 | 6471 | 6472 | SNP |
| bah20d03 | 6475 | 6476 | SNP |
| baet19F0212 | 6479 | 6480 | SNP |
| bags12j05 | 6483 | 6484 | SNP |
| BaSD24D17 | 6487 | 6488 | SNP |
| BaGS24K10 | 6491 | 6492 | SNP |
| baal9e05 | 6495 | 6496 | SNP |
| BaGS33M23 | 6499 | 6500 | SNP |
| bah46g14 | 6503 | 6504 | SNP |
| bags33h05 | 6507 | 6508 | SNP |
| baak24h12 | 6511 | 6512 | SNP |
| BaH50N19 | 6515 | 6516 | SNP |
| BaAK31O05 | 6519 | 6520 | SNP |
| BaGS39L14 | 6523 | 6524 | SNP |
| BaGS27C22 | 6527 | 6528 | SNP |
| bags20o24 | 6531 | 6532 | SNP |
| bags34j05 | 6535 | 6536 | CAPS |
| bah56l03 | 6539 | 6540 | CAPS |
| basd12k03 | 6543 | 6544 | CAPS |
| BaAK39I18 | 6547 | 6548 | CAPS |
| bags21h06 | 6551 | 6552 | CAPS |
| bah56k04 | 6555 | 6556 | CAPS |
| bah60e11 | 6559 | 6560 | CAPS |
| baak22i05 | 6563 | 6564 | CAPS |
| baal5i02 | 6567 | 6568 | CAPS |
| BaAK2E05 | 6571 | 6572 | CAPS |
| baak33g12 | 6575 | 6576 | CAPS |
| bags4e05 | 6579 | 6580 | CAPS |
| bast42C0806 | 6583 | 6584 | SNP |
| baak26c05 | 6587 | 6588 | SNP |

TABLE 8-5

| Name | Primers used (SEQ ID NO:) | | marker type |
|---|---|---|---|
| bags19a16 | 6591 | 6592 | SNP |
| kr11F1212 | 6595 | 6596 | SNP |
| BaH28K13 | 6599 | 6600 | CAPS |
| baak20d06 | 6603 | 6604 | size_poly (codominant) |
| BaSD1I24 | 6607 | 6608 | CAPS |
| baak35l20 | 6611 | 6612 | SNP |
| bah57m07 | 6615 | 6616 | SNP |
| bah60k11 | 6619 | 6620 | SNP |
| basd20o09 | 6623 | 6624 | SNP |
| basd24i22 | 6627 | 6628 | SNP |
| bags30g20 | 6631 | 6632 | SNP |
| bags1m11 | 6635 | 6636 | SNP |
| bags23g20 | 6639 | 6640 | SNP |
| BaGS15B05 | 6643 | 6644 | SNP |
| BaGS24P05 | 6647 | 6648 | SNP |
| bags10g06 | 6651 | 6652 | SNP |
| bah32o04 | 6655 | 6656 | SNP |
| BaGS32P08 | 6659 | 6660 | SNP |
| bags4e02 | 6663 | 6664 | CAPS |
| bast04H0315 | 6667 | 6668 | CAPS |
| BaGS37L06 | 6671 | 6672 | CAPS |
| basd2b18 | 6675 | 6676 | CAPS |
| bags3h12 | 6679 | 6680 | SNP |
| bags1e21 | 6683 | 6684 | SNP |
| BaAK27M21 | 6687 | 6688 | SNP |
| BaSD18F05 | 6691 | 6692 | size_poly (codominant) |
| BaH35B05 | 6695 | 6696 | SNP |
| basd21h11 | 6699 | 6700 | SNP |
| BaH32E20 | 6703 | 6704 | SNP |
| BaGS22A20 | 6707 | 6708 | SNP |
| BaSD14B13 | 6711 | 6712 | CAPS |
| bags29l04 | 6715 | 6716 | SNP |
| bags22g16 | 6719 | 6720 | SNP |
| BaAL4B14 | 6723 | 6724 | size_poly (codominant) |
| bah61h20 | 6727 | 6728 | SNP |
| bah15p01 | 6731 | 6732 | SNP |
| baak41p03 | 6735 | 6736 | SNP |
| BaSD12L06 | 6739 | 6740 | SNP |
| BaSD23P07 | 6743 | 6744 | SNP |
| BaGS7J05 | 6747 | 6748 | SNP |
| bah29b06 | 6751 | 6752 | SNP |
| BaGS31N17 | 6755 | 6756 | SNP |
| BaGS13F08 | 6759 | 6760 | SNP |
| BaAK39G10 | 6763 | 6764 | CAPS |
| BaAK39G03 | 6767 | 6768 | CAPS |
| baak2a18 | 6771 | 6772 | CAPS |
| bags39d12 | 6775 | 6776 | SNP |
| basd17l04 | 6779 | 6780 | CAPS |
| BaAK20B19 | 6783 | 6784 | SNP |
| bags15j15 | 6787 | 6788 | SNP |
| BaAK30F02 | 6791 | 6792 | CAPS |

TABLE 8-6

| Name | Primers used (SEQ ID NO:) | | marker type |
|---|---|---|---|
| BaGS22A21 | 6795 | 6796 | SNP |
| baet45E0410 | 6799 | 6800 | SNP |
| BaGS22C14 | 6803 | 6804 | SNP |
| bah23k12 | 6807 | 6808 | SNP |
| BaH15O13 | 6811 | 6812 | SNP |
| kr24F0412 | 6815 | 6816 | SNP |
| BaGS28O21 | 6819 | 6820 | SNP |
| BaAL15N19 | 6823 | 6824 | SNP |
| bags10j15 | 6827 | 6828 | CAPS |
| bags32j03 | 6831 | 6832 | SNP |
| bags20e14 | 6835 | 6836 | SNP |
| bags3c15 | 6839 | 6840 | CAPS |
| basd27n01 | 6843 | 6844 | SNP |
| BaGS6M19 | 6847 | 6848 | SNP |
| baak13e03 | 6851 | 6852 | SNP |
| BaH15M10 | 6855 | 6856 | CAPS |
| bags14k12 | 6859 | 6860 | size_poly (codominant) |
| bast61E0509 | 6863 | 6864 | CAPS |
| BaGS31N04 | 6867 | 6868 | CAPS |

TABLE 8-6-continued

| Name | Primers used (SEQ ID NO:) | | marker type |
|---|---|---|---|
| BaAK27D22 | 6871 | 6872 | CAPS |
| baal5o19 | 6875 | 6876 | CAPS |
| bah55b18 | 6879 | 6880 | CAPS |
| bah23i02 | 6883 | 6884 | SNP |
| BaAK15H22 | 6887 | 6888 | SNP |
| bags32b03 | 6891 | 6892 | SNP |
| baak30c15 | 6895 | 6896 | SNP |
| BaGS22A05 | 6899 | 6900 | SNP |
| bah16m01 | 6903 | 6904 | SNP |
| bags15e08 | 6907 | 6908 | CAPS |
| BaGS37D12 | 6911 | 6912 | SNP |
| BaAL37N24 | 6915 | 6916 | SNP |
| BaH28B09 | 6919 | 6920 | SNP |
| bah47h08 | 6923 | 6924 | SNP |
| BaH57N07 | 6927 | 6928 | SNP |
| baak38o02 | 6931 | 6932 | SNP |
| baak20f16 | 6935 | 6936 | SNP |
| baak28n19 | 6939 | 6940 | SNP |
| bah59j07 | 6943 | 6944 | SNP |
| bah44j20 | 6947 | 6948 | SNP |
| BaH47J05 | 6951 | 6952 | CAPS |
| baet39B0303 | 6955 | 6956 | SNP |
| BaAK27D19 | 6959 | 6960 | SNP |
| basd25g01 | 6963 | 6964 | SNP |
| BaAL34K17 | 6967 | 6968 | SNP |
| basd21i17 | 6971 | 6972 | SNP |
| bags15o12 | 6975 | 6976 | SNP |
| baal2j10 | 6979 | 6980 | CAPS |
| baak44n10 | 6983 | 6984 | SNP |
| baak21e08 | 6987 | 6988 | SNP |
| BaGS37F14 | 6991 | 6992 | CAPS |
| BaAK41I21 | 6995 | 6996 | SNP |

TABLE 8-7

| Name | Primers used (SEQ ID NO:) | | marker type |
|---|---|---|---|
| BaGS19C07 | 6999 | 7000 | SNP |
| BaGS15O08 | 7003 | 7004 | SNP |
| baak40p22 | 7007 | 7008 | SNP |
| BaH21K05 | 7011 | 7012 | CAPS |
| baal40n03 | 7015 | 7016 | SNP |
| bags23b08 | 7019 | 7020 | SNP |
| BaGS39L18 | 7023 | 7024 | SNP |
| BaGS25K24 | 7027 | 7028 | CAPS |
| bags1a18 | 7031 | 7032 | CAPS |
| baal15k07 | 7035 | 7036 | size_poly (codominant) |
| bags14o13 | 7039 | 7040 | size_poly (dominant) |
| BaH18D15 | 7043 | 7044 | SNP |
| bastl04F0911 | 7047 | 7048 | SNP |
| BaGS31E03 | 7051 | 7052 | SNP |
| BaGS19J21 | 7055 | 7056 | SNP |
| BaGS39P08 | 7059 | 7060 | SNP |
| BaH56B06 | 7063 | 7064 | SNP |
| baal13m24 | 7067 | 7068 | SNP |
| bags15h14 | 7071 | 7072 | SNP |
| bags35j22 | 7075 | 7076 | CAPS |
| baak20h22 | 7079 | 7080 | CAPS |
| baal34b14 | 7083 | 7084 | SNP |
| bah16j04 | 7087 | 7088 | CAPS |
| BaH54J03 | 7091 | 7092 | CAPS |
| bast58C1206 | 7095 | 7096 | SNP |
| BaH26M05 | 7099 | 7100 | CAPS |
| bastl20B0404 | 7103 | 7104 | SNP |
| baak14e23 | 7107 | 7108 | CAPS |
| BaH15P22 | 7111 | 7112 | SNP |
| BaGS17I22 | 7115 | 7116 | SNP |
| bags15h01 | 7119 | 7120 | SNP |
| bags7p13 | 7123 | 7124 | SNP |
| BaGS29H13 | 7127 | 7128 | SNP |
| bah47b01 | 7131 | 7132 | SNP |
| bastl45E1109 | 7135 | 7136 | CAPS |
| bags32m15 | 7139 | 7140 | SNP |
| basd12c09 | 7143 | 7144 | size_poly (codominant) |
| baal27m11 | 7147 | 7148 | SNP |

TABLE 8-7-continued

| Name | Primers used (SEQ ID NO:) | | marker type |
|---|---|---|---|
| basd12k01 | 7151 | 7152 | CAPS |
| baak41n15 | 7155 | 7156 | size_poly (codominant) |
| bags1b01 | 7159 | 7160 | SNP |
| BaH56O11 | 7163 | 7164 | size_poly (codominant) |
| bah15k16 | 7167 | 7168 | CAPS |
| bags31a22 | 7171 | 7172 | CAPS |
| bags21e21 | 7175 | 7176 | SNP |
| baak32n05 | 7179 | 7180 | size_poly (codominant) |
| baet02B0503 | 7183 | 7184 | SNP |
| BaH29L05 | 7187 | 7188 | SNP |
| baet43H1016 | 7191 | 7192 | SNP |
| BaGS38N20 | 7195 | 7196 | CAPS |
| BaGS23O09 | 7199 | 7200 | CAPS |

TABLE 8-8

| Name | Primers used (SEQ ID NO:) | | marker type |
|---|---|---|---|
| bastl26E0410 | 7203 | 7204 | CAPS |
| BaH15N14 | 7207 | 7208 | CAPS |
| baak20b06 | 7211 | 7212 | SNP |
| BaH16I04 | 7215 | 7216 | SNP |
| bah22p07 | 7219 | 7220 | SNP |
| baak21j02 | 7223 | 7224 | SNP |
| bah30o13 | 7227 | 7228 | CAPS |
| bags38fl8 | 7231 | 7232 | CAPS |
| bah13o05 | 7235 | 7236 | CAPS |
| baak36b12 | 7239 | 7240 | CAPS |
| bags18o09 | 7243 | 7244 | CAPS |
| BaAK16L10 | 7247 | 7248 | CAPS |
| BaAK38E16 | 7251 | 7252 | size_poly (dominant) |
| bah13e15 | 7255 | 7256 | CAPS |
| bags1f22 | 7259 | 7260 | CAPS |
| bags21o12 | 7263 | 7264 | SNP |
| BaGS9B14 | 7267 | 7268 | SNP |
| BaAL1N23 | 7271 | 7272 | CAPS |
| baaK1a17 | 7275 | 7276 | SNP |
| BaH32B01 | 7279 | 7280 | CAPS |
| BaSD18L13 | 7283 | 7284 | CAPS |
| baak12p07 | 7287 | 7288 | size_poly (codominant) |
| BaH58A04 | 7291 | 7292 | CAPS |
| bags1p04 | 7295 | 7296 | SNP |
| BaAL17O03 | 7299 | 7300 | SNP |
| baal8e17 | 7303 | 7304 | SNP |
| BaH50I05 | 7307 | 7308 | CAPS |
| bastl28A0101 | 7311 | 7312 | CAPS |
| BaH39L18 | 7315 | 7316 | SNP |
| bags18e18 | 7319 | 7320 | SNP |
| WMCIE8 | — | — | SSR |

TABLE 9-1

| Name | Primers used (SEQ ID NO:) | | marker type |
|---|---|---|---|
| BaGS20L10 | 7323 | 7324 | SNP |
| BaSD15P22 | 7327 | 7328 | SNP |
| bags7b16 | 7331 | 7332 | SNP |
| BaAK34H02 | 7335 | 7336 | CAPS |
| BaAK22H13 | 7339 | 7340 | SNP |
| BaGS37P19 | 7343 | 7344 | CAPS |
| BaAL19P17 | 7347 | 7348 | CAPS |
| BaH41L14 | 7351 | 7352 | SNP |
| BaAK24H17 | 7355 | 7356 | SNP |
| bast21A0602 | 7359 | 7360 | SNP |
| BaAL27L20 | 7363 | 7364 | SNP |
| Bmac134 | — | — | SSR |
| cMWG682 | — | — | STS |
| bags34p10 | 7367 | 7368 | SNP |
| basd18b14 | 7371 | 7372 | size_poly (codominant) |
| bags38p20 | 7375 | 7376 | CAPS |
| BaAK41N22 | 7379 | 7380 | CAPS |
| BaAK21D17 | 7383 | 7384 | CAPS |
| BaAL29B07 | 7387 | 7388 | SNP |

TABLE 9-1-continued

| Name | Primers used (SEQ ID NO:) | | marker type |
|---|---|---|---|
| baak20o16 | 7391 | 7392 | SNP |
| bast42A0602 | 7395 | 7396 | CAPS |
| BaH36B07 | 7399 | 7400 | SNP |
| BaAK26L07 | 7403 | 7404 | CAPS |
| baal12a06 | 7407 | 7408 | CAPS |
| BaSD3C20 | 7411 | 7412 | SNP |
| bastl17G0113 | 7415 | 7416 | SNP |
| baak11h14 | 7419 | 7420 | SNP |
| baal12m14 | 7423 | 7424 | CAPS |
| baal33a18 | 7427 | 7428 | SNP |
| bah28a18 | 7431 | 7432 | SNP |
| bags39o04 | 7435 | 7436 | SNP |
| BaH48H04 | 7439 | 7440 | SNP |
| BaGS6B11 | 7443 | 7444 | size_poly (dominant) |
| bags4p16 | 7447 | 7448 | SNP |
| basd24j22 | 7451 | 7452 | SNP |
| basd16p15 | 7455 | 7456 | SNP |
| bags15k16 | 7459 | 7460 | SNP |
| bast23D1208 | 7463 | 7464 | SNP |
| BaAL32B22 | 7467 | 7468 | SNP |
| BaGS39D07 | 7471 | 7472 | size_poly (codominant) |
| BaH19L09 | 7475 | 7476 | SNP |
| bags38a17 | 7479 | 7480 | SNP |
| BaAK39I11 | 7483 | 7484 | SNP |
| BaSD3I24 | 7487 | 7488 | SNP |
| BaH35F01 | 7491 | 7492 | CAPS |
| BaAL30K02 | 7495 | 7496 | CAPS |
| bah13l23 | 7499 | 7500 | SNP |
| BaAL26H21 | 7503 | 7504 | SNP |
| BaGS22H22 | 7507 | 7508 | CAPS |
| bags13n11 | 7511 | 7512 | CAPS |
| bags1h03 | 7515 | 7516 | CAPS |

TABLE 9-2

| Name | Primers used (SEQ ID NO:) | | marker type |
|---|---|---|---|
| baak32l16 | 7519 | 7520 | SNP |
| baal19a12 | 7523 | 7524 | CAPS |
| BaAK45G16 | 7527 | 7528 | CAPS |
| BaGS37N19 | 7531 | 7532 | CAPS |
| baak3f03 | 7535 | 7536 | CAPS |
| bags5c02 | 7539 | 7540 | SNP |
| BaGS35P07 | 7543 | 7544 | SNP |
| HVM36 | — | — | SSR |
| bah45e07 | 7547 | 7548 | size_poly (codominant) |
| BaAK24B09 | 7551 | 7552 | SNP |
| bags33a11 | 7555 | 7556 | SNP |
| bah62i11 | 7559 | 7560 | CAPS |
| BaH56A24 | 7563 | 7564 | SNP |
| BaSD21D14 | 7567 | 7568 | SNP |
| basd1a17 | 7571 | 7572 | SNP |
| bah17n24 | 7575 | 7576 | CAPS |
| kr70G0113 | 7579 | 7580 | SNP |
| basd15f08 | 7583 | 7584 | SNP |
| BaGS4J04 | 7587 | 7588 | CAPS |
| baak33f06 | 7591 | 7592 | CAPS |
| basd14f16 | 7595 | 7596 | CAPS |
| BaH59K20 | 7599 | 7600 | CAPS |
| baal35h05 | 7603 | 7604 | SNP |
| BaGS20M01 | 7607 | 7608 | CAPS |
| BaH25N22 | 7611 | 7612 | size_poly (codominant) |
| baak14a24 | 7615 | 7616 | SNP |
| baak30d07 | 7619 | 7620 | SNP |
| bah11n18 | 7623 | 7624 | CAPS |
| kr14C0305 | 7627 | 7628 | SNP |
| baet18F0911 | 7631 | 7632 | CAPS |
| BaGS4J18 | 7635 | 7636 | CAPS |
| bast74C0705 | 7639 | 7640 | SNP |
| BaAL4G17 | 7643 | 7644 | SNP |
| bastl43H0515 | 7647 | 7648 | SNP |
| BaH58M22 | 7651 | 7652 | SNP |
| bags10i21 | 7655 | 7656 | SNP |
| bah20h16 | 7659 | 7660 | SNP |
| BaH17P13 | 7663 | 7664 | SNP |

TABLE 9-2-continued

| Name | Primers used (SEQ ID NO:) | | marker type |
|---|---|---|---|
| baak41d10 | 7667 | 7668 | CAPS |
| BaGS14F01 | 7671 | 7672 | CAPS |
| BaAK16E24 | 7675 | 7676 | SNP |
| BaSD18F09 | 7679 | 7680 | SNP |
| baet42A0501 | 7683 | 7684 | SNP |
| BaAK20L07 | 7687 | 7688 | SNP |
| baak16e20 | 7691 | 7692 | SNP |
| BaGS13N14 | 7695 | 7696 | size_poly (codominant) |
| basd13m14 | 7699 | 7700 | SNP |
| bags20g23 | 7703 | 7704 | SNP |
| basd1l17 | 1707 | 7708 | SNP |
| basd26l01 | 7711 | 7712 | SNP |
| BaAL37J18 | 7715 | 7716 | SNP |

TABLE 9-3

| Name | Primers used (SEQ ID NO:) | | marker type |
|---|---|---|---|
| bags7i05 | 7719 | 7720 | SNP |
| bah60m17 | 7723 | 7724 | SNP |
| bags21l01 | 7727 | 7728 | SNP |
| baet31E0109 | 7731 | 7732 | SNP |
| bags34m12 | 7735 | 7736 | SNP |
| bah50n02 | 7739 | 7740 | SNP |
| BaH50M11 | 7743 | 7744 | SNP |
| bast27E1010 | 7747 | 7748 | SNP |
| bags23c12 | 7751 | 7752 | SNP |
| bah51m11 | 7755 | 7756 | SNP |
| baak20d17 | 7759 | 7760 | SNP |
| bags23l21 | 7763 | 7764 | SNP |
| BaH52K04 | 7767 | 7768 | CAPS |
| BaAL37F24 | 7771 | 7772 | CAPS |
| bags23d01 | 7775 | 7776 | CAPS |
| BaSD11K22 | 7779 | 7780 | CAPS |
| baal29m02 | 7783 | 7784 | SNP |
| bah17e21 | 7787 | 7788 | SNP |
| bah56j18 | 7791 | 7792 | SNP |
| bags38n06 | 7795 | 7796 | CAPS |
| baet44D1208 | 7799 | 7800 | CAPS |
| BaAL34O13 | 7803 | 7804 | SNP |
| BaGS4N05 | 7807 | 7808 | SNP |
| BaSD15P20 | 7811 | 7812 | SNP |
| baal13d11 | 7815 | 7816 | CAPS |
| bah27g02 | 7819 | 7820 | SNP |
| basd27m10 | 7823 | 7824 | SNP |
| basd23f16 | 7827 | 7828 | SNP |
| bah16i19 | 7831 | 7832 | SNP |
| BaH50I20 | 7835 | 7836 | SNP |
| BaH34M23 | 7839 | 7840 | CAPS |
| bah28b24 | 7843 | 7844 | SNP |
| BaH50P13 | 7847 | 7848 | CAPS |
| basd11m16 | 7851 | 7852 | CAPS |
| bags10p15 | 7855 | 7856 | CAPS |
| bags4g01 | 7859 | 7860 | CAPS |
| bags10k08 | 7863 | 7864 | CAPS |
| bags5e16 | 7867 | 7868 | CAPS |
| bags18l02 | 7871 | 7872 | CAPS |
| baak44k02 | 7875 | 7876 | CAPS |
| bags35a20 | 7879 | 7880 | CAPS |
| BaGS26M11 | 7883 | 7884 | CAPS |
| basd14h21 | 7887 | 7888 | CAPS |
| BaSD13D12 | 7891 | 7892 | CAPS |
| bags38k23 | 7895 | 7896 | size_poly (codominant) |
| BaH42E05 | 7899 | 7900 | CAPS |
| bastl55A0701 | 7903 | 7904 | CAPS |
| bags13g18 | 7907 | 7908 | SNP |
| BaH15D23 | 7911 | 7912 | SNP |
| kr28B0604 | 7915 | 7916 | CAPS |
| bags10f01 | 7919 | 7920 | size_poly (codominant) |

TABLE 9-4

| Name | Primers used (SEQ ID NO:) | | marker type |
|---|---|---|---|
| BaGS33I07 | 7923 | 7924 | SNP |
| BaSD27B02 | 7927 | 7928 | SNP |
| BaGS30N12 | 7931 | 7932 | SNP |
| basd3h13 | 7935 | 7936 | SNP |
| BaGS37L19 | 7939 | 7940 | SNP |
| bah16g18 | 7943 | 7944 | CAPS |
| bags20i15 | 7947 | 7948 | SNP |
| bags35c23 | 7951 | 7952 | CAPS |
| bah56k07 | 7955 | 7956 | SNP |
| bags37d02 | 7959 | 7960 | SNP |
| BaAK19K05 | 7963 | 7964 | CAPS |
| bah11i16 | 7967 | 7968 | CAPS |
| bags22l23 | 7971 | 7972 | SNP |
| kr33A0901 | 7975 | 7976 | SNP |
| bastl38C0606 | 7979 | 7980 | SNP |
| baak11j13 | 7983 | 7984 | SNP |
| BaH58E19 | 7987 | 7988 | SNP |
| BaGS31G22 | 7991 | 7992 | SNP |
| bah37h01 | 7995 | 7996 | SNP |
| BaAL29P13 | 7999 | 8000 | SNP |
| bags39a22 | 8003 | 8004 | SNP |
| bah19g10 | 8007 | 8008 | SNP |
| BaAL31A14 | 8011 | 8012 | SNP |
| BaH50G15 | 8015 | 8016 | SNP |
| BaH51M12 | 8019 | 8020 | SNP |
| bags18k22 | 8023 | 8024 | SNP |
| BaGS20N21 | 8027 | 8028 | SNP |
| BaSD17O21 | 8031 | 8032 | SNP |
| BaH37G17 | 8035 | 8036 | SNP |
| bags30l22 | 8039 | 8040 | SNP |
| baak22b17 | 8043 | 8044 | CAPS |
| bags20f22 | 8047 | 8048 | CAPS |
| bast72G0113 | 8051 | 8052 | SNP |
| BaH30B05 | 8055 | 8056 | SNP |
| BaH60B14 | 8059 | 8060 | SNP |
| BaH17B16 | 8063 | 8064 | SNP |
| basd12n23 | 8067 | 8068 | SNP |
| BaH61A21 | 8071 | 8072 | SNP |
| BaAK19H17 | 8075 | 8076 | SNP |
| bah47l12 | 8079 | 8080 | SNP |
| baak18p11 | 8083 | 8084 | SNP |
| baet29H0715 | 8087 | 8088 | SNP |
| BaH13D11 | 8091 | 8092 | SNP |
| baet39D1107 | 8095 | 8096 | SNP |
| BaH53E15 | 8099 | 8100 | SNP |
| bags32o15 | 8103 | 8104 | SNP |
| bast48A0701 | 8107 | 8108 | SNP |
| bast62D0907 | 8111 | 8112 | SNP |
| BaH45P22 | 8115 | 8116 | SNP |
| BaGS32L16 | 8119 | 8120 | SNP |
| BaAK30J05 | 8123 | 8124 | SNP |

TABLE 9-5

| Name | Primers used (SEQ ID NO:) | | marker type |
|---|---|---|---|
| bah52a14 | 8127 | 8128 | SNP |
| bah58i22 | 8131 | 8132 | SNP |
| BaH56L16 | 8135 | 8136 | SNP |
| bah52a21 | 8139 | 8140 | SNP |
| BaSD14G11 | 8143 | 8144 | SNP |
| bags6a03 | 8147 | 8148 | SNP |
| bast72E0109 | 8151 | 8152 | SNP |
| bags21a21 | 8155 | 8156 | SNP |
| BaH58P13 | 8159 | 8160 | SNP |
| bah27n22 | 8163 | 8164 | SNP |
| bags20c13 | 8167 | 8168 | SNP |
| bags30i14 | 8171 | 8172 | SNP |
| BaAK17E11 | 8175 | 8176 | SNP |
| baal1d17 | 8179 | 8180 | CAPS |
| bags22f06 | 8183 | 8184 | CAPS |
| baal10l01 | 8187 | 8188 | SNP |
| baak26e17 | 8191 | 8192 | SNP |
| bah16a03 | 8195 | 8196 | CAPS |
| BaAL11F18 | 8199 | 8200 | CAPS |

TABLE 9-5-continued

| Name | Primers used (SEQ ID NO:) | | marker type |
|---|---|---|---|
| BaAK29E10 | 8203 | 8204 | CAPS |
| bags32d21 | 8207 | 8208 | SNP |
| bah54j22 | 8211 | 8212 | SNP |
| baak16f14 | 8215 | 8216 | CAPS |
| baak44c12 | 8219 | 8220 | CAPS |
| bah13f11 | 8223 | 8224 | SNP |
| baal39m19 | 8227 | 8228 | CAPS |
| baak4e02 | 8231 | 8232 | CAPS |
| baak46f04 | 8235 | 8236 | CAPS |
| BaAK13N23 | 8239 | 8240 | size_poly (codominant) |
| BaGS20E09 | 8243 | 8244 | size_poly (codominant) |
| baal4f01 | 8247 | 8248 | CAPS |
| BaSD19I17 | 8251 | 8252 | CAPS |
| baal4l21 | 8255 | 8256 | SNP |
| BaAK19P01 | 8259 | 8260 | CAPS |
| BaAK31O14 | 8263 | 8264 | SNP |
| BaH26P22 | 8267 | 8268 | CAPS |
| baal13d17 | 8271 | 8272 | SNP |
| bags22j12 | 8275 | 8276 | SNP |
| bags33p05 | 8279 | 8280 | SNP |
| bags38j07 | 8283 | 8284 | SNP |
| kr59F0311 | 8287 | 8288 | CAPS |
| baal13e10 | 8291 | 8292 | CAPS |
| bags15d19 | 8295 | 8296 | SNP |
| BaGS5K11 | 8299 | 8300 | CAPS |
| BaGS10J14 | 8303 | 8304 | CAPS |
| baak41m17 | 8307 | 8308 | CAPS |
| bah57o03 | 8311 | 8312 | SNP |
| baak41d22 | 8315 | 8316 | CAPS |
| bah61c16 | 8319 | 8320 | CAPS |
| BaAL7M13 | 8323 | 8324 | CAPS |
| BaAK31F11 | 8327 | 8328 | CAPS |

TABLE 9-6

| Name | Primers used (SEQ ID NO:) | | marker type |
|---|---|---|---|
| basd22k05 | 8331 | 8332 | Size_poly (codominant) |
| basd3p19 | 8335 | 8336 | Size_poly (dominant) |
| baak17o09 | 8339 | 8340 | CAPS |
| baal33d23 | 8343 | 8344 | CAPS |
| BaAK12F04 | 8347 | 8348 | SNP |
| bah53j16 | 8351 | 8352 | SNP |
| BaSD2E24 | 8355 | 8356 | SNP |
| bags39h08 | 8359 | 8360 | SNP |
| BaSD1N02 | 8363 | 8364 | SNP |
| bags20m21 | 8367 | 8368 | SNP |
| baal10h19 | 8371 | 8372 | SNP |
| basd12m11 | 8375 | 8376 | SNP |
| bah29d24 | 8379 | 8380 | SNP |
| BaGS39P09 | 8383 | 8384 | SNP |
| BaGS31F17 | 8387 | 8388 | SNP |
| BaGS23D08 | 8391 | 8392 | SNP |
| bags39d15 | 8395 | 8396 | SNP |
| BaGS34I17 | 8399 | 8400 | SNP |
| BaH32N02 | 8403 | 8404 | SNP |
| BaSD18H19 | 8407 | 8408 | SNP |
| bast63A0101 | 8411 | 8412 | SNP |
| BaH50N04 | 8415 | 8416 | SNP |
| baal4a13 | 8419 | 8420 | SNP |
| baal41l18 | 8423 | 8424 | SNP |
| BaH31A03 | 8427 | 8428 | CAPS |
| bastl39A0901 | 8431 | 8432 | CAPS |
| baet46D0507 | 8435 | 8436 | CAPS |
| baal27e20 | 8439 | 8440 | SNP |
| bags37l16 | 8443 | 8444 | SNP |
| baak34o06 | 8447 | 8448 | SNP |
| BaAL30I11 | 8451 | 8452 | SNP |
| BaH62C15 | 8455 | 8456 | SNP |
| basd12i15 | 8459 | 8460 | CAPS |
| BaAK40I03 | 8463 | 8464 | CAPS |
| BaAK23E14 | 8467 | 8468 | CAPS |
| BaAL21F11 | 8471 | 8472 | size_poly (codominant) |
| BaAK16L19 | 8475 | 8476 | SNP |
| baal27a24 | 8479 | 8480 | CAPS |

TABLE 9-6-continued

| Name | Primers used (SEQ ID NO:) | | marker type |
|---|---|---|---|
| kr41H0315 | 8483 | 8484 | SNP |
| BaH62I23 | 8487 | 8488 | SNP |
| bah52i24 | 8491 | 8492 | SNP |
| bastl33A0301 | 8495 | 8496 | SNP |
| BaH28J15 | 8499 | 8500 | CAPS |
| bastl56A0301 | 8503 | 8504 | SNP |
| baal39a03 | 8507 | 8508 | SNP |
| baal5b15 | 8511 | 8512 | CAPS |
| baak34l03 | 8515 | 8516 | SNP |
| BaSD20J15 | 8519 | 8520 | SNP |
| bastl30F0711 | 8523 | 8524 | SNP |
| baal11p07 | 8527 | 8528 | size_poly (codominant) |
| BaH28J10 | 8531 | 8532 | CAPS |

TABLE 9-7

| Name | Primers used (SEQ ID NO:) | | marker type |
|---|---|---|---|
| baak34p05 | 8535 | 8536 | CAPS |
| bast56G0713 | 8539 | 8540 | SNP |
| bah27d18 | 8543 | 8544 | CAPS |
| bastl02H0715 | 8547 | 8548 | SNP |
| bah37e07 | 8551 | 8552 | size_poly (codominant) |
| bags4d18 | 8555 | 8556 | size_poly (codominant) |
| bags8i05 | 8559 | 8560 | SNP |
| BaH50A15 | 8563 | 8564 | CAPS |
| kr06D0907 | 8567 | 8568 | size_poly (codominant) |
| basd18m04 | 8571 | 8572 | SNP |
| basd2f22 | 8575 | 8576 | CAPS |
| BaH47K06 | 8579 | 8580 | CAPS |
| BaH28G01 | 8583 | 8584 | SNP |
| BaSD1M13 | 8587 | 8588 | SNP |
| bags37h19 | 8591 | 8592 | SNP |
| bags29b01 | 8595 | 8596 | CAPS |
| BaH21A10 | 8599 | 8600 | SNP |
| bags23d06 | 8603 | 8604 | SNP |
| basd2a21 | 8607 | 8608 | CAPS |
| BaGS19G10 | 8611 | 8612 | SNP |
| cMWG699 | — | — | STS |
| bah11b24 | 8615 | 8616 | SNP |
| bast39D0408 | 8619 | 8620 | SNP |
| baak33e08 | 8623 | 8624 | SNP |
| bags33m15 | 8627 | 8628 | CAPS |
| BaAL33B08 | 8631 | 8632 | SNP |
| bags39e12 | 8635 | 8636 | SNP |
| baak41e24 | 8639 | 8640 | CAPS |
| bah63c08 | 8643 | 8644 | CAPS |
| bags33n09 | 8647 | 8648 | SNP |
| Bmag125 | — | — | SSR |
| baal32h09 | 8651 | 8652 | SNP |
| BaAK20O17 | 8655 | 8656 | SNP |
| BaGS32G10 | 8659 | 8660 | SNP |
| baet33E1210 | 8663 | 8664 | SNP |
| BaH50O08 | 8667 | 8668 | SNP |
| bast46F0711 | 8671 | 8672 | SNP |
| BaH16F05 | 8675 | 8676 | SNP |
| baal17e18 | 8679 | 8680 | CAPS |
| cMWG694 | — | — | STS |
| bah13o11 | 8683 | 8684 | SNP |
| basd11g04 | 8687 | 8688 | CAPS |
| bah32c06 | 8691 | 8692 | size_poly (codominant) |
| basd27i13 | 8695 | 8696 | SNP |
| kr14F0911 | 8699 | 8700 | size_poly (codominant) |
| BaGS36A04 | 8703 | 8704 | CAPS |
| bags13a16 | 8707 | 8708 | CAPS |
| bags26e20 | 8711 | 8712 | SNP |
| baet45G1214 | 8715 | 8716 | SNP |
| BaAK35F14 | 8719 | 8720 | CAPS |
| BaAK23N21 | 8723 | 8724 | size_poly (codominant) |

TABLE 9-8

| Name | Primers used (SEQ ID NO:) | | marker type |
|---|---|---|---|
| basd13j22 | 8727 | 8728 | SNP |
| BaAK46E10 | 8731 | 8732 | SNP |
| bastl55F0812 | 8735 | 8736 | SNP |
| baak46l06 | 8739 | 8740 | CAPS |
| BaAL2D11 | 8743 | 8744 | size_poly (codominant) |
| baak15p17 | 8747 | 8748 | CAPS |
| BaGS33J16 | 8751 | 8752 | CAPS |
| bags7p21 | 8755 | 8756 | CAPS |
| BaAK22E05 | 8759 | 8760 | CAPS |
| bah42m05 | 8763 | 8764 | CAPS |
| BaAK25L01 | 8767 | 8768 | CAPS |
| bags39e24 | 8771 | 8772 | CAPS |
| BaH56N24 | 8775 | 8776 | size_poly (codominant) |
| baak44i12 | 8779 | 8780 | SNP |
| bah21j03 | 8783 | 8784 | SNP |
| kr71B0103 | 8787 | 8788 | SNP |
| BaGS16D15 | 8791 | 8792 | CAPS |
| baak21p23 | 8795 | 8796 | SNP |
| BaGS6G09 | 8799 | 8800 | SNP |
| BaSD15M02 | 8803 | 8804 | SNP |
| basd13f02 | 8807 | 8808 | SNP |
| BaH19F21 | 8811 | 8812 | CAPS |
| bags20b10 | 8815 | 8816 | CAPS |
| bah26j10 | 8819 | 8820 | SNP |
| bast65G0113 | 8823 | 8824 | SNP |
| baak4k13 | 8827 | 8828 | SNP |
| baal19j23 | 8831 | 8832 | size_poly (codominant) |
| bags34h11 | 8835 | 8836 | SNP |
| bags37j03 | 8839 | 8840 | SNP |
| baal15e13 | 8843 | 8844 | size_poly (codominant) |
| BaAL5O10 | 8847 | 8848 | size_poly (dominant) |
| BaGS29J10 | 8851 | 8852 | CAPS |
| bah22o08 | 8855 | 8856 | SNP |
| bags6k13 | 8859 | 8860 | SNP |
| bastl43C0705 | 8863 | 8864 | SNP |
| BaAL4D10 | 8867 | 8868 | size_poly (codominant) |
| basd12n12 | 8871 | 8872 | CAPS |
| bags23h03 | 8875 | 8876 | SNP |
| bags6l02 | 8879 | 8880 | CAPS |
| bast63B0703 | 8883 | 8884 | SNP |
| BaSD13E02 | 8887 | 8888 | SNP |
| BaSD14P15 | 8891 | 8892 | CAPS |
| bah13a17 | 8895 | 8896 | SNP |
| BaH50L23 | 8899 | 8900 | SNP |
| bags19g04 | 8903 | 8904 | CAPS |
| bast73E0210 | 8907 | 8908 | SNP |
| BaH50O21 | 8911 | 8912 | SNP |
| basd21g05 | 8915 | 8916 | SNP |
| bah33p11 | 8919 | 8920 | CAPS |
| baal5i19 | 8923 | 8924 | SNP |
| bah16e04 | 8927 | 8928 | SNP |

TABLE 9-9

| Name | Primers used (SEQ ID NO:) | | marker type |
|---|---|---|---|
| baak32p24 | 8931 | 8932 | SNP |
| EBmac415 | — | — | SSR |
| bags38f12 | 8935 | 8936 | CAPS |
| basd26p18 | 8939 | 8940 | CAPS |
| baak45h16 | 8943 | 8944 | CAPS |
| bah28p12 | 8947 | 8948 | CAPS |
| bah19a10 | 8951 | 8952 | CAPS |
| baak13d11 | 8955 | 8956 | SNP |
| bah49p10 | 8959 | 8960 | SNP |
| baal32n15 | 8963 | 8964 | SNP |
| bast09C0305 | 8967 | 8968 | size_poly (codominant) |
| basd16l09 | 8971 | 8972 | CAPS |
| BaAK22H04 | 8975 | 8976 | SNP |
| BaGS15J13 | 8979 | 8980 | SNP |
| kr66G0414 | 8983 | 8984 | SNP |
| BaSD22C07 | 8987 | 8988 | SNP |
| kr71C1105 | 8991 | 8992 | SNP |
| bags34i11 | 8995 | 8996 | SNP |
| BaH23K17 | 8999 | 9000 | SNP |

TABLE 9-9-continued

| Name | Primers used (SEQ ID NO:) | | marker type |
|---|---|---|---|
| bast39D0107 | 9003 | 9004 | SNP |
| BaH44K24 | 9007 | 9008 | SNP |
| BaGS18N21 | 9011 | 9012 | CAPS |
| baak32k15 | 9015 | 9016 | SNP |
| bah61a13 | 9019 | 9020 | SNP |
| bags35n11 | 9023 | 9024 | SNP |
| BaAK24I03 | 9027 | 9028 | SNP |
| baal4h20 | 9031 | 9032 | size_poly (codominant) |
| BaH28N23 | 9035 | 9036 | SNP |
| bags10e13 | 9039 | 9040 | SNP |
| baak27i10 | 9043 | 9044 | size_poly (codominant) |
| bags19d13 | 9047 | 9048 | SNP |
| baak19d04 | 9051 | 9052 | SNP |
| BaAL34O19 | 9055 | 9056 | SNP |
| baal12l02 | 9059 | 9060 | CAPS |
| BaAK1P04 | 9063 | 9064 | SNP |
| baak35m13 | 9067 | 9068 | SNP |
| bags35a12 | 9071 | 9072 | CAPS |
| bah41n09 | 9075 | 9076 | SNP |
| BaGS23I12 | 9079 | 9080 | SNP |
| BaH16P20 | 9083 | 9084 | SNP |
| BaAK42L17 | 9087 | 9088 | CAPS |
| baak36d23 | 9091 | 9092 | CAPS |
| bast78C1006 | 9095 | 9096 | CAPS |
| BaH45O16 | 9099 | 9100 | SNP |
| bah21h09 | 9103 | 9104 | SNP |
| bah58p22 | 9107 | 9108 | SNP |
| bags20l19 | 9111 | 9112 | SNP |
| bah13i10 | 9115 | 9116 | SNP |
| BaAK36B07 | 9119 | 9120 | CAPS |
| baak26b05 | 9123 | 9124 | CAPS |
| baal7c15 | 9127 | 9128 | SNP |

TABLE 9-10

| Name | Primers used (SEQ ID NO:) | | marker type |
|---|---|---|---|
| bah63f05 | 9131 | 9132 | SNP |
| bags15l16 | 9135 | 9136 | SNP |
| BaGS6N10 | 9139 | 9140 | CAPS |
| bah41e10 | 9143 | 9144 | SNP |
| BaH54D08 | 9147 | 9148 | SNP |
| baak18c01 | 9151 | 9152 | SNP |
| basd21o07 | 9155 | 9156 | SNP |
| bah41b23 | 9159 | 9160 | CAPS |
| basd18g15 | 9163 | 9164 | size_poly (codominant) |
| baak43o03 | 9167 | 9168 | SNP |
| bastl30D0408 | 9171 | 9172 | CAPS |
| bah17p16 | 9175 | 9176 | CAPS |
| baal13f18 | 9179 | 9180 | SNP |
| bags18i22 | 9183 | 9184 | SNP |
| bags9b02 | 9187 | 9188 | SNP |
| bah11e22 | 9191 | 9192 | SNP |
| bah58h09 | 9195 | 9196 | SNP |
| basd16e16 | 9199 | 9200 | CAPS |
| BaAK4C12 | 9203 | 9204 | SNP |
| bags37a05 | 9207 | 9208 | SNP |
| bags9p10 | 9211 | 9212 | CAPS |
| baak24m01 | 9215 | 9216 | size_poly (codominant) |
| basd27d09 | 9219 | 9220 | CAPS |
| baak34a14 | 9223 | 9224 | size_poly (codominant) |
| baak36a20 | 9227 | 9228 | SNP |
| BaSD17P09 | 9231 | 9232 | CAPS |
| bags5m04 | 9235 | 9236 | CAPS |
| BaGS5E06 | 9239 | 9240 | CAPS |
| MWG2076 | — | — | STS |
| bags15f03 | 9243 | 9244 | size_poly (dominant) |
| bags18j23 | 9247 | 9248 | size_poly (dominant) |
| baal13m04 | 9251 | 9252 | SNP |
| bags9o24 | 9255 | 9256 | SNP |
| kr49E0610 | 9259 | 9260 | CAPS |
| bah12h16 | 9263 | 9264 | SNP |
| baak33n16 | 9267 | 9268 | SNP |
| BaGS22E05 | 9271 | 9272 | CAPS |
| bah26n01 | 9275 | 9276 | SNP |

TABLE 9-10-continued

| Name | Primers used (SEQ ID NO:) | | marker type |
|---|---|---|---|
| BaGS39E07 | 9279 | 9280 | SNP |
| BaH45O03 | 9283 | 9284 | CAPS |
| BaH38A09 | 9287 | 9288 | SNP |

TABLE 10-1

| Name | Primers used (SEQ ID NO:) | | marker type |
|---|---|---|---|
| BaAL15P01 | 9291 | 9292 | SNP |
| BaAK42D06 | 9295 | 9296 | size_poly (dominant) |
| bags12k16 | 9299 | 9300 | size_poly (codominant) |
| BaAL36H19 | 9303 | 9304 | size_poly (codominant) |
| bags1d06 | 9307 | 9308 | SNP |
| bast18A0602 | 9311 | 9312 | SNP |
| basd22i04 | 9315 | 9316 | CAPS |
| BaGS31M01 | 9319 | 9320 | CAPS |
| BaH63H24 | 9323 | 9324 | SNP |
| basd15n13 | 9327 | 9328 | CAPS |
| MWG848 | — | — | STS |
| BaAK13C16 | 9331 | 9332 | SNP |
| BaGS32C19 | 9335 | 9336 | SNP |
| baak36f08 | 9339 | 9340 | SNP |
| bastl04C0406 | 9343 | 9344 | CAPS |
| bastl42D1107 | 9347 | 9348 | SNP |
| BaGS31B20 | 9351 | 9352 | size_poly (codominant) |
| baak39l17 | 9355 | 9356 | CAPS |
| BaAL17J24 | 9359 | 9360 | CAPS |
| bah15p03 | 9363 | 9364 | CAPS |
| baak20g06 | 9367 | 9368 | SNP |
| baal22c16 | 9371 | 9372 | CAPS |
| baak46o05 | 9375 | 9376 | SNP |
| basd15h22 | 9379 | 9380 | SNP |
| BaSD19C07 | 9383 | 9384 | SNP |
| bags22i13 | 9387 | 9388 | CAPS |
| baak39a14 | 9391 | 9392 | SNP |
| bah31e12 | 9395 | 9396 | SNP |
| BaSD15L22 | 9399 | 9400 | SNP |
| BaGS20D21 | 9403 | 9404 | CAPS |
| bags39o21 | 9407 | 9408 | CAPS |
| basd21j11 | 9411 | 9412 | SNP |
| BaH48C10 | 9415 | 9416 | SNP |
| BaH54J07 | 9419 | 9420 | SNP |
| BaSD19H23 | 9423 | 9424 | CAPS |
| baak35n06 | 9427 | 9428 | CAPS |
| bags35b22 | 9431 | 9432 | CAPS |
| BaAK30H06 | 9435 | 9436 | CAPS |
| BaAL15M07 | 9439 | 9440 | CAPS |
| BaGS20N02 | 9443 | 9444 | CAPS |
| BaAL19L12 | 9447 | 9448 | CAPS |
| bags25b05 | 9451 | 9452 | CAPS |
| HvLTPPB | — | — | SSR |
| baal1h04 | 9455 | 9456 | CAPS |
| baet46B0903 | 9459 | 9460 | SNP |
| BaGS19F16 | 9463 | 9464 | SNP |
| baak13g18 | 9467 | 9468 | SNP |
| BaH45N12 | 9471 | 9472 | CAPS |
| bast74H0216 | 9475 | 9476 | SNP |
| bah24l06 | 9479 | 9480 | size_poly (dominant) |
| BaAK45C14 | 9483 | 9484 | SNP |

TABLE 10-2

| Name | Primers used (SEQ ID NO:) | | marker type |
|---|---|---|---|
| baal5k12 | 9487 | 9488 | CAPS |
| kr63F0111 | 9491 | 9492 | SNP |
| baak13h18 | 9495 | 9496 | SNP |
| baak12j16 | 9499 | 9500 | CAPS |
| BaAK28J20 | 9503 | 9504 | CAPS |
| BaH27G14 | 9507 | 9509 | CAPS |
| BaH49B13 | 9511 | 9512 | SNP |
| BaGS35A09 | 9515 | 9516 | CAPS |
| BaGS38L24 | 9519 | 9520 | size_poly (dominant) |

TABLE 10-2-continued

| Name | Primers used (SEQ ID NO:) | | marker type |
|---|---|---|---|
| BaAK43H20 | 9523 | 9524 | CAPS |
| bast16A0802 | 9527 | 9528 | SNP |
| basd18k01 | 9531 | 9532 | SNP |
| BaH58D17 | 9535 | 9536 | SNP |
| BaAK30M07 | 9539 | 9540 | CAPS |
| bags6a04 | 9543 | 9544 | CAPS |
| kr15H0915 | 9547 | 9548 | CAPS |
| bags26d01 | 9551 | 9552 | SNP |
| basd14k04 | 9555 | 9556 | SNP |
| BaSD24D11 | 9559 | 9560 | SNP |
| BaH53L10 | 9563 | 9564 | SNP |
| BaH60D22 | 9567 | 9568 | size_poly (codominant) |
| BaSD1G06 | 9571 | 9572 | size_poly (codominant) |
| BaAK21L13 | 9575 | 9576 | size_poly (codominant) |
| bah57m03 | 9579 | 9580 | SNP |
| baal30b10 | 9583 | 9584 | SNP |
| bah62n16 | 9587 | 9588 | SNP |
| BaGS22F15 | 9591 | 9592 | SNP |
| BaH50J14 | 9595 | 9596 | SNP |
| bah19d23 | 9599 | 9600 | SNP |
| bags38c06 | 9603 | 9604 | SNP |
| BaGS25N05 | 9607 | 9608 | SNP |
| bastl29B0503 | 9611 | 9612 | SNP |
| baak27d01 | 9615 | 9616 | CAPS |
| baak43n21 | 9619 | 9620 | SNP |
| BaAL4F05 | 9623 | 9624 | size_poly (codominant) |
| baal4a06 | 9627 | 9628 | SNP |
| bast17D1008 | 9631 | 9632 | SNP |
| BaGS16B17 | 9635 | 9636 | SNP |
| BaGS27P18 | 9639 | 9640 | CAPS |
| BaGS4J14 | 9643 | 9644 | CAPS |
| BaAK16B19 | 9647 | 9648 | SNP |
| baal40p07 | 9651 | 9652 | SNP |
| bah49c19 | 9655 | 9656 | SNP |
| bast58C0406 | 9659 | 9660 | SNP |
| BaAK35M24 | 9663 | 9664 | SNP |
| bags19h13 | 9667 | 9668 | SNP |
| bah57c21 | 9671 | 9672 | SNP |
| BaH53P15 | 9675 | 9676 | SNP |
| BaGS20A10 | 9679 | 9680 | SNP |
| bast02D0808 | 9683 | 9684 | SNP |
| bags31c04 | 9687 | 9688 | SNP |

TABLE 10-3

| Name | Primers used (SEQ ID NO:) | | marker type |
|---|---|---|---|
| BaH32J06 | 9691 | 9692 | CAPS |
| bah60o22 | 9695 | 9696 | SNP |
| BaH50C16 | 9699 | 9700 | SNP |
| BaH57K23 | 9703 | 9704 | CAPS |
| bags21g23 | 9707 | 9708 | size_poly (codominant) |
| HVM9 | — | — | SSR |
| Bmac67 | — | — | SSR |
| baak43e04 | 9711 | 9712 | SNP |
| kr17G1113 | 9715 | 9716 | SNP |
| bags19k19 | 9719 | 9720 | SNP |
| baak38b13 | 9723 | 9724 | SNP |
| baak1d12 | 9727 | 9728 | SNP |
| BaH28M14 | 9731 | 9732 | SNP |
| BaH48I15 | 9735 | 9736 | SNP |
| basd27h23 | 9739 | 9740 | SNP |
| BaAK21A11 | 9743 | 9744 | SNP |
| bast04B0804 | 9747 | 9748 | SNP |
| bah45f13 | 9751 | 9752 | SNP |
| BaAL8J18 | 9755 | 9756 | SNP |
| BaGS9D01 | 9759 | 9760 | SNP |
| baal12d12 | 9763 | 9764 | CAPS |
| baal4i06 | 9767 | 9768 | SNP |
| bah26i01 | 9771 | 9772 | SNP |
| BaGS15C17 | 9775 | 9776 | SNP |
| baak1k08 | 9779 | 9780 | SNP |
| bags9b03 | 9783 | 9784 | SNP |
| baet42G1214 | 9787 | 9788 | SNP |
| bah18d12 | 9791 | 9792 | SNP |

TABLE 10-3-continued

| Name | Primers used (SEQ ID NO:) | | marker type |
|---|---|---|---|
| BaSD14G02 | 9795 | 9796 | CAPS |
| bags22b22 | 9799 | 9800 | SNP |
| bah13f10 | 9803 | 9804 | size_poly (codominant) |
| baal36g05 | 9807 | 9808 | SNP |
| bags33j15 | 9811 | 9812 | SNP |
| BaAL12H04 | 9815 | 9816 | size_poly (codominant) |
| BaGS16I18 | 9819 | 9820 | CAPS |
| bast61D0707 | 9823 | 9824 | SNP |
| bah11k22 | 9827 | 9828 | CAPS |
| baak32p21 | 9831 | 9832 | CAPS |
| bah63l21 | 9835 | 9836 | CAPS |
| BaGS38D03 | 9839 | 9840 | CAPS |
| BaSD23A04 | 9843 | 9844 | SNP |
| BaSD14C15 | 9847 | 9848 | SNP |
| bast63C0105 | 9851 | 9852 | SNP |
| bast23C1105 | 9855 | 9856 | SNP |
| bags23b01 | 9859 | 9860 | CAPS |
| bags29c09 | 9863 | 9864 | CAPS |
| bags6b06 | 9867 | 9868 | CAPS |
| BaAK27G06 | 9871 | 9872 | CAPS |
| BaAK39D07 | 9875 | 9876 | CAPS |
| BaGS20G21 | 9879 | 9880 | CAPS |
| bastl22E0810 | 9883 | 9884 | size_poly (codominant) |

TABLE 10-4

| Name | Primers used (SEQ ID NO:) | | marker type |
|---|---|---|---|
| bah11m03 | 9887 | 9888 | CAPS |
| BaAL3C04 | 9891 | 9892 | CAPS |
| BaAL19H10 | 9895 | 9896 | SNP |
| bags24n16 | 9899 | 9900 | CAPS |
| BaSD24B15 | 9903 | 9904 | SNP |
| bah48n17 | 9907 | 9908 | SNP |
| bags9i05 | 9911 | 9912 | SNP |
| bags1l22 | 9915 | 9916 | SNP |
| bah62p18 | 9919 | 9920 | SNP |
| bah55n21 | 9923 | 9924 | SNP |
| bah44a05 | 9927 | 9928 | SNP |
| bah19c13 | 9931 | 9932 | SNP |
| baal12b04 | 9935 | 9936 | CAPS |
| Bmag136 | — | — | SSR |
| Bmac209 | — | — | SSR |
| BaAK28A10 | 9939 | 9940 | size_poly (dominant) |
| kr28B0703 | 9943 | 9944 | SNP |
| bastl50C0606 | 9947 | 9948 | SNP |
| BaGS36B01 | 9951 | 9952 | CAPS |
| BaH19A05 | 9955 | 9956 | SNP |
| baal10c06 | 9959 | 9960 | SNP |
| bags19p04 | 9963 | 9964 | SNP |
| BaAK21A17 | 9967 | 9968 | SNP |
| bah20j14 | 9971 | 9972 | SNP |
| BaAK19A03 | 9975 | 9976 | SNP |
| BaGS30E19 | 9979 | 9980 | SNP |
| BaAK28C21 | 9983 | 9984 | size_poly (codominant) |
| bags11o14 | 9987 | 9988 | SNP |
| BaGS13P22 | 9991 | 9992 | SNP |
| kr27A1101 | 9995 | 9996 | SNP |
| HVM27 | — | — | SSR |
| baal12i18 | 9999 | 10000 | CAPS |
| BaAL8G07 | 10003 | 10004 | CAPS |
| bast58F0412 | 10007 | 10008 | SNP |
| bags3f23 | 10011 | 10012 | CAPS |
| baal4m06 | 10015 | 10016 | CAPS |
| baal32p23 | 10019 | 10020 | SNP |
| basd23m17 | 10023 | 10024 | SNP |
| bastl30E0509 | 10027 | 10028 | SNP |
| bah44b0B | 10031 | 10032 | SNP |
| BaGS14N10 | 10035 | 10036 | SNP |
| BaGS32B13 | 10039 | 10040 | SNP |
| BaH30B03 | 10043 | 10044 | SNP |
| basd1l23 | 10047 | 10048 | CAPS |
| basd11o06 | 10051 | 10052 | SNP |
| bah17f24 | 10055 | 10056 | SNP |
| BaAK26L17 | 10059 | 10060 | SNP |

TABLE 10-4-continued

| Name | Primers used (SEQ ID NO:) | | marker type |
|---|---|---|---|
| bags23f03 | 10063 | 10064 | SNP |
| bags20o06 | 10067 | 10068 | SNP |
| bags19n12 | 10071 | 10072 | SNP |
| baal12a09 | 10075 | 10076 | size_poly (codominant) |

TABLE 10-5

| Name | Primers used (SEQ ID NO:) | | marker type |
|---|---|---|---|
| bast14F0612 | 10079 | 10080 | SNP |
| baak13p20 | 10083 | 10084 | CAPS |
| BaGS16K13 | 10087 | 10088 | SNP |
| baak22c16 | 10091 | 10092 | SNP |
| baal40m06 | 10095 | 10096 | SNP |
| BaH29I03 | 10099 | 10100 | CAPS |
| bah16h01 | 10103 | 10104 | CAPS |
| bah57a11 | 10107 | 10108 | SNP |
| BaH41E23 | 10111 | 10112 | SNP |
| baal11c11 | 10115 | 10116 | size_poly (dominant) |
| BaSD14L18 | 10119 | 10120 | SNP |
| bah14d17 | 10123 | 10124 | SNP |
| BaGS1N17 | 10127 | 10128 | SNP |
| bags27h17 | 10131 | 10132 | CAPS |
| bah47p22 | 10135 | 10136 | SNP |
| BaH50A16 | 10139 | 10140 | SNP |
| bags7b20 | 10143 | 10144 | SNP |
| bags22a02 | 10147 | 10148 | SNP |
| HvBRI1 | — | — | dCAPS |
| basd12g02 | 10151 | 10152 | SNP |
| basd15o18 | 10155 | 10156 | SNP |
| baal25d19 | 10159 | 10160 | SNP |
| bast52G0414 | 10163 | 10164 | SNP |
| baal11c20 | 10167 | 10168 | CAPS |
| bags37k06 | 10171 | 10172 | SNP |
| bags6e22 | 10175 | 10176 | SNP |
| basd15a02 | 10179 | 10180 | CAPS |
| bags7b06 | 10183 | 10184 | CAPS |
| bah15k11 | 10187 | 10188 | CAPS |
| bast46C0406 | 10191 | 10192 | SNP |
| bastl45E0509 | 10195 | 10196 | SNP |
| baal35p14 | 10199 | 10200 | CAPS |
| BaH41G07 | 10203 | 10204 | SNP |
| bast46H1016 | 10207 | 10208 | SNP |
| bah60d12 | 10211 | 10212 | SNP |
| baal39a19 | 10215 | 10216 | SNP |
| baak11n24 | 10219 | 10220 | CAPS |
| bast14E0909 | 10223 | 10224 | SNP |
| baet13G0713 | 10227 | 10228 | SNP |
| HVM33 | — | — | SSR |
| BaSD14L04 | 10231 | 10232 | CAPS |
| baak13c05 | 10235 | 10236 | SNP |
| bastl41G0513 | 10239 | 10240 | SNP |
| BaGS39M09 | 10243 | 10244 | CAPS |
| baal19b12 | 10247 | 10248 | SNP |
| BaAL39B05 | 10251 | 10252 | SNP |
| BaAL1J03 | 10255 | 10256 | SNP |
| basd11k09 | 10259 | 10260 | SNP |
| BaGS33N15 | 10263 | 10264 | SNP |
| baet43H0416 | 10267 | 10268 | SNP |
| bah11m06 | 10271 | 10272 | SNP |

TABLE 10-6

| Name | Primers used (SEQ ID NO:) | | marker type |
|---|---|---|---|
| baak31a24 | 10275 | 10276 | CAPS |
| bags27h20 | 10279 | 10280 | SNP |
| basd27c09 | 10283 | 10284 | SNP |
| BaAL25O01 | 10287 | 10288 | SNP |
| bags7f08 | 10291 | 10292 | CAPS |
| BaGS13O12 | 10295 | 10296 | size_poly (codominant) |
| bags38b06 | 10299 | 10300 | CAPS |
| BaAK19J09 | 10303 | 10304 | SNP |

TABLE 10-6-continued

| Name | Primers used (SEQ ID NO:) | | marker type |
|---|---|---|---|
| bags9e16 | 10307 | 10308 | size_poly (codominant) |
| bags20n14 | 10311 | 10312 | SNP |
| bah42o12 | 10315 | 10316 | SNP |
| baak31k16 | 10319 | 10320 | SNP |
| bags4p14 | 10323 | 10324 | SNP |
| bah27a22 | 10327 | 10328 | CAPS |
| bags21n02 | 10331 | 10332 | size_poly (codominant) |
| BaH62B09 | 10335 | 10336 | SNP |
| BaGS19J10 | 10339 | 10340 | SNP |
| bags15k18 | 10343 | 10344 | SNP |
| BaAK29G03 | 10347 | 10348 | CAPS |
| baak23e11 | 10351 | 10352 | CAPS |
| bags31k04 | 10355 | 10356 | CAPS |
| bast56C0305 | 10359 | 10360 | size_poly (dominant) |
| basd26o09 | 10363 | 10364 | SNP |
| BaSD20B11 | 10367 | 10368 | SNP |
| HVM60 | — | — | SSR |
| BaH46F11 | 10371 | 10372 | SNP |
| BaH30F03 | 10375 | 10376 | SNP |
| BaSD27G02 | 10379 | 10380 | CAPS |
| Bmag225 | — | — | SSR |
| BaAK33I12 | 10383 | 10384 | SNP |
| baak32m10 | 10387 | 10388 | CAPS |
| BaAL4L02 | 10391 | 10392 | CAPS |
| kr44F0911 | 10395 | 10396 | size_poly (codominant) |
| BaGS37A16 | 10399 | 10400 | SNP |
| bags39p06 | 10403 | 10404 | SNP |
| BaAL12N06 | 10407 | 10408 | SNP |
| bags22p05 | 10411 | 10412 | size_poly (codominant) |
| bags9a03 | 10415 | 10416 | SNP |
| baet24F1212 | 10419 | 10420 | SNP |
| baak29d10 | 10423 | 10424 | SNP |
| bags13i12 | 10427 | 10428 | SNP |
| BaAL16A23 | 10431 | 10432 | SNP |
| bastl16B1204 | 10435 | 10436 | SNP |
| bastl29F0711 | 10439 | 10440 | SNP |
| BaGS32M17 | 10443 | 10444 | CAPS |
| baal15e10 | 10447 | 10448 | SNP |
| basd3g08 | 10451 | 10452 | CAPS |
| baal33m18 | 10455 | 10456 | SNP |
| baak24e23 | 10459 | 10460 | SNP |
| baak46j13 | 10463 | 10464 | SNP |
| bah49o05 | 10467 | 10468 | SNP |

TABLE 10-7

| Name | Primers used (SEQ ID NO:) | | marker type |
|---|---|---|---|
| baal15e05 | 10471 | 10472 | SNP |
| BaAK1O08 | 10475 | 10476 | SNP |
| BaGS30P02 | 10479 | 10480 | SNP |
| BaSD15D05 | 10483 | 10484 | SNP |
| BaAL7B16 | 10487 | 10488 | CAPS |
| bags38n23 | 10491 | 10492 | SNP |
| baak36a14 | 10495 | 10496 | SNP |
| baak34g01 | 10499 | 10500 | CAPS |
| baak12f01 | 10503 | 10504 | CAPS |
| BaGS30I18 | 10507 | 10508 | CAPS |
| bags35n24 | 10511 | 10512 | SNP |
| bah37j21 | 10515 | 10516 | SNP |
| bah31e13 | 10519 | 10520 | SNP |
| bags22g10 | 10523 | 10524 | size_poly (dominant) |
| bags22f17 | 10527 | 10528 | size_poly (codominant) |
| baal30l05 | 10531 | 10532 | SNP |
| bags38o10 | 10535 | 10536 | SNP |
| baak40o04 | 10539 | 10540 | CAPS |
| BaH49L21 | 10543 | 10544 | SNP |
| bastl30A0701 | 10547 | 10548 | SNP |
| bags19l03 | 10551 | 10552 | SNP |
| bah18m13 | 10555 | 10556 | SNP |
| baak44p03 | 10559 | 10560 | SNP |
| kr10H0216 | 10563 | 10564 | SNP |
| bags11i04 | 10567 | 10568 | CAPS |
| bah52o06 | 10571 | 10572 | CAPS |
| bah35c14 | 10575 | 10576 | size_poly (codominant) |

TABLE 10-7-continued

| Name | Primers used (SEQ ID NO:) | | marker type |
|---|---|---|---|
| BaAL30C02 | 10579 | 10580 | size_poly (dominant) |
| bah11i21 | 10583 | 10584 | SNP |
| BaAK36B11 | 10587 | 10588 | size_poly (codominant) |
| BaAK20K23 | 10591 | 10592 | SNP |
| basd14n22 | 10595 | 10596 | SNP |
| BaAL25p17 | 10599 | 10600 | CAPS |
| BaH49A01 | 10603 | 10604 | size_poly (codominant) |
| basd13p12 | 10607 | 10608 | size_poly (codominant) |
| bags39m17 | 10611 | 10612 | size_poly (codominant) |
| baet44D0707 | 10615 | 10616 | SNP |
| BaH16P10 | 10619 | 10620 | SNP |
| BaAK42J01 | 10623 | 10624 | SNP |
| kr24E0709 | 10627 | 10628 | CAPS |
| BaAK38O08 | 10631 | 10632 | SNP |
| BaAL13N01 | 10635 | 10636 | CAPS |
| baak12c12 | 10639 | 10640 | size_poly (codominant) |
| BaGS31N06 | 10643 | 10644 | CAPS |
| baal15f24 | 10647 | 10648 | CAPS |
| BaSD18B21 | 10651 | 10652 | SNP |
| BaSD17G23 | 10655 | 10656 | SNP |
| baak41k22 | 10659 | 10660 | SNP |
| baak21o03 | 10663 | 10664 | SNP |
| BaSD16B18 | 10667 | 10668 | SNP |
| bast79C1105 | 10671 | 10672 | SNP |

TABLE 10-8

| Name | Primers used (SEQ ID NO:) | | marker type |
|---|---|---|---|
| BaAK4J17 | 10675 | 10676 | SNP |
| BaAL37H08 | 10679 | 10680 | SNP |
| BaH36L17 | 10683 | 10684 | CAPS |
| BaH46A12 | 10687 | 10688 | size_poly (codominant) |
| bags11i15 | 10691 | 10692 | SNP |
| baak20g24 | 10695 | 10696 | CAPS |
| baak20h23 | 10699 | 10700 | size_poly (codominant) |
| baak35b18 | 10703 | 10704 | SNP |
| Bmag13 | — | — | SSR |
| baak41o03 | 10707 | 10708 | SNP |
| baet46C0206 | 10711 | 10712 | CAPS |
| bags10i20 | 10715 | 10716 | size_poly (dominant) |
| baal1b16 | 10719 | 10720 | SNP |
| baal5i05 | 10723 | 10724 | CAPS |
| BaH27B05 | 10727 | 10728 | size_poly (codominant) |
| bah14a11 | 10731 | 10732 | CAPS |
| basd19k10 | 10735 | 10736 | size_poly (codominant) |
| bags30n17 | 10739 | 10740 | CAPS |
| bags31e24 | 10743 | 10744 | CAPS |
| BaGS5B16 | 10747 | 10748 | SNP |
| BaAL5F06 | 10751 | 10752 | SNP |
| bags34a11 | 10755 | 10756 | CAPS |
| bags6c16 | 10759 | 10760 | CAPS |
| bah42g19 | 10763 | 10764 | SNP |
| BaH47O14 | 10767 | 10768 | SNP |
| BaH12L06 | 10771 | 10772 | SNP |
| basd11a10 | 10775 | 10776 | CAPS |
| BaH50I12 | 10779 | 10780 | CAPS |
| BaH51A21 | 10783 | 10784 | SNP |
| baak45p02 | 10787 | 10788 | CAPS |
| BaSD12P12 | 10791 | 10792 | SNP |
| bags9l16 | 10795 | 10796 | CAPS |
| BaSD26O20 | 10799 | 10800 | CAPS |
| bags5d10 | 10803 | 10804 | CAPS |
| baal0e07 | 10807 | 10808 | CAPS |
| baak14e02 | 10811 | 10812 | CAPS |
| BaH63F14 | 10815 | 10816 | size_poly (codominant) |
| bah33f19 | 10819 | 10820 | CAPS |
| bags19l10 | 10823 | 10824 | SNP |
| BaH56J21 | 10827 | 10828 | SNP |
| baal40i22 | 10831 | 10832 | CAPS |
| kr42C0105 | 10835 | 10836 | size_poly (codominant) |
| bags16i19 | 10839 | 10840 | SNP |
| BaH54H01 | 10843 | 10844 | SNP |
| kr69E0810 | 10847 | 10848 | CAPS |
| bags17i14 | 10851 | 10852 | CAPS |

TABLE 10-8-continued

| Name | Primers used (SEQ ID NO:) | | marker type |
|---|---|---|---|
| bags20e19 | 10855 | 10856 | SNP |
| bast74C0206 | 10859 | 10860 | SNP |
| BaAK13L10 | 10863 | 10864 | SNP |
| bags20i01 | 10867 | 10868 | SNP |
| basd19n14 | 10871 | 10872 | SNP |

TABLE 10-9

| Name | Primers used (SEQ ID NO:) | | marker type |
|---|---|---|---|
| baak42g21 | 10875 | 10876 | SNP |
| BaAK39A15 | 10879 | 10880 | CAPS |
| basd18o21 | 10883 | 10884 | CAPS |
| BaAK22K17 | 10887 | 10888 | SNP |
| baal6o24 | 10891 | 10892 | SNP |
| BaH22C09 | 10895 | 10896 | SNP |
| HVM62 | — | — | SSR |
| bags23k14 | 10899 | 10900 | CAPS |
| baal24n12 | 10903 | 10904 | SNP |
| BaGS21H17 | 10907 | 10908 | CAPS |
| BaSD16D09 | 10911 | 10912 | SNP |
| BaAL13B22 | 10915 | 10916 | SNP |
| bah41l03 | 10919 | 10920 | CAPS |
| bastl30F0111 | 10923 | 10924 | SNP |
| BaH15L04 | 10927 | 10928 | SNP |
| baak40c12 | 10931 | 10932 | SNP |
| kr23D0408 | 10935 | 10936 | CAPS |
| bah57d15 | 10939 | 10940 | SNP |
| baak31e03 | 10943 | 10944 | SNP |
| BaAL13O01 | 10947 | 10948 | SNP |
| BaSD26P04 | 10951 | 10952 | SNP |
| bags20f18 | 10955 | 10956 | SNP |
| BaH42J22 | 10959 | 10960 | SNP |
| BaAL3K03 | 10963 | 10964 | size_poly (codominant) |
| kr30B1103 | 10967 | 10968 | SNP |
| baak14i02 | 10971 | 10972 | CAPS |
| bags28c17 | 10975 | 10976 | CAPS |
| baal4e21 | 10979 | 10980 | SNP |
| BaGS29D05 | 10983 | 10984 | SNP |
| bah54d24 | 10987 | 10988 | SNP |
| basd22g20 | 10991 | 10992 | CAPS |
| BaH62H20 | 10995 | 10996 | CAPS |
| bags38h17 | 10999 | 11000 | SNP |
| BaAK30B23 | 11003 | 11004 | SNP |
| BaAK24P09 | 11007 | 11008 | SNP |
| baak23i12 | 11011 | 11012 | CAPS |
| BaGS22D06 | 11015 | 11016 | SNP |
| BaAL34P18 | 11019 | 11020 | SNP |
| BaAL39F24 | 11023 | 11024 | CAPS |
| BaGS4L04 | 11027 | 11028 | CAPS |
| bah12e02 | 11031 | 11032 | CAPS |
| BaAL15F23 | 11035 | 11036 | SNP |
| BaGS25O15 | 11039 | 11040 | SNP |
| BaGS7G14 | 11043 | 11044 | CAPS |
| basd24i11 | 11047 | 11048 | CAPS |
| baak20l21 | 11051 | 11052 | size_poly (dominant) |
| bags33m02 | 11055 | 11056 | SNP |
| BaH48G21 | 11059 | 11060 | SNP |
| bags27p13 | 11063 | 11064 | SNP |

TABLE 11-1

| Name | Primers used (SEQ ID NO:) | | marker type |
|---|---|---|---|
| BaGS10N17 | 11067 | 11068 | size_poly (dominant) |
| BaAK38K23 | 11071 | 11072 | size_poly (codominant) |
| bah14a22 | 11075 | 11076 | SNP |
| BaAL19O06 | 11079 | 11080 | CAPS |
| BaGS32P17 | 11083 | 11084 | SNP |
| bah11j04 | 11087 | 11088 | CAPS |
| baak35b06 | 11091 | 11092 | SNP |
| basd21f17 | 11095 | 11096 | SNP |
| BaAK44O11 | 11099 | 11100 | size_poly (dominant) |

TABLE 11-1-continued

| Name | Primers used (SEQ ID NO:) | | marker type |
|---|---|---|---|
| bastl14D0408 | 11103 | 11104 | size_poly (codominant) |
| BaAK42C15 | 11107 | 11108 | CAPS |
| baak40n12 | 11111 | 11112 | CAPS |
| basd2j05 | 11115 | 11116 | CAPS |
| baak46n05 | 11119 | 11120 | size_poly (codominant) |
| baak24g04 | 11123 | 11124 | CAPS |
| BaAL22H02 | 11127 | 11128 | SNP |
| bah56g24 | 11131 | 11132 | SNP |
| BaAL2I22 | 11135 | 11136 | CAPS |
| bags20c22 | 11139 | 11140 | CAPS |
| BaH50O22 | 11143 | 11144 | CAPS |
| baak32f06 | 11147 | 11148 | SNP |
| bags35i24 | 11151 | 11152 | CAPS |
| BaSD21D13 | 11155 | 11156 | SNP |
| bast46D0408 | 11159 | 11160 | SNP |
| bast55B1204 | 11163 | 11164 | SNP |
| BaGS39M07 | 11167 | 11168 | size_poly (dominant) |
| bags39b15 | 11171 | 11172 | SNP |
| baak37p11 | 11175 | 11176 | CAPS |
| bah29o22 | 11179 | 11180 | SNP |
| baak12k14 | 11183 | 11184 | size_poly (codominant) |
| baet31E1010 | 11187 | 11188 | SNP |
| HVM40 | — | — | SSR |
| baal39h14 | 11191 | 11192 | SNP |
| bags14g22 | 11195 | 11196 | size_poly (codominant) |
| baal18m18 | 11199 | 11200 | SNP |
| BaSD24E02 | 11203 | 11204 | SNP |
| BaH50N14 | 11207 | 11208 | CAPS |
| kr70A0202 | 11211 | 11212 | CAPS |
| baak11d04 | 11215 | 11216 | SNP |
| MWG2033 | — | — | STS |
| bags20h01 | 11219 | 11220 | CAPS |
| BaH39P15 | 11223 | 11224 | CAPS |
| BaAK46O20 | 11227 | 11228 | CAPS |
| baal33m06 | 11231 | 11232 | SNP |
| bastl50E0309 | 11235 | 11236 | SNP |
| bags20i17 | 11239 | 11240 | SNP |
| BaGS22A07 | 11243 | 11244 | SNP |
| bah41b09 | 11247 | 11248 | SNP |
| kr18G0913 | 11251 | 11252 | CAPS |
| BaGS19O23 | 11255 | 11256 | SNP |
| bags15e12 | 11259 | 11260 | CAPS |

TABLE 11-2

| Name | Primers used (SEQ ID NO:) | | marker type |
|---|---|---|---|
| bags29i09 | 11263 | 11264 | CAPS |
| baak19m23 | 11267 | 11268 | CAPS |
| bags14h12 | 11271 | 11272 | SNP |
| bah32e15 | 11275 | 11276 | SNP |
| bah11l02 | 11279 | 11280 | CAPS |
| bags39e16 | 11283 | 11284 | SNP |
| bags10l12 | 11287 | 11288 | CAPS |
| BaGS31M13 | 11291 | 11292 | CAPS |
| baal32m10 | 11295 | 11296 | SNP |
| basd12b23 | 11299 | 11300 | SNP |
| baal39e15 | 11303 | 11304 | SNP |
| baal16l11 | 11307 | 11308 | CAPS |
| BaGS31B01 | 11311 | 11312 | SNP |
| BaSD17F09 | 11315 | 11316 | CAPS |
| BaH48L11 | 11319 | 11320 | SNP |
| BaSD14M08 | 11323 | 11324 | CAPS |
| bah56c09 | 11327 | 11328 | SNP |
| baak17g07 | 11331 | 11332 | size_poly (codominant) |
| bags20k09 | 11335 | 11336 | SNP |
| BaSD25B08 | 11339 | 11340 | SNP |
| bast27E0309 | 11343 | 11344 | SNP |
| baet20D0107 | 11347 | 11348 | SNP |
| BaAL17L08 | 11351 | 11352 | CAPS |
| bah61p18 | 11355 | 11356 | CAPS |
| bah63d12 | 11359 | 11360 | CAPS |
| BaAK26A03 | 11363 | 11364 | CAPS |
| baak26n10 | 11367 | 11368 | SNP |
| bast22B0204 | 11371 | 11372 | SNP |

TABLE 11-2-continued

| Name | Primers used (SEQ ID NO:) | | marker type |
|---|---|---|---|
| BaAL3C05 | 11375 | 11376 | SNP |
| BaGS38H14 | 11379 | 11380 | size_poly (codominant) |
| BaAL4D19 | 11383 | 11384 | CAPS |
| BaAK20B09 | 11387 | 11388 | SNP |
| BaAK37H01 | 11391 | 11392 | SNP |
| BaGS33P13 | 11395 | 11396 | SNP |
| basd13l12 | 11399 | 11400 | CAPS |
| bags11m01 | 11403 | 11404 | CAPS |
| BaGS18H09 | 11407 | 11408 | SNP |
| basd3d13 | 11411 | 11412 | CAPS |
| baal9m23 | 11415 | 11416 | CAPS |
| bags23f08 | 11419 | 11420 | CAPS |
| BaGS15L23 | 11423 | 11424 | CAPS |
| baak2k13 | 11427 | 11428 | CAPS |
| baak17d18 | 11431 | 11432 | SNP |
| bags13a12 | 11435 | 11436 | SNP |
| baak44g22 | 11439 | 11440 | CAPS |
| kr34F0212 | 11443 | 11444 | SNP |
| baal16d11 | 11447 | 11448 | SNP |
| bah22d04 | 11451 | 11452 | SNP |
| bah48m23 | 11455 | 11456 | size_poly (codominant) |
| basd15p13 | 11459 | 11460 | CAPS |
| BaGS6O07 | 11463 | 11464 | SNP |

TABLE 11-3

| Name | Primers used (SEQ ID NO:) | | marker type |
|---|---|---|---|
| BaH37O10 | 11467 | 11468 | SNP |
| bags21k10 | 11471 | 11472 | CAPS |
| bah56n18 | 11475 | 11476 | CAPS |
| baal9i11 | 11479 | 11480 | SNP |
| BaAL39N06 | 11483 | 11484 | SNP |
| bags9d05 | 11487 | 11488 | size_poly (codominant) |
| BaAL19I19 | 11491 | 11492 | SNP |
| basd12l11 | 11495 | 11496 | SNP |
| bastl46D1008 | 11499 | 11500 | SNP |
| BaH50H16 | 11503 | 11504 | SNP |
| bags9n05 | 11507 | 11508 | SNP |
| kr61B1103 | 11511 | 11512 | SNP |
| kr27B0103 | 11515 | 11516 | SNP |
| kr33H1115 | 11519 | 11520 | SNP |
| baak30l02 | 11523 | 11524 | SNP |
| bah55a12 | 11527 | 11528 | SNP |
| BaH26K14 | 11531 | 11532 | SNP |
| HVM3 | — | — | SSR |
| BaAK33K19 | 11535 | 11536 | CAPS |
| basd18m17 | 11539 | 11540 | SNP |
| BaH50G09 | 11543 | 11544 | CAPS |
| BaH53B03 | 11547 | 11548 | SNP |
| BaH54L11 | 11551 | 11552 | CAPS |
| basd13i14 | 11555 | 11556 | CAPS |
| bah56g09 | 11559 | 11560 | CAPS |
| bah41b06 | 11563 | 11564 | CAPS |
| bags14d19 | 11567 | 11568 | SNP |
| baal20f05 | 11571 | 11572 | SNP |
| BaH18H12 | 11575 | 11576 | SNP |
| baal9o21 | 11579 | 11580 | SNP |
| bags21a02 | 11583 | 11584 | SNP |
| BaAL3G19 | 11587 | 11588 | SNP |
| baal7a09 | 11591 | 11592 | SNP |
| BaAL29I16 | 11595 | 11596 | size_poly (codominant) |
| bast70B0804 | 11599 | 11600 | SNP |
| bags14n08 | 11603 | 11604 | CAPS |
| bastl14F0412 | 11607 | 11608 | SNP |
| BaAK36I12 | 11611 | 11612 | CAPS |
| baal3f19 | 11615 | 11616 | SNP |
| baal1e10 | 11619 | 11620 | SNP |
| bags6k02 | 11623 | 11624 | SNP |
| kr42H0315 | 11627 | 11628 | SNP |
| bah39p02 | 11631 | 11632 | SNP |
| BaGS9L14 | 11635 | 11636 | SNP |
| baal35l03 | 11639 | 11640 | SNP |
| basd12m15 | 11643 | 11644 | SNP |
| BaAK35P01 | 11647 | 11648 | SNP |

TABLE 11-3-continued

| Name | Primers used (SEQ ID NO:) | | marker type |
|---|---|---|---|
| basd11d18 | 11651 | 11652 | SNP |
| BaH38E07 | 11655 | 11656 | SNP |
| BaGS18H13 | 11659 | 11660 | SNP |
| bags18g16 | 11663 | 11664 | SNP |

TABLE 11-4

| Name | Primers used (SEQ ID NO:) | | marker type |
|---|---|---|---|
| bags27f21 | 11667 | 11668 | SNP |
| BaGS7M13 | 11671 | 11672 | CAPS |
| baal39c19 | 11675 | 11676 | SNP |
| baak46j05 | 11679 | 11680 | SNP |
| BaAK32D20 | 11683 | 11684 | CAPS |
| MWG058 | — | — | STS |
| BaGS18M02 | 11687 | 11688 | SNP |
| bags9c05 | 11691 | 11692 | size_poly (dominant) |
| baak46m13 | 11695 | 11696 | CAPS |
| bags35n16 | 11699 | 11700 | CAPS |
| bags39g08 | 11703 | 11704 | SNP |
| baal33a06 | 11707 | 11708 | CAPS |
| BaSD17F20 | 11711 | 11712 | CAPS |
| bags22i21 | 11715 | 11716 | CAPS |
| bah32g18 | 11719 | 11720 | SNP |
| BaAL37O23 | 11723 | 11724 | CAPS |
| bags22p03 | 11727 | 11728 | CAPS |
| bags38l18 | 11731 | 11732 | SNP |
| BaGS35C13 | 11735 | 11736 | SNP |
| bah47h04 | 11739 | 11740 | SNP |
| bags30m11 | 11743 | 11744 | SNP |
| BaH22L15 | 11747 | 11748 | SNP |
| bags39e15 | 11751 | 11752 | SNP |
| kr65H0816 | 11755 | 11756 | CAPS |
| basd11h11 | 11759 | 11760 | SNP |
| baak2b06 | 11763 | 11764 | SNP |
| Bmag353 | — | — | SSR |
| bags37j11 | 11767 | 11768 | CAPS |
| BaAK46L15 | 11771 | 11772 | CAPS |
| BaSD14A23 | 11775 | 11776 | SNP |
| bast25C0705 | 11779 | 11780 | SNP |
| bast21B1204 | 11783 | 11784 | SNP |
| bags1l16 | 11787 | 11788 | CAPS |
| BaAK21G02 | 11791 | 11792 | SNP |
| bastl26E1109 | 11795 | 11796 | SNP |
| basd13k24 | 11799 | 11800 | SNP |
| BaAL13F02 | 11803 | 11804 | SNP |
| bags13c10 | 11807 | 11808 | SNP |
| bags11o11 | 11811 | 11812 | SNP |
| BaAK36P01 | 11815 | 11816 | SNP |
| bah52d09 | 11819 | 11820 | SNP |
| BaGS26D18 | 11823 | 11824 | SNP |
| baak33c22 | 11827 | 11828 | SNP |
| basd1d10 | 11831 | 11832 | CAPS |
| baak11c22 | 11835 | 11836 | CAPS |
| bags34l06 | 11839 | 11840 | SNP |
| baak33j06 | 11843 | 11844 | CAPS |
| bags23a11 | 11847 | 11848 | CAPS |
| bags34f02 | 11851 | 11852 | CAPS |
| bags20p21 | 11855 | 11856 | SNP |
| bah52m01 | 11859 | 11860 | SNP |

TABLE 11-5

| Name | Primers used (SEQ ID NO:) | marker type |
|---|---|---|
| basd15d07 | 11863 11864 | SNP |
| BaAL20A14 | 11867 11868 | CAPS |
| BaGS21B04 | 11871 11872 | CAPS |
| HVM68 | — — | SSR |
| BaAL30B07 | 11875 11876 | SNP |
| basd11p10 | 11879 11880 | CAPS |
| BaGS33E17 | 11883 11884 | CAPS |

TABLE 11-5-continued

| Name | Primers used (SEQ ID NO:) | | marker type |
|---|---|---|---|
| kr67C0206 | 11887 | 11888 | SNP |
| bags15j20 | 11891 | 11892 | SNP |
| BaH15E05 | 11895 | 11896 | SNP |
| BaH58K02 | 11899 | 11900 | SNP |
| basd13d17 | 11903 | 11904 | SNP |
| BaGS17A15 | 11907 | 11908 | CAPS |
| BaAK30F13 | 11911 | 11912 | SNP |
| baal17m22 | 11915 | 11916 | CAPS |
| baak42f04 | 11919 | 11920 | CAPS |
| baal2n22 | 11923 | 11924 | SNP |
| kr30C0705 | 11927 | 11928 | SNP |
| BaSD19J21 | 11931 | 11932 | SNP |
| BaH34N22 | 11935 | 11936 | SNP |
| BaAK2I20 | 11939 | 11940 | CAPS |
| BaGS1E22 | 11943 | 11944 | SNP |
| baak34b17 | 11947 | 11948 | SNP |
| BaSD11L18 | 11951 | 11952 | CAPS |
| kr32A0202 | 11955 | 11956 | SNP |
| bags27h21 | 11959 | 11960 | SNP |
| bah62d17 | 11963 | 11964 | SNP |
| bah43e22 | 11967 | 11968 | SNP |
| BaAL30I23 | 11971 | 11972 | SNP |
| BaSD13H20 | 11975 | 11976 | CAPS |
| BaSD14O04 | 11979 | 11980 | CAPS |
| baak34p06 | 11983 | 11984 | SNP |
| bah63b08 | 11987 | 11988 | SNP |
| bastl03F0812 | 11991 | 11992 | SNP |
| basd14m17 | 11995 | 11996 | SNP |
| BaSD2J03 | 11999 | 12000 | SNP |
| bah13b17 | 12003 | 12004 | size_poly (codominant) |
| baal32b23 | 12007 | 12008 | SNP |
| bastl50D1208 | 12011 | 12012 | size_poly (codominant) |
| BaGS9H13 | 12015 | 12016 | CAPS |
| baal33e04 | 12019 | 12020 | CAPS |
| BaAL40L16 | 12023 | 12024 | CAPS |
| bah44n03 | 12027 | 12028 | SNP |
| bags20h05 | 12031 | 12032 | SNP |
| bags20l15 | 12035 | 12036 | SNP |
| BaGS7E03 | 12039 | 12040 | SNP |
| bags9k13 | 12043 | 12044 | CAPS |
| bast55E0709 | 12047 | 12048 | SNP |
| bags8a14 | 12051 | 12052 | CAPS |
| baak38k04 | 12055 | 12056 | SNP |
| BaH33B15 | 12059 | 12060 | CAPS |

TABLE 11-6

| Name | Primers used (SEQ ID ND:) | | marker type |
|---|---|---|---|
| bags29m17 | 12063 | 12064 | size_poly (codominant) |
| BaSD23P08 | 12067 | 12068 | CAPS |
| BaH42L12 | 12071 | 12072 | SNP |
| bast79G0313 | 12075 | 12076 | CAPS |
| baet46C0905 | 12079 | 12080 | SNP |
| baal4o09 | 12083 | 12084 | CAPS |
| bah26e10 | 12087 | 12088 | SNP |
| BaH32J04 | 12091 | 12092 | SNP |
| bags20l07 | 12095 | 12096 | SNP |
| kr18C0505 | 12099 | 12100 | SNP |
| basd11m24 | 12103 | 12104 | SNP |
| basd1i15 | 12107 | 12108 | SNP |
| bah45b02 | 12111 | 12112 | size_poly (codominant) |
| bast40C0206 | 12115 | 12116 | CAPS |
| baal40g05 | 12119 | 12120 | CAPS |
| bah13i21 | 12123 | 12124 | SNP |
| basd27o20 | 12127 | 12128 | SNP |
| BaAK12L24 | 12131 | 12132 | CAPS |
| BaAL12F24 | 12135 | 12136 | CAPS |
| baak45l08 | 12139 | 12140 | SNP |
| BaAL36N04 | 12143 | 12144 | SNP |
| baak41d17 | 12147 | 12148 | SNP |
| kr39E0810 | 12151 | 12152 | CAPS |
| BaGS32G16 | 12155 | 12156 | CAPS |

TABLE 11-6-continued

| Name | Primers used (SEQ ID ND:) | | marker type |
|---|---|---|---|
| BaGS25M06 | 12159 | 12160 | SNP |
| BaH36F21 | 12163 | 12164 | SNP |
| BaAK13B12 | 12167 | 12168 | SNP |
| baal29j18 | 12171 | 12172 | size_poly (codominant) |
| bast63B0604 | 12175 | 12176 | SNP |
| baak11n06 | 12179 | 12180 | SNP |
| kr13F1012 | 12183 | 12184 | SNP |
| bags20k06 | 12187 | 12188 | SNP |
| baak15p20 | 12191 | 12192 | SNP |
| bah18n11 | 12195 | 12196 | size_poly (codominant) |
| BaH23J08 | 12199 | 12200 | SNP |
| baet30B1004 | 12203 | 12204 | SNP |
| bags34p06 | 12207 | 12208 | size_poly (codominant) |
| bastl33H0816 | 12211 | 12212 | SNP |
| BaSD17I17 | 12215 | 12216 | size_poly (codominant) |
| basd19p22 | 12219 | 12220 | CAPS |
| bags4e03 | 12223 | 12224 | CAPS |
| BaAK36A13 | 12227 | 12228 | CAPS |
| bags33i03 | 12231 | 12232 | CAPS |
| BaAK14F03 | 12235 | 12236 | CAPS |
| BaAK42K19 | 12239 | 12240 | SNP |
| bast60A1101 | 12243 | 12244 | SNP |
| bah52l06 | 12247 | 12248 | SNP |
| bah23h10 | 12251 | 12252 | SNP |
| BaGS15O23 | 12255 | 12256 | SNP |
| BaAK20E08 | 12259 | 12260 | SNP |
| kr61A1202 | 12263 | 12264 | SNP |

TABLE 11-7

| Name | Primers used (SEQ ID NO:) | | marker type |
|---|---|---|---|
| bast03F0212 | 12267 | 12268 | SNP |
| bags39m22 | 12271 | 12272 | CAPS |
| BaAK30O17 | 12275 | 12276 | SNP |
| baak29a01 | 12279 | 12280 | CAPS |
| basd1e04 | 12283 | 12284 | CAPS |
| BaGS23K09 | 12287 | 12288 | CAPS |
| BaAL2N04 | 12291 | 12292 | SNP |
| BaH42C12 | 12295 | 12296 | CAPS |
| bah39o14 | 12299 | 12300 | size_poly (codominant) |
| bast26A1202 | 12303 | 12304 | size_poly (codominant) |
| BaGS30N15 | 12307 | 12308 | SNP |
| BaAL34D18 | 12311 | 12312 | SNP |
| baak15k23 | 12315 | 12316 | CAPS |
| bags37i06 | 12319 | 12320 | SNP |
| BaGS19N09 | 12323 | 12324 | SNP |
| BaSD13H09 | 12327 | 12328 | SNP |
| bags3h19 | 12331 | 12332 | CAPS |
| baak28o08 | 12335 | 12336 | SNP |
| BaH15K08 | 12339 | 12340 | SNP |
| HVM67 | — | — | SSR |
| bah17h20 | 12343 | 12344 | CAPS |
| BaAL5L13 | 12347 | 12348 | CAPS |
| BaGS31P13 | 12351 | 12352 | size_poly (dominant) |
| BaH28A11 | 12355 | 12356 | SNP |
| BaSD25E01 | 12359 | 12360 | SNP |
| sh | — | — | Trait |
| baet23F0111 | 12363 | 12364 | SNP |
| VRN2 | — | — | size_poly |
| bastl41C0806 | 12367 | 12368 | CAPS |
| basd11o04 | 12371 | 12372 | SNP |
| bags22kl7 | 12375 | 12376 | SNP |
| bastl27A1101 | 12379 | 12380 | size_poly (dominant) |
| bags22a16 | 12383 | 12384 | CAPS |
| BaAL5E04 | 12387 | 12388 | CAPS |
| baal39f20 | 12391 | 12392 | CAPS |
| baak43d13 | 12395 | 12396 | CAPS |
| baak41l23 | 12399 | 12400 | CAPS |
| baet23B0604 | 12403 | 12404 | CAPS |
| BaAK28I08 | 12407 | 12408 | CAPS |
| bastl26C1206 | 12411 | 12412 | SNP |
| bah27p20 | 12415 | 12416 | SNP |

TABLE 11-7-continued

| Name | Primers used (SEQ ID NO:) | | marker type |
|---|---|---|---|
| baal12d24 | 12419 | 12420 | SNP |
| bastl41F0511 | 12423 | 12424 | SNP |
| BaGS17E03 | 12427 | 12428 | CAPS |

TABLE 12-1

| Name | Primers used (SEQ ID NO:) | | marker type |
|---|---|---|---|
| baal10j04 | 12431 | 12432 | SNP |
| BaAK33J17 | 12435 | 12436 | SNP |
| BaAL21J19 | 12439 | 12440 | CAPS |
| bast17H0515 | 12443 | 12444 | SNP |
| bags22c02 | 12447 | 12448 | size_poly (codominant) |
| BaAK35A06 | 12451 | 12452 | SNP |
| BaGS11K08 | 12455 | 12456 | CAPS |
| bastl30A0602 | 12459 | 12460 | size_poly (codominant) |
| BaGS39H16 | 12463 | 12464 | CAPS |
| MWG502 | — | — | STS |
| BaAK18M22 | 12467 | 12468 | SNP |
| bast26G0614 | 12471 | 12472 | SNP |
| BaSD22F13 | 12475 | 12476 | SNP |
| BaAK28L16 | 12479 | 12480 | CAPS |
| bags35o06 | 12483 | 12484 | CAPS |
| bags13d07 | 12487 | 12488 | CAPS |
| BaAL24F18 | 12491 | 12492 | size_poly (codominant) |
| bah63l18 | 12495 | 12496 | SNP |
| BaGS9H22 | 12499 | 12500 | SNP |
| BaAK18A05 | 12503 | 12504 | CAPS |
| BaH38D03 | 12507 | 12508 | CAPS |
| BaH17N17 | 12511 | 12512 | SNP |
| bah18d08 | 12515 | 12516 | SNP |
| bags34a05 | 12519 | 12520 | SNP |
| bags1m23 | 12523 | 12524 | SNP |
| BaH50B05 | 12527 | 12528 | SNP |
| bags1h11 | 12531 | 12532 | SNP |
| BaH47G19 | 12535 | 12536 | CAPS |
| BaAK38H10 | 12539 | 12540 | CAPS |
| bah47e01 | 12543 | 12544 | SNP |
| bast52E0109 | 12547 | 12548 | SNP |
| bags1o08 | 12551 | 12552 | SNP |
| BaH31H16 | 12555 | 12556 | CAPS |
| baaK32l14 | 12559 | 12560 | SNP |
| BaH50O06 | 12563 | 12564 | SNP |
| BaSD26I01 | 12567 | 12568 | SNP |
| bags1h24 | 12571 | 12572 | SNP |
| basd27g16 | 12575 | 12576 | SNP |
| BaGS16G24 | 12579 | 12580 | CAPS |
| BaGS34C19 | 12583 | 12584 | SNP |
| bah20k17 | 12587 | 12588 | SNP |
| bah54e13 | 12591 | 12592 | size_poly (codominant) |
| bags35i06 | 12595 | 12596 | CAPS |
| bah29g09 | 12599 | 12600 | size_poly (codominant) |
| BaAK29C12 | 12603 | 12604 | SNP |
| bah56c06 | 12607 | 12608 | CAPS |
| baal6a09 | 12611 | 12612 | SNP |
| bags6j06 | 12615 | 12616 | CAPS |
| BaH30P15 | 12619 | 12620 | SNP |
| baak30k04 | 12623 | 12624 | CAPS |
| basd25d22 | 12627 | 12628 | SNP |

TABLE 12-2

| Name | Primers used (SEQ ID NO:) | | marker type |
|---|---|---|---|
| BaGS39M02 | 12631 | 12632 | CAPS |
| baak13n10 | 12635 | 12636 | SNP |
| BaGS18J21 | 12639 | 12640 | SNP |
| BaSD22G22 | 12643 | 12644 | size_poly (codominant) |
| bags18b17 | 12647 | 12648 | size_poly (codominant) |
| bags33j02 | 12651 | 12652 | SNP |

TABLE 12-2-continued

| Name | Primers used (SEQ ID NO:) | | marker type |
|---|---|---|---|
| baak36b16 | 12655 | 12656 | CAPS |
| bags37f05 | 12659 | 12660 | SNP |
| BaAL17L15 | 12663 | 12664 | SNP |
| BaGS20H12 | 12667 | 12668 | SNP |
| kr65A0802 | 12671 | 12672 | SNP |
| BaGS13E12 | 12675 | 12676 | size_poly (dominant) |
| basd3h06 | 12679 | 12680 | size_poly (codominant) |
| basd22j16 | 12683 | 12684 | SNP |
| bah39n18 | 12687 | 12688 | SNP |
| bags20d19 | 12691 | 12692 | SNP |
| BaGS34H19 | 12695 | 12696 | SNP |
| baak42n10 | 12699 | 12700 | SNP |
| BaSD24F03 | 12703 | 12704 | SNP |
| BaGS23N21 | 12707 | 12708 | SNP |
| BaAK45E04 | 12711 | 12712 | SNP |
| bags5n23 | 12715 | 12716 | SNP |
| bast52H1216 | 12719 | 12720 | SNP |
| bags22f23 | 12723 | 12724 | SNP |
| BaH38E02 | 12727 | 12728 | SNP |
| BaH50O07 | 12731 | 12732 | SNP |
| kr07C1006 | 12735 | 12736 | SNP |
| baak26a02 | 12739 | 12740 | SNP |
| BaAK2J22 | 12743 | 12744 | SNP |
| bah45h23 | 12747 | 12748 | SNP |
| bah11h09 | 12751 | 12752 | size_poly (dominant) |
| BaAK46M16 | 12755 | 12756 | SNP |
| bah55m23 | 12759 | 12760 | SNP |
| bah59c05 | 12763 | 12764 | SNP |
| basd11l17 | 12767 | 12768 | SNP |
| bah19e08 | 12771 | 12772 | SNP |
| BaAK21N24 | 12775 | 12776 | SNP |
| BaH50E09 | 12779 | 12780 | SNP |
| BaAK17P18 | 12783 | 12784 | SNP |
| BaAL7A04 | 12787 | 12788 | SNP |
| bast47B0303 | 12791 | 12792 | SNP |
| bah28o17 | 12795 | 12796 | SNP |
| bah37k03 | 12799 | 12800 | SNP |
| bastl38A0501 | 12803 | 12804 | SNP |
| bags23c03 | 12807 | 12808 | SNP |
| basd13j01 | 12811 | 12812 | SNP |
| bags21c02 | 12815 | 12816 | SNP |
| bah28l03 | 12819 | 12820 | CAPS |
| BaAK36B17 | 12823 | 12824 | CAPS |
| bags6k10 | 12827 | 12828 | SNP |
| BaAK32J23 | 12831 | 12832 | size_poly (codominant) |

TABLE 12-3

| Name | Primers used (SEQ ID NO:) | | marker type |
|---|---|---|---|
| bags9k18 | 12835 | 12836 | SNP |
| baal18c19 | 12839 | 12840 | CAPS |
| baak27p14 | 12843 | 12844 | SNP |
| BaGS30N21 | 12847 | 12848 | SNP |
| bah55p23 | 12851 | 12852 | SNP |
| bah54p22 | 12855 | 12856 | SNP |
| bags34f05 | 12859 | 12860 | SNP |
| Bmac113 | — | — | SSR |
| bags15i11 | 12863 | 12864 | CAPS |
| BaH26I21 | 12867 | 12868 | size_poly (codominant) |
| BaSD20M22 | 12871 | 12872 | CAPS |
| bah14a24 | 12875 | 12876 | SNP |
| BaH50J11 | 12879 | 12880 | SNP |
| bags7a20 | 12883 | 12884 | CAPS |
| bah25l12 | 12887 | 12888 | CAPS |
| bags6k09 | 12891 | 12892 | CAPS |
| BaGS29P21 | 12895 | 12896 | CAPS |
| bah58f18 | 12899 | 12900 | CAPS |
| bags39i18 | 12903 | 12904 | CAPS |
| basd22l21 | 12907 | 12908 | SNP |
| bags4o22 | 12911 | 12912 | CAPS |
| kr27E0909 | 12915 | 12916 | SNP |
| bastl41H0216 | 12919 | 12920 | SNP |

TABLE 12-3-continued

| Name | Primers used (SEQ ID NO:) | | marker type |
|---|---|---|---|
| baak36o17 | 12923 | 12924 | SNP |
| BaH31P15 | 12927 | 12928 | SNP |
| kr07D0208 | 12931 | 12932 | CAPS |
| bags9h03 | 12935 | 12936 | SNP |
| BaGS38M11 | 12939 | 12940 | CAPS |
| kr26C0705 | 12943 | 12944 | size_poly (dominant) |
| bags3k24 | 12947 | 12948 | CAPS |
| bah53e16 | 12951 | 12952 | CAPS |
| bags21n10 | 12955 | 12956 | CAPS |
| BaGS25E06 | 12959 | 12960 | CAPS |
| bah38n03 | 12963 | 12964 | CAPS |
| BaAK38G14 | 12967 | 12968 | CAPS |
| baal5a06 | 12971 | 12972 | CAPS |
| basd26d19 | 12975 | 12976 | CAPS |
| BaSD26D07 | 12979 | 12980 | SNP |
| BaH50G14 | 12983 | 12984 | CAPS |
| bah21h17 | 12987 | 12988 | SNP |
| bags5d21 | 12991 | 12992 | SNP |
| BaAK34D14 | 12995 | 12996 | SNP |
| baak18a16 | 12999 | 13000 | SNP |
| bags4b01 | 13003 | 13004 | SNP |
| bags38c19 | 13007 | 13008 | SNP |
| BaGS38J23 | 13011 | 13012 | CAPS |
| kr42D0208 | 13015 | 13016 | SNP |
| BaH33A16 | 13019 | 13020 | CAPS |
| bags10e03 | 13023 | 13024 | CAPS |
| bags14f17 | 13027 | 13028 | CAPS |
| BaAK35N11 | 13031 | 13032 | SNP |

TABLE 12-4

| Name | Primers used (SEQ ID NO:) | | marker type |
|---|---|---|---|
| bags26n10 | 13035 | 13036 | SNP |
| bags37n02 | 13039 | 13040 | SNP |
| baal39l05 | 13043 | 13044 | size_poly (dominant) |
| BaAK26L11 | 13047 | 13048 | SNP |
| BaH57C19 | 13051 | 13052 | SNP |
| bags7a01 | 13055 | 13056 | SNP |
| bah19l15 | 13059 | 13060 | SNP |
| baal4o02 | 13063 | 13064 | SNP |
| bah58a12 | 13067 | 13068 | SNP |
| HVM30 | — | — | SSR |
| bah11b08 | 13071 | 13072 | SNP |
| bags14m15 | 13075 | 13076 | SNP |
| baak1e17 | 13079 | 13080 | CAPS |
| bags14i11 | 13083 | 13084 | size_poly (codominant) |
| bastl04B1103 | 13087 | 13088 | SNP |
| bags13g08 | 13091 | 13092 | SNP |
| basd27p03 | 13095 | 13096 | SNP |
| bast38D0707 | 13099 | 13100 | SNP |
| baak35j18 | 13103 | 13104 | CAPS |
| baal19k05 | 13107 | 13108 | SNP |
| BaH19C21 | 13111 | 13112 | SNP |
| bah49g10 | 13115 | 13116 | SNP |
| bags14h08 | 13119 | 13120 | CAPS |
| bags23g18 | 13123 | 13124 | SNP |
| bags22o22 | 13127 | 13128 | SNP |
| BaAL20A03 | 13131 | 13132 | SNP |
| bags5e24 | 13135 | 13136 | SNP |
| bags5f11 | 13139 | 13140 | SNP |
| BaAK33B10 | 13143 | 13144 | SNP |
| BaSD15J20 | 13147 | 13148 | CAPS |
| bags38b22 | 13151 | 13152 | size_poly (codominant) |
| bah39b06 | 13155 | 13156 | CAPS |
| bags19j08 | 13159 | 13160 | CAPS |
| BaGS1G09 | 13163 | 13164 | CAPS |
| bah63j06 | 13167 | 13168 | CAPS |
| BaAL39J02 | 13171 | 13172 | SNP |
| BaSD27H14 | 13175 | 13176 | SNP |
| BaH50M01 | 13179 | 13180 | SNP |
| BaSD24E13 | 13183 | 13184 | SNP |
| baal5j24 | 13187 | 13188 | CAPS |

TABLE 12-4-continued

| Name | Primers used (SEQ ID NO:) | | marker type |
|---|---|---|---|
| bah15h18 | 13191 | 13192 | CAPS |
| bast62E0610 | 13195 | 13196 | CAPS |
| bah28k24 | 13199 | 13200 | SNP |
| bah47c11 | 13203 | 13204 | SNP |
| BaSD26M15 | 13207 | 13208 | SNP |
| bah60o02 | 13211 | 13212 | SNP |
| BaH50G06 | 13215 | 13216 | SNP |
| bast15G0913 | 13219 | 13220 | SNP |
| bah62n12 | 13223 | 13224 | size_poly (codominant) |
| baal10n23 | 13227 | 13228 | CAPS |
| bags20c12 | 13231 | 13232 | SNP |

TABLE 12-5

| Name | Primers used (SEQ ID NO:) | | marker type |
|---|---|---|---|
| basd16f13 | 13235 | 13236 | SNP |
| baak21h06 | 13239 | 13240 | CAPS |
| bags3b05 | 13243 | 13244 | CAPS |
| bags22p08 | 13247 | 13248 | SNP |
| BaH23N06 | 13251 | 13252 | SNP |
| bags29c08 | 13255 | 13256 | SNP |
| BaGS11O23 | 13259 | 13260 | SNP |
| baak16a11 | 13263 | 13264 | CAPS |
| baak15n22 | 13267 | 13268 | CAPS |
| BaAL18J13 | 13271 | 13272 | SNP |
| bah15m02 | 13275 | 13276 | SNP |
| baak38d20 | 13279 | 13280 | CAPS |
| BaSD12L21 | 13283 | 13284 | CAPS |
| kr68B1103 | 13287 | 13288 | SNP |
| BaAK28L22 | 13291 | 13292 | CAPS |
| bags15b10 | 13295 | 13296 | SNP |
| bags20h21 | 13299 | 13300 | SNP |
| BaAK29K06 | 13303 | 13304 | SNP |
| bags21l05 | 13307 | 13308 | CAPS |
| bah56j14 | 13311 | 13312 | SNP |
| basd15e02 | 13315 | 13316 | CAPS |
| bags3j24 | 13319 | 13320 | SNP |
| bags38m08 | 13323 | 13324 | SNP |
| bah11m18 | 13327 | 13328 | CAPS |
| bags35g06 | 13331 | 13332 | SNP |
| bags37b01 | 13335 | 13336 | SNP |
| BaAL19F02 | 13339 | 13340 | SNP |
| BaAL4D09 | 13343 | 13344 | SNP |
| BaAK30H10 | 13347 | 13348 | CAPS |
| bags38b16 | 13351 | 13352 | CAPS |
| bags27f15 | 13355 | 13356 | SNP |
| bags10k14 | 13359 | 13360 | SNP |
| bags22f10 | 13363 | 13364 | CAPS |
| baak38n21 | 13367 | 13368 | SNP |
| baak30e05 | 13371 | 13372 | SNP |
| bastl04A0101 | 13375 | 13376 | SNP |
| BaAK28P18 | 13379 | 13380 | SNP |
| BaGS34E01 | 13383 | 13384 | SNP |
| BaH54H04 | 13387 | 13388 | SNP |
| bah13o19 | 13391 | 13392 | SNP |
| BaAK29B22 | 13395 | 13396 | CAPS |
| BaAK27C16 | 13399 | 13400 | CAPS |
| BaGS22H13 | 13403 | 13404 | CAPS |
| BaSD27A15 | 13407 | 13408 | SNP |
| BaAK27E07 | 13411 | 13412 | CAPS |
| BaGS9N02 | 13415 | 13416 | SNP |
| Bmag223 | — | — | SSR |
| bags28o18 | 13419 | 13420 | CAPS |
| baal25b05 | 13423 | 13424 | CAPS |
| bastl30A0202 | 13427 | 13428 | SNP |
| bags37d20 | 13431 | 13432 | CAPS |

TABLE 12-6

| Name | Primers used (SEQ ID NO:) | | marker type |
|---|---|---|---|
| BaGS22K12 | 13435 | 13436 | SNP |
| BaAK13G12 | 13439 | 13440 | SNP |
| basd2a02 | 13443 | 13444 | CAPS |
| BaGS31L06 | 13447 | 13448 | CAPS |
| bags17j17 | 13451 | 13452 | CAPS |
| baal12j15 | 13455 | 13456 | SNP |
| BaAK19H14 | 13459 | 13460 | CAPS |
| BaH34J11 | 13463 | 13464 | SNP |
| BaGS30I11 | 13467 | 13468 | SNP |
| BaH49L06 | 13471 | 13472 | CAPS |
| baal18m24 | 13475 | 13476 | CAPS |
| baak15l06 | 13479 | 13480 | SNP |
| basd18o14 | 13483 | 13484 | SNP |
| bags24p22 | 13487 | 13488 | SNP |
| BaAL37A09 | 13491 | 13492 | SNP |
| bags5l01 | 13495 | 13496 | SNP |
| BaAK12P03 | 13499 | 13500 | SNP |
| baak21f10 | 13503 | 13504 | SNP |
| bastl30E0410 | 13507 | 13508 | SNP |
| kr25C0206 | 13511 | 13512 | SNP |
| baak4j01 | 13515 | 13516 | CAPS |
| BaAK27E01 | 13519 | 13520 | CAPS |
| bah54n06 | 13523 | 13524 | SNP |
| bags19p05 | 13527 | 13528 | CAPS |
| bast22F0311 | 13531 | 13532 | SNP |
| basd1m04 | 13535 | 13536 | SNP |
| bags35i04 | 13539 | 13540 | CAPS |
| baak41d01 | 13543 | 13544 | SNP |
| baal19m08 | 13547 | 13548 | CAPS |
| baak13j10 | 13551 | 13552 | SNP |
| baak44h11 | 13555 | 13556 | SNP |
| baal19j09 | 13559 | 13560 | SNP |
| baet37C1105 | 13563 | 13564 | SNP |
| baak12d06 | 13567 | 13568 | CAPS |
| basd23f10 | 13571 | 13572 | SNP |
| BaH41P07 | 13575 | 13576 | SNP |
| baak1g13 | 13579 | 13580 | SNP |
| basd14b04 | 13583 | 13584 | CAPS |
| bags22l14 | 13587 | 13588 | SNP |
| bast26E1210 | 13591 | 13592 | SNP |
| baet25F0911 | 13595 | 13596 | SNP |
| BaAK32N13 | 13599 | 13600 | SNP |
| BaSD2C09 | 13603 | 13604 | size_poly (codominant) |
| BaGS31P01 | 13607 | 13608 | SNP |
| baak30m11 | 13611 | 13612 | SNP |
| BaAK4N16 | 13615 | 13616 | size_poly (codominant) |
| bastl46F1012 | 13619 | 13620 | SNP |
| bags3e06 | 13623 | 13624 | SNP |
| bags31o10 | 13627 | 13628 | CAPS |
| bags33j12 | 13631 | 13632 | CAPS |
| BaGS30N07 | 13635 | 13636 | CAPS |

TABLE 12-7

| Name | Primers used (SEQ ID NO:) | | marker type |
|---|---|---|---|
| BaH37I18 | 13639 | 13640 | CAPS |
| baak46p24 | 13643 | 13644 | CAPS |
| baak46o19 | 13647 | 13648 | SNP |
| basd3c19 | 13651 | 13652 | SNP |
| bags30f01 | 13655 | 13656 | SNP |
| BaGS20F10 | 13659 | 13660 | CAPS |
| BaGS32D08 | 13663 | 13664 | SNP |
| BaAK23M23 | 13667 | 13668 | SNP |
| bah21a16 | 13671 | 13672 | SNP |
| BaAL3M08 | 13675 | 13676 | SNP |
| BaAK21I09 | 13679 | 13680 | SNP |
| baet33A0301 | 13683 | 13684 | SNP |
| baak24k02 | 13687 | 13688 | SNP |
| bah33p03 | 13691 | 13692 | CAPS |
| bast75D1208 | 13695 | 13696 | SNP |
| BaSD12K20 | 13699 | 13700 | size_poly (codominant) |
| bags34f06 | 13703 | 13704 | SNP |
| bags6f09 | 13707 | 13708 | SNP |
| bags7b10 | 13711 | 13712 | SNP |
| BaGS25H01 | 13715 | 13716 | CAPS |
| baak33m08 | 13719 | 13720 | CAPS |
| bags37e01 | 13723 | 13724 | SNP |
| bags32n20 | 13727 | 13728 | CAPS |
| BaH47A11 | 13731 | 13732 | CAPS |
| BaGS24M06 | 13735 | 13736 | SNP |
| bags22m23 | 13739 | 13740 | SNP |
| basd18d18 | 13743 | 13744 | SNP |
| bastl06F0212 | 13747 | 13748 | SNP |
| BaH49O16 | 13751 | 13752 | SNP |
| bags39e22 | 13755 | 13756 | CAPS |
| BaH38N06 | 13759 | 13760 | SNP |
| BaH56P16 | 13763 | 13764 | SNP |
| BaSD13O13 | 13767 | 13768 | SNP |
| bags19i06 | 13771 | 13772 | CAPS |
| bah34f11 | 13775 | 13776 | SNP |
| bags37g04 | 13779 | 13780 | SNP |
| basd11k21 | 13783 | 13784 | CAPS |
| HvLOX | — | — | SSR |
| baak43o03 | 13787 | 13788 | SNP |
| BaAL4J21 | 13791 | 13792 | SNP |
| BaH51J22 | 13795 | 13796 | SNP |
| bah58l03 | 13799 | 13800 | SNP |
| BaGS21M18 | 13803 | 13804 | SNP |
| BaGS31K06 | 13807 | 13808 | SNP |
| baal4o01* VRN2(sh2) | 13811 | 13812 | SNP |
| BaAK24H19 | 13815 | 13816 | size_poly (codominant) |
| BaGS17D21 | 13819 | 13820 | size_poly (codominant) |
| bah39o04 | 13823 | 13824 | SNP |
| baak46e06 | 13827 | 13828 | size_poly (codominant) |
| basd13j03 | 13831 | 13832 | CAPS |

TABLE 12-8

| Name | Primers used (SEQ ID NO:) | | marker type |
|---|---|---|---|
| bast14H0416 | 13835 | 13836 | SNP |
| BaSD18I03 | 13839 | 13840 | CAPS |
| bastl44H1115 | 13843 | 13844 | SNP |
| bast34D0608 | 13847 | 13848 | CAPS |
| BaGS30F06 | 13851 | 13852 | CAPS |
| bags21k16 | 13855 | 13856 | CAPS |
| BaH48G01 | 13859 | 13860 | CAPS |
| bags39a24 | 13863 | 13864 | CAPS |
| bags15i03 | 13867 | 13868 | size_poly (dominant) |
| bags23f02 | 13871 | 13872 | SNP |
| bastl40E1010 | 13875 | 13876 | SNP |
| bags17p10 | 13879 | 13880 | CAPS |
| BaH57L13 | 13883 | 13884 | CAPS |
| bags10e22 | 13887 | 13888 | size_poly (codominant) |
| bags4p07 | 13891 | 13892 | CAPS |
| bah63a08 | 13895 | 13896 | CAPS |
| baak12f13 | 13899 | 13900 | size_poly (dominant) |
| bah56j15 | 13903 | 13904 | CAPS |
| bah15e16 | 13907 | 13908 | SNP |
| BaH50F21 | 13911 | 13912 | CAPS |
| basd27o16 | 13915 | 13916 | SNP |
| kr66G0713 | 13919 | 13920 | SNP |
| baak46c17 | 13923 | 13924 | SNP |
| baet19C1206 | 13927 | 13928 | SNP |
| bags34e15 | 13931 | 13932 | CAPS |
| baal4d18 | 13935 | 13936 | size_poly (dominant) |
| bah13b13 | 13939 | 13940 | CAPS |
| BaGS26G20 | 13943 | 13944 | SNP |
| BaGS28C14 | 13947 | 13948 | SNP |
| kr61G1214 | 13951 | 13952 | SNP |
| bags9g08 | 13955 | 13956 | SNP |
| bags5p01 | 13959 | 13960 | SNP |
| BaAL4D04 | 13963 | 13964 | SNP |
| bah26p09 | 13967 | 13968 | CAPS |

TABLE 12-8-continued

| Name | Primers used (SEQ ID NO:) | | marker type |
|---|---|---|---|
| bah11e02 | 13971 | 13972 | SNP |
| MWG2077 | — | — | STS |
| bast41F0311 | 13975 | 13976 | SNP |
| bastl54D0307 | 13979 | 13980 | SNP |
| BaSD3F21 | 13983 | 13984 | size_poly (codominant) |
| bah56f18 | 13987 | 13988 | size_poly (codominant) |
| BaH41C21 | 13991 | 13992 | CAPS |
| basd19g21 | 13995 | 13996 | CAPS |
| kr33H0816 | 13999 | 14000 | SNP |
| BaH38F16 | 14003 | 14004 | SNP |
| BaGS21P09 | 14007 | 14008 | SNP |
| BaGS36M20 | 14011 | 14012 | CAPS |
| bags21m10 | 14015 | 14016 | CAPS |
| BaAK14G11 | 14019 | 14020 | CAPS |
| BaGS30L20 | 14023 | 14024 | CAPS |
| basd21g02 | 14027 | 14028 | SNP |
| bah22m17 | 14031 | 14032 | SNP |

TABLE 12-9

| Name | Primers used (SEQ ID NO:) | | marker type |
|---|---|---|---|
| BaGS9H19 | 14035 | 14036 | SNP |
| bah26m24 | 14039 | 14040 | SNP |
| BaH56D01 | 14043 | 14044 | SNP |
| bah53j08 | 14047 | 14048 | CAPS |
| bags21d10 | 14051 | 14052 | CAPS |
| bags9a01 | 14055 | 14056 | CAPS |
| baal9m13 | 14059 | 14060 | SNP |
| baak20m05 | 14063 | 14064 | size_poly (codominant) |
| baak21k16 | 14067 | 14068 | SNP |
| bags34d17 | 14071 | 14072 | CAPS |
| baal40k24 | 14075 | 14076 | CAPS |
| BaGS19O14 | 14079 | 14080 | SNP |
| baak35m03 | 14083 | 14084 | SNP |
| baak33o23 | 14087 | 14088 | SNP |
| kr57F1012 | 14091 | 14092 | SNP |
| bah53i05 | 14095 | 14096 | size_poly (codominant) |
| bags22l16 | 14099 | 14100 | SNP |
| baet43C0505 | 14103 | 14104 | SNP |
| BaH33H02 | 14107 | 14108 | CAPS |
| bastl22E1010 | 14111 | 14112 | SNP |
| BaH53N24 | 14115 | 14116 | SNP |
| baal8e24 | 14119 | 14120 | SNP |
| BaH62H21 | 14123 | 14124 | SNP |
| BaH42K01 | 14127 | 14128 | SNP |
| basd26p09 | 14131 | 14132 | SNP |
| bags4p18 | 14135 | 14136 | SNP |
| BaH60H14 | 14139 | 14140 | size_poly (codominant) |
| bast70D1107 | 14143 | 14144 | SNP |
| bah26i23 | 14147 | 14148 | SNP |
| baal39g02 | 14151 | 14152 | SNP |
| bags10e02 | 14155 | 14156 | CAPS |
| bags22c13 | 14159 | 14160 | SNP |
| bags35n03 | 14163 | 14164 | CAPS |
| BaAL16H03 | 14167 | 14168 | SNP |
| BaAL15N07 | 14171 | 14172 | CAPS |
| bags18o20 | 14175 | 14176 | SNP |
| bags37g12 | 14179 | 14180 | CAPS |
| bags22l12 | 14183 | 14184 | CAPS |
| BaAK44K01 | 14187 | 14188 | CAPS |
| BaAK31G07 | 14191 | 14192 | CAPS |
| bah53n21 | 14195 | 14196 | CAPS |
| BaGS19C02 | 14199 | 14200 | SNP |
| BaH52E20 | 14203 | 14204 | SNP |
| BaAL4N05 | 14207 | 14208 | SNP |
| bags7p06 | 14211 | 14212 | SNP |
| bast70C0905 | 14215 | 14216 | SNP |
| BaSD15J01 | 14219 | 14220 | SNP |
| BaH56H18 | 14223 | 14224 | SNP |
| BaGS4N04 | 14227 | 14228 | SNP |
| bags31o13 | 14231 | 14232 | SNP |
| kr29D0107 | 14235 | 14236 | CAPS |

TABLE 12-10

| Name | Primers used (SEQ ID NO:) | | marker type |
|---|---|---|---|
| BaAK21A15 | 14239 | 14240 | size_poly (codominant) |
| bags7h14 | 14243 | 14244 | SNP |
| basd26b20 | 14247 | 14248 | size_poly (codominant) |
| baal1g06 | 14251 | 14252 | size_poly (codominant) |
| bags5n14 | 14255 | 14256 | SNP |
| BaAK34H17 | 14259 | 14260 | size_poly (dominant) |
| bastl32H0816 | 14263 | 14264 | SNP |
| basd18m12 | 14267 | 14268 | size_poly (codominant) |
| baak31p06 | 14271 | 14272 | SNP |
| bah52i03 | 14275 | 14276 | CAPS |
| BaAK33K05 | 14279 | 14280 | CAPS |
| BaAK44J08 | 14283 | 14284 | SNP |
| baak18g16 | 14287 | 14288 | SNP |
| baak11a11 | 14291 | 14292 | SNP |
| BaH25B20 | 14295 | 14296 | size_poly (codominant) |
| bastl12G0113 | 14299 | 14300 | CAPS |
| baal9n02 | 14303 | 14304 | SNP |
| bags20f08 | 14307 | 14308 | SNP |
| BaGS9C24 | 14311 | 14312 | SNP |
| BaGS22O02 | 14315 | 14316 | SNP |
| baak13k16 | 14319 | 14320 | CAPS |
| MWG2249 | — | — | STS |
| bah41b17 | 14323 | 14324 | SNP |
| bah63m11 | 14327 | 14328 | SNP |
| BaGS28P07 | 14331 | 14332 | SNP |
| bags1h15 | 14335 | 14336 | CAPS |
| kr26H0515 | 14339 | 14340 | CAPS |
| bags6n05 | 14343 | 14344 | size_poly (codominant) |
| BaH24P17 | 14347 | 14348 | CAPS |
| bast03D0408 | 14351 | 14352 | SNP |
| BaAL17G06 | 14355 | 14356 | SNP |
| BaH32G11 | 14359 | 14360 | CAPS |
| BaGS4P17 | 14363 | 14364 | SNP |
| baal31o21 | 14367 | 14368 | SNP |
| BaGS36A16 | 14371 | 14372 | CAPS |
| bags4d11 | 14375 | 14376 | SNP |
| basd13n18 | 14379 | 14380 | SNP |
| basd0a08 | 14383 | 14384 | SNP |
| BaGS32P24 | 14387 | 14388 | SNP |
| baak12i02 | 14391 | 14392 | CAPS |
| kr06H0315 | 14395 | 14396 | SNP |
| BaAL26B09 | 14399 | 14400 | SNP |
| kr32C1105 | 14403 | 14404 | SNP |
| BaH53B15 | 14407 | 14408 | SNP |
| bags13h04 | 14411 | 14412 | SNP |
| baal15i11 | 14415 | 14416 | SNP |
| bags1m19 | 14419 | 14420 | CAPS |
| HVM6 | — | — | SSR |

TABLE 13-1

| Name | Primers used (SEQ ID NO:) | | marker type |
|---|---|---|---|
| MWG620 | — | — | STS |
| basd14f03 | 14423 | 14424 | CAPS |
| BaH30P12 | 14427 | 14428 | SNP |
| BaH59J05 | 14431 | 14432 | SNP |
| BaAL39O22 | 14435 | 14436 | SNP |
| baal16i24 | 14439 | 14440 | CAPS |
| BaAL30P12 | 14443 | 14444 | CAPS |
| BaGS21H12 | 14447 | 14448 | CAPS |
| BaAK15J05 | 14451 | 14452 | size_poly (codominant) |
| BaGS9G15 | 14455 | 14456 | CAPS |
| BaAK41J04 | 14459 | 14460 | CAPS |
| baak43j24 | 14463 | 14464 | SNP |
| bah26n19 | 14467 | 14468 | size_poly (dominant) |
| Bmac316 | — | — | SSR |
| bags38a05 | 14471 | 14472 | CAPS |
| BaH43I06 | 14475 | 14476 | CAPS |
| bags9j07 | 14479 | 14480 | CAPS |
| baak31p11 | 14483 | 14484 | CAPS |
| BaGS17P19 | 14487 | 14488 | CAPS |
| baal32j05 | 14491 | 14492 | CAPS |

TABLE 13-1-continued

| Name | Primers used (SEQ ID NO:) | | marker type |
|---|---|---|---|
| baal16l16 | 14495 | 14496 | CAPS |
| baal6a11 | 14499 | 14500 | CAPS |
| bah55p06 | 14503 | 14504 | CAPS |
| bags8f03 | 14507 | 14508 | CAPS |
| bags3m02 | 14511 | 14512 | SNP |
| BaAL36L08 | 14515 | 14516 | SNP |
| baet19E0309 | 14519 | 14520 | SNP |
| BaSD18J06 | 14523 | 14524 | size_poly (codominant) |
| bast48D0307 | 14527 | 14528 | SNP |
| kr55D0707 | 14531 | 14532 | SNP |
| BaAL4B09 | 14535 | 14536 | CAPS |
| bags32f21 | 14539 | 14540 | CAPS |
| BaGS24F04 | 14543 | 14544 | SNP |
| BaGS10G07 | 14547 | 14548 | CAPS |
| BaGS26P07 | 14551 | 14552 | SNP |
| bags12f11 | 14555 | 14556 | SNP |
| MWG2218 | — | — | STS |
| BaH63O04 | 14559 | 14560 | CAPS |
| BaGS26D21 | 14563 | 14564 | CAPS |
| bags20o14 | 14567 | 14568 | SNP |
| baak36d08 | 14571 | 14572 | SNP |
| bast75H0616 | 14575 | 14576 | SNP |
| basd16g17 | 14579 | 14580 | SNP |
| baal4k16 | 14583 | 14584 | CAPS |
| bags32b14 | 14587 | 14588 | CAPS |
| baal4d01 | 14591 | 14592 | CAPS |
| baal7d23 | 14595 | 14596 | CAPS |
| BaH62C20 | 14599 | 14600 | size_poly (codominant) |
| BaH21K13 | 14603 | 14604 | SNP |
| BaAK14J02 | 14607 | 14608 | SNP |
| bah22c08 | 14611 | 14612 | SNP |

TABLE 13-2

| Name | Primers used (SEQ ID NO:) | | marker type |
|---|---|---|---|
| baak25d07 | 14615 | 14616 | CAPS |
| BaAK29M05 | 14619 | 14620 | CAPS |
| BaGS31I08 | 14623 | 14624 | CAPS |
| bah12n12 | 14627 | 14628 | SNP |
| baal30o06 | 14631 | 14632 | CAPS |
| baak13n14 | 14635 | 14636 | CAPS |
| bags7a09 | 14639 | 14640 | CAPS |
| baak32l04 | 14643 | 14644 | SNP |
| bah31o16 | 14647 | 14648 | CAPS |
| BaAL7C19 | 14651 | 14652 | SNP |
| BaAK23F04 | 14655 | 14656 | SNP |
| kr40D0707 | 14659 | 14660 | CAPS |
| basd0g08 | 14663 | 14664 | SNP |
| BaAL30H03 | 14667 | 14668 | CAPS |
| BaAL21B21 | 14671 | 14672 | SNP |
| BaGS30E05 | 14675 | 14676 | SNP |
| BaAK13G04 | 14679 | 14680 | SNP |
| BaGS27N11 | 14683 | 14684 | size_poly (dominant) |
| BaGS9A04 | 14687 | 14688 | SNP |
| BaAK23M11 | 14691 | 14692 | SNP |
| basd3f22 | 14695 | 14696 | CAPS |
| baak41p21 | 14699 | 14700 | SNP |
| BaAK41K07 | 14703 | 14704 | CAPS |
| BaH53I11 | 14707 | 14708 | CAPS |
| baak26j14 | 14711 | 14712 | SNP |
| BaAL18N03 | 14715 | 14716 | CAPS |
| baak40c08 | 14719 | 14720 | CAPS |
| bags17l19 | 14723 | 14724 | CAPS |
| BaSD25N02 | 14727 | 14728 | size_poly (codominant) |
| BaAK37E04 | 14731 | 14732 | SNP |
| baal33h17 | 14735 | 14736 | CAPS |
| bags20d08 | 14739 | 14740 | CAPS |
| BaGS4J01 | 14743 | 14744 | CAPS |
| bah48o03 | 14747 | 14748 | SNP |
| bastl31A0901 | 14751 | 14752 | SNP |
| bah20k22 | 14755 | 14756 | SNP |
| BaGS15J17 | 14759 | 14760 | size_poly (dominant) |

TABLE 13-2-continued

| Name | Primers used (SEQ ID NO:) | | marker type |
|---|---|---|---|
| BaAK17I01 | 14763 | 14764 | CAPS |
| BaAK30F08 | 14767 | 14768 | CAPS |
| bah47a17 | 14771 | 14772 | SNP |
| basd15e10 | 14775 | 14776 | SNP |
| BaH56C11 | 14779 | 14780 | SNP |
| BaH18C17 | 14783 | 14784 | SNP |
| BaGS20G24 | 14787 | 14788 | SNP |
| bags19g17 | 14791 | 14792 | CAPS |
| BaAK21L02 | 14795 | 14796 | CAPS |
| BaH52H21 | 14799 | 14800 | SNP |
| bags9l13 | 14803 | 14804 | CAPS |
| BaSD18C12 | 14807 | 14808 | SNP |
| baak23k07 | 14811 | 14812 | SNP |
| bags16j16 | 14815 | 14816 | SNP |

TABLE 13-3

| Name | Primers used (SEQ ID NO:) | | marker type |
|---|---|---|---|
| BaSD15O17 | 14819 | 14820 | SNP |
| baak12i20 | 14823 | 14824 | CAPS |
| BaAK3M04 | 14827 | 14828 | CAPS |
| BaGS4N23 | 14831 | 14832 | SNP |
| baak34k24 | 14835 | 14836 | CAPS |
| bah15n23 | 14839 | 14840 | CAPS |
| baak45i02 | 14843 | 14844 | CAPS |
| basd13i08 | 14847 | 14848 | SNP |
| BaSD17P01 | 14851 | 14852 | SNP |
| HVM31 | — | — | SSR |
| baak13d19 | 14855 | 14856 | SNP |
| baal3h14 | 14859 | 14860 | SNP |
| bags33j18 | 14863 | 14864 | SNP |
| BaH45B01 | 14867 | 14868 | CAPS |
| baak21n07 | 14871 | 14872 | SNP |
| BaH36H18 | 14875 | 14876 | size_poly (codominant) |
| BaAL23O14 | 14879 | 14880 | CAPS |
| bah53f05 | 14883 | 14884 | SNP |
| baak12d02 | 14887 | 14888 | SNP |
| bags11h12 | 14891 | 14892 | SNP |
| baet01F1212 | 14895 | 14896 | SNP |
| baak17l11 | 14899 | 14900 | SNP |
| basd20e17 | 14903 | 14904 | SNP |
| bah29p24 | 14907 | 14908 | SNP |
| bags30o05 | 14911 | 14912 | SNP |
| kr68D0208 | 14915 | 14916 | SNP |
| bags37l11 | 14919 | 14920 | SNP |
| baal4d14 | 14923 | 14924 | CAPS |
| BaH58I23 | 14927 | 14928 | SNP |
| bags39l04 | 14931 | 14932 | SNP |
| baak29j13 | 14935 | 14936 | CAPS |
| bags20p18 | 14939 | 14940 | CAPS |
| BaAK12J13 | 14943 | 14944 | CAPS |
| BaH13K17 | 14947 | 14948 | size_poly (codominant) |
| bah60p09 | 14951 | 14952 | SNP |
| BaH27N11 | 14955 | 14956 | CAPS |
| BaGS34D11 | 14959 | 14960 | CAPS |
| BaGS39G07 | 14963 | 14964 | CAPS |
| bah22o14 | 14967 | 14968 | SNP |
| bah14l20 | 14971 | 14972 | SNP |
| bah42p22 | 14975 | 14976 | SNP |
| BaAK21G03 | 14979 | 14980 | SNP |
| BaAL35D24 | 14983 | 14984 | SNP |
| baak45h14 | 14987 | 14988 | SNP |
| bags28o05 | 14991 | 14992 | SNP |
| BaAK31P07 | 14995 | 14996 | SNP |
| bah36c06 | 14999 | 15000 | SNP |
| BaGS37H24 | 15003 | 15004 | SNP |
| bast65B0303 | 15007 | 15008 | SNP |
| BaH51A22 | 15011 | 15012 | SNP |
| BaGS39K23 | 15015 | 15016 | SNP |

TABLE 13-4

| Name | Primers used (SEQ ID NO:) | | marker type |
|---|---|---|---|
| BaSD14O12 | 15019 | 15020 | SNP |
| BaH57F12 | 15023 | 15024 | SNP |
| BaGS32G02 | 15027 | 15028 | CAPS |
| BaAL40N06 | 15031 | 15032 | SNP |
| bah11b14 | 15035 | 15036 | SNP |
| bah15j14 | 15039 | 15040 | SNP |
| bast21C1105 | 15043 | 15044 | CAPS |
| bags29f03 | 15047 | 15048 | CAPS |
| BaAK46B16 | 15051 | 15052 | CAPS |
| basd11p22 | 15055 | 15056 | CAPS |
| baal16h16 | 15059 | 15060 | CAPS |
| BaSD21L07 | 15063 | 15064 | SNP |
| BaH42D07 | 15067 | 15068 | SNP |
| BaGS23K24 | 15071 | 15072 | SNP |
| BaAK24L01 | 15075 | 15076 | SNP |
| BaAL11H22 | 15079 | 15080 | SNP |
| BaAL13O24 | 15083 | 15084 | CAPS |
| BaAL6M22 | 15087 | 15088 | SNP |
| BaH56I06 | 15091 | 15092 | size_poly (codominant) |
| BaSD19A18 | 15095 | 15096 | size_poly (dominant) |
| BaSD20P03 | 15099 | 15100 | SNP |
| BaH19B13 | 15103 | 15104 | SNP |
| kr59H0416 | 15107 | 15108 | SNP |
| BaGS14A02 | 15111 | 15112 | SNP |
| BaH34P05 | 15115 | 15116 | SNP |
| bah61o16 | 15119 | 15120 | SNP |
| BaH24N07 | 15123 | 15124 | SNP |
| BaAL20M22 | 15127 | 15128 | CAPS |
| BaAL11H20 | 15131 | 15132 | SNP |
| bah54b04 | 15135 | 15136 | SNP |
| BaAK14H23 | 15139 | 15140 | size_poly (dominant) |
| BaSD20M23 | 15143 | 15144 | SNP |
| BaAL15B12 | 15147 | 15148 | CAPS |
| baal15d09 | 15151 | 15152 | SNP |
| baak39n20 | 15155 | 15156 | SNP |
| BaH43N16 | 15159 | 15160 | SNP |
| bags39h18 | 15163 | 15164 | CAPS |
| BaAL3L23 | 15167 | 15168 | CAPS |
| basd22c03 | 15171 | 15172 | SNP |
| bast55G0913 | 15175 | 15176 | CAPS |
| kr47F0511 | 15179 | 15180 | SNP |
| bah15l24 | 15183 | 15184 | size_poly (codominant) |
| bast77A0402 | 15187 | 15188 | SNP |
| BaH58F04 | 15191 | 15192 | SNP |
| BaAK30L09 | 15195 | 15196 | SNP |
| kr39G1113 | 15199 | 15200 | SNP |
| baak1c16 | 15203 | 15204 | SNP |
| basd20e05 | 15207 | 15208 | SNP |
| BaAK12F18 | 15211 | 15212 | SNP |
| BaH50L11 | 15215 | 15216 | CAPS |
| bast50G0814 | 15219 | 15220 | CAPS |

TABLE 13-5

| Name | Primers used (SEQ ID NO:) | | marker type |
|---|---|---|---|
| bast70D0107 | 15223 | 15224 | SNP |
| baal17d05 | 15227 | 15228 | SNP |
| baak46g03 | 15231 | 15232 | SNP |
| bah63m17 | 15235 | 15236 | SNP |
| BaH15L15 | 15239 | 15240 | SNP |
| BaGS19N01 | 15243 | 15244 | SNP |
| BaAK32P07 | 15247 | 15248 | SNP |
| bags14l13 | 15251 | 15252 | SNP |
| bags37o24 | 15255 | 15256 | SNP |
| baal5e24 | 15259 | 15260 | CAPS |
| BaH46B06 | 15263 | 15264 | CAPS |
| bags11a16 | 15267 | 15268 | CAPS |
| baal27m03 | 15271 | 15272 | SNP |
| BaAK1C18 | 15275 | 15276 | SNP |
| BaAK38H16 | 15279 | 15280 | size_poly (codominant) |
| BaGS37K02 | 15283 | 15284 | CAPS |
| bah28a10 | 15287 | 15288 | CAPS |

TABLE 13-5-continued

| Name | Primers used (SEQ ID NO:) | | marker type |
|---|---|---|---|
| bah27c03 | 15291 | 15292 | CAPS |
| BaH52B11 | 15295 | 15296 | SNP |
| bah27f05 | 15299 | 15300 | SNP |
| bags37g15 | 15303 | 15304 | CAPS |
| bah59c10 | 15307 | 15308 | SNP |
| bags38j06 | 15311 | 15312 | SNP |
| basd14e01 | 15315 | 15316 | SNP |
| BaGS24L06 | 15319 | 15320 | size_poly (codominant) |
| bags17b02 | 15323 | 15324 | CAPS |
| BaH54L03 | 15327 | 15328 | CAPS |
| BaAK21J17 | 15331 | 15332 | CAPS |
| BaGS23G08 | 15335 | 15336 | CAPS |
| basd18e06 | 15339 | 15340 | SNP |
| baak19o02 | 15343 | 15344 | size_poly (codominant) |
| basd2o16 | 15347 | 15348 | SNP |
| baak16e08 | 15351 | 15352 | SNP |
| bags18h01 | 15355 | 15356 | SNP |
| BaGS4L20 | 15359 | 15360 | SNP |
| BaAL2M19 | 15363 | 15364 | CAPS |
| BaH36F15 | 15367 | 15368 | CAPS |
| bah58l07 | 15371 | 15372 | CAPS |
| baet29C0406 | 15375 | 15376 | CAPS |
| BaAK35B04 | 15379 | 15380 | CAPS |
| bags34k13 | 15383 | 15384 | CAPS |
| baal29i08 | 15387 | 15388 | CAPS |
| baak11p10 | 15391 | 15392 | CAPS |
| BaH30J08 | 15395 | 15396 | SNP |
| bags4e12 | 15399 | 15400 | CAPS |
| bastl05C1206 | 15403 | 15404 | size_poly (codominant) |
| bast22G0313 | 15407 | 15408 | SNP |
| basd24b08 | 15411 | 15412 | CAPS |
| bastl16C0206 | 15415 | 15416 | size_poly (codominant) |
| bags33n21 | 15419 | 15420 | SNP |
| baak33c11 | 15423 | 15424 | SNP |

TABLE 13-6

| Name | Primers used (SEQ ID NO:) | | marker type |
|---|---|---|---|
| baal13o10 | 15427 | 15428 | CAPS |
| BaH36P06 | 15431 | 15432 | SNP |
| basd12l01 | 15435 | 15436 | SNP |
| baet25H0115 | 15439 | 15440 | SNP |
| bags15d14 | 15443 | 15444 | CAPS |
| BaGS37E09 | 15447 | 15448 | CAPS |
| BaAK29I15 | 15451 | 15452 | SNP |
| BaAK18I01 | 15455 | 15456 | SNP |
| bast62B0404 | 15459 | 15460 | SNP |
| bah25l03 | 15463 | 15464 | SNP |
| BaGS19I11 | 15467 | 15468 | CAPS |
| baal1n11 | 15471 | 15472 | SNP |
| baak16l07 | 15475 | 15476 | SNP |
| BaGS18P04 | 15479 | 15480 | CAPS |
| bags19e06 | 15483 | 15484 | CAPS |
| baak35n07 | 15487 | 15488 | CAPS |
| BaAK29K23 | 15491 | 15492 | SNP |
| baal13c18 | 15495 | 15496 | SNP |
| bags7d17 | 15499 | 15500 | SNP |
| bags20j08 | 15503 | 15504 | SNP |
| baal9c20 | 15507 | 15508 | SNP |
| bags20l05 | 15511 | 15512 | SNP |
| bah63k05 | 15515 | 15516 | size_poly (codominant) |
| BaAK14C17 | 15519 | 15520 | CAPS |
| Bmac40 | — | — | SSR |
| baal15j23 | 15523 | 15524 | SNP |
| BaAK1N06 | 15527 | 15528 | CAPS |
| bags38d10 | 15531 | 15532 | CAPS |
| BaAK19J15 | 15535 | 15536 | CAPS |
| BaH50L14 | 15539 | 15540 | SNP |
| BaGS37E11 | 15543 | 15544 | SNP |
| BaSD27E20 | 15547 | 15548 | SNP |
| basd17f18 | 15551 | 15552 | SNP |
| baal32m04 | 15555 | 15556 | SNP |

TABLE 13-6-continued

| Name | Primers used (SEQ ID NO:) | | marker type |
|---|---|---|---|
| BaSD12L12 | 15559 | 15560 | CAPS |
| BaGS37D24 | 15563 | 15564 | CAPS |
| BaGS9K15 | 15567 | 15568 | CAPS |
| BaGS33L03 | 15571 | 15572 | CAPS |
| BaAK24G10 | 15575 | 15576 | SNP |
| kr58F0511 | 15579 | 15580 | CAPS |
| BaH50F16 | 15583 | 15584 | SNP |
| basd17d11 | 15587 | 15588 | SNP |
| BaH37P24 | 15591 | 15592 | SNP |
| bah47l21 | 15595 | 15596 | SNP |
| baet45C1105 | 15599 | 15600 | SNP |
| baak39o18 | 15603 | 15604 | CAPS |
| bags20p12 | 15607 | 15608 | CAPS |
| bags38f23 | 15611 | 15612 | CAPS |
| baak14b08 | 15615 | 15616 | SNP |
| bah54n10 | 15619 | 15620 | SNP |
| bags3k09 | 15623 | 15624 | CAPS |

TABLE 13-7

| Name | Primers used (SEQ ID NO:) | | marker type |
|---|---|---|---|
| bags34p08 | 15627 | 15628 | SNP |
| baal1e06 | 15631 | 15632 | SNP |
| baak34p14 | 15635 | 15636 | CAPS |
| baak14k12 | 15639 | 15640 | CAPS |
| BaSD13G17 | 15643 | 15644 | size_poly (codominant) |
| MWG897 | — | — | STS |
| bags27h05 | 15647 | 15648 | size_poly (codominant) |
| basd15m11 | 15651 | 15652 | CAPS |
| BaH28G09 | 15655 | 15656 | CAPS |
| bags21b06 | 15659 | 15660 | CAPS |
| basd12g17 | 15663 | 15664 | size_poly (codominant) |
| BaH18F07 | 15667 | 15668 | CAPS |
| BaH44A23 | 15671 | 15672 | CAPS |
| bags3d07 | 15675 | 15676 | CAPS |
| BaAL6A21 | 15679 | 15680 | SNP |
| BaAK24E07 | 15683 | 15684 | CAPS |
| BaAL29L09 | 15687 | 15688 | SNP |
| kr66D1107 | 15691 | 15692 | SNP |
| bastl47C0606 | 15695 | 15696 | SNP |
| BaH50M03 | 15699 | 15700 | SNP |
| basd27k17 | 15703 | 15704 | SNP |

TABLE 14-1

| Name | Primers used (SEQ ID NO:) | | marker type |
|---|---|---|---|
| basd2p19 | 15707 | 15708 | SNP |
| BaAK38B18 | 15711 | 15712 | size_poly (dominant) |
| bah42i06 | 15715 | 15716 | CAPS |
| bags6f02 | 15719 | 15720 | SNP |
| BaAK39J07 | 15723 | 15724 | SNP |
| BaAK1L23 | 15727 | 15728 | CAPS |
| baak17e10 | 15731 | 15732 | SNP |
| BaH50H08 | 15735 | 15736 | SNP |
| baal17e10 | 15739 | 15740 | SNP |
| BaSD17C05 | 15743 | 15744 | SNP |
| BaGS14P02 | 15747 | 15748 | SNP |
| bastl42H0115 | 15751 | 15752 | SNP |
| BaAK19C08 | 15755 | 15756 | SNP |
| bastl40H1115 | 15759 | 15760 | SNP |
| bags12l21 | 15763 | 15764 | CAPS |
| baak12j24 | 15767 | 15768 | CAPS |
| bags14d22 | 15771 | 15772 | CAPS |
| BaAK21P12 | 15775 | 15776 | SNP |
| baal6b02 | 15779 | 15780 | CAPS |
| baak29f13 | 15783 | 15784 | CAPS |
| bast79C0406 | 15787 | 15788 | SNP |
| BaH45M08 | 15791 | 15792 | SNP |

TABLE 14-1-continued

| Name | Primers used (SEQ ID NO:) | | marker type |
|---|---|---|---|
| kr28A0301 | 15795 | 15796 | SNP |
| bags19e04 | 15799 | 15800 | CAPS |
| BaH28L07 | 15803 | 15804 | CAPS |
| baak21m18 | 15807 | 15808 | CAPS |
| baak21l22 | 15811 | 15812 | SNP |
| basd15h01 | 15815 | 15816 | SNP |
| BaH19O11 | 15819 | 15820 | SNP |
| BaH59A20 | 15823 | 15824 | CAPS |
| bags39l05 | 15827 | 15828 | SNP |
| BaAK31N06 | 15831 | 15832 | CAPS |
| BaH58P03 | 15835 | 15836 | SNP |
| bags29c18 | 15839 | 15840 | CAPS |
| BaAL4O04 | 15843 | 15844 | SNP |
| bags37n23 | 15847 | 15848 | CAPS |
| BaAL39N03 | 15851 | 15852 | size_poly (codominant) |
| BaAK14C23 | 15855 | 15856 | SNP |
| kr61A1101 | 15859 | 15860 | SNP |
| BaH42J17 | 15863 | 15864 | SNP |
| BaH58H08 | 15867 | 15868 | SNP |
| bast78A0202 | 15871 | 15872 | SNP |
| BaGS21E20 | 15875 | 15876 | CAPS |
| bags22k18 | 15879 | 15880 | size_poly (codominant) |
| BaGS33H15 | 15883 | 15884 | size_poly (codominant) |
| HVM4 | — | — | SSR |
| BaSD18O16 | 15887 | 15888 | SNP |
| baak22j11 | 15891 | 15892 | SNP |
| BaAK20K04 | 15895 | 15896 | SNP |
| bags29l11 | 15899 | 15900 | SNP |
| BaAK17G18 | 15903 | 15904 | size_poly (dominant) |

TABLE 14-2

| Name | Primers used (SEQ ID NO:) | | marker type |
|---|---|---|---|
| baak14o13 | 15907 | 15908 | SNP |
| baal8d17 | 15911 | 15912 | size_poly (codominant) |
| BaAK37P20 | 15915 | 15916 | CAPS |
| bags28k04 | 15919 | 15920 | SNP |
| bah34b22 | 15923 | 15924 | CAPS |
| BaGS37M03 | 15927 | 15928 | SNP |
| BaGS18C14 | 15931 | 15932 | SNP |
| bast23G0214 | 15935 | 15936 | SNP |
| bah47p02 | 15939 | 15940 | SNP |
| baak42a24 | 15943 | 15944 | CAPS |
| baak16f06 | 15947 | 15948 | CAPS |
| bah11m12 | 15951 | 15952 | CAPS |
| kr66H0216 | 15955 | 15956 | SNP |
| BaGS23D15 | 15959 | 15960 | SNP |
| baal22c17 | 15963 | 15964 | SNP |
| baak33d06 | 15967 | 15968 | CAPS |
| bags34l17 | 15971 | 15972 | SNP |
| BaGS25G03 | 15975 | 15976 | CAPS |
| bah14j16 | 15979 | 15980 | CAPS |
| bah34a23 | 15983 | 15984 | size_poly (codominant) |
| BaAK21B17 | 15987 | 15988 | SNP |
| bast42C0406 | 15991 | 15992 | CAPS |
| baak21m13 | 15995 | 15996 | SNP |
| baet45H0115 | 15999 | 16000 | size_poly (codominant) |
| BaH38E01 | 16003 | 16004 | SNP |
| bast03G0313 | 16007 | 16008 | SNP |
| baak38p18 | 16011 | 16012 | size_poly (codominant) |
| basd18g06 | 16015 | 16016 | SNP |
| baak40i22 | 16019 | 16020 | SNP |
| baal2n12 | 16023 | 16024 | SNP |
| BaSD3C24 | 16027 | 16028 | SNP |
| BaAK46M07 | 16031 | 16032 | SNP |
| BaGS17N04 | 16035 | 16036 | SNP |
| bags12d09 | 16039 | 16040 | SNP |
| basd20c08 | 16043 | 16044 | SNP |
| bags17i04 | 16047 | 16048 | CAPS |
| baak15p03 | 16051 | 16052 | CAPS |
| baak24b20 | 16055 | 16056 | size_poly (codominant) |
| baal18g11 | 16059 | 16060 | SNP |

TABLE 14-2-continued

| Name | Primers used (SEQ ID NO:) | | marker type |
|---|---|---|---|
| baal40b06 | 16063 | 16064 | CAPS |
| baak40g02 | 16067 | 16068 | SNP |
| baal1m11 | 16071 | 16072 | size_poly (codominant) |
| BaH26B16 | 16075 | 16076 | SNP |
| baal5n08 | 16079 | 16080 | SNP |
| BaSD27F05 | 16083 | 16084 | size_poly (codominant) |
| bags9c08 | 16087 | 16088 | SNP |
| baak3c01 | 16091 | 16092 | CAPS |
| basd1j22 | 16095 | 16096 | SNP |
| BaH23N03 | 16099 | 16100 | SNP |
| bast46D0808 | 16103 | 16104 | SNP |
| bast22A0802 | 16107 | 16108 | SNP |

TABLE 14-3

| Name | Primers used (SEQ ID NO:) | | marker type |
|---|---|---|---|
| bast34D0808 | 16111 | 16112 | SNP |
| bast48E0509 | 16115 | 16116 | SNP |
| bast26F1012 | 16119 | 16120 | SNP |
| baal30e07 | 16123 | 16124 | SNP |
| bags23n06 | 16127 | 16128 | CAPS |
| BaGS18I05 | 16131 | 16132 | SNP |
| BaH52L11 | 16135 | 16136 | CAPS |
| baal18b16 | 16139 | 16140 | CAPS |
| bags1a17 | 16143 | 16144 | size_poly (dominant) |
| HVCMA | — | — | SSR |
| bags8o06 | 16147 | 16148 | SNP |
| baak46e14 | 16151 | 16152 | SNP |
| BaGS38N08 | 16155 | 16156 | SNP |
| BaH49P17 | 16159 | 16160 | SNP |
| bah60l22 | 16163 | 16164 | CAPS |
| bags21m22 | 16167 | 16168 | CAPS |
| BaH54E07 | 16171 | 16172 | CAPS |
| BaAK39A20 | 16175 | 16176 | CAPS |
| bags21d11 | 16179 | 16180 | SNP |
| kr39H0816 | 16183 | 16184 | SNP |
| baet32B1103 | 16187 | 16188 | CAPS |
| BaAK31O16 | 16191 | 16192 | CAPS |
| bags39l20 | 16195 | 16196 | CAPS |
| BaGS15L12 | 16199 | 16200 | CAPS |
| kr67D0208 | 16203 | 16204 | SNP |
| BaAK1H16 | 16207 | 16208 | SNP |
| BaH26F10 | 16211 | 16212 | SNP |
| bags14n02 | 16215 | 16216 | SNP |
| bah36f01 | 16219 | 16220 | CAPS |
| bast79F0711 | 16223 | 16224 | size_poly (codominant) |
| BaGS29G21 | 16227 | 16228 | size_poly (codominant) |
| bast79D1107 | 16231 | 16232 | SNP |
| BaGS26O20 | 16235 | 16236 | SNP |
| bags11h08 | 16239 | 16240 | CAPS |
| bags22h11 | 16243 | 16244 | SNP |
| baet19D0608 | 16247 | 16248 | SNP |
| bags23a14 | 16251 | 16252 | CAPS |
| cMWG704 | — | — | STS |
| bah62d14 | 16255 | 16256 | size_poly (codominant) |
| BaGS37C09 | 16259 | 16260 | SNP |
| bags20a01 | 16263 | 16264 | SNP |
| bah53m11 | 16267 | 16268 | SNP |
| BaGS26L01 | 16271 | 16272 | SNP |
| bags21p23 | 16275 | 16276 | SNP |
| BaAK24B01 | 16279 | 16280 | SNP |
| BaAK13L03 | 16283 | 16284 | CAPS |
| MWG511 | — | — | CAPS |
| bastl56C0105 | 16287 | 16238 | SNP |
| basd20j22 | 16291 | 16292 | CAPS |
| bags28d11 | 16295 | 16296 | SNP |
| BaGS4I11 | 16299 | 16300 | size_poly (codominant) |

TABLE 14-4

| Name | Primers used (SEQ ID NO:) | | marker type |
|---|---|---|---|
| BaH52G15 | 16303 | 16304 | size_poly (codominant) |
| baak11d12 | 16307 | 16308 | SNP |
| BaH42A07 | 16311 | 16312 | SNP |
| BaGS38F01 | 16315 | 16316 | CAPS |
| BaAK32I05 | 16319 | 16320 | CAPS |
| bah60f18 | 16323 | 16324 | SNP |
| baal2n10 | 16327 | 16328 | CAPS |
| BaAK14F01 | 16331 | 16332 | CAPS |
| bah57o01 | 16335 | 16336 | CAPS |
| basd12f05 | 16339 | 16340 | CAPS |
| bah58e21 | 16343 | 16344 | CAPS |
| bags1d07 | 16347 | 16348 | CAPS |
| BaH23J15 | 16351 | 16352 | CAPS |
| baak1p09 | 16355 | 16356 | CAPS |
| BaAK32C23 | 16359 | 16360 | SNP |
| baal9e06 | 16363 | 16364 | SNP |
| baal18g23 | 16367 | 16368 | CAPS |
| bastl47E0309 | 16371 | 16372 | SNP |
| baak30o08 | 16375 | 16376 | SNP |
| baet44C0606 | 16379 | 16380 | SNP |
| bags39g18 | 16383 | 16384 | SNP |
| BaH50P14 | 16387 | 16388 | CAPS |
| bags38m06 | 16391 | 16392 | SNP |
| baal33e12 | 16395 | 16396 | size_poly (codominant) |
| bags3i04 | 16399 | 16400 | SNP |
| BaAL1A11 | 16403 | 16404 | SNP |
| BaSD2M23 | 16407 | 16408 | SNP |
| Bmag359 | — | — | SSR |
| BaAK23L23 | 16411 | 16412 | CAPS |
| bags7a23 | 16415 | 16416 | CAPS |
| bah56l04 | 16419 | 16420 | CAPS |
| basd12k23 | 16423 | 16424 | SNP |
| bast22C0105 | 16427 | 16428 | SNP |
| BaGS38H20 | 16431 | 16432 | SNP |
| bah61p21 | 16435 | 16436 | SNP |
| basd11h13 | 16439 | 16440 | SNP |
| BaAL41J12 | 16443 | 16444 | size_poly (codominant) |
| baal0f04 | 16447 | 16448 | SNP |
| kr18E0810 | 16451 | 16452 | SNP |
| BaH15J07 | 16455 | 16456 | size_poly (codominant) |
| BaAL6G08 | 16459 | 16460 | CAPS |
| BaGS24F02 | 16463 | 16464 | SNP |
| baal19m12 | 16467 | 16468 | CAPS |
| bah34h16 | 16471 | 16472 | size_poly (codominant) |
| baak2e06 | 16475 | 16476 | SNP |
| bast10C0406 | 16479 | 16480 | CAPS |
| baak12l16 | 16483 | 16484 | SNP |
| baak29d01 | 16487 | 16488 | SNP |
| BaAK19N06 | 16491 | 16492 | SNP |
| BaAK4I02 | 16495 | 16496 | SNP |
| BaH49K10 | 16499 | 16500 | SNP |

TABLE 14-5

| Name | Primers used (SEQ ID NO:) | | marker type |
|---|---|---|---|
| baal2o03 | 16503 | 16504 | SNP |
| baak28g14 | 16507 | 16508 | SNP |
| bah62n05 | 16511 | 16512 | CAPS |
| bags16e11 | 16515 | 16516 | SNP |
| bags23g13 | 16519 | 16520 | SNP |
| BaSD23C05 | 16523 | 16524 | SNP |
| BaH19F17 | 16527 | 16528 | SNP |
| BaH15J02 | 16531 | 16532 | size_poly (codominant) |
| baak20d11 | 16535 | 16536 | CAPS |
| BaAL6D19 | 16539 | 16540 | CAPS |
| baak43e16 | 16543 | 16544 | CAPS |
| baak40b02 | 16547 | 16548 | CAPS |
| bah62m03 | 16551 | 16552 | CAPS |
| BaGS26G17 | 16555 | 16556 | SNP |
| baal6j16 | 16559 | 16560 | SNP |
| bags29b09 | 16563 | 16564 | SNP |
| baal20e03 | 16567 | 16568 | SNP |

TABLE 14-5-continued

| Name | Primers used (SEQ ID NO:) | | marker type |
|---|---|---|---|
| BaGS9L23 | 16571 | 16572 | SNP |
| bah32e22 | 16575 | 16576 | SNP |
| BaAK17O14 | 16579 | 16580 | SNP |
| bah56g23 | 16583 | 16584 | CAPS |
| basd22f14 | 16587 | 16588 | CAPS |
| BaH42O04 | 16591 | 16592 | SNP |
| bast74F0111 | 16595 | 16596 | SNP |
| BaSD21F13 | 16599 | 16600 | SNP |
| BaAK26G13 | 16603 | 16604 | CAPS |
| BaAK44D07 | 16607 | 16608 | CAPS |
| bast61C0206 | 16611 | 16612 | size_poly (codominant) |
| BaAL29L08 | 16615 | 16616 | SNP |
| BaH34B20 | 16619 | 16620 | CAPS |
| baak21a04 | 16623 | 16624 | SNP |
| BaGS37F18 | 16627 | 16628 | SNP |
| baal12h12 | 16631 | 16632 | SNP |
| BaAK42B16 | 16635 | 16636 | CAPS |
| BaAK26F12 | 16639 | 16640 | SNP |
| BaH27B21 | 16643 | 16644 | size_poly (codominant) |
| BaGS12B05 | 16647 | 16648 | SNP |
| baal12h24 | 16651 | 16652 | SNP |
| baal35j16 | 16655 | 16656 | SNP |
| BaGS37C07 | 16659 | 16660 | SNP |
| BaAK45D23 | 16663 | 16664 | SNP |
| BaH42G09 | 16667 | 16668 | SNP |
| BaAL40P01 | 16671 | 16672 | SNP |
| kr61A0901 | 16675 | 16676 | SNP |
| baal4d05 | 16679 | 16680 | CAPS |
| basd20l03 | 16683 | 16684 | CAPS |
| baal31b03 | 16687 | 16688 | CAPS |
| bags27k21 | 16691 | 16692 | CAPS |
| bah55n15 | 16695 | 16696 | CAPS |
| BaH44B17 | 16699 | 16700 | SNP |
| BaSD2K11 | 16703 | 16704 | SNP |

TABLE 14-6

| Name | Primers used (SEQ ID NO:) | | marker type |
|---|---|---|---|
| BaAK20B23 | 16707 | 16708 | CAPS |
| BaGS23E20 | 16711 | 16712 | SNP |
| bags33i10 | 16715 | 16716 | SNP |
| bags35k06 | 16719 | 16720 | SNP |
| bags22c18 | 16723 | 16724 | CAPS |
| MWG2031 | — | — | STS |
| BaGS22M17 | 16727 | 16728 | SNP |
| baak21j24 | 16731 | 16732 | SNP |
| BaH29D20 | 16735 | 16736 | CAPS |
| bah44f20 | 16739 | 16740 | CAPS |
| BaAL16O08 | 16743 | 16744 | SNP |
| BaAL27L17 | 16747 | 16748 | SNP |
| sKT3 | — | — | size_poly |
| sKT9 | — | — | size_poly |
| baet31B1103 | 16751 | 16752 | SNP |
| MWG975 | — | — | STS |
| BaAL4A11 | 16755 | 16756 | CAPS |
| BaGS22I18 | 16759 | 16760 | CAPS |
| BaGS24K08 | 16763 | 16764 | SNP |
| bah16c17 | 16767 | 16768 | SNP |
| bah42m04 | 16771 | 16772 | size_poly (codominant) |
| bags28l21 | 16775 | 16776 | SNP |
| basd12f23 | 16779 | 16780 | size_poly (codominant) |
| bah31m22 | 16783 | 16784 | SNP |
| BaAL30C17 | 16787 | 16788 | SNP |
| BaAK40P18 | 16791 | 16792 | CAPS |
| baak37n01 | 16795 | 16796 | SNP |
| BaGS24O11 | 16799 | 16800 | SNP |
| BaH27K19 | 16803 | 16804 | CAPS |
| BaGS15J07 | 16807 | 16808 | CAPS |
| bah19a07 | 16811 | 16812 | CAPS |
| BaH50I23 | 16815 | 16816 | SNP |
| BaH56D06 | 16819 | 16820 | SNP |
| BaAK39M05 | 16823 | 16824 | SNP |

TABLE 14-6-continued

| Name | Primers used (SEQ ID NO:) | | marker type |
|---|---|---|---|
| bah11m16 | 16827 | 16828 | SNP |
| bah49d03 | 16831 | 16832 | SNP |
| bah62l23 | 16835 | 16836 | SNP |
| BaAK38J13 | 16839 | 16840 | SNP |
| BaH37N04 | 16843 | 16844 | SNP |
| basd27c06 | 16847 | 16848 | SNP |
| bah39g10 | 16851 | 16852 | SNP |
| BaSD18P05 | 16855 | 16856 | size_poly (codominant) |
| BaGS20A13 | 16859 | 16860 | SNP |
| bah44n05 | 16863 | 16864 | CAPS |
| EBmac764 | — | — | SSR |
| BaH27L15 | 16867 | 16868 | SNP |
| BaAK21I02 | 16871 | 16872 | size_poly (codominant) |
| Bmac0064 | — | — | SSR |
| BaH59F07 | 16875 | 16876 | SNP |
| bags9l05 | 16879 | 16880 | SNP |
| BaGS13H12 | 16883 | 16884 | CAPS |

TABLE 14-7

| Name | Primers used (SEQ ID NO:) | | marker type |
|---|---|---|---|
| BaAL19B06 | 16887 | 16888 | CAPS |
| BaSD15P23 | 16891 | 16892 | CAPS |
| bah53j21 | 16895 | 16896 | SNP |
| bah21f16 | 16899 | 16900 | SNP |
| baet39E0309 | 16903 | 16904 | SNP |
| bags5l04 | 16907 | 16908 | SNP |
| bags7g10 | 16911 | 16912 | SNP |
| BaGS9D22 | 16915 | 16916 | SNP |
| kr27H1216 | 16919 | 16920 | CAPS |
| BaAK25O11 | 16923 | 16924 | CAPS |
| bah18j14 | 16927 | 16928 | SNP |
| bags37k14 | 16931 | 16932 | SNP |
| baak26n19 | 16935 | 16936 | size_poly (codominant) |
| bah42k03 | 16939 | 16940 | SNP |
| BaH36N15 | 16943 | 16944 | CAPS |
| Bmag120 | — | — | SSR |
| bags12i02 | 16947 | 16948 | SNP |
| BaAK38E05 | 16951 | 16952 | CAPS |
| baet25B0604 | 16955 | 16956 | SNP |
| BaAK46E21 | 16959 | 16960 | SNP |
| BaGS37J12 | 16963 | 16964 | SNP |
| bast60C0105 | 16967 | 16968 | CAPS |
| baak30b08 | 16971 | 16972 | SNP |
| BaAL29N13 | 16975 | 16976 | size_poly (codominant) |
| BaAL24O04 | 16979 | 16980 | CAPS |
| baak20o12 | 16983 | 16984 | SNP |
| basd14k23 | 16987 | 16988 | SNP |
| BaAK23L05 | 16991 | 16992 | SNP |
| BaGS31G02 | 16995 | 16996 | CAPS |
| bags33o01 | 16999 | 17000 | SNP |
| basd18g14 | 17003 | 17004 | CAPS |
| bah24d24 | 17007 | 17008 | SNP |
| BaGS12F09 | 17011 | 17012 | SNP |
| BaAK33H23 | 17015 | 17016 | SNP |
| bah47p03 | 17019 | 17020 | SNP |
| BaSD14F09 | 17023 | 17024 | SNP |
| bah11k13 | 17027 | 17028 | CAPS |
| BaSD22F10 | 17031 | 17032 | SNP |
| bags32a01 | 17035 | 17036 | CAPS |
| bags27o20 | 17039 | 17040 | SNP |
| baak31o10 | 17043 | 17044 | SNP |
| bags10f16 | 17047 | 17048 | SNP |
| baal37j12 | 17051 | 17052 | CAPS |
| BaGS9H02 | 17055 | 17056 | SNP |
| BaAK40H10 | 17059 | 17060 | CAPS |
| bah56m09 | 17063 | 17064 | size_poly (codominant) |
| kr66C0705 | 17067 | 17068 | SNP |
| BaGS33M05 | 17071 | 17072 | SNP |
| bast60B0204 | 17075 | 17076 | size_poly (codominant) |
| bah56p08 | 17079 | 17080 | CAPS |
| baak12e19 | 17083 | 17084 | CAPS |

TABLE 14-8

| Name | Primers used (SEQ ID NO:) | | marker type |
|---|---|---|---|
| BaGS1D05 | 17087 | 17088 | CAPS |
| BaH29M21 | 17091 | 17092 | CAPS |
| bags21c04 | 17095 | 17096 | CAPS |
| baak32p09 | 17099 | 17100 | CAPS |
| BaAL24B02 | 17103 | 17104 | SNP |
| BaGS34F08 | 17107 | 17108 | SNP |
| bast36D1208 | 17111 | 17112 | SNP |
| kr25B1103 | 17115 | 17116 | SNP |
| kr08D0303 | 17119 | 17120 | size_poly (dominant) |
| baal19g05 | 17123 | 17124 | SNP |
| BaH22B15 | 17127 | 17128 | CAPS |
| bags19c10 | 17131 | 17132 | SNP |
| bags29k01 | 17135 | 17136 | SNP |
| bastl54G0414 | 17139 | 17140 | SNP |
| BaGS23J01 | 17143 | 17144 | CAPS |
| bags34b15 | 17147 | 17148 | SNP |
| baak46i07 | 17151 | 17152 | CAPS |
| BaAL6J13 | 17155 | 17156 | CAPS |
| bah31l17 | 17159 | 17160 | SNP |
| BaAK32A05 | 17163 | 17164 | SNP |
| BaGS30N22 | 17167 | 17168 | SNP |
| BaH54J20 | 17171 | 17172 | CAPS |
| BaGS7F20 | 17175 | 17176 | CAPS |
| bah63p18 | 17179 | 17180 | size_poly (codominant) |
| bags11p11 | 17183 | 17184 | CAPS |
| BaH27L17 | 17187 | 17188 | SNP |
| basd17e11 | 17191 | 17192 | SNP |
| bags15i06 | 17195 | 17196 | SNP |
| BaAK36F09 | 17199 | 17200 | SNP |
| bast57A0101 | 17203 | 17204 | SNP |
| baak26h17 | 17207 | 17208 | CAPS |
| basd13b15 | 17211 | 17212 | SNP |
| bags9d11 | 17215 | 17216 | SNP |
| BaH20K03 | 17219 | 17220 | size_poly (codominant) |
| BaSD27N21 | 17223 | 17224 | size_poly (codominant) |
| baal13a10 | 17227 | 17228 | size_poly (dominant) |
| kr30F1212 | 17231 | 17232 | SNP |
| bastl45B0903 | 17235 | 17236 | SNP |
| Bmac156 | — | — | SSR |
| bah60k06 | 17239 | 17240 | size_poly (codominant) |
| BaGS32I12 | 17243 | 17244 | SNP |
| BaGS4H02 | 17247 | 17248 | CAPS |
| bah44k12 | 17251 | 17252 | size_poly (codominant) |
| baak27p06 | 17255 | 17256 | SNP |
| bags21m21 | 17259 | 17260 | SNP |
| BaSD14J15 | 17263 | 17264 | CAPS |
| HVM49 | — | — | SSR |
| basd16e11 | 17267 | 17268 | SNP |
| BaAK21N09 | 17271 | 17272 | SNP |
| baal0e10 | 17275 | 17276 | size_poly (codominant) |
| baak1g17 | 17279 | 17280 | SNP |

TABLE 14-9

| Name | Primers used (SEQ ID NO:) | | marker type |
|---|---|---|---|
| BaH14K12 | 17283 | 17284 | size_poly (codominant) |
| BaAK31G05 | 17287 | 17288 | size_poly (codominant) |
| MWG2062 | — | — | STS |
| BaH50G17 | 17291 | 17292 | size_poly (codominant) |
| HVM5 | — | — | SSR |
| bags38n21 | 17295 | 17296 | CAPS |
| bastl04B0303 | 17299 | 17300 | size_poly (codominant) |
| baal35f12 | 17303 | 17304 | SNP |
| BaH49M02 | 17307 | 17308 | CAPS |
| baak38f04 | 17311 | 17312 | CAPS |
| bah29b02 | 17315 | 17316 | SNP |
| basd15d20 | 17319 | 17320 | CAPS |
| kr61C0305 | 17323 | 17324 | CAPS |
| BaH23B08 | 17327 | 17328 | SNP |
| kr40H1115 | 17331 | 17332 | CAPS |
| bah51g17 | 17335 | 17336 | SNP |
| BaSD22E19 | 17339 | 17340 | SNP |

Table 8-1 through Table 14-9 show 7 kinds of polymorphisms: CAPS, SNP, size_poly, SSR (simple sequence repeat), STS, dCAPS, and trait. SSR, STS, dCAPS, and trait are known genetic markers. The polymorphisms specified by the inventors of the present invention are classified into 3 categories: CAPS, SNP, and size_poly. The third category, size_poly, is a polymorphism based on differences in the length of amplified fragments, and it includes polymorphisms that are detected based on whether the primer sets have successfully amplified the fragments. In any case, the polymorphism can be detected by running electrophoresis for the amplified DNA fragments, and detecting differences in band positions, or the presence or absence of bands.

CAPS is a polymorphism based on the presence or absence of a restriction enzyme recognition sequence. Most CAPS are based on single nucleotide polymorphism in the restriction enzyme recognition sequence; however, CAPS also includes those based on insertion/deletion of one or more bases. In Table 8-1 through Table 14-9, the marker type designated as SNP is the marker that does not have single nucleotide polymorphism or insertion/deletion in the restriction enzyme recognition sequence. CAPS can be detected by running electrophoresis for the amplified DNA fragments after restriction enzyme treatment and then detecting the number of bands, or band positions. Non-CAPS SNPs can be detected by typing, i.e., by actually confirming the base at the site of SNP or insertion/deletion. CAPS can also be detected by SNP typing.

Table 15-1 through Table 21-6 show base sequences in the vicinity of SNP or insertion/deletion that occurs between Haruna Nijo and H602. Names of restriction enzymes and recognition sequences of the restriction enzymes are also shown. Tables 15-1 through 15-5 are for 1H chromosome, Tables 16-1 through 16-7 for 2H chromosomes, Tables 17-1 through 17-6 for 3H chromosomes, Tables 18-1 through 18-5 for 4H chromosome, Tables 19-1 through 19-6 for 5H chromosome, Tables 20-1 through 20-5 for 6H chromosome, and Tables 21-1 through 21-6 for 7H chromosome. Table 22-1 through Table 28-25 show base sequences in the vicinity of SNPs of the SNP markers (non-CAPS). Tables 22-1 through 22-20 show polymorphisms in 1H chromosome, Tables 23-1 through 23-30 in 2H chromosome, Tables 24-1 through 24-27 in 3H chromosome, Tables 25-1 through 25-18 in 4H chromosome, Tables 26-1 through 26-28 in 5H chromosome, Tables 27-1 through 27-16 in 6H chromosome, and Tables 28-1 through 28-25 in 7H chromosome. Some of these polymorphisms occur at more than one location in one fragment.

In Table 15-1 through Table 28-25, bases that represent SNP or insertion/deletion are indicated by underline. Note that, in the sequence listing, bases at SNP sites are indicated by "universal codes." Where applicable, the universal codes are also used for bases in the restriction enzyme recognition sequence.

In Table 15-1 through Table 28-25, bases with SNPs are indicated by N in cases where the base is identified only for one of Haruna Nijo and H602 but not for the other. In this case, the unidentified base is one of the remaining three bases.

Universal codes are defined as follows.
m: A or C
r: G or A
w: A or T
s: G or C
y: T or C
k: G or T
v: A, G or C
h: A, C, or T
d: A, G, or T
b: G, C, or T
n: (A, C, G, or T) or (unidentified other bases)

[Table 15-1]

| Clones | Haruna Nijo H602 | SEQ ID NO: | Restriction enzyme | Recognition sequence |
|---|---|---|---|---|
| baak2l03 | AGCTTACATCCTGGAATCTTC<br>AGCTTACATCGTGGAATCTTC | 17342 | MvaI | CCWGG |
| BaGS32E23 | TGATTGCATCAAAATGGCATG<br>TGATTGCATCGAAATGGCATG | 17353 | TaqI | TCGA |
| basd13k20 | CCAGGTGCCGCGGITGTTGCA<br>CCAGGTGCCGGGGITGTTGCA | 17354 | HapII | CCGG |
| baak24o11 | GGAAGTTCTCGTCCTTGA-GC<br>GGAANGTCTCATCCTTGAAGG | 17355<br>17356 | FokI | NNNNNNNNNNNNNCATCC |
| BaSD2D08 | GGGAGCTGCATCAGCAGCCCC<br>GGGAGCTGCAGCAGCAGCCCC | 17359 | PstI | CTGCAG |
| bah11b15 | CGGCGCACCCAGCCCTCTCGT<br>CGGCGCACCCGGCCCTCTCGT | 17361 | BCnI | CCSGG |
| BaGS17B21 | AGCAGCATGCACATGTGATGG<br>AGCAGCATGCGCATGTGATGG | 17375 | HhaI | GCGC |
| BaAK21D02 | CAATGAGGCCATACAGGGCAA<br>CAATGAGGCCGTACAGGGCAA | 17382 | AfaI | GTAC |
| baal4f12 | CGAGACCGGCGCTCGATTAAG<br>CGAGACCGGCCCTCGATTAAG | 17385 | HaeIII | GGCC |
| BaGS11I03 | GGGCGACCCGGTATGAACAAC<br>GGGCGACCCGATATGAACAAC | 17386 | HapII | CCGG |
| bah19f01 | CGAAGTTCCAGGCGTCATTGA<br>CGAAGTTCCAAGCGTCATTGA | 17387 | MvaI | GCMG |
| BaAK27F07 | GGAGCGATCGATCGACGGGAC<br>GGAGCGATCGGTCGACGGGAC | 17388 | ClaI | ATCGAT |
| BaH36O18 | AGACGAGGGCACTGCTGAGGA<br>AGACGAGGGCGCTGCTGAGGA | 17403 | HhaI | GCGC |
| BaAK20A06 | ACAGTAATATCGATTATGAAT<br>ACAGTAATATTGATTATGAAT | 17404 | ClaI | ATCGAT |
| bah25n06 | AATCCCTTGACCCAAACAAAG<br>AATCCCTTGATCCAAACAAAG | 17405 | MboI | GATC |
| BaGS11J13 | GCACGACACCGGCGTCCTTGC<br>GCACGACACCCGCGTCCTTGC | 17413 | HapII | CCGG |
| baa138123 | TGGGTGAGCCTGAGCCGCGAA<br>TGGGTGAGCCAGAGCCGCGAA | 17414 | DdeI | CTNAG |
| BaAL36B15 | AGCCTCCATGGCCGCCCATCA<br>AGCCTCCATGTCCGCCCATCA | 17415 | HaeIII | GGCC |
| bast60D0610 | CGTCCCAGCTCACAAACTTTG<br>CGTCCCAGCTGACAAACTTTG | 17416 | PvuII | CAGCTG |
| kr22D0808 | ATTTGGGGCTGGGTGTCTTTT<br>ATTTGGGGCTAGGTGTCTTTT | 17417 | XspI | CTAG |
| basd23o02 | GACCGGATCTGGACGCCAGGA<br>GACCGGATCTAGACGCCAGGA | 17422 | XspI | CTAG |
| baak1j14 | ATCTTCTGCAGGCACTTGTCG<br>ATCTTCTGCAACCACTTGICG | 17423 | PstI | CTGCAG |
| baak24k18 | CCCCCTGTGGCCACCTCTGGC<br>CCCCCTGTGGTCACCTCTGGC | 17424 | HphI | NNNNNNNTCACC |
| BaH38H09 | ATCTTCTGCAAGCACTTGTCG<br>ATCTTCTGCAGGCACTTGTCG | 17426 | PstI | CTGCAG |
| basd17m22 | AAGACCCTGTACACCTTGTCC<br>AAGACCCTGTCCACCTTGTCC | 17450 | AfaI | GTAC |

[Table 15-2]

| Clones | Harunz Nijo H602 | SED ID NO: | Restriction enzyme | Recognition sequence |
|---|---|---|---|---|
| bags15g01 | TGATCCGAGATATGCAAAGAG<br>TGATCCGAGACATGCAAAGAG | 17451 | BsmAI | NNNNNGAGAC |
| BaH57E12 | AATGCCTCGACTTAGTTATGA<br>AATGCCTCGAATTAGTTATGA | 17453 | DdeI | CTNAG |
| baal19m17 | ATCTCTCATC-TATCTCGA-A<br>TTCTCTCATCCTATCTCGAAA | 17461<br>17462 | FokI | NNNNNNNNNNNNNNCATCC |
| bags3p11 | ATATGGTCAGTGAAGCCAGGG<br>ATATGGTCAGCGAAGCCAGGG | 17472 | TspRI | CASTGNN |
| bags3p11 | TTGAAGGGTCGGTGTTATGGT<br>TTGAAGGGTCAGTGTTATGGT | 17473 | TspRI | CASTGNN |
| BaAK14J21 | GCCGCCGCCCGCTGGCAGGAT<br>GCCGCCGCCCACTGGCAGGAT | 17474 | TspRI | CASTGNN |
| baak37g19 | AGGAGCAGATGAGGGAGCCGA<br>AGGAGCAGATGAGGGAGCCGA | 17478 | MboI | GATC |
| BaSD16G03 | AAATATTGCTCAGCTTTAAA<br>AAATATTGCGCAGCTTTAAA | 17482 | HhaI | GCGC |
| BaH13F14 | TTTTGTCGTCAACAGATGAAA<br>TTTTGTCGTCGACAGATGAAA | 17491 | TaqI | TCG A |
| basd18l16 | CTGCTGAGCACATAGTGGGGC<br>CTGCTGAGCACATAGTGGGGC | 17496 | Bsp1286I | GDGCHC |
| BaAL19J14 | AGTCATAGTCAACTACACAAT<br>AGTCATAGTCGACTACACAAT | 17497 | TaqI | TCGA |
| basd17m16 | CGATGATGGATGGCTGGAAGA<br>CGATGATGGAAGGCTGGAAGA | 17507 | FokI | GGATGNNNNNNNNN |
| baak13n06 | ACCATGTCGCTGGGAAGAGCC<br>ACCATGTCGCTGGGAAGAGCC | 17509 | HapII | CCGG |
| BaGS27M04 | CTTGCGTACAGAATCTTGTTG<br>CTTGCGTACAAAATCTTGTTG | 17511 | HinfI | GANTC |
| bags15d20 | TATGGACAGTCTAGACAAGCA<br>TATGGACAGTTTAGACAAGCA | 17522 | XbaI | TCTAGA |
| bags37e17 | GCTTTGCTTACGAACGGATCT<br>GCTTTGCTTAGGAACGGATCT | 17563 | DdeI | CTNAG |
| BaSD11P04 | TAAGGATAATAGACCATTCCA<br>TAAGGATAATGGACCATTCCA | 17569 | AvaII | GGWCC |
| bah12j09 | TCTCATGCCGGTATCTTATAG<br>TCTCATGCCGATATCTTATAG | 17570 | EcoRV | GATATC |
| bags14j09 | ATGGTATAATTATTCTGTGAG<br>ATGGTATAATGATTCTGTGAG | 17573 | HinfI | GANTC |
| bags14j09 | TCGGCGACCGACTCCCAACCA<br>TCGGCGACCGTCTCCCAACCA | 17574 | HinfI | GANTC |
| kr26E0610 | GCAAGATGTACCCTGACTTGG<br>GCAAGATGTATCCTGACTTGG | 17575 | AfaI | GTAC |
| BaGS17A18 | GGGGGTTGTCACGGCTTTGGT<br>GGGGGTTGTCGCGGCTTTGGT | 17579 | BstUI | CGCG |
| BaSD22O13 | GGCAGAGGACCGCCAGAAACG<br>GGCAGAGGACTGCCAGAAACG | 17581 | AvaII | GGWCC |
| bags15a22 | TCCAGTGGAGACCCTCGTGGA<br>TCCAGTGGAGGCCCTCGTGGA | 17582 | HaeIII | GGCC |
| baet21H1016 | GCTGTTGAGCCACTCCTTTGC<br>GCTGTTGAGCTACTCCTTTGC | 17583 | AluI | AGCT |

[Table 15-3]

| Clones | Haruna Nijo H602 | SEQ ID NO: | Restriction enzyme | Recognition sequence |
|---|---|---|---|---|
| baak34k14 | CCGGCACGCCGTCGACCTTCA<br>CCGGCACGCCATCGACCTTCA | 17593 | SalI | GTCGAC |
| bags22f12 | CGCCGGATTCCATGCTGCTGC<br>CGCCGGATTCGATGCTGCTGC | 17595 | TaqI | TCGA |
| BaH45P03 | CGGCAACGGGATCTTCAGGCC<br>CGGCAACGGGATCTTCAGGCC | 17596 | MboI | GATC |
| basd11d13 | CTTGACGCTGAACTCCACGAA<br>CTTGACGCTGTACTCCACGAA | 17597 | AfaI | GTAC |
| bags34j05 | CTCAGCCAAGCTCTCCCTAAC<br>CTCAGCCAAGTTCTCCCTAAC | 17639 | AluI | AGCT |
| bah56l03 | CTGCTCCTCGAACTCATTGAC<br>CTGCTCCTCGCACTCATTGAC | 17640 | TaqI | TCGA |
| basd12k03 | TTCCTAGGACGTTCTTCAAAT<br>TTCCTAGGACCTTCTTCAAAT | 17641 | Cfr13I | GGNCC |
| BaAK39I18 | CGGCAACGGGATCTTCAGGCC<br>CGGCAACGGGGTCTTCAGGCC | 17642 | MflI | RGATCY |
| bags21h06 | GGAGCTTTTTAAAGCTCCGCG<br>GGAGCTTTTTGAAGCTCCGCG | 17643 | DraI | TTTAAA |
| bah56k04 | ACACTAACAAAATTCAGCAAG<br>ACACTAACAAGATTCAGCAAG | 17644 | HinfI | GANTG |
| bah60e11 | AGTACAGGTCAAGAAGTTAAA<br>AGTACAGGTCCAGAAGTTAAA | 17645 | Cfr13I | GGNCC |
| baak22i05 | TCGGGATAGGCCCAAAACCCA<br>TCGGGATAGGTCCAAAACCCA | 17646 | HaeIII | GGCC |
| baal5i02 | TTCATGACCATGGCCUCTGC<br>TTCATGACCACGGCCCTCTGC | 17647 | NcoI | CCATGG |
| BaAK2E05 | GCTGCCAACCTAGTACTCTTT<br>GCTGCCAACCAAGTACTCTTT | 17648 | XspI | CTAG |
| baak33g12 | CGACCTCGTAGGGCCCGACGA<br>CGACCTCGTAAGGCCCGACGA | 17649 | BanII | GRGCYC |
| bags4e05 | ACTAAGTTAGCACATATATCA<br>ACTAAGTTAGTACATATATCA | 17650 | AfaI | GTAC |
| BaH28K13 | GGCCGTGGCCGTGAGAGTCGT<br>GGCCGTGGCCCTGAGAGTCGT | 17658 | Cfr13I | GGNCC |
| BaSD1I24 | GGCCGTCGAGGGCCATGAACT<br>GGCCGTCGAGAGCCATGAACT | 17659 | Cfr13I | GGNCC |
| bags4e02 | TATGAGACTACACTGTGTCCT<br>T-TGAGA-TAAACTGG---TT | 17682<br>17683 | TspRI | CASTGNN |
| bast04H0315 | CCGTCGACTCGGGCGGATTTA<br>CCGTCGACTCCGGCGGATTTA | 17684 | AvaI | CYCGRG |
| basd2b18 | CGAAATATGGCCGCACCTGTG<br>CGAAATATGGTCGCACCTGTG | 17688 | Hae111 | GGCC |
| BaSD14B13 | GCCCTGCCCGCCGGCTCCGCA<br>GCCCTGCCCGTCGGCTCCGCA | 17700 | HapII | CCGG |
| BaAK39G10 | CAGATGGAGCTGGCGCCTTCA<br>CAGATGGAGCCGGCGCCTTCA | 17724 | HapII | CCGG |
| BaAK39G03 | GTACTCCCTCTTGGTGTCGAA<br>GTACTCCCTCCTGGTGTCGAA | 17725 | MvaI | CCWGG |
| baak2a18 | TAGACATTACCGGGAGAATCC<br>TAGACATTACTGGGAGAATCC | 17726 | HapII | CCGG |

[Table 15-4]

| Clones | Harunz Nijo H602 | SEQ ID NO: | Restriction enzyme | Recognition sequence |
|---|---|---|---|---|
| basd17104 | CTCCATGGTGCGCCGACGGTG<br>CTCCATGGTGAGCCGACGGTG | 17730 | HhaI | GCGC |
| BaAK30F02 | GACTAATAGAGGCCTATATGA<br>GACTAATAGAAGCCTATATGA | 17735 | HaeIII | GGCC |
| bags10j15 | GGGTAGTTTCCAAGCTGAAGT<br>GGGTAGTTTCGAAGCTGAAGT | 17754 | BspT104I | TTCGAA |
| bags3c15 | ACGGCGTCACATACAGCACGA<br>ACGGCGTCACGTACAGCACGA | 17759 | AfaI | GTAC |
| BaH15M10 | TCTCACATTCAAAGATTGTAG<br>TCTCACATTCGAAGATTGTAG | 17767 | BspT104I | TTCGAA |
| bast61E0509 | TTTGICTGAGCGCATGAGCTT<br>TTTGICTGAGTGCATGAGCTT | 17768 | HhaI | GCGC |
| BaGS31N04 | CAAGTGAGTACACTGACTGTT<br>CAAGTGAGTAAACTGACTGTT | 17769 | TspRI | CASTGNN |
| BaAK27D22 | CGATTGACGTTGCACCCTCTG<br>CGATTGACGTGGCACCCTCTG | 17770 | BanI | GGYRCC |
| baa15o19 | AGGAATTTTGCATGATAAACT<br>AGGAATTTTGGATGATAAACT | 17771 | FokI | GGATGNNNNNNNNN |
| bah55b18 | AT--CCGCAGTGG-ACGCATT<br>GTTTCTGCAGGGGCACGCATC | 17772<br>17773 | TspRI | CASTGNN |
| bags15e08 | CATTTGTCTCTTGTTTTCTC<br>CATTTTGTCTTTTGTTTTCTC | 17786 | BsmAI | GTCTCN |
| BaH47J05 | TAGTAAAACTCTAAAAAGACT<br>TAGTAAAACTTTAAAAAGACT | 17814 | DraI | TTTAAA |
| baa12j10 | TTACATGTCCACTGTGTCTGC<br>TTACATGTCCTCTGTGTCTGC | 17827 | TspRI | CASTGNN |
| BaGS37F14 | ACAAACAGCTGCAATTTCCAT<br>ACAAACAGCTTCAATTTCCAT | 17831 | PvuII | CAGCTG |
| BaH21K05 | GCCAACAACATTGCACGTACT<br>GCCAACAACAGTGCACGTACT | 17842 | Bsp1286I | GDGCHC |
| BaGS25K24 | TTGTTTTGTAGAGCTGCAAAG<br>TTGTTTTGTACAGCTGCAAAG | 17851 | AfaI | GTAC |
| bags1a18 | TGGAGTTGGATATCATGCACA<br>TGGAGTTGGAGATCATGCACA | 17852 | EcoRV | GATATC |
| bags35j22 | TATTGTTGGGAACCATCTAGT<br>TATTGTTGGGGACCATCTAGT | 17866 | Cfr13I | GGNCC |
| baak20h22 | AGTCAACGAGCTCGCCCCACT<br>AGTCAACGAGATCGCCCCACT | 17867 | SacI | GAGCTC |
| bah16j04 | CCCTCAGGAAGGCCAATGTGA<br>CCCTCAGGAAAGCCAATGTGA | 17872 | HaeIII | GGCC |
| BaH54J03 | ATCTCCTCAACTTGTTCAC<br>ATCTCCTCCTCGACTTGTTCAC | 17873 | TaqI | TCGA |
| BaH26M05 | GTGCTGTCGCAAGCATGACCG<br>GTGCTGTCGCGAGCATGACCG | 17876 | BstUI | CGCG |
| baak14e23 | TTAGGGATGCCGGATCAAGTA<br>TTAGGGATGCTGGATCAAGTA | 17880 | HapII | CCGG |
| bast145e1109 | ATCCGAGGATTCACCAGGCTG<br>ATCCGAGGATCCAGC AGGCTG | 17892 | MboI | GATC |
| bah15k16 | CCATTGCATTGAACGATTCCA<br>CCATTGCATTTAACGATTCCA | 17902 | MseI | TTAA |

[Table 15-5]

| Clones | Haruna Nijo H602 | SEQ ID NO: | Restriction enzyme | Recognition sequence |
|---|---|---|---|---|
| bags31a22 | AAATAACTTGTGICATGTTCA<br>AAATAACTTGAGTCATGTTCA | 17903 | HinfI | GANTC |
| BaGS38N20 | GACGGGGTCGGCGATGTGGTC<br>GACGGGGTCGACGATGIGGTC | 17917 | TaqI | TCGA |
| BaGS23O09 | AGCCAAACATCGAGAACATGG<br>AGCCAAACATTGAGAACATGG | 17918 | TaqI | TCGA |
| bastl26E0410 | AGAGTGCGGGGGGCTCAGTAG<br>AGAGTOCGGGCGGCTCAGTAG | 17919 | BanII | GRGCYC |
| BaH15N14 | CTGCGCAATGGCCAACGGTAA<br>CTGCGCAATGACCAACGGTAA | 17920 | HaeIII | GGCC |
| bah30o13 | CAAGCCCAGCTCCAAACTACC<br>CAAGCCCAGC-CCAAACTACC | 17927<br>17928 | AluI | AGCT |
| bags38f18 | GGACAATGGGGATGTTCTCAC<br>GGACAATGGGAATGTTCTCAC | 17929 | FokI | GGATGNNNNNNNNN |
| bah13o05 | CTTGTGGACTTGAGTCATCAC<br>CTTGTGGACTCGAGTCATCAC | 17930 | XhoI | CTCGAG |
| baak36b12 | GGAGCTCCGGGCGCACGAAGT<br>GGAGCTCCGGACGCACGAAGT | 17931 | BcnI | CCSGG |
| bags18o09 | CGTGCTGGCGTTCCAGTAGCC<br>CGTGCTGGCGCTCCAGTAGCC | 17932 | HhaI | GCGC |
| BaAK16L10 | CAGCTTAAGCACATTCATAAC<br>CAGCTTAAGCGCATTCATAAC | 17933 | HhaI | GCGC |
| bah13e15 | CTTATGTGATCATAATACTGC<br>CTTATGTGATAATAATACTGC | 17934 | MboI | GATC |
| bags1f22 | AGCCTTCCACTGGTATCATTT<br>AGCCTTCCACCGGTATCATTT | 17935 | HapII | CCGG |
| BaAL1N23 | CGTAGACATGATCGCCATCGC<br>CGTAGACATGGTCGCCATCGC | 17945 | MboI | GATC |
| BaH32B01 | ATCACAACTGCGCTACTTTTT<br>ATCACAACTGTGCTACTTTTT | 17948 | HhaI | GCGC |
| BaSD18L13 | CCGCTCCTCCATACGATGATG<br>CCGCTCCTCCGTACGATGATG | 17949 | AfaI | GTAC |
| BaH58A04 | GGAATGACTCGATCAGGTCGC<br>GGAATGACTCAATCAGGTCGC | 17950 | MboI | GATC |
| bah50l05 | ATTTTGACTTAGGTCGCACCT<br>ATTTTGACTTCGGTCGCACCT | 17956 | DdeI | CTNAG |
| bastl28a0101 | AAAACAGGATGTACACGGCAC<br>AAAACAGGATATACACGGCAC | 17957 | FokI | GGATGNNNNNNNNN |

TABLE 16-1

| Clones | Haruna Nijo H602 | SEQ ID NO: | Restriction enzyme | Recognition sequence |
|---|---|---|---|---|
| BaAK34H02 | ACTTGTGAGACGGTACGTACC<br>ACTTGTGAGATGGTACGTACC | 17968 | BsmAI | NNNNNGAGAC |
| BaGS37P19 | CTTCCTCCGATCGATTGCCGC<br>CTTCCTCCGACCGATTGCCGC | 17971 | ClaI | ATCGAT |
| BaAL19P17 | TTCCGCTGTAACTCGTGGAGC<br>TTCCGCTGTACCTCGTGGAGC | 17972 | AfaI | GTAC |
| bags38p20 | ATTGCTTGAAGGCCTCGAGGT<br>ATTGCTTGAAAGCCTCGAGGT | 17983 | HaeIII | GGCC |

TABLE 16-1-continued

| Clones | Haruna Nijo H602 | SEQ ID NO: | Restriction enzyme | Recognition sequence |
|---|---|---|---|---|
| BaAK41N22 | AGTATCCGCCATACGTCCACA<br>AGTATCCGCCGTACGTCCACA | 17984 | AfaI | GTAC |
| BaAK21D17 | AGGCGTCCTCTAGGGCGCGCT<br>AGGCGTCCTCCAGGGCGCGCT | 17985 | XspI | CTAG |
| bast42A0602 | GCACCACCCGCCGGCCGTCGA<br>GCACCACCCGTCGGCCGTCGA | 17989 | HapII | CCGG |
| bast42A0602 | GGCAGCAGCCTGTGCGGCACC<br>GGCAGCAGCCGGTGCGGCACC | 17990 | HapII | CCGG |
| BaAK26L07 | ACCTTCTACAGGTGCCAAGGC<br>ACCTTCTACAAGTGCCAAGGC | 17995 | BanI | GGYRCC |
| baal12a06 | GCAGATATGTTCACATCCCGT<br>GCAGATATGTACACATCCCGT | 17996 | AfaI | GTAC |
| baal12m14 | TTCGTCCACTACCTCGATGAA<br>TTCGTCCACTGCCTCGATGAA | 18003 | TspRI | CASTGNN |
| BaH35F01 | CGGCGTAGGCGAGCTTGTCGT<br>CGGCGTAGGCCAGCTTGTCGT | 18044 | HaeIII | GGCC |
| BaAL30K02 | CAAGGACATCCCTTTGCATTT<br>CAAGGACATCTCTTTGCATTT | 18045 | FokI | NNNNNNNNNNNNNCATCC |
| bags22h22 | TACGCAGACAGTGAGATTTTA<br>TACGCAGACAATGAGATTTTA | 18057 | TspRI | CASTGNN |
| bags13n11 | CCTGCAGAATCGACAAACTAT<br>CCTGCAGAATGGACAAACTAT | 18058 | HinfI | GANTC |
| bags1h03 | GTGGCAAGGCTTGTAGATCTG<br>GTGGCAAGGCCTGTAGATCTG | 18059 | HaeIIE | GGCC |
| baal19a12 | GGTCGCCTACGGGTGAGCATT<br>GGTCGCCTACCGGTGAGCATT | 18069 | HapII | CCGG |
| BaAK45G16 | TGCTGAACTCCAGGCAGGGCA<br>TGCTGAACTCGAGGCAGGGCA | 18070 | MvaI | CCWGG |
| BaGS37N19 | ACAGCAGGATGCACAATGGAA<br>ACAGCAGGATCCACAATGGAA | 18071 | MflI | RGATCY |
| baak3f03 | GAAGGCCTGGAGCCTGGGGGT<br>GAAGGCCTGGCGCCTGGGGGT | 18072 | HhaI | GCGC |
| bah62i11 | CTGCGGAGGCTGAACGGCTTG<br>CTGCGGAGGCCGAACGGCTTG | 18081 | HaeII | GGCC |
| bah17n24 | ACAAAGAAGGTCGTTCATGAT<br>ACAAAGAAGGCCGTTCATGAT | 18091 | HaeIII | GGCC |
| BaGS4J04 | GGAAACAGCAAATCAAGTACA<br>GGAAACAGCAGATCAAGTACA | 18096 | MboI | GATC |
| baak33f06 | ACGTCAAGGGATTCCATTCTT<br>ACGTCAAGGGGTTCCATTCTT | 18097 | HinfI | GANTC |

TABLE 16-2

| Clones | Haruna Nijo H602 | SEQ ID No: | Restriction enzyme | Recognition sequence |
|---|---|---|---|---|
| basd14f16 | GGATGCCCTAGCATAAACTGA<br>GGATGCCCTACCATAAACTGA | 18098 | XspI | CTAG |
| BaH59K20 | CTAGCGCCGGCCCGCAGGCAG<br>CTAGCGCCGGACCGCAGGCAG | 18099 | HaeIII | GGCC |
| BaH59K20 | TTGTCGGTGGTCTCGTCGCCG<br>TTGTCGGTGGCCTCGTCGCCG | 18100 | HaeIII | GGCC |

TABLE 16-2-continued

| Clones | Haruna Nijo H602 | SEQ ID No: | Restriction enzyme | Recognition sequence |
|---|---|---|---|---|
| BaGS20M01 | CATCAGATATGGAATGATGCA<br>CATCAGATATCGAATGATGCA | 18107 | EcoRV | GATATC |
| bah11n18 | TCGGAGCACGGTTCGGCGCTC<br>TCGGAGCACGATTCGGCGCTC | 18111 | HinfI | GANTC |
| baet18F0911 | GCGAGATTTGACCTCACGATA<br>GCGAGATTTGGCCTCACGATA | 18113 | HaeIII | GGCC |
| BaGS4J18 | AGTCATAGTCCGCGTCCATGT<br>AGTCATAGTCAGCGTCCATGT | 18114 | BstUI | CGCG |
| baak41d10 | GGCAAAATCATTGTAGCAAGG<br>GGCAAAATCAGTGTAGCAAGG | 18127 | TspRI | CASTGNN |
| BaGS14F01 | GCAGGTGGTCGACACTGTTAA<br>GCAGGTGGTCAACACTGTTAA | 18128 | TaqI | TCGA |
| BaH52K04 | GCAACCAAAATATATTAGCAA<br>GCAACCAAAAAATATTAGCAA | 18202 | SspI | AATATT |
| BaAL37F24 | GCAACCAAAATATATTAGCAA<br>GCAACCAAAAAATATTAGCAA | 18203 | SspI | AATATT |
| BaSD11K22 | GTTACTTCGGTTCGTCGCCAG<br>GTTACTTCGGATCGTCGCCAG | 18206 | MboI | GATC |
| bags38n06 | GATAGGCAACCAGACCAGATT<br>GATAGGCAACTAGACCAGATT | 18213 | XspI | CTAG |
| baet44D1208 | AATACAACGCGAATTAATTTA<br>AATACAACGCCAATTAATTTA | 18214 | BstUI | CGCG |
| baal13d11 | GCGACGATCCCTGCAGAGCCC<br>GCGACGATCCTTGCAGAGCCC | 18220 | PstI | CTGCAG |
| bah34m23 | AAACTTTGTCGGATGCGTCGA<br>AAACTTTGTCAGATGCGTCGA | 18240 | FokI | GGATGNNNNNNNNN |
| BaH50P13 | CGACTGCAGCAGCCATGAAGA<br>CGACTGCAGCTGCCATGAAGA | 18242 | AluI | AGCT |
| basd11m16 | CTTTCGTGTATAAAGCTGGAG<br>CTTTCGTGTACAAAGCTGGAG | 18243 | AfaI | GTAC |
| bags10p15 | AACGAGCATTGAAGATTATTT<br>AACGAGCATTAAAGATTATTT | 18244 | MseI | TTAA |
| bags4g01 | GTCGATCAGTGCACGTTTCGC<br>GTCGATCAGTACACGTTTCGC | 18245 | ApaLI | GTGCAC |
| bags10k08 | CACATACACTCAATGCCCCGT<br>CACATAGACTTAATGCCCCGT | 18246 | MseI | TTAA |
| bags5e16 | ACTTCTTCTCAAGCTCAATCT<br>ACTTCTTCTCGAGCTCAATCT | 18247 | BanII | GRGCYC |
| bags18l02 | TGTAGAATACTTCAGTGTCCA<br>TGTAGAATACCTCAGTGTCCA | 18248 | DdeI | CTNAG |
| baak44k02 | TGCTTGAACGCGCAGTGAGCC<br>TGCTTGAACGTGCAGTGAGCC | 18249 | HhaI | GCGC |

TABLE 16-3

| Clones | Haruna Nijo H602 | SEQ ID NO: | Restriction enzyme | Recognition sequence |
|---|---|---|---|---|
| bags35a20 | CTCATTGTTCCGGTTTCACAG<br>CTCATTGTTCTGGTTTCACAG | 18250 | HapII | CCGG |
| BaGS26M11 | TAAACAAGTGCGCCCTGAGCC<br>TAAACAAGTGTGCCCTGAGCC | 18251 | HhaI | GCGC |

TABLE 16-3-continued

| Clones | Haruna Nijo H602 | SEQ ID NO: | Restriction enzyme | Recognition sequence |
|---|---|---|---|---|
| BaSD13D12 | CGTGCTGCTCCGCGAACCGGA<br>CGTGCTGCTCTGCGAACCGGA | 18259 | BstUI | CGCG |
| BaH42E05 | TTCGCATGATTGCATCTACAG<br>TTCGCATGATCGCATCTACAG | 18260 | MboI | GATC |
| bast155A0701 | ACCCCGTATGATACAACAGCG<br>ACCCCGTATGGTACAACAGCG | 18261 | AfaI | GTAC |
| kr28B0604 | CCGCGTTTCTTGGGGGGTGCT<br>CCGCGTTTCTCGGGGGGTGCT | 18265 | AvaI | CYCGRG |
| bah16g18 | AAGTGCTACACCCTIGGCTGT<br>AAGTGCTACATCCTTGGCTGT | 18278 | FokI | NNNNNNNNNNNNNCATCC |
| bags35c23 | CAACCATCAGCTGGCTACCAA<br>CAACCATCAGTTGCCTACCAA | 18284 | A luI | AGCT |
| BaAK19K05 | AAAGGAGTACTGACTTGATA<br>AAAGGACTATTGACTTGATA | 18293 | AfaI | GTAC |
| bah11i16 | CTTGTGCTGGGGACGGCTGAG<br>CTTGTGCTGGTGACGGCTGAG | 18294 | HphI | GGTGANNNNNNN |
| baak22b17 | GAGCTCGACGGGTCCTTTAGC<br>GAGCTCGACGAGTCCTTTAGC | 18325 | Eco0109I | RGGNCCY |
| bags20f22 | AACTACTACCNGGTNNGCGAC<br>AACTACTACCGGGTNNGCGAC | 18326 | BcnI | CCSGG |
| baal1d17 | CAAACATCCGGAAATGCACAG<br>CAAACATCCGAAAATGCACAG | 18397 | HapII | CCGG |
| bags22f06 | ATTAAGAGATCGCCCGAACAA<br>ATCAAGAGATTGCCCGAACAA | 18398 | MboI | GATC |
| bah16a03 | TTCCCAGCGGTCGCTGCTGCC<br>TTCCCAGCGGCCGCTGCTGCC | 18404 | HaeIII | GGCC |
| BaAL11F18 | AACTTAAGAGATCTACAGCTT<br>AACTTAAGAGGTCTACAGCTT | 18405 | BglII | AGATCT |
| BaAK29E10 | CCGCGTTGCGCTGGAACTCGA<br>CCGCGTTGCGTTGGAACTCGA | 18406 | HhaI | GCGC |
| baak16f14 | AAGAAGTAGATCAATCCTCAG<br>AAGAAGTAGACCAATCCTCAG | 18415 | MboI | GATC |
| baak44c12 | TATAAGAGCATTTGGGTCACT<br>TATAAGAGCACTTGGGTCACT | 18416 | Bsp1286I | GDGCHC |
| baal39m19 | AACTATGAATATTAGACCCTT<br>AACTATGAATCTTAGACCCTT | 18418 | SspI | AATATT |
| baak4e02 | TTACAAAATCAAGAAACAAGT<br>TTACAAAATCGAGAAACAAGT | 18419 | TaqI | TCGA |
| baak46f04 | TCGATATAGATCAAATAAGAA<br>TCGATATAGACCAAATAAGAA | 18420 | MboI | GATC |
| BaSD19I17 | GGTGCGAATCGATGGICCTIC<br>GGTGCGAATCCATGGICCTIC | 18425 | ClaI | ATCGAT |
| BaAK19P01 | CAAAAGAGTCTAGTAAATTTG<br>CAAAAGAGTCCAGTAAATTTG | 18427 | XspI | CTAG |

TABLE 16-4

| Clones | Haruna Nijo H602 | SEQ ID NO: | Restriction enzyme | Recognition sequence |
|---|---|---|---|---|
| BaH26P22 | AGAAGCATTGGTCAGATGACC<br>ACAAGCATTGATCAGATGACC | 18429 | MboI | GATC |

TABLE 16-4-continued

| Clones | Haruna Nijo H602 | SEQ ID NO: | Restriction enzyme | Recognition sequence |
|---|---|---|---|---|
| kr59F0311 | TTTAGTGAAT<u>CC</u>GTATTTTGT<br>TTTAGTGAATTCGTATTTTGT | 18439 | E co RI | GAATTC |
| baal13e10 | TTGCTTACAG<u>C</u>TATGGTTCCC<br>TTGCTTACAG<u>T</u>TATGGTTCCC | 18440 | AluI | AGCT |
| BaGS5K11 | TCTAGGCCG<u>CC</u>AAGCTCACGA<br>TCTAGGCCGCTAAGCTCACGA | 18442 | DdeI | CTNAG |
| BaGS10J14 | TCCCAGCTGA<u>C</u>CCAACCATTA<br>TCCCAGCTGATCCAACCATTA | 18443 | MboI | GATC |
| BaGS10J14 | ACTCTACAAGATCTTGAA-TT<br>ACTCTACAAG<u>TT</u>CTTGAAATT | 18444<br>18445 | MboI | GATC |
| baak41m17 | TGATGTGCCG<u>A</u>TGAAATCCCT<br>TGATGTGCCGGTGAAATCCCT | 18446 | HapII | CCGG |
| baak41d22 | CACGTCTCTA<u>A</u>GACAAGAAAC<br>CACGTCTCTA<u>G</u>GACAAGAAAC | 18449 | XspI | CTAG |
| bah61c16 | GGTCGCTCCCAGGTCC<u>I</u>TCGC<br>GGTCGCTCCCGGGTCCTTCGC | 18450 | HapII | CCGG |
| BaAL7M13 | GGACCGTGTG<u>C</u>CCCTTTGGGT<br>GGACCGTGTGGCCCTTTGGGT | 18451 | HaeIII | GGCC |
| BaAK31F11 | GGTCGCTCCCAGGTCCTTCGC<br>GGTCGCTCCC<u>GGG</u>TCCTTCGC | 18452 | AvaI | CYCGRG |
| baal33d23 | TGGTGGTGAC<u>G</u>GCGGCCTGCA<br>TGGTGGTGACCGCGGCCIGCA | 18453 | S ac If | CCGCGG |
| BaH31A03 | GCTTGGCATG<u>A</u>ATGGCGCACA<br>GCTTGGCATG<u>G</u>ATGGCGCACA | 18495 | FokI | GGATGNNNNNNNNN |
| bast139A0901 | CAAAATAAAAGGCTATCAACT<br>CAAAATAAAAGCTATCAACT | 18496 | AluI | AGCT |
| basd12i15 | CTCTAGGCGA<u>T</u>AATCACCATC<br>CTCTAGGCGAGAATCACCATC | 18509 | HinfI | GANTC |
| BaAK40I03 | CACAATGATTCTATTTTAAAA<br>CACAATGATT<u>TT</u>TATTTTAAAA | 18510 | H hfI | GANTC |
| BaAK23E14 | GATTCTTCTC<u>A</u>ATCTGACGGA<br>GATTCTTCTCGATCTGACGGA | 18511 | TaqI | TOGA |
| baal27a24 | TCATCTTGGC<u>A</u>GTTTCACCAC<br>TCATCTTGGC<u>C</u>GTTTCACCAC | 18513 | HaeIII | GGCC |
| BaH28J15 | CCTTGGTGTCGAAATGAGACG<br>CCTTGGTGTC<u>A</u>AAATGAGACG | 18518 | TaqI | TOGA |
| baal5b15 | CTGGAGACTC<u>A</u>AGCAGATGCA<br>CTGGAGACTCGAGCAGATGCA | 18526 | XhoI | CTCGAG |
| BaH28J10 | GCATCGTGCGCGGTGCTCACC<br>GCATCGTGCG<u>T</u>GGTGCTCACC | 18537 | HhaI | GCGC |
| baak34p05 | GACACTCAAGTAGTGCGTCGA<br>GACACTCAAGCAGTGCGTCGA | 18538 | TspRI | CASTGNN |
| bah27d18 | TCAGTCTGAG<u>T</u>ACTAATCAAA<br>TCAGTCTGAG-ACTAATCAAA | 18541<br>18542 | AfaI | GTAC |
| BaH50A15 | ATAAAAAAAATTCGATCTITA<br>ATAAAAAAA<u>A</u>TCGATCTITA | 18546 | ClaI | ATCGAT |

TABLE 16-5

| Clones | Haruna Nijo H602 | SEQ ID NO: | Restriction enzyme | Recognition sequence |
|---|---|---|---|---|
| basd2f22 | CATGCCTCCACGCCAATCTCC<br>CATGCCTCCAGGCCAATCTCC | 18548 | HaeIII | GGCC |
| BaH47K06 | TCCTTCTTTTAAAAAAAAAAA<br>TCCTTCTTTTCAAAAAAAAAA | 18549 | DraI | TTTAAA |
| bags29b01 | TTTTTTTAAAAATCCTGGGGG<br>TTCTTTTCAACATCCTCGCGC | 18555 | FokI | NNNNNNNNNNNNNCATCC |
| basd2a21 | ACCAAGCAACGCGCATCAACT<br>ACCAAGCAACTCGCATCAACT | 18559 | HhaI | GCGC |
| bags33m15 | TACACCTTGTGGATTAATATA<br>TACACCTTGTCGATTAATATA | 18574 | DraIII | CACNNNGTG |
| baak41e24 | GCCACTTGTCAATGCAGGCGC<br>GCCACTTGTCGATGCAGGCGC | 18584 | TaqI | TCGA |
| bah63c08 | AAGGTCTCATTAAAAAGGTGA<br>AAGGTCTCATCAAAAAGGTGA | 18585 | MseI | TTAA |
| baal17e18 | GCTAAGATCCAGAGAAAAGGA<br>GCTAAGATCCGGAGAAAAGGA | 18606 | HapII | CCGG |
| basd11g04 | TTTGGATGGTGCCCCAACACT<br>TTTGGATGGTCCCCCAACACT | 18608 | BanI | GGYRCC |
| BaGS36A04 | GTTCAGTCTTGAAATGCCCGA<br>GTTCAGTCTTTAAATGCCCGA | 18611 | DraI | TTTAAA |
| bags13a16 | GCATCCTTGTCAAGGTACCCT<br>GCATCCTTGTTAAGGTACCCT | 18612 | MseI | TTAA |
| BaAK35F14 | TGCACCCTCATGCATCCATAC<br>TGCACCCTCAGGCATCCATAC | 18618 | DdeI | CTNAG |
| baak46l06 | GGCCGAGAGGTGTCCGGTAAA<br>GGCCGAGAGGGGTCCGGTAAA | 18624 | AvaII | GGWCC |
| baak15p17 | GACTTTGGCCGGGGATCGCT<br>GACTTTGGCCAGGGGATCGCT | 18625 | HapII | CCGG |
| BaGS33J16 | CTATGCTCTGTGCTATAACCA<br>CTATGCTCTGCGCTATAACCA | 18626 | HhaI | GCGC |
| bags7p21 | AGAGCAGTGCACACACTTGTG<br>AGAGCAGTGCGCACACTTGTG | 18627 | ApaLI | GTGCAC |
| BaAK22E05 | TGAGATAGGGCCCCCAGGAAT<br>TGAGATAGGGACCCCAGGAAT | 18628 | HaeIII | GGCC |
| bah42m05 | TGTACTGGTGCTAAGCATGCC<br>TGTACTGGTGATAAGCATGCC | 18629 | HphI | GGTGANNNNNNNN |
| BaAK25L01 | CGGCACCGGCGCCGTGTGCCG<br>CGGCACCGGCACCGTGTGCCG | 18630 | HaeII | RGCGCY |
| bags39e24 | AAGAAGATGCACGAGGATAGC<br>AAGAAGATGCGCGAGGATAGC | 18631 | BstUI | CGCG |
| bags16d15 | GAAGAAACAACTACCCCACTG<br>GAAGAAACAAGTACCCCACTG | 18638 | AfaI | GTAC |
| bah19f21 | TTTACAGCCGAGAGATGAGCA<br>TTTACAGCCGGGAGATGAGCA | 18648 | HapII | CCGG |
| bags20b10 | TACCTGCATGTTAACACAAGG<br>TACCTGCATGATAACACAAGG | 18649 | MseI | TTAA |
| BaGS29J10 | CCATGGTGGTTCATTTTTGCT<br>CCATGGTGGTCCATTTTTGCT | 18660 | Cfr13I | GGNCC |

TABLE 16-6

| Clones | Haruna Nijo H602 | SEQ ID NO: | Restriction enzyme | Recognition sequence |
|---|---|---|---|---|
| basd12n12 | CCCTGTTCCTGGAAAATGGAA<br>CCCTGTTCCTAGAAAATGGAA | 18675 | MvaI | CCWGG |
| bags6l02 | ATTAGGGTATCAATCCTATAC<br>ATTAGGTCATTAATGCTATAC | 18677 | AseI | ATTAAT |
| basd14p15 | AAACACAAATATTCCTACAAT<br>AGACACAAATCTTCCTACAAT | 18680 | SspI | AATATT |
| bags19g04 | ATCATCCTTCGAACAACATCC<br>ATCATCCTTCAAACAACATCC | 18685 | BspT104I | TTCGAA |
| bah33p11 | AGGTAACCAGCTTTAGCCATT<br>AGGTAACCAGTTTTAGCCATT | 18693 | AluI | AGCT |
| bags38f12 | TTTACAGTCCGGTAGATTTGG<br>TTTACAGTCCAGTAGATTTGG | 18704 | HapII | CCGG |
| basd26p18 | CCTTTGAATTATTTGTAATTT<br>CCTTTGAATTCTTTGTAATTT | 18705 | EcoRI | GAATTC |
| baak45h16 | CAGATTGACCGTACCTGGTTA<br>CAGATTGACCATACCTGGTTA | 18706 | AfaI | GTAC |
| bah28p12 | AAGGCATGTACGTATGTCATC<br>AAGGCATGTAAGTATGTCATC | 18707 | Afal | GTAC |
| bah19a10 | CATGCGCAGCACAGAGAAGTG<br>CATGCGCAGCTGAGAGAAGTG | 18708 | AluI | AGCT |
| basd16l09 | CTTCTGAAAGATTACTTTTCG<br>CTTCTGAGAGCTTACTTTTCG | 18717 | AluI | AGCT |
| BaGS18N21 | CAATGGCTTCAACAATCCGGA<br>CAATGGCTTCGACAATCCGGA | 18742 | TaqI | TCGA |
| baal12l02 | ATTTTATCTAACTAGTCTGTA<br>ATTTTATCTAGCTAGTCTGTA | 18768 | AluI | AGCT |
| bags35a12 | GCATGGAACCAGTGTCGGCTT<br>GCATGGAACCGGTGTCGGCTT | 18775 | HapII | CCGG |
| baak42l17 | CCCTGTGGCGCGTCTCCTGCT<br>CCCTGTGGCGGGTCTCCTGCT | 18785 | HhaI | GCGC |
| baak36d23 | CTTGTCTTCGAGCTGCAAAGA<br>CTTGTCTTCGGGCTGCAAAGA | 18786 | AluI | AGCT |
| bast78C1006 | GCACCCAGGGTCGTCTGCCAC<br>GCACCCAGGGCCGTCTGCCAC | 18787 | HaeIII | GGCC |
| BaAK36B07 | GGCCATGCAGGATCAGTCCAG<br>GGCCATGCAGTATCACTCCAG | 18799 | MboI | GATC |
| baak26b05 | AAGGCTGGCGTCGGCTTGGAC<br>AAGGCTGGCGCCGGCTTGGAC | 18800 | HapII | CCGG |
| bags6n10 | ACCACAATTAATACCTGGAGC<br>ACCACAATTAGTACCTGGAGC | 18809 | AseI | ATTAAT |
| bah41b23 | TGGCATCCTCAATTGAGTCAA<br>TGGCATCCTCGATTGAGTCAA | 18820 | TaqI | TCGA |
| bast130D0408 | GCCTTTTTCGATAAACAAGAA<br>GCCTTTTTCGGTAAACAAGAA | 18822 | TaqI | TCGA |
| bah17p16 | CTGGATTTCCGGCTGCCCGAT<br>CTGGATTTCCTGCTGCCCGAT | 18823 | HapII | CCGG |
| basd16e16 | TCATTCAAGCTGGCAATAGCA<br>TCATTCAAGCCGGCAATAGCA | 18835 | HapII | CCGG |

TABLE 16-7

| Clones | Haruna Nijo H602 | SEQ ID NO: | Restriction enzyme | Recognition sequence |
|---|---|---|---|---|
| bags9p10 | CTCACAGAGCGCGGCACGCAG<br>CTCACAGAGCACGGCACGCAG | 18838 | Bsp1286I | GDGCHC |
| basd27d09 | AGTTTTTAACTAAGTGCTTCC<br>AGTTTTTAACAAAGTGCTTCC | 18839 | DdeI | CTNAG |
| basd17p09 | CCTGTGAAGAGCCCGGATGCT<br>CCTGTGAAGATCCCGGATGCT | 18844 | BanII | GRGCYC |
| bags5m04 | AGCCTGCAATTGATATCACTC<br>AGCCTGCAATCGATATCACTC | 18845 | ClaI | ATCGAT |
| BaGS5E06 | GGTCATCCGCCGCGCCGTGGT<br>GGTCATCCGCGGCGCCGTGGT | 18846 | SacII | CCGCGG |
| kr49E0610 | AGGGATACCATGGAAACAAAA<br>AGGGATACCACGGAAACAAAA | 18850 | NcoI | CCATGG |
| BaGS22E05 | AATCATCTGCACTAGCATTTC<br>AATCATCTGCGCTAGCATTTC | 18859 | HhaI | GCGC |
| BaH45O03 | CTGCTCAAGCGCTGTGTGAAA<br>CTGCTCAAGCACTGTGTGAAA | 18862 | HhaI | GCGC |

TABLE 17-1

| Clones | Haruna Nijo H602 | SEQ ID NO: | Restriction enzyme | Recognition sequence |
|---|---|---|---|---|
| basd22i04 | TCCTGTACTCAGGTTTCACCA<br>TCCTGTACTCGGGTTTCACCA | 18870 | AvaI | CYCGRG |
| BaGS31M01 | ACACGTGCCATGGGTTGGCGG<br>ACACGTGCCACGGGTTGGCGG | 18871 | NcoI | CCATGG |
| basd15n13 | AGCTGCCCGGGGAAAAACCCA<br>AGCTGCCCGGCGAAAAACCCA | 18873 | AvaI | CYCGRG |
| bast104C0406 | GACGTGACGGTTCGGGTTGAT<br>GACGTGACGGCTCGGGTTGAT | 18883 | AvaI | CYCGRG |
| baak39117 | CGAGAGCTGGACCATAATGGA<br>CGAGAGCTGGGCCATAATGGA | 18886 | HaeIII | GGCC |
| BaAL17J24 | CGACGTACTGATCCTGGCAGA<br>CGACGTACTGGTCCTGGCAGA | 18887 | AvaII | GGWCC |
| bah15p03 | GTAAAACCGGATGACAGTTAT<br>GTAAAACCGGCTGACAGTTAT | 18888 | FokI | GGATGNNNNNNNNN |
| baal22c16 | ATAGATAATTCGATATGTGAA<br>ATAGATAATTAGATATGTGAA | 18890 | TaqI | TCGA |
| bags22i13 | TGAAGACATCGAGTGATCCCA<br>TGAAGACATCAAGTGATCCCA | 18902 | TaqI | TCGA |
| BaGS20D21 | CCACCTTGGCATCCTCCGGCA<br>CCACCTTGGCGTCCTCCGGCA | 18906 | FokI | NNNNNNNNNNNNNCATCC |
| bags39o21 | ATCTGCTATAACTATATGAAA<br>ATCTGCTATAGCTATATGAAA | 18907 | AluI | AGCT |
| BaSD19H23 | TTCCAGATTCGAAATCATTTC<br>TTCCAGATTCCAAATCATTTC | 18914 | BspT104I | TTCGAA |
| baak35n06 | ACGGCACGGTCAGTGTCAGGT<br>ACGGCACGGTTAGTGTCAGGT | 18915 | TspRI | CASTGNN |
| baak35n06 | ATTTTAGACATTGTTTGGATC<br>ATTTTAGACAGTGTATGGATC | 18916 | TspRI | CASTGNN |
| bags35b22 | AACACTGGTACCTTGTTAGCT<br>AACACTGGTAACTTGTTAGCT | 18917 | AfaI | GTAC |

TABLE 17-1-continued

| Clones | Haruna Nijo H602 | SEQ ID NO: | Restriction enzyme | Recognition sequence |
|---|---|---|---|---|
| BaAK30H06 | CTAAACTCGTGGTCCGTCAAC<br>CTAAACTCGTCGTCCGTCAAC | 18918 | Cfr13I | GGNCC |
| BaAL15M07 | AACACTGGTACCTTGTTAGCT<br>AACACTGGTAACTTGTTAGCT | 18919 | KpnI | GGTACC |
| BaGS20N02 | GATCGCTGGG-GCTATAGGCA<br>GATCGCTGGGCGCTATAGGCA | 18920<br>18921 | HhaI | GCGC |
| BaAL19L12 | TCTGCACAGCGCCTGGTTGCT<br>TCTGCACAGCACCTGGTTGCT | 18922 | HhaI | GCGC |
| baal1h04 | CAGTCGACACTGGCGCTGATC<br>CAGTCGACACCGGCGCTGATC | 18923 | HapII | CCGG |
| bah45n12 | GTTGCCCGCGAATCTGCACCG<br>GTTGCCCGCGGATCTGCACCG | 18933 | SacII | CCGCGG |
| baal5k12 | CGACCACACGTGTCCCAGCAG<br>CGACCACACGCGTCCCAGCAG | 18936 | BstUI | CGCG |
| baak12j16 | AGGTGAACTCGAGGTTTGGGC<br>AGGTGAACTCAAGGTTTGGGC | 18939 | XhoI | CTCGAG |
| BaAK28J20 | TCATGGTAAGCTTGCAATGTG<br>TCATGGTAAGTTTGCAATGTG | 18940 | HindIII | AAGCTT |

TABLE 17-2

| Clones | Haruna Nijo H602 | SEQ ID NO: | Restriction enzyme | Recognition sequence |
|---|---|---|---|---|
| BaH27G14 | TCATGGTAAGCTTGCAATGTG<br>TCATGGTAAGTTTGCAATGTG | 18941 | HindIII | AAGCTT |
| baak43h20 | TCTGACCATCTTCAGCAGTCT<br>TCTGACCATCCTCAGCAGTCT | 18947 | FokI | NNNNNNNNNNNNNCATCC |
| BaAK30M07 | CTGTAGTGCTTCTTCGTCAGG<br>CTGTACTGCTCCTTCGTCAGG | 18951 | Bsp1286 | GDGCHC |
| bags6a04 | AATAATTCATCGATTAACAAA<br>AATAATTCATTGATTAACAAA | 18952 | ClaI | ATCGAT |
| baak27d01 | TCTAGACGTACTTAGTGCTAC<br>TCTAGACGTATTTAGTGCTAC | 19001 | AfaI | GTAC |
| BaGS27P18 | ATGGAGATTTTTAAACTTCCA<br>ATGGAGATTTATAAACTTCCA | 19016 | DraI | TTTAAA |
| BaGS4J14 | GGACTTCATGCCGCCACTCCAG<br>GGACTTCATGTGCCACTCCAG | 19017 | HhaI | GCGC |
| BaH32J06 | ACCAAATGAGTTCATGGAATC<br>ACCAAATGAGCTCATGGAATC | 19034 | BanII | GRGCYC |
| BaH57K23 | GTATATGTTTGGCGCCAGGAG<br>GTATATGTTTCGCGCCAGGAG | 19040 | HaeII | RGCGCY |
| baal12d12 | TGGCCCAAGATCCCTAGCTGG<br>TGGCCCAAGAACCCTAGCTGG | 19057 | MflI | RGATCY |
| BaSD14G02 | ACATGCGAATATTTTTTTAAT<br>ACATGCGAATCTTTTTTTAAT | 19070 | SspI | AATATT |
| BaGS16I18 | CAAAAGAGATGAGGCGAGGC<br>CAAAAGAGACGAGGCGAGGC | 19081 | BsmAI | NNNNNGAGAC |
| bah11k22 | TTATCTTTCCTGGGGTAACCA<br>TTATCTTTCCGGGGGTAACCA | 19083 | BcnI | CCSGG |
| baak32p21 | TGTCCCACGCACTGTTGATCG<br>TGTCCCACGCGCTGTTGATCG | 19084 | HhaI | GCGC |

TABLE 17-2-continued

| Clones | Haruna Nijo H602 | SEQ ID NO: | Restriction enzyme | Recognition sequence |
|---|---|---|---|---|
| bah63121 | GAAAAAACTGTGCCTCTACAA<br>GAAAAAACTGCGCCTCTACAA | 19085 | HhaI | GCGC |
| BaGS38D03 | CGAGCTTCACTCGGTCACCAT<br>CGAGCTTCACCCGGTCACCAT | 19086 | HapII | CCGG |
| bags23b01 | AGTCAAACTCAAGTGAGGAAC<br>AGTCAAACTCCAGTGAGGAAC | 19093 | TspRI | CASTGNN |
| bags29c09 | GATGATTGGGGATCTGTTGAT<br>GATGATTGGGCATCTGTTGAT | 19094 | MflI | RGATCY |
| bags6b06 | ACAGATTTTGTGCAGCATGTT<br>ACAGATTTTGCGCAGCATGTT | 19095 | HhaI | GCGC |
| BaAK27G06 | AGGCCTTGGCAAGCACGTCGT<br>AGGCCTTGGCGAGCACGTCGT | 19096 | Bsp1286I | GDGCHC |
| BaAK39I07 | TTGTGCTACCAGGCTTGAATA<br>TTGTGCTACCGGGCTTGAATA | 19097 | BcnI | CCSGG |
| BaGS20G21 | AGCTGAGCGCAATTCCTTGTG<br>AGCTGAGCGCGATTCCTTGTG | 19098 | HinfI | GANTC |
| bah11m03 | CAGGTGTAGCTCCATATCTGG<br>CAGGTGTAGCCCCATATCTGG | 19099 | AluI | AGCT |
| BaAL3C04 | TTCCGGGGATCCTTCCAGCTA<br>TTCCGGGGATTCTTCCAGCTA | 19100 | HinfI | GANTC |

TABLE 17-3

| Clones | Haruna Nijo H602 | SEQ ID NO: | Restriction enzyme | Recognition sequence |
|---|---|---|---|---|
| bags24n16 | CATGGTGAACCGGGGAGTCTT<br>CATGGTGAACAGGTGAGTCTT | 19103 | HapII | CCGG |
| baal12b04 | AATATTCATAGTTAATACACA<br>AATATTCATAATTAATACACA | 19124 | AseI | ATTAAT |
| BaGS36B01 | AAAACGATTCACGGTTCAGCT<br>AAAACGATTCGCGGTTCAGCT | 19131 | BstUI | CGCG |
| baal12i18 | AGAACTGTGGAGCATACTACT<br>AGAACTGTGGCGCATACTACT | 19150 | HhaI | GCGC |
| BaAL8G07 | ACCAGCTGCAGGTTATACCCT<br>ACCAGCTGCACCTTATACCCT | 19151 | PstI | CTGCAG |
| bags3f23 | CATTGTGTCTCGAGTCAATGG<br>CATTGTGTCTTGAGTCAATGG | 19157 | XhoI | CTCGAG |
| baal4m06 | GGAGAACAAGATCTGCCTCGA<br>GGAGAACAAGGTCTGCCTCGA | 19158 | MflI | RGATCY |
| basd1123 | TTCATTTACTAGATACTCCAT<br>TTCATTTACTGGATACTCCAT | 19177 | XspI | CTAG |
| baak13p20 | TATCGTCGGCGTGAATCTGAT<br>TATCGTCGGCCTGAATCTGAT | 19196 | HaeIII | GGCC |
| BaH29I03 | TGCAAGGTACCATCCCAGGAT<br>TGCAAGGTACTATCCCAGGAT | 19211 | KpnI | GGTACC |
| bah16h01 | CAGCACCGCCAGGAGTTTTGCT<br>CAGCACCGCCGGGAGTTTTGCT | 19212 | MvaI | CCWGG |
| baal11c20 | TTGCTACGAATCCAAGAGAAA<br>TTGCTACGAAACCAAGAGAAA | 19249 | HinfI | GANTC |
| basd15a02 | CAGCGGAGCCGGTCATAGGTT<br>CAGCGGAGCCAGTCATAGGTT | 19254 | HapII | CCGG |

TABLE 17-3-continued

| Clones | Haruna Nijo H602 | SEQ ID NO: | Restriction enzyme | Recognition sequence |
|---|---|---|---|---|
| bah15k11 | CACAAACGAAAGCGCGTCTTG<br>CACAAACGAANGCGCGTCTTG | 19259 | HhaI | GCGC |
| bah15k11 | GCCACGCATGCCGCACAAGAAA<br>GCCACGCATGTGCACAAGAAA | 19260 | HhaI | GCGC |
| baal35p14 | AGACGACTTCAGCTCTTGATG<br>AGACGACTTCTGCTCTTGATG | 19266 | AluI | AGCT |
| baak11n24 | AGTCAAAGGGTTTAGAAACCA<br>AGTCAAAGGGCTTAGAAACCA | 19286 | DdeI | CTNAG |
| BaGS39M09 | TGGCAATAAGCATCCCGATGC<br>TGGCAATAAGAATCCCGATGC | 19291 | HinfI | GANTC |
| baak31a24 | GTCTTAATAAACTAATGATAG<br>GTCTTAATAAGCTAATGATAG | 19307 | AluI | AGCT |
| baak31a24 | TTAAATCTGAGCTTATGAAGA<br>TTAAATCTGACCTTATGAAGA | 19308 | AluI | AGCT |
| baak31a24 | TGGAATGCAGCTTCATATGCG<br>TGGAATGCAGTTTCATATGCG | 19309 | AluI | AGCT |
| bags7f08 | GGTAAGCGTCGAACAGAGATG<br>GGTAAGCGTCAAACAGAGATG | 19314 | TaqI | TCGA |
| bags38b06 | TTGCGACGTTTAAGATATTCG<br>TTGCGACGTTGAAGATATTCG | 19318 | MseI | TTAA |
| bah27a22 | AACACCAAGCTTCGTGAGAAT<br>AACACCAAGCCTCGTGAGAAT | 19330 | AluI | AGCT |

TABLE 17-4

| Clones | Haruna Nijo H602 | SEQ ID NO: | Restriction enzyme | Recognition sequence |
|---|---|---|---|---|
| BaAK29G03 | CCATGGAGGGCCGATCAGCAG<br>CCATGGAGGGACGATCAGCAG | 19335 | Cfr13I | GGNCC |
| baak23e11 | CTGATGATACTAGAGCAGCCA<br>CTGATGATACCAGAGCAGCCA | 19340 | XspI | CTAG |
| bags31k04 | TTGTAGAGCTTGCACAATCTT<br>TTGTAGAGCTCGCACAATCTT | 19341 | BanII | GRGCYC |
| BaSD27G02 | GCTGCTGTGGACCGAAGGTCG<br>CCTGCTGTGGGCCGAAGGTCG | 19350 | HaeIII | GGCC |
| baak32m10 | CCTCGAGGCCAGACTTGAGGC<br>CCTCGAGGCCGGACTTGAGGC | 19352 | HapII | CCGG |
| baak32m10 | TGTTGGCCACCCGGATCATGT<br>TGTTGGCCACACGGATCATGT | 19353 | HapII | CCGG |
| BaAL4L02 | GCTCGTACTCCCGGCGCGGTGT<br>GCTCGTACTCTGGCGCGGTGT | 19355 | HapII | CCGG |
| BaGS32M17 | ATACTCCATCCGTCCCGAATT<br>ATACTCCATCGGTCCCGAATT | 19375 | AvaII | GGWCC |
| basd3g08 | AGGACTTTGGAATATTATTAA<br>AGGACTTTGGTATATTATTAA | 19377 | SspI | AATATT |
| BaAL7816 | CATCAAACATCCATTCCTTCT<br>CATCAAACATACATTCCTTCT | 19398 | FokI | NNNNNNNNNNNNNCATCC |
| baak34g01 | TAGATGAAGATACATCCATTT<br>TAGATGAAGAGACATCCATTT | 19406 | BsmAI | NNNNNGAGAC |
| baak12f01 | AGAAGGTGGGATGATTATCAG<br>AGAAGGTGGGGTGATTATCAG | 19407 | FokI | GGATGNNNNNNNNN |

TABLE 17-4-continued

| Clones | Haruna Nijo H602 | SEQ ID NO: | Restriction enzyme | Recognition sequence |
|---|---|---|---|---|
| BaGS30I18 | CAAATATTTCAATGAAAATAC<br>CAAAT-TTTCGATGAAAATAC | 19408<br>19409 | TaqI | TCGA |
| baak40o04 | TTGGCGGATTCTTGACGCGGC<br>TTGCCGGATTGTTGACGCGGC | 19424 | HinfI | GANTC |
| bags11i04 | GATCATCAACGTACTCAAACT<br>GATCATCAACATACTCAAACT | 19432 | AfaI | GTAC |
| bah52o06 | AGAATGGCACCGGAGACTAGA<br>AGAATGGCACGGGAGACTAGA | 19435 | HapII | CCGG |
| BaAL25P17 | TGGCGAAGTGACAACTGATCT<br>TGGCGAAGTGGCAACTGATCT | 19441 | MboI | GATC |
| BaAL25P17 | TGGGTGCTGACCAACGACACA<br>TGGGTGCTGATCAACGACACA | 19442 | MboI | GATC |
| kr24E0709 | TACCTTGAATTATCCATCATA<br>TACCTTGAATGATCCATCATA | 19454 | MboI | GATC |
| BaAL13N01 | TCTTGGTCGC-CCCGGGCGA<br>TCTTGGTCGCGCCCGGGCGA | 19458<br>19459 | HhaI | GCGC |
| BaGS31N06 | AATGAGTGGTACACGGTCGTG<br>AATGAGTGGTGCACGGTCGTG | 19460 | ApaLI | GTGCAC |
| BaH36L17 | GGGTGAACTCAAAAATGCTAA<br>GGGTGAACTCGAAAATGCTAA | 19490 | TaqI | TCGA |
| baak20g24 | CCAGGCCATAGCGGGTGCTGT<br>CCAGGCCATACCGGGTGCTGT | 19494 | HapII | CCGG |
| baet46C0206 | TGTTGAAGTCTCGGGTGTTGT<br>TGTTGAAGTCCCGGGTGTTGT | 19503 | BcnI | CCSGG |

TABLE 17-5

| Clones | Haruna Nijo H602 | SEQ ID NO: | Restriction enzyme | Recognition sequence |
|---|---|---|---|---|
| baal5i05 | TGAGCTTGTCTCGCTTGGACC<br>TGAGCTTGTCGCGCTTGGACC | 19509 | HhaI | GCGC |
| bah14a11 | CTGCGTCTATAGCCCCGATGT<br>CTGCGTCTATGGCCCCGATGT | 19510 | HaeIII | GGCC |
| bags31e24 | AGGAAGGGCTTTCGACTCGGA<br>AGGAAGGGCTCTCGACTCGGA | 19513 | BanII | GRGCYC |
| basd11a10 | AGGCGTCCCCGGCCTGCGCGG<br>AGGCGTCCCCAGCCTGCGCGG | 19526 | HapII | CCGG |
| bah50i12 | CGGCGGCGGCACTGTTTGTTG<br>CGGCGGCGGCGCTGTTTGTTG | 19527 | HhaI | GCGC |
| baak45p02 | TTTATTACAGTGACTTTCCAA<br>TTTATTACAGCGACTTTCCAA | 19530 | TspRI | CASTGNN |
| bags9l16 | TGTTGCAGCAGTCGACGGCAT<br>TGTTGCAGCACTCGACGGCAT | 19531 | SalI | GTCGAC |
| BaSD26o20 | TTTCAGTGTCGAACTAAGGGC<br>TTTCAGTGTCCAACTAAGGGC | 19533 | TaqI | TOGA |
| bags5d10 | TACCCAGTGAAGCTATAACAA<br>TACCCAGTGACGCTATAACAA | 19534 | AluI | AGCT |
| baal0e07 | AGTTTCTTGGCCTGGCAGGGA<br>AGTTTCTTGGACTGGCAGGGA | 19535 | MvaI | CCWGG |
| baak14e02 | AAATAGTAAGCTCATGTCCAG<br>AAATAGTAAGTTCATGTCCAG | 19536 | AluI | AGCT |

TABLE 17-5-continued

| Clones | Haruna Nijo H602 | SEQ ID NO: | Restriction enzyme | Recognition sequence |
|---|---|---|---|---|
| bah33f19 | GTGCAATTGGNTACAAATGCC<br>GTGCAATTGGGTACAAATGCC | 19537 | AfaI | GTAC |
| baal40i22 | GTCATCAGCGGCCCCCCGCAA<br>GTCATCAGCGCCCCCCCGCAA | 19543 | HhaI | GCGC |
| kr69E0810 | GATTGTTGATCTATGCAGCAA<br>GATTGTTGATGTATGCAGCAA | 19547 | MboI | GATC |
| BaAK39A15 | ACAGTGCCGGCCAGACTGTTC<br>ACAGTGCCGGACAGACTGTTC | 19568 | HaeIII | GGCC |
| basd18o21 | TGTCTCTCACTGGGAGCTCCC<br>TGTCTCTCACCGGGAGCTCCC | 19569 | BcnI | CCSGG |
| bags23k14 | ACATGTGGACTCCAGATATAA<br>ACATGTGGACCCCAGATATAA | 19575 | AvaII | GGWCC |
| BaGS21H17 | GATCACTGGATGACCAACCTC<br>GATCACTGGAGGACCAACCTC | 19576 | FokI | GGATGNNNNNNNNN |
| bah41l03 | TGCCGTGGCCGTGCACGATGA<br>TGCCGTGGCCATGCACGATGA | 19585 | ApaLI | GTGCAC |
| kr23D0408 | TGTACAGACTCAGCTGAGAGA<br>TGAACAGACTGAGCTGAGAGA | 19592 | HinfI | GANTC |
| baak14i02 | ATTACTCAGCTACACACCTAT<br>ATTACTCAGCCACACACCTAT | 19617 | AluI | AGCT |
| bags28c17 | TCAACTCCGCGAACGACACTT<br>TCAACTCCGCANACGACACTT | 19622 | BstUI | CGCG |
| bags28c17 | TCGATTCCTCGCGCATCTATA<br>TCGATTCCTCCCGCATCTATA | 19623 | BstUI | CGCG |
| basd22g20 | TCTTCCCCTCCGGGTACTTCA<br>TCTTCCCCTCTGGGTACTTCA | 19633 | HapII | CCGG |

TABLE 17-6

| Clones | Haruna Nijo H602 | SEQ ID NO: | Restriction enzyme | Recognition sequence |
|---|---|---|---|---|
| BaH62H20 | CTCAAAAGTTTGAAGGATTGA<br>CTCAAAAGTTCGAAGGATTGA | 19634 | TaqI | TCGA |
| baak23i12 | AGCATGCTGAGTTTTGTTTAC<br>AGCATGCTGATTTTTGITTAC | 19639 | DdeI | CTNAG |
| BaAL39F24 | CCGTTCTCCGCCGCCATCTCC<br>CCGTTCTCCGGCGCCATCTCC | 19648 | HapII | CCGG |
| BaGS4L04 | CTAACAATCTTAAACCCAAAA<br>CTAACAATCTCAAACCCAAAA | 19649 | MseI | TTAA |
| BaGS7G14 | TTTATGTGCCTGTAGCGGTTG<br>TTTATGTGCCGGTAGCGCTTG | 19655 | HapII | CCGG |
| basd24i11 | CTCTGCACCGGCGGCCTGGCC<br>CTCTGCACCGCCGGCCTGGCC | 19656 | AciI | CCGC |

TABLE 18-1

| Clones | Haruna Nijo H602 | SEQ ID NO: | Restriction enzyme | Recognition sequence |
|---|---|---|---|---|
| BaAL19006 | TACCAAGCGCGTGTCTAGTGA<br>TACCAAGCGCATGTCTAGTGA | 19666 | BstUI | CGCG |

TABLE 18-1 -continued

| Clones | Haruna Nijo H602 | SEQ ID NO: | Restriction enzyme | Recognition sequence |
|---|---|---|---|---|
| baak42c15 | TAAATCTCGAGGCCAGTATGA<br>TAAATCTCGAAGCCAGTATGA | 19675 | XhoI | CTCGAG |
| baak40n12 | GGAGATATGCTGAGATCCTGC<br>GGAGATATGCGGAGATCCTGC | 19676 | DdeI | CTNAG |
| basd2j05 | ACCAACACTCGCCACCATAAG<br>ACCAACACTCACCACCATAAG | 19677 | HphI | NNNNNNNTCACC |
| baak24g04 | AACAAGACGCGGCCGTCCTTG<br>AACAAGACGCTGCCGTCCTTG | 19678 | HaeIII | GGCC |
| baal2i22 | CGGAAGCAGCACAAAAAAAAA<br>CGGAAGCAGCGCAAAAAAAA- | 19684<br>19685 | HhaI | GCGC |
| bags20c22 | TTAGTAAGCAATGATGAAGAG<br>TTAGTAAGCAGTGATGAAGAG | 19686 | TspRI | CASTGNN |
| BaH50O22 | ATAACTGGACTCAATTCCTTG<br>ATAACTGGACACAATTCCTTG | 19687 | HinfI | GANTC |
| bags35i24 | AGAATTTGCCAGTCTCTCCAT<br>AGAATTTGCCGGTCTCTCCAT | 19689 | HapII | CCGG |
| baak37p11 | GCTGCCAGCCGATCTGTGCGA<br>GCTGCCAGCCAATCTG-GCGA | 19699<br>19700 | MboI | GATC |
| BaH50N14 | CTTCAAGGACTTTGCTGTTCC<br>CTTCAAGGACCTTGCTGTTCC | 19712 | AvaII | GGWCC |
| kr70A0202 | ACCTGCAGATCAGCCTCGCCG<br>ACCTGCAGATTAGCCTCGCCG | 19713 | MboI | GATC |
| bags20h01 | TTAAAATATAAATTCATTGAA<br>TTAAAATATAGATTCATTGAA | 19716 | HinfI | GANTC |
| BaH39P15 | GATCAACGGACGATATCGAGA<br>GATCAACGGATGATATCGAGA | 19717 | FokI | GGATGNNNNNNNNN |
| BaAK46020 | TATACCTCATGCGCTTCTCTG<br>TATACCTCATACGCTTCTCTG | 19718 | HhaI | GCGC |
| kr18G0913 | GGGCTTAGTTTCGGCCAGGTT<br>GGGCTTAGTTCCGGCCAGGTT | 19734 | HapII | CCGG |
| bags15e12 | AGCTGACCCGCGCGCATCAGT<br>AGCTGACCCGAGCGCATCAGT | 19737 | AvaI | CYCGRG |
| bags29i09 | CGCGCGTGAGGCCCCCCGGCT<br>CGCGCGTGAGCCCCCCCGGCT | 19738 | HaeIII | GGCC |
| baak19m23 | GTGCTGAATTTATGTTTCAGC<br>GTGCTGAATTCATGTTTCAGC | 19739 | EcoRI | GAATTC |
| bah11l02 | GAATCGCTTCGACAAAAAGTT<br>GAATCGCTTCCACAAAAAGTT | 19746 | TaqI | TCGA |
| bags10l12 | GGCTGGATTTTACCTCTCTAA<br>GGCTGGATTTCACCTCTCTAA | 19750 | HphI | NNNNNNNTCACC |
| bags31m13 | GCACCCACCTTGGCAGGTCGA<br>GCACCCACCTGGGCAGGTCGA | 19751 | MvaI | CCWGG |
| baal16l11 | CATTTTGTAGATTCTTCTATA<br>CATTTTGTAGCTTCTTCTATA | 19762 | HinfI | GANTC |
| BaSD17F09 | TGTCAATCTTCATCCTCACCG<br>ACTGATAACTGATCCT-ACAG | 19765<br>19766 | FokI | NNNNNNNNNNNNNCATCC |
| BaSD14M08 | CGTGCTTGGCGAGCTCGCCGG<br>CGTGCTTGGCAAGCTCGCCGG | 19769 | BanII | GRGCYC |

TABLE 18-2

| Clones | Haruna Nijo H602 | SEQ ID NO: | Restriction enzyme | Recognition sequence |
|---|---|---|---|---|
| BaAL17L08 | GTTCAGTCAGTGTTTCTCCCA<br>GTTCAGTCAGAGTTTCTCCCA | 19785 | TspRI | CASTGNN |
| bah61p18 | TCAGCTCGGCGGAAGTCAGGT<br>TCAGCTCGGCAGAAGTCAGGT | 19786 | AciI | GCGG |
| bah61p18 | TTGTTACCACCGCTGTCTCCG<br>TTGTTACCACTGCTGTCTCCG | 19787 | AciI | CCGC |
| bah63d12 | GCGAGGGGCACACGCCGCGGC<br>GCGAGGGGCAGACGCCGCGGC | 19788 | Bsp1286I | GDGCHC |
| BaAK26A03 | AAAGAATGAACCAGTTTTTCC<br>AAAGAATGAATCAGTTTTTCC | 19789 | HinfI | GANTC |
| BaAL4D19 | TGTTTCTCGGAGCACACCTTG<br>TGTTTCTCGGGGCACACCTTG | 19797 | AvaI | CYCGRG |
| basd13l12 | GATATTCCATTGAAGTGAAGA<br>GATATTCCATCGAAGTGAAGA | 19804 | TaqI | TCGA |
| bags11m01 | ATAATTTCACTGATCAGAAGT<br>ATAATTTCACAGATCAGAAGT | 19805 | TspRI | CASTGNN |
| basd3d13 | GATCGAAGGGCGTATCATATA<br>GATCGAAGGGAGTCTCATATA | 19807 | HinfI | GANTC |
| bags23f08 | CTCGTCCATGGTCTGCATCGG<br>CTCGTCCATGCTCTGCATCGG | 19809 | NcoI | CCATGG |
| BaGS15L23 | CTGCAC-ACTCGATTGCTTAA<br>CTGCACGACTTGACTGCTTGA | 19810<br>19811 | TaqI | TCGA |
| BaGS15L23 | TACAGTTGTCGAACAATTACA<br>TACAGTTGTCAAACAATTACA | 19812 | TaqI | TCGA |
| baak2k13 | ACCCACGAGTACCGTCTGGCA<br>ACCCACGAGTGCCGTCTGGCA | 19813 | AfaI | GTAC |
| baak44g22 | TTGTCAACTATGCGAGGATAT<br>TTGTCAACTACGCGAGGATAT | 19817 | BstUI | CGCG |
| basd15p13 | CTATGTCTAATTAATGTCTAA<br>CTATGTCTAACTAATGTCTAA | 19829 | AseI | ATTAAT |
| bags21k10 | CTAAATCAGTTGACAGCAAAA<br>CTAAATCAGTCGACAGCAAAA | 19832 | TaqI | TCGA |
| bah56n18 | TGATGTAGTCAACGATCTCGT<br>TGATGTAGTCGACGATCTCGT | 19833 | TaqI | TCGA |
| baak33k19 | GGACGTACGGTTAGACCTCGA<br>GGACGTACGGCTAGACCTCGA | 19856 | XspI | CTAG |
| bah50g09 | GCCGCCCGCCCCGATTTGTTT<br>GCCGCCCGCCTCGATTTGTTT | 19858 | TaqI | TOGA |
| bah54l11 | CAAAACGCAGGTCCTCAGCCC<br>CAAAACGCAGATCCTCAGCCC | 19860 | AvaII | GGWCC |
| basd13i14 | TCGGCGGGATCACTTGGCCAT<br>TCGGCGGGATTACTTGGCCAT | 19861 | MboI | GATC |
| bah56g09 | ATAGGAGAGTCCGGCCTGGAG<br>ATAGGAGAGTTCGGCCTGGAG | 19862 | HinfI | GANTC |
| bah41b06 | GCCCCTCCCTCGAGTTGACGA<br>GCCCCTCCCTGGAGTTGACGA | 19863 | MvaI | CCWGG |
| bags14n08 | TGAACGATCCGGATAAAGAAC<br>TGAACGATCCAGATAAAGAAC | 19880 | HapII | CCGG |
| BaAK36I12 | TTAAGTGGACGAGTGATTGCA<br>TTAAGTGGACTAGTGATTGCA | 19882 | XspI | CTAG |

TABLE 18-3

| Clones | Haruna Nijo H602 | SEQ ID NO: | Restriction enzyme | Recognition sequence |
|---|---|---|---|---|
| BaGS7M13 | ATGATCCTGAGGCTGAACATG<br>ATGATCCTGATGCTGAACATG | 19908 | DdeI | CTNAG |
| BaAK32D20 | TCCTTGGGTACTATATCAGGT<br>TCCTTGGGTATTATATCAGGT | 19914 | AfaI | GTAC |
| baak46m13 | ATGCCCGGAAACTGGGATGTT<br>ATGCCCGGAATCTGGGATGTT | 19916 | HinfI | GANTC |
| bags35n16 | GGAAAATTCTCGATTCATAAA<br>GGAAAATTCTTGATTCATAAA | 19917 | TaqI | TCGA |
| baal33a06 | CCGCGGCCTGAGCGGTTTGCG<br>CCGCGGCCTGTGCGGTTTGCG | 19920 | DdeI | CTNAG |
| BaSD17F20 | AGAGCAACACGATCATCTATT<br>AGAGCAACACAATCATCTATT | 19921 | MboI | GATC |
| bags22i21 | AGTTGTGCGCATTGAAACAAA<br>AGTTGTGCGCGTTGAAACAAA | 19922 | BstUI | CGCG |
| BaAL37O23 | GGACGAGCCGAGCATCGACTC<br>GGACGAGCCGGGCATCGACTC | 19925 | BcnI | CCSGG |
| bags22p03 | CTGCCTTGCGTATCAAGGGGA<br>CTGCCTTGCGGATCAAGGGGA | 19926 | MboI | GATC |
| kr65H0816 | CCATGATGGACCTATATACAA<br>CCATGATGGATCTATATACAA | 19946 | Cfr13I | GGNCC |
| bags37j11 | ATCGCCCTCCGGATTCCTTTT<br>ATCGCCCTCCTGATTCCTTTT | 19956 | HapII | CCGG |
| bags37j11 | TTTGGTCTACAGGGTTACCGC<br>TTTGGTCTACCGGGTTACCGC | 19957 | HapII | CCGG |
| BaAK46L15 | GATTATAGTACAGCGGCGACC<br>GATTATAGTATAGCGGCGACC | 19958 | AfaI | GTAC |
| bags1l16 | AGTGCACTGGCGCTAAGTATG<br>AGTGCACTGGTGCTAAGTATG | 19967 | HhaI | GCGC |
| basd1d10 | AGAGATTTCGGGACGTACCAG<br>AGAGATTTCGCGACGTACCAG | 19998 | BstUI | CGCG |
| baak33j06 | GGGCTTGAGCGCAAGTGACAG<br>GGGCTTGAGCACAAGTGACAG | 20002 | HhaI | GCGC |
| bags23a11 | CCCAGTAAAGCATGTTGGAAG<br>CCCAGTAAAGGATGTTGGAAG | 20003 | FokI | GGATGNNNNNNNNN |
| bags34f02 | TACGACTCGAGCATTGGGCCT<br>TACGACTCGAACATTGGGCCT | 20004 | XhoI | CTCGAG |
| baal20a14 | TAGCACAAATATTCAAGAATC<br>TAGCACAAATGTTCAAGAATC | 20009 | SspI | AATATT |
| BaGS21B04 | ACCCTGTATTAAGAAGAGTAA<br>ACCCTGTATTCAGAAGAGTAA | 20010 | MseI | TTAA |
| basd11p10 | ATTAGAATTCCAGTACACAAG<br>ATTAGAATTCTAGTACACAAG | 20013 | XspI | CTAG |
| BaG333E17 | CTGGGGCGCCCCGAGCCGACGC<br>CTGGGGCGCCGGAGCCGACGC | 20014 | AvaI | CYCGRG |
| BaGS17A15 | AGTGGGCAGCCCTGATCTCAG<br>AGTGGGCAGCTCTGATCTCAG | 20029 | AluI | AGCT |
| baal17m22 | TCAGGTTGGAGCCATGGAGGT<br>TCAGGTTGGATCCATGGAGGT | 20031 | MboI | GATC |
| baak42f04 | AGTGGGCAGCCCTGATCTCAG<br>AGTGGGCAGCTCTGATCTCAG | 20032 | AlUI | AGCT |

TABLE 18-4

| Clones | Haruna Nijo H602 | SEQ ID NO: | Restriction enzyme | Recognition sequence |
|---|---|---|---|---|
| BaAK2I20 | CCGGAGGGACGCCCCACAGCA<br>CCGGAGGGACTCCCCACAGCA | 20045 | HinfI | GANTC |
| basd11l18 | TCAGGACTCAAGACCACATAG<br>TCAGGACTCAGGACCATATAG | 20050 | AvaII | GGWCC |
| BaSD13H20 | CTCCGGGCAAGAATCTTCAGG<br>CTCCGGGCAACAATCTTCAGG | 20057 | HinfI | GANTC |
| BaSD14O04 | TTGGCGGCCTGGCCGGCGAGC<br>TTGGCGGCCTCGCCGGCGAGC | 20058 | MvaI | CCWGG |
| BaGS9H13 | ATACTCTGGTGGAACTGGAGG<br>ATACTCTGGTCGAACTGGAGG | 20071 | TaqI | TCGA |
| baal33e04 | GAAGACATGTCAACCACACCA<br>GAAGACATGTTAACCACACCA | 20072 | MseI | TTAA |
| BaAL40L16 | TATACTCCGGATCTTCATGCT<br>TATACTCCGGTTCTTCATGCT | 20073 | MboI | GATC |
| bags9k13 | AGGAGCAGGCACGAGAACGTT<br>AGGAGCAGGCGCGAGAACGTT | 20079 | HhaI | GCGC |
| bags8a14 | CTGCGAGCTCCGAAGATGTTG<br>CTGCGAGCTCAGAAGATGTTG | 20081 | DdeI | CTNAG |
| BaH33B15 | TGCACCCATTCGACACCATGT<br>TGCACCCATTTGACACCATGT | 20084 | TaqI | TCGA |
| BaSD23P08 | TCGTCATGTTGGCCCTCTGCA<br>TCGTCATGTTAGCCCTCTGCA | 20085 | HaeIII | GGCC |
| bast79G0313 | CGTTCTGCGGTGCCTCGGCCA<br>CGTTCTGCGGCGCCTCGGCCA | 20088 | HhaI | GCGC |
| baal4o09 | TGCCTCTGAATCTCTGCTTGC<br>TGCCTCTGAACCTCTGCTTGC | 20091 | HinfI | GANTC |
| bast40C0206 | CTCCACTCCCGCGCCTTCTTC<br>CTCCACTCCCTCGCCTTCTTC | 20117 | BstUI | CGCG |
| baal40g05 | GGAACGTGTCGAATTCCTCAT<br>GGAACGTGTCAAATTCCTCAT | 20118 | EcoRI | GAATTC |
| BaAK12L24 | TGAACCCACCAGGTTCGCAGC<br>TGAACCCACCGGGTTCGCAGC | 20121 | MvaI | CCWGG |
| BaAL12F24 | GAAATCCTCGATCGGTCCTGG<br>GAAATCCTCGGTCGGTCCTGG | 20122 | MboI | GATC |
| BaGS32G16 | ACTCGTCGCCAGCGAGGTACT<br>ACTCGTCGCCGGCGAGGTACT | 20138 | HapII | CCGG |
| basd19p22 | CTTTACCCACGACTCGAGCGT<br>CTTTACCCACAACTCGAGCGT | 20157 | HinfI | GANTC |
| bags4e03 | TTTCATCTACGTACTACCTGC<br>TTTCATCTACTTACTACCTGC | 20158 | AfaI | GTAC |
| BaAK36A13 | ATCCTCACGCGAGCTTGCAAG<br>ATCCTCACGCAAGCTTGCAAG | 20159 | HindIII | AAGCTT |
| bags33i03 | ATTTGAGTGCTCAGCCTATAT<br>ATTTGAGTGCGCAGCCTATAT | 20160 | HhaI | GCGC |
| BaAK14F03 | ATATATGAAACTGAGACGACC<br>ATATATGAAATTGAGACCACC | 20161 | DdeI | CTNAG |
| bags39m22 | CGGACGATATCAGCTAGCTAG<br>CGGACGATATGAGCTAGCTAG | 20180 | EcoRV | GATATC |
| baak29a01 | CCTCACCGGCCCTTGCAACGG<br>CCTCACCGGCGCTTGCAACGG | 20183 | Cfr13I | GGNCC |

TABLE 18-5

| Clones | Haruna Nijo H602 | SEQ ID NO: | Restriction enzyme | Recognition sequence |
|---|---|---|---|---|
| basd1e04 | GAAAACATGCCGGTGAACTCA<br>GAAAACATGCAGGTGAACTCA | 20184 | HapII | CCGG |
| BaGS23K09 | TGGCGGCCGCGTCGCCTTTCA<br>TGGCGGCCGCATCGCCTTTCA | 20185 | BstUI | CGCG |
| BaH42C12 | TCACAAAACATTAAACCCCCA<br>TCACAAAACAATAAACCCCCA | 20187 | MseI | TTAA |
| baak15k23 | GTCACCCAAATCATGGTCATT<br>GTCACCCAAACCATGGTCATT | 20190 | NcoI | CCATGG |
| bags3h19 | GCGGGCGCCGTGGGTCGAGCG<br>GCGGGCGCCGCGGGTCGAGCG | 20196 | SacII | CCGCGG |
| bah17h20 | GCACCTTGGGAGCCTTACCTT<br>GCACCTTGGGGGCCTTACCTT | 20199 | HaeIII | GGCC |
| BaAL5L13 | TTGAGATCGTGTACTCGAGAA<br>TTGAGATCGTATACTCGAGAA | 20200 | AfaI | GTAC |
| bast141C0806 | GCGTGCGGGCGCCCTTCTGGC<br>GCGTGCGGCCACCCTTCTGGC | 20207 | HhaI | GCGC |
| BaAL5E04 | ATTCAGTTGGTGCAGTTCTTA<br>ATTCACTTGGCGCAGTTCTTA | 20216 | HhaI | GCGC |
| baal39f20 | ACCGGCACCATGGCTAAGATC<br>ACCGGCACCACGGCTAAGATC | 20217 | NcoI | CCATGG |
| baak43d13 | CAGTCTCCCCAGCAATTGCAG<br>CAGTCTCCCCGGCAATTGCAG | 20218 | HapII | CCGG |
| baet23B0604 | GCTCCCGCCGGCAGCAGGTTC<br>GCTCCCGCCGCCAGCAGGTTC | 20221 | HapII | CCGG |
| BaAK28I08 | ACAATGAGTTCGAAAACACGT<br>ACAATGAGTTTGAAAACACGT | 20222 | BspT104I | TTCGAA |
| BaGS17E03 | AAAGAACACAATGGTTGTTTT<br>AAAGAACACACTGGTTGTTTT | 20229 | TspRI | CASTGNN |

TABLE 19-1

| Clones | Haruna Nijo H602 | SEQ ID NO: | Restriction enzyme | Recognition sequence |
|---|---|---|---|---|
| BaAL21J19 | GTGTCGACGCAGAACTCGCCG<br>GTGTCGACGCGGAACTCGCCG | 20232 | BstUI | CGCG |
| BaGS11K08 | CCTTGAATCACTGAATTTCCT<br>CCTTGAATCATTGAATTTCCT | 20236 | TspRI | CASTGNN |
| BaGS11K08 | TACTCCTACAGTGCTGCCAAG<br>TACTCCTACAATGCTGCCAAG | 20237 | TspRI | CASTGNN |
| BaGS39H16 | CATTGTCCGCCGGGCGTTCT<br>CATTGTCCGCTGGGCGTTCT | 20238 | HapIII | CCGG |
| BaAK28L16 | AGAAGGTTTTTGCCACCGAAG<br>AGAAGGTTTTGGCCACCGAAG | 20246 | HaeIII | GGCC |
| bags35o06 | GAGGGAAGTCAAAAAATAGGA<br>GAGGGAAGTCGAAAAATAGGA | 20247 | TaqI | TCGA |
| bags13d07 | TTCTGTTTGTGCTCCTGCTGC<br>TTCTGTTTGTCCTCCTGCTGC | 20248 | Bsp1286I | GDGCHC |
| BaAK18A05 | TTTGCGCGCTTGAGGAGTCTC<br>TTTGCGCGCTCGAGGAGTCTC | 20257 | TaqI | TCGA |
| BaH38D03 | TTTGCGCGCTTGAGGAGTCTC<br>TTTGCGCGCTCGAGGAGTCTC | 20258 | XhoI | CTCGAG |

TABLE 19-1-continued

| Clones | Haruna Nijo H602 | SEQ ID NO: | Restriction enzyme | Recognition sequence |
|---|---|---|---|---|
| BaH47G19 | TGGCGGCCTCGACCATGTTGG<br>TGGCGGCCTCAACCATGTTGG | 20272 | TaqI | TCGA |
| BaAK38H10 | TCTAATGAATGGCCGCGACGA<br>TCTAATGAATCGCCGCGACGA | 20273 | HaeIII | GGCC |
| BaH31H16 | GTGGTCTGTCAAGTCTCAAAT<br>GTGGTCTGTCGAGTCTCAAAT | 20278 | HinfI | GANTC |
| bags16g24 | GATGATGGACCCCCGGGCGGT<br>GATGATGGACACCCGGGCGGT | 20293 | AvaII | GGWCC |
| bags35i06 | TCTTGGGGCATTAAAATATAT<br>TCTTGGGGCAATAAAATATAT | 20298 | MseI | TTAA |
| bah56c06 | TCCTAGCCTCGAGGAGTGAAT<br>TCCTAGCCTCAAGGAGTGAAT | 20303 | XhoI | CTCGAG |
| bags6j06 | GTGGGTATGCGCTTCCCAGCT<br>GTGGGTATGCACTTCCCAGCT | 20305 | HhaI | GCGC |
| baak30k04 | AAGTGCTCCATCCTGGTCTTT<br>AAGTGCTCCAGCCTGGTCTTT | 20307 | FokI | NNNNNNNNNNNNNCATCC |
| bags39m02 | AGACGTCGCCGTCGATGAAGG<br>AGACGTCGCCATCGATGAAGG | 20309 | ClaI | ATCGAT |
| baak36b16 | ACACGTAGTAATGCACGTCAA<br>ACACGTAGTAGTGCACGTCAA | 20315 | ApaLI | GTGCAC |
| bah28l03 | CACGTACCAGTTCATTAGCAC<br>CACGTACCAGCTCATTAGCAC | 20392 | AluI | AGCT |
| BaAK36B17 | ACTTACAATCTGCGACATAAA<br>ACTTACAATCGGCGACATAAA | 20393 | BstUI | CGCG |
| bags15i11 | CGGTGGCCGCACTCCCTGTAC<br>CGGTGGCCGCGCTCCCTGTAC | 20414 | HhaI | GCGC |
| BaSD20M22 | TCACCACCTTTTGAAAATGCT<br>TCACCACCTTGTGAAAATGCT | 20415 | DraIII | CACNNNGTG |
| bags7a20 | TATGAACTGCACCATCTAGTG<br>TATGAACTGCGCCATCTAGTG | 20418 | HhaI | GCGC |
| bah25l12 | CTGCTGATTTCACCCAATCCC<br>CTGCTGATTTGACCCAATCCC | 20419 | HphI | NNNNNNNTCACC |

TABLE 19-2

| Clones | Haruna Nijo H602 | SEQ ID NO: | Restriction enzyme | Recognition sequence |
|---|---|---|---|---|
| bags6k09 | TAACCACCGTACCTGTGGGCC<br>TAACCACCGTGCCTGTGGGCC | 20420 | AfaI | GTAC |
| BaGS29P21 | AGCATATATTCGAAAGATGAC<br>AGCATATATTTGAAAGATGAC | 20421 | BspT104I | TTCGAA |
| bah58f18 | TGCACCGGCGCCACCGACAAC<br>TGCACCGGCGGCACCGACAAC | 20422 | HhaI | GCGC |
| bags39i18 | CGGGAATTTTCAATTTTATAA<br>CGGGAATTTTAAATTTTATAA | 20423 | DraI | TTTAAA |
| kr07D0208 | CCTTGTCATGGTCCTGAATTC<br>CCTTGTCATGATCCTGAATTC | 20430 | MboI | GATC |
| BaGS38M11 | CAAAGACATCTGGACGAACCA<br>CAAAGACATCCGGACGAACCA | 20432 | HapII | CCGG |
| bags3k24 | GGTGCCCGCGACAAATGCAAA<br>GGTGCCCGCGGCAAATGCAAA | 20433 | SacII | CCGCGG |

TABLE 19-2 -continued

| Clones | Haruna Nijo H602 | SEQ ID NO: | Restriction enzyme | Recognition sequence |
|---|---|---|---|---|
| bah53e16 | CACAAGCTGAGGCTACTAAAA<br>CACAAGCTGAAGCTACTAAAA | 20434 | DdeI | CTNAG |
| bags21n10 | CCCATGACCGATACGACTGGG<br>CCCATGACCGGTACGACTGGG | 20435 | HapII | CCGG |
| bags21n10 | TGGTGCTCGCCGGGCGGTAGT<br>TGGTGCTCGCNGGGCGGTAGT | 20436 | HapII | CCGG |
| BaGS25E06 | ACAGATGGGGACGCAATGCAA<br>ACAGATGGGGCGCAATGCAA | 20437 | HhaI | GCGC |
| bah38n03 | CTCTGTAGGGGTGCTGTGGAG<br>CTCTGTAGGGATGCTGTGGAG | 20438 | FokI | GGATGNNNNNNNNN |
| BaAK38G14 | GGTGCCCGCGACAAATGCAAA<br>GGTGCCCGCGGCAAATGCAAA | 20439 | SacII | CCGCGG |
| baa5a06 | CAACAGGGAGCAGCTTTTGGC<br>CAACAGGGAGAAGCTTTTGGC | 20440 | HindIII | AAGCTT |
| basd26d19 | AAGAATACTGGACCTCGAGAC<br>AAGAATACTGCACCTCGAGAC | 20441 | Cfr13I | GGNCC |
| BaH50G14 | GCAACAAGATCGAGAAATTTG<br>GCAACAAGATTGAGAAATTTG | 20443 | MboI | GATC |
| BaGS38J23 | GAGCGCGCTCGATATGCTTAG<br>GAGCGCGCTCAATATGCTTAG | 20455 | TaqI | TCGA |
| BaH33A16 | ATGCAACTCTAAACACAAAAT<br>ATGCAACTCTTAACACAAAAT | 20457 | MseI | TTAA |
| bags10e03 | ATAATCAGTCAACCAAAATTG<br>ATAATCAGTCGACCAAAATTG | 20458 | TaqI | TCGA |
| bags14f17 | GAAGCAGGCGCTTCGACAAAA<br>GAAGCAGGCGTTTCGACAAAA | 20459 | HhaI | GCGC |
| baak1e17 | CTGCCCCATCAACCAAGCACT<br>CTGCCCCATCGACCAAGCACT | 20485 | TaqI | TCGA |
| baak35j18 | CTTGGCACCAATGTGACCTGT<br>CTTGGCACCAGTGTGACCTGT | 20495 | TspRI | CASTGNN |
| bags14h08 | TCATCAACTAGCTAAGCTACG<br>TCATCAACTAACTAAGCTACG | 20508 | XspI | CTAG |
| BaSD15J20 | ATCAACCGTGATCTCCAGGTG<br>ATCAACCGTGCTCTCCAGGTG | 20532 | MboI | GATC |
| bah39b06 | AACATTCTCCAGGACAATCCT<br>AACATTCTCCGGGACAATCCT | 20533 | BcnI | CCSGG |

TABLE 19-3

| Clones | Haruna Nijo H602 | SEQ ID NO: | Restriction enzyme | Recognition sequence |
|---|---|---|---|---|
| bags19j08 | AGGGAGGGCTCGGTAGCTGTG<br>AGGGAGGGCTTGGTAGCTGTG | 20534 | BanII | GRGCYC |
| BaGS1009 | ACCGCATGCGCGTCTACGTCT<br>ACCGCATGCGTGTCTACGTCT | 20535 | HhaI | GCGC |
| bah63j06 | GGTGCATAACATCCATCTCGA<br>GGTGCATAACTTCCATCTCGA | 20536 | FokI | NNNNNNNNNNNNNCATCC |
| baa5j24 | CATGAGTGCGCTGTGTCCTGA<br>CATGAGTGCGTTGTGTCCTGA | 20542 | HhaI | GCGC |
| bah15h18 | TCATCGCCACAAATCACATGA<br>TCATCGCCACGAATCACATGA | 20543 | HinfI | GANTC |

TABLE 19-3-continued

| Clones | Haruna Nijo H602 | SEQ ID NO: | Restriction enzyme | Recognition sequence |
|---|---|---|---|---|
| bast62E0610 | CATGAGTGCGTTGTGTCCTGA<br>CATGAGTGCGCTGTGTCCTGA | 20544 | HhaI | GCGC |
| bast62E0610 | TCANGACACAACGCACCNNAG<br>NCANGACACAGCGCANNGGGG | 20545 | HhaI | GCGC |
| baak21h06 | TCCAGTTGCGGTTGAGGGTGG<br>TCCAGTTGCGCTTGAGGGTGG | 20562 | HhaI | GCGC |
| bags3b05 | AGAAAAGAGTCGACAGATTAT<br>AGAAAAGAGTTGACAGATTAT | 20563 | HinfI | GANTC |
| baak16a11 | CTCTGTGAACCGGGCTCCTAA<br>CTCTGTGAACTGGGCTCCTAA | 20569 | HapII | CCGG |
| baak15n22 | CGCCTTTGGCTCCCTTGAGAG<br>CGCCTTTGGCGCCCTTGAGAG | 20570 | HhaI | GCGC |
| baak38d20 | AGGCTCAAACACGAATTTTAA<br>AGGCTCAAACGCGAATTTTAA | 20578 | BstUI | CGCG |
| BaSD12L21 | GGCCGCACGGTGCCGAGAACC<br>GGCCGCACGGCGCCGAGAACC | 20579 | HhaI | GCGC |
| BaAK28L22 | TGTAATTGTACACAAGATTGG<br>TGTAATTGTAGACAAGATTGG | 20582 | AfaI | GTPC |
| bags21l05 | CTTCACCGGGTCTCAGTGCAC<br>CTTCACCGGGCCTCAGTGCAC | 20590 | Cfr13I | GGNCC |
| basd15e02 | ATTTGGGTGTTGAAAGCTCAG<br>ATTTGGGTGTCGAAAGCTCAG | 20594 | TaqI | TCGA |
| bah11m18 | TGGCACTATTTATCTCTCAGG<br>TGGCACTATTAATCTCTCAGG | 20597 | AseI | ATTAAT |
| BaAK30H10 | CACAGATGAAGAATCGTTCTT<br>CACAGATGAATAATCGTTCTT | 20608 | HinfI | GANTC |
| bags38b16 | ATTCTCGGTGTGCCGAAGCTT<br>ATTCTCGGTGCGCCGAAGCTT | 20609 | HhaI | GCGC |
| bags22f10 | TACGACGACGGGCAGCCTTGG<br>TACGACGACGCGCAGCCTTGG | 20614 | BstUI | CGCG |
| BaAK29B22 | CCTACTCGGCTATGCAGGGGT<br>CCTACTCGGCCATGCAGGGGT | 20628 | HaeIII | GGCC |
| BaAK27C16 | CCATACGTGTAAATTCGAATG<br>CCATACGTGTGAATTCGAATG | 20629 | EcoRI | GAATTC |
| BaGS22H13 | CCTGGCTATACTACTCATCTT<br>CCTGGCTATAGTACTCATCTT | 20630 | AfaI | GTAC |
| BaAK27E07 | CTACATGGGCTAGCCAAGAAG<br>CTACATGGGCCAGCCAAGAAG | 20638 | Cfr13I | GGNCC |
| bags28o18 | GGCATCTTCGTGGGGGAGTTC<br>GGCATCTTCGCGGGGGAGTTC | 20640 | BstUI | CGCG |

TABLE 19-4

| Clones | Haruna Nijo H602 | SEQ ID NO: | Restriction enzyme | Recognition sequence |
|---|---|---|---|---|
| baal25b05 | CCGCAGAACTCCGGACGTAGA<br>CCGCAGAACTGCGGACGTAGA | 20641 | HapII | CCGG |
| bags37d20 | CAGGTGAGTACAGAAGCACCA<br>CAGGTGAGTAAAGAAGCACCA | 20645 | AfaI | GTAC |
| basd2a02 | CCTTGATGTCCACTCCGGTCG<br>CCTTGATGTCGACTCCGGTCG | 20652 | HinfI | GANTC |

TABLE 19-4-continued

| Clones | Haruna Nijo H602 | SEQ ID NO: | Restriction enzyme | Recognition sequence |
|---|---|---|---|---|
| BaGS31L06 | TGCTTATGTCAAAGTACTTGG<br>TGCTTATGTCGAAGTACTTCG | 20653 | TaqI | TCGA |
| BaAK19H14 | TGATTGATTCAGCTGAAAGTA<br>TGATTGATTCGGCTGAAAGTA | 20661 | PvuII | CAGCTG |
| BaH49L06 | TTAGGATCGACGAGCACCGGG<br>TTAGGATCGATGAGCACCGGG | 20667 | ClaI | ATCGAT |
| baak4j01 | TGTTGGCTTGTTGCAGCATAG<br>TGTTGGCTTGCTGCAGCATAG | 20688 | PstI | CTGCAG |
| BaAK27E01 | ATACCATGTCTATTTGGAAGC<br>ATACCATGTCGATTTGGAAGC | 20689 | TaqI | TCGA |
| bags19p05 | TGTCACATTCATAGCTTGTAC<br>TGTCACATTCGTAGCTTGTAC | 20691 | AfaI | GTAC |
| bags35i04 | TCCCCATAAGCATCATCCTCC<br>TCCCCATAAGAATCATCCTCC | 20698 | HinfI | GANTC |
| baal19m08 | TCAAGTGGATGAATAACTGGG<br>TCAAGTGGATAAATAACTGGG | 20703 | FokI | GGATGNNNNNNNNN |
| baak12d06 | CACCAAATCGACGCAGCAAGG<br>CACCAAATCGGCGCAGCAAGG | 20711 | HhaI | GCGC |
| basd14b04 | CATAACCATTAGAAATGTTTC<br>CATAACCATTCGAAATGTTTC | 20722 | BspT104I | TTCGAA |
| bags33j12 | CCAGAGGGAGCTCCTATACCC<br>CCAGAGGGAGTTCCTATACCC | 20745 | BanII | GRGCYC |
| BaGS30N07 | TGAGCACGCCGCGGGTCTCCT<br>TGAGCACGCCCCGGGTCTCCT | 20746 | BcnI | CCSGG |
| BaH37I18 | TTCTGAATGGCCCTTTGACTA<br>TTCTGAATGGTCCTTTGACTA | 20747 | HaeIII | GGCC |
| baak46p24 | TTCTGAATGGCCCTTTGACTA<br>TTCTGAATGGTCCTTTGACTA | 20748 | HaeIII | GGCC |
| BaGS20F10 | GACGGTTAACTCAGCAAAGGA<br>GACGGTTAACCCAGCAAAGGA | 20757 | DdeI | CTNAG |
| bah33p03 | TTTATCCCAGCTGGTGCGCAT<br>TTTATCCCAGTTGGTGCGCAT | 20774 | PvUII | CAGCTG |
| bags25h01 | AATCCACATCAAGGATGCCTC<br>AATCCACATCTAGGATGCCTC | 20789 | XspI | CTAG |
| baak33m08 | TTCTTTTAAGTTAAAAGTGGG<br>TTCTTTTAAGCTAAAAGTGGG | 20790 | AluI | AGCT |
| BaH47A11 | GAACGGCCTCAAGAGCCTTGC<br>GAACGGCCTCGAGAGCCTTGC | 20793 | XhoI | CTCGAG |
| bags39e22 | CGAATGGCTTTAACGACCTTA<br>CGAATGGCTTCAACGACCTTA | 20810 | MseI | TTAA |
| bags19i06 | CCTAGTAGTACGCAAAAACAC<br>CCTAGTAGTATGCAAAAACAC | 20815 | AfaI | GTAC |
| basd11k21 | AACGGGGCGCAAGAGTGAAGT<br>AACGGGGCGCGAGAGTGAAGT | 20819 | BstUI | CGCG |

TABLE 19-5

| Clones | Haruna Nijo H602 | SEQ ID NO: | Restriction enzyme | Recognition sequence |
|---|---|---|---|---|
| basd13j03 | AATCCTGGAGTCGACTGATGT<br>AATCCTGGAGGCGACTGATGT | 20840 | SaII | GTCGAC |

TABLE 19-5-continued

| Clones | Haruna Nijo H602 | SEQ ID NO: | Restriction enzyme | Recognition sequence |
|---|---|---|---|---|
| BaSD18I03 | GACAGATTTATAAGAAGTTTT<br>GACAGATTTAAAAGAAGTTTT | 20842 | DraI | TTTAAA |
| bast34D0608 | GTAACACAGAACGAGTACCCC<br>GTAACACAGATCGAGTACCCC | 20844 | MboI | GATC |
| BaGS30F06 | CATCGGTGTTTGACTTACCAT<br>CATCGGTGTTCGACTTACCAT | 20845 | TaqI | TCGA |
| bags21k16 | GAATTGTTTCAGCCTTCTTTT<br>GAATTGTTTCGGCCTTCTTTT | 20846 | HaeIII | GGCC |
| BaH48GC1 | CCAGGTTCGGCGCCGACCCGG<br>CCAGGTTCGGGGCCGACCCGG | 20847 | HaeIII | GGCC |
| bags39a24 | AGAGAACATCGGTGATGCTCT<br>AGAGAACATCAGTGATGCTCT | 20848 | TspRI | CASTGNN |
| bags17p10 | CATCAGGCATGTGCAGATAGT<br>CATCAGGCATCTGCAGATAGT | 20851 | PstI | CTGCAG |
| BaH57L13 | TCGGACGGTAATACTTGTTGG<br>TCGGACGGTAGTACTTGTTGG | 20852 | AfaI | GTAC |
| bags4p07 | CTTCTTTTGCGCTGCATCTCA<br>CTTCTTTTGCACTGCATCTCA | 20853 | HhaI | GCGC |
| bah63a08 | ACTTCAAGTGCAATCGTGCTA<br>ACTTCAAGTGGAATCGTGCTA | 20854 | HinfI | GANTC |
| bah56j15 | CGCCCTTGATGACACCAACAG<br>CGCCCTTGATCACACCAACAG | 20855 | MboI | GATC |
| BaH50F21 | TGTGGAAGTTTGAGACCACCA<br>TGTGGAAGTTCGAGACCACCA | 20857 | TaqI | TCGA |
| bags34e15 | TCCATCGGTCAAGCATTCCTG<br>TCCATCGGTCGAGCATTCCTG | 20868 | TaqI | TCGA |
| bah13b13 | CAGTTGGACTTGCGCAGAAAT<br>CAGTTGGACTCGCGCAGAAAT | 20869 | HinfI | GANTC |
| bah26p09 | TATAGATAGCTGAACAATTGC<br>TATAGATAGCCGAACAATTGC | 20889 | AluI | AGCT |
| BaH41C21 | CATTGTCTTCCGCAGCAGATT<br>CATTGTCTTCTGCAGCAGATT | 20897 | PstI | CTGCAG |
| basd19g21 | ATCCTGTTGCACCCGCCTTCT<br>ATCCTGTTGCGCCCGCCTTCT | 20898 | HhaI | GCGC |
| BaGS36M20 | AGGCATAAGATATCGCTCACA<br>AGGCATAAGAAATCGCTCACA | 20905 | EcoRV | GATATC |
| bags21m10 | ATTTGCTCGGCGCTCTTTTTG<br>ATTTGCTCGGTGCTCTTTTTG | 20906 | Bsp1286I | GDGCHC |
| BaAK14G11 | TACATTCGTTCAAAAATTCTT<br>TACATTCGTTTAAAAATTCTT | 20907 | DraI | TTTAAA |
| BaGS30L20 | ATACAAGACCCGAGATAAACC<br>ATACAAGACCTGAGATAAACC | 20908 | AvaI | CYCGRG |
| bah53j08 | AGCGTTTAGACCGGGTTGCCG<br>AGCGTTTAGATCGGGTTGCCG | 20923 | BcnI | CCSGG |
| bags21d10 | AACAAGAATAGATTCAACCTG<br>AACAAGAATACATTCAACCTG | 20924 | HinfI | GANTC |
| bags9a01 | CGAGCCCGGCGTACTGCACGA<br>CGAGCCCGGCATACTGCACGA | 20925 | AfaI | GTAC |

TABLE 19-6

| Clones | Haruna Nijo H602 | SEQ ID NO: | Restriction enzyme | Recognition sequence |
|---|---|---|---|---|
| bags34d17 | AACTAATCAGCTTAACAATTG<br>AACTAATCAGATTAACAATTG | 20933 | AluI | AGCT |
| baal40k24 | AAGTTCCCATTTGAGTGTCTG<br>AAGTTCCCATCTGAGTGTCTG | 20934 | DdeI | CTNAG |
| BaH33H02 | ACTCAGCAAGGTATCAAATAA<br>ACTCAGCAAGATATCAAATAA | 20948 | EcoRV | GATATC |
| bags10e02 | CGTTGGTGCTCGCGTACGTCA<br>CGTTGGTGCTTGCGTACGTCA | 20976 | BstUI | CGCG |
| bags35n03 | TGAATATCAGTTGGCATTTCC<br>TGAATATCAGCTGGCATTTCC | 20980 | AluI | AGCT |
| BaAL15N07 | AGGCGACAAAGATCCACACCA<br>AGGCGACAAAAATCCACACCA | 20982 | MboI | GATC |
| BaAL15N07 | AGACTGGTGATCTGGAGCCGG<br>AGACTGGTGACCTGGAGCCGG | 20983 | MboI | GATC |
| bags37g12 | CAGAATAACCACGCATGTACC<br>CAGAATAACCGCGCATGTACC | 20986 | HhaI | GCGC |
| bags22l12 | GGCCCACGAAGCTTAGAGGAT<br>GGCCCACGAAACTTAGAGGAT | 20987 | AluI | AGCT |
| BaAK44K01 | GGTTTTGAGTACTTGTGTTTG<br>GGTTTTGAGTGCTTGTGTTTG | 20988 | AfaI | GTAC |
| BaAK31G07 | CATCAGAGATTGCAGGAACCT<br>CATCAGAGATCGCAGGAACCT | 20989 | MboI | GATC |
| bah53n21 | TTGAGTGATTTGATGATGCTT<br>TTGAGTGATTCGATGATGCTT | 20990 | HinfI | GANTC |
| kr29d0107 | TGCTCGAGCTCTAGGGTATTT<br>TGCTCGAGCTGTAGGCTATTT | 21005 | XspI | CTAG |
| bah52iC3 | CGTCGGAGAGTCCAAGGCCCC<br>CGTCGGAGAGCCCAAGGCCCC | 21019 | BanII | GRGCYC |
| BaAK33K05 | TGTTGCTCCCGGTCACAACAT<br>TGTTGCTCCCTGTCACAACAT | 21020 | BcnI | CCSGG |
| bast12G0113 | TTCAGCTGGTGCTAAGGGTAT<br>TTCAGCTCGTACTAAGGGTAT | 21028 | AfaI | GTAC |
| baak13k16 | AGCCACTCGAGAAGCAGGACT<br>AGCCACTCGAAAAGCAGGACT | 21041 | XhoI | CTCGAG |
| bags1h15 | CTGGATAGCGCGAGGGAGCTA<br>CTGGATAGCGTGAGGGAGCTA | 21047 | HhaI | GCGC |
| kr26H0515 | CCACAGGGCTGGAGCTCAACA<br>CCACAGGGCTAGAGCTCAACA | 21048 | XspI | CTAG |
| BaH32G11 | GTCAGATGTGGTCCACCACGT<br>GTCAGATCTGATCCACCACGT | 21054 | Cfr13I | GGNCC |
| BaGS36A16 | GGTGGTCCGCGGTGGCTGGCT<br>GGTGGTCCGCAGTGGCTGGCT | 21065 | SacII | CCGCGG |
| baak1202 | TAAGCATTCCGGTGCAAATCC<br>TAAGCATTCCAGTGCAAATCC | 21073 | HapII | CCGG |
| bags1m19 | ATATGTTCATAGATGTCAATC<br>ATATGTTCATGGATGTCAATC | 21082 | FokI | GGATGNNNNNNNNN |

TABLE 20-1

| Clones | Haruna Nijo H602 | SEQ ID NO: | Restriction enzyme | Recognition sequence |
|---|---|---|---|---|
| basd14f03 | ATCATTCAGGATGTAAAATGT<br>ATCATTCAGGGTGTAAAATGT | 21083 | FokI | GGATGNNNNNNNNN |
| BaAL30P12 | CCTCCTCCTCGGGTGTAAAGT<br>CCTCCTCCTCAGGTGTAAAGT | 21093 | AvaI | CYCGRG |
| BaGS21H12 | AGTAATTTGATCCACAAGTAT<br>AGTAATTTGAACCACAAGTAT | 21094 | MboI | GATC |
| BaGS9G15 | TAGGACCTGACCTTTCAAGCT<br>TAGGACCTGATCTTTCAAGCT | 21095 | MboI | GATC |
| baak41j04 | CCCGGCACCTGTCAGACACGC<br>CCCGGCACCTCTCAGACACGC | 21096 | DdeI | CTNAG |
| bags38a05 | TTCCTACTCAGATCTGCCAGG<br>TTCCTACTCAAATCTGCCAGG | 21099 | MboI | GATC |
| BaH43I06 | CGCGGCCGCGCGCCTGCCACA<br>CGCGGCCGCGTGCCTGCCACA | 21100 | HhaI | GCGC |
| bags9j07 | TTCACACTTAAAAGGCACACA<br>TTCACACTTAGAAGGCACACA | 21101 | DdeI | CTNAG |
| baak31p11 | TTGCGCCTTCGAACAATGAAT<br>TTGCGCCTTCAAACAATGAAT | 21102 | BspT104I | TTCGAA |
| BaGS17P19 | GATGGTCCTCAATTTCACTTG<br>GATGGTCCTCGATTTCACTTG | 21103 | TaqI | TCGA |
| baal32j05 | CGAGGCCTCTTGCGACGTAGA<br>CGAGGCCTCTCGCGACGTAGA | 21104 | BstUI | CGCG |
| baal16l16 | ACTGACTCGCGATTTATTTTA<br>ACTGACTCGCAATTTATTTTA | 21105 | BstUI | CGCG |
| baal6a11 | TCACCGTGGATCTCCCGCCCA<br>TCACCGTGGACCTCCCGCCCA | 21106 | MflI | RGATCY |
| bah55p06 | ACGGTCTCTCATCGATGCGCT<br>ACGGTCTCTCGTCGATGCGCT | 21107 | ClaI | ATCGAT |
| bags8f03 | TTCAGGGCCAAAGTCTCCACC<br>TTCAGGGCCAGAGTCTCCACC | 21108 | HinfI | GANTC |
| BaAL4B09 | CAACACCAATATAGAAATCAG<br>CAACACCAATCTAGAAATCAG | 21117 | XbaI | TCTAGA |
| bags32f21 | AAGTGAAGATCTCAGTAATGA<br>AAGTGAAGATTTCAGTAATGA | 21118 | MflI | RGATCY |
| BaGS10G07 | TGTTGGGGATGACGCCGCCGT<br>TGTTGGGGATCACGCCGCCGT | 21121 | FokI | GGATGNNNNNNNNN |
| BaH63O04 | GTAAGTCCGCAACACATGGCG<br>GTAAGTCCGCGACACATGGCG | 21125 | BstUI | CGCG |
| BaG326D21 | AGGTATTGAGTTCAAGTGAGA<br>AGGTATTGAGATCAAGTGAGA | 21126 | MboI | GATC |
| baal4k16 | GTAAATCCATTGATTCATGCA<br>GTAAATCCATCGATTCATGCA | 21138 | ClaI | ATCGAT |
| bags32b14 | GTCACGGCCGGCCTCTTCCGC<br>GTTACGGCCGCCCTCTTCCGC | 21139 | HapII | CCGG |
| baal4d01 | AGTTTAAGGCCCCGAAGGTTC<br>AGTTTAAGGCTCCGAAGGTTC | 21140 | HaeIII | GGCC |
| baal4d01 | TGCT--AAGGTCCTTGGATGA<br>TGCTATAAGGGCCTTGGATGA | 21141<br>21142 | HaeIII | GGCC |
| baak25d07 | CATCGTGAGGGGCGGTGGAGT<br>CATCGTGAGGCGCGGTGGAGT | 21154 | HhaI | GCGC |

TABLE 20-2

| Clones | Haruna Nijo H602 | SEQ ID NO: | Restriction enzyme | Recognition sequence |
|---|---|---|---|---|
| BaAK29M05 | AGACGCAGGATCTGTCGAAGT<br>AGACGCAGGACCTGTCGAAGT | 21155 | AvaII | GGWCC |
| BaGS31I08 | CTCAAGCATGCGCTTCTTTGC<br>CTCAAGCATGTGCTTCTTTGC | 21156 | HhaI | GCGC |
| baal30o06 | CCTTCTTCTCACCGGCGGCGC<br>CCTTCTTCTCTCCGGCGGCGC | 21158 | HphI | NNNNNNNTCACC |
| baak13n14 | GCGAGCACCGCCGGATAAACT<br>GCGAGCACCGTCGGATAAACT | 21159 | HapII | CCGG |
| bags7a09 | TAAAAGACAGCTTGCTAACTC<br>TAAAAGACAGTTTGCTAACTC | 21160 | AluI | AGCT |
| bah31o16 | GTGCTTCAACACGATTTAGCA<br>GTGCTTCAACGCGATTTAGCA | 21166 | BstUI | CGCG |
| kr40D0707 | GTCTTCCGGACGTTGAGGAAA<br>GTCTTCCGGATGTTGAGGAAA | 21170 | FokI | GCATGNNNNNNNNN |
| BaAL30H03 | AGAAACTGGGAAATTCTGGGT<br>AGAAACTGGGGAATTCTGGGT | 21175 | EcoRI | GAATTC |
| basd3f22 | TAGTCCAAGGGCACATCACAC<br>TAGTCCAAGGACACATCACAC | 21192 | Bsp1286I | GDGCHC |
| BaAK41K07 | GCTGGTCCGGNGGGATGCCTT<br>GCTGGTCCGGGGGGATGCCTT | 21196 | HapII | CCGG |
| BaAK41K07 | TGGTCTTGCCGGTGAGGGTCT<br>TGGTCTTGCCTGTGAGGGTCT | 21197 | HapII | CCGG |
| BaH53I11 | ATCATCTCCTTGAGCACCAGC<br>ATCATCTCCTGGAGCACCAGC | 21198 | MvaI | CCWGG |
| BaAL18N03 | TCGGAACTCCGGACGGGCTCG<br>TCGGAACTCCAGACGGGCTCG | 21201 | HapII | CCGG |
| baak40c08 | ATATATAACANGAAGAGAGCT<br>ATATATAACAAGAAGAGAGCT | 21202 | AluI | AGCT |
| baak40c08 | CTGCATTGCAGCTCTGTGTTA<br>CTGCATTGCAACTCTGTGTTA | 21203 | AluI | AGCT |
| baal33h17 | TAGACCGATAGATCCTACTTA<br>TAGACCGATAAATCCTACTTA | 21207 | MfII | RGATCY |
| bags20d08 | TCAGGACGGCCTTGTCAACCT<br>TCAGGACGGCTTTGTCAACCT | 21208 | HaeIII | GGCC |
| BaGS4J01 | TCGCGCCGTAAGCCTCGGTGC<br>TCGCGCCGTAGGCCTCGGTGC | 21209 | HaeIII | GGCC |
| BaAK17I01 | GTGGGTCCACAATCTCACCGA<br>GTGGGTCCACGATCTCACCGA | 21215 | MboI | GATC |
| BaAK30F08 | TTGCTCAGAGCCTGGGCCGCG<br>TTGCTCAGAGTCTGGGCCGCG | 21216 | HinfI | GANTC |
| bags19g17 | TGACAGCAGCCGATGTCGTGC<br>TGACAGCAGCTGATGTCGTGC | 21225 | AluI | AGCT |
| baak21I02 | CGTCCCATTCGAGGGTATCGG<br>CGTCCCATTCAAGGGTATCGG | 21226 | TaqI | TCGA |
| bags9I13 | ATATGTCCGCAAAAGGCGTTC<br>ATATGTCCGCGAAAGGCGTTC | 21232 | BstUI | CGCG |
| baak12i20 | CAAGAGACGCGGAGGATGACA<br>CAAGAGACGCAGAGGATGACA | 21241 | BstUI | CGCG |
| BaAK3M04 | AGCAAGGTACATCCAATACTT<br>AGCAAGGTACCTCCAATACTT | 21242 | BanI | GGYRCC |

TABLE 20-3

| Clones | Haruna Nijo H602 | SEQ ID NO: | Restriction enzyme | Recognition sequence |
|---|---|---|---|---|
| bah15n23 | GGCAGGGCAGATTTCCCACAA<br>GGCAGGGCAGCTTTCCCACAA | 21244 | AluI | AGCT |
| baak45i02 | CCGCAAGGGTGCGACCATCCT<br>CCGCAAGGGTCCGACCATCCT | 21245 | AvaII | GGWCC |
| BaH45B01 | AACCAAGCACAGTACCAGGAC<br>AACCAAGCACGGTACCAGGAC | 21253 | KpnI | GGTACC |
| baal23o14 | CCGCAAGGGTGCGACCATCCT<br>CCGCAAGGGTCCGACCATCCT | 21255 | AvaII | GGWCC |
| baal4d14 | AAGACTGAAAAAGCACCCCCT<br>AAGACTGAAAGAGCACCCCCT | 21271 | Bsp1286I | GDGCHC |
| baak29j13 | AGCAACCTTACAAACTGAAAG<br>AGCAACCTTAAAAACTGAAAG | 21280 | MseI | TTAA |
| bags20p18 | GTTTCGACTCGGATGCCGCTC<br>GTTTCGACTCAGATGCCGCTC | 21281 | FokI | GGATGNNNNNNNNN |
| BaAK12J13 | TGGTGACTCCGGTGATGCTGA<br>TGGTGACTCCCGTGATGCTGA | 21282 | HapII | CCGG |
| BaH27N11 | ACTAACCATGGAAAAGGCTTA<br>ACTAACCATGTAAAAGGCTTA | 21286 | NcoI | CCATGG |
| BaGS34D11 | CTATCTGCCAGATCCTGTCAC<br>CTATCTGCCATATCCTGTCAC | 21287 | MflI | RGATCY |
| BaGS39G07 | ATTTTGTCATTCAGATAATTT<br>ATTTTGTCATCCAGATAATTT | 21288 | FokI | NNNNNNNNNNNNNCATCC |
| BaGS32G02 | ATGCTGAAAGGACTCTTCTAG<br>ATGCTGAAAGAACTCTTCTAG | 21320 | HinfI | GANTC |
| bast21C1105 | TATATCCGTCAATATGTGGTA<br>TATATCCGTCGATATGTGGTA | 21326 | TaqI | TCGA |
| bags29f03 | CGCCATTAGGTGCTATGGAGG<br>CGCCATTAGGAGCTATGGAGG | 21327 | AluI | AGCT |
| BaAK46B16 | TCTGAACTGTCGATATGCCTA<br>TCTGAACTGTGGATATGCCTA | 21328 | TaqI | TCGA |
| baal16h16 | TTTCTTTCTGACGCAAGCAAA<br>TTTCTTTCTGGCGCAAGCAAA | 21329 | HhaI | GCGC |
| BsAL13O24 | CGCAGTTTTCCACTTGATTCT<br>CGCAGTTTTCGACTTGATTCT | 21338 | TaqI | TCGA |
| BaAL20M22 | GCGTCCTTGAACGCCGCTCTC<br>GCGTCCTTGAGCGCCGCTCTC | 21347 | HaeII | RGCGCY |
| BaAL151B12 | TCAAGAAGCATCCCTGAATAT<br>TCAAGAAGCAGCCCTGAATAT | 21353 | FokI | NNNNNNNNNNNNNCATCC |
| bags39h18 | TTTACCTGTTTGAATTTGCAA<br>TTTACCTGTTCGAATTTGCAA | 21360 | BspT104I | TTCGAA |
| BaAL3L23 | TCCACCTCACCAAGGAATTCA<br>TCCACCTCACTAAGGAATTCA | 21362 | DdeI | CTNPCT |
| BaH50L11 | ATCATAAAATCTTTTGAATCA<br>ATCATAAAATATTTTGAATCA | 21380 | SspI | AATATT |
| bast50G0814 | CTACAGCACAGTACTCTGCCG<br>CTACAGCACACTACTCTGCCG | 21381 | ScaI | AGTACT |
| BaH46B06 | AGACTCTGTCCCGGACTCCAG<br>AGACTCTGTCACGGACTCCAG | 21403 | HapII | CCGG |
| baal5e24 | TGAAGCGGATCGATCTAATGG<br>TGAAGCGGATTGATCTAATGG | 21404 | ClaI | ATCGAT |

TABLE 20-4

| Clones | Haruna Nijo H602 | SEQ ID NO: | Restriction enzyme | Recognition sequence |
|---|---|---|---|---|
| bags11a16 | GTTGTCCTGCCTAGGGTCGCC<br>GTTGTCCTGCTTAGGGTCGCC | 21405 | EcoT14lI | CCWWGG |
| BaGS37K02 | TCTTTGTCACGCGAACTGCCG<br>TCTTTGTCACACGAACTGCCG | 21413 | BstUI | CGCG |
| bah28a10 | ACTATCAGAGTCACACTATGA<br>ACTATCAGAGCCACACTATGA | 21414 | HinfI | GANTC |
| bah27c03 | GGCTGCCATCGGATGCAAACG<br>GGCTGCCATCCGATGCAAACG | 21415 | FokI | NNNNNNNNNNNNNCATCC |
| bags37g15 | GAGCTTTCGCGCTAAGTGACA<br>GAGCTTTCGCACTAAGTGACA | 21418 | BstUI | CGCG |
| BaH54L03 | CACACGGCGATCGGAGCTTCA<br>CACACGGCGACCGGAGCTTCA | 21426 | MboI | GATC |
| BaAK21J17 | GTGCATCGTAAATCATCAGGG<br>GTGCATCGTACATCATCAGGG | 21427 | AfaI | GTAC |
| bags23g08 | ATGATGCAGGCGCTCAGTGGA<br>ATGATGCAGGGGCTCAGTGGA | 21428 | HhaI | GCGC |
| BaAL2M19 | CCTAGTGGGCATCCTCCTCCT<br>CCTAGTGGGCGTCCTCCTCCT | 21440 | FokI | NNNNNNNNNNNNNCATCC |
| BaH36F15 | CGAGGCCCTGGGCGACGTACC<br>CGAGGCCCTGCGCGACGTACC | 21442 | MvaI | CCWGG |
| bah58l07 | GCTCAAACTGTGCTGACAGGC<br>GCTCAAACTGCGCTGACAGGC | 21443 | HhaI | GCGC |
| baet29C0406 | ACGGGAGCGACCGGCACCCAC<br>ACGGGAGCGAGCGGCACCCAC | 21444 | HapII | CCGG |
| BaAK35804 | ATCCCCTGCCCCGCCTTGAGG<br>ATCCCCTGCCGCGCCTTGAGG | 21445 | HhaI | GCGC |
| bags34k13 | ACAATTCTGACCGAACATAGC<br>ACAATTCTGATCGAACATAGC | 21446 | TaqI | TCGA |
| baal29i08 | CCTGTTGCTGCAGCTATATCT<br>CCTGTTGCTGTAGCTATATCT | 21447 | PstI | CTGCAG |
| baak11p10 | AAACGAGATGTGCTGTCTAGT<br>AAACGAGATGCGCTGTCTAGT | 21448 | HhaI | GCGC |
| bags4e12 | GGAACTTGCGGAGTTTCAGGA<br>GGAACTTGCGCAGTTTCAGGA | 21449 | HhaI | GCGC |
| basd24b08 | TAAAGATTGGCCTGATTTGTT<br>TAAAGATTGGTCTGATTTGTT | 21457 | HaeIII | GGCC |
| baalf3o10 | GTCGATCTCCGGCTGCGCCAC<br>GTCGATCTCCAGCTGCGCCAC | 21463 | AluI | AGCT |
| bags15d14 | CTATTTTTANAGGATGGGAC<br>CTATTTTTTAAAGGATGGGAC | 21471 | FokI | GGATGNNNNNNNNN |
| bags15d14 | CTTTGTCATCCGTATTTCTTA<br>CTTTGTCATCTGTATTTCTTA | 21472 | FokI | NNNNNNNNNNNNNCATCC |
| BaGS37E09 | GGGCAGAGTCTCGCCAGTAGC<br>GGGCAGAGTCGCGCCAGTAGC | 21473 | HhaI | GCGC |
| BaGS19I11 | ATGCTGTTAATGCTTGACGAT<br>ATGCTGTTAAAGCTTGACGAT | 21481 | HindIII | AAGCTT |
| BaGS18P04 | ATTCACTGGTACAGACGATGA<br>ATTCACTGGTGCAGACGATGA | 21491 | AfaI | GTAC |
| bags19e06 | GCGAGTAGATCATTAAGAATT<br>GCGAGTAGATTATTAAGAATT | 21492 | MboI | GATC |

TABLE 20-5

| Clones | Haruna Nijo H602 | SEQ ID NO: | Restriction enzyme | Recognition sequence |
|---|---|---|---|---|
| baak35n07 | TTCCGCTCTCACCAACCGAGG<br>TTCCGCTCTCCCCAACCGAGG | 21493 | HphI | NNNNNNNTCACC |
| BaAK14C17 | GTGCAGGCCGACGAACAATGG<br>GTGCAGGCCGTCGAACAATGG | 21519 | TaqI | TCGA |
| BaAK1N06 | CAATTGCATCCTAGTTAGCCG<br>CAATTGCATCTTAGTTAGCCG | 21525 | XspI | CTAG |
| bags38d10 | ATACCTCAGCTAATCTCTGGC<br>ATACCTCAGCCAATCTCTGGC | 21526 | AluI | AGCT |
| BaAK19J15 | GGAAGGTGGGTACCTCCACGA<br>GGAAGGTGGGCACCTCCACGA | 21527 | AfaI | GTAC |
| BaGS37D24 | TCGTTCAGGGACAAGGAGTTG<br>TCGTTCAGGGCCAAGGAGTTG | 21544 | HaeIII | GGCC |
| BaGS9K15 | GAAACTTCCACGGAAGGACTG<br>GAAACTTCCAGGGAAGGACTG | 21545 | MvaI | CCWGG |
| BaGS33L03 | ACACACGCCGTCGGAAGGCCC<br>ACACACGCCGCCGGGAAGGCCC | 21546 | SacII | CCGCGG |
| kr58F0511 | GCTTCGTTGTGTACTGGGTCT<br>GCTTCGTTGTTTACTGGGTCT | 21548 | AfaI | GTAC |
| baak39o18 | AGCCAACATGATACTCTCTAT<br>AGCCAACATGGTACTCTCTAT | 21566 | AfaI | GTAC |
| bags20p12 | GCACCCGGGCTCCGACCACGT<br>GCACCCGGGCGCCGACCACGT | 21567 | BanII | GRGCYC |
| bags38f23 | TCAATGATAGCTACTTTCAAG<br>TCAATGATAGTTACTTTCAAG | 21568 | AluI | AGCT |
| bags3k09 | TGAACATACAATGAGAGAGCT<br>TGAACATACAGTGAGAGAGCT | 21575 | TspRI | CASTGNN |
| baak34p14 | CAATGTCCCGGAGGATACGGA<br>CAATGTCCCGAAGGATACGGA | 21580 | BcnI | CCSGG |
| basd15m11 | CAGCACAGGTCCATAGATGGA<br>CAGCACAGGTTCATAGATGGA | 21583 | AvaII | GGWCC |
| bags21b06 | AAGAACAGCTAAAACATATAT<br>AAGAACAGCTGAAACATATAT | 21584 | PvuII | CAGCTG |
| BaH18F07 | TGGGGGCGGCGCCCAGCACTC<br>TGGGGGCGGCTCCCAGCACTC | 21585 | HhaI | GCGC |
| BaH44A23 | CAGCATCTTCGAATGCTGAGA<br>CAGCATCTTCAAATGCTGAGA | 21586 | BspT104I | TTTCGAA |
| bags3d07 | AGACACCGACCGCAGTTGACG<br>AGACACCGACTGCAGTTGACG | 21587 | PstI | CTGCAG |
| baak24e07 | CGGTAGGCACCCAAGAGCTCC<br>CGGTAGGCACGCAAGAGCTCC | 21589 | BanI | GGYRCC |

TABLE 21-1

| Clones | Haruna Nijo H602 | SEQ ID NO: | Restriction enzyme | Recognition sequence |
|---|---|---|---|---|
| bah42i06 | CTTGCTTGCTCACATGGTGAG<br>CTTGCTTGCTGACATGGTGAG | 21600 | DraIII | CACNNNGTG |
| bagsl2l21 | TCCTTGCATCTGTCTCACCAT<br>TCCTTGCATCCGTCTCACCAT | 21629 | FokI | NNNNNNNNNNNNNCATCC |
| baak12j24 | GTTCGGCCCGTGGAAAGGCAG<br>GTTCGGCCCGCGGAAAGGCAG | 21630 | SacII | CCGCGG |

TABLE 21-1-continued

| Clones | Haruna Nijo H602 | SEQ ID NO: | Restriction enzyme | Recognition sequence |
|---|---|---|---|---|
| bags14d22 | TTAGGAAGAGGGCGAGATAGG<br>TTAGGAAGAGCGCGAGATAGG | 21631 | BstUI | CGCG |
| baa16b02 | AGTGTTCCGGGAGAAGCTCCG<br>AGTGTTCCGGCAGAAGCTCCG | 21633 | BcnI | CCSGG |
| baak29f13 | AGATCCACTAACATCTCCGTA<br>AGATCCACTAGCATCTCCGTA | 21634 | XspI | CTAG |
| bags19e04 | TTATAAGGCCGTAAATCTAAA<br>TTATAAGGCCCTAAATCTAAA | 21643 | Cfr13I | GGNCC |
| BaH28L07 | CCATGCTTCCCAGGACAGAGC<br>CCATGCTTCCGAGGACAGAGC | 21644 | MvaI | CCWGG |
| baak21m18 | TGATGATCCGCGGGGAAGGT<br>TGATGATCCGTGGGGAAGGT | 21645 | SacII | CCGCGG |
| BaH59A20 | AGTTCTGGGATGGCGGGTTGA<br>AGTTCTGGGACGGCGGGTTGA | 21657 | FokI | GGATGNNNNNNNNN |
| BaAK31N06 | AGATTTTGTTGACTGACCGAC<br>AGATTTTGTTCACTGACCGAC | 21662 | TspRI | CASTGNN |
| bags29c18 | ATACTACTGAAACACGATATC<br>ATACTACTGAGACACGATATC | 21666 | DdeI | CTNAG |
| bags37n23 | GCCGGCGTTAACAGAGCCAGC<br>GCCGGCGTTAGCAGAGCCAGG | 21670 | MseI | TTAA |
| BaGS21E20 | AAACAACACGACCGAGACGGT<br>AAACAACACGGCCGAGACCGT | 21681 | HaeIII | GGCC |
| BaAK37P20 | ATTGCTTCTCAGA-TCAAACC<br>ATTGCTTCTCGGAGTCAAACC | 21694<br>21695 | DdeI | CTNAG |
| bah34b22 | TACCGTCGCTTAAATACCATC<br>TACCGTCGCTNAAATACCATC | 21699 | MseI | TTAA |
| bah34b22 | TCTTCACTTAAACAAATCCAG<br>TCTTCACTTACACAAATCCAG | 21700 | MseI | TTAA |
| baak42a24 | ATGACTCCGGAGCTTTACCAA<br>ATGACTCCGGCGCTTTACCAA | 21708 | HhaI | GCGC |
| baak16f06 | AAGCAGCACAGCGCCGTGAAC<br>AAGCAGCACAACGCCGTGAAC | 21709 | HhaI | GCGC |
| baak16f06 | TGGGGGTCTCCGCTGCGCCTT<br>TGGGGGTCTCTGCTGCGCCTT | 21710 | HhaI | GCGC |
| bah11m12 | GTGCTAGCTAGTAATATGCAG<br>GTGCTAGCTATTAATATGCAG | 21711 | AsaI | ATTAAT |
| baak33d06 | TTCAGACACTAATGCTCCGTA<br>TTCAGACACTGATGCTCCGTA | 21719 | TspRI | CASTGNN |
| BaGS25G03 | ACAGCTCTGGACTGTGGTGGC<br>ACAGCTCTGGCCTGTGGTGGC | 21725 | HaeIII | GGCC |
| bast42C0406 | AGTGCCTCCTCGCCAGCGACA<br>AGTGCCTCCTAGCCAGCGACA | 21728 | XspI | CTAG |

TABLE 21-2

| Clones | Haruna Nijo H602 | SEQ ID NO: | Restriction enzyme | Recognition sequence |
|---|---|---|---|---|
| bags17i04 | TGCAACAGATGCGTCTAACTT<br>TGCAACAGATCCGTCTAACTT | 21758 | MboI | GATC |
| baa140b06 | AGACTCCGTCAACTTCCAGCA<br>AGACTCCGTCGACTTCCAGCA | 21762 | TaqI | TCGA |

TABLE 21-2-continued

| Clones | Haruna Nijo H602 | SEQ ID NO: | Restriction enzyme | Recognition sequence |
|---|---|---|---|---|
| baal40b06 | TCCATCTGCAATTTCAGTAAA<br>TCGATCTGCATTTTCAGTAAA | 21763 | TaqI | TCGA |
| baak3c01 | CGGGCCGTAGCTGGCCTGGTT<br>CGGGCCGTAGGTGGCCTGGTT | 21770 | AluI | AGCT |
| baak3c01 | CTCCTTGAGCTTGAACGGTCC<br>CTCCTTGAGCCTGAACGGTCC | 21771 | AluI | AGCT |
| BaH52L11 | GACATGACTTGGAACTATCCT<br>AACATGACTTAGAACTATCCT | 21788 | DdeI | CTNAG |
| BaH52L11 | GTGTACCTGAGCATT-CAGAA<br>GTGTACCTGACCATTTCAGAA | 21789<br>21790 | DdeI | CTNAG |
| BaH52L11 | TCAGCCTCTCTGAGTAGAGCT<br>TCAGCCTCTCCGAGTAGAGCT | 21791 | DdeI | CTNAG |
| baaI8b16 | TTGCTCCCCTCATCAGAGGTA<br>TTGCTCCCCTGATCAGAGGAA | 21792 | MboI | GATC |
| bah60l22 | CGCCAAACTAGTAGGACAAAA<br>CGCCAAACTAATAGGACAAAA | 21801 | XspI | CTAG |
| bags21m22 | TAAAAGAAGCACAATATGAT<br>TAAAAGAAGTACAATATGAT | 21802 | AfaI | GTAC |
| BaH54E07 | GGCAGTACACGAGCTTCCGAG<br>GGCAGTACACAAGCTTCCGAG | 21803 | HindIII | AAGCTT |
| BaAK39A20 | AGTCTTTTTAAAGATTCCACT<br>AGTCTTTTTAGAGATTCCACT | 21804 | DraI | TTTAAA |
| baet32B1103 | CAGTTCCTCTAGAACAGAGCT<br>CAGTTCCTCTGGAACAGAGCT | 21810 | XbaI | TCTAGA |
| BaAK31O16 | TATATGAAGCGCTCCAGCACG<br>TATATGAAGCACTCCAGCACG | 21811 | HhaI | GCGC |
| bags39l20 | TGTCCTGAGTTGCAGCCCTTG<br>TGTCCTGAGTCGCAGCCCTTG | 21812 | HinfI | GANTC |
| BaGS15L12 | ATCTCTTCCTCGGGAACCGCT<br>ATCTCTTCCTTGGGAACCGCT | 21813 | AvaI | CYCGRG |
| bags11h08 | CAATGCGGTACCCCTCGACGG<br>CAATGCGGTATCCCTCGACGG | 21831 | AfaI | GTAC |
| BaAK13L03 | CAAGAAAGTACTTTTGGAAAA<br>CAAGAAAGTAATTTTGGAAAA | 21851 | AfaI | GTAC |
| basd20j22 | ACAGCAGGTACTGTGATTAAG<br>ACAGCAGGTATTGTGATTAAG | 21854 | AfaI | GTAC |
| BaGS38F01 | TGAGACATCTTAAACCTTCAC<br>TGAGACATCTCAAACCTTCAC | 21861 | MseI | TTAA |
| BaAK32I05 | CCCCAAACTAATAGATGAAAA<br>CCCCAAACTAGTAGATGAAAA | 21862 | XspI | CTAG |
| BaAK14F01 | TTCAAACATCGGCGGAAGATT<br>TTCAAACATCCGCGGAAGATT | 21870 | SacII | CCGCGG |
| bah57o01 | TCTCGCCGGCATCCTCCTCCA<br>TCTCGCCGGCGTCCTCCTCCA | 21871 | FokI | NNNNNNNNNNNNNCATCC |

TABLE 21-3

| Clones | Haruna Nijo H602 | SEQ ID NO: | Restriction enzyme | Recognition sequence |
|---|---|---|---|---|
| basd12f05 | GCACCGGGAGCTCTTGGCTCC<br>GCACCGGGAGTTCTTGGCTCC | 21872 | SacI | GAGCTC |

TABLE 21-3-continued

| Clones | Haruna Nijo H602 | SEQ ID NO: | Restriction enzyme | Recognition sequence |
|---|---|---|---|---|
| bah58e21 | TAAACTTGGTGCTCCTGTAAC<br>TAAACTTGGTTCTCCTGTAAC | 21873 | Bsp1286I | GDGCHC |
| bags1d07 | CAATGAGGATTCTATGTGGTG<br>CAATGAGGATCCTATGTGGTG | 21874 | MboI | GATC |
| BaH23J15 | TTCAAACATCGGCGGAAGATT<br>TTCAAACATCCGCGGAAGATT | 21875 | SKII | CCGCGG |
| baal18g23 | TCTCGCCGGCATCCTCCTCCA<br>TCTCGCCGGCGTCCTCCTCCA | 21882 | FokI | NNNNNNNNNNNNNCATCC |
| BaH50P14 | TCAGCGTGGACGTGGTGGAGT<br>TCAGCGTGGATGTGGTGGAGT | 21892 | FokI | GGATGNNNNNNNNN |
| BaAK23L23 | TCGGATATCCCGGGTAACCAA<br>TCGGATATCCTGGGTAACCAA | 21902 | AvaI | CYCGRG |
| bags7a23 | CCGGCTCATATTGCAGCATTT<br>CCGGCTCATACTGCAGCATTT | 21903 | PstI | CTGCAG |
| bah56l04 | AGCAACTCTAACCTACCTCGA<br>AGCAACTCTAGCCTACCTCGA | 21904 | XspI | CTAG |
| BaAL6G08 | ATCAAAAACGCGATGCCACCA<br>ATCAAAAACGAGATGCCACCA | 21923 | BstUI | CGCG |
| bast10C0406 | TGCTAGGTTCCATCATCCTGC<br>TGCTAGGTTCGATCATCCTGC | 21931 | TaqI | TCGA |
| bah62n05 | GAAAAAACGCATGAGTCTAAC<br>GAAAAAACGCGTGAGTCTAAC | 21945 | BstUI | CGCG |
| baak20d11 | GTGGCAGTGCGCCGCCAATGG<br>GTGGCAGTGCTCCGCCAATGG | 21958 | HhaI | GCGC |
| BaAL6D19 | GTAACTTGGCCTTTCATCGAC<br>GTAACTTGGCTTTTCATCGAC | 21959 | HaeIII | GGCC |
| baak43e16 | ACATGTTGTATAGGTCTTCGA<br>ACATGTTGTACAGGTCTTCGA | 21960 | AfaI | GTAC |
| baak40b02 | GCAATTTCAGTGCTAGATTGG<br>GCAATTTCAGAGCTAGATTGG | 21961 | AkAI | AGCT |
| bah62m03 | AGCTTCGCGGAGCTATGACCT<br>AGCTTCGCGGCGCTATGACCT | 21962 | HhaI | GCGC |
| bah56g23 | ACTGTTCCTG_ATGTCGAGAA<br>ACTGTTCCTGGATGTCGAGAA | 21977<br>21978 | MvaI | CCWGG |
| bah56g23 | GAGAAACCTGGCGAAACCGCA<br>GAGAAACCTGACGAAACCGCA | 21979 | MvaI | CCWGG |
| basd22f14 | TTCATTCACAGGCCAGCTTGG<br>TTCATTCACACGCCAGCTTGG | 21980 | HaeIII | GGCC |
| BaAK26G13 | CAAGACCGAACTAATCTTGCT<br>CAAGACCGAATTAATCTTGCT | 21984 | AseI | ATTAAT |
| BaAK44D07 | CCTCCTCTGGGCCGTCGACGT<br>CCTCCTCTGGTCCGTCGACGT | 21985 | HaeII | GGCC |
| bah34b20 | AGATGGTCTCCGATCGGTGGG<br>AGATGGTCTCAGATCGGTGGG | 21987 | DdeI | CTNAG |
| BaAK42B16 | AATGCTTTCGAAATCAGTNNT<br>AATGCTTTGGGAATCAGTTTA | 21992 | TaqI | TCGA |

TABLE 21-4

| Clones | Haruna Nijo H602 | SEQ ID NO: | Restriction enzyme | Recognition sequence |
|---|---|---|---|---|
| BaAK42816 | GGAAATCTCGGTTTTGAATAC<br>GGAAATCTCGATTTTGAATAC | 21993 | TaqI | TCGA |
| baal4d05 | TGCCGGAATCACCAGGTTGGC<br>TGCCGGAATCCCCACCTTCGC | 22022 | HphI | NNNNNNNTCACC |
| basd20103 | AGCGCCAGAGCCCCATCTTGA<br>AGCGCCAGAGGCCCATCTTGA | 22023 | Cfr13I | GGNCC |
| baal31b03 | ACTTTCTAGCGCGTGCTTCTG<br>ACTTTCTAGCCCGTGCTTCTG | 22024 | HhaI | GCGC |
| bags27k21 | TCCTGGCAGCTGTCAACTATG<br>TCCTGGCAGCCGTCAACTATG | 22025 | AluI | AGCT |
| bah55n15 | CAGCAAACTTTAAATGTTTTT<br>CAGCAAACTTCAAATGTTTTT | 22026 | DraI | TTTAAA |
| BaAK20B23 | ATCAATACTCAGAAGGCGTTA<br>ATCAATACTCGGAAGGCGTTA | 22031 | DdeI | CTNAG |
| bags22c18 | ATGACATTTCGAAATTTTGCT<br>ATGACATTTCAAAATTTTGCT | 22036 | BspT104I | TTCGAA |
| bah29d20 | ACCCAAAAGCTCTATCCTACG<br>ACCCAAAAGCCCTATCCTACG | 22040 | AluI | AGCT |
| bah44f20 | CCTACACCCGAGCGTAATGGA<br>CCTACACCCGCGCGTAATGGA | 22041 | BstUI | CGCG |
| BaAL4A11 | GCTGAGGTACACGCGCTGGAG<br>GCTGAGGTACCCGCGCTGGAG | 22049 | KpnI | GGTACC |
| BaGS22I18 | CCAATTTATACTCAGCCATTC<br>CCAATTTATAGTCACCCATTC | 22050 | DdeI | CTNAG |
| BaAK40P18 | CCCTTTGGTCAAGGCTCAGAC<br>CCCTTTGGTCGAGGCTCAGAC | 22065 | TaqI | TCGA |
| BaH27K19 | TCTAAGAAGGGGACTCGTGTC<br>TCTAAGAAGGAGACTCGTGTC | 22070 | BsmAI | NNNNNGAGAC |
| bags15j07 | CATTTTGCCACACATAGTGAG<br>CATTTTGCCAGACATAGTGAG | 22071 | DraIII | CACNNNGTG |
| bah19a07 | GGTCTTGGTCGCGTCGTCGAG<br>GGTCTTGGTCACGTCGTCGAG | 22072 | BstUI | CGCG |
| bah44n05 | AGATGAAGCGCCATCGACATA<br>AGATGAAGCGTCATCGACATA | 22103 | HhaI | GCGC |
| BaGS13H12 | GACAAAGTTAATCAGTAATTG<br>GACAAACTTATTCACTAATTG | 22113 | MseI | TTAA |
| BaAL19B06 | ATATGTTCTCGACAGCCCGCA<br>ATATGTTCTCCACAGCCCGCA | 22114 | TaqI | TCGA |
| BaSD15P23 | GTGTCCCTCCGGTGCCTTCTC<br>GTGTCCCTCCTGTGCCTTCTC | 22115 | BanI | GGYRCC |
| kr27H1216 | CTGCGTCGTCAACTATCTGAA<br>CTGCGTCGTCGACTATCTGAA | 22130 | SaII | GTCGAC |
| BaAK25O11 | GGGCTACTGTCTCTGCATGCT<br>GGGCTACTGTATCTGCATGCT | 22131 | BsmAI | GTCTCN |
| BaH36N15 | CACTTCCGGCGCTGGATTTGC<br>CACTTCCGGCCCTGGATTTGC | 22138 | HaeIII | GGCC |
| BaAK38E05 | CTTGTATGTCGAGCGACAACG<br>CTTGTATGTCAAGCGACAACG | 22144 | TaqI | TCGA |

TABLE 21-5

| Clones | Haruna Nijo H602 | SEQ ID NO: | Restriction enzyme | Recognition sequence |
|---|---|---|---|---|
| bast60C0105 | CAGCCGCCTCATCCAGCGCCC<br>CAGCCGCCTCGTCCAGCGCCC | 22152 | FokI | NNNNNNNNNNNNNCATCC |
| BaAL24O04 | CCTGCAACGCGAAGTTCTGGC<br>CCTGCAACGCAAAGTTCTGGC | 22154 | BstUI | CGCG |
| BaGS31G02 | CCACAGAAGAGAGCTGGTGAT<br>CCACAGAAGACAGCTGGTGAT | 22164 | PvuII | CAGCTG |
| basd18g14 | TGGCATTGGACGTCTCGAACA<br>TGGCATTGGATGTCTCGAACA | 22167 | FokI | GGATGNNNNNNNNN |
| bah11k13 | GGCCATCCTCAAGCTGCTTGC<br>GGCCATCCTCGAGCTGCTTGC | 22178 | XhoI | CTCGAG |
| bags32a01 | GCGCTTTCCCAGATCCCTTAG<br>GCGCTTCCCCGGATCCCTTAG | 22184 | HapII | CCGG |
| bags32a01 | GAGTAACCGCTGCCATTGTTG<br>GAGTAACCGCCGGCATTGTTG | 22185 | HapII | CCGG |
| baal37j12 | CATAGCCTTCCACGCTAGCAT<br>CATAGCCTTCGACGCTAGCAT | 22193 | TaqI | TCGA |
| BaAK40H10 | TATTGAGCATTGAGCCCTCTC<br>TATTGAGCATCGAGCCCTCTC | 22195 | TaqI | TCGA |
| BaAK40H10 | TTAAGAACTTCGAATCATCAC<br>TCAAGAACTTTGAATCATCAC | 22196 | TaqI | TCGA |
| bah56p08 | GCTTATCATCCCGGTCGTATC<br>GCTTATCATCACGGTCGTATC | 22203 | HapII | CCGG |
| bags1i05 | ACAGAGACTACGGCATCACTG<br>ACAGACACTAGGGCATCACTG | 22204 | XspI | CTAG |
| BaH29M21 | CCAGCAGCTCTAGGCTTGCGC<br>CCAGCAGCTCCAGGCTTGCGC | 22205 | MvaI | CCWGG |
| bags21c04 | AGCATGAGCCTGCTTACATCC<br>ACCATGAGCCAGCTTACATCC | 22206 | AluI | AGCT |
| baak32p09 | CGCCTTCTGCAGGGTCTTCGA<br>CGCCTTCTGCGGGGTCTTCGA | 22207 | PstI | CTGCAG |
| BaH22B15 | ACACAAACTCCGGTGAAGCAA<br>ACACAAACTCTGCTCAAGCAA | 22221 | HapII | CCGG |
| BaGS23J01 | TGCCGATGTCGGGGTGCACCT<br>TGCCGATGTCCGGGTGCACCT | 22239 | HapII | CCGG |
| baak46i07 | GCCACCCTCGCGATGATGTCT<br>GCCACCCTCGTGATGATGTCT | 22242 | BstUI | CGCG |
| BaAL6J13 | GATCTCACTGTACCGCGAGCC<br>GATCTCACTGCACCGCGAGCC | 22243 | AfaI | GTAC |
| BaH54J20 | ATTTCAGCCAGGGTCATCATC<br>ATTTCAGCCATGGTCATCATC | 22254 | NcoI | CCATGG |
| BaGS7F20 | AGTCAATCACGATTCAAGGCG<br>ACTCAATCACAATTCAAGGCG | 22255 | HinfI | GANTC |
| bags11p11 | CCTTTGTTTCGACAACATGTC<br>CCTTTGTTTCAACAACATGTC | 22256 | TaqI | TCGA |
| bags11p11 | CTTCTCATCGTGCAGAACAAG<br>CTTCTCATCGAGCAGAACAAG | 22257 | TaqI | TCGA |
| baak26h17 | TTTCCTGGTCCGGATTGGACT<br>TTTCCTGGTCTGGATTGGACT | 22277 | HapII | CCGG |

TABLE 21-6

| Clones | Haruna Nijo H602 | SEQ ID NO: | Restriction enzyme | Recognition sequence |
|---|---|---|---|---|
| BaGS4H02 | CGGCGAGGTACCCTCCTCCAC<br>CGGCGAGGTATCCTCCTCCAC | 22295 | KpnI | GGTACC |
| BaSD14J15 | CAAACATGACTGGTCCTAATG<br>CAAACATGACAGGTCCTAATG | 22302 | Cfr13I | GGNCC |
| BaSD14J15 | GTTGACGGCCTCTCGTGAACA<br>GTTGACGGCCCCTCGTGAACA | 22303 | Cfr13I | GGNCC |
| bags38n21 | AGAGCCCGCTCGAGTTTACAC<br>AGAGCCCGCTTGAGTTTACAC | 22314 | XhoI | CTCGAG |
| BaH49M02 | CAGCACGTTCCAAACAATAGG<br>CAGCACGTTCGAAACAATAGG | 22318 | BspT104I | TTCGAA |
| baak38f04 | CCCCCTCGCCTGCTCTTCTCC<br>CCCCCTCGCCGGCTCTTCTCC | 22319 | HapII | CCGG |
| basd15d20 | TCATGGAGTCGTACCTCATGA<br>TCATGGAGTCATACCTCATGA | 22324 | AfaI | GTAC |
| kr40H1115 | AAGTAAATTAAATTCAGAGTA<br>AAGTAAATTAGATTCAGAGTA | 22329 | HinfI | GANTC |

TABLE 22-1

| Clones | Haruna Nijo H602 | SEQ ID NO: |
|---|---|---|
| bags30b07 | GCAACCACGACGTACATCGTT<br>GCAACCACGAGGTACATCGTT | 17341 |
| BaAK17D13 | AGCTCGCGGCACCGTTCACCT<br>AGCTCGCGGCGCCGTTCACCT | 17343 |
| basd26l20 | CCTCCACGACCGCCCCGGGCT<br>CCTCCACGACGGCCCCGGGCT | 17344 |
| bah61p17 | ATAATGTATCCACATTCTCGC<br>ATAATGTATCGACATTCTCGC | 17345 |
| bah61p17 | TTTTCTGAAACGCAAACAATA<br>TTTTCTGAAATGCAAACAATA | 17346 |
| bah61p17 | CGCTTGCCCACGTGTGCAACA<br>CGCTTGCCCAAGTGTGCAACA | 17347 |
| kr12h0216 | TCCTCGGCGCAACCGCCTACA<br>TCCTCGGCGCGACCGCCTACA | 17348 |
| kr12h0216 | CACTTGTATGTAGTTCACCAA<br>CACTTGTATGCAGTTCACCAA | 17349 |
| kr12h0216 | ACCAGAGCAACTGACTCACTG<br>ACCAGAGCAAATGACTCACTG | 17350 |
| kr12h0216 | ACTTCACCCTTGTCCAGCACA<br>ACTTCACCCTCGTCCAGCACA | 17351 |
| kr12h0216 | GCGGCATCTTCCTATGGTACT<br>GCGGCATCTTTCTATGGTACT | 17352 |
| kr26d0507 | TGCTAACATGTTTGTACGACC<br>TGCTAACATGCTTGTACGACC | 17357 |
| kr26d0507 | TCCACTCCATACTCCAGTGGT<br>TCCACTCCATGCTCCAGTGGT | 17358 |
| baak41n21 | ACCAGACGGGAGACTACGAGG<br>ACCAGACGGGCGACTACGAGG | 17360 |
| kr24b0903 | ACGCGTAAACTCCAAGTGCAT<br>ACGCGTAAACGCCAAGTGCAT | 17362 |
| kr24b0903 | TATTCAAGAACAAACACATG<br>TATTCAAGAAGAAACACATG | 17363 |
| kr24b0903 | AGTGCATTGATAGACTCCCCA<br>AGTGCATTGACAGAGTCCCGA | 17364 |
| kr24b0903 | CTGGAACCTGACTGCTAAAAG<br>CTGGAACCTGGCTGCTAAAAG | 17365 |
| kr24b0903 | TGCTGGAAACGAAAGTGGGGC<br>TGCTGGAAACTAAAGTGGGGC | 17366 |
| baal17o01 | CAAACATTAGCCAGTTACTTC<br>CAAACATTAGTCAGTTACTTC | 17367 |
| baak41a04 | GCTCTCAAGCGTCTGTTCATC<br>GCTCTCAAGCATCTGTTCATC | 17368 |
| baak41a04 | AAATAAACAGGAGGAAAGGA<br>AAATAAACAAGAGGAAAGGA | 17369 |
| baak41a04 | ATATGTCAGACATGCGTGGCA<br>ATATGTCAGAAATGCGTGGCA | 17370 |
| bags16g18 | CTCGCGGACGTACCCACCATT<br>CTCGCGGACGCACCCACCATT | 17371 |
| bags16g18 | CAGGTCTGGGTTTGCCAGGAA<br>CAGGTCTGGGATTGCCAGGAA | 17372 |

TABLE 22-2

| Clones | Haruna Nijo H602 | SEQ ID NO: |
|---|---|---|
| BaSD3C22 | AGCGTCCCTTGCCGGGATGGC<br>AGCGTCCCTTACCGGGATGGC | 17373 |
| BaSD3C22 | TGACGCAGTACCTTGATGCAA<br>TGACGCAGTATCTTGATGCAA | 17374 |
| basd27b10 | GGAGCGACGACCTTGATCTTC<br>GGAGCGACGAACTTGATCTTC | 17376 |

TABLE 22-2-continued

| Clones | Haruna Nijo H602 | SEQ ID NO: |
|---|---|---|
| basd27b10 | GGCGTATCCCAAGAGTACCCA<br>GGCGTATCCCGAGAGTACCCA | 17377 |
| bah47d23 | TGTCACCGGCATCAGCATAGT<br>TGTCACCGGCGTCAGCATAGT | 17378 |
| bah47d23 | GGTTTGGCGCAATGTCACCGG<br>GGTTTGGCGCAATGTCACCGG | 17379 |
| bah47d23 | GGGCCCTGTGCGCTTGGTTTG<br>GGGCCCTGTGTGCTTGGTTTG | 17380 |
| bah47d23 | CTGGTTCTTCGCACCACTGGT<br>CTGGTTCTTCACACCACTGGT | 17381 |
| BaH17D02 | CATGACCACCATCTCGTGCCG<br>CATGACCACCGTCTCGTGCCG | 17383 |
| BaH17D02 | TGCATCATCCCTGACTACTTC<br>TGCATCATCCGTGACTACTTC | 17384 |
| BaAK12I12 | TCCCATCATGGTATGTTCAAC<br>TCCCATCATGTTATGTTCAAC | 17389 |
| BaAK12I12 | GTTCTAAGGCACTTTAATAAT<br>GTTCTAAGGCTCTTTAATAAT | 17390 |
| BaAK12I12 | TGAACCGATTTGATACACTGC<br>TGAACCGATTCGATACACTGC | 17391 |
| baal6n04 | CCGTTGGAACGCACGGGTCT<br>CCGTTGGAACACACGGGTCT | 17392 |
| baal6n04 | CTTTGGAGTAGCCAAGCTCTC<br>CTTTGGAGTATCCAAGCTCTC | 17393 |
| baal6n04 | CCACGGTGGCAAACTTGTCGT<br>CCACGGTGGCGAACTTGTCGT | 17394 |
| baal6n04 | ACCTCCAGACGGCGGTTGTCT<br>ACCTCCAGACAGCGGTTGTCT | 17395 |
| baal6n04 | CCGTGTCCGAAGCTCGCCTCA<br>CCGTGTCCGAGGCTCGCCTCA | 17396 |
| baal6n04 | GGCACCCTGCAACTCATCTGT<br>GGCACCCTGCGACTCATCTGT | 17397 |
| baal16l05 | GAAGGGATTGGAGAGTATGTC<br>GAAGGGATTGCAGAGTATGTC | 17398 |
| baal16l05 | CTATCACTCTTATCAGTGAAG<br>CTATCACTCTGATCAGTGAAG | 17399 |
| BaSD3J13 | AGTGACGCTGCCTTCTGGGCC<br>AGTGACGCTGTCTTCTGGGCC | 17400 |
| BaSD3J13 | CGCCCAGACGAGGGTCCAGCA<br>CGCCCAGACGGGGGTCCAGCA | 17401 |
| BaSD3J13 | CCTTGGCGTCATGGAGCTGCT<br>CCTTGGCGTCGTGGAGCTGCT | 17402 |
| BaAK16M07 | GCTTCGCCCTCGCTGTAGACG<br>GCTTCGCCCTTGCTGTAGACG | 17406 |

TABLE 22-3

| Clones | Haruna Nijo H602 | SEQ ID NO: |
|---|---|---|
| BaAK16M07 | TCATTGCTTCCTGCACACCAT<br>TCATTGCTTCATGCACACCAT | 17407 |

TABLE 22-3-continued

| Clones | Haruna Nijo H602 | SEQ ID NO: |
|---|---|---|
| BaH36M15 | CTGACCATGCAACGAAGAATA<br>CTGACCATGCGACGAAGAATA | 17408 |
| baal39c22 | AGCACACAGCCGAGGCTCGCT<br>AGCACACAGCAGAGGCTCGCT | 17409 |
| kr68b0303 | CCTCGTCCTCCTCGCCGGAGA<br>CCTCGTCCTCGTCGCCGGAGA | 17410 |
| baak24d09 | GGCGAGGTACCGCACGACCTG<br>GGCGAGGTACGGCACGACCTG | 17411 |
| baak24d09 | GCACGACCTGGCTCCTCTTCC<br>GCACGACCTGCCTCCTCTTCC | 17412 |
| baal19i12 | GGCTTACAGTCGACAGTAATC<br>GGCTTACAGTTGACAGTAATC | 17418 |
| baal19i12 | GAATCTGGGTTGGATGATGGC<br>GAATCTGGGTCGGATGATGGC | 17419 |
| baal19i12 | ATGGCACACCTTTGTTCAATG<br>ATGGCACACCCTTGTTCAATG | 17420 |
| baal19i12 | GAAACATCTATTAGGCTTACA<br>GAAACATCTACTAGGCTTACA | 17421 |
| kr18g0814 | GTGAAATTGGCGGGTGGGAT<br>GTGAAATTGGTGGGTGGGGAT | 17425 |
| BaGS8B13 | TGGTGCCAGCACCGTCGACGG<br>TGGTGCCAGCGCCGTCGACGG | 17427 |
| BaGS8B13 | TACCGATCCCAATAAGCGCCT<br>TACCGATCCCGATAAGCGCCT | 17428 |
| BaGS8B13 | AAGCGGACGAGCGCCTCTTCA<br>AAGCGGACGAACGCCTCTTCA | 17429 |
| BaGS8B13 | TTGGTGAGCAGATTCTTACCG<br>TTGGTGAGCACATTCTTACCG | 17430 |
| BaGS8B13 | GGTTGGTTTGGCGCAGCTTGC<br>GGTTGGTTTGACGCAGCTTGC | 17431 |
| BaH25J08 | AAGATGCACAGGAACATATTT<br>AAGATGCACAAGAACATATTT | 17432 |
| BaH25J08 | TGTAAGTAAAGAGATCGATAG<br>TGTAAGTAAACAGATCGATAG | 17433 |
| baak3d11 | ACATGCGAAACCACAAGAGAT<br>ACATGCGAAATCACAAGAGAT | 17434 |
| baak3d11 | ATACTATTAGAGTCTTCGGTA<br>ATACTATTAGGGTCTTCGGTA | 17435 |
| baak3d11 | CTTTGTAGCATTGCTGCCTAA<br>CTTTGTAGCAATGCTGCCTAA | 17436 |
| baak3d11 | ATGCAGATGAACAATTATAGT<br>ATGCAGATGAGCAATTATAGT | 17437 |
| baak3d11 | CTGCCTAACACATTAAAATTT<br>CTGCCTAACAAATTAAAATTT | 17438 |
| baal12p08 | AGTCTCAGAANGATGGGATGA<br>AGTCTCAGAAGGATGGGATGA | 17439 |
| baal12p08 | AGTGAGCTTTCATGTATCAGG<br>AGTGAGCTTTNATGTATCAGG | 17440 |

TABLE 22-4

| Clones | Haruna Nijo / H602 | SEQ ID NO: |
|---|---|---|
| bags39i20 | GGTTGTCAGACTCGTGCACCT<br>GGTTGTCAGATTCGTGCACCT | 17441 |
| bags39i20 | TCTGGCACGGCCAAGGGGAAC<br>TCTGGCACGGTCAAGGGGAAC | 17442 |
| bags39i20 | AGGGGAACTCGAACTCTTGAT<br>AGGGGAACTCTAACTCTTGAT | 17443 |
| kr15a0402 | ATAGTAGAAATGCATGGTCAC<br>ATAGTAGAAACGCATGGTCAC | 17444 |
| baal3c01 | CATCAACACATTTCAGCAAGA<br>CATCAACACAGTTCAGCAAGA | 17445 |
| baal3c01 | CCACGGTGGGGACGCCGGGT<br>CCACGGTGGGAACGCCGGGT | 17446 |
| baal3c01 | CGTTGTTGTACGTGAACGCAC<br>CGTTGTTGTAGGTGAACGCAC | 17447 |
| baak41i03 | TCTCGGCACTTTTATGAGTTG<br>TCTCGGCACTCTTATGAGTTG | 17448 |
| BaGS29M13 | AGGAAGAAAAGGTAGAGATCT<br>AGGAAGAAAAGTAGAGATCT | 17449 |
| BaH24I06 | TCATACTAATGCCCCACACGA<br>TCATACTAATACCCCACACGA | 17452 |
| basd25c22 | AGACTGCTTATTCATGCATTG<br>AGACTGCTTACTCATGCATTG | 17454 |
| basd25c22 | AATTCCGAACAGAGGGAGTAT<br>AATTCCGAACGGAGGGAGTAT | 17455 |
| basd25c22 | GGGTGGCTGCGTGTGACAACA<br>GGGTGGCTGCATGTGACAACA | 17456 |
| basd25c22 | AATGCCTCGAATTAGTTATGA<br>AATGCCTCGACTTAGTTATGA | 17457 |
| basd25c22 | TTTTTCCTTAACTATTATATC<br>TTTTTCCTTATCTATTATATC | 17458 |
| basd25c22 | TAACTATCTCCTCATCTGGGT<br>TAACTATCTCATCATCTGGGT | 17459 |
| basd25c22 | ATGACAGATGCAACCAAGCAT<br>ATGACAGATGGAACCAAGCAT | 17460 |
| bah46p14 | TATTCCAGGTAAAGCTACCCC<br>TATTCCAGGTGAAGCTACCCC | 17463 |
| bags18d19 | ATGGAACAGCACTGAGCATTT<br>ATGGAACAGCGCTGAGCATTT | 17464 |
| bags18d19 | ACAGAACTTTCTGCACAACAG<br>ACAGAACTTTTTGCACAACAG | 17465 |
| bags18d19 | GCAAAGAGATCAAATACAATA<br>GCAAAGAGATAAAATACAATA | 17466 |
| bags18d19 | TTACTTACAGCTCTCTTTCCA<br>TTACTTACAGGTCTCTTTCCA | 17467 |
| bags18d19 | GGACTTTATCGTTAACCGGGC<br>GGACTTTATCATTAACCGGGC | 17468 |
| bags18d19 | GATCTGAATATTAGCATACTC<br>GATCTGAATACTAGCATACTC | 17469 |
| baak34j19 | TTTTCTTCTTGTAGTGTGTTT<br>TTTTCTTCTTTTAGTGTGTTT | 17470 |

TABLE 22-5

| Clones | Haruna Nijo / H602 | SEQ ID NO: |
|---|---|---|
| baak34j19 | TGAAGAAACATGAACAATATA<br>TGAAGAAACAGGAACAATATA | 17471 |
| baak2m05 | ACCTTTTTAATGAAGCATAC<br>ACCTTTTTATTGAAGCATAC | 17475 |
| baak2m05 | AGACACATAAAATGACGAGCT<br>AGACACATAAGATGACGAGCT | 17476 |
| baak2m05 | GAGTACATCGTAATAGACATA<br>GAGTACATCGCAATAGACATA | 17477 |
| BaGS31B11 | GCAAGGAATTGGAAACAGAAG<br>GCAAGGAATTAGAAACAGAAG | 17479 |
| BaAL35M08 | CAAGCCGCGCGCGAGCTAGCT<br>CAAGCCGCGCACGAGCTAGCT | 17480 |
| BaAL35M08 | CTGTATATGTCCGACCTGCAA<br>CTGTATATGTGCGACCTGCAA | 17481 |
| BaH58J20 | TGCCATGGTGTCTGAAATTCT<br>TGCCATGGTGCCTGAAATTCT | 17483 |
| BaGS22B13 | GTTCCTGCTTCTGACGAAGAG<br>GTTCCTGCTTTTGACGAAGAG | 17484 |
| BaGS22B13 | AACCCATATCCCACACACACC<br>AACCCATATCTCACACACACC | 17485 |
| BaGS22B13 | TAGGAGTAATTCACAACCCAT<br>TAGGAGTAATCCACAACCCAT | 17486 |
| BaAK43M01 | ATACACACTGAAAACCAGCGA<br>GAACACACTGGAAACCAGCGA | 17487 |
| bah14i07 | AGCCGGAAGATAATAACATGA<br>AGCCGGAAGAAAATAACATGA | 17488 |
| bah14i07 | TCAAGAATCGCCTTTGGGGT<br>TCAAGAATCGTCTTTGGGGT | 17489 |
| bah14i07 | GGTGTTTGGACCCAATACCAN<br>GGTGTTTGGAACCAATACCAN | 17490 |
| baal9j16 | CTGGCCAAAGAGTCTCCTCGG<br>CTGGCCAAAGTGTCTCCTCGG | 17492 |
| baal9j16 | CGGCGCGAAGGGATCGCGCTC<br>CGGCGCGAAGCGATCGCGCTC | 17493 |
| baal9j16 | TTGAACTATGCCCGGATGAGC<br>TTGAACTATGACCGGATGAGC | 17494 |
| BaAK2O24 | CCTTCCACTGCGAAGAAGTCA<br>CCTTCCACTGTGAAGAAGTCA | 17495 |
| bags22j15 | ATTGGCTTGCAGAATTCTCTC<br>ATTGGCTTGCGGAATTCTCTC | 17498 |
| baak44a23 | AAAATTCTATATTATGCTAGG<br>AAAATTCTATGTTATGCTAGG | 17499 |
| baak32n04 | GTGAAAAGTGACCGCTTCTC<br>GTGAAAAGTCACCGCTTCTC | 17500 |
| basd21e22 | CTCGTGTTTTTGCACTGCTCT<br>CTCGTGTTTTGGCACTGCTCT | 17501 |
| basd21e22 | CATGTACAACAAGAACGCGAC<br>CATGTACAACGAGAACGCGAC | 17502 |
| baak42e22 | GAAAATCGCGGGCGTTCATC<br>GAAAATCGCAGGCGTTCATC | 17503 |

TABLE 22-6

| Clones | Haruna Nijo / H602 | SEQ ID NO: |
|---|---|---|
| baake42e22 | ACACCCACGTTTGAAAATCTG<br>ACACCCACGTCTGAAAATCTG | 17504 |
| bast75e0610 | TCGGAGAAGAGACGGAGGGCG<br>TCGGAGAAGAAACGGAGGGCG | 17505 |
| baet16a1002 | TCCGCTGAGCCGCGCTTCTAG<br>TCCGCTGAGCGGCGCTTCTAG | 17506 |
| baak21i01 | GGCCCTCCTCTGCCCTAGCCG<br>GGCCCTCCTCCGCCCTAGCCG | 17508 |
| baak22o23 | GAAAAGAGTCTGCACCTTATC<br>GAAAAGAGTCCGCACCTTATC | 17510 |
| bah52h18 | ATATATACGAACTCATGTAGC<br>ATATATACGACCTCATGTAGC | 17512 |
| bah52h18 | AGGCTTCTGCACCCCTTGCTG<br>AGGCTTCTGCGCCCCTTGCTG | 17513 |
| bah52h18 | CGTACAGAGAAGAAACAGACA<br>CGTACAGAGAGGAAACAGACA | 17514 |
| baak33k20 | ATTTTGACTACGGTAGCTTGG<br>ATTTTGACTATGGTAGCTTGG | 17515 |
| baak33k20 | TTTGAACTATCTGGGACTGGG<br>TTTGAACTATGTGGGACTGGG | 17516 |
| baak33k20 | AAAGCTTAGATAATAACTGGT<br>AAAGCTTAGAGAATAACTGGT | 17517 |
| bags21f16 | ATAGATGCTTCACCAGTGCAC<br>ATAGATGCTTTACCAGTGCAC | 17518 |
| bags21f16 | GTAGAACCTCATGAACATTTC<br>GTAGAACCTCGTGAACATTTC | 17519 |
| bags34e05 | CCGCGTCCACAGCGAAGTCCA<br>CCGCGTCCACGGCGAAGTCCA | 17520 |
| bags34e05 | GTCAACGCAGCTCTGGGCATC<br>GTCAACGCAGTTCTGGGCATC | 17521 |
| bags19a02 | GGCTTTTGCCACTATCAACTG<br>GGCTTTTGCCGCTATCAACTG | 17523 |
| bags19a02 | TCGGGTAGACGAAAAAACCCG<br>TCGGGTAGACCAAAAAACCCG | 17524 |
| bags35k02 | CCAACGGCACAATCATCCCTC<br>CCAACGGCACGATCATCCCTC | 17525 |
| bah35a22 | CTCTCCCTGCTGAAATGCCAT<br>CTCTCCCTGCGGAAATGCCAT | 17526 |
| bah35a22 | CAGCAACAGCTATAAAACAAT<br>CAGCAACAGCCATAAAACAAT | 17527 |
| bags17h13 | ACACTTGACCTTGGCTGCTGC<br>ACACTTGACCGTGGCTGCTGC | 17528 |
| bah47n12 | CGATGGGTACCGCAGCTTGAA<br>CGATGGGTACGGCAGCTTGAA | 17529 |
| bah47n12 | CTGCTTCTTCCGCTGGGGGCC<br>CTGCTTCTTCTGCTGGGGGCC | 17530 |
| bah47n12 | CTACACGTACACAAGCTGCAG<br>CTACACGTACGCAAGCTGCAG | 17531 |
| baak12p11 | AGAAGTAGTGAGTATGATTGT<br>AGAAGTAGTGGGTATGATTGT | 17532 |

TABLE 22-7

| Clones | Haruna Nijo / H602 | SEQ ID NO: |
|---|---|---|
| baet38B1004 | ACCGAGACCCGACTCCACGGA<br>ACCGAGACCCAACTCCACGGA | 17533 |
| baet38B1004 | ATTTTCCCACACAGCCCTTTT<br>ATTTTCCCACGCAGCCCTTTT | 17534 |
| BaGS13K12 | TCGAGACGGCAGTCCACCAGC<br>TCGAGACGGCGGTCCACCAGC | 17535 |
| baal25a05 | GGTAGTTTATATGTGCAGCAT<br>GGTAGTTTATGTGTGCAGCAT | 17536 |
| baal25a05 | AGTGAACCAAATATCATAAAT<br>AGTGAACCAAGTATCATAAAT | 17537 |
| baal25a05 | TCATAAATGAGATGGTTTACG<br>TCATAAATGAAATGGTTTACG | 17538 |
| baal25a05 | TCGCCTTCTCAGTGTCCTTGT<br>TCGCCTTCTCGGTGTCCTTGT | 17539 |
| BaAK24J12 | TTCAGAGAATGAATGGATTAA<br>TTCAGAGAATAAATGGATTAA | 17540 |
| BaAK24J12 | CACCCACCTTTTTATTTATTGT<br>CACCCACCTTCTATTTATTGT | 17541 |
| basd1 4m22 | GCAGTTATAAATTGCTACTGT<br>GCAGTTATAATTTGCTACTGT | 17542 |
| basd1 4m22 | AGCACTTCATAAGTGCTTCCA<br>AGCACTTCATCAGTGCTTCCA | 17543 |
| bah17l24 | TCCCCCACAGTCGTGTTTCTC<br>TCCCCCACAGGCGTGTTTCTC | 17544 |
| bah17l24 | AAAGGTAAGTAAACATAAACT<br>AAAGGTAAGTGAACATAAACT | 17545 |
| baal29j09 | AGCCCTATGTAAAAACATTTC<br>AGCCCTATGTGAAAACATTTC | 17546 |
| baal29j09 | TAGGGCACCAAACAAACTAGA<br>TAGGGCACCAGACAAACTAGA | 17547 |
| baal29j09 | TATGTACACATTTTGCACAG<br>TATGTACACAATTTTGCACAG | 17548 |
| baal29j09 | TCATTCAGAGTCGTATATGTA<br>TCATTCAGAGCCGTATATGTA | 17549 |
| baal29j09 | AATGGTAATTACTCCAGAAGA<br>AATGGTAATTGCTCCAGAAGA | 17550 |
| bah16d09 | CATGTTGGATAGCTGCAACAC<br>CATGTTGGATTGCTGCAACAC | 17551 |
| bah16d09 | TTGCGCTCTCGGCAAGGCATA<br>TTGCGCTCTCTGCAAGGCATA | 17552 |
| bah60d03 | GGGCAACAAGATCGCCTGCAT<br>GGGCAACAAGGTCGCCTGCAT | 17553 |
| bah60d03 | ACAAATAATTTTGACAGTTCA<br>ACAAATAATTCTGACAGTTCA | 17554 |
| bah60d03 | TTATGGGCTCCGCGGCTTCTG<br>TTATGGGCTCTGCGGCTTCTG | 17555 |
| bah45i13 | GCAAAAGCAGCTTGAAGTATA<br>GCAAAAGCAGTTTGAAGTATA | 17556 |
| bah11h03 | GCGCCAAGATCAGGCGGCTGA<br>GCGCCAAGATAAGGCGGCTGA | 17557 |

TABLE 22-8

| Clones | Haruna Nijo H602 | SEQ ID NO: |
|---|---|---|
| bah47h17 | CATCCACCATTACAAGACAAG<br>CATCCACCATAACAAGACAAG | 17558 |
| bah47h17 | CACTCCCTCAGGAACTCAACA<br>CACTCCCTCAAGAACTCAACA | 17559 |
| bags35d02 | ATCAGTTTATATGCCTCGTGT<br>ATCAGTTTATTTGCCTCGTGT | 17560 |
| bags35d02 | AATAAAATTGCCTTATTTTTG<br>AATAAAATTGTCTTATTTTTG | 17561 |
| bags35d02 | GATGTAGAAGTTGGAGAGCAT<br>GATGTAGAAGCTGGAGAGCAT | 17562 |
| baak14c12 | TCAAGTTCTCGGTGTCGTAGA<br>TCAAGTTCTCAGTGTCGTAGA | 17564 |
| baak34c01 | GCATGTCGTCATTGTCCCCAT<br>GCATGTCGTCGTTGTCCCCAT | 17565 |
| bah35a11 | AGTTATATTAAGGTTGAGACA<br>AGTTATATTATGGTTGAGACA | 17566 |
| bah35a11 | ACCACACAAGGCTCAGATCTT<br>ACCACACAAGCCTCAGATCTT | 17567 |
| BaAK30M16 | GTTTACTGCCGAAATTAGCAG<br>GTTTACTGCCAAAATTAGCAG | 17568 |
| BaAL2G20 | GTAAATATGCAATAATGCTGT<br>GTAAATATGCTATAATGCTGT | 17571 |
| BaAL2G20 | GCTAATTCAGGTTCACTGTAG<br>GCTAATTCAGATTCACTGTAG | 17572 |
| bah37f01 | AAGCTGGCGCCTGTACTATGT<br>AAGCTGGCGCATGTACTATGT | 17576 |
| bah37f01 | GACGTGGCCGTATATTCTTCT<br>GACGTGGCCGCATATTCTTCT | 17577 |
| bags29m05 | CAAACGTCACACCCTTCTTGT<br>CAAACGTCACGCCCTTCTTGT | 17578 |
| baet34A0501 | TGGTAGATGCTCGCGAATCCT<br>TGGTAGATGCCCGCGAATCCT | 17580 |
| BaH30E13 | GCTGGCCTGGCCGTTTTGTCG<br>GCTGGCCTGGTCGTTTTGTCG | 17584 |
| BaH30E13 | CGAGCATATGTTTGATTTTTG<br>CGAGCATATGGTTGATTTTTG | 17585 |
| bags4e23 | GTCCAGTTTGTTGGGGGGAGA<br>GTCCAGTTTGCTGGGGGGAGA | 17586 |
| baak45b03 | TGGCCGTGTAGAAGGCGTCCA<br>TGGCCGTGTACAAGGCGTCCA | 17587 |
| baak45b03 | TATACGCGCGTGCGTACGTAC<br>TATACGCGCGCGCGTACGTAC | 17588 |
| baak45b03 | AGGCGTCCACGGTGGTGTCGA<br>AGGCGTCCACTGTGGTGTCGA | 17589 |
| bah12o12 | GATCATCAGTTGGTCTAACAC<br>GATCATCAGTCGGTCTAACAC | 17590 |
| bah12o12 | TAGAAATGAAGTCAAGTGCTC<br>TAGAAATGAAATCAAGTGCTC | 17591 |
| bah12o12 | GAATCGGAACCGTTATAATCA<br>GAATCGGAACTGTTATAATCA | 17592 |

TABLE 22-9

| Clones | Haruna Nijo H602 | SEQ ID NO: |
|---|---|---|
| baal3e14 | GTCGGAGCATTGCTCACATAT<br>GTCGGAGCATCGCTCACATAT | 17594 |
| basd1 j14 | CAGAATAAAACGGAGGAACAT<br>CAGAATAAAATGGAGGAACAT | 17598 |
| basd1 j14 | TTTGGCCATAAAGCATGGCAC<br>TTTGGCCATAGAGCATGGCAC | 17599 |
| bags35b18 | GAGGAGGTGCTGGCTTTCTTA<br>GAGGAGGTGCCGGCTTTCTTA | 17600 |
| baal41i11 | AACCAAATCAAATCGGTTACA<br>AACCAAATCAGATCGGTTACA | 17601 |
| baal41i11 | CATCTCTTGTGTACGTACCAT<br>CATCTCTTGTTTACGTACCAT | 17602 |
| baal41i11 | GCCAGGCTTACATATTTTGGA<br>GCCAGGCTTAGATATTTTGGA | 17603 |
| baal41i11 | ATGTGATTGGGGCTCAACTGA<br>ATGTGATTGGTGCTCAACTGA | 17604 |
| bags13e23 | AACATAATTTTCAATCTGTTA<br>AACATAATTTCCAATCTGTTA | 17605 |
| bags13e23 | GGCCTGCACATTGGGGAAAAT<br>GGCCTGCACAGTGGGGAAAAT | 17606 |
| bah20d03 | TCGCCCTTGGGGGAGACAGCG<br>TCGCCCTTGGAGGAGACAGCG | 17607 |
| baet19f0212 | AGCAGAAAGGAGCAGCTCAAC<br>AGCAGAAAGGGGCAGCTCAAC | 17608 |
| basd12j05 | AAGAAGAACAACACAGAAGTT<br>AAGAAGAACAGCACAGAAGTT | 17609 |
| basd24d17 | CCTAAGCAGTAGGTGCATTCT<br>CCTAAGCAGTCGGTGCATTCT | 17610 |
| basd24d17 | GACACAACAGAGGGCTCCTGG<br>GACACAACAGGGGGCTCCTGG | 17611 |
| basd24d17 | AGGCGTTGAGGACGGCTGATA<br>AGGCGTTGAGAACGGCTGATA | 17612 |
| bags24k10 | AAAAAAACACATGTACCTTAT<br>AAAAAAACACGTGTACCTTAT | 17613 |
| baal9e05 | GTAAAATGCCAGCGCGTCTAC<br>GTAAAATGCCGGCGCGTCTAC | 17614 |
| baal9e05 | TGCCCCACCACTTGCGCTTGG<br>TGCCCCACCATTTGCGCTTGG | 17615 |
| baal9e05 | TGCCACCGGCACTGCCGCCGC<br>TGCCACCGGCCCTGCCGCCGC | 17616 |
| bags33m23 | AATACAAGTAGGATCATCCTA<br>AATACAAGTACGATCATCCTA | 17617 |
| bags33m23 | TGTCCTCTCTCCTGACAAAAC<br>TGTCCTCTCTTCTGACAAAAC | 17618 |
| bags33m23 | AATAAATGAATGAAGACAACA<br>AATAAATGAACGAAGACAACA | 17619 |
| bah46g14 | AAATCAATGAGCAGGTAGAAT<br>AAATCAATGAACAGGTAGAAT | 17620 |
| bah46g14 | AGCTCAGATCGAAACCGGCTT<br>AGCTCAGATCAAAACCGGCTT | 17621 |

TABLE 22-10

| Clones | Haruna Nijo / H602 | SEQ ID NO: |
|---|---|---|
| bags33h05 | GCTGGAAATTTTTCCACGGGG<br>GCTGGAAATTGTTCCACGGGG | 17622 |
| bags33h05 | TGGCAATGCTATGCCGGCTCA<br>TGGCAATGCTTTGCCGGCTCA | 17623 |
| baak24h12 | ATATGCTACCACTAAGCTGCA<br>ATATGCTACCCCTAAGCTGCA | 17624 |
| baak24h12 | CACACTAGATGAGATGGAGGG<br>CACACTAGATAAGATGGAGGG | 17625 |
| bah50n19 | ACGGCGCCGATAGGGCGGAGA<br>ACGGCGCCGAGAGGGCGGAGA | 17626 |
| baak31o05 | GATCGAGGTAGCCGACGGAAT<br>GATCGAGGTATCCGACGGAAT | 17627 |
| baak31o05 | ACGCTGTAAATTGGCTACCGG<br>ACGCTGTAAACTGGCTACCGG | 17628 |
| bags39l14 | CCCCTGCGTGATCACCGTGTC<br>CCCCTGCGTGGTCACCGTGTC | 17629 |
| bags39l14 | TCAATATTTGAAGGTGCTTGA<br>TCAATATTTGCAGGTGCTTGA | 17630 |
| bags39l14 | TGGATCTACCATCAATATTTG<br>TGGATCTACCTTCAATATTTG | 17631 |
| bags39l14 | AATAAGTTGAGAGACTGGATC<br>AATAAGTTGAAAGACTGGATC | 17632 |
| bags39l14 | CGTGCATGTTCGCCTGCACAG<br>CGTGCATGTTTGCCTGCACAG | 17633 |
| bags39l14 | GTTTGCAAACAAAAGAAGCT<br>GTTTGCAAACGAAAAGAAGCT | 17634 |
| BaGS27C22 | GTTACAACTCGGTTCAATTCC<br>GTTACAACTCAGTTCAATTCC | 17635 |
| bags20o24 | TGTCAACTCATCTTAGTGTCG<br>TGTCAACTCAACTTAGTGTCG | 17636 |
| bags20o24 | TCTACATAGAATGTACTAGCT<br>TCTACATAGACTGTACTAGCT | 17637 |
| bags20o24 | CAATCGACAGTGGCTCCAGGG<br>CAATCGACAGCGGCTCCAGGG | 17638 |
| bast42c0806 | CCATATAAAAGGGTTCAGCTA<br>CCATATAAAAGGTTCAGCTA | 17651 |
| baak26c05 | CAGTTCGATGCCGATTGCAAA<br>CAGTTCGATGTCGATTGCAAA | 17652 |
| baak26c05 | ATGCGTTCAACATTTAGCCTG<br>ATGCGTTCAAAATTTAGCCTG | 17653 |
| bags19a16 | GGTGTTGACATTACAACAAAG<br>GGTGTTGACACTACAACAAAG | 17654 |
| bags19a16 | TCAAAGCTACGCACGACTGCG<br>TCAAAGCTACCCACGACTGCG | 17655 |
| bags19a16 | GAGTGATTCACATGTGATTGC<br>GAGTGATTCAGATGTGATTGC | 17656 |
| kr11f1212 | CACACTCGTTCACACACGACA<br>CACACTCGTTAACACACGACA | 17657 |
| baak35l20 | GGATGCAGTCAGCGAACTTGC<br>GGATGCAGTCGGCGAACTTGC | 17660 |

TABLE 22-11

| Clones | Haruna Nijo / H602 | SEQ ID NO: |
|---|---|---|
| bah57m07 | CTCGTGAAGAATGACACAGGC<br>CTCGTGAAGAGTGACACAGGC | 17661 |
| bah60k11 | TCCATGAGGCCGAACCTAACT<br>TCCATGAGGCTGAACCTAACT | 17662 |
| bah60k11 | ATAAGAAATCGTCAGAAACAG<br>ATAAGAAATCATCAGAAACAG | 17663 |
| bah60k11 | AGAAACAGTGAGAAAACCTAG<br>AGAAACAGTGGGAAAACCTAG | 17664 |
| basd20o09 | ATATAAGTTCACTAATTTTGC<br>ATATAAGTTCTCTAATTTTGC | 17665 |
| basd20o09 | TCTAAACGATTATTACCACCA<br>TCTAAACGATCATTACCACCA | 17666 |
| basd24i22 | GCCTACACTTCACTGATGATT<br>GCCTACACTTTACTGATGATT | 17667 |
| basd24i22 | ATGACTCACAATGTGACAGCA<br>ATGACTCACATTGTGACAGCA | 17668 |
| bags30g20 | CGGACTGAAACGAGTGAACAA<br>CGGACTGAAATGAGTGAACAA | 17669 |
| bags30g20 | TAAGAAAGATGACATGAAAAT<br>TAAGAAAGATCACATGAAAAT | 17670 |
| bags1 m11 | GTTCATTCTCGGCCAAGGTCA<br>GTTCATTCTCAGCCAAGGTCA | 17671 |
| bags23g20 | GACAGACGCCGATGGACATGC<br>GACAGACGCCAATGGACATGC | 17672 |
| bags23g20 | GTATTTCCGGGAATTCTGCAG<br>GTATTTCCGGAAATTCTGCAG | 17673 |
| bags15b05 | GCACGCATGTGTCCTTGAATT<br>GCACGCATGTATCCTTGAATT | 17674 |
| bags15b05 | CCTCCGACTAGTCGATCTTAT<br>CCTCCGACTACTCGATCTTAT | 17675 |
| bags15b05 | GCTGGCGGCGGCGCCGTTGCC<br>GCTGGCGGCGCCGCCGTTGCC | 17676 |
| BaGS24P05 | TCACTCGTAATGACATGATCA<br>TCACTCGTAACGACATGATCA | 17677 |
| bags10g06 | ACGTCCTGTGATTTGCGTGCC<br>ACGTCCTGTGCTTTGCGTGCC | 17678 |
| bah32o04 | GCGACCGCCATCTCAGGCTCG<br>GCGACCGCCACCTCAGGCTCG | 17679 |
| bah32o04 | CGACGGGAGAGTGGCCAGCCA<br>CGACGGGAGACTGGCCAGCCA | 17680 |
| bags32p08 | CACCACTGCTCGATTGTTCAT<br>CACCACTGCTTGATTGTTCAT | 17681 |
| BaGS37L06 | TCTCGGCCTCGGTGAACTCCA<br>TCTCGGCCTCAGTGAACTCCA | 17685 |
| BaGS37L06 | AAAGCACAATGCCACATAAAT<br>AAAGCACAATACCACATAAAT | 17686 |
| BaGS37L06 | CATTCATGTTGCTCTCGGCCT<br>CATTCATGTTACTCTCGGCCT | 17687 |
| bags3h12 | AAGAAAAATGTGAGGAGAGAA<br>AAGAAAAATGAGAGGAGAGAA | 17689 |

TABLE 22-12

| Clones | Haruna Nijo / H602 | SEQ ID NO: |
|---|---|---|
| bags3h12 | ACAAGTCAAGCAAGCCGTACG<br>ACAAGTCAAGTAAGCCGTACG | 17690 |
| bags1e21 | CACCATTGTTTGGCAATTTAC<br>CACCATTGTTGGGCCATTTAC | 17691 |
| bags1e21 | ATTGTTTGGCAATTTACAGCA<br>ATTGTTGGGCCATTTACAGCA | 17692 |
| baak27m21 | CCAACCAGCAGAAAACAGTTT<br>CCAACCAGCACAAAACAGTTT | 17693 |
| bah35b05 | GCACGGACCAACATCAAAGGT<br>GCACGGACCAGCATCAAAGGT | 17694 |
| basd21h11 | ATCATAAGAACGATTTGGAGA<br>ATCATAAGAATGATTTGGAGA | 17695 |
| BaH32E20 | TCGTGCCCCATCTCCCTCGTT<br>TCGTGCCCCACCTCCCTCGTT | 17696 |
| BaH32E20 | TGTCTGGGCAGGTGTGGAGCG<br>TGTCTGGGCAAGTGTGGAGCG | 17697 |
| bags22a20 | GAAGCTACTCGTCAGTTAGGA<br>GAAGCTACTCATCAGTTAGGA | 17698 |
| bags22a20 | AATCCGCATGATGCAGCGATG<br>AATCCGCATGGTGCAGCGATG | 17699 |
| bags29l04 | CACCTGATACAATGAAGATGT<br>CACCTGATACGATGAAGATGT | 17701 |
| bags22g16 | AAAACTCGTCGGCGCTGCTGT<br>AAAACTCGTCAGCGCTGCTGT | 17702 |
| bags22g16 | CCACACTTGTAATTAGCAACC<br>CCACACTTGTGATTAGCAACC | 17703 |
| bah61h20 | CGTTCATAACACATCACCATT<br>CGTTCATAACGCATCACCATT | 17704 |
| bah61h20 | CGTGCCTAACGACCTGAAACG<br>CGTGCCTAACAACCTGAAACG | 17705 |
| bah61h20 | TCTGAATGATGGTGTGAAAGA<br>TCTGAATGATAGTGTGAAAGA | 17706 |
| bah15p01 | CTGCATTTGGGTTGGITCCAG<br>CTGCATTTGGATTGGTTCCAG | 17707 |
| baak41p03 | TCTGGACTTGTGACGCCACGA<br>TCTGGACTTGCGACGCCACGA | 17708 |
| BaSD12L06 | ACACAGTTTAGTAATACTGTA<br>ACACAGTTTAATAATACTGTA | 17709 |
| BaSD12L06 | TTCTGTACTACAAGAGATGAC<br>TTCTGTACTAAAAGAGATGAC | 17710 |
| BaSD23P07 | CCCTGAAGTCACTGCCCTTGA<br>CCCTGAAGTCGCTGCCCTTGA | 17711 |
| BaGS7J05 | GGGATGAGTCCAGCGACTCGA<br>GGGATGAGTCGAGCGACTCGA | 17712 |
| BaGS7J05 | AGTCACACTTTCAGGGTCGAC<br>AGTCACACTTCCAGGGTCGAC | 17713 |
| BaGS7J05 | TTTGAGACGCTCGACTAGTCG<br>TTTGAGACGCCCGACTAGTCG | 17714 |
| BaGS7J05 | TGAAATTATCGTGAAACGGAA<br>TGAAATTATCATGAAACGGAA | 17715 |

TABLE 22-13

| Clones | Haruna Nijo / H602 | SEQ ID NO: |
|---|---|---|
| bah29b06 | AGAGGAAGCCGTCCCTGCGAT<br>AGAGGAAGCCATCCCTGCGAT | 17716 |
| bags31n17 | TAAACACAGACGCAGCTTAGC<br>TAAACACAGATGCAGCTTAGC | 17717 |
| bags31n17 | CATGCTGATCCATACTGCTCT<br>CATGCTGATCAATACTGCTCT | 17718 |
| bags31n17 | TTGCCAGTAACTACAGCAGTT<br>TTGCCAGTAATTACAGCAGTT | 17719 |
| bags31n17 | TACTTTGAGATGCAGAAAGCA<br>TACTTTGAGACGCAGAAAGCA | 17720 |
| bags31n17 | ATGAACATACGAAAATCTAAC<br>ATGAACATACTAAAATCTAAC | 17721 |
| bags31n17 | ACAAGTAGAGCCAAAAGGTGA<br>ACAAGTAGAGACAAAAGGTGA | 17722 |
| BaGS13F08 | CAAAACAATTTAGCCACAAAA<br>CAAAACAATTCAGCCACAAAA | 17723 |
| bags39d12 | ATGTCCAAAAAGAAAGTCAGC<br>ATGTCCAAAAGGAAAGTCAGC | 17727 |
| bags39d12 | TCATGGTACAGAAATCTTACA<br>TCATCGTACATAAATCTTACA | 17728 |
| bags39d12 | TTACTTGTTTTGTTGATAGAC<br>TTACTTGTTTCGTTGATAGAC | 17729 |
| BaAK20B19 | ACATCTTGCCATCGAACTTGT<br>ACATCTTGCCGTCGAACTTGT | 17731 |
| BaAK20B19 | TCCGCACGGCGACCGCCCTGC<br>TCCGCACGGCCACCGCCCTGC | 17732 |
| bags15j15 | TCTTCCTCGTCGTCGTCGAGA<br>TCTTCCTCGTTGTCGTCGAGA | 17733 |
| bags15j15 | GAAGTACTTGTTCCTCTCGGC<br>GAAGTACTTGCTCCTCTCGGC | 17734 |
| BaGS22A21 | ACATATCGCACATATCTGAGC<br>ACATATCGCATATATCTGAGC | 17736 |
| BaGS22A21 | GGCAACCATCATTAGGCACAA<br>GGCAACCATCGTTAGGCACAA | 17737 |
| BaGS22A21 | CAAAGGCAGCGATCTTCTTCC<br>CAAAGGCAGCAATCTTCTTCC | 17738 |
| BaGS22A21 | TCTTCTTCCCATTCTTCACCA<br>TCTTCTTCCCGTTCTTCACCA | 17739 |
| BaGS22A21 | ACTTCAGGTTGTATAGGACAT<br>ACTTCAGGTTATATAGGACAT | 17740 |
| BaGS22A21 | CCTTAACAGTCCATTCCATCC<br>CCTTAACAGTGCATTCCATCC | 17741 |
| baet45e0410 | CAAGCGGTAAGCATAACTACA<br>CAAGCGGTAATCATAACTACA | 17742 |
| bags22c14 | AGGTTCATCAGTTCCCTTTCC<br>AGGTTCATCAATTCCCTTTCC | 17743 |
| bags22c14 | TAATCCACCGCCCCTCAATCT<br>TAATCCACCGACCCTCAATCT | 17744 |
| bah23k12 | GCTAGGACTGTAAAATAAACG<br>GCTAGGACTGCAAAATAAACG | 17745 |

TABLE 22-14

| Clones | Haruna Nijo / H602 | SEQ ID NO: |
|---|---|---|
| bah15o13 | ATCCAAATTACAACCACTTCC<br>ATCCAAATTAGAACCACTTCC | 17746 |
| kr24f0412 | GAACAGAAGATTGCCATTAAC<br>GAACAGAAGAATGCCATTAAC | 17747 |
| kr24f0412 | TAGCTGGCGGGTAACAGTTTC<br>TAGCTGGCGGATAACAGTTTC | 17748 |
| bags28o21 | TCCTCTTCGAACTGTAGGGGA<br>TCCTCTTCGAGCTGTAGGGGA | 17749 |
| bags28o21 | CGCCCTTGCCCAGACCCTTGC<br>CGCCCTTGCCGAGACCCTTGC | 17750 |
| bags28o21 | AGATCTTGAGCACGCCGCGGG<br>AGATCTTGAGGACGCCGCGGG | 17751 |
| baal15n19 | CAACGGAGGCAGCGCACTGTC<br>CAACGGAGGCGGCGCACTGTC | 17752 |
| baal15n19 | CCGCGATGGCAAGGGCGGCGC<br>CCGCGATGGCGAGGGCGGCGC | 17753 |
| bags32j03 | CAAATTGATCGCAGACTCCAC<br>CAAATTGATCACAGACTCCAC | 17755 |
| bags32j03 | ACTACTAAGAGAGTCCAGCTG<br>ACTACTAAGAAAGTCCAGCTG | 17756 |
| bags32j03 | CAGACCAGACAACAGAGATGA<br>CAGACCAGACCACAGAGATGA | 17757 |
| bags20e14 | ACCTGTCCTGTTTCAGCGCGT<br>ACCTGTCCTGCTTCAGCGCGT | 17758 |
| basd27n01 | AACCCCGCCAGTTGTATAAGA<br>AACCCCGCCACTTGTATAAGA | 17760 |
| basd27n01 | TATCAGGGATCCAGGAGGGGA<br>TATCAGGGATTCAGGAGGGGA | 17761 |
| basd27n01 | TTCACGAGTGCACACTACAAT<br>TTCACGAGTGTACACTACAAT | 17762 |
| basd27n01 | CAGGAGGGGAGGAGCGATCGC<br>CAGGAGGGGACGAGCGATCGC | 17763 |
| bags6m19 | GAATAACGACCTACAAATCCA<br>GAATAACGACGTACAAATCGA | 17764 |
| bags6m19 | CCTACAAATCCAGTATACTAG<br>CGTACAAATCGAGTATACTAG | 17765 |
| baak13e03 | CATAGGGCTCCTCGTTATCAA<br>CATAGGGCTCGTCGTTATCAA | 17766 |
| bah23i02 | AGAATGGCGACATTAGAAATA<br>AGAATGGCGAGATTAGAAATA | 17774 |
| bah23i02 | CCTGGCCGCGCGACCTTTATA<br>CCTGGCCGCGGGACCTTTATA | 17775 |
| baak15h22 | ATTTTGATTCGCACCTGCACT<br>ATTTTGATTCACACCTGCACT | 17776 |
| baak15h22 | CAGAGTATACTAGACGTAGTA<br>CAGAGTATACCAGACGTAGTA | 17777 |
| baak15h22 | TATTGTCGACCCTCACACAGC<br>TATTGTCGACACTCACACAGC | 17778 |
| bags32b03 | AATACCAAGTCACCCGTTGTG<br>AATACCAAGTAACCCGTTGTG | 17779 |

TABLE 22-15

| Clones | Haruna Nijo / H602 | SEQ ID NO: |
|---|---|---|
| baak30c15 | ATGAATGGCCGGGCACAATGC<br>ATGAATGGCCAGGCAGAATGC | 17780 |
| baak30c15 | TGGCCGGGCACAATGCATATT<br>TGGCCAGGCAGAATGCATATT | 17781 |
| BaGS22A05 | AGCTAACTAGGGCCAACGCCT<br>AGCTAACTAGCGCCAACGCCT | 17782 |
| BaGS22A05 | CAAGGCGCCCGTTCTTGACCT<br>CAAGGCGCCCATTCTTGACCT | 17783 |
| BaGS22A05 | CGAAGCTGCCGCCAGGGTAGA<br>CGAAGCTGCCACCAGGGTAGA | 17784 |
| bah16m01 | GTTTTGGCTCTCCTAGCAAGG<br>GTTTTGGCTCGCCTAGCAAGG | 17785 |
| bags37d12 | CTCGGACCCCCGGAGCAGCAG<br>CTCGGACCCCTGGAGCAGCAG | 17787 |
| baal37n24 | CTCCCTCCTCTGTTCCTGATT<br>CTCCCTCCTCCGTTCCTGATT | 17788 |
| baal37n24 | CCATGAGGCCGATGATCCACC<br>CCATGAGGCCAATGATCCACC | 17789 |
| baal37n24 | TTGCCGTGCTCTGTATCGGAC<br>TTGCCGTGCTTTGTATCGGAC | 17790 |
| BaH28B09 | CAACAAATACAAAAGTGAGTT<br>CAACAAATACGAAAGTGAGTT | 17791 |
| BaH28B09 | AATCGGCCGGGGACCATCAGA<br>AATCGGCCGGAGACCATCAGA | 17792 |
| BaH28B09 | ACGATGCAGCGGACACAAGCT<br>ACGATGCAGCAGACACAAGCT | 17793 |
| BaH28B09 | TTGTCTTTTATAATAAGCATT<br>TTGTCTTTTAAAATAAGCATT | 17794 |
| BaH28B09 | TTTTATTGACGGTGCAAAACA<br>TTTTATTGACAGTGCAAAACA | 17795 |
| BaH28B09 | AAACTCTGACGTGGGATAGAA<br>AAACTCTGACATGGGATAGAA | 17796 |
| bah47h08 | ATGTGTTGATCACAGCTGCTC<br>ATGTGTTGATTACAGCTGCTC | 17797 |
| bah57n07 | TGGTGCAGACAGGCGCGGTGA<br>TGGTGCAGACGGGCGCGGTGA | 17798 |
| baak38o02 | CCACGACGTAGGTACGTCGTT<br>CCACGACGTACGTACGTCGTT | 17799 |
| baak20f16 | AGTCATTTATTTGGAATGAAG<br>AGTCATTTATCTGGAATGAAG | 17800 |
| baak20f16 | ACTCAACTAACTTTAGGTGG<br>ACTCAACTAATTTTAGGTGG | 17801 |
| baak28n19 | CGAAGCTGCCGCCAGGGTAGA<br>CGAAGCTGCCACCAGGGTAGA | 17802 |
| baak28n19 | CGAGGCCACCCTCGCTGAAGA<br>CGAGGCCACCGTCGCTGAAGA | 17803 |
| bah59j07 | AGCTAGTTCAGACATCGTCCT<br>AGCTAGTTCACACATCGTCCT | 17804 |
| bah59j07 | GGAATCTTGGATAGTTGGAGC<br>GGAATCTTGGGTAGTTGGAGC | 17805 |

TABLE 22-16

| Clones | Haruna Nijo H602 | SEQ ID NO: |
|---|---|---|
| bah59j07 | TCCATGACGATTCCACACACC<br>TCCATGACGAATCCACACACC | 17806 |
| bah59j07 | GGTACTGGCAACATCCATGAC<br>GGTACTGGCAGCATCCATGAC | 17807 |
| bah59j07 | TCCTCTTGCTGTCTTACAGTC<br>TCCTCTTGCTATCTTACAGTC | 17808 |
| bah59j07 | AGACAAAGAAGATTGCAAGTC<br>AGACAAAGAAAATTGCAAGTC | 17809 |
| bah59j07 | CAGGTCGTTCGGGGGAAGCAG<br>CAGGTCGTTCTGGGGAAGCAG | 17810 |
| bah59j07 | CTGCTTGAAACATCACCATAA<br>CTGCTTGAAATATCACCATAA | 17811 |
| bah59j07 | CAAATGCCTTGTGTGCACTGC<br>CAAATGCCTTATCTGCACTGC | 17812 |
| bah44j20 | AAGGTCTTGCAACTGAAGGCG<br>AAGGTCTTGCGACTGAAGGCG | 17813 |
| baet39b0303 | CCATCTCCGCATTGGCCCAGT<br>CCATCTCCGCCTTGGCCCAGT | 17815 |
| baet39b0303 | GCTTTCTTGGCAGGGTAAGGA<br>GCTTTCTTGGTAGGGTAAGGA | 17816 |
| baet39b0303 | GCTCGCCGTCGAGCACGCTGC<br>CCTCGCCGTCCAGCACGCTGC | 17817 |
| baak27d19 | ACGAGTGGTCGTCCCAGCCAG<br>ACGAGTGGTCTTCCCAGCCAG | 17818 |
| baak27d19 | TTAACAGCCGGCGGCTGAACG<br>TTAACAGCCGACGGCTGAACG | 17819 |
| basd25g01 | TCCCTACCTTCCCTGGCCTCC<br>TCCCTACCTTACCTGGCCTCC | 17820 |
| basd25g01 | TCCCGGAGCTCGCGTTCGCGT<br>TCCCGGAGCTAGCGTTCGCGT | 17821 |
| baal34k17 | TCTTTCGGAGCTGCTACTCTA<br>TCTTTCGGAGATGCTACTCTA | 17822 |
| baal34k17 | AGTTTCGGGGTAAATTTATCC<br>AGTTTCGGGGAAAATTTATCC | 17823 |
| basd21i17 | CCTCCCCGCACCGCAGTGTGG<br>CCTCCCCGCATCGCAGTGTGG | 17824 |
| basd21i17 | GGCAGCATCTCACGAAACACC<br>GGCAGCATCTGACGAAACACC | 17825 |
| bags15o12 | GAAAAGAGTGAAAACATACAA<br>GAAAAGAGTGGAAACATACAA | 17826 |
| baak44n10 | GTGATGGCAATGAATTTTATG<br>GTGATGGCAAGGAATTTTATG | 17828 |
| baak44n10 | GTGACCTCGTCGAAACTTGGT<br>GTGACCTCGTTGAAACTTGGT | 17829 |
| baak21e08 | TGCGGTACACTGCGCTCAGCC<br>TGCGGTACACCGCGCTCAGCC | 17830 |
| baak41i21 | CGAGCCGACAGTGCACACCGC<br>CGAGCCGACACTGCACACCGC | 17832 |
| BaGS19C07 | CCGCGCCTCTCGGGTCACCGG<br>CCGCGCCTCTTGGGTCACCGG | 17833 |

TABLE 22-17

| Clones | Haruna Nijo H602 | SEQ ID NO: |
|---|---|---|
| BaGS19C07 | TGAAAAATGTCATATCATTCA<br>TGAAAAATGTTATATCATTCA | 17834 |
| BaGS19C07 | GACAGGATGAGCAACTTGCCT<br>GACAGGATGAACAACTTGCCT | 17835 |
| BaGS19C07 | CTCGATTGCCAATGTATATGA<br>CTCGATTGCCGATGTATATGA | 17836 |
| BaGS19C07 | CTTTCCTGATCATGGAGCAAT<br>CTTTCCTGATAATGGAGCAAT | 17837 |
| BaGS19C07 | CTGGTATTGGAGGCAATGGGA<br>CTGGTATTGGCGGCAATGGGA | 17838 |
| BaGS15O08 | CCCTGCCGGCAATCTCACCGA<br>CCCTGCCGGCGATCTCACCGA | 17839 |
| BaGS15O08 | CAGACATCTCATCTGTCCAGG<br>CAGACATCTCGTCTGTCCAGG | 17840 |
| baak40p22 | ATATGGCACCCATACAACCCT<br>ATATGGCACCGATACAACCCT | 17841 |
| baal40n03 | TAGTAATTGTAATGTAGTAGG<br>TAGTAATTGTTATGTAGTAGG | 17843 |
| baal40n03 | GGCCTCGGCCACCATAGAACC<br>GGCCTCGGCCGCCATAGAACC | 17844 |
| bags23b08 | CAGATCACTTGCAAATGTGGT<br>CAGATCACTTACAAATGTGGT | 17845 |
| bags23b08 | GTTTGTGTATGAGAAGAAGAG<br>GTTTGTGTATCAGAAGAAGAG | 17846 |
| bags23b08 | AGTCGTTGTCCATCTGGTCAT<br>AGTCGTTGTCTATCTGGTCAT | 17847 |
| BaGS39L18 | TGGCCTTCAGCTCAGGCTTCA<br>TGGCCTTCAGTTCAGGCTTCA | 17848 |
| BaGS39L18 | CCAGGGCATACTCCTTCCTAC<br>CCAGGGCATAGTCCTTCCTAC | 17849 |
| BaGS39L18 | CCTCCAAGTCAGAAGAGATGA<br>CCTCCAAGTCGGAAGAGATGA | 17850 |
| bah18d15 | AGAAGAGATCATTCGCCGCCA<br>AGAAGAGATCGTTCGCCGCCA | 17853 |
| bastl04f0911 | TCTTGCACGAGCAATGAGGTG<br>TCTTGCACGACCAATGAGGTG | 17854 |
| BaGS31E03 | CCTTGAAAACTGACGAGTAGT<br>CCTTGAAAACCGACGAGTAGT | 17855 |
| BaGS19J21 | ACTGCGGCACACTCCAGGTCT<br>ACTGCGGCACGCTCCAGGTCT | 17856 |
| BaGS19J21 | GAGTGCCAAGCTTCCATAGCA<br>GAGTGCCAAGTTTCCATAGCA | 17857 |
| BaGS19J21 | GGCTTGGAGTTGGAGGTACTG<br>GGCTTGGAGTCGGAGGTACTG | 17858 |
| bags39p08 | GAATCAGATGAACAAGACAGT<br>GAATCAGATGCACAAGACAGT | 17859 |
| BaH56B06 | TCAGTCCTCATCAAGTAGCAT<br>TCAGTCCTCACCAAGTAGCAT | 17860 |
| baaL13m24 | ACAACACAAGCAAATGAAGGG<br>ACAACACAAGGAAATGAAGGG | 17861 |

TABLE 22-18

| Clones | Haruna Nijo / H602 | SEQ ID NO: |
|---|---|---|
| baal13m24 | GATCAGGATCGTCACTTTTCC<br>GATCAGGATCATCACTTTTCC | 17862 |
| baal13m24 | ATACGCTCTTTATATGCTACA<br>ATACGCTCTTAATATGCTACA | 17863 |
| baal13m24 | ATGAAGGGGGTAAAACAGGTT<br>ATGAAGGGGGCAAAACAGGTT | 17864 |
| bags15h14 | AGGAGGAGGCGTCGTCAGAAA<br>AGGAGGAGGCATCGTCAGAAA | 17865 |
| baal34b14 | ACTGAGAGTCAACCACTGTAT<br>ACTGAGAGTCGACCACTGTAT | 17868 |
| baal34b14 | TGTCGATGCACAAGTTGCGAC<br>TGTCGATGCAGAAGTTGCGAC | 17869 |
| baal34b14 | AATAGTCTGTCTCAGTCTCAC<br>AATAGTCTGTTTCAGTCTCAC | 17870 |
| baal34b14 | CAAACCAAGATAGCATCAGTC<br>CAAACCAAGAAAGCATCAGTC | 17871 |
| bast58C1206 | TTCTTCTTCTTGGGCAACGTA<br>TTCTTCTTCTAGGGCAACGTA | 17874 |
| bast58C1206 | TTTAGGTAAACTGAACCTCAA<br>TTTAGGTAAATTGAACCTCAA | 17875 |
| bastl20B0404 | AAAAAAAAAAAAAAAAAAAA<br>AAAAAAAAAAGAAAAAAAAA | 17877 |
| bastl20B0404 | AAGAGCTGACCGTGGAAACCA<br>AAGAGCTGACTGTGGAAACCA | 17878 |
| bastl20B0404 | AAAAAAAAAGAAAAAAAAAA<br>AAAAAAAAAAAAAAAAAAAA | 17879 |
| BaH15P22 | TGGGGGCACCGACCTTTCGGA<br>TGGGGGCACCAACCTTTCGGA | 17881 |
| BaGS17I22 | AAACAAGTGCAGACCATGGCC<br>AAACAAGTGCCGACCATGGCC | 17882 |
| BaGS17I22 | GCATGTACTCATTGGAGGAAC<br>GCATGTACTCGTTGGAGGAAC | 17883 |
| BaGS17I22 | CTCAACATCAAACATACTGCT<br>CTCAACATCATACATACTGCT | 17884 |
| bags15h01 | CAGGAGGAATGCTAAACTGCT<br>CAGGAGGAATACTAAACTGCT | 17885 |
| bags15h01 | GCTAGAATGTTCTAGATCAGT<br>GCTAGAATGTACTAGATCAGT | 17886 |
| bags7p13 | TGGTCACTCAGGCAGAAAGGA<br>TGGTCACTCAAGCAGAAAGGA | 17887 |
| bags29h13 | TGGGGGCACCAACCTTTCGGA<br>TGGGGGCACCGACCTTTCGGA | 17888 |
| bags29h13 | TGTGAGGGACAAGTCAATACT<br>TGTGAGGGACGAGTCAATACT | 17889 |
| bah47b01 | AGTAGATGCAAGGGTTCGAAG<br>AGTAGATGCAGGGGTTCGAAG | 17890 |
| bah47b01 | TGAGCACATATATGTAGTAGA<br>TGAGCACATACATGTAGTAGA | 17891 |
| bags32m15 | TATGATTGACACTACGACTTT<br>TATGATTGACGCTACGACTTT | 17893 |

TABLE 22-19

| Clones | Haruna Nijo / H602 | SEQ ID NO: |
|---|---|---|
| bags32m15 | ATGACCATCCAGTGGGGTAGT<br>ATGACCATCCGGTGGGGTAGT | 17894 |
| bags32m15 | TCATGCTTGAAACGGTGCAGA<br>TCATGCTTGAGACGGTGCAGA | 17895 |
| bags32m15 | GACTTCAAGGGGGTCCACAA<br>GACTTCAAGGTGGTTCCACAA | 17896 |
| baal27m11 | ACAGTATATCGCACGAGAAAA<br>ACAGTATATCACACGAGAAAA | 17897 |
| baal27m11 | GCTGGCCTGTGGCACCATTCG<br>GCTGGCCTGTCGCACCATTCG | 17898 |
| baal27m11 | TGTCTGCAGAGTGATTCTGCA<br>TGTCTGCAGAATGATTCTCCA | 17899 |
| basdl2k01 | GAGTGAACAGCCTTGGAAAGC<br>GAGTGAAGAGTCTTGGAAAGG | 17900 |
| bags1b01 | TCGCCAGCTCGCCGACACCAC<br>TCGCCAGCTCACCGACACCAC | 17901 |
| bags21e21 | GGTGCACACGGGACACATAAC<br>GGTGCACACGAGACACATAAC | 17904 |
| baes21e21 | TCTGTGGCTTCGCAGGATCTT<br>TCTGTGGCTTGGCAGGATCTT | 17905 |
| bags21e21 | TCATCATGTCAGCGCCAGATA<br>TCATCATGTCCGCGCCAGATA | 17906 |
| bags21e21 | ACATGTTTGCGGTGTTGAGGT<br>ACATGTTTGCAGTGTTGAGGT | 17907 |
| baes21e21 | TGAAGTGGTCTCGGGGGTGCA<br>TGAAGTGGTCGCGGGGGTGCA | 17908 |
| baet02b0503 | CCACCAGCACTCCGGCACCTG<br>CCACCAGCACGCCGGCACCTG | 17909 |
| baet02b0503 | GGCCGTATGGATCCATTGGCG<br>GGCCGTATGGCTCCATTGGCG | 17910 |
| bah29l05 | GATTTCTTGAGTTGTAATCCG<br>GATTTCTTGAATTGTAATCCG | 17911 |
| bah29l05 | GCAACATCCGCCTAGATTTCT<br>GCAACATCCGACTAGATTTCT | 17912 |
| bah29l05 | TGTAGTCCCCATGCAACTTCC<br>TGTAGTCCCCGTGCAACTTCC | 17913 |
| bah29l05 | TTTTATTAAAGAAATAGAAAT<br>TTTTATTAAAAAAATAGAAAT | 17914 |
| baet43H1016 | GACAGGGTCGGCAATGTGGTC<br>GACAGGGTCGACAATGTGGTC | 17915 |
| baet43H1016 | TAATATACATCGTTGGTGTTA<br>TAATATACATAGTTGGTGTTA | 17916 |
| baak20b06 | CACACTCATCGATCCATTCGC<br>CACACTCATCAATCCATTCGC | 17921 |
| BaH16l04 | CCACATCAAAGAGCAGTCAG<br>CCACATCAAA-GAGCAGTCAG | 17922<br>17923 |
| bah22p07 | GGTGGAATTCTTTGGTGTCCC<br>GGTGGAATTCCTTGGTGTCCC | 17924 |
| bah22p07 | CCAGATGCTTTCATCCTCTCA<br>CCAGATGCTTCCATCCTCTCA | 17925 |

TABLE 22-20

| Clones | Haruna Nijo / H602 | SEQ ID NO: |
|---|---|---|
| baak21j02 | GCTCTTTGTCGGTGCCTTGCA<br>GCTCTTTGTCCGTGCCTTGCA | 17926 |
| bags21o12 | TGCCAAACGGAACGGTGCCGA<br>TGCCAAACGGGACGGTGCCGA | 17936 |
| bag21o12 | TGAGCGACCGCGTGTATATGT<br>TGAGCGACCGTGTGTATATGT | 17937 |
| bags21o12 | TCTTCTGCCCTGCCGGAACAT<br>TCTTCTGCCCCGCCGGAACAT | 17938 |
| bags9b14 | ATGTGCAGCAGATGAGATGAG<br>ATGTGCAGCAAATGAGATGAG | 17939 |
| bags9b1 | CTGCCCAGATATATGATTAGG<br>CTGCCCAGATGTATGATTAGG | 17940 |
| bags9b14 | GGAATGGAATATGCGAAATAG<br>GGAATGGAATGTGCGAAATAG | 17941 |
| bags9b14 | GATTTAAAAGGCTTCTTCCAG<br>GATTTAAAAGACTTCTTCCAG | 17942 |
| bags9b14 | AGATGAGAAACGACGCGACAC<br>AGATGAGAAATGACGCGACAC | 17943 |
| bags9b14 | ACTCACATACGCAGCTTTCAA<br>ACTCACATACACAGCTTTCAA | 17944 |
| baak1a17 | CAGGGGGCAGAGTCATAAGAT<br>CAGGGGGCAGCGTCATAAGAT | 17946 |
| baak1a17 | AGCACTATAATCGTCCGAAAC<br>AGCACTATAACCGTCCGAAAC | 17947 |
| bags1p04 | AAACTTACTTGGTGCACGACT<br>AAACTTACTTAGTGCACGACT | 17951 |
| bags1p04 | TAATAAATTTACAAACTCAAA<br>TAATAAATTTCCAAACTCAAA | 17952 |
| BaAL17O03 | TAAGGTAGGTAGGTTGGTTGG<br>TAAGGTAGGTTGGTTGGTTGG | 17953 |
| baal8e17 | CTACTGGCTCTGTCGCTGGAT<br>CTACTGGCTCCGTCGCTGGAT | 17954 |
| baal839e17 | TGGTGGTGGACAAACATATAT<br>TGGTGGTGGATAAACATATAT | 17955 |
| BaH39L18 | CAATGGGCGGCGCGGCGCAGC<br>CAATGGGCGGGGCGGCGCAGC | 17958 |
| BaH39L18 | CGCAGACAAGTCACTGGCAGC<br>CGCAGACAAGCCACTGGCAGC | 17959 |
| bags18e18 | CCAGTTGCCCCCACGCTGCAG<br>CCAGTTGCCCGCACGCTGCAG | 17960 |
| bags18e18 | TTGAGCAGATGGTCAGTGTTT<br>TTGAGCAGATTGTCAGTGTTT | 17961 |
| bags18e18 | CTGTAGGCAATGTGTGGATGT<br>CTGTAGGCAAAGTGTGGATGT | 17962 |

TABLE 23-1

| Clones | Haruna Nijo / H602 | SEQ ID NO: |
|---|---|---|
| BaGS20L10 | CGCGACAAACCGCGGAGCACA<br>CGCGACAAACAGCGGAGCACA | 17963 |
| BaGS20L10 | CTACCGATGACCAACCGAGTG<br>CTACCGATGATCAACCGAGTG | 17964 |
| basd15p22 | ACAGGTGCTCCATCGACTCAC<br>ACAGGTGCTCGATCGACTCAC | 17965 |
| bags7b16 | TCGTCACTGTTGCAAATCATA<br>TCGTCACTGTCGCAAATCATA | 17966 |
| bags7b16 | AGGACACTGTTACAGGTTAAG<br>AGGACACTGTGACAGGTTAAG | 17967 |
| BaAK22H13 | TTTCAGTTCTGTCGATGCAGT<br>TCTCAGTTCTATCGATGCAGT | 17969 |
| BaAK22H13 | TTATCTACCTTTCAGTTCTGT<br>TTATCTACCTCTCAGTTCTAT | 17970 |
| BaH41L14 | ATCAAGCTTACAAAACAGAAT<br>ATCAAGCTTATAAAACAGAAT | 17973 |
| BaH41L14 | TTGCAACCCCACCACCATCAA<br>TTGCAACCCCGCCACCATCAA | 17974 |
| BaAK24H17 | TGCATCAGAACGAATGTGCAT<br>TGCATCAGAATGAATGTGCAT | 17975 |
| bast21A0602 | ATATACCTTCTACCTTACATA<br>ATATACCTTCCACCTTACATA | 17976 |
| BaAL27L20 | ACCGCTGCAAGGGATCCTGCT<br>ACCGCTGCAAAGGATCCTGCT | 17977 |
| BaAL27L20 | CTCATTTCTGTGACGACCGCT<br>CTCATTTCTGGGACGACCGCT | 17978 |
| BaAL27L20 | ATGTCGGTCCAATAAATACTT<br>ATGTCGGTCCGATAAATACTT | 17979 |
| BaAL27L20 | GAGATTCACAAAACTACATG<br>GAGATTCACGAAACTACATG | 17980 |
| bags34p10 | TGCATCAGAACGAATGTGCAT<br>TGCATCAGAATGAATGTGCAT | 17981 |
| baes34p10 | ACCACCATGGGTTCTATGTCC<br>ACCACCATGGATTCTATGTCC | 17982 |
| BaAL29B07 | GGTTGTGTTGCCGCACGAACG<br>GGTTGTGTTGTCGCACGAACG | 17986 |
| baak20o16 | TAACAGCATTGTCGACAGTCA<br>TAACAGCATTATCGACAGTCA | 17987 |
| baak20o16 | GGATGTGCAGTGGCACCTACA<br>GGATGTGCAGGGGCACCTACA | 17988 |
| BaH36B07 | AGCAGCATGATGAGGTCCTTG<br>AGCAGCATGACGAGGTCCTTG | 17991 |
| BaH36B07 | AGCCGGAGGTTAGCAGGGCCG<br>AGCCGGAGGTGAGCAGGGCCG | 17992 |
| BaH36B07 | CGGCGTCCTCTTCCTCGGCAT<br>CGGCGTCCTCCTCCTCGGCAT | 17993 |
| BaH36B07 | GACCTCCTCCATCTTGCTCTC<br>GACCTCCTCCGTCTTGCTCTC | 17994 |
| BaSD3C20 | TCATACAGTAGCGGCGGCGGG<br>TCATACAGTACCGGCGGCGGG | 17997 |

TABLE 23-2

| Clones | Haruna Nijo H602 | SEQ ID NO: |
|---|---|---|
| BaSD3C20 | CCATGTATCAGATTGTCTCAT<br>CCATGTATCAAATTGTCTCAT | 17998 |
| BaSD3C20 | TAAAAATCCCTTGCGTTCACC<br>TAAAAATCCCCTGCGTTCACC | 17999 |
| bastl17G0113 | ATTATAGAAGGTTATCTTTCA<br>ATTATAGAAGATTATCTTTCA | 18000 |
| baak11h14 | CAATGGTGTGCAGACACAGGT<br>CAATGGTGTGTAGACACAGGT | 18001 |
| baak11h14 | CGGAGAAGAATGCTTCAAGGT<br>CGGAGAAGAAGGCTTCAAGGT | 18002 |
| baal33a18 | CATCCTTTGAGGTGCTGATAC<br>CATCCTTTGAAGTCCTGATAC | 18004 |
| baal33a18 | TCTCAAGAGGTTCAACTAACG<br>TCTCAAGAGGCTCAACTAACG | 18005 |
| baal33a18 | AGAATCAATCGTCAACTAGTA<br>AGAATCAATCATCAACTAGTA | 18006 |
| baal33a18 | AGAAGTGGACATTATCTTGCT<br>AGAAGTGGACGTTATCTTGCT | 18007 |
| baal33a18 | ACTTGACTCATCTATGTCCTA<br>ACTTGACTCAACTATGTCCTA | 18008 |
| bah28a18 | TGTTGAGTGCGTGTTCTTCCA<br>TGTTGAGTGCATCTTCTTCCA | 18009 |
| bah28a18 | GTTCACAGAAAAAAGTAGCTC<br>GTTCACAGAAGAAAGTAGCTC | 18010 |
| bah28a18 | CGCCGTCATACGCAGAGAGGA<br>CGCCGTCATATGCAGAGAGGA | 18011 |
| bah28a18 | CATCGTTTGCCTCATTGCTTC<br>CATCGTTTGCTTCATTGCTTC | 18012 |
| bags39o04 | CATTGTATCAGCATCTCGGAT<br>CATTGTATCAACATCTCGGAT | 18013 |
| bags39o04 | GGGGGTCCTCGACGACGTCCT<br>GGGGGTCCTCAACGACGTCCT | 18014 |
| bags39o04 | AATAAGGCTTCCGTAGACACC<br>AATAAGGCTTTCGTAGACACC | 18015 |
| bags39o04 | GTCAATTGACAGCGCCCCCTC<br>GTCAATTGACGGCGCCCCCTC | 18016 |
| BaH48H04 | CCCCTCCGATCAGCGGATCAT<br>CCCCTCCGATTAGCGGATCAT | 18017 |
| bags4p16 | CCGTTCCTTCGTGCGTATGCT<br>CCTTTCCTTCCTGCGTATGCT | 18018 |
| bags4p16 | TTGCTCCACCGTTCCTTCGTG<br>TTGCTCCACCTTTCCTTCCTG | 18019 |
| basd24j22 | TTGCCTGCTTTGTCAGGCGAG<br>TTGCCTGCTTCGTCAGGCGAG | 18020 |
| basd16p15 | ATACACCACAGGACGCCATTA<br>ATACACCACATGACGCCATTA | 18021 |
| basd16p15 | AGTACAGGTACAAGAAATGAT<br>AGTACAGGTATAAGAAATGAT | 18022 |
| bags15k16 | CTTTGTCCTCTAATGTCAGAT<br>CTTTGTCCTCCAATGTCAGAT | 18023 |

TABLE 23-3

| Clones | Haruna Nijo H602 | SEQ ID NO: |
|---|---|---|
| bags15k16 | GCCTTGCCATCGGTCTTCCTC<br>GCCTTGCCATTGGTCTTCCTC | 18024 |
| bast23D1208 | TGTGCTCGACGGTCTTCAGTT<br>TGTGCTCGACAGTCTTCAGTT | 18025 |
| bast23D1208 | AAACATAACCAATCGTGACGA<br>AAACATAACCGATCGTGACGA | 18026 |
| baaG2b22 | TTAGTCGTCCATATATCTTTT<br>TTAGTCGTCCCTATATCTTTT | 18027 |
| baaB2b22 | CATCATCTCTGTTGTATACTT<br>CATCATCTCTATTGTATACTT | 18028 |
| baaB2b22 | TGTATACTTGCCACACACCCG<br>TGTATACTTGTCACACACCCG | 18029 |
| baaB2b22 | ACGAAGTGCTGAGAGATAATA<br>ACGAAGTGCTCAGAGATAATA | 18030 |
| baaB2b22 | ACAAAATGACATGTTAATACA<br>ACAAAATGACCTGTTAATACA | 18031 |
| baaB2b22 | ACTTAGTTGATGGGTTAAAAG<br>ACTTAGTTGACGGGTTAAAAG | 18032 |
| baaB2b22 | CCACTGATATTATAGTACCTA<br>CCACTGATATGATAGTACCTA | 18033 |
| baaB2b22 | GTGACGGGTTACCCAAATATA<br>GTGACGGGTTGCCCAAATATA | 18034 |
| baaB2b22 | CACTCAATATGTATACTACTT<br>CACTCAATATATATACTACTT | 18035 |
| BaH19L09 | CACCCGACTCCATCAGGTTCT<br>CACCCGACTCGATCAGGTTCT | 18036 |
| BaH19L09 | ACACCGAGGCAGCGTTCTGGA<br>ACACCGAGGCGGCGTTCTGGA | 18037 |
| BaH19L09 | CGCATCTCGTTACCTTGGCGG<br>CGCATCTCGTCACCTTGGCGG | 18038 |
| bags38a17 | CAGATAAACTCTCAAGAATGA<br>CAGATAAACTTTCAAGAATGA | 18039 |
| BaAK39I11 | GCTTGCTGCCGTCGGTCGTGA<br>GCTTGCTGCCATCGGTCGTGA | 18040 |
| BaSD3I24 | CTCTAAGGAGGATAGAGCAAC<br>CTCTAAGGAGAATAGAGCAAC | 18041 |
| BaSD3I24 | TGACGACGACATCGTACATGT<br>TGACGACGACGTCGTACATGT | 18042 |
| BaSD3I24 | TCATCAGGAACACAAGGGTAT<br>TCATCAGGAATACAAGGGTAT | 18043 |
| bah13123 | CCATATGGTAGACAGTATGCC<br>CCATATGGTATACAGTATGCC | 18046 |
| bah13123 | ATAAAATTTCCGAGAACCCAA<br>ATAAAATTTCTGAGAACCCAA | 18047 |
| bah13123 | TTTCATAAATACTCTATTCTT<br>TTTCATAAATTCTCTATTCTT | 18048 |
| bah13123 | TTGTGCATCCATTTTTTATGT<br>TTGTGCATCCGTTTTTTATGT | 18049 |
| bah13123 | TCGAGTTTGCGGATCTCCGTA<br>TCGAGTTTGCAGATCTCCGTA | 18050 |

TABLE 23-4

| Clones | Haruna Nijo H602 | SEQ ID NO: |
|---|---|---|
| bah13123 | ACCCAAGTAATCCATATGGTA<br>ACCCAAGTAACCCATATGGTA | 18051 |
| BaAL26H21 | TGCATCGCTCATCAAACATGA<br>TGCATCGCTCGTCAAACATGA | 18052 |
| BaAL26H21 | CACACTGCACGGCAGAAAACT<br>CACACTGCACCGCAGAAAACT | 18053 |
| BaAL26H21 | CGCCGAAAAGCGTCGCGGCGG<br>CGCCGAAAAGTGTCGCGGCGG | 18054 |
| BaAL26H21 | CGAGATCTTCCGAAGGGTATA<br>CGAGATCTTCTGAAGGGTATA | 18055 |
| BaAL26H21 | AATCCAGACACCCTAAGACAC<br>AATCCAGACATCCTAAGACAC | 18056 |
| baak32l16 | GCAGGTTGTCAAAGCCGATGA<br>GCAGGTTGTCGAAGCCGATGA | 18060 |
| baak32l16 | ACTGCACCTGCCGCAGGTTGT<br>ACTGCACCTGACGCAGGTTGT | 18061 |
| baak32l16 | AGCCGATGATGCGGACGTAGG<br>AGCCGATGATACGGACGTAGG | 18062 |
| baak32l16 | GGTTACTTCAACTTGCACTTT<br>GGTTACTTCATCTTGCACTTT | 18063 |
| baak32l16 | TCAGGTAGTCGACCTGCTTCA<br>TCAGGTAGTCAACCTGCTTCA | 18064 |
| baak32l16 | TGTGTGGCGTGGGTGCACCCG<br>TGTGTGGCGTCGGTGCACCCG | 18065 |
| baak32l16 | AGTATCGGCCATCGTAGTACC<br>AGTATCGGCCGTCGTAGTACC | 18066 |
| baak32l16 | TGACCTCCTCGACCTCATTGA<br>TGACCTCCTCGACCTCATTGA | 18067 |
| baak32l16 | GGAGGGCCTCAGTGGTGAGGG<br>GGAGGGCCTCCGTGGTGAGGG | 18068 |
| bags5c02 | TCCCAGGCCACAACTCCTCTC<br>TCCCAGGCCAAAACTCCTCTC | 18073 |
| bags35p07 | GCTTCGGTGGGACTGGCTTCT<br>GCTTCGGTGGCACGGCTTCT | 18074 |
| bags35p07 | TCGGTGGGACTGGCTTCTTGT<br>TCGGTGGCACGGGCTTCTTGT | 18075 |
| BaAK24B09 | CCTGTGGGAAGACCATGATGT<br>CCTGTGGGAACACCATGATGT | 18076 |
| BaAK24B09 | CGGCGGACGGCAGGTTGTTGG<br>CGGCGGACGGGAGGTTGTTGG | 18077 |
| BaAK24B09 | AGAGCTTGATTAGCCGCTGCC<br>AGAGCTTGATCAGCCGCTGCC | 18078 |
| bags33a11 | TTTCGTCATCATCAAAGCGAG<br>TTTCGTCATCGTCAAAGCGAG | 18079 |
| bags33a11 | TCCGAGTAAGTCCGTGCAAGT<br>TCCGAGTAAGGCCGTGCAAGT | 18080 |
| bah56a24 | ACTTGGGCGCTGCCTCCAGCT<br>ACTTGGGCGCTGCCTCCAGCT | 18082 |
| bah56a24 | GCTCCTTCTTTTCCACGCTCT<br>GCTCCTTCTTCTCCACGCTCT | 18083 |

TABLE 23-5

| Clones | Haruna Nijo H602 | SEQ ID NO: |
|---|---|---|
| BaSD21D14 | GACTCCATTCGGTTCCAGCAA<br>GACTCCATTCCGTTCCAGCAA | 18084 |
| BaSD21D14 | ACATTGCTTCTCCCACATGGT<br>ACATTGCTTCCCCCACATGGT | 18085 |
| BaSD21D14 | ACAAAGAAGGCCGTTCATGAT<br>ACAAAGAAGGTCGTTCATGAT | 18086 |
| BaSD21D14 | TGATGATCCAGCAAACAAGGG<br>TGATGATCCAACAAACAAGGG | 18087 |
| basd1a17 | TCTGTTGTACTTTATGACAAT<br>TCTGTTGTACCTTATGACAAT | 18088 |
| basd1a17 | TCATGTCAATGCAAATCTTTA<br>TCATGTCAATACAAATCTTTA | 18089 |
| basd1a17 | TGGTTCTATTTTAGTTTTATT<br>TGGTTCTATTGTAGTTTTATT | 18090 |
| kr70g0113 | CTTGTTATTCCGAATTGGAAA<br>CTTGTTATTC-GAATTGGAAA | 18092<br>18093 |
| basd15f08 | ATAATATAAGTGTGTTTTTGT<br>ATAATATAAGAGTGTTTTTGT | 18094 |
| basd15f08 | GCTTCTTGACGTTGGTTCGGT<br>GCTTCTTGACATTGGTTCGGT | 18095 |
| baal35h05 | GGATCTTGTGATATAGCACTT<br>GGATCTTGTGGTATAGCACTT | 18101 |
| baal35h05 | AGCTTCCTCATCCCAAGCGTC<br>AGCTTCCTCAGCCCAAGCGTC | 18102 |
| baal35h05 | AAGATAGATACTTGCAGCAAC<br>AAGATAGATAGTTGCAGCAAC | 18103 |
| baal35h05 | ACCAGCTAGACCACCAGCTTC<br>ACCAGCTAGATCACCAGCTTC | 18104 |
| baal35h05 | CTGATTCAATTGACTCCTAAC<br>CTGATTCAATCGACTCCTAAC | 18105 |
| baal35h05 | ACGGGATTCAAAGAGGGATCT<br>ACGGGATTCAGAGAGGGATCT | 18106 |
| baak14a24 | CGTGGTACTTGTCGCCGTTGA<br>CGTGGTACTTATCGCCGTTGA | 18108 |
| baak30d07 | AAAAACATGTCGCATACCACA<br>AAAAACATGTTGCATACCACA | 18109 |
| baak30d07 | CGTGCACTCAGCAAGTTCCTC<br>CGTGCACTCACCAAGTTCCTC | 18110 |
| kr14c0305 | GAGACCGGGCCGGATCCGGCC<br>GAGACCGGGCGGATCCGGCC | 18112 |
| bast74c0705 | CTAGCAGCAGCAGGAGGACTA<br>CTAGCAGCAGGAGGAGGACTA | 18115 |
| baal4g17 | TCGCAAGGCATCACACGCAAA<br>TCGCAAGGCAACACACGCAAA | 18116 |
| baal4g17 | CTAGCAGCAGCAGGAGGACTA<br>CTAGCAGCAGGAGGAGGACTA | 18117 |
| bast143H0515 | AAGCCGATCATACACACACAC<br>AAGCCGATCACACACACACAC | 18118 |
| BaH58M22 | GCGTACGTGCACGAGCCATGC<br>GCGTACGTGCGCGAGCCATGC | 18119 |

TABLE 23-6

| Clones | Haruna Nijo / H602 | SEQ ID NO: |
|---|---|---|
| BaH58M22 | CGTGGTACTTATCGCCGTTGA<br>CGTGGTACTTGTCGCCGTTGA | 18120 |
| bags10i21 | CGAACGCGTCACTGTAAGGAA<br>CGAACGCGTCGCTGTAAGGAA | 18121 |
| bags10i21 | ACAAAATGGCAACTTCAGGGG<br>ACAAAATGGCGACTTCAGGGG | 18122 |
| bah20h16 | CGTCGCAAACATTATTGCCAA<br>CGTCGCAAACGTTATTGCCAA | 18123 |
| bah20h16 | ATGGGTCAGGTATCGAAGCCG<br>ATGGGTCAGGAATCGAAGCCG | 18124 |
| bah20h16 | ATCCTACGGTTAACGGTGAAG<br>ATCCTACGGTCAACGGTGAAG | 18125 |
| BaH17P13 | GCTGAACATACCCCTTTTCAC<br>GCTGAACATATCCCTTTTCAC | 18126 |
| baak16e24 | ACTCGCATGCCTTCAACAGCA<br>ACTCGCATGCTTTCAACAGCA | 18129 |
| baak16e24 | CTGAGCTGACACACACAAGAT<br>CTGAGCTGACCCACACAAGAT | 18130 |
| baak16e24 | ATGCTCACAT-TTTCTACACA<br>ATGCTCACATATTTCTACACA | 18131<br>18132 |
| baak16e24 | TATTCGAACC-CTGCTATGCT<br>TATTCGAACCACTGCTATGCT | 18133<br>18134 |
| BaSD18F09 | CCGCGCTGGATGCGAAGTTCC<br>CCGCGCTGGACGCGAAGTTCC | 18135 |
| BaSD18F09 | CGAGGTTCGCCAGGTTGCCGT<br>CGAGGTTCGCTAGGTTGCCGT | 18136 |
| BaSD18F09 | GAAGGCGCTGGTGAAGGCCGC<br>GAAGGCGCTGCTGAAGGCCGC | 18137 |
| BaSD18F09 | GCGCGATGTTGCCCATCTTGA<br>GCGCGATGTTTCCCATCTTGA | 18138 |
| baet42A0501 | AGCTGATCCTCACCTGGCCCT<br>AGCTGATCCTGACCTGGCCCT | 18139 |
| baet42A0501 | GCCGTTGATCACCTTGTTAAT<br>GCCGTTGATCGCCTTGTTAAT | 18140 |
| baet42A0501 | AATTCACCTTGGAGCAGCTGA<br>AATTCACCTTCGAGCAGCTGA | 18141 |
| baet42A0501 | GGCCCTGCGAGCCGGTCAACG<br>GGCCCTGCGAACCGGTCAACG | 18142 |
| baet42A0501 | CACCATGGCCGAGGCGAAGGC<br>CACCATGGCCAAGGCGAAGGC | 18143 |
| baak20l07 | GCTTGCGAGCCCTGCCGACTA<br>GCTTGCGAGCGCTGCCGACTA | 18144 |
| baak16e20 | TTCAAAAGTGAGAAAATACCA<br>TTCAAAAGTGGGAAAATACCA | 18145 |
| baak16e20 | AATTCTGCTTGGGCTGTTCCG<br>AATTCTGCTTCGGCTGTTCCG | 18146 |
| basd13m14 | GGACATCAAAGCTACTTGTAT<br>GGACATCAAATCTACTTGTAT | 18147 |
| basd13m14 | GGTAACCTGAATTTATTATAG<br>GGTAACCTGATTTTATTATAG | 18148 |

TABLE 23-7

| Clones | Haruna Nijo / H602 | SEQ ID NO: |
|---|---|---|
| basd13m14 | TACCTACAGATGAGGCAAGTT<br>TACCTACAGACGAGGCAAGTT | 18149 |
| basd13m14 | TTTCACAGCCCGTGAGGGACA<br>TTTCACAGCCGGTGAGGGACA | 18150 |
| bags20g23 | TAAATAAATATAATTCTGAAG<br>TAAATAAATACAATTCTGAAG | 18151 |
| bags20g23 | TTCTGAAGGTTGTTACTCCCT<br>TTCTGAAGGTCGTTACTCCCT | 18152 |
| basd1l17 | CGATGGCGAATGACTTCAAGA<br>CGATGGCGAACGACTTCAAGA | 18153 |
| basd1l17 | AACGGACCCTGCGGCGGCTCA<br>AACGGACCCTTCGGCGGCTCA | 18154 |
| basd1l17 | AGGAGTGGCCGATGATGTACG<br>AGGAGTGGCCAATGATGTACG | 18155 |
| basd1l17 | GAAGGAACGAATAGGCGTAGT<br>GAAGGAACGAGTAGGCGTAGT | 18156 |
| basd1l17 | GCGTCACCGACGGGCCCTGC<br>GCGTCACCGATGGGCCCTGC | 18157 |
| basd26l01 | TGCCATAGGTTTATCGTTCCG<br>TGCCATAGGTCTATCGTTCCG | 18158 |
| basd26l01 | TATCGTTCCGTTTACCTGTTT<br>TATCGTTCCGATTACCTGTTT | 18159 |
| basd26l01 | CGTTCCAAGGGCGCGCTCTTG<br>CGTTCCAAGGTCGCGCTCTTG | 18160 |
| basd26l01 | TCGCCTGTAGTGACGAGGACG<br>TCGCCTGTAGCGACGAGGACG | 18161 |
| baal37j18 | GGGTGGTCCAGATGACTAAGT<br>GGGTGGTCCAAATGACTAAGT | 18162 |
| baal37j18 | GGAGGGCAGATCTGATCTCTT<br>GGAGGGCAGACCTGATCTCTT | 18163 |
| baal37j18 | GACAGAAAGAGGACACACGGA<br>GACAGAAAGAAGACACACGGA | 18164 |
| baal37j18 | CAAGCCAGTTCATATACATAT<br>CAAGCCAGTTGATATACATAT | 18165 |
| bags7i05 | AAAAGGGATGATGGAATACAA<br>AAAAGGGATGGTGGAATACAA | 18166 |
| bags7i05 | CGGGTTCAGGCTTGGGCTCTG<br>CGGGTTCAGGTTTGGGCTCTG | 18167 |
| bags7i05 | ATCAATTGTCCGTCATCGGCG<br>ATCAATTGTCAGTCATCGGCG | 18168 |
| bags7i05 | CAAGGAATGCAAAAAAGATGC<br>CAAGGAATGCTAAAAAGATGC | 18169 |
| bah60m17 | AAATCTGTTCAGTTGTGTTGC<br>AAATCTGTTCGGTTGTGTTGC | 18170 |
| bah60m17 | GAGAATGTTATAACTAGGAGC<br>GAGAATGTTAGAACTAGGAGC | 18171 |
| bah60m17 | TTGAGGTGCACGGAAGGTGTG<br>TTGAGCTGCAAGGAAGGTCTG | 18172 |
| bah60m17 | TTGGATCTTCACCGCTGGCAT<br>TTGGATCTTCGCCGCTGGCAT | 18173 |

TABLE 23-8

| Clones | Haruna Nijo H602 | SEQ ID NO: |
|---|---|---|
| bah60m17 | GTTGCCGTCACAATCATCGAT<br>GTTGCCGTCAGAATCATCGAT | 18174 |
| bah60m17 | GAGGCACCTACTAAAATGGTA<br>GAGGCACCTAGTAAAATGGTA | 18175 |
| bah60m17 | AAAACCTGCACCAGTTTGGAT<br>AAAACCTGCAGCAGTTTGGAT | 18176 |
| bags21l01 | GCCTCCGCGTAGGTTCTTCC<br>GCCTCCGCGGGAGGTTCTTCC | 18177 |
| bags21l01 | ACTCGTCAGCATGCTTCTTCT<br>ACTCGTCAGCGTGCTTCTTCT | 18178 |
| baes21l01 | TTCCTCTTGGTGCTTCCTCTT<br>TTCCTCTTGGGGCTTCCTCTT | 18179 |
| baes21l01 | TTGGACTTCTCTTTCTCCTGC<br>TTGGACTTCTGTTTCTCCTGC | 18180 |
| bags21l01 | GCTAGCATCAGCATCAGCTGC<br>GCTAGCATCAACATCAGCTGC | 18181 |
| baet31e0109 | CAATATTTCTGACCCGTCGTG<br>CAATATTTCTAACCCGTCGTG | 18182 |
| baet31e0109 | CATATGCGCGATCGTGCACAT<br>CATATGCGCGGTCGTGCACAT | 18183 |
| bags34m12 | GTACGTCTTCGTACCGGATTC<br>GTACGTCTTCATACCGGATTC | 18184 |
| bags34m12 | CCTAGTTTTTATAGTTAGCTA<br>CCTAGTTTTTGTAGTTAGCTA | 18185 |
| bags34m12 | TTTATTCTGGGATCCTTATTT<br>TTTATTCTGGAATCCTTATTT | 18186 |
| bags34m12 | TTCGCTGGATTCTAGGAGTCC<br>TTCGCTGGATACTAGGACTCC | 18187 |
| bags34m12 | ATACCACTCAGAATCTAGGTC<br>ATACCACTCAAAATCTAGGTC | 18188 |
| bah50n02 | CTGCTCCCACTGAGGCGCCA<br>CTGCTCCCACCGAGGCGCCA | 18189 |
| BaH50M11 | TGCTTCATCACCTATCACTAT<br>TGCTTCATCATCTATCACTAT | 18190 |
| BaH50M11 | AATTTTGGGGTGGAGGGAGTA<br>AATTTTGGGGCGGAGGGAGTA | 18191 |
| bast27e1010 | TACCTTTCGCAAGGCGGAGCG<br>TACCTTTCGCGAGGCGGAGCG | 18192 |
| bast27e1010 | TACTGGTCATGAGGCGGGAGC<br>TACTGGTCATCAGGCGGGAGC | 18193 |
| bags23c12 | TCTCGGTTCCAGTTTCAGCCT<br>TCTCGGTTCCCGTTTCAGCCT | 18194 |
| bah51m11 | ATTTATCCGTCGAGACCGAGA<br>ATTTATCCGTGGAGACCGAGA | 18195 |
| baak20d17 | GCGCAGGGTCAGTTCTCCTG<br>GCGCAGGGTGTAGTTCTCCTG | 18196 |
| bags23l21 | GCCTCAATTAAAAGATTGGAA<br>GCCTCAATTATAAGATTGGAA | 18197 |
| bags23l21 | CAGGGCATCCCATGTGACAAC<br>CAGGGCATCCGATGTGACAAC | 18198 |

TABLE 23-9

| Clones | Haruna Nijo H602 | SEQ ID NO: |
|---|---|---|
| bags23l21 | CGTGCCATATCAGGTTCAATC<br>CGTGCCATATGAGGTTCAATC | 18199 |
| bags23l21 | ATGCTCGTCTCGCCTCGAGAA<br>ATGCTCGTCTTGCCTCGAGAA | 18200 |
| bags23l21 | CTAGCTATCTAAAGGATGTCT<br>CTAGCTATCTGAAGCATGTCT | 18201 |
| bags23d01 | TTACTCTGAANAGAAATGAGT<br>TTACTCTGAAGAGAAATGAGT | 18204 |
| bags23d01 | TTTGAACACCACGGAGAGCCT<br>TTTGAACACCGCGGACAGCCT | 18205 |
| baal29m02 | ATACTCGAGGAGAAGAAGGGA<br>ATACTCGACGGGAAGAAGGGA | 18207 |
| baal29m02 | TATTGTTGCCTATACTCACGC<br>TATTGTTGCCTATACTCACGC | 18208 |
| baal29m02 | GGGTAGGGCTCCACATATTGT<br>GGGTAGGGGTTGAGATATTGT | 18209 |
| bah17e21 | CATGCGTAGAAAACCTTGGTA<br>GGAGCTGAGAGAAGGTTGGTA | 18210 |
| bah56j18 | GAGGCAAAAGGAGAAGGATA<br>GAGGGAAAAAGAGAAGGATA | 18211 |
| bah56j18 | GGTTAATTTTGGTGGTGGGAC<br>GGTTAATTTTCCTCCTGGGAC | 18212 |
| BaAL34O13 | AATAAGGGCGGTCGGTTAATT<br>AATAAGGGGGATGGGTTAATT | 18215 |
| BaAL34O13 | TTAGTAAGTGAATGTGTGGTA<br>TTAGTAAGTGGATGTGTGGTA | 18216 |
| bags4n05 | GCACCAACGCGCTCCAGACTA<br>GCACCAACGCCCTCCAGACTA | 18217 |
| bags4n05 | GCCACCTGTGGGCAATTATGA<br>GCCACCTGTGCGCAATTATGA | 18218 |
| BaSD15P20 | GCAAGCCATCATCATCCTCCT<br>GCAAGCCATCGTCATCCTCCT | 18219 |
| bah27g02 | TTAAAATGGCGAGATTGCCCA<br>TTAAAATGGCCAGATTGCCCA | 18221 |
| bah27e02 | TCATAGTAGAGACTACTACTC<br>TCATAGTAGAAACTACTACTC | 18222 |
| bah27g02 | AATCTACACTGAACAACATGC<br>AATCTACACTAAACAACATGC | 18223 |
| bah27g02 | GCAAGCGGGCGGCGTTGCAAT<br>GCAAGCGGGCAGCGTTGCAAT | 18224 |
| bah27g02 | CCTTCTAGACTAGCACACAGA<br>CCTTCTAGACAAGCACACAGA | 18225 |
| bah27g02 | CCCAGGAAAACCTCTACGCAC<br>CCCAGGAAAAACTCTACGCAC | 18226 |
| bah27g02 | TCTCAAAATATAAACAACCCA<br>TCTCAAAATAGAAACAACCCA | 18227 |
| basd27m10 | TTGCTTCCTCATAAACCCAGT<br>TTGCTTCCTCGTAAACCCAGT | 18228 |
| basd23f16 | TTGCCGAGTCGGAGCAAAAGC<br>TTGCCGAGTCCGAGCAAAAGC | 18229 |

TABLE 23-10

| Clones | Haruna Nijo / H602 | SEQ. ID NO: |
|---|---|---|
| basd23f16 | TAATTTGCCGCGTTAGCTTGT<br>TAATTTGCCGTGTTAGCTTGT | 18230 |
| basd23f16 | TGGCCTCCATATTGCCGCCAC<br>TGGCCTCCATTTTGCCGCCAC | 18231 |
| basd23f16 | AGCACCTTGGAGCTGCTGAAC<br>AGCACCTTGGTGCTGCTGAAC | 18232 |
| basd23f16 | CATTGCATGTTTAGCACAACC<br>CATTGCATGTATAGCACAACC | 18233 |
| basd23f16 | TCGTATTCAGGATTCATTGCA<br>TCGTATTCAGAATTCATTGCA | 18234 |
| bah16i19 | ATACATTATCTTGAGTGACTA<br>ATACATTATCGTGAGTGACTA | 18235 |
| bah16i19 | GATTGTAGCAGTTAGATACAT<br>GATTGTAGCAATTAGATACAT | 18236 |
| bah16i19 | ATGATGCACAATTGCATCTCT<br>ATGATGCACATTTGCATCTCT | 18237 |
| bah16i19 | GTCTTTCTCTGGATAGAATAA<br>GTCTTTCTCTCGATAGAATAA | 18238 |
| BaH50I20 | GGCAAGTAGCAACATATGTCG<br>GGCAAGTAGCGACATATGTCG | 18239 |
| bah28b24 | CTGGTTGTCATCGGTAGCTCC<br>CTGGTTGTCACCGGTAGCTCC | 18241 |
| basd14h21 | CAAGTCATTTTACTTACTGAC<br>CAAGTCATTTAACTTACTGAC | 18252 |
| basd14h21 | GGGACGACAGATGACATCTTA<br>GGGACGACAGGTGACATCTTA | 18253 |
| basd14h21 | AATTTCACACATGTCATGGGA<br>AATTTCACACGTGTCATGGGA | 18254 |
| basd14h21 | GGGACTCTATGTCTCCCATCA<br>GGGACTCTATATCTCCCATCA | 18255 |
| basd14h21 | CAGAGCATTCTGAAAGCATCT<br>CAGAGCATTCGGAAAGCATCT | 18256 |
| basd14h21 | CTAACAATCCAAAGCTAAAG<br>CTAACAATCCGAAGCTAAAG | 18257 |
| basd14h21 | AGGCAATTTAAACACCACACG<br>AGGCAATTTATACACCACACG | 18258 |
| bags13g18 | CTCTAACCAGAGTCAGGATAT<br>CTCTAACCAGCGTCAGGATAT | 18262 |
| BaH15D23 | ACATTGCTTAAACACTATAGA<br>ACATTGCTTATACACTATAGA | 18263 |
| BaH15D23 | TTTCAGAATGCTGGAGGAATA<br>TTTCAGAATGTTGGAGGAATA | 18264 |
| BaGS33I07 | GAGTGTGGTAACGGTCACCCA<br>GAGTGTGGTAGCGGTCACCCA | 18266 |
| BaGS33I07 | GAGACTGTGATGCATTCAGCC<br>GAGACTGTGACGCATTCAGCC | 18267 |
| BaGS33I07 | ACCGCTTGCAGATGCCAACTA<br>ACCGCTTGCAAATGCCAACTA | 18268 |
| BaGS33I07 | AGTACCAATACCTCATAAGCA<br>AGTACCAATAGCTCATAAGCA | 18269 |

TABLE 23-11

| Clones | Haruna Nijo / H602 | SEQ. ID NO: |
|---|---|---|
| basd27b02 | TTGGCTTCAGGGCGGCATTCG<br>TTGGCTTCAGAGCGGCATTCG | 18270 |
| bags30n12 | GTACACACCCTGGGCTCTCAC<br>GTACACACCCGGGGCTCTCAC | 18271 |
| bags30n12 | CTTTGTCACCAAATCCAAGTT<br>CTTTGTCACCGAATCCAAGTT | 18272 |
| basd3h13 | TAAAGGCATCATTTAGCTAAT<br>TAAAGGCATCCTTTAGCTAAT | 18273 |
| BaGS37L19 | AGTAAAATGAATGAATTTACG<br>AGTAAAATGAGTGAATTTACG | 18274 |
| BaGS37L19 | GGGAAGTGATTTCTAGGCGCC<br>GGGAAGTGATGTCTAGGCGCC | 18275 |
| BaGS37L19 | GCTAGTTCTTAAAGAAAATCA<br>GCTAGTTCTTTAAGAAAATCA | 18276 |
| BaGS37L19 | TCAAGCATTGCGATGCATGTT<br>TCAAGCATTGTGATGCATGTT | 18277 |
| bags20i15 | TTATTGTTTGCGCTGCTGCAT<br>TTATTGTTTGTGCTGCTGCAT | 18279 |
| bags20i15 | TCAACGTTACCAAACACAAGT<br>TCAACGTTACAAACACAAGT | 18280 |
| bags20i15 | TACAGCCAATACAACTAGGAT<br>TACAGCCAATGCAACTAGGAT | 18281 |
| bags20i15 | GCTGCATTGTTCACCGACCGC<br>GCTGCATTGTCCACCGACCGC | 18282 |
| bags20i15 | GCATCACCAAAATTGAAGTAC<br>GCATCACCAACATTGAAGTAC | 18283 |
| bah56k07 | GCATACTTCACCGTTGCAGCG<br>GCATACTTCATCGTTGCAGCG | 18285 |
| bah56k07 | GTCGCAGTCTCGTTCATCATC<br>GTCGCAGTCTTGTTCATCATC | 18286 |
| bah56k07 | CCAAACTTCACGGCTTGCTGA<br>CCAAACTTCAGGGCTTGCTGA | 18287 |
| bags37d02 | CATTCAGGTTCTTTTTGTTCT<br>CATTCAGGTTTTTTTTGTTCT | 18288 |
| bags37d02 | TATTTTCCACGGTAAATGGGA<br>TATTTTCCACAGTAAATGGGA | 18289 |
| bags37d02 | GAAATGAGTCGAGCGATGGTA<br>GAAATGAGTCCAGCGATGGTA | 18290 |
| bags37d02 | ACAAAGATCAGCGGGGAGGAC<br>ACAAAGATCATCGGGGAGGAC | 18291 |
| bags37d02 | ATAAGCCACAGCAAAGACAGA<br>ATAAGCCACATCAAAGACAGA | 18292 |
| bags22l23 | ATGGTTTGGTGTTTAGGGCTG<br>ATGGTTTGGTTTTTAGGGCTG | 18295 |
| kr33a0901 | CGCTGCCCAAGGTCGAGCTAC<br>CGCTGCCCAATGTCGAGCTAC | 18296 |
| kr33a0901 | ATGGCTTCAACAAACGCCGCA<br>ATGGCTTCAAAAAACGCCGCA | 18297 |
| bast138C0606 | AGAGAAACGCTTCCTTTGGCC<br>AGAGAAACGCGTCCTTTGGCC | 18298 |

TABLE 23-12

| Clones | Haruna Nijo H6102 | SEQ ID NO: |
|---|---|---|
| bast138C0606 | AGATGTTGCATCTGTCGTACC<br>AGATGTTGCACCTGTCGTACC | 18299 |
| baak11J13 | GATTGGCTGACTCTTGCAAGG<br>GATTGGCTGATTCTTGCAAGG | 18300 |
| baak11j13 | TTCCCTTCCTGTCACCGGTTC<br>TTCCCTTCCTATCACCGGTTC | 18301 |
| bah58e19 | TATTTTTCAATAACCAAGGAC<br>TATTTTTCAACAACCAAGGAC | 18302 |
| BaGS31G22 | AGAAAGAGACATGACAAATCA<br>AGAAAGAGACGTGACAAATCA | 18303 |
| BaGS31G22 | ACGCTGATGGTGAATCCGGAC<br>ACGCTGATGGCGAATCCGGAC | 18304 |
| bah37h01 | CAGATAGCATGTGTAGCTTCT<br>CAGATAGCATTTGTAGCTTCT | 18305 |
| bah37h01 | CCACAGGTGGGTCACTATCCA<br>CCACAGGTGGTTCACTATCCA | 18306 |
| bah37h01 | TCAGGCCAAAGACGATCATCT<br>TCAGGCCAAAAACGATCATCT | 18307 |
| bah37h01 | TAGCCTAATAGAATTTTTAGT<br>TAGCCTAATATAATTTTTAGT | 18308 |
| baal29p13 | AGTTTTTTAGGTTTCACTTAG<br>AGTTTTTTAGATTTCACTTAG | 18309 |
| bags39a22 | CTCTTTTTCCCAGCCCCATAA<br>CTCTTTTTCCAAGCCCCATAA | 18310 |
| bah19g10 | GTATGCAGAGTGCTCCTGCCC<br>GTATGCAGAGCGCTCCTGCCC | 18311 |
| baal31a14 | TCGCTATGGCTGCAAAGAAGA<br>TCGCTATGGCGGCAAAGAAGA | 18312 |
| bah50g15 | AAGCTGAGGCAGCTCGCTCTT<br>AAGCTGAGGCTGCTCGCTCTT | 18313 |
| bah50g15 | TCCTTGTCCCGGTATTTTCTT<br>TCCTTGTCCCAGTATTTTCTT | 18314 |
| bah51m12 | TTGAATGAAGGTTTAAAAACT<br>TTGAATGAAGATTTAAAAACT | 18315 |
| bags18k22 | ACGATCTAACGCTGTACGAAA<br>ACGATCTAACACTGTACGAAA | 18316 |
| bags18k22 | CCTTCAGCGGTGCATCAGGTA<br>CCTTCAGCGGAGCATCAGGTA | 18317 |
| bags20n21 | CCTTTCCATCAGAGAATATGT<br>CCTTTCCATCGGAGAATATGT | 18318 |
| basd17o21 | CCCGATCTGCATAACCAAGAA<br>CCCGATCTGCGTAACCAAGAA | 18319 |
| basd17o21 | TCAAAAGTGACGGAAAGAAAA<br>TCAAAAGTGATGGAAAGAAAA | 18320 |
| bah37g17 | AAAATTGGACAAGGTTCTCTA<br>AAAATTGGACGAGGTTCTCTA | 18321 |
| bags30l22 | AGTAAGAAACATCAGCTAATA<br>AGTAAGAAACGTCAGCTAATA | 18322 |
| bags30l22 | GCTTCTTCTATGGTTGCATAT<br>GCTTCTTCTACGGTTGCATAT | 18323 |

TABLE 23-13

| Clones | Haruna Nijo H602 | SEQ ID NO: |
|---|---|---|
| bags30l22 | ATCTAGGATTCATCCCTTCCT<br>ATCTAGGATTTATCCCTTCCT | 18324 |
| bast72G0113 | CTTCCCATACGGACAGCACAA<br>CTTCCCGTACAGACAGCACAA | 18327 |
| bast72G0113 | TTAGCTTCCCATACGGACAGC<br>TTAGCTTCCCGTACAGACAGC | 18328 |
| BaH30B05 | CATGCTTCCGCTCAGATAATG<br>CATGCTTCCGTTCAGATAATG | 18329 |
| BaH60B14 | ACCCCTCCCTACCCAACCTGC<br>ACCCCTCCCTCCCCAACCTGC | 18330 |
| BaH60B14 | TTGCAATATGGGACCTTACAT<br>TTGCAATATGTGACCTTACAT | 18331 |

TABLE 23-13-continued

| Clones | Haruna Nijo H602 | SEQ ID NO: |
|---|---|---|
| BaH60B14 | CTGCACCTGATCTGCATGTCT<br>CTGCACCTGACCTGCATGTCT | 18332 |
| BaH17B16 | CAAAAAGATACGAGTGTTTGT<br>CAAAAAGATATGAGTGTTTGT | 18333 |
| basd12n23 | AGTTCGGCAGCTTTGTTGCCA<br>AGTTCGGCAGTTTTGTTGCCA | 18334 |
| basd12n23 | AAACGATGGAGATTAATCGTG<br>AAACGATGGAAATTAATCGTG | 18335 |
| basd12n23 | GATGTAGCAGATGATCTTACA<br>GATGTAGCAGTTGATCTTACA | 18336 |
| basd12n23 | GATGACATTTCACATGTCATT<br>GATGACATTTTACATGTCATT | 18337 |
| basd12n23 | CCTTGAGTTTCTTGCAAATAA<br>CCTTGAGTTTATTGCAAATAA | 18338 |
| basd12n23 | GATTCACTGGTCCATTCGGAT<br>GATTCACTGGCCCATTCGGAT | 18339 |
| basd12n23 | CAACAGCTTGTTCAGTGGTGC<br>CAACAGCTTGATCAGTGGTGC | 18340 |
| basd12n23 | TTGTGCGGACTTCAACAGCTT<br>TTGTGCGGACATCAACAGCTT | 18341 |
| bah61a21 | GCTATTTTATATCAATGATGA<br>GCTATTTTATCTCAATGATGA | 18342 |
| baak19h17 | TTCTAATCAGTGGTATAATAG<br>TTCTAATCAGGGGTATAATAG | 18343 |
| baak19h17 | GTCGTGCAGAGCGCCGTTTGT<br>GTCGTGCAGAGCGCCGTTTGT | 18344 |
| bah47H2 | AAGAGTTAGGAAAGAAGAGGC<br>AAGAGTTAGGCAAGAAGAGGC | 18345 |
| bah47l12 | AGCAGCGAGAAGACAGCTGGA<br>AGCAGCGAGAAGACAGCTGGA | 18346 |
| baak18p11 | AGCTGGCGTTTGATCTGTTGA<br>AGCTGGCGTTGGATCTGTTGA | 18347 |
| baak18p11 | ACAACAGAGAGATTATCACAA<br>ACAACAGAGAAATTATCACAA | 18348 |
| baak18p11 | AAAAGTTCTTCCTTTTAATCC<br>AAAAGTTCTTTCTTTTAATCC | 18349 |
| baak18p11 | TGGATCTGCTAGTGCTGGCGC<br>TGGATCTGCTGGTGCTGGCGC | 18350 |

TABLE 23-14

| Clones | Haruna Nijo H602 | SEQ ID NO: |
|---|---|---|
| baet29h0715 | CCTCCTTGGCCGCCGCGGATA<br>CCTCCTTGGCTGCCGCGG-TA | 18351<br>18352 |
| BaH13D11 | GAAATCCTTCAGCATAGTTTG<br>GAAATCCTTCGGCATAGTTTG | 18353 |
| BaH13D11 | GTCTCAGACAAGGTACTTCCA<br>GTCTCAGACACGGTACTTCCA | 18354 |
| BaH13D11 | ACAGTACACACCGACTGAATA<br>ACAGTACACAACGACTGAATA | 18355 |

TABLE 23-14-continued

| Clones | Haruna Nijo H602 | SEQ ID NO: |
|---|---|---|
| BaH13D11 | ATAGAAGCACAATTGTTGAGA<br>ATAGAAGCACGATTGTTGAGA | 18356 |
| baet39D1107 | GACCGCCAACATTAGCGCGCC<br>GACCGCCAACGTTAGCGCGCC | 18357 |
| BaH53E15 | TATTAAGCTATGAAAAATATT<br>TATTAAGCTATGAAAAATATT | 18358 |
| bags32o15 | TTACTGCGACGCACGCACAGA<br>TTACTGCGACCCACGCACAGA | 18359 |
| bags32o15 | TAGAGTCGCGGCATCTTTTGT<br>TAGAGTCGCGCCATCTTTTGT | 18360 |
| bags32o15 | GTCTTACACCAGATACTTGGG<br>GTCTTACACCCGATACTTGGG | 18361 |
| bast48a0701 | AAGCTAGCAGCTCTCAAGGAC<br>AAGCTAGCAGGTCTCAAGGAC | 18362 |
| bast62d0907 | GTACTAGGGACACCTCCCACA<br>GTACTAGGGAGACCTCCCACA | 18363 |
| bast62d0907 | ACAGCGCACAGCGAGACGACG<br>ACAGCGCACACCGAGACGACG | 18364 |
| bah45p22 | TCTGTGCTCACATGGAATGGG<br>TCTGTGCTCATATGGAATGGG | 18365 |
| bah45p22 | AATATGAAAATGAGAAGTAAC<br>AATATGAAAACGAGAAGTAAC | 18366 |
| bags32H6 | CAAAAAACTACCACGAGCAGA<br>CAAAAAACTAACACGAGCAGA | 18367 |
| baak30j05 | AACTAAAATACACTTTAACGG<br>AACTAAAATATACTTTAACGG | 18368 |
| baak30j05 | GTCTCTGACGAGCATTCATGA<br>GTCTCTGACGGGCATTCATGA | 18369 |
| bah52a14 | TTTCTCATCGATATCTCCCGA<br>TTTCTCATCGGTATCTCCCGA | 18370 |
| bah52a14 | TGTAACTTGGAACCACTCTTG<br>TGTAACTTGGCACCACTCTTG | 18371 |
| bah58i22 | AGGTGTGTATGAAATACCACT<br>AGGTGTGTATCAAATACCACT | 18372 |
| BaH56L16 | GTTTAGACTGAACAGCAAAGC<br>GTTTAGACTGGACAGCAAAGC | 18373 |
| BaH56L16 | TTTCTTTTTCCAATCCAGAAA<br>TTTCTTTTTCAAATCCAGAAA | 18374 |
| bah52a21 | CTGAAATTATTTTACTAACAT<br>CTGAAATTATATTACTAACAT | 18375 |
| bah52a21 | CCATAGATTTAGGTGACTGGA<br>CCATAGATTTGGGTGACTGGA | 18376 |

TABLE 23-15

| Clones | Haruna Nijo H602 | SEQ ID NO: |
|---|---|---|
| bah52a21 | ATAATATTAACACCTTGATAT<br>ATAATATTAAAACCTTGATAT | 18377 |
| basd14g11 | AACAACAGTTCCTGTTGACAG<br>AACAACAGTTGCTGTTGACAG | 18378 |

TABLE 23-15-continued

| Clones | Haruna Nijo H602 | SEQ ID NO: |
|---|---|---|
| bags6a03 | ACAAGAGGCAGATAAATTGAG<br>ACAAGAGGCACATAAATTGAG | 18379 |
| bast72e0109 | TTTTTTTTTATTTTTTTTTT<br>TTTTTTTTTTTTTTTTTTTT | 18380 |
| bags21a21 | CCTGGATCATTGCATAGATGT<br>CCTGGATCATAGCATAGATGT | 18381 |
| bags21a21 | AGTTGGGGTGCAACTCTGATA<br>AGTTGGGGTGTAACTCTGATA | 18382 |
| bags21a21 | CTACTTGGGTGTAAAGGTGTT<br>CTACTTGGGTATAAAGGTGTT | 18383 |
| bah58p13 | CTACATAGAAGCATGCAGGTG<br>CTACATAGAAACATGCAGGTG | 18384 |
| bah58p13 | TCGGAGGGAGAATTATAATTT<br>TCGGAGGGAGTATTATAATTT | 18385 |
| bah58p13 | TGTATGCCAACCGTACCTTCT<br>TGTATGCCAATCGTACCTTCT | 18386 |
| bah27n22 | GTACAAAATATCATACATATA<br>GTACAAAATACCATACATATA | 18387 |
| bags20c13 | GGTTATTGCACATAAAGTGA<br>GGTTATTGCAAATAAAGTGA | 18388 |
| bags20c13 | AACAAATGCAGGAGTTGCAGA<br>AACAAATGCATGAGTTGCAGA | 18389 |
| bags20c13 | GATATGTTCCCATGCATTTTT<br>GATATGTTCCGATGCATTTTT | 18390 |
| bags20c13 | TTTATCTCGTTATATGACGCT<br>TTTATCTCGTCATATGACGCT | 18391 |
| bags30i14 | TCGCACGCCGACTCAATTTTA<br>TCGCACGCCGTCTCAATTTTA | 18392 |
| bass30i14 | GATACGGAATCTACCTCTCAG<br>GATACGGAATTTACCTCTCAG | 18393 |
| bags30i14 | GCTCGTCCGGATGGATACGGA<br>GCTCGTCCGGTTGGATACGGA | 18394 |
| BaAK17E11 | GCGTAAGTAGGTCATCAAAAC<br>GCGTAAGTAGAGTCATCAAAAC | 18395 |
| BaAK17E11 | GAAATCCTTCAGCATAGTTTG<br>GAAATCCTTCGGCATAGTTTG | 18396 |
| baal10l01 | CACCACTAAG-GACAGACCAC<br>CACCACTAAGAGACAGACCAC | 18399<br>18400 |
| baal10l01 | TGCGAAATCTCTGGTTCCTGA<br>TGCGAAATCTTTGGTTCCTGA | 18401 |
| baak26e17 | AAAGCACAATGGACTATCTCG<br>AAAGCACAATAGACTATCTCG | 18402 |
| baak26e17 | TATCTCCAGATGAGGTGATAC<br>TATCTCCAGACGAGGTGATAC | 18403 |
| bags32d21 | CTTCCTTTTCACCTTATAACG<br>CTTCCTTTTCGCCTTATAACG | 18407 |

TABLE 23-16

| Clones | Haruna Nijo H602 | SEQ ID NO: |
|---|---|---|
| bags32d21 | CTCTTTCCAGCAGTTTGGTCC<br>CTCTTTCCAGAAGTTTGGTCC | 18408 |
| bags32d21 | GTTAAGCAGGTGCTGGATCCT<br>GTTAAGCAGGGGCTGGATCCT | 18409 |
| bah54j22 | TAACTGACTTCTACAAGAAAA<br>TAACTGACTTTTACAAGAAAA | 18410 |
| bah54j22 | AGATTATTGAACGGACCACAT<br>AGATTATTGATCGGACCACAT | 18411 |
| bah54j22 | GCCAAAACTAAGAGAGGACGA<br>GCCAAAACTATGAGAGGACGA | 18412 |
| bah54j22 | GTTGGTGTCATAGAAGATTAT<br>GTTGGTGTCACAGAAGATTAT | 18413 |
| bah54j22 | TTTTGGAGCAATGACACGAGC<br>TTTTGGAGCACTGACACGAGC | 18414 |
| bah13f11 | GCTTATTGGTAAACTGCATCA<br>GCTTATTGGTGAACTGCATCA | 18417 |
| baal4f01 | AAACGCACTCGTGGCCCACAC<br>AAACGCACTC-TGGCCCACAC | 18421<br>18422 |
| baal4f01 | AAACTCTAAGTTGGGAGACCA<br>AAACTCTAAGATGGGAGACCA | 18423 |
| baal4f01 | CTCGATTGGCATGGGATCAAC<br>CTCGATTGGCNTGGGATCAAC | 18424 |
| baal4l21 | TCTTCGCTTTTTGATTGATGG<br>TCTTCGCTTTCTGATTGATGG | 18426 |
| BaAK31O14 | CAGCTCATCCGCATCGCTGGA<br>CAGCTCATCCACATCGCTGGA | 18428 |
| baafl3d17 | TCCACACGATTTCAGCAACTT<br>TCCACACGATCTCAGCAACTT | 18430 |
| baal13d17 | TGAGCCCCTGGGCGAGCGTGC<br>TGAGCCCCTGCGCGAGCGTGC | 18431 |
| baal13d17 | AGGCTTCAGAATGGCCGTTTG<br>AGGCTTCAGAGTGGCCGTTTG | 18432 |
| baal13d17 | GCTTATTTCCCCACGGGTTCT<br>GCTTATTTCGAGACCCGTTCT | 18433 |
| bags22j12 | CCCACGCACAATTCGGAAGCA<br>CCCACGCACAGTTCGGAAGCA | 18434 |
| bags33p05 | AAGACGCCATGTCAGAATAAG<br>AAGACGCCATATCAGAATAAG | 18435 |
| bags33p05 | CAAAATGACCGAACACATGAA<br>CAAAATGACCAAACACATGAA | 18436 |
| bags33p05 | TTCGATCACTTCTCAGATCAT<br>TTCGATCACTCCTCAGATCAT | 18437 |
| bags33j07 | TCGGGTTCAGACATGCAATGA<br>TCGGGTTCAGGCATGCAATGA | 18438 |
| bags15d19 | TGCCACGGCTGCCGTAAGGGT<br>TGCCACGGCTACGGTAAGGGT | 18441 |
| bah57o03 | AAAAGAACTTTATGTTGTCGC<br>AAAAGAACTTCATGTTCTCGC | 18447 |
| bah57o03 | GGATTGGGCAAAGATGATATT<br>GGATTGGGCACAGATGATATT | 18448 |

TABLE 23-17

| Clones | Haruna Nijo H602 | SEQ ID NO: |
|---|---|---|
| BaAK12F04 | CTTGAAAACTCTGGCAGTATC<br>CTTGAAAACTATGGCAGTATC | 18454 |
| BaAK12F04 | TATGGTACAACAGAAACAATT<br>TATGGTACAATAGAAACAATT | 18455 |
| BaAK12F04 | TAAACCGACCCTTGATGTAGC<br>TAAACCGACCATTGATGTAGC | 18456 |
| bah53j16 | GCTCGAGTCTCAATCGTCTCC<br>GCTCGAGTCTAAATCGTCTCC | 18457 |
| bah53j16 | TTCATTCATCTGTTCTAACAC<br>TTCATTCATCGGTTCTAACAC | 18458 |
| bah53j16 | CTCCTAGGGACTCAAGACCCT<br>CTCCTAGGGATTCAAGACCCT | 18459 |
| BaSD2E24 | TCTCTCTTTTTCAGCATGAAG<br>TCTCTCTTTTCCAGCATGAAG | 18460 |
| BaSD2E24 | CGTAATCTTAAGATTCATATA<br>CGTAATCTTAGGATTCATATA | 18461 |
| bags39h08 | AGGATCTAGCGATACACCGTT<br>AGGATCTAGCAATACACCGTT | 18462 |
| basd1n02 | TGGCGGACGCGCCGTCGCGCA<br>TGGCGGACGCACCGTCGCGCA | 18463 |
| bags20m21 | CGCACACGGGTTGCAGTTCAC<br>CGCACACGGGGTGCAGTTCAC | 18464 |
| baat10h19 | GGATACCAAGAGTCCTGGAGA<br>GGATACCAAGGGTCCTGGAGA | 18465 |
| basd12m11 | CTTGCATACCTCTTACCGATT<br>CTTGCATACCGCTTACCGATT | 18466 |
| basd12m11 | ATTAGCATTTTTCTTAACATC<br>ATTAGCATTTCTGTTAACATG | 18467 |
| bah29d24 | CCTCCCTGCTTCTTTGCTGGC<br>CCTCCCTGCTGCTTTGCTGGC | 18468 |
| bah29d24 | TTACATACCTACCCCCCTCCT<br>TTACATACCTTCCCCCCTCCT | 18469 |
| BaGS39P09 | CAGATATTCTAAGCTAGATTA<br>CAGATATTCTGAGCTAGATTA | 18470 |
| BaGS39P09 | ATCCCTGTCGACATATCTTGG<br>ATCCCTGTCGCCATATCTTGG | 18471 |
| BaGS31F17 | CATGGGTGCCAATGAGCCCAA<br>CATGGGTGCCGATGAGCCCAA | 18472 |
| BaGS23D08 | ATTGAGTGATTGGTCTATGAC<br>ATTGAGTGATGGGTCTATGAC | 18473 |
| BaGS23D08 | CGTCACCAAATTGTCAGAAA<br>CGTCACCAAACTGTCAGAAA | 18474 |
| bags39d15 | ATGGTTGGAGCGCGACGCTGG<br>ATGGTTGGAGTGCGACGCTGG | 18475 |
| BaGS34I17 | ACCACAAAAATTCTGGCTTTC<br>ACCACAAAAAATCTGGCTTTC | 18476 |
| BaGS34I17 | ATGCATGATCCGTGTTGCCTG<br>ATCCATGATCTGTGTTGCCTG | 18477 |
| BaH32N02 | GCTGCCTGGAGGCAATTTTCC<br>GCTGCCTGGAAGCAATTTTCC | 18478 |

TABLE 23-18

| Clones | Haruna Nijo H602 | SEQ ID NO: |
|---|---|---|
| BaSD18H19 | CACGATCTATACATGTGTTCC<br>CACGATCTATGCATGTGTTCC | 18479 |
| bast63A0101 | GGCCCGAGTGGTTGCGATGCA<br>GGCCCGAGTGATTGCGATGCA | 18480 |
| BaH50N04 | GAGCGGCGCGCGGTACGGTGG<br>GAGCGGCGCGTGGTACGGTGG | 18481 |
| BaH50N04 | GTACGTAGCTTGCTTGGTCGC<br>GTACGTAGCTCGCTTGGTCGC | 18482 |
| baal4a13 | TATCGTATTGAGTGCTTTTCA<br>TATCGTATTGTGTGCTTTTCA | 18483 |
| baal4a13 | TTTATCAGCTGTGCATAAGTT<br>TTTATCAGCTTTGCATAAGTT | 18484 |
| baal4a13 | GAATGGATGACAACCACGATG<br>GAATGGATGAGAACCACGATG | 18485 |
| baal4a13 | TACCAGAACAGATGTCATTTT<br>TACCAGAACAAATGTCATTTT | 18486 |
| baal41118 | GCCATCTAATAGTATTAGCAT<br>GCCATCTAATGGTATTAGCAT | 18487 |
| baal41118 | TCCTCTTTCTTCCTTCTCCTT<br>TCCTCTTTCTCCCTTCTCCTT | 18488 |
| baal41118 | ATATCTATTCGCAGGTAAGAC<br>ATATCTATTCACAGGTAAGAC | 18489 |
| baal41118 | TTAAACAGGAAAGATAGAGAG<br>TTAAACAGGAGAGATAGAGAG | 18490 |
| baal41118 | GTGTTACTGGTTACTTATCAT<br>GTGTTACTGGGTACTTATCAT | 18491 |
| baal41118 | GTACTAHCAGTTAGCCGCCAT<br>GTACTACCAGGTAGCCGCCAT | 18492 |
| baal41118 | ATAGAGAGAGTTTTATTTATA<br>ATAGAGAGAGGTTTATTTATA | 18493 |
| baal41118 | TTGACAACTAGTTATATCTAT<br>TTGACAACTAATTATATCTAT | 18494 |
| baal27e20 | AAATGCATGTAAAGCACCAGC<br>AAATGnATGTGAAGCACCAGC | 18497 |
| baal27e20 | TCAGCTGGCAAGCTTGAAGGC<br>TCAGCTGGCATGCTTGAAGGC | 18498 |
| baal27e20 | GTTGCGTTTTCTCACCATCTT<br>GTTGCGTTTTTTCACCATCTT | 18499 |
| baal27e20 | GCCTACTTACCGTGATGAAAA<br>GCCTACTTACTGTGATGAAAA | 18500 |
| bags37116 | CAGCACCAGGAGATGATGCAT<br>CAGCACCAGGGGATGATGCAT | 18501 |
| baak34o06 | TCGGAAGAGTAAATGTATCTT<br>TCGGAAGAGTGAATGTATCTT | 18502 |
| baak34o06 | TGATCACAGCAGTGAGGATTC<br>TGATCACAGCCGTGAGGATTC | 18503 |
| baak34o06 | CATCTTTGGAGCATGCTACAG<br>CATCTTTGGAACATGCTACAG | 18504 |
| baak34o06 | CGACAACTAACTCCGGACGGA<br>CGACAACTAATTCCGGACGGA | 18505 |

TABLE 23-19

| Clones | Haruna Nijo H602 | SEQ ID NO: |
|---|---|---|
| baak34o06 | ATCGGCGATACGATATTACAT<br>ATCGGCGATATGATATTAGAT | 18506 |
| baal30i11 | TATTGGTCAACTTTATACTAC<br>TATTGGTCAAATTTATACTAC | 18507 |
| BaH62C15 | GAATTAACTCCTGCCCCTCCT<br>GAATTAACTCTTGCCCCTCCT | 18508 |
| baak16l19 | TGCGCCACCGTCTCCGGGTTG<br>TGCGCCACCGCCTCCGGGTTG | 18512 |
| kr41h0315 | GTCGCTGTTCCGTCTGTGGAA<br>GTCGCTGTTCAGTCTGTGGAA | 18514 |
| bah62i23 | TTCCACAGACGGAACAGCGAC<br>TTCCACAGACTGAACAGCGAC | 18515 |
| bah52i24 | CGTCTGGTGATTCTGCCTTTG<br>CGTCTGGTGACTCTGCCTTTG | 18516 |
| bastl33a0301 | CGTCTGGTGACTCTGCCTTTG<br>CGTCTGGTGATTCTGCCTTTG | 18517 |
| bastl56A0301 | TGCCACTACAAGTATATGCAG<br>TGCCACTACAGGTATATGCAG | 18519 |
| baal39a03 | ACTCAAGCTTCCATTTTTTCT<br>ACTCAAGCTTGCATTTTTTCT | 18520 |
| baal39a03 | CTTTCTCTGACGAAGAAACAA<br>CTTTCTCTGAAGAAGAAACAA | 18521 |
| baal39a03 | GTGGTATATTTTCCAAACTCA<br>GTGGTATATTCTCCAAACTCA | 18522 |
| baal39a03 | TCTCACAATCCCTGATATGTT<br>TCTCACAATCGCTGATATGTT | 18523 |
| baal39a03 | ATGCACATTTTCCGTGCGCGC<br>ATGCACATTTACCGTGCGCGC | 18524 |
| baal39a03 | ATTGTCGGGGAAAAATGTATG<br>ATTGTCGGGGGAAAATGTATG | 18525 |
| baak34l03 | TTCTTAGACATGCATTATGTG<br>TTCTTAGACACGCATTATGTG | 18527 |
| baak34l03 | TGCACATGAAGGAAATAGATG<br>TGCACATGAAAGAAATAGATG | 18528 |
| baak34l03 | ATGTCTGTTGATGTACTTGTG<br>ATGTCTGTTGGTGTACTTGTG | 18529 |
| baak34l03 | CATGGAAGTTCTCATAGGGAT<br>CATGGAAGTTTTCATAGGGAT | 18530 |
| baak34l03 | TACATCTATACAATGTCATGG<br>TACATCTATATAATGTCATGG | 18531 |
| baak34l03 | GTGATAAATTTTCTGTGTCAT<br>GTGATAAATTCTCTGTGTCAT | 18532 |
| baak34l03 | TAAACAAGAAAAGCTTGATG<br>TAAACAAGATAAGCTTGATG | 18533 |
| BaSD20J15 | ACTATGTATGCACAGACGCGC<br>ACTATGTATGTACAGACGCGC | 18534 |
| bastl30f0711 | CACAAACAAACGGGACCCCCA<br>CACAAACAAAGGGGACCCCCA | 18535 |
| bastl30f0711 | GTTTGCTTATATACTATACAC<br>GTTTGCTTATTTACTATACAC | 18536 |

TABLE 23-20

| Clones | Haruna Nijo H602 | SEQ ID NO: |
|---|---|---|
| bast56G0713 | ACCAGAAGCTCTCTACTACCA<br>ACCAGAAGCTTTCTACTACCA | 18539 |
| bast56G0713 | CAGCCGAACCCCTGGCTGGCT<br>CAGCCGAACCCGCTGGCTGGCT | 18540 |
| bast102H0715 | GATTTGGCATCAATGTTACAA<br>GATTTGGCATTAATGTTACAA | 18543 |
| bast102H0715 | GTGTCAAAGGAAACTCCAAAA<br>GTGTCAAAGGGAACTCCAAAA | 18544 |
| bags8i05 | CACCGCACCGACTTTCTCGTT<br>CACCGCACCGGCTTTCTCGTT | 18545 |
| basd18m04 | GGCGACGCCGGAACCAACGAA<br>GGCGACGCCGAAACCAACGAA | 18547 |
| bah28g01 | CGTAGTCTTCCGGTGTTAGTG<br>CGTAGTCTTCAGGTGTTAGTG | 18550 |
| basd1m13 | ACGGCAAACCGAGACGAGAAC<br>ACGGCAAACCCAGACGAGAAC | 18551 |
| bags37h19 | AAGAAGGATATCTATGAGACG<br>AAGAAGGATAACTATGAGACG | 18552 |
| bags37h19 | TGTGTGTGTGATGATCGGTTT<br>TGTGTGTGTGGTGATCGGTTT | 18553 |
| bags37h19 | CTACGTCACCAACGACAGAAA<br>CTACGTCACCGACGACAGAAA | 18554 |
| bah21a10 | GATGCCTCCTGGCCCTCGGCG<br>GATGCCTCCTCGCCCTCGGCG | 18556 |
| bah21a10 | CTCAGTCTCAGACCACACCTA<br>CTCAGTCTCAAACCACACCTA | 18557 |
| bags23d06 | AAAATCAATACTAAATACTCC<br>AAAATCAATATTAAATACTCC | 18558 |
| BaGS19G10 | TTTGCTTCACACCGGGGTTCT<br>TTTGCTTCACGCCGGGGTTCT | 18560 |
| bah11b24 | TCAAAAAGCAGAAGTGGGCTC<br>TCAAAAAGCAAAAGTGGGCTC | 18561 |
| bah11b24 | TAAGAAAGCTATGTATCAGCA<br>TAAGAAACCTCTGTATCAGCA | 18562 |
| bah11b24 | TACAAACAGTGAATAAGCCTG<br>TACAAACAGTAAATAAGCCTG | 18563 |
| bah11b24 | CAGGAAGTTCGTGCAGATTGC<br>CAGGAAGTTGTTGGAGATTGC | 18564 |
| bah11b24 | ATAATAATAGTTCAAACAGGG<br>ATAATAATAGCTCAAACAGGG | 18565 |
| bah11b24 | GTGGGCTCCGATGTATGTAAC<br>GTGGGCTCCGGTGTATGTAAC | 18566 |
| bah11b24 | TTAACACTTGATTACTGGTGA<br>TTAACACTTGGTTACTGGTGA | 18567 |
| bah11b24 | ATAAGCCTGTAATCTAGATAT<br>ATAAGCCTGTGATCTAGATAT | 18568 |
| bast39d0408 | TGAGTTTGTATTGCTGCAAAT<br>TGAGTTTGTACTGCTGCAAAT | 18569 |
| bast39d0408 | TGCTACAATACAAATGGAATG<br>TGCTACAATATAAATGGAATG | 18570 |

TABLE 23-21

| Clones | Haruna Nijo H602 | SEQ ID NO: |
|---|---|---|
| bast39d0408 | GAATGATCGCATAGCGAGAAC<br>GAATGATCGCGTAGCGAGAAC | 18571 |
| bast39d0408 | CAATAATCGCGAGTTGGTGCA<br>CAATAATCGCAAGTTGGTGCA | 18572 |
| baak33e08 | TGAGAAACACAGCAAACGATG<br>TGAGAAACACGGCAAACGATG | 18573 |
| BaAL33B08 | ACTCAAATTGAACGGTCAGTA<br>ACTCAAATTGCACGGTCAGTA | 18575 |
| BaAL33B08 | CGTTCACTGTATACGGGCCAA<br>CGTTCACTGTGTACGGGCCAA | 18576 |
| BaAL33B08 | CCTCGGTCTCTCCTTGTCTCT<br>CCTCGGTCTCCCCTTGTCTCT | 18577 |
| BaAL33B08 | CGGTCAGTAACTGTGTCTCCG<br>GGGTCAGTAATTGTGTCTCGG | 18578 |
| bags39e12 | TGAGTACACTTATTAACCTGT<br>TGAGTACACTCATTAACCTGT | 18579 |
| bags39e12 | ACAGAGCTTCAGATAATTGGT<br>ACAGAGCTTCTGATAATTGGT | 18580 |
| bags39e12 | TGTCAATCAATGACTTGTACT<br>TGTCAATCAAGGACTTGTACT | 18581 |
| bags39e12 | TTCAGCAAGTCATTGAAGTGT<br>TTCAGCAAGTAATTGAAGTGT | 18582 |
| bags39e12 | ATCACGTGCCCGCAACCGCCA<br>ATCACGTGCCTGCAACCGCCA | 18583 |
| bags33n09 | ACCTTCCAATAAATTTAGTT<br>ACCTTCCAATGAAATTTAGTT | 18586 |
| baal32h09 | ACTTGGCCAGTGGTCACAGCA<br>ACTTGGCCAGNGGTCACAGCA | 18587 |
| baal32h09 | CACCACCTGATCATCAGATTG<br>CACCACCTGACCATCAGATTG | 18588 |
| baal32h09 | CCGAGTCCGGTTGATTCTGGC<br>CCGAGTCCGGNTGATTCTGGC | 18589 |
| baal32h09 | GATTCTGGCGGGCTCCTGCTC<br>GATTCTGGCGAGCTCCTGCTC | 18590 |
| BaAK20017 | ACTGCCCTCCGTCCTTTTACG<br>ACTGCCCTCCCTCCTTTTACG | 18591 |
| BaAK20017 | GGAGTAGTTTGCAACACTGCC<br>GGAGTAGTTTACAACACTGCC | 18592 |
| BaAK20017 | ATTTCTAAAATGTCTTATATT<br>ATTTCTAAAGGTCTTATATT | 18593 |
| bags32g10 | CCGCATTCTCCCCTTCAAACA<br>CCGCATTCTCTCCTTCAAACA | 18594 |
| baet33E1210 | GAGCTCGTGCCGCTGCCGTCA<br>GAGCTCGTGCGGCTGCCGTCA | 18595 |
| baet33E1210 | GCCCGTGTGGGCACTGGGCAC<br>GCCCGTGTGGACACTGGGCAC | 18596 |
| bah50o08 | TTGATTCCTGCAGCCTTTTCC<br>TTGATTCCTGTACCCTTTTCC | 18597 |
| bah50o08 | CCGGCATCTCCGGTACTGCTT<br>CCGGCATCTCTGGTACTGTTT | 18598 |

TABLE 23-22

| Clones | Haruna Nijo / H602 | SEQ ID NO: |
|---|---|---|
| bah50o08 | GATTCCTGCAGCCTTTTCCTG<br>GATTCCTGTACCCTTTTCCTG | 18599 |
| bast46F0711 | ATAACCCTACGACTCAGAAGG<br>ATAACCCTACAACTCAGAAGG | 18600 |
| bast46F0711 | GCCGACCCCGATACTAGCACG<br>GCCGACCCCGTTACTAGCACG | 18601 |
| bast46F0711 | GAGAGCAGGAAATATCTATCA<br>GAGAGCAGGACATATCTATCA | 18602 |
| bast46F0711 | ATCTATCATTTCAGGCCAAAT<br>ATCTATCATTCCAGGCCAAAT | 18603 |
| bah16f05 | TATCTCCTGGCCAGCGTTTT<br>TATCTCCTGGGACAGCGTTTT | 18604 |
| bah16f05 | GGAGCGTCAGGAACTGATTCA<br>GGAGCGTCACAAACTGATTCA | 18605 |
| bah13o11 | GCACCGTAGCGGAGGACATCC<br>GCACCGTAGCAGAGGACATCC | 18607 |
| basd27i13 | AAACTGTTACTCTACCGAACA<br>AAACTGTTACGCTACCGAACA | 18609 |
| basd27i13 | CTAGGATCTCGGTCAGCAGCT<br>CTAGGATCTCAGTCAGCAGCT | 18610 |
| bags26e20 | AAATGCTTCAAAAAGATATCA<br>AAATGCTTCACAAAGATATCA | 18613 |
| bags26e20 | GCGTGCATGTCACCAGTATAG<br>GCGTGCATGTTACCAGTATAG | 18614 |
| bags26e20 | CATCAAGAACGGTATGAACCA<br>CATCAAGAACAGTATGAACCA | 18615 |
| baet45g1214 | ACATAACATATTCCGTATACG<br>ACATAACATAGTCCGTATACG | 18616 |
| baet45g1214 | ATTACACATGCCACATAACAT<br>ATTACACATGTCACATAACAT | 18617 |
| basd13j22 | CCCTGCGGCAGTTGTTCCTCA<br>CCCTGCGGCAATTGTTCCTCA | 18619 |
| baak46e10 | GGGCGGCCCAGGTTCCAGGGG<br>GGGCGGCCCATGTTCCAGGGG | 18620 |
| baak46e10 | CCGACGGAACCAAACAATCAG<br>CCGACGGAACAAAACAATCAG | 18621 |
| baak46e10 | TAATACGAGGACACGTGTG<br>TAATACGACGACACGTGTG | 18622 |
| bastE5f0812 | AAAGGGTTATGAAATTACCC<br>AAAGGGTTAGGAAATTACCC | 18623 |
| baak44i12 | CGAGCGATCCGAAGGTGTTCT<br>CGAGCGATCCAAAGGTGTTCT | 18632 |
| bah21j03 | AACGTGTCTCATTCCAGCTTC<br>AACGTGTCTCGTTCCAGCTTC | 18633 |
| bah21j03 | TCAGTCCCGAAGCAGAGGAA<br>TCAGTCCCGTAGCAGAGGAA | 18634 |
| bah21j03 | TGAGTCTTCAAGACAGAGTGT<br>TCACTCTTCAGGACAGAGTGT | 18635 |
| bah21j03 | ACCTCTCAGCTTCAAGCATCG<br>ACCTCTCAGCCTCAAGCATCG | 18636 |

TABLE 23-23

| Clones | Haruna Nijo / H602 | SEQ ID NO: |
|---|---|---|
| kr71b0103 | HGCGCGTCCTTGCCGGCAAGG<br>CGCGCGTCCTCGCCGGCAAGG | 18637 |
| baak21p23 | CTACTTTATCCACATGCTGCG<br>CTACTTTATCAACATGCTGCG | 18639 |
| baak21p23 | AATACATCAGACCCTGAGCTA<br>AATACATCAGCCCCTGAGCTA | 18640 |
| bags6g09 | AAAAGGAAAATCAACACATGA<br>AAAAGGAAAAGCAACACATGA | 18641 |
| BaSD15M02 | GGCCGATAGCAGGGATCCCAG<br>GGCCGATAGCGGGGATCCCAG | 18642 |
| basd13f02 | ATGCCTGTACATGGACACCAG<br>ATGCCTGTACTTGGACACCAG | 18643 |
| basd13f02 | AAGCTCATATGAAGTTAATCA<br>AAGCTCATATAAAGTTAATCA | 18644 |
| basd13f02 | GGTCAAACCATCAAAAAGATT<br>GGTCAAACCACCAAAAAGATT | 18645 |
| basd13f02 | TTACTCCTTCACAGTGATGCA<br>TTACTCCTTCGCAGTGATGCA | 18646 |
| basd13f02 | TAACAAGTAACGGTAAAAACT<br>TAACAAGTAATGGTAAAAACT | 18647 |
| bah26j10 | TCACCATGACTGGTTTAGACT<br>TCACCATGACAGGTTTAGACT | 18650 |
| bah26j10 | CAGATTCCCAGATGGCTCGTC<br>CAGATTCCCAAATGGCTCGTC | 18651 |
| bast65g0113 | TTCGTGCCGCGTGATGCAGCC<br>TTCGTGCCGCCTGATGCAGCC | 18652 |
| baak4k13 | GCTCACTTGCTTTTCAGTGTG<br>GCTCACTTGCGTTTCAGTGTG | 18653 |
| baak4k13 | GGAGGTCGCCGAACGTCTTGG<br>GGAGGTCGCCAAACGTCTTGG | 18654 |
| bags34h11 | CATCCCGAAACTTGTCACAGA<br>CATCCCGAAATTTGTCACAGA | 18655 |
| bags37j03 | CTAACTTATTATTGTTACTAA<br>CTAACTTATTTTTGTTACTAA | 18656 |
| bags37j03 | CATCCTGACAAAAGAGAGCAA<br>CATCCTGACAGAAGAGAGCAA | 18657 |
| bags37j03 | TCAAATAGAGCGTGCAGCTAC<br>TCAAATAGAGTGTGCAGCTAC | 18658 |
| bags37j03 | AGCAAAATCAAGACAGGCAGT<br>AGCAAAATCAGGACAGGCAGT | 18659 |
| bah22o08 | TGATCTTCTGCCTGTAGAATA<br>TGATCTTCTGTCTGTAGAATA | 18661 |
| bah22o08 | CTGATAGGTAGGCTGATTCAT<br>CTGATAGGTAAGCTGATTCAT | 18662 |
| bah22o08 | TCCATAACTTTCCCTTGCACA<br>TCCATAACTTCCCCTTGCACA | 18663 |
| bah22o08 | TACAGGGTGTGCGAATTCAGA<br>TACAGGGTGTCCGAATTCAGA | 18664 |
| bah22o08 | GCAACATTTGCGTCACCATCC<br>GCAACATTTGTGTCACCATCC | 18665 |

TABLE 23-24

| Clones | Haruna Nijo H602 | SEQ ID NO: |
|---|---|---|
| bags6k13 | TGACTGTTACAAGAAATACTG<br>TGACTGTTACGAGAAATACTG | 18666 |
| bags6k13 | AAATCAGCCAGACACTGACTG<br>AAATCAGCCACACACTGACTG | 18667 |
| bags6k13 | CCCTCTCTCTCTCTATCGACA<br>CCCTCTCTCTGTCTATCGACA | 18668 |
| bags6k13 | TTCAGTATGCGAGAATTAACC<br>TTCAGTATGCAAGAATTAACC | 18669 |
| bags6k13 | GCACCGGCAGTAGCACCTGCA<br>GCACCGGCAGCAGCACCTGCA | 18670 |
| bags6k13 | ATAGTAACCAGCAGCAGCACC<br>ATAGTAACCACCAGCAGCACC | 18671 |
| bast143C0705 | TTGCTGAAACAATTAAAAGTA<br>TTGCTGAAACGATTAAAAGTA | 18672 |
| bast143C0705 | ATATGTTGCACATACAAGTGC<br>ATATGTTGCAGATACAAGTGC | 18673 |
| bast143C0705 | TACAAGTGCCCACAAATGCTG<br>TACAAGTGCCGACAAATGCTG | 18674 |
| bags23h03 | TGCTTCTGAACATTTGAGCCC<br>TGCTTCTGAATATTTGAGCCC | 18676 |
| bast63B0703 | TCAAGTCCATGTGCCTCTGAT<br>TCAAGTCCATATGCCTCTGAT | 18678 |
| BaSD13E02 | AGAGACTCAGAAAACTAGAAG<br>AGAGACTCAGGAAACTAGAAG | 18679 |
| bah13a17 | AATCATCAAGTTCGATCAAGG<br>AATCATCAAGGTCGATCAAGG | 18681 |
| bah50123 | CTGGCCTCTTTGCTGGCCTGT<br>CTGGCCTCTTGGCTGGCCTGT | 18682 |
| bah50123 | TTGCATACGATACTGAAACAT<br>TTGCATACGAAACTGAAACAT | 18683 |
| bah50123 | TTTCGACTTTGGCTGACTCTG<br>TTTCGACTTTTGCTGACTCTG | 18684 |
| bast73e0210 | GGCATTGCGCGGCGGCCAACA<br>GGCATTGCGCCGCGGCCAACA | 18686 |
| BaH50021 | TTCCATTTCAGATCTGATGCT<br>TTCCATTTCAAATCTGATGCT | 18687 |
| BaH50021 | TTCACTACACTTATTTGAGCA<br>TTCACTACACATATTTGAGCA | 18688 |
| BaH50021 | TGGAGTACTAGACTTGGATCT<br>TGGAGTACTACACTTGGATCT | 18689 |
| BaH50021 | TTGAGCATGAAGCACTATATT<br>TTGAGCATGAGGCACTATATT | 18690 |
| BaH50021 | GCACCCTCCTCTTCCCCGCCA<br>GCACCCTCCTTTTCCCCGCCA | 18691 |
| basd21g05 | GTTGGCAACATCATAAACTAG<br>GTTGGCAACAGCATAAACTAG | 18692 |
| baal5i19 | TATAACCCGGGGAGAGATAGA<br>TATAACCCGGAGAGAGATAGA | 18694 |
| baal5i19 | CACGCACATGGCCCTGTTCAA<br>CACGCACATGTCCCTGTTCAA | 18695 |

TABLE 23-25

| Clones | Haruna Nijo H602 | SEQ ID NO: |
|---|---|---|
| baal5i19 | ATTATACCTGAAATTCAAGGA<br>ATTATACCTGTAATTCAAGGA | 18696 |
| baal5i19 | TCTTTGTTGGGATTACACCCA<br>TCTTTGTTGGAATTACACCCA | 18697 |
| bah16e04 | TTATACCACATGCGGCCCGGG<br>TTATACCACAGGCGGCCCGGG | 18698 |
| bah16e04 | ACCTGTACCATACAGAGCAGT<br>ACCTGTACCAAACAGAGCAGT | 18699 |
| bah16e04 | GCACCGTCAGCACAGAAGAAC<br>GCACCGTCAGTACAGAAGAAC | 18700 |
| bah16e04 | TAGTAGTCATCTCTGGAAATA<br>TAGTAGTCATGTCTGGAAATA | 18701 |
| bah16e04 | GAAGAACAGAAACTGAATCAG<br>GAAGAACAGATACTGAATCAG | 18702 |
| baak32p24 | GCACCTTTCTCCGCTGCCCTG<br>GCACCTTTCTTCGCTGCCCTG | 18703 |
| baak13d11 | ATATACATAGCCAAGAGGTTT<br>ATATACATAGGCAAGAGGTTT | 18709 |
| baak13d11 | GGGTTGTCATAATTTTATTTG<br>GGGTTGTCATGATTTTATTTG | 18710 |
| bah49p10 | TTCACCACGGAGCCGTCGACC<br>TTCACCACGGTGCCGTCGACC | 18711 |
| bah49p10 | ACTGGAGCTGTAGCTCGACCT<br>ACTGGAGCTGGAGCTCGACCT | 18712 |
| bah49p10 | GCCTGACGCGCCCTTGGAGCC<br>GCCTGACGCGCCCTTGGAGCC | 18713 |
| bah49p10 | TCCACCAGCGACCCGATGTCC<br>TCCACCAGCGGCCCGATGTCC | 18714 |
| baal32n15 | TCTATGTCTGATCCAACCTGC<br>TCTATGTCTGTTCCAACCTGC | 18715 |
| baal32n15 | TCTCGTTCTCATTAGCCAGTT<br>TCTCGTTCTCGTTAGCCAGTT | 18716 |
| BaAK22H04 | TCCCGGTGCCGTAGGGAGCTT<br>TCCCGGTGCCATAGGGAGCTT | 18718 |
| bags15j13 | AGGTGGCGCCCGGGCGGGTGT<br>AGGTGGCGCCGGGGCGGGTGT | 18719 |
| bags15j13 | CGACCTGCGCTTTCGGATTCC<br>CGACCTGCGCCTTCGGATTCC | 18720 |
| kr66G0414 | AGGACATGTTTCGTATGGTCC<br>AGGACATGTTCCGTATGGTCC | 18721 |
| basd22c07 | CGCTCTGAAACTGACAGACAG<br>CGCTCTGAAAATGACAGACAG | 18722 |
| kr71c1105 | TCTAAAACCTTAATCTTATTG<br>TCTAAAACCTCAATCTTATTG | 18723 |
| bags34i11 | CGGCAAAACCACTCTAAGGTG<br>CGGCAAAACCGCTCTAAGGTG | 18724 |
| bags34i11 | TCCAAGATTATGACACGGAGT<br>TCCAAGATTACGACACGGAGT | 18725 |
| bags34i11 | CACATTTATTCTGTACTAGAA<br>CACATTTATTTTGTACTAGAA | 18726 |

TABLE 23-26

| Clones | Haruna Nijo / H602 | SEQ ID NO: |
|---|---|---|
| bah23k17 | CTCATCATCTAGTTCTCTACA<br>CTCATCATCTGGTTCTCTACA | 18727 |
| bah23k17 | TTTGTTTTCAATCACATTCCA<br>TTTGTTTTCATTCACATTCCA | 18728 |
| bah23k17 | TGTATCATTGGTACATGGATA<br>TGTATCATTGATACATGGATA | 18729 |
| bah23k17 | ACAATGTGTCCCTCTGTATCA<br>ACAATGTGTCTCTCTGTATCA | 18730 |
| bah23k17 | GAAAGTACATAATTTGAGTGT<br>GAAAGTACATGATTTGAGTGT | 18731 |
| bah23k17 | AAACACTGAAAATAGGGATGA<br>AAACACTGAAGATAGGGATGA | 18732 |
| bast39D0107 | GGATGCATCAGAGGAGACTCA<br>GGATGCATCATAGGAGACTCA | 18733 |
| bast39D0107 | TCCTACCAGAAAAGGGACGAT<br>TCCTACCAGAGAAGGGACGAT | 18734 |
| bast39D0107 | TCTTGGTACAAGGATGCATCA<br>TCTTGGTACAGGGATGCATCA | 18735 |
| bast39D0107 | ATGTTACTCAAGAGTTGAGAT<br>ATGTTACTCACGAGTTGAGAT | 18736 |
| bast39D0107 | CCTAGGAGAACTCTTCCTACC<br>CCTAGGAGAATTCTTCCTACC | 18737 |
| bast39D0107 | AGTATTAGAAAACTGAGAGCT<br>AGTATTAGAATACTGAGAGCT | 18738 |
| BaH44K24 | CTGCCTGAGGTGGTGGAATAT<br>CTGCCTGAGGCGGTGGAATAT | 18739 |
| BaH44K24 | TGCTGGGAATATAGAGGCCAG<br>TGCTGGGAATGTAGAGGCCAG | 18740 |
| BaH44K24 | TAGAAAATGGTGCCAGAATGC<br>TAGAAAATGGCGCCAGAATGC | 18741 |
| baak32k15 | TTATAAAGAACATACTTGAGA<br>TTATAAAGAAGATACTTGAGA | 18743 |
| baak32k15 | TGACATCATAACCACATTAAT<br>TGACATCATACCCACATTAAT | 18744 |
| baak32k15 | CATGAAGCAATAAAACCAGTT<br>CATGAAGCAACAAAACCAGTT | 18745 |
| bah61a13 | CCTCGCATAATTATCAACATG<br>CCTCGCATAACTATCAACATG | 18746 |
| bah61a13 | CTTTGTGCGTCCCGAAACTTT<br>CTTTGTGCGTACCGAAACTTT | 18747 |
| bags35n11 | TCAGATGTAAATAGGTGTTTT<br>TCAGATGTAATTAGGTGTTTT | 18748 |
| bags35n11 | CCATACCATCATCAGTTATCA<br>CCATACCATCGTCAGTTATCA | 18749 |
| bags35n11 | CATCGTCTAATTTGGGGCGGA<br>CATCGTCTAACTTGGGGCGGA | 18750 |
| bags35n11 | CAGCCTGCAGATGTGTCCATA<br>CAGCCTGCAGGTGTGTCCATA | 18751 |
| baak24i03 | CAGCCTGCAGATGTGTCCATA<br>CAGCCTGCAGGTGTGTCCATA | 18752 |

TABLE 23-27

| Clones | Haruna Nijo / H602 | SEQ ID NO: |
|---|---|---|
| baak24i03 | CATCGTCTAATTTGGGGCGGA<br>CATCGTCTAACTTGGGGCGGA | 18753 |
| baak24i03 | CCATACCATCATCAGTTATCA<br>CCATACCATCGTCAGTTATCA | 18754 |
| bah28n23 | CGTTCTTATGGATTTTACTCC<br>CGTTCTTATGAATTTTACTCC | 18755 |
| bah28n23 | TTCTTTGCATACTCGGCATCA<br>TTCTTTGCATGCTCGGCATCA | 18756 |
| bags10e13 | ATGTAACTCAATCCGCATCAT<br>ATGTAACTCAGTCCGCATCAT | 18757 |
| bags10e13 | TTTGTTTTCAATCACATTCCA<br>TTTGTTTTCATTCACATTCCA | 18758 |
| bags10e13 | CTCATCATCTAGTTCTCTACA<br>CTCATCATCTGGTTCTCTACA | 18759 |
| bags10e13 | GAAAGTACATAATTTGAGTGT<br>GAAAGTACATGATTTGAGTGT | 18760 |
| bags10e13 | GGATGCCTCACGCTTGTCGAT<br>GGATGCCTCAGGCTTGTCGAT | 18761 |
| bags10e13 | CCATTTTGCATACAGAAACAT<br>CCATTTTGCAGACAGAAACAT | 18762 |
| bags19d13 | CCTCACCCTCGCCTATTTGTT<br>CCTCACCCTCACCTATTTGTT | 18763 |
| bags19d13 | GGACGTCGAAGGGCTTCACTT<br>GGACGTCGAATGGCTTCACTT | 18764 |
| baak19d04 | GCATGAAGTCGTGCCGTGTTA<br>GCATGAAGTCATGCCGTGTTA | 18765 |
| baak19d04 | CATGATTATAAACAACTTGCC<br>CATGATTATAGACAACTTGCC | 18766 |
| BaAL34019 | CGATCTTGACGATCTTCTCCG<br>CGATCTTGACAATCTTCTCCG | 18767 |
| BaAK1P04 | CGTTCTTATGAATTTTACTCC<br>CGTTCTTATGGATTTTACTCC | 18769 |
| BaAK1P04 | TTCTTTGCATGCTCGGCATCA<br>TTCTTTGCATACTCGGCATCA | 18770 |
| baak35m13 | TGAACTCCTCAGCTATCGAGA<br>TGAACTCCTCGGCTATCGAGA | 18771 |
| baak35m13 | TCGACTGAATTTACTCTGCCA<br>TCGACTGAATGTACTCTGCCA | 18772 |
| baak35m13 | TGTTAAGACTCCAGAATGACT<br>TGTTAAGACTTCAGAATGACT | 18773 |
| baak35m13 | CGATAAGTAACTTGCCCGTGA<br>CGATAAGTAATTTGCCCGTGA | 18774 |
| bah41n09 | TGGCATAGGAGAACACATATA<br>TGGCATAGGAAAACACATATA | 18776 |
| bah41n09 | CGAAATACCACCAGTGAAGTG<br>CGAAATACCAACAGTGAAGTG | 18777 |
| bah41n09 | ACGCTTGTTTGGGAGTCGGC<br>ACGCTTGTTGGGGAGTCGGC | 18778 |
| bah41n09 | CACCAGCTCATGACGGACCAA<br>CACCAGCTCAGGACGGACCAA | 18779 |

TABLE 23-28

| Clones | Haruna Nijo / H602 | SEQ ID NO: |
|---|---|---|
| bah41n09 | TTCACTATGAGAGTCATGCAG<br>TTCACTATGAAAGTCATGCAG | 18780 |
| BaGS23I12 | GGAACCTTACTGACATTACCC<br>GGAACCTTACCGACATTACCC | 18781 |
| BaGS23I12 | CTCCACCGCGCGGCGGGTACCT<br>CTCCACCGGCAGCGGGTACCT | 18782 |
| bah16p20 | CGACGGTGCCGACCACCGTCA<br>CGACGGTGCCCACCACCGTCA | 18783 |
| bah16p20 | CCTCCTTGGCAGGGCCGACGG<br>CCTCCTTGGCCGGGCCGACGG | 18784 |
| BaH45O16 | ACAGGCAGGATAGGACAGCGA<br>ACAGGCAGGACAGGACAGCGA | 18788 |
| BaH45O16 | CTATCGATGCAGTGCAACTGG<br>CTATCGATGCGGTGCAACTGG | 18789 |
| bah21h09 | TTGTCTGGTGGCTAGGTAGAT<br>TTGTCTGGTGTCTAGGTAGAT | 18790 |
| bah21h09 | ATAAAACTGAATTGGAAAAGT<br>ATAAAACTGATTTGGAAAAGT | 18791 |
| bah21h09 | CAGTTCATCTAATTTTGGTTT<br>CAGTTCATCTGATTTTGGTTT | 18792 |
| bah58p22 | ACCCGAAATATAGGTGATCCA<br>ACCCGAAATAGAGGTGATCCA | 18793 |
| bah58p22 | CAGCAACATCAAAGCTAACAT<br>CAGCAACATCTAAGCTAACAT | 18794 |
| bags20l19 | ACAGGCTACAGCATTTACAGG<br>ACAGGCTACATCATTTACAGG | 18795 |
| bah13i10 | AGGCTTTCAAAGGCTTGAAGT<br>AGGCTTTCAAGGGCTTGAAGT | 18796 |
| bah13i10 | TCGATTACTACCTGAGACTGC<br>TCGATTACTATCTGAGACTGC | 18797 |
| bah13i10 | CTCGGCCTGTCGAATAACCAT<br>CTCGGCCTGTTGAATAACCAT | 18798 |
| baal7c15 | GGGTCGCTACGAAGGCGAGGT<br>GGGTCGCTACTAAGGCGAGGT | 18801 |
| baal7c15 | GATCCGGGCATGGGACGATCC<br>GATCCGGGCACGGGACGATCC | 18802 |
| bah63f05 | GTATGCTATGTTGTGCAACAA<br>GTATGCTATGCTGTGCAACAA | 18803 |
| bah63f05 | GTTTCCCCTACGACATTATAT<br>GTTTCCCCTAGGACATTATAT | 18804 |
| bah63f05 | TTCCCCTCGACACCGTATGGA<br>TTCCCCTCGAAACCGTATGGA | 18805 |
| bags15j16 | GAGCGGAACCGGATATAAGCT<br>GAGCGGAACCCGATATAAGCT | 18806 |
| bags15j16 | GGCAGATCGATGCGACCGGCT<br>GGCAGATCGACGCGACCGGCT | 18807 |
| bags15j16 | GTCACGCCGTAAACGACGCGT<br>GTCACGCCGTCAACGACGCGT | 18808 |
| bah41e10 | GGATGGGCTGCCCCGAAGTGGA<br>GGATGGGCTGGCCGAAGTGGA | 18810 |

TABLE 23-29

| Clones | Haruna Nijo / H602 | SEQ ID NO: |
|---|---|---|
| bah54d08 | GTACAGTGCTCAACGGTGTGC<br>GTACAGTGCTAAACGGTGTGC | 18811 |
| bah54d08 | CCACGTTCAGATTCACCAAGG<br>CCACGTTCAGCTTCACCAAGG | 18812 |
| baak18c01 | ACTGCGAAGAGTATGAAATTT<br>ACTGCGAAGAATATGAAATTT | 18813 |
| baak18c01 | AGGAGCCGAGCGAGTTGGGGT<br>AGGAGCCGAGGGAGTTGGGGT | 18814 |
| baak18c01 | CGTGCACAGATCCAGAGTGGT<br>CGTGCACAGACCCAGAGTGGT | 18815 |
| baak18c01 | AGTTGGGGTCGGTTCCCCACC<br>AGTTGGGGTCAGTTCCCCACC | 18816 |
| baak18c01 | ATCTAAAGCTTTACCGGCTCG<br>ATCTAAAGCTATACCGGCTCG | 18817 |
| baak18c01 | GACATTAGCGATTAGAACCTG<br>GACATTAGCGGTTAGAACCTG | 18818 |
| basd21o07 | ATGCTGCAGCGAAAATAAACA<br>ATGCTGCAGCAAAAATAAACA | 18819 |
| baak43c03 | CACACATGTCAGTGGTTATTT<br>CACACATGTCGGTGGTTATTT | 18821 |
| baal13f18 | GCCGGAAGGTGCTCTTGAATC<br>GCCGGAAGGTACTCTTGAATC | 18824 |
| baal13f18 | CAACAAGCTCGGCAGCTTCGA<br>CAACAAGCTCAGCAGCTTCGA | 18825 |
| baal13f18 | ATGTGAGGCACAGGTACATGT<br>ATGTGAGGCAAAGGTACATGT | 18826 |
| bags18i22 | CTATTACTCACGAGCTAGCGT<br>CTATTACTCATGAGCTAGCGT | 18827 |
| bags18i22 | AAGATTGAAGATGTCTTGAGA<br>AAGATTGAAGGTGTCTTGAGA | 18828 |
| bags9b02 | ATGGCATACAGTCTGCGCAAC<br>ATGGCATACAATCTGCGCAAC | 18829 |
| bags9b02 | TATTTTTCCACAAATAAATAT<br>TATTTTTCCAAAAATAAATAT | 18830 |
| bah11e22 | CCTGGTTTACCCTGTCATCAT<br>CCTGGTTTACTCTGTCATCAT | 18831 |
| bah11e22 | GAATGCCTACCTCGATCGTCT<br>GAATGCCTACATCGATCGTCT | 18832 |
| bah11e22 | GCGCTTACATACGGCGCGGCT<br>GCGCTTACATGCGGCGCGGCT | 18833 |
| bah58h09 | GACGCCACTGGTGATCTCTTG<br>GACGCCACTGCTGATCTCTTT | 18834 |
| baak4c12 | GGACGACGACAGCATCGCCGG<br>GGACGACGACGGCATCGCCGG | 18836 |
| bags37a05 | TTCGGTGTGGCCGATGACAAG<br>TTCGGTGTGGGCGATGACAAG | 18837 |
| baak36a20 | TTGCTTGAGGAAGAGACGTCT<br>TTGCTTGAGGCAGAGACGTCT | 18840 |
| baak36a20 | TTTATTATTATAACCAATCCC<br>TTTATTATTACAACCAATCCC | 18841 |

TABLE 23-30

| Clones | Haruna Nijo H602 | SEQ ID NO: |
|---|---|---|
| baak36a20 | TTACTGAGGCAATGTGTACTT<br>TTACTGAGGCGATGTGTACTT | 18842 |
| baak36a20 | ACCAATCCCATTTCTTCCTGC<br>ACCAATCCCAGTTCTTCCTGC | 18843 |
| baal13m04 | ACCTCCTCCTCCTTGTGCCTG<br>ACCTCCTCCTGCTTGTGCCTG | 18847 |
| basl13m04 | TTTCCGTTAATGCCGTCTAAT<br>TTTCCGTTAACGCCGTCTAAT | 18848 |
| bags9o24 | ACTCAGTCACGCTACACTTTT<br>ACTCAGTCACACTACACTTTT | 18849 |
| bah12h16 | TGATGCTGCCGCTGCTCCGGT<br>TGATGCTGCCACTGCTCCGGT | 18851 |
| bah12h16 | GGGGGCCGCAAAGAAGAAGCT<br>GGGGGCCGCAGAGAAGAAGCT | 18852 |
| bah12h16 | ATGCCTGTTCCTAAGCTGATC<br>ATGCCTGTTCTTAAGCTGATC | 18853 |
| baak33n16 | GAAACATAATACAGCTACAAA<br>GAAACATAATTCAGCTACAAA | 18854 |
| baak33n16 | AACGCTGCCGGGGACGCTACC<br>AACGCTGCCGTGGACGCTACC | 18855 |
| baak33n16 | CACCGAGGGCACACTCGGATA<br>CACCGAGGGCTCACTCGGATA | 18856 |
| baak33n16 | AGCGGGTTCTTGAGGCCCACA<br>AGCGGGTTCTCGAGGCCCACA | 18857 |
| baak33n16 | TGAACAGGATCGCCCAGTATC<br>TGAACAGGATAGCCCAGTATC | 18858 |
| bah26n01 | CACTCTCAGCGTTCCTTGTGA<br>CACTCTCAGCATTCCTTGTGA | 18860 |
| BaGS39E07 | ATGCACGCAGCGAAGAAGAGC<br>ATGCACGCAGTGAAGAAGAGC | 18861 |
| BaH33A09 | ATACTATCTAGGGTGCAATCT<br>ATACTATCTATGGTGCAATCT | 18863 |
| BaH38A09 | AGAGGCTATCACTTCCGTCGG<br>AGAGGCTATCGCTTCCGTCGG | 18864 |
| BaH33A09 | TCTTGTCTTAGGATTGTCTAG<br>TCTTGTCTTAAGATTGTCTAG | 18865 |

TABLE 24-1

| Clones | Haruna Nijo H602 | SEQ ID NO: |
|---|---|---|
| BaAL15P01 | TGCAAGGCGCATGCCAAAAG<br>TGCAAGGCGCCTGCCAAAAG | 18866 |
| bags1d06 | TATTATATTAGGACTGCTCAT<br>TATTATATTATGACTGCTCAT | 18867 |
| bags1d06 | AGCATGGCAGGAAGTAGCAGA<br>AGCATGGCAGCAAGTAGCAGA | 18868 |
| bast18A0602 | CATACTAGTAATGCTTACGGC<br>CATACTAGTAGTGCTTACGGC | 18869 |
| bah63h24 | TAGAGCGTGTGGCATGCCATC<br>TAGAGCGTGTAGCATGCCATC | 18872 |

TABLE 24-1-continued

| Clones | Haruna Nijo H602 | SEQ ID NO: |
|---|---|---|
| BaAK13C16 | CTCATGTACAATTAGTACACA<br>CTCATGTACAGTTAGTACACA | 18874 |
| BaGS32C19 | TGCAGGTCGGAGCACACTGCT<br>TGCAGGTCGGGGCACACTGCT | 18875 |
| baak36f08 | TTACCGCCGGCGGCAACGTCC<br>TTACCGCCGGTGGCAACGTCC | 18876 |
| baak36f08 | CCATGGACGGTCCGCAGGACT<br>CCATGGACGGCCCGCAGGACT | 18877 |
| baak36f08 | GCATGCGGTAACTAGTTACCG<br>GCATGCGGTACCTAGTTACCG | 18878 |
| baak36f08 | GGGCGTGCATCGGGGCGGGAC<br>GGGCGTGCATAGGGGCGGGAC | 18879 |
| baak36f08 | CGACCTGGACAGCAGGCAGGT<br>CGACCTGGACGGCAGGCAGGT | 18880 |
| baak36f08 | TGCAGGTTTTGGGGCACTCGA<br>TGCAGGTTTTCGGGCACTCGA | 18881 |
| baak36f08 | CGACGTACTGATCCTGGCAGA<br>CGACGTACTGGTCCTGGCAGA | 18882 |
| bast142D1107 | TCTCCTATGCCTCGATGTGCA<br>TCTCCTATGCTTCGATGTGCA | 18884 |
| bast142D1107 | GCTCTATAAAATTAAATTAGA<br>GCTCTATAAATTTAAATTAGA | 10885 |
| baak20g06 | CAGAGAAACAAGCAAAAACAG<br>CAGAAAAACAGGCAAAAACAG | 18889 |
| baak46o05 | GCCGCAACGAATCACAGTCCG<br>GCCGCAACGATTCACAGTCCG | 18891 |
| baak46o05 | CATCCAATACGTATATATGTT<br>CATCCAATACTTATATATGTT | 18892 |
| baak46o05 | GAATGCTGCTACAAGCATGTG<br>GAATGCTGCTCCAAGCATGTG | 18893 |
| baak46o05 | TTTCACATGAATGGTCATACC<br>TTTCACATGAGTGGTCATACC | 18894 |
| basd15h22 | AGAGAGCGCCCTCCACGATCT<br>AGAGAGCGCCGTCCACGATCT | 18895 |
| basd15h22 | TCGCTCATCAACTTGTACATG<br>TCGCTCATCAGCTTGTACATG | 18896 |
| basd15h22 | GCAGTCTAATTAATGAACATC<br>GCAGTCTAATGAATGAACATC | 18897 |
| basd15h22 | CCGGATCGCCGCACCGGATGT<br>CCGGATCGCCACACCGGATGT | 18898 |

TABLE 24-2

| Clones | Haruna Nijo H602 | SEQ ID NO: |
|---|---|---|
| basd15h22 | CATCCCAGCTAACGCTCTTGG<br>CATCCCAGCTCACGCTCTTGG | 18899 |
| basd19c07 | CAACAATCAAACAAACTTTAT<br>CAACAATCAAGCAAACTTTAT | 18900 |
| basd19c07 | TCAAGGCACCGGCCTTTGGGT<br>TCAAGGCACCTGCCTTTGGGT | 18901 |

TABLE 24-2-continued

| Clones | Haruna Nijo H602 | SEQ ID NO: |
|---|---|---|
| baak39a14 | TCTCTGATTCTTTCAAATACT<br>TCTCTGATTCCTTCAAATACT | 18903 |
| bah31e12 | GAGACAGGTCCAGCGATTCTA<br>GAGACAGGTCGAGCGATTCTA | 18904 |
| BaSD15L22 | ACGCCTTCTTCCTCATGCTCT<br>ACGCCTTCTTTTCTCATGCTCT | 18905 |
| basd21j11 | AACACAGCAGCTCTTTGATTC<br>AACACAGCAGTTCTTTGATTC | 18908 |
| BaH48C10 | TTCTCTGGAAAGAGGCATATG<br>TTCTCTGGAACGAGGCATATG | 18909 |
| BaH48C10 | AAATAGAAATTTGGGAGAAAT<br>AAATAGAAATGTGGGAGAAAT | 18910 |
| BaH48C10 | AGTTATTGCACAATATTAATT<br>AGTTATTGCATAATATTAATT | 18911 |
| BaH54J07 | TGCCCAATCATACCATCCAAT<br>TGCCCAATCACACCATCCAAT | 18912 |
| BaH54J07 | ACTCCAGATGCATGCTTGATT<br>ACTCCAGATGAATGCTTGATT | 18913 |
| baet46b0903 | CCGTGTGCCATGCATTGCCTC<br>CCGTGTGCCACGCATTGCCTC | 18924 |
| baet46b0903 | TAAGGCGAAGTCACCTAGGGC<br>TAAGGCGAAGGCACCTAGGGC | 18925 |
| BaGS19F16 | AAAATCATACAGATCCATTCT<br>AAAATCATACGGATCCATTCT | 18926 |
| BaGS19F16 | AGGCCCACACAGTAACGTCGG<br>AGGCCCACACCGTAACGTCGG | 18927 |
| BaGS19F16 | AACATTTCAAAAATTCTAAAT<br>AACATTTCAAGAATTCTAAAT | 18928 |
| BaGS19F16 | ATTCTAAATTCTGTGGTAGAA<br>ATTCTAAATTTTGTGGTAGAA | 18929 |
| BaGS19F16 | GAGATATCTGTGGAACAACAA<br>GAGATATCGCGGAACAACAA | 18930 |
| baak13g18 | CTTGCTTGTCGGCGGTGCTCT<br>CTTGCTTGTCAGCGGTGCTCT | 18931 |
| baak13g18 | GCCTTGCCAGTGTTTAACCCA<br>GCCTTGCCAGCGTTTAACCCA | 18932 |
| bast74h0216 | CTTAATTTCACCTATCTGAGC<br>CTTAATTTCAACTATCTGAGC | 18934 |
| BaAK45C14 | TCTCTTTCATTCTTGTTCTTT<br>TCTCTTTCATCCTTGTTCTTT | 18935 |
| kr63f0111 | GCATAAATATGAATTACATGC<br>GCATAAATATTAATTACATGC | 18937 |
| baak13h18 | TGGTGCTAGGGTGCTTGCAGA<br>TGGTGCTAGGATGCTTGCAGA | 18938 |

TABLE 24-3

| Clones | Haruna Nijo H602 | SEQ ID NO: |
|---|---|---|
| BaH49B13 | GATAAGCATGTACATACACAT<br>GATAAGCATGCACATACACAT | 18942 |

TABLE 24-3-continued

| Clones | Haruna Nijo H602 | SEQ ID NO: |
|---|---|---|
| BaH49B13 | CAAGCATATAGAACATCAGCA<br>CAAGCATATACAACATCAGCA | 18943 |
| BaH49B13 | CAAGCTATGGCTTGTGTTCTT<br>CAAGCTATGGTTTGTGTTCTT | 18944 |
| BaH49B13 | TTACCCAGGACATTGAAATGG<br>TTACCCAGGAAATTGAAATGG | 18945 |
| BaGS35A09 | TGGTGGCAACAAGCTCCATCA<br>TGGTGGCAACGAGCTCCATCA | 18946 |
| bast16a0802 | AATTCAAGTGGTTGGAATTAC<br>AATTCAAGTGATTGGAATTAC | 18948 |
| basd18k01 | GCCGCCACGGTAAGGAAGACG<br>GCCGCCACGGCAAGGAAGACG | 18949 |
| BaH58D17 | CTGTAGTGCTTCTTCGTCAGG<br>CTGTAGTGCTCCTTCGTCAGG | 18950 |
| bags26d01 | GGATTGCTTGGACATACCGAG<br>GGATTGCTTGCACATACCGAG | 18953 |
| bags26d01 | TCTGCTTTGTCGGTGTCATCT<br>TCTGCTTTGTTGGTGTCATCT | 18954 |
| bags26d01 | AGACCAGTGACGTTCAGCAAT<br>AGACCAGTGATGTTCAGCAAT | 18955 |
| bags26d01 | CAGAAAGTCGACCATGAGGGA<br>CAGAAAGTCGTCCATGAGGGA | 18956 |
| bags26d01 | CCTACGCCTTTCCCTTCTTTC<br>CCTACGCCTTCCCCTTCTTTC | 18957 |
| bags26d01 | GCGGCTCGCTTTGAAGGTGTC<br>GCGGCTCGCTCTGAAGGTGTC | 18958 |
| bags26d01 | CTGGCTGACTCAGAAAAAGGA<br>CTGGCTGACTGAGAAAAAGGA | 18959 |
| bags26d01 | CTGAAACCCTAGATGCGGCTC<br>CTGAAACCCTGGATGCGGCTC | 18960 |
| basd14k04 | ATGCTGCCTAGAACCACTTTG<br>ATGCTGCCTAAAACCACTTTG | 18961 |
| basd14k04 | TGGCCTAGAAGCATGCTGCCT<br>TGGCCTAGAATCATGCTGCCT | 18962 |
| basd14k04 | GGCCTTCGACGCTAAGCTTTG<br>GGCCTTCGACACTAAGCTTTG | 18963 |
| BaSD24D11 | ATATTTGCATGATATCAAGGT<br>ATATTTGCATCATATCAAGGT | 18964 |
| BaSD24D11 | CGGTCAAGGCTATGAGATGCC<br>CGGTCAAGGCAATGAGATGCC | 18965 |
| BaSD24D11 | CGAGGTGTTATACTTCATAGC<br>CGAGGTGTTACACTTCATAGC | 18966 |
| BaSD24D11 | CTTTTCTGACAAAGCGCATGT<br>CTTTTCTGACCAAGCGCATGT | 18967 |
| BaSD24D11 | GCACGCTTCAAAAGATTAACG<br>GCACGCTTCACAAGATTAACG | 18968 |
| BaSD24D11 | GTGGTGTTGCCGCAGACTGCG<br>GTGGTGTTGCGGCAGACTGCG | 18969 |

TABLE 24-4

| Clones | Haruna Nijo H602 | SEQ ID NO: |
|---|---|---|
| BaSD24D11 | GGCAGGAAACGGAACATTGAG<br>GGCAGGAAACAGAACATTGAG | 18970 |
| BaH53L10 | GCGATCCTACCGTAATGTACT<br>GCGATCCTACTGTAATGTACT | 18971 |
| BaH53L10 | GACCTTTTGCGCTTCTTTCCA<br>GACCTTTTGCCCTTCTTTCCA | 18972 |
| bah57m03 | TGGAACAAGTCCAGTAGAAAT<br>TGGAACAAGTTCAGTAGAAAT | 18973 |
| bah57m03 | GATGAAATAGAGGCGTCGTTA<br>GATGAAATAGTGGCGTCGTTA | 18974 |
| bah57m03 | ACTTGCGCGATGCGATCGCAT<br>ACTTGCGCGACGCGATCGCAT | 18975 |
| bah57m03 | CGGATTTCTATCAGACAAGAA<br>CGGATTTCTACCAGACAAGAA | 18976 |
| bah57m03 | ATTTTTAGAATTAGGTGCAGA<br>ATTTTTAGAAATAGGTGCAGA | 18977 |
| bah57m03 | TAAGATGAGCATGCCATTTTT<br>TAAGATGAGCGTGCCATTTTT | 18978 |
| baal30b10 | AAGATTGGGTTTCTACTTAT<br>AAGATTGGGCTTCTACTTAT | 18979 |
| bah62n16 | ACATATATTATTGGCTGCTTT<br>ACATATATTACTGGCTGCTTT | 18980 |
| bah62n16 | TATGGATCTACGGCGCAGCTT<br>TATGGATCTATGGCGCAGCTT | 18981 |
| bah62n16 | ATCAGCGTGGCTGCTGATGAC<br>ATCAGCGTGGTTGCTGATGAC | 18982 |
| BaGS22F15 | CTCCGTACTTTGCAACAAGTT<br>CTCCGTACTTCGCAACAAGTT | 18983 |
| BaGS22F15 | AGAGGAGTTCACACTGGTAAT<br>AGAGGAGTTCGCACTGGTAAT | 18984 |
| BaGS22F15 | ACTTTGAGCCGGAAGATTTCG<br>ACTTTGAGCCAGAAGATTTCG | 18985 |
| BaGS22F15 | TGAATACGAAGGGTGAGATCC<br>TGAATACGAATGGTGAGATCC | 18986 |
| BaGS22F15 | CACATAGACAGTCTCTTAGAA<br>CACATAGACATTCTCTTAGAA | 18987 |
| BaH50J14 | CAAGGCTTTGTTAGGTACTAC<br>CAAGGCTTTGCTAGGTACTAC | 18988 |
| BaH50J14 | CCAAGATGCATGGTCTACTTC<br>CCAAGATGCACGGTCTACTTC | 18989 |
| BaH50J14 | TATCATTTCATAACCCAAGAT<br>TATCATTTCACAACCCAAGAT | 18990 |
| BaH50J14 | AGCTCATGGTTGAAGCCGCGA<br>AGCTCATGGTCGAAGCCGCGA | 18991 |
| bah19d23 | CCACATCTGGAAGGTGTTCAG<br>CCACATCTGGCAGGTGTTCAG | 18992 |
| bah19d23 | GCCTTCAAGCTTTCATACGCA<br>GCCTTCAAGCCTTCATACGCA | 18993 |
| bah19d23 | CTGCTGTAGCCTAGCTGAGAC<br>CTGCTGTAGCTTAGCTGAGAC | 18994 |

TABLE 24-5

| Clones | Haruna Nijo H602 | SEQ ID NO: |
|---|---|---|
| bags38c06 | TGCTGCAAGCAAATTTCTTTT<br>TGCTGCAAGCCAATTTCTTTT | 18995 |
| bags38c06 | CCCCCTCCTATTTCTTTGTTT<br>CCCCCTCCTACTTCTTTGTTT | 18996 |
| bags38c06 | GGGAAGCTCAACTGTGGTGGT<br>GGGAAGCTCAGCTGTGGTGGT | 18997 |
| BaGS25N05 | CGAGCTTGACGACCTGCTTGC<br>CGAGCTTGACAACCTGCTTGC | 18998 |
| bast129B0503 | AGGTTCAAGGGCCGGGAGATT<br>AGGTTCAAGG-CCGGGAGATT | 18999<br>19000 |
| baak43n21 | CCCAAAGCTGAATCCACCACA<br>CCCAAAGCTGGATCCACCACA | 19002 |
| baak43n21 | TTCACCTATTCAGGGAACTAA<br>TTCACCTATTGAGGGAACTAA | 19003 |
| baal4a06 | ATTTTCTTTCGGCTCCTTATG<br>ATTTTCTTTCAGCTCCTTATG | 19004 |
| baal4a06 | CGATTTCGATTGCCTTGGGTT<br>CGATTTCGATCGCCTTGGGTT | 19005 |
| baal4a06 | CGAGGGCACCAAATCTGCAGT<br>CGAGGGCACCGAATCTGCAGT | 19006 |
| baal4a06 | TCTGTTCCACGTCCATGTCGC<br>TCTGTTCCACCTCCATGTCGC | 19007 |
| baal4a06 | TTATGATCGCGTTGCCTCGGG<br>TTATGATCGCCTTGCCTCGGG | 19008 |
| baal4a06 | ATAGCCTGCTCGTTCTGCCTA<br>ATAGCCTGCTTGTTCTGCCTA | 19009 |
| baal4a06 | CTCCTTCTGGTGATTTTCATT<br>CTCCTTCTGGAGATTTTCATT | 19010 |
| baal4a06 | CCATGACAGTATCCCTTGTCT<br>CCATGACAGTCTCCCTTGTCT | 19011 |
| bast17D1008 | CAAACACAAGCAAACTCTTGG<br>CAAACACAAGTAAACTCTTGG | 19012 |
| bast17D1008 | TACGGCCGGGCACGTTACTC<br>TACGGCCGGGTACGTTACTC | 19013 |
| BaGS16B17 | TCTTGTCGAGGCCTGATGTGT<br>TCTTGTCGAGACCTGATGTGT | 19014 |
| BaGS16B17 | CTTGATGATGATATAAGGGCC<br>CTTGATGATGTTATAAGGGCC | 19015 |
| BaAK16B19 | ATCCGCGCTAGCTTTTAGCTA<br>ATCCGCGCTACCTTTTAGCTA | 19018 |
| baal40p07 | CCATCGAGTAAGGTGAATCGA<br>CCATCGAGTAGGGTGAATCGA | 19019 |
| baal40p07 | GGCAAAAGAATTGAAGAAACT<br>GGCAAAAGAACTGAAGAAACT | 19020 |
| baal40p07 | ACCCTGCATGCAAGTCACCGG<br>ACCCTGCATGTAAGTCACCGG | 19021 |
| baal40p07 | CCATCTTACCGCCTGCATCGA<br>CCATCTTACCACCTGCATCGA | 19022 |
| bah49c19 | GAACGGTGGTTTATGGTGTTG<br>GAACGGTGGTGTATGGTGTTG | 19023 |

TABLE 24-6

| Clones | Haruna Nijo / H602 | SEQ ID NO: |
|---|---|---|
| bah49c19 | CGAGCTGTTAGAAAATAGCTG<br>CGAGCTGTTAAAAAATAGCTG | 19024 |
| bast58C0406 | AGACTCGTCAGAAGACGACCA<br>AGACTCGTCAAAAGACGACCA | 19025 |
| baak35m24 | GCCCGTAAACATCTTGCTGGC<br>GCCCGTAAACGTCTTGCTGGC | 19026 |
| bags19h13 | TGGGAGGATTGAAAACTTACT<br>TGGGAGGATTTAAAACTTACT | 19027 |
| bags19h13 | GATTCGTCTCGGATTTGCAGG<br>GATTCGTCTCAGATTTGCAGG | 19028 |
| bah57c21 | CGACCTTCGCGCCGCCCTTGC<br>CGACCTTCGCACCGCCCTTGC | 19029 |
| BaH53P15 | ATCTGACAACCTCAAAATCGT<br>ATCTGACAACTTCAAAATCGT | 19030 |
| bags20a10 | GGAAGAGAAAGCANAACANAG<br>GGAAGAGAAAACAAAACAAAG | 19031 |
| bast02d0808 | TCACTTTCCGGACAGAAAACA<br>TCACTTTCCGAACAGAAAACA | 19032 |
| bags31c04 | AACCTTTGTAAACTTGGCACC<br>AACCTTTGTACACTTGGCACC | 19033 |
| bah60o22 | CCTTCCGACAGATTCAACACC<br>CCTTCCGACAAATTCAACACC | 19035 |
| bah60o22 | ATTCGCCGTTCACTGCGTCAT<br>ATTCGCCGTTTACTGCGTCAT | 19036 |
| bah60o22 | AGCATATCTCCTCTTCGGGTC<br>AGCATATCTCTTCTTCGGGTC | 19037 |
| BaH50C16 | TCTCTGCTCACAAGCTTCATA<br>TCTCTGCTCATAAGCTTCATA | 19038 |
| BaH50C16 | CGGTACGCCCGAATTTCCTGG<br>CGGTACGCCCTAATTTCCTGG | 19039 |
| baak43e04 | AAGCTCCTGACGGCGACGCAG<br>AAGCTCCTGATGGCGACGCAG | 19041 |
| kr17g1113 | TTGTAGCTACCGCCTGCGTGT<br>TTGTAGCTACGGCCTGCGTGT | 19042 |
| bags19k19 | TTCCATTGTCAGAACATAAGC<br>TTCCATTGTCGGAACATAAGC | 19043 |
| baak38b13 | GCAGCTTCAGCAGCTCCTCTC<br>GCAGCTTCAGGAGCTCCTCTC | 19044 |
| baak38b13 | TCAAGAAGGATTATACGTTTA<br>TCAAGAAGGAGTATACGTTTA | 19045 |
| baak1d12 | ATTATCAAACGGAATAGTCCC<br>ATTATCAAACAGAATAGTCCC | 19046 |
| baak1d12 | ATTTGGCATGTCTCAGAAATT<br>ATTTGGCATGCCTCAGAAATT | 19047 |
| baak1d12 | TGCATTCTCTCGTTCGACAGG<br>TGCATTCTCTTGTTCGACAGG | 19048 |
| bah28m14 | AGTCCCACTCGCTGAGCAGAT<br>AGTCCCACTCACTGAGCAGAT | 19049 |
| bah48i15 | TAATAATATAGTTAAGCGCAA<br>TAATAATATAATTAAGCGCAA | 19050 |

TABLE 24-7

| Clones | Haruna Nijo / H602 | SEQ ID NO: |
|---|---|---|
| basd27h23 | AGCTCACTCCTTTTGAGCCAC<br>AGCTCACTCCGTTTGAGCCAC | 19051 |
| baak21a11 | AGCAATAAAAGACGTATTGGC<br>AGCAATAAAAAACGTATTGGC | 19052 |
| bast04b0804 | TTGCTATGTCCGGCCGATGCT<br>TTGCTATGTCGGGCCGATGCT | 19053 |
| bah45f13 | TGCGATTTTATATAACGAAAT<br>TGCGATTTTACATAACGAAAT | 19054 |
| BaAL8J18 | TAATAATATAATTAAGCGCAA<br>TAATAATATAGTTAAGCGCAA | 19055 |
| BaGS9D01 | CATGTAAAAGTGACCTCCTG<br>CATGTAAAAACTGACCTCCTG | 19056 |
| baal4i06 | CTTGCTCTTTCTTCTTATCT<br>CTTGCTCTTTCCTTCTTATCT | 19058 |
| baal4i06 | TGAGCTACGAAGGATATTATA<br>TGAGCTACGAGGGATATTATA | 19059 |
| baal4i06 | CCATCTGCGTGTTCGTGCATC<br>CCATCTGCGTTTTCGTGCATC | 19060 |
| bah26i01 | CTGTAAAGAAGATCAAACAG<br>CTGTAAAGAGGATCAAACAG | 19061 |
| bah26i01 | CATCATCCTTCGCTCGAGGAA<br>CATCATCCTTTGCTCGAGGAA | 19062 |
| bah26i01 | CCTCTTCATTCGACAATACAT<br>CCTCTTCATTTGACAATACAT | 19063 |
| bah26i01 | TACGTTGGGCGGATGACAAGT<br>TACGTTGGGCAGATGACAAGT | 19064 |
| bags15c17 | GCTGCAACACAAATGGAAAG<br>GCTGCAACACCAATGGAAAG | 19065 |
| baak1k08 | CCGTGGCTTCGCTGTCAAACG<br>CCGTGGCTTCACTGTCAAACG | 19066 |
| bags9b03 | ACTCCTCAAGCTCGACGATTA<br>ACTCCTCAAGTTCGACGATTA | 19067 |
| bags9b03 | TAATTATGACCAGAGAGACAA<br>TAATTATGACGAGAGAGACAA | 19068 |
| baet42G1214 | AGCACCTGCGGGGAGTAAGTG<br>AGCACCTGCGAGGAGTAAGTG | 19069 |
| bags22b22 | GCATTCATGCCGCTCATCTTT<br>GCATTCATGCGGCTCATCTTT | 19071 |
| bags22b22 | GACAAACTAGTCATCAAATGC<br>GACAAACTAGCCATCAAATGC | 19072 |
| bags22b22 | GATGGACACTCGGTAGCAAAA<br>GATGGACACTTGGTAGCAAAA | 19073 |
| baal36g05 | ACCACCCAGATTATATAATCC<br>ACCACCCAGAATATATAATCC | 19074 |
| baal36g05 | ACTAGCACTAGCACTAGCACT<br>ACTAGCACTATCACTAGCACT | 19075 |
| baal36g05 | GATGTATCTACACACGTTTTA<br>GATGTATCTAGACACGTTTTA | 19076 |
| baal36g05 | TCATGTACGCGAAGAAAACAG<br>TCATGTACGCAAAGAAAACAG | 19077 |

TABLE 24-8

| Clones | Haruna Nijo H602 | SEQ ID NO: |
|---|---|---|
| bags33j15 | AAAGCAATGTCCGGTTAAGTT<br>AAAGCAATGTGTGGTTAAGTT | 19078 |
| bags33j15 | CTTGTGGATTCAAGTACATGA<br>CTTGTGGATTGAAGTACATGA | 19079 |
| bags33j15 | GGGTTCTGGTTGACATACAAA<br>GGGTTCTGGTGGACATACAAA | 19080 |
| bast61d0707 | TCGAACGCGGCAGGCAACGGC<br>TCGAACGCGGAAGGCAACGGC | 19082 |
| basd23a04 | GATGATAACTTCATTTGCGCA<br>GATGATAACTCCATTTGCGCA | 19087 |
| basd14c15 | CACTTACAAAAGACTTCATCA<br>CACTTACAAAGGACTTCATCA | 19088 |
| basd14c15 | TGTTAACACTCACGACCAGGA<br>TGTTAACACTTACGACCAGGA | 19089 |
| bast63c0105 | ACTCTACGGAACGGTCGACCT<br>ACTCTACGGAGCGGTCGACCT | 19090 |
| bast23c1105 | ATGTTTATAACATGATACAGG<br>ATGTTTATAATATGATACAGG | 19091 |
| bast23c1105 | ACGAGTGTTCTAACGAGTGGT<br>ACGAGTGTTCCAACGAGTGGT | 19092 |
| BaAL19H10 | TCTGGTACAAATCCTTCAACC<br>TCTGGTACAAGTCCTTCAACC | 19101 |
| BaAL19H10 | GTTAAATAAAACCTCAAAATT<br>GTTAAATAAAGCCTCAAAATT | 19102 |
| BaSD24B15 | ACATACAAGAAGCAATAAAAA<br>ACATACAAGAGGCAATAAAAA | 19104 |
| BaSD24B15 | GTAATCAACTAATTCCTTTGG<br>GTAATCAACTGATTCCTTTGG | 19105 |
| bah48n17 | GAAAACAGGAACCAAAGGACG<br>GAAAACAGGAGCCAAAGGACG | 19106 |
| bah48n17 | CAACATTCCGTTTCGAAAGAA<br>CAACATTCCGCTTCGAAAGAA | 19107 |
| bags9i05 | GCCAACTTGTCGTCGATGTAG<br>GCCAACTTGTTGTCGATGTAG | 19108 |
| bags9i05 | TCTCTTTTCTGAGCTTCAGAT<br>TCTCTTTTCTAAGCTTCAGAT | 19109 |
| bags1l22 | GTGTAGCACAAATACAGTTAG<br>GTGTAGCACATATACAGTTAG | 19110 |
| bags1l22 | TACTGGGCTCACACTGATGAG<br>TACTGGGCTCCCACTGATGAG | 19111 |
| bags1l22 | AGAAAGTGCTTTACTGGGCTC<br>AGAAAGTGCTGTACTGGGCTC | 19112 |
| bags1l22 | ACTGCATGGCAAATAATGCAG<br>ACTGCATGGCGAATAATGCAG | 19113 |
| bags1l22 | TACTGCCGTAAAGTATATTTA<br>TACTGCCGTACAGTATATTTA | 19114 |
| bah62p18 | CCGATAGGCCACACTTGTCAA<br>CCGATAGGCCTCACTTGTCAA | 19115 |
| bah62p18 | CAGAATTCTGCTCCTTAGTGC<br>CAGAATTCTGTTCCTTAGTGC | 19116 |

TABLE 24-9

| Clones | Haruna Nijo H602 | SEQ ID NO: |
|---|---|---|
| bah62p18 | CAGGAGAATACGGAAGTCAGA<br>CAGGAGAATATGGAAGTCAGA | 19117 |
| bah55n21 | TCGAGGTTTCCACTTTCTAGA<br>TCGAGGTTTCGACTTTCTAGA | 19118 |
| bah55n21 | ATCATGTACAAATATGTCAGG<br>ATCATGTACAGATATGTCAGG | 19119 |
| bah44a05 | GTGGACTGTGTAACCCAGTTA<br>GTGGACTGTGCAACCCAGTTA | 19120 |
| bah19c13 | AATGGTAGTGGTTTGGGAAAA<br>AATGGTAGTGCTTTGGGAAAA | 19121 |
| bah19c13 | TGTGCTTCAACTTCCTCGTCA<br>TGTGCTTCAATTTCCTCGTCA | 19122 |
| bah19c13 | GATCATCATAAGCAACAGGCA<br>GATCATCATACGCAACAGGCA | 19123 |
| kr28B0703 | ATATTGCAGCAGTCATTTACT<br>ATATTGCAGCGGTCATTTACT | 19125 |
| kr28B0703 | GACCTACCAAGGTTTGCTAAA<br>GACCTACCAACGTTTGCTAAA | 19126 |
| kr28B0703 | CTTGTATATAGTGACCTACCA<br>CTTGTATATAATGACCTACCA | 19127 |
| kr28B0703 | TACTCCCTTCCAGTTCAGTTT<br>TACTCCCTTCTAGTTCAGTTT | 19128 |
| bast150C0606 | CTTGCAATTAGTAAATGAATG<br>CTTGCAATTAATAAATGAATG | 19129 |
| bast150C0606 | AATTTCTGAACGATTCACCTG<br>AATTTCTGAATGATTCACCTG | 19130 |
| bah19a05 | CAAGAGAAAGGATCATGTGG<br>CAAGAGAAAAGATCATGTGG | 19132 |
| baal10c06 | ATCCGTAGCC-CAAGGATCCT<br>ATCCGTAGCCACAAGGATCCT | 19133<br>19134 |
| bags19p04 | GCATCCCACAGCCGAAGAAGT<br>GCATCCCACAACCGAAGAAGT | 19135 |
| baak21a17 | TTTTTAACACAATTTTTAACA<br>TTTTTAACACGATTTTTAACA | 19136 |
| bah20j14 | GATTTAAACACCTCATTTCGT<br>GATTTAAACAGCTCATTTCGT | 19137 |
| bah20j14 | CATAGCACTCCGATTTCCTTC<br>CATAGCACTCGGATTTCCTTC | 19138 |
| baak19a03 | AGCTTTAGGGTAAATACATAT<br>AGCTTTAGGGAAAATACATAT | 19139 |
| baak19a03 | ATTTCCCGTGCTGTCTGAAAC<br>ATTTCCCGTGATGTCTGAAAC | 19140 |
| baak19a03 | TAACATACAACACCAGAGAAA<br>TAACATACAAAACCAGAGAAA | 19141 |
| bags30e19 | CGATTTCTGTATACCTTCTTC<br>CGATTTCTGTGTACCTTCTTC | 19142 |
| bags11o14 | GAACCAGATACCATGGTGTAT<br>GAACCAGATATCATGGTGTAT | 19143 |
| bags13p22 | TACAGGCAAGTGAACCACCTC<br>TACAGGCAAGCGAACCACCTC | 19144 |

TABLE 24-10

| Clones | Haruna Nijo / H602 | SEQ ID NO: |
|---|---|---|
| bags13p22 | ATCAGCTAGATTTGGCATACA<br>ATCAGCTAGAGTTGGCATACA | 19145 |
| kr27A1101 | ACGCCTACTCACCGCGCCCG<br>ACGCCTACTCCCCGCGCCCG | 19146 |
| kr27A1101 | ACCCCTCCGCCTCCCGATCTC<br>ACCCCTCCGCGTCCCGATCTC | 19147 |
| kr27A1101 | CCTAGAGGAGGGAAGGCAAGA<br>CCTAGAGGAGAGAAGGCAAGA | 19148 |
| kr27A1101 | CCCTCGCCTATAACCCCTCCG<br>CCCTCGCCTAGAACCCCTCCG | 19149 |
| bast58f0412 | CGGGGCCGCAGATATACATTG<br>CGGGGCCGCAAATATACATTG | 19152 |
| bast58f0412 | AATGAACCCATAAAGGAGATT<br>AATGAACCCAGAAAGGAGATT | 19153 |
| bast58f0412 | ACAGGGAACGACTATAAAAGC<br>ACAGGGAACGGCTATAAAAGC | 19154 |
| bast58f0412 | CCTAACAGTATAAATGCTATG<br>CCTAACAGTAGAAATGCTATG | 19155 |
| bast58f0412 | TACTACTAACGCGTTACTGGG<br>TACTACTAACACGTTACTGGG | 19156 |
| baal32p23 | CTCCCTCTGTAAAACTTTCAG<br>CTCCCTCTGTGAAACTTTCAG | 19159 |
| baal32p23 | GACATAACCACTATTAGTTGC<br>GACATAACCATTATTAGTTGC | 19160 |
| baal32p23 | CAGAGCTCCTCTGAAGTTTCG<br>CAGAGCTCCTATGAAGTTTCG | 19161 |
| basd23m17 | CTGCATTAAAAAATTGAGTGT<br>CTGCATTAAACAATTGAGTGT | 19162 |
| basd23m17 | CATTCGGAACATACCAACCAC<br>CATTCGGAACGTACCAACCAC | 19163 |
| bastl30E0509 | ACCTGGAATATAAAAACATCG<br>ACCTGGAATACAAAAACATCG | 19164 |
| bastl30E0509 | TCGCTTCAGAAAGCATCATTA<br>TCGCTTCAGACAGCATCATTA | 19165 |
| bah44b08 | AGGCCGGGCCGGGCCGGAGAT<br>AGGCCGGGCCAGGCCGGAGAT | 19166 |
| bah44b08 | CAAAAATCACGGAACAGCAAG<br>CAAAAATCACAGAACAGCAAG | 19167 |
| BaGS14N10 | GCCTGGGCCAGCGGACGATGA<br>GCCTGGGCCAACGGACGATGA | 19168 |
| BaGS14N10 | CAGCAGGTGACTTCGGGGACT<br>CAGCAGGTGATTTCGGGGACT | 19169 |
| BaGS14N10 | GGCCACATTACTCTTGGTGGC<br>GGCCACATTATTCTTGGTGGC | 19170 |
| BaGS32B13 | ATTTGCTCCATATGTAGACT<br>ATTTGCTCCGTATGTAGACT | 19171 |
| BaGS32B13 | ATAAGTCATTTGCGTAGTTTT<br>ATAAGTCATTCGCGTAGTTTT | 19172 |
| BaGS32B13 | AGAGAAAATACGGGACGGCAG<br>AGAGAAAATATGGGACGGCAG | 19173 |

TABLE 24-11

| Clones | Haruna Nijo / H602 | SEQ ID NO: |
|---|---|---|
| BaH30B03 | TCAAGCCTGAAAATACGACAA<br>TCAAGCCTGACAATACGACAA | 19174 |
| BaH30B03 | TTCACATGTTTGCTTTCCTCT<br>TTCACATGTTCGCTTTCCTCT | 19175 |
| BaH30B03 | GGCCATAAGATATTTCACACC<br>GGCCATAAGAAATTTCACACC | 19176 |
| basd11o06 | GTAGCACTGACATGGAAGTTC<br>GTAGCACTGAAATGGAAGTTC | 19178 |
| basd11o06 | TCTGCATACTTTCGATTTGGT<br>TCTGCATACTGTCGATTTGGT | 19179 |
| basd11o06 | ATAAAGAGGAAATGGTTAGGC<br>ATAAAGAGGAGATGGTTAGGC | 19180 |
| basd11o06 | GAACGCTCACGAGGACTGAAC<br>GAACGCTCACAAGGACTGAAC | 19181 |
| basd11o06 | CTCTAGGTGAAAACGTGACTA<br>CTCTAGGTGAGAACGTGACTA | 19182 |
| bah17f24 | GATCTGTTACATCTACAGCAT<br>GATCTGTTACGTCTACAGCAT | 19183 |
| bah17f24 | TAACAATCCTCATATTGTGGA<br>TAACAATCCTTATATTGTGGA | 19184 |
| bah17f24 | AAATACAACAGCATATGAAAA<br>AAATACAACAACATATGAAAA | 19185 |
| bah17f24 | AAGCCACGCACATAGATCTGT<br>AAGCCACGCAAATAGATCTGT | 19186 |
| bah17f24 | CTTACAAAATGTAGACAAGCA<br>CTTACAAAATTTAGACAAGCA | 19187 |
| BaAK26L17 | TCGATCCGGTTCCAAAGAGCT<br>TCGATCCGGTCCCAAAGAGCT | 19188 |
| BaAK26L17 | GACATGACACTAGGTCCAGCA<br>GACATGACACCAGGTCCAGCA | 19189 |
| BaAK26L17 | CTCCATCAGCGAGGAACTTCA<br>CTCCATCAGCAAGGAACTTCA | 19190 |
| bags23f03 | CAGCTATAGTCATGGAAATAA<br>CAGCTATAGTTATGGAAATAA | 19191 |
| bags20o06 | TTTTCTCCTGTACTCTAGCTG<br>TTTTCTCCTGCACTCTAGCTG | 19192 |
| bags20o06 | GTGCCGGACATCGCTGTTGTT<br>GTGCCGGACACCGCTGTTGTT | 19193 |
| bags19n12 | GAAGGCTAGCGTGAAGTTGCA<br>GAAGGCTAGCATGAAGTTGCA | 19194 |
| bast14f0612 | ATATAGTTTCCCAGCATACTA<br>ATATAGTTTCACAGCATACTA | 19195 |
| bags16k13 | CTTTCACAGTTTTGATTTGAG<br>CTTTCACAGTCTTGATTTGAG | 19197 |
| bags16k13 | TGAATCGATGAGTAGTGACTA<br>TGAATCGATGGGTAGTGACTA | 19198 |
| baak22c16 | GCTCCCTGCAGTCCATATTAA<br>GCTCCCTGCAATCCATATTAA | 19199 |
| baak22c16 | CATTGCAATCATAGCAAAAAG<br>CATTGCAATCGTAGCAAAAAG | 19200 |

TABLE 24-12

| Clones | Haruna Nijo / H602 | SEQ ID NO: |
|---|---|---|
| baak22c16 | TGAAGACATAATAATCAGCAG<br>TGAAGACATAGTAATCAGCAG | 19201 |
| baak22c16 | CAGGGCTTGTTAATAGTTTTA<br>CAGGGCTTGTGAATAGTTTTA | 19202 |
| baak22c16 | ATCTCACTGAAAACAGAGCAT<br>ATCTCACTGAGAACAGAGCAT | 19203 |
| baak22c16 | GGGAACATGTTCATGCTTCGG<br>GGGAACATGTACATGCTTCGG | 19204 |
| baak22c16 | TCCGCAGGGCCTGTCTCCCAG<br>TCCGCAGGGC-TGTCTCCCAG | 19205<br>19206 |
| baak22c16 | TGCATCACAGCACGATCAACA<br>TGCATCACAG-ACGATCAACA | 19207<br>19208 |
| baal40m06 | GAATCGTCCTCTTTTGCTGCC<br>GAATCGTCCTATTTTGCTGCC | 19209 |
| baal40m06 | CCTTTCCTGTCGCCTCCCTTG<br>CCTTTCCTGTTGCCTCCCTTG | 19210 |
| bah57a11 | ACATCAAAGGATCACTATAAT<br>ACATCAAAGGGTCACTATAAT | 19213 |
| bah57a11 | TGAAACTGGTGAGGAGATATA<br>TGAAACTGGTAAGGAGATATA | 19214 |
| bah41e23 | AAACTACCAAGGTTGTATCCA<br>AAACTACCAAAGTTGTATCCA | 19215 |
| bah41e23 | TGATACAAAAAATGTTTGCAT<br>TGATACAAAAGATGTTTGCAT | 19216 |
| bah41e23 | CCTGGTATTTTGCTATCAGAA<br>CCTGGTATTTCGCTATCAGAA | 19217 |
| BaSD14L18 | ACATATGAGTTAGTCCGATGA<br>ACATATGAGTAAGTCCGATGA | 19218 |
| BaSD14L18 | TTGTCACTCATGAAATACTCA<br>TTGTCACTCAAGAAATACTCA | 19219 |
| BaSD14L18 | CTCAGCTTCAGTATTTCTGAA<br>CTCAGCTTCACTATTTCTGAA | 19220 |
| BaSD14L18 | TTTTACGTTTTCCTCAGCTTC<br>TTTTACGTTTCCCTCAGCTTC | 19221 |
| BaSD14L18 | GCCCAGCAGTGTTCTCCTGAA<br>GCCCAGCAGTATTCTCCTGAA | 19222 |
| bah14d17 | CCACCCCTCTTCCATCTCCTT<br>CCACCCCTCTACCATCTCCTT | 19223 |
| bah14d17 | CCATGTCGACGTCGGCCGGCT<br>CCATGTCGACATCGGCCGGCT | 19224 |
| bah14d17 | CGGCAGCTCGCGGTACCGCTC<br>CGGCAGCTCGTGGTACCGCTC | 19225 |
| BaGS1N17 | ACACACACACGAAGAGAGAGA<br>ACACACACACAAAGAGAGAGA | 19226 |
| BaGS1N17 | CTTTGTCAGATGCAGCCACAG<br>CTTTGTCAGACGCAGCCACAG | 19227 |
| BaGS1N17 | AGAGCTCACATATCCATTTTC<br>AGAGCTCACAAATCCATTTTC | 19228 |
| bags27h17 | CAGCTCTGAA-GAACCTCGTN<br>CAGCTCTGAAAGAACCTCGTN | 19229<br>19230 |

TABLE 24-13

| Clones | Haruna Nijo / H602 | SEQ ID NO: |
|---|---|---|
| bah47p22 | GTATCGAATA-GTTAATTAAT<br>GAATCGAATAAGTTAATTAAT | 19231<br>19232 |
| bah47p22 | CCTGTATGTG-AAAATGAAAA<br>CCTGTATGTGTAAAATGAGAA | 19233<br>19234 |
| bah50a16 | GTTGTTTGGGCGTGCAGAGAA<br>GTTGTTTGGGGGTGCAGAGAA | 19235 |
| bags7b20 | TTAGAACTTAGGCATGCAATG<br>TTAGAACTTACGCATGCAATG | 19236 |
| bags7b20 | CCTGGTATTTCGCTATCAGAA<br>CCTGGTATTTTGCTATCAGAA | 19237 |
| bags7b20 | TTGTTTCAGAAAGACTTAGTA<br>TTGTTTCAGACAGACTTAGTA | 19238 |
| bags22a02 | TGTCTTAGTTGTACATTAATC<br>TGTCTTAGTTATACATTAATC | 19239 |
| bags22a02 | TATACAGAGAGGGTTTTACTA<br>TATACAGAGATGGTTTTACTA | 19240 |
| bags22a02 | ATCACACAAATCGTACATGAA<br>ATCACACAAACCGTACATGAA | 19241 |
| basd12g02 | GGATCAGCAGAGGCAAACAGA<br>GGATCAGCAGTGGCAAACAGA | 19242 |
| basd12g02 | CAATTAAGTGAAACTGCACCT<br>CAATTAAGTGGAACTGCACCT | 19243 |
| basd12g02 | GTGCCGAGTATGCCACTTGTA<br>GTGCCGAGTACGCCACTTGTA | 19244 |
| basd15o18 | AAACGCTTGTGGGCAACCGCC<br>AAACGCTTGTAGGCAACCGCC | 19245 |
| basd15o18 | TAGCGGAGCCACCGGAATCGT<br>TAGCGGAGCCGCCGGAATCGT | 19246 |
| baal25d19 | GTTCCTCGTTTGGTTTTGTCG<br>GTTCCTCGTTCGGTTTTGTCG | 19247 |
| bast52g0414 | AATCGTAATGCAGCACGGATG<br>AATCGTAATGAAGCACGGATG | 19248 |
| bags37k06 | CACATAGAAACTATCACGCCA<br>CACATAGAAATTATCACGCCA | 19250 |
| bags6e22 | ACCTGGAGACAACATAGATTA<br>ACCTGGAGACTACATAGATTA | 19251 |
| bags6e22 | AGATATCTAAAACCTGGAGAC<br>AGATATCTAACACCTGGAGAC | 19252 |
| bags6e22 | TTTCTCATTATCTGCAAAAAA<br>TTTCTCATTAGCTGCAAAAAA | 19253 |
| bags7b06 | ATATTTCTGGTTCATGGATTT<br>ATATTTCTGGGTCATGGATTT | 19255 |
| bags7b06 | GGTCGGGGCCTGGCTGGCTAT<br>GGTCGGGGCCGGGCTGGCTAT | 19256 |
| bags7b06 | TGGCTATCGAGCTCCGGCGAC<br>TGGCTATCGAACTCCGGCGAC | 19257 |
| bags7b06 | AGCATGTGCTAGAAATGCCGG<br>AGCATGTGCTTGAAATGCCGG | 19258 |
| bast46c0406 | CAGACGCCATAACCCATCTGA<br>CAGACGCCATGACCCATCTGA | 19261 |

TABLE 24-14

| Clones | Haruna Nijo H602 | SEQ ID NO: |
|---|---|---|
| bast46c0406 | TCAAGGTCAATAAGTTTCACA<br>TCAAGGTCAACAAGTTTCACA | 19262 |
| bast46c0406 | GAGGAATTGGTCAAACGCCAA<br>GAGGAATTGGACAAACGCCAA | 19263 |
| bast145e0509 | ACATAGAGGAGAGGATACACC<br>ACATAGAGGATAGGATACACC | 19264 |
| bast145e0509 | GGATTTACACGACCGATTTTG<br>GGATTTACACAACCGATTTTG | 19265 |
| BaH41G07 | CTTCTTCCCCCACATCTGCAT<br>CTTCTTCCCCTACATCTGCAT | 19267 |
| bast46H1016 | AATTCCACCCTAGAAAATCCA<br>AATTCCACCCCAGAAAATCCA | 19268 |
| bah60d12 | GAGCCCTCTGTCCTTGGTCCT<br>GAGCCCTCTGCCCTTGGTCCT | 19269 |
| bah60d12 | CCCTGAGTGCCTTGCCGCCCT<br>CCCTGAGTGCATTGCCGCCCT | 19270 |
| bah60d12 | TGCCGCCCTCAGACGCCATGA<br>TGCCGCCCTCGGACGCCATGA | 19271 |
| bah60d12 | CGGCAGCTGCAACCTTCGCCG<br>CGGCAGCTGCGACCTTCGCCG | 19272 |
| bah60d12 | CCGCGTACAGAGGCCAGCATA<br>CCGCGTACAGCGGCCAGCATA | 19273 |
| bah60d12 | CTTCATTGTATCCTCTCATCT<br>CTTCATTGTAGCCTCTCATCT | 19274 |
| bah60d12 | CCCTTAACCACCTCTTCATTG<br>CCCTTAACCAGCTCTTCATTG | 19275 |
| bah60d12 | TTCCACCTCCTCGCCCTTAAC<br>TTCCACCTCCACGCCCTTAAC | 19276 |
| bah60d12 | CCTTGAGCGCGTCGGCAGCTG<br>CCTTGAGCGCCTCGGCAGCTG | 19277 |
| baal39a19 | GTAGGGTCTCCTCTTGGGCAG<br>GTAGGGTCTCTTCTTGGGCAG | 19278 |
| baal39a19 | TGACGGGGATCGCGGGAGGCC<br>TGACGGGGATGGCGGGAGGCC | 19279 |
| baal39a19 | GACACTCTGACTCTCAACCGC<br>GACACTCTGAGTCTCAACCGC | 19280 |
| baal39a19 | TGCCGCTCCGAGCCATCATCA<br>TGCCGCTCCGCGCCATCATCA | 19281 |
| baal39a19 | TCATCAGGTTCGCGCAGGAGC<br>TCATCAGGTTTGCGCAGGAGC | 19282 |
| baal39a19 | ACCTCACCTCGGACATGCACG<br>ACCTCACCTCCGACATGCACG | 19283 |
| baal39a19 | GGGCAGGTCCGCCAGGCACCT<br>GGGCAGGTCCTCCAGGCACCT | 19284 |
| baal39a19 | TGCACGCGAACGACTGGGACT<br>TGCACGCGAAGGACTGGGACT | 19285 |
| bast14e0909 | GACACACAAAAATAATGGTAC<br>GACACACAAAGATAATGGTAC | 19287 |
| baet13g0713 | CGTCGCCGGCCGGCTTGATGC<br>CGTCGCCGGCTGGCTTGATGC | 19288 |

TABLE 24-15

| Clones | Haruna Nijo H602 | SEQ ID NO: |
|---|---|---|
| baak13c05 | GGAGGACGTGCAGATCATCCC<br>GGAGGACGTGGAGATCATCCC | 19289 |
| bast141g0513 | ACTTGCTCAGGGAGGAGTGGT<br>ACTTGCTCAGCGAGGAGTGGT | 19290 |
| baal19b12 | TAGTGCATCTTTTGCAATGGC<br>TAGTGCATCTCTTGCAATGGC | 19292 |
| baal19b12 | TTACATGATAGGGTCATTACC<br>TTACATGATAAGGTCATTACC | 19293 |
| baal19b12 | TAGAGTATCAGATGGAAATAT<br>TAGAGTATCAAATGGAAATAT | 19294 |
| baal19b12 | TTCATGAGTTTACAATTATTT<br>TTCATGAGTTCACAATTATTT | 19295 |
| baal19b12 | ATAGAATCCAGAGTGTCAACT<br>ATAGAATCCAAAGTGTCAACT | 19296 |
| baal19b12 | TGGAAATATTGTAAATGACGA<br>TGGAAATATTATAAATGACGA | 19297 |
| baal19b12 | TGACGAAATAGAGTACACAGC<br>TGACGAAATAAAGTACACAGC | 19298 |
| baal39b05 | CCTGGTCACCTCCACCCTGCG<br>CCTGGTCACCGCCACCCTGCG | 19299 |
| baal1j03 | CAACCTACGCTGTGGCTATCA<br>CAACCTACGCCGTGGCTATCA | 19300 |
| BaGS33N15 | TAAAGAAGGGAAAAATTAACG<br>TAAAGAAGGGGAAAATTAACG | 19301 |
| basd11k09 | CCTGGTCACCTCCACCCTGCG<br>CCTGGTCACCGCCACCCTGCG | 19302 |
| basd11k09 | GACGGCCTTAACTTCTTCACC<br>GACGGCCTTACCTTCTTCACC | 19303 |
| baet43H0416 | GAACTAGCCACAGGTTGCACT<br>GAACTAGCCATAGGTTGCACT | 19304 |
| bah11m06 | CAGATAGTACCTCGATCCTCT<br>CAGATAGTACTTCGATCCTCT | 19305 |
| bah11m06 | GAATAAGGAACGTTCTTAGAA<br>GAATAAGGAATGTTCTTAGAA | 19306 |
| bags27h20 | ATTAGCATCGTTTTAGACAAG<br>ATTAGCATCGGTTTAGACAAG | 19310 |
| basd27c09 | GAACTAGCCACAGGTTGCACT<br>GAACTAGCCATAGGTTGCACT | 19311 |
| basd27c09 | TCAACACTTTTGTATAGAAGG<br>TCAACACTTTGGTATAGAAGG | 19312 |
| basd27c09 | TCTCCAGGTGGTTCTGCATGA<br>TCTCCAGGTGTTTCTGCATGA | 19313 |
| baal25o01 | TTAACATAATTAGAGGATTGA<br>TTAACATAATCAGAGGATTGA | 19315 |
| baal25o01 | AAACAACTAGGTAGTGAAAAC<br>AAACAACTAGATAGTGAAAAC | 19316 |
| baal25o01 | TTATCACTGCCCCAGATCCTT<br>TTATCACTGCACCAGATCCTT | 19317 |
| BaAK19J09 | GGGCTTTGTTCTCCACTCAGG<br>GGGCTTTGTTTTCCACTCAGG | 19319 |

TABLE 24-16

| Clones | Haruna Nijo H602 | SEQ ID NO: |
|---|---|---|
| BaAK19J09 | CCATTTTGACGTATGTTTGTG<br>CCATTTTGACATATGTTTGTG | 19320 |
| bags20n14 | CCGTCATGACGGATATACAGG<br>CCGTCATGACAGATATACAGG | 19321 |
| baak31k16 | AGAATTGAGCAGCGACTCTAA<br>AGAATTGAGCGGCGACTCTAA | 19322 |
| baak31k16 | CCATCCCCACCGTTTCTTTCA<br>CCATCCCCACTGTTTCTTTCA | 19323 |
| baak31k16 | CGTAGTAGGCGTGCGTCCGGT<br>CGTAGTAGGCNTGCGTCCGGT | 19324 |
| bah42o12 | TAGCGTGAGTTATGAAGTTAT<br>TAGCGTGAGTGATGAAGTTAT | 19325 |
| bags4p14 | TGATAGTTCATATACAAAACA<br>TGATAGTTCAGATACAAAACA | 19326 |
| bags4p14 | CCTGTGTGCAACCCAAAAACA<br>CCTGTGTGCAGCCCAAAAACA | 19327 |
| bags4p14 | ATAAAATTTGAACTAACGTAG<br>ATAAAATTTGTACTAACGTAG | 19328 |
| bags4p14 | GCTAGAGAAGCCAACAAGTAG<br>GCTAGAGAAGTCAACAAGTAG | 19329 |
| BaH62B09 | AATCCCTTGCCCAAGGCTTGA<br>AATCCCTTGCTCAAGGCTTGA | 19331 |
| BaH62B09 | ATATGTAGAAAGAGCATGACA<br>ATATGTAGAAGGAGCATGACA | 19332 |
| BaH62B09 | GAAATCCAAAGCCCTAGCCCA<br>GAAATCCAAAACCCTAGCCCA | 19333 |
| bags19j10 | CCTTCCTGCTGGGGTCTTCAT<br>CCTTCCTGCTCGGGTCTTCAT | 19334 |
| bags15k18 | CAAACCAGCAGTGGGAAGCGA<br>CAAACCAGCAATGGGAAGCGA | 19336 |
| bags15k18 | GTTGACAAACAGTATAGCGTG<br>GTTGACAAACGGTATAGCGTG | 19337 |
| bags15k18 | AACACACTGTGCGCTGAATAC<br>AACACACTGTACGCTGAATAC | 19338 |
| bags15k18 | TCCCTATAATCAGTATGAAAC<br>TCCCTATAATGAGTATGAAAC | 19339 |
| basd26c09 | ACTCCAAGAGCGTCCGCCTTC<br>ACTCCAAGAGTGTCCGCCTTC | 19342 |
| basd26c09 | ATGGAAAAGAGCAATGTCGAC<br>ATGGAAAAGAACAATGTCGAC | 19343 |
| basd26c09 | CCATGTGGCTCACCATGGAAA<br>CCATGTGGCTTACCATGGAAA | 19344 |
| basd20b11 | TCCGGACGGAAGGAGTACTAC<br>TCCGGACGGAGGGAGTACTAC | 19345 |
| basd20b11 | CCTAGAAATGAATGTATCTAG<br>CCTAGAAATGGATGTATCTAG | 19346 |
| BaH46F11 | CATTTTCTATCTGAAATCTTG<br>CATTTTCTATTTGAAATCTTG | 19347 |
| BaH46F11 | AAACACACACACGCAACCCAA<br>AAACACACACCCGCAACCCAA | 19348 |

TABLE 24-17

| Clones | Haruna Nijo H602 | SEQ ID NO: |
|---|---|---|
| BaH46F11 | ACTTCAGGAATACCGAGTTCT<br>ACTTCAGGAACACCGAGTTCT | 19349 |
| bah30f03 | GGTTGTAAACGTCATGTGTCT<br>GGTTGTAAACATCATGTGTCT | 19351 |
| baak33i12 | ATAAAGTTCTGGAAACAATGG<br>ATAAAGTTCTTGAAACAATGG | 19354 |
| bags37a16 | TTCCTGGCCGCCGGCGCCCTC<br>TTCCTGGCCGGCGGCGCCCTC | 19356 |
| bags37a16 | TGGCGATGCCGCTGCCGCGCT<br>TGGCGATGCCCCTGCCGCGCT | 19357 |
| bags39p06 | TCGGCCCATTCCCGCAGGGCC<br>TCGGCCCATTTCCGCAGGGCC | 19358 |
| baal12n06 | TCAGCAGTTTCCATCCCTCAC<br>TCAGCAGTTTTCATCCCTCAC | 19359 |
| bags9a03 | GGCAATCTCAAGGACGAGAGG<br>GGCAATCTCAGGGACGAGAGG | 19360 |
| bags9a03 | AGGGTCGTCCCGGTTAGGGTC<br>AGGGTCGTCCGGGTTAGGGTC | 19361 |
| bags9a03 | GCAGCGAGCACATTGAAAGCA<br>GCAGCGAGCAGATTGAAAGCA | 19362 |
| bags9a03 | CATACTTCTGGGTCCAGCTGC<br>CATACTTCTGCGTCCAGCTGC | 19363 |
| bags9a03 | TGCGGGCTGTTGTCTCGTACT<br>TGCGGGCTGTCGTCTCGTACT | 19364 |
| baet24F1212 | GTTTCCACAATGCAAGGCTAC<br>GTTTCCACAACGCAAGGCTAC | 19365 |
| baak29d10 | AGCATTGTCAGTTCTTGGACG<br>AGCATTGTCAATTCTTGGACG | 19366 |
| bags13i12 | CCGTGGAAGCTTGTCGGGTCC<br>CCGTGGAAGCCTGTCGGGTCC | 19367 |
| baal16a23 | CCTGGAAGCCGTGGAGGTTCA<br>CCTGGAAGCCATGGAGGTTCA | 19368 |
| baal16a23 | CAGGCTGAAGCGTGTGCGAGG<br>CAGGCTGAAGTGTGTGCGAGG | 19369 |
| bastl29F0711 | GGCCCAGAGAGGAAGATTTCA<br>GGCCCAGAGAAGAAGATTTCA | 19370 |
| bastl29F0711 | GCTTGGCCGCCTCTCCCCTGC<br>GCTTGGCCGCGTCTCCCCTGC | 19371 |
| bastl29F0711 | CTCTTCAGCAGGCTCTGCAGC<br>CTCTTCAGCAAGCTCTGCAGC | 19372 |
| bastl29F0711 | CGTACAGTAGCCATACTGTGA<br>CGTACAGTAGTCATACTGTGA | 19373 |
| bastl16b1204 | TTTTGGACGACCAGATTTGTG<br>TTTTGGACGAGCAGATTTGTG | 19374 |
| baal15e10 | GATTCATGACGAAATTCCTTC<br>GATTCATGACAAAATTCCTTC | 19376 |
| baal33m18 | CACCATCAGACGTGCTGCCTG<br>CACCATCAGATGTGCTGCCTG | 19378 |
| baak24e23 | TAATGTCAGAAATCATGAGAA<br>TAATGTCAGACATCATGAGAA | 19379 |

TABLE 24-18

| Clones | Haruna Nijo H602 | SEQ ID NO: |
|---|---|---|
| baak24e23 | CCACACTGCTCAAGGGACTCC CCACACTGCTAAAGGGACTCC | 19380 |
| baak24e23 | AAAAATGTTCGCAAGGATGTT AAAAATGTTCTCAAGGATGTT | 19381 |
| baak24e23 | CAGAAACAAGTCATTATGGTC CAGAAACAAGACATTATGGTC | 19382 |
| baak24e23 | ATTTGCAATAGTTAGTATATC ATTTGCAATAATTAGTATATC | 19383 |
| baak24e23 | ACACGCTACTCATAGTCGACA ACACGCTACTTATAGTCGACA | 19384 |
| baak24e23 | AACTCCCACAGGTATAAATGA AACTCCCACATGTATAAATGA | 19385 |
| baak24e23 | TGATGGTCAGTGGATAATAAT TGATGGTCAGCGGATAATAAT | 19386 |
| baak46j13 | TCATACACATAGTCGCACAAA TCATACACATGGTCGCACAAA | 19387 |
| baak46j13 | CGAGGAGGGTAAAGAGGATGA CGAGGAGGGTGAAGAGGATGA | 19388 |
| bah49o05 | GTTCATTGATAGTGTAAAATT GTTCATTGATCGTGTAAAATT | 19389 |
| bah49o05 | CAAGGTGCGGTGGACATCAGC CAAGGTGCGGAGGACATCAGC | 19390 |
| bah49o05 | CTGTCTGCCGCCGGACATGAA CTGTCTGCCGTCGGACATGAA | 19391 |
| bah49o05 | GACCATCAGAAATGGAGTGTT GACCATCAGATATGGAGTGTT | 19392 |
| baal15e05 | TGTTATCGTCGCCCTCGTATG TGTTATCGTCCCCCTCGTATG | 19393 |
| BaGS30P02 | CCTCGCTCTCAAACTGCACGA CCTCGCTCTCGAACTGCACGA | 19394 |
| BaGS30P02 | GATCCCTCGAGCTTGCTCGCA GATCCCTCGATCTTGCTCGCA | 19395 |
| baak1o08 | CCTAACCACAGAAATAAATAA CCTAACCACACAAATAAATAA | 19396 |
| BaSD15D05 | TTTTTGACCCTGCACTCTCCT TTTTTGACCCCGCACTCTCCT | 19397 |
| bags38n23 | ACGCAAATGCTATCGCCAATT ACGCAAATGCCATCGCCAATT | 19399 |
| bags38n23 | ACTGATGCACCTGACCCTTAA ACTGATGCACTTGACCCTTAA | 19400 |
| bags38n23 | AATCTCTCGACCAGTGACCTG AATCTCTCGAGCAGTGACCTG | 19401 |
| bags38n23 | GCCTTGGATGGGATTTATCTC GCCTTGGATGAGATTTATCTC | 19402 |
| bags38n23 | AGGAACTCCTCCAGGTAAGCT AGGAACTCCTTCAGGTAAGCT | 19403 |
| baak36a14 | CTATGAATCACGCTCATAACA CTATGAATCATGCTCATAACA | 19404 |
| baak36a14 | TCCTAATAGCGGCAGCAACAA TCCTAATAGCAGCAGCAACAA | 19405 |

TABLE 24-19

| Clones | Haruna Nijo H602 | SEQ ID NO: |
|---|---|---|
| bags35n24 | GGTCGAGCGTGATGCGATGCA GGTCGAGCGTCATGCGATGCA | 19410 |
| bags35n24 | GCCATGAGAAGGAGCTCGAGG GCCATGAGAAAGAGCTCGAGG | 19411 |
| bah37j21 | AGTACTTGTCTTCACTCGCCT AGTACTTGTCCTCACTCGCCT | 19412 |
| bah31e13 | ATCATCAAATCGTTTACTATA ATCATCAAATTGTTTACTATA | 19413 |
| bah31e13 | TGAAGCACACGATGTGGCAGT TGAAGCACACAATGTGGCAGT | 19414 |
| bah31e13 | TCCGACTTATACAGCGGAAAG TCCGACTTATGCAGCGGAAAG | 19415 |
| bah31e13 | CTACACCGCCTTTTATTCTCT CTACACCGCCATTTATTCTCT | 19416 |
| baal30l05 | AATACCTATCCACTTGTTGTA AATACCTATCAACTTGTTGTA | 19417 |
| baal30l05 | TGTATAATGACACAATGCATG TGTATAATGAGACAATGCATG | 19418 |
| baal30l05 | TAGACCCAAGTGAGCCAAAAG TAGACCCAAGCGAGCCAAAAG | 19419 |
| baal30l05 | GATCGTATATAAAATAAAACA GATCGTATATCAAATAAAACA | 19420 |
| bags38o10 | CCAGTGCAGATGTCTCAAGGA CCAGTGCAGAGGTCTCAAGGA | 19421 |
| bags38o10 | CTTTCTCAGAAAATGCTTGGC CTTTCTCAGAGAATGCTTGGC | 19422 |
| bags38o10 | CGTTAATAGTGCTTTCCTTGC CGTTAATAGTCCTTTCCTTGC | 19423 |
| bast130A0701 | CTCCTCCCCTCTTTACACCTA CTCCTCCCCTTTTTACACCTA | 19425 |
| bah49l21 | AGCACTTCACCTTCTCCCGCG AGCACTTCACTTTCTCCCGCG | 19426 |
| bah49l21 | TGCACTAACTGTTCCTGTGAA TGCACTAACTATTCCTGTGAA | 19427 |
| bags19l03 | GACAACATAGTAAAATAGTAT GACAACATAGCAAAATAGTAT | 19428 |
| bags19l03 | AACAAAAAGGAAAATGAACT AACAAAAAGAAAAATGAACT | 19429 |
| bags19l03 | TAACCAAGTCATCTAGAACAA TAACCAAGTCGTCTAGAACAA | 19430 |
| baak44p03 | AGGAGGAGGAGGAAGAAGAAG AGGAGGAGGAAGAAGAAGAAG | 19431 |
| kr10h0216 | CCATAATCCTGCAAGAATTCC CCATAATCCTCCAAGAATTCC | 19433 |
| kr10h0216 | CGTCCCGGCGCCCCAGATCCA CGTCCCGGCGTCCCAGATCCA | 19434 |
| bah11i21 | ATGTACATATGGTTCGTGTAT ATGTACATATAGTTCGTGTAT | 19436 |
| bah11i21 | TTTTAGCCGTGAGAAAAGAAT TTTTAGCCGTAAGAAAAGAAT | 19437 |

TABLE 24-20

| Clones | Haruna Nijo H602 | SEQ ID NO: |
|---|---|---|
| bah11i21 | AATTTCATGTCTTCTTTCCCG<br>AATTTCATGTTTTCTTTCCCG | 19438 |
| baak20k23 | GGAATTTATGCGGCTGCGCTA<br>GGAATTTATGTGGCTGCGCTA | 19439 |
| baak20k23 | CATCCTGCAAGCAGTGTTGAC<br>CATCCTGCAAACAGTGTTGAC | 19440 |
| basd14n22 | ACGACTGAGATCTTGTGTACC<br>ACGACTGAGACCTTGTGTACC | 19443 |
| basd14n22 | ATTTGCAGCACACAGAGAGCA<br>ATTTGCAGCATACAGAGAGCA | 19444 |
| basd14n22 | ACAGAGTTCAGGGCCGATATC<br>ACAGAGTTCACGGCCGATATC | 19445 |
| basd14n22 | TATTAGATGTGCGGTTTGATG<br>TATTAGATGTTCGGTTTGATG | 19446 |
| basd14n22 | CGCGGCAGAATGGGCACGACT<br>CGCGGCAGAAAGGGCACGACT | 19447 |
| basd14n22 | TGTCGGGGACTATGAGGGGCA<br>TGTCGGGGACGATGAGGGGCA | 19448 |
| basd14n22 | TAGTAGACCAACAGGAGGTTG<br>TAGTAGACCAGCAGGAGGTTG | 19449 |
| basd14n22 | AAAGCCAGAGAAACAAATAAT<br>AAAGCCAGAGCAACAAATAAT | 19450 |
| baet44D0707 | CGCTTGCTGGTGGCAGCTTGC<br>CGCTTGCTGGCGGCAGCTTGC | 19451 |
| bah16p10 | CATTCATCAGGGAATGCACAG<br>CATTCATCAGCGAATGCACAG | 19452 |
| bah16p10 | TGTGTCACCCGCAACCTCCAG<br>TGTGTCACCCTCAACCTCCAG | 19453 |
| baak42j01 | CCAGCTGGACCCCAGTGCTTAG<br>CCAGCTGGACACAGTGCTTAG | 19455 |
| baak42j01 | ACAAATAGACACATGATTTAG<br>ACAAATAGACCCATGATTTAG | 19456 |
| BaAK38008 | TGGTGCTAAAGAAGTGTTTGC<br>TGGTGCTAAAAAAGTGTTTGC | 19457 |
| baal15f24 | ATAACTTTTAGCTGCTTTCAG<br>ATAACTTTTATCTGCTTTCAG | 19461 |
| baal15f24 | TCTCATATCTCTAGTCTCGAG<br>TCTCATATCTGTAGTCTCGAG | 19462 |
| baal15f24 | AACACCTGAAACCACTTTTCT<br>AACACCTGAAGCCACTTTTCT | 19463 |
| baal15f24 | AGGTGCTGATGGTGTTTTTG<br>AGGTGCTGATAGTGTTTTTG | 19464 |
| baal15f24 | CTCTTTTGCTTGAGCAATTAG<br>CTCTTTTGCTAGAGCAATTAG | 19465 |
| baal15f24 | TCTAACAACAAATAGATACGT<br>TCTAACAACATATAGATACGT | 19466 |
| baal15f24 | GATGAATTTAGATAAATGACA<br>GATGAATTTACATAAATGACA | 19467 |
| baal15f24 | GCAATTAGCTCTGCTTGCATC<br>GCAATTAGCTGTGCTTGCATC | 19468 |

TABLE 24-21

| Clones | Haruna Nijo H602 | SEQ. ID NO: |
|---|---|---|
| basd18b21 | TGGCATAGCATGTCAGAGGTC<br>TGGCATAGCAAGTCAGAGGTC | 19469 |
| basd18b21 | GGCGGATCATCGGTATGCATC<br>GGCGGATCATTGGTATGCATC | 19470 |
| basd18b21 | TCAGAGGTCAACCATAACACA<br>TCAGAGGTCATCCATAACACA | 19471 |
| basd17g23 | GCAGCTCATTGAGCTCCGTCT<br>GCAGCTCATTTAGCTCCGTCT | 19472 |
| basd17g23 | TGGTCTTCTTCCGCAGCTCAT<br>TGGTCTTCTTTCGCAGCTCAT | 19473 |
| basd17g23 | GCCTGGCGACGCAGACATGTC<br>GCCTGGCGACACAGACATGTC | 19474 |
| baak41k22 | TCATGTTAAACTCACGGTTCA<br>TCATGTTAAATTCACGGTTCA | 19475 |
| baak41k22 | GTTCAGGAAAAAGCACAAAGT<br>GTTCAGGAAATAGCACAAAGT | 19476 |
| baak41k22 | ATACACCAATTTGAACCTACT<br>ATACACCAATGTGAACCTACT | 19477 |
| BaSD16B18 | GGTGGAAACAGTTCACGGTTA<br>GGTGGAAACAATTCACGGTTA | 19478 |
| BaSD16B18 | GCTGATTTTACCATACATGAT<br>GCTGATTTTATCATACATGAT | 19479 |
| BaSD16B18 | TACATGATATCTGTGAAGTAC<br>TACATGATATGTGTGAAGTAC | 19480 |
| BaSD16B18 | CCATCTGATCTGCAGCACCCG<br>CCATCTGATCAGCAGCACCCG | 19481 |
| BaSD16B18 | TGCAGACTGGGCAGCTAAACT<br>TGCAGACTGGACAGCTAAACT | 19482 |
| BaSD16B18 | TGTGGCCACAGATGGTTGATG<br>TGTGGCCACATATGGTTGATG | 19483 |
| baak21o03 | CTTCAGTACTGAAGTTAAACA<br>CTTCAGTACTTAAGTTAAACA | 19484 |
| baak21o03 | GCATGCTGGACTACTACTACT<br>GCATGCTGGAATACTACTACT | 19485 |
| bast79C1105 | AGTCTGTTTTTATTCAGGTAG<br>AGTCTGTTTTCATTCAGGTAG | 19486 |
| BaAL37H08 | CGGAAATTACTTCCTGGATAC<br>CGGAAATTACCTCCTGGATAC | 19487 |
| baak4j17 | AGACCCCATCGGGGCCGCCA<br>AGACCCCATTGGGGCCGCCA | 19488 |
| baak4j17 | GCGACGCCGACCGGGAGTAGC<br>GCGACGCCGAGCGGGAGTAGC | 19489 |
| bags11i15 | TCACCAGACTCGCAAGCCTGT<br>TCACCAGACTTGCAAGCCTGT | 19491 |
| bags11i15 | GAGGGGTCGCCACATGGACAT<br>GAGGGGTCGCGACATGGACAT | 19492 |
| bags11i15 | ATGAGGGGTCACAACGTGGAC<br>ATGAGGGGTCGCAACGTGGAC | 19493 |
| baak35b18 | TATGCAAGTTTTTGGCTGAAA<br>TATGCAAGTTATTGGCTGAAA | 19495 |

TABLE 24-22

| Clones | Haruna Nijo H602 | SEQ ID NO: |
|---|---|---|
| baak35b18 | GCTGCTACCAAATCAGCTACT<br>GCTGCTACCAGATCAGCTACT | 19496 |
| baak35b18 | TGGTACTTAACGCCCCTGAGG<br>TGGTACTTAAAGCCCCTGAGG | 19497 |
| baak35b18 | GCTTTTACTGCCCTTCAGGCC<br>GCTTTTACTGTCCTTCAGGCC | 19498 |
| baak35b18 | CAGAGAAGTGAAAAAAAAAAG<br>CAGAGAAGTGGAAAAAAAAAG | 19499 |
| baak35b18 | ACTACAAAGCTTATGGTACTT<br>ACTACAAAGCATATGGTACTT | 19500 |
| baak41o03 | GCAGGTGACAAAACTGGCAGT<br>GCAGGTGACAGAACTGACAGT | 19501 |
| baak41o03 | GACAAAACTGGCAGTAACAAC<br>GACAGAACTGACAGTAACAAC | 19502 |
| baal1b16 | ATGCAGTGCTCAATTCCAAGC<br>ATGCAGTGCTAAATTCCAAGC | 19504 |
| baalb16 | AGATGCAGGTAAACTTCATGC<br>AGATGCAGGTCAACTTCATGC | 19505 |
| baalb16 | AGTACAAGACGGAAAACGGAA<br>AGTACAAGACAGAAAACGGAA | 19506 |
| baalb16 | TTTCATCTATATTACCTTCCA<br>TTTCATCTATGTTACCTTCCA | 19507 |
| baalb16 | AGCTTCGAGCAAAGAACACAT<br>AGCTTCGAGCTAAGAACACAT | 19508 |
| bags30n17 | GGGCATCCTCAAGCCTTGCCC<br>GGGCATCCTCGAGCCTTGCCC | 19511 |
| bags30n17 | TTGCCCTGGAATCCTCAAGCT<br>TTGCCCTGGAGTCCTCAAGCT | 19512 |
| bags5b16 | GCTTCGACAAAGACACAACAT<br>GCTTCGACAACGACACAACAT | 19514 |
| baal5f06 | ACTTGCCATTCTCTTGGACAT<br>ACTTGCCATTTTCTTGGACAT | 19515 |
| bah42g19 | TGGTAAAACAACTGAGACACA<br>TGGTAAAACATCTGAGACACA | 19516 |
| bah42g19 | GGTCGTTAGCTATGCAGGAAC<br>GGTCGTTAGCCATGCAGGAAC | 19517 |
| bah42g19 | TCGACCAAGTTACCTTCACTG<br>TCGACCAAGTCACCTTCACTG | 19518 |
| BaH47O14 | CGTACCGTGCCTGATACCCCG<br>CGTACCGTGCTTGATACCCCG | 19519 |
| BaH47O14 | TGTGGATGGATAATAACACGA<br>TGTGGATGGAGAATAACACGA | 19520 |
| BaH47O14 | TGCCATCCTGCATTGTTGAGC<br>TGCCATCCTGTATTGTTGAGC | 19521 |
| BaH47O14 | TGTTGAATTACTGACCTTATT<br>TGTTGAATTATTGACCTTATT | 19522 |
| BaH47O14 | AACACGAGGAATTTTTGTTGT<br>AACACGAGGATTTTTTGTTGT | 19523 |
| BaH12L06 | TTGGTATGGACGTCAGGATGC<br>TTGGTATGGATGTCAGGATGC | 19524 |

TABLE 24-23

| Clones | Haruna Nijo H602 | SEQ ID NO: |
|---|---|---|
| BaH12L06 | ATGGGATGGCATCGGCGAAGG<br>ATGGGATGGCGTCGGCGAAGG | 19525 |
| bah51a21 | GTGCATCCCAATCGGTAGTGT<br>GTGCATCCCAGTCGGTAGTGT | 19528 |
| bah51a21 | CTTCCCTTTGGTTTAGCAATA<br>CTTCCCTTTGTTTTAGCAATA | 19529 |
| basd12p12 | TACATAACTTATTTACATGGG<br>TACATAACTTCTTTACATGGG | 19532 |
| bags19l10 | TTGCCTCAATCGACGGGAACA<br>TTGCCTCAATTGACGGGAACA | 19538 |
| BaH56J21 | GCGAGCCGCGGGTATGCCTTG<br>GCGAGCCGCGAGTATGCCTTG | 19539 |
| BaH56J21 | AAACAACCTTTGATAAAGTAT<br>AAACAACCTTCGATAAAGTAT | 19540 |
| BaH56J21 | GCAGGAACCAGGTGATGAACG<br>GCAGGAACCACGTGATGAACG | 19541 |
| BaH56J21 | GTGACACTACGATCATCGACA<br>GTGACACTACAATCATCGACA | 19542 |
| bags16i19 | GCAGGCATGTGTTACGGCACT<br>GCAGGCATGTTTTACGGCACT | 19544 |
| bags16i19 | CGCTGCTGCGGCCAGAGCATC<br>CGCTGCTGCGCCCAGAGCATC | 19545 |
| bags16i19 | GCATCCTGAGCGAGGCAGGCC<br>GCATCCTGAGAGAGGCAGGCC | 19546 |
| bah54h01 | AGCTGGATGCTTATGTGCACC<br>AGCTGGATGCATATGTGCACC | 19548 |
| bah54h01 | TAATAATTCAAAGCAAATCAA<br>TAATAATTCAGAGCAAATCAA | 19549 |
| bags20e19 | CCATTCCGGCGACACAAGCAT<br>CCATTCCGGCAACACAAGCAT | 19550 |
| bags20e19 | TACTCAACAAAGTCGATGGCC<br>TACTCAACAAGGTCGATGGCC | 19551 |
| bags20e19 | GAACCTTGTCCCTTCAGCCAG<br>GAACCTTGTCACTTCAGCCAG | 19552 |
| bags20e19 | CCTTTCTCGAGGTCCGGCAGC<br>CCTTTCTCGACGTCCGGCAGC | 19553 |
| bast74c0206 | TGAACAGCCCAAAGTTCTTCT<br>TGAACAGCCCGAAGTTCTTCT | 19554 |
| bast74c0206 | TTATTCGACCACGAAATATCC<br>TTATTCGACCGCGAAATATCC | 19555 |
| bast74c0206 | GCGTGCCATTGCCGACGTGGT<br>GCGTGCCATTCCCGACGTGGT | 19556 |
| bags20i01 | GTGTGCTCGAAGGCTGTATCT<br>GTGTGCTCGAGGGCTGTATCT | 19557 |
| bags20i01 | GAAAGAGCAATCTATCAAGG<br>GAAAGAGCAGTCTATCAAGG | 19558 |
| baak13l10 | TGGACAGACCATTATCGCTTC<br>TGGACAGACCGTTATCGCTTC | 19559 |
| baak42g21 | CAGTAGAGGC-ATCACTTATG<br>CAGTAGAGGCCATCACTTATG | 19560<br>19561 |

TABLE 24-24

| Clones | Haruna Nijo H602 | SEQ ID NO: |
|---|---|---|
| baak42g21 | CTAGATTTGCGAATATAGCGC<br>CTAGATTTGCAAATATAGCGC | 19562 |
| basd19n14 | TAAAGGATAGTTGCAGCTGCA<br>TAAAGGATAGCTGCAGCTGCA | 19563 |
| basd19n14 | TACAAGCATATCTTTTGTTTA<br>TACAAGCATACCTTTTGTTTA | 19564 |
| basd19n14 | GACCCACAAATTTGACAGACA<br>GACCCACAAACTTGACAGACA | 19565 |
| basd19n14 | TGTAGTGGTACCATCACAACT<br>TGTAGTGGTAGCATCACAACT | 19566 |
| basd19n14 | ATGCTTCATCACACGGTAATG<br>ATGCTTCATCGCACGGTAATG | 19567 |
| BaAK22K17 | TTGCTACGTACGTACGCGTAT<br>TTGCTACGTATGTACGCGTAT | 19570 |
| baal6o24 | GAGTTTGCTCATAGGGACGTA<br>GAGTTTGCTCGTAGGGACGTA | 19571 |
| baal6o24 | TCATAAGCCAAAACCAGTTGT<br>TCATAAGCCAGAACCAGTTGT | 19572 |
| baal6o24 | TTTGCATCGCGTCACATGAAA<br>TTTGCATCGCATCACATGAAA | 19573 |
| BaH22C09 | CAAAGGCCAATAATGAAATGA<br>CAAAGGCCAACAATGAAATGA | 19574 |
| baal24n12 | GCGCGCGACTTATAACTTGTT<br>GCGCGCGACTAATAACTTGTT | 19577 |
| baal24n12 | TGATACATTACGCAAAGAAAT<br>TGATACATTATGCAAAGAAAT | 19578 |
| BaSD16I09 | TATGATATACATGTGCGAGAG<br>TATGATATACGTGTGCGAGAG | 19579 |
| BaSD16I09 | CTGGCTCCTCGGTGATGGTAA<br>CTGGCTCCTCAGTGATGGTAA | 19580 |
| BaSD16I09 | TACATCCACCGCAGGACCAAA<br>TACATCCACCCCAGGACCAAA | 19581 |
| BaAL13B22 | CATCAGGTTGGAATATGCCGG<br>CATCAGGTTGAACTATGCCGG | 19582 |
| BaAL13B22 | TTGACATGGTCGGTCGATCGT<br>TTGACATGGTTGGTCGATCGT | 19583 |
| BaAL13B22 | TTGAACTAATGCAGAAATATA<br>TTGAACTAATACAGAAATATA | 19504 |
| bastl30f0111 | GCATGCCGGGGCCTTAACACC<br>GCATGCCGGGACCTTAACACC | 19586 |
| baak40c12 | ACAGCAGAGTGGCAATTACAT<br>ACAGCAGAGTCGCAATTACAT | 19587 |
| baak40c12 | AAGATAGCCCTTTGAAAAAAG<br>AAGATAGCCCCTTGAAAAAAG | 19588 |
| baak40c12 | CGTCAGCTTTGTCAGAATGA<br>CGTCTAGCTTCGTCAGAATGA | 19589 |
| baak40c12 | CCCCTTCGCCTACACCAACAA<br>CCCCTTCGCCGACACCAACAA | 19590 |
| bah15l04 | ATGTGCAATTGCGGTGCATCG<br>ATGTGCAATTCCGGTGCATCG | 19591 |

TABLE 24-25

| Clones | Haruna Nijo H602 | SEQ ID NO: |
|---|---|---|
| baak31e03 | TTGTCCGACTACATAAGGAAA<br>TTGTCCGACTGCATAAGGAAA | 19593 |
| baak31e03 | CTCCCTCGCAACCGCTCATCC<br>CTCCCTCGCACCCGCTCATCC | 19594 |
| baak31e03 | ACAGAACATTATCCTCCCTCG<br>ACAGAACATTTTCCTCCCTCG | 19595 |
| baak31e03 | TGATTAAGATTCATCTAAATT<br>TGATTAAGATCCATCTAAATT | 19596 |
| bah57d15 | AATTCTGCTGCGTTCCAGTTA<br>AATTCTGCTGTGTTCCAGTTA | 19597 |
| baal13o01 | CTACTGATATAATTAAACTAA<br>CTACTGATATGATTAAACTAA | 19598 |
| baal13o01 | TGAGGCCACAGGGTTATTATT<br>TGAGGCCACATGGTTATTATT | 19599 |
| baal13o01 | ACCAGAACAGAGCTTAGTTTA<br>ACCAGAACAGGGCTTAGTTTA | 19600 |
| bags20f18 | TCTAGGCTAGCATACAACAAT<br>CTTATTCTAG-ATACAACAAT | 19601<br>19602 |
| bags20f18 | AACAATTGGCTACAAATAACG<br>AACAATTGGC-ACAAATAACA | 19603<br>19604 |
| basd26p04 | AGAACTAGCCATGCAAGTTTC<br>AGAACTAGCCGTGCAAGTTTT | 19605 |
| basd26p04 | TTGTCAAAACCAAAAACAGAT<br>TTGTCAAAACTAAAAACACAT | 19606 |
| basd26p04 | ACCAAAAACAGATGATGAATG<br>ACTAAAAACACATGATGAATG | 19607 |
| basd26p04 | CGCATCATGAAAATTTTGCTA<br>CGCATCATGACAAGTTTGCTA | 19608 |
| basd26p04 | ATCATGAAAATTTTGCTAAGA<br>ATCATGACAAGTTTGCTAAGA | 19609 |
| basd26p04 | TGATAGCTGAATAACTGTCAG<br>TGATAGCTGAGTTACTGTCAG | 19610 |
| basd26p04 | TATCTTATTCTAACCTCATAA<br>TATGTTATTCAAACCTCATAA | 19611 |
| basd26p04 | CTGCAGATATCTTATTCTAAC<br>CTGCAGATATGTTATTCAAAC | 19612 |
| basd26p04 | TAAATCAGTGAAATGGGAATA<br>TAAATCGGTGGAATGGGAATA | 19613 |
| BaH42J22 | ATTTGGCCAGACGAACAACCG<br>ATTTGGCCAGGCGAACAACCG | 19614 |
| BaH42J22 | CGCCCCTCTCGACTGCATCCC<br>CGCCCCTCTCAACTGCATCCC | 19615 |
| BaH42J22 | TCATGTGTTTTCCTATGATCC<br>TCATGTGTTTGCCTATGATCC | 19616 |
| kr30b1103 | TCCCACCAGGCATCGCTCCCT<br>TCCCACCAGGTATCGCTCCCT | 19618 |
| kr30b1103 | TTCCAACTTCTAATTTGCAT<br>TTCCAACTTATAATTTGCAT | 19619 |
| kr30b1103 | CTGCAATGTCTTTGCACCACC<br>CTGCAATGTCGTTGCACCACC | 19620 |

TABLE 24-26

| Clones | Haruna Nijo H602 | SEQ ID NO: |
|---|---|---|
| kr30b1103 | AGGTCTATGTAATCTTTGTTT<br>AGGTCTATGTTATCTTTGTTT | 19621 |
| baal4e21 | CTCCATTTTTTTTAATCAACT<br>CTCCATTTTTCTTAATCAACT | 19624 |
| baal4e21 | TCTACCACAATCCAGAATATC<br>TCTACCACAACCCAGAATATC | 19625 |
| BaGS29D05 | GAAGATAACACCATCTTAGAA<br>GAAGATAACAACATCTTAGAA | 19626 |
| BaGS29D05 | TTAGAAAACGCTGTGACGTCA<br>TTAGAAAACGATGTGACGTCA | 19627 |
| BaGS29D05 | GTGACGTCATCTAGGGTCAGT<br>GTGACGTCATTTAGGGTCAGT | 19628 |
| bah54d24 | TGCATCAAGACTCATCCAATT<br>TGCATCAAGAATCATCCAATT | 19629 |
| bah54d24 | GGCTCTGTGATTCTGCATCAA<br>GGCTCTGTGACTCTGCATCAA | 19630 |
| bah54d24 | TCCGGGGCGATGTTGGCCGCG<br>TCCGGGGCGACGTTGGCCGCG | 19631 |
| bah54d24 | GGGGGCATCCAGGGGCTCCGG<br>GGGGGCATCCTGGGGCTCCGG | 19632 |
| bags38h17 | AACCGGTTTTCCGAGGCTTCA<br>AACCGGTTTTGCGAGGCTTCA | 19635 |
| baak30b23 | CGTCCTCCGATGGCAGGAAGT<br>CGTCCTCCGACGGCAGGAAGT | 19636 |
| baak30b23 | TGGCCTCGTATGCGTCCTCCG<br>TGGCCTCGTAGGCGTCCTCCG | 19637 |
| baak30b23 | GGTAGATAACGCTCTTGACAC<br>GGTAGATAACTCTCTTGACAC | 19638 |
| baak24p09 | CTCCCTCTATTAACTAATATA<br>CTCCCTCTATAAACTAATATA | 19640 |
| baak24p09 | GCAGCTAAACTGGCTAGGCAT<br>GCAGCTAAACAGGCTAGGCAT | 19641 |
| baak24p09 | TATGCTTGCAGACCCTCTGCA<br>TATGCTTGCACACCCTCTGCA | 19642 |
| BaGS22I06 | TGTAAATAAATTTTGTAATAA<br>TGTAAATAAACTTTGTAATAA | 19643 |
| BaGS22I06 | CACTACAAAATTATGATGCTA<br>CACTACAAAACTATGATGCTA | 19644 |
| BaAL34P18 | AAATCCCCACGAAAAACTTAT<br>AAATCCCCACTAAAAACTTAT | 19645 |
| BaAL34P18 | TCTCGCCGACGTAGTACTCGT<br>TCTCGCCGACATAGTACTCGT | 19646 |
| BaAL34P18 | AACTTATTCATCTCTTGAACC<br>AACTTATTCAGCTCTTGAACC | 19647 |
| bah12e02 | GGTTTGCTCCTACTGCTACTT<br>GGTTTGCTCCCACTGCTACTT | 19650 |
| BaAL15F23 | GGATGGTCAGCATTTCTGTGC<br>GGATGGTCAGTATTTCTGTGC | 19651 |
| BaAL15F23 | TCATGTCATTCCACTGATGAC<br>TCATGTCATTACACTGATGAC | 19652 |

TABLE 24-27

| Clones | Haruna Nijo H602 | SEQ ID NO: |
|---|---|---|
| BaGS25015 | TGCAATAGCTGAAATTGTGAC<br>TGCAATAGCTAAAATTGTGAC | 19653 |
| BaGS25015 | ATGGGTTGGTCGGGATGCTCG<br>ATGGGTTGGTTGGGATGCTCG | 19654 |
| bags33m02 | GCATATAATCAACACTCAACA<br>GCATATAATCGACACTCAACA | 19657 |
| bags33m02 | GAGTAGTTTCGATGCGAGAGT<br>GAGTAGTTTCAATGCGAGAGT | 19658 |
| bags27p13 | GCTATTTTGCCGTTCTCAACA<br>GCTATTTTGCTGTTCTCAACA | 19659 |
| bags27p13 | TCAACAGAGTATAAACGATAA<br>TCAACAGACTGTAAACGATAA | 19660 |
| bags27p13 | AAACCCATCTTCATACATCAG<br>AAACCCATCTCCATACATCAG | 19661 |
| bah48g21 | TGTAGTTGACTAAGCAAAGAT<br>TGTAGTTGACGAAGCAAAGAT | 19662 |
| bah48g21 | AAGGCGGCGGAACGATCATGG<br>AAGGCGGCGGGACGATCATGG | 19663 |

TABLE 25-1

| Clones | Haruna Nijo H602 | SEQ ID NO: |
|---|---|---|
| bah14a22 | CTCGGACAGCATCCACGGCTT<br>CTCGGACAGCGTCCACGGCTT | 19664 |
| bah14a22 | CTTCAAGGGGTTCGACGCCGT<br>CTTCAAGGGGCTCGACGCCGT | 19665 |
| BaGS32P17 | TGGAGTGGATCGACACCATCC<br>TGGAGTGGATAGACACCATCC | 19667 |
| BaGS32P17 | GAGAACACAGGCATAGAACAC<br>GAGAACACAGCCATAGAACAC | 19668 |
| BaGS32P17 | CCCTCTCCATAAGGTCCTTGA<br>CCCTCTCCATCAGGTCCTTGA | 19669 |
| BaGS32P17 | ACACCATCCTGATGAGCCCCC<br>ACACCATCCTAATGAGCCCCC | 19670 |
| baak35b06 | TCAATTTTGCGAAACCCGCCT<br>TCAATTTTGCAAAACCCGCCT | 19671 |
| basd21f17 | AGGAGGAGGATTGAAGAGGAG<br>AGGAGGAGGACTGAAGAGGAG | 19672 |
| basd21f17 | CCCTTTCCCTCTCCCTCTCCC<br>CCCTTTCCCTTTCCCTCTCCC | 19673 |
| basd21f17 | AGAATCCGACAATGGATGCTG<br>AGAATCCGACGATGGATGCTG | 19674 |
| baal22h02 | TCTTCTTCTTCTCCTTCTTCT<br>TCTTCTTCTTGTCCTTCTTCT | 19679 |
| bah56g24 | ATCTCTCCTCGCATACTTGCT<br>ATCTCTCCTCACATACTTGCT | 19680 |
| bah56g24 | CATTGGCCGGCGGCGGGTTCA<br>CATTGGCCGGTGGCGGGTTCA | 19681 |
| bah56g24 | CGCGCACGTCGGCAATCAGCG<br>CGCGCACGTCAGCAATCAGCG | 19682 |

TABLE 25-1-continued

| Clones | Haruna Nijo H602 | SEQ ID NO: |
|---|---|---|
| bah56g24 | CTTCCGCCTCTGGGGAGACCT<br>CTTCCGCCTCCGGGGAGACCT | 19683 |
| baak32f06 | CGAACGACGGTTTCACGCGAG<br>CGAACGACGGCTTCACGCGAG | 19688 |
| basd21d13 | CATCATCACACGGCGCACTCA<br>CATCATCACAAGGCGCACTCA | 19690 |
| basd21d13 | TACAGCTAAAGTAAAATAGTT<br>TACAGCTAAAATAAAATAGTT | 19691 |
| bast46d0408 | CGAAAAGGATGGATCGATAAC<br>CGAAAAGGATAGATCGATAAC | 19692 |
| bast55B1204 | TCTACTCCTACTTTGTTTTTA<br>TCTACTCCTAGTTTGTTTTTA | 19693 |
| bast55B1204 | ACCTTGGCAATGATGTCCTCC<br>ACCTTGGCAACGATGTCCTCC | 19694 |
| bast55B1204 | GATAACAATGTCAGTTCAGTT<br>GATAACAATGCCAGTTCAGTT | 19695 |
| bast55B1204 | GTGAATTCTGTCCAAAGATGC<br>GTGAATTCTGCCCAAAGATGC | 19696 |
| bags39b15 | CTTAATGACAGTAAGGGTTAT<br>CTTAATGACACTAAGGGTTAT | 19697 |
| bags39b15 | GAAAACCTAAAAATTGCATGC<br>GAAAACCTAACAATTGCATGC | 19698 |

TABLE 25-2

| Clones | Haruna Nijo H602 | SEQ ID NO: |
|---|---|---|
| bah29o22 | GTAGATATCCTCTTCCCCGCC<br>GTAGATATCCCCTTCCCCGCC | 19701 |
| bah29o22 | TGCAGCAGAGGCGACGGCTCA<br>TGCAGCAGAGCCGACGGCTCA | 19702 |
| baet31e1010 | TCTATTGCATGTTGTGCAAA<br>TCTATTGCATCGTTGTGCAAA | 19703 |
| baal39h14 | AGATCAAAACTGCTTTATTTA<br>AGATCAAAACCGCTTTATTTA | 19704 |
| baal39h14 | TACATGAAGAAACACAGTGAT<br>TACATGAAGACACACAGTGAT | 19705 |
| baal18m18 | CTGCAAAGACGAAACAGTCTC<br>CTGCAAAGACAAAACAGTCTC | 19706 |
| baal18m18 | TATCAAAATTTTCTTTTGAGA<br>TATCAAAATTGTCTTTTGAGA | 19707 |
| baal18m18 | CGATCATCAGGCTGTCAAGAA<br>CGATCATCAGACTGTCAAGAA | 19708 |
| basd24e02 | AGGCTTGCTAGAATCCGCCGG<br>AGGCTTGCTACAATCCGCCGG | 19709 |
| basd24e02 | AAAGTAAAGGTGTCAGCGAGT<br>AAAGTAAAGGCGTCAGCGAGT | 19710 |
| basd24e02 | AGAGGATGACGACGAGCTTCA<br>AGAGGATGACCACGAGCTTCA | 19711 |
| baak11d04 | AGTCAAGGCTTGCCGAGGATT<br>AGTCAAGGCT_GCCGAGGATT | 19714<br>19715 |

TABLE 25-2-continued

| Clones | Haruna Nijo H602 | SEQ ID NO: |
|---|---|---|
| baal33m06 | TTAAGGTGAANGGCAATAGAT<br>TTAAGGTGAAAGGCAATAGAT | 19719 |
| baal33m06 | TTGTACCTGGCTCGTGAGCAA<br>TTGTACCTGGTTCGTGAGCAA | 19720 |
| bast150E0309 | GCTCCGGGTCGTGGTTCATGC<br>GCTCCGGGTCATGGTTCATGC | 19721 |
| bast150E0309 | CGTGGCGAACACCCTTTATTC<br>CGTGGCGAACGCCCTTTATTC | 19722 |
| bags20i17 | GAATCTTGACATAGGGCAACA<br>GAATCTTGACGTAGGGCAACA | 19723 |
| bags20i17 | GCCACCATGCGTGTCCCTGCG<br>GCCACCATGCATGTCCCTGCG | 19724 |
| BaGS22A07 | ATATACACACCCTGATGCAAA<br>ATATACACACTCTGATGCAAA | 19725 |
| BaGS22A07 | GCACAAAAACGTGGATGGAA<br>GCACAAAAATGTGGATGGAA | 19726 |
| bah41b09 | CTCCCAGCCTGTGCCCCCGGC<br>CTCCCAGCCTCTGCCCCCGGC | 19727 |
| bah41b09 | CCCTTCTTGGGCTTCTTGCTA<br>CCCTTCTTGGCCTTCTTGCTA | 19728 |
| bah41b09 | TGCCAACCCGAGCTCGTCGG<br>TGCCAACCCAAGCTCGTCGG | 19729 |
| bah41b09 | CCCCCCTCGGGCTTGCCCTTC<br>CCCCCCTCGGCCTTGCCCTTC | 19730 |
| bah41b09 | GTCGATCTCGATGCTCTCCTT<br>GTCGATCTCGTTGCTCTCCTT | 19731 |

TABLE 25-3

| Clones | Haruna Nijo H602 | SEQ ID NO: |
|---|---|---|
| bah41b09 | TGTCGGACTTGGTGGCCTCGA<br>TGTCGGACTTAGTGGCCTCGA | 19732 |
| bah41b09 | CCCCCGGCCTGCTTCTTGCTC<br>CCCCCGGCCTCCTTCTTGCTC | 19733 |
| BaGS19023 | CGACCGTGCCGTCTTTCGAGC<br>TGACCGTGCCATCTTTCGAGC | 19735 |
| BaGS19023 | GCTTGGGTGCCGCCAGAAGCG<br>GCTTGGGTGCTGCCAGAAGTG | 19736 |
| bags14h12 | CGACGGGAATCATTTGAAGG<br>CGACGGGAAACATTTGAAGG | 19740 |
| bags14h12 | CTTCCTTTGGTTTGGTTCAAG<br>CTTCCTTTGGATTGGTTCAAG | 19741 |
| bags14h12 | ACAAGAGTCAAAACTGCATCC<br>ACAAGAGTCAGAACTGCATCC | 19742 |
| bah32e15 | GGGCACGAGACGTCCTTTTGG<br>GGGCACGAGATGTCCTTTTGG | 19743 |
| bah32e15 | TGCACTGCTGTTGCACCTGCC<br>TGCACTGCTGCTGCACCTGCC | 19744 |
| bah32e15 | CAGCCTCGCAAAGTGCTCGGC<br>CAGCCTCGCATAGTGCTCGGC | 19745 |

TABLE 25-3-continued

| Clones | Haruna Nijo / H602 | SEQ ID NO: |
|---|---|---|
| bags39e16 | TGTATAGCTTTATGAGGATAG<br>TGTATAGCTTCATGAGGATAG | 19747 |
| bags39e16 | TTTTGAGTGGTTGGCATAGTT<br>TTTTGAGTGGCTGGCATAGTT | 19748 |
| bags39e16 | CAGGAAATAGTTTTTGAGGGG<br>CAGGAAATAGGTTTTGAGGGG | 19749 |
| baal32m10 | ATCAGTGGATCTTATCCCTGA<br>ATCAGTGGATGTTATCCCTGA | 19752 |
| baal32m10 | CCTTGTTTAATTATCTTTTAG<br>CCTTGTTTAAGTATCTTTTAG | 19753 |
| baal32m10 | CTTTTAGGGAGTGACAATTTG<br>CTTTTAGGGATTGACAATTTG | 19754 |
| baal32m10 | AAAAAATTAGCTCAGTATTGC<br>AAAAAATTAGTTCAGTATTGC | 19755 |
| basd12p12 | ATGCACATAGTGCATGTATTA<br>ATGCACATAGGGCATGTATTA | 19756 |
| basd12p12 | CGGCAAGATCGGCATCTATTT<br>CGGCAAGATCAGCATCTATTT | 19757 |
| basd12p12 | CTATTTGCAACTTACAAATCA<br>CTATTTGCAAGTTACAAATCA | 19758 |
| basd12p12 | CAGATGTATATCAGCAGCAAT<br>CAGATGTATAGCAGCAGCAAT | 19759 |
| baal39e15 | GTGCGTGTGCATGCGCCGGAG<br>GTGCGTGTGCGTGCGCCGGAG | 19760 |
| baal39e15 | CCAAACCGTAAAGTGGTAACC<br>CCAAACCGTAGAGTGGTAACC | 19761 |
| BaGS31B01 | AGCACGATGCCGTAATGTTTA<br>AGCACGATGCTGTAATGTTTA | 19763 |
| BaGS31B01 | ACTCAGCCTTCGCAATCCACA<br>ACTCAGCCTTTGCAATCCACA | 19764 |

TABLE 25-4

| Clones | Haruna Nijo / H602 | SEQ ID NO: |
|---|---|---|
| BaH48L11 | CTGCTTTCAAGTTTCGCTGCT<br>CTGCTTTCAAATTTCGCTGCT | 19767 |
| BaH48L11 | CAAATTTATACTCCCAGCCAA<br>CAAATTTATATTCCCAGCCAA | 19768 |
| bah56c09 | TCAGTGAAGCCCATGAACTTC<br>TCAGTGAAGCTCATGAACTTC | 19770 |
| bags20k09 | GAAGTGCGGGCGGCATCAGC<br>GAAGTGCGGGACGGCATCAGC | 19771 |
| bags20k09 | GGCCCTTTCAAGGGGAAGTGC<br>GGCCCTTTCAGGGGGAAGTGC | 19772 |
| bags20k09 | TGTGGTCGTCGGGCGCCAGGC<br>TGTGGTCGTCAGGCGCCAGGC | 19773 |
| bags20k09 | GAGTTACATTGCAACACAGCT<br>GAGTTACATTTCAACACAGCT | 19774 |
| basd25b08 | TCGCCGCCTGAGACGACGCTG<br>TCGCCGCCTGGGACGACGCTG | 19775 |

TABLE 25-4-continued

| Clones | Haruna Nijo / H602 | SEQ ID NO: |
|---|---|---|
| basd25b08 | TGGGGCACCAGTCGACGAACT<br>TGGGGCACCAATCGACGAACT | 19776 |
| basd25b08 | GCACACGGCCATCTGGACCTT<br>GCACACGGCCCTCTGGACCTT | 19777 |
| basd25b08 | TGCCCTCGCCGACGTACCAGT<br>TGCCCTCGCCCACGTACCAGT | 19778 |
| basd25b08 | CGTCGCCCTCGTCACCGTCCT<br>CGTCGCCCTCATCACCGTCCT | 19779 |
| basd25b08 | TGAGACAGCAGGCCATGTACT<br>TGAGACAGCATGCCATGTACT | 19780 |
| bast27e0309 | CAAGCTGCTTGGGCCAACCAG<br>CAAGCTGCTTCGGCCAACCAG | 19781 |
| baet20D0107 | AAATTTACAATACACTACAGG<br>AAATTTACAACACACTACAGG | 19782 |
| baet20D0107 | GCAGAGAAAACAATAATGAG<br>GCAGAGAAAACCATAATGAG | 19783 |
| baet20D0107 | AACGAGCAGAATTGCATTCTA<br>AACGAGCAGAGTTGCATTCTA | 19784 |
| baak26n10 | CTTCTTCTTTCGGATAAGAAA<br>CTTCTTCTTTGGGATAAGAAA | 19790 |
| baak26n10 | GTGTGCCTTTCAGTGTGTAGT<br>GTGTGCCTTTNAGTGTGTAGT | 19791 |
| baak26n10 | TATATTTTAG-CCTTCATCAT<br>TATATTTTAGGCCTTCATCAT | 19792<br>19793 |
| bast22b0204 | CTTCGTTGCCGGCCGGCCAGC<br>CTTCGTTGCCAGCCGGCCAGC | 19794 |
| baal3c05 | TTTTAGGACCGCAACATCTCG<br>TTTTAGGACCACAACATCTCG | 19795 |
| baal3c05 | GTGACGCTGAAGATTCGCTCT<br>GTGACGCTGACGATTCGCTCT | 19796 |
| BaAK20B09 | CCATCTGTTGTTCCCTCCATT<br>CCATCTGTTGCTCCCTCCATT | 19798 |
| BaAK37H01 | AAAATGAAAAATTGAAAGCTC<br>AAAATGAAAATTTGAAAGCTC | 19799 |

TABLE 25-5

| Clones | Haruna Nijo / H602 | SEQ ID NO: |
|---|---|---|
| BaAK37H01 | CGGCCTGGTCATGGATTCGGG<br>CGGCCTGGTCTTGGATTCGGG | 19800 |
| BaAK37H01 | GAAAGCTCTCACTGGAATTGT<br>GAAAGCTCTCGCTGGAATTGT | 19801 |
| BaGS33P13 | GTAGCCCAACTCATGCTACTA<br>GTAGCCCAACGCATGCTACTA | 19802 |
| BaGS33P13 | TGCCCCTTATGATCTTGAAGT<br>TGCCCCTTATAATCTTGAAGT | 19803 |
| bags18h09 | GGGATGGACATCAAACAATAA<br>GGGATGGACACCAAACAATAA | 19806 |
| baal9m23 | CCTGTTTCCTCGACAGGAAAT<br>CCTGTTTCCTTGACAGGAAAT | 19808 |

TABLE 25-5-continued

| Clones | Haruna Nijo H602 | SEQ ID NO: |
|---|---|---|
| baak17d18 | TCTTTTGCTTCGGGTTGGGAC<br>TCTTTTGCTTTGGGTTGGGAC | 19814 |
| bags13a12 | CAAGTGTTGGAGATATATGGT<br>CAAGTGTTGGTGATATATGGT | 19815 |
| bags13a12 | TTCCAGCCTCAAAGTACATGT<br>TTCCAGCCTCGAAGTACATGT | 19816 |
| kr34f0212 | AATTACGGCCCATCCATGTGG<br>AATTACGGCCTATCCATGTGG | 19818 |
| kr34f0212 | GTGAAATTGTATTACTTTACT<br>GTGAAATTGTCTTACTTTACT | 19819 |
| kr34f0212 | AACGGAGGGACTATTTAATAT<br>AACGGAGGGAGTATTTAATAT | 19820 |
| kr34f0212 | CACGACAAGTATTTTGGAACG<br>CACGACAAGTGTTTTGGAACG | 19821 |
| kr34f0212 | AATTCATTTAAAAGAAGAAGA<br>AATTCATTTACAAGAAGAAGA | 19822 |
| baal16d11 | GCTTGCTGTTGCTAACTAGCA<br>GCTTGCTGTTCCTAACTAGCA | 19823 |
| baal16d11 | CGAGAGCAACAGAAGGTATGT<br>CGAGAGCAACCGAAGGTATGT | 19824 |
| baal16d11 | ATCCATCATCGAGAAATTTAC<br>ATCCATCATCAAGAAATTTAC | 19825 |
| bah22d04 | CATAAGGTTCGTCGAAGTATT<br>CATAAGGTTCATCGAAGTATT | 19826 |
| bah22d04 | GCGAGGCGACGAATGCGAGTG<br>GCGAGGCGACAAATGCGAGTG | 19827 |
| bah22d04 | CCTGCCACGCTCTGAGGAACA<br>CCTGCCACGCCCTGAGGAACA | 19828 |
| BaGS6007 | ATGGCCATAGCAGCAGCAGCA<br>ATGGCCATAGTAGCAGCAGCA | 19830 |
| BaH37O10 | GACATTGAACGCGAGGTTTGT<br>GACATTGAACACGAGGTTTGT | 19831 |
| baal9i11 | GGCACGGGCTTGTAATTCTGG<br>GGCACGGGCTCGTAATTCTGG | 19834 |
| BaAL39NO6 | CCCGAGTAACCATCCCTTGAC<br>CCCGAGTAACTATCCCTTGAC | 19835 |
| BaAL19I19 | CTATCTGTACGTGATTTTCTT<br>CTATCTGTACATGATTTTCTT | 19836 |

TABLE 25-6

| Clones | Haruna Nijo H602 | SEQ ID NO: |
|---|---|---|
| BaAL19I19 | TGCCAGGTGCATTATACCACA<br>TGCCAGGTGCTTTATACCACA | 19837 |
| basd12I11 | GCAGTTACTATGAAGCTTAGG<br>GCAGTTACTACGAAGCTTAGG | 19838 |
| bastl46D1008 | AAACAACTAGTGTAAAGGAGA<br>AAACAACTAGCGTAAAGGAGA | 19839 |
| BaH50H16 | TTGTCAGGCAAAGTAATATTA<br>TTGTCAGGCAGAGTAATATTA | 19840 |

TABLE 25-6-continued

| Clones | Haruna Nijo H602 | SEQ ID NO: |
|---|---|---|
| bags9n05 | GCTTCAGGTCCTCTTGCTCTG<br>GCTTCAGGTCATCTTGCTCTG | 19841 |
| bags9n05 | ATGAGAGACCAAATATTTGCT<br>ATGAGAGACCGAATATTTGCT | 19842 |
| kr61b1103 | AACCTTTATTTATATTATGTG<br>AACCTTTATT-ATATTATGTG | 19843<br>19844 |
| kr27b0103 | CTGCACTGCA-TCGCGCAATG<br>CTGCACTGCAGTCGCGCAATG | 19845<br>19846 |
| kr33h1115 | CCCAAATGGCGGCGTCGGCGG<br>CCCAAATGGCCGCGTCGGCGG | 19847 |
| baak30l02 | GAGCAGCAGAGATTGTGCATG<br>GAGCAGCAGACATTGTGCATG | 19848 |
| baak30l02 | CACTCAGATGCTGTCCTCGTC<br>CACTCAGATGTTGTCCTCGTC | 19849 |
| bah55a12 | GTTCCAGAAGGACACAATGAT<br>GTTCCAGAAGTACACAATGAT | 19850 |
| bah55a12 | CACGGGGCCGACATATTCACC<br>CACGGGGCCGCCATATTCACC | 19851 |
| bah55a12 | AAGTAAATGTCATCTTTTTCT<br>AAGTAAATGTTATCTTTTTCT | 19852 |
| bah26k14 | TAAAACCTGAAAACCACTAAT<br>TAAAACCTGAGAACCACTAAT | 19853 |
| bah26k14 | ATGTCCATGTACATCAATAGG<br>ATGTCCATGTGCATCAATAGG | 19854 |
| bah26k14 | ATTTATCTAGAAATGGATATA<br>ATTTATCTAGCAATGGATATA | 19855 |
| basd18m17 | AAGACTGGGTATTATCCATAT<br>AAGACTGGGTGTTATCCATAT | 19857 |
| BaH53B03 | GAAGGCTGAGACGAAGCTGTC<br>GAAGGCTGAGGCGAAGCTGTC | 19859 |
| bags14d19 | ATGAGCACGTATTAGGTGGTA<br>ATGAGCACGTCTTAGGTGGTA | 19864 |
| bags14d19 | TGCTGAGCTATATGTTGCACA<br>TGCTGAGCTACATGTTGCACA | 19865 |
| baal20f05 | TACCTCCTTCCGCTCCTTTCT<br>-ACCTCCTTCGGCTCCTTTCT | 19866<br>19867 |
| baal20f05 | ACTGATGATCCTGGG-AAAG<br>ACTGATGATCTTTGGGAAAG | 19868<br>19869 |
| BaH18H12 | TTGGAGTTATGAGCCAGAGGA<br>TTGGAGTTATAAGCCAGAGGA | 19870 |
| baal9o21 | GTGTGTATCCACCGTCAGTTC<br>GTGTGTATCCTCCGTCAGTTC | 19871 |

TABLE 25-7

| Clones | Haruna Nijo H602 | SEQ ID NO: |
|---|---|---|
| baal9o21 | GCGTGCCACCGACGTTGAGGC<br>GCGTGCCACCTACGTTGAGGC | 19872 |
| baal9o21 | TTGAGGCTGGTGAATCCATCT<br>TTGAGGCTGGCGAATCCATCT | 19873 |

TABLE 25-7-continued

| Clones | Haruna Nijo H602 | SEQ ID NO: |
|---|---|---|
| bags21a02 | ACTTCATCAGGGCTACGTCGA<br>ACTTCATCAGCGCTACGTCGA | 19874 |
| BaAL3G19 | GAAATTCTGCTACAGACCACA<br>GAAATTCTGCCACAGACCACA | 19875 |
| baal7a09 | CACTTGGACAATTCTATGCAA<br>CACTTGGACACTTCTATGCAA | 19876 |
| baal7a09 | ATCTAGTATAGGTTTGGATGC<br>ATCTAGTATAAGTTTGGATGC | 19877 |
| baal7a09 | CTGTCTTCGCAGCAGATGCGA<br>CTGTCTTCGCGGCAGATGCGA | 19878 |
| bast70b0804 | GACCGGTGATCCGTCCGCCTC<br>GACCGGTGATGCGTCCGCCTC | 19879 |
| bastl14f0412 | CCAACGACTACGCAAATTATA<br>CCAACGACTAGGCAAATTATA | 19881 |
| baal3f19 | TGCCTCCTTTCCCCGATAGGC<br>TGCCTCCTTTTCCCGATAGGC | 19883 |
| baal3f19 | TCGTATCAGCGATAACTATGC<br>TCGTATCAGCAATAACTATGC | 19884 |
| baal3f19 | GTATGTGGATCTTCGTATCAG<br>GTATGTGGATATTCGTATCAG | 19885 |
| baal3f19 | ACAGGTCATCTAGACGAAGCA<br>ACAGGTCATCAAGACGAAGCA | 19886 |
| baal3f19 | AATCCCTGGCAACCTTGATGT<br>AATCCCTGGCTACCTTGATGT | 19887 |
| baal1e10 | TCTTCTGAGTCGGGAATTTCA<br>TCTTCTGAGTGGGGAATTTCA | 19888 |
| baal1e10 | GACTTGGATCGACAGCAGCTT<br>GACTTGGATCAACAGCAGCTT | 19889 |
| bags6k02 | CAGAAGACCCCATGTGGGTTC<br>CAGAAGACCCGATGTGGGTTC | 19890 |
| kr42h0315 | ATCAATAGTCTTAATATTGTA<br>ATCAATAGTCCTAATATTGTA | 19891 |
| kr42h0315 | GTGAGTAACCTCTCTTCTCTC<br>GTGAGTAACCGCTCTTCTCTC | 19892 |
| bah39p02 | AAGGTCCAGACCATGCCCTGT<br>AAGGTCCAGAGCATGCCCTGT | 19893 |
| bah39p02 | AAGCAGTGAATTCTCTCTCAT<br>AAGCAGTGAAATCTCTCTCAT | 19894 |
| BaGS9L14 | ATGATGTCTCCGCAATCTCAT<br>ATGATGTCTCTGCAATCTCAT | 19895 |
| baal35l03 | TGGACTAGATTCGAAAAGGCA<br>TGGACTAGATCCGAAAAGGCA | 19896 |
| baal35l03 | GCACAAACATTATCGTTTTGT<br>GCACAAACATCATCGTTTTGT | 19897 |
| basd12m15 | CAGCCGAACTTCTAAAATATA<br>CAGCCGAACTGCTAAAATATA | 19898 |

TABLE 25-8

| Clones | Haruna Nijo H602 | SEQ ID NO: |
|---|---|---|
| baak35p01 | GTTGATCTTGGACAGCGACTC<br>GTTGATCTTGCACAGCGACTC | 19899 |
| baak35p01 | GCTAGGTACATTCGTGACATC<br>GCTAGGTACACTCGTGACATC | 19900 |
| basd11d18 | AGCTACAAAAGCAATGATGGA<br>AGCTACAAAAACAATGATGGA | 19901 |
| BaH38E07 | GTTACATCCCATCTGCTCAAA<br>GTTACATCCCGTCTGCTCAAA | 19902 |
| bags18h13 | ACAACAGATAAGTGCAATGCA<br>ACAACAGATATGTGCAATGCA | 19903 |
| bags18h13 | GTTTGTAAAACAGCAAACGTA<br>GTTTGTAAAAAAGCAAACGTA | 19904 |
| bags18g16 | GTGAAGTTGGCCCACTTGAAG<br>GTGAAGTTGGTCCACTTGAAG | 19905 |
| bags27f21 | CTGTCACCGCACCTTCAGCTG<br>CTGTCACCGCGCCTTCAGCTG | 19906 |
| bags27f21 | TTTTCGCTCGTTTCACTCTTC<br>TTTTCGCTCGATTCACTCTTC | 19907 |
| baal39c19 | TCACCCGGTGCGACGTGCCAA<br>TCACCCGGTGTGACGTGCCAA | 19909 |
| baak46j05 | ATTCTGAAGCCTACAGAAACA<br>ATTCTGAAGCTTACAGAAACA | 19910 |
| baak46j05 | GTATGCAAATCACATTAGAAA<br>GTATGCAAATTACATTAGAAA | 19911 |
| baak46j05 | TTATATTGTGGTTTAACTCAT<br>TTATATTGTGTTTAACTCAT | 19912 |
| baak46j05 | TAACTCATGAAATACATGGG<br>TAACTCATGGGAATACATGGG | 19913 |
| BaGS18M02 | CATCCATTGATAGGCACTGCA<br>CATCCATTGACAGGCACTGCA | 19915 |
| bags39g08 | TTCTTCGGACACATAATTTTT<br>TTCTTCGGACGCATAATTTTT | 19918 |
| bags39g08 | GCTGCATTACAGATCGCAACA<br>GCTGCATTACGGATCGCAACA | 19919 |
| bah32g18 | CTTCTCTGCCAAGCTGCGGCT<br>CTTCTCTGCCGAGCTGCGGCT | 19923 |
| bah32g18 | GGATCTGAGGCAGTGCACTTG<br>GGATCTGAGGAAGTGCACTTG | 19924 |
| bags38l18 | CATCTAAAGAAAAATGATGCT<br>CATCTAAAGACAAATGATGCT | 19927 |
| bags38l18 | TGATGATGACGGTGATGACGG<br>TGATGATGACAGTGATGACGG | 19928 |
| bags35c13 | AACAAAAGAAACATGTATTGT<br>AACAAAAGAATCATGTATTGT | 19929 |
| bags35c13 | AATGTCTTTCGAACATTGCTA<br>AATGTCTTTCAAACATTGCTA | 19930 |
| bags35c13 | GCCCACCTCAGGCATCTTGAT<br>GCCCACCTCACGCATCTTGAT | 19931 |
| bags35c13 | TGAATCAGTAAAAGAACATTC<br>TGAATCAGTAGAAGAACATTC | 19932 |

TABLE 25-9

| Clones | Haruna Nijo / H602 | SEQ ID NO: |
|---|---|---|
| bags35c13 | AATATCTGGCAAATATGCTTG<br>AATATCTGGCGAATATGCTTG | 19933 |
| bah47h04 | TCCTGTGTATGTGGCGCCACT<br>TCCTGTGTATCTGGCGCCACT | 19934 |
| bah47h04 | CTTTGCAAGAGATCGGTGAAT<br>CTTTGCAAGAAATCGGTGAAT | 19935 |
| bah47h04 | GATAAAATGGAAACAGTATTA<br>GATAAAATGGGAACAGTATTA | 19936 |
| bags30m11 | AGCATTTGTGCCGATGTCTCC<br>AGCATTTGTGGCGATGTCTCC | 19937 |
| bah22l15 | CGGCCGAGCCGATCTCTTAAA<br>CGGCCGAGCCAATCTCTTAAA | 19938 |
| bah22l15 | CTGCGTTTGGTAATGGTGGGA<br>CTGCGTTTGGCAATGGTGGGA | 19939 |
| bah22l15 | GGGAGCACAATTTTGGATTCG<br>GGGAGCACAAATTTGGATTCG | 19940 |
| bags39e15 | ATGTACCTTTTTCTGGGTTAG<br>ATGTACCTTTATCTGGGTTAG | 19941 |
| bags39e15 | CTTGATGACCATTACGTTCAT<br>CTTGATGACCGTTACGTTCAT | 19942 |
| bags39e15 | GTTGGTTAAGATTATGATGAA<br>GTTGGTTAAGGTTATGATGAA | 19943 |
| bags39e15 | TTAGGAGGATTTGTTAGTGGA<br>TTAGGAGGATCTGTTAGTGGA | 19944 |
| bags39e15 | AAATCATCGACCCAGCAGTCA<br>AAATCATCGAACCAGCAGTCA | 19945 |
| basd11h11 | TCACAAACACCAAGAGAGTTG<br>TCACAAACACAAAGAGAGTTG | 19947 |
| baak2b06 | TCAATTTGATCGATCATTTCC<br>TCAATTTGATTGATCATTTCC | 19948 |
| baak2b06 | ACACTAGACCAAGGTAAAGTC<br>ACACTAGACCCAGGTAAAGTC | 19949 |
| baak2b06 | GAATGAGGACAACGCGATGGG<br>GAATGAGGACCACGCGATGGG | 19950 |
| baak2b06 | AACAAAAAGAAGCACCATCTA<br>AACAAAAAGACGCACCATCTA | 19951 |
| baak2b06 | ATCATTTCCTAAAAAAAATTG<br>ATCATTTCCTGAAAAAAATTG | 19952 |
| baak2b06 | ACTGGAAGAGAAGTACCTCTC<br>ACTGGAAGAGGAGTACCTCTC | 19953 |
| baak2b06 | TCTGGATTGAAAAAGAATGAG<br>TCTGGATTGAGAAAGAATGAG | 19954 |
| baak2b06 | ACGCGATGGGGGAGAAGGAAC<br>ACGCGATGGGAGAGAAGGAAC | 19955 |
| basd14a23 | GCGCACGGCGGCTGCCACGTC<br>GCGCACGGCGTCTGCCACGTC | 19959 |
| basd14a23 | ACAAGCATCTCATAAGCTAAT<br>ACAAGCATCTTATAAGCTAAT | 19960 |
| basd14a23 | CAAGCATCAGATCAGCTCTAC<br>CAAGCATCAGTTCAGCTCTAC | 19961 |

TABLE 25-10

| Clones | Haruna Nijo / H602 | SEQ ID NO: |
|---|---|---|
| bast25c0705 | TTCCACGCTCACTAATTACTA<br>TTCCACGCTCGCTAATTACTA | 19962 |
| bast25c0705 | TGCTAAACAGTAACTTTACCG<br>TGCTAAACAGCAACTTTACCG | 19963 |
| bast25c0705 | ACCGCATATCGCCTTCTTCA<br>ACCGCATATCACCTTCTTCA | 19964 |
| bast21b1204 | CACTACTAAGGTAGATATAGC<br>CACTACTAAGATAGATATAGC | 19965 |
| bast21b1204 | ACCGAACAAGATGCATGCACA<br>ACCGAACAAGGTGCATGCACA | 19966 |
| BaAK21G02 | ATTCAAACTCTTCCAGCACGC<br>ATTCAAACTCCTCCAGCACGC | 19968 |
| bastl26e1109 | TCTAGAGCAAGCACTGCTGCT<br>TCTAGAGCAACCACTGCTGCT | 19969 |
| basd13k24 | CAACAGATGTGGCAGCACGTA<br>CAACAGATGTCGCAGCACGTA | 19970 |
| baal13f02 | CTAATTGGTCCGGTGTAGAGT<br>CTAATTGGTCAGGTGTAGAGT | 19971 |
| baal13f02 | ATGCAATGCATAGTCGCTTTA<br>ATGCAATGCACAGTCGCTTTA | 19972 |
| baal13f02 | CATAGCTGCCTTCAAATAAAA<br>CATAGCTGCCGTCAAATAAAA | 19973 |
| baal13f02 | CGCCAACATTTATGACACCTA<br>CGCCAACATTGATGACACCTA | 19974 |
| bags13c10 | GCATGCATGA-AGATACAGGC<br>GCATGCATGACAGATACAGGC | 19975<br>19976 |
| bags13c10 | CGTATCTGCA-GCGATACATG<br>CGTATCTGCAAGCGATACATG | 19977<br>19978 |
| bags13c10 | TTCACAAATC-ATCATGGCCT<br>TTCACAAATCCATCATGGCCT | 19979<br>19980 |
| bags11o11 | GTCCTTTGCCGTCCTGCTCTT<br>GTCCTTTGCCATCCTGCTCTT | 19981 |
| bags11o11 | CCCAGTGTCACCGTTAAATTT<br>CCCAGTGTCATCGTTAAATTT | 19982 |
| bags11o11 | CTAGATCTTGAGTTGGTTGGT<br>CTAGATCTTGCGTTGGTTGGT | 19983 |
| baak36p01 | CCTGCTGTTCTTCTTGGCATG<br>CCTGCTGTTCCTCTTGGCATG | 19984 |
| bah52d09 | GGCTGTAATTAGGATCTGCTC<br>GGCTGTAATTTGGATCTGCTC | 19985 |
| bah52d09 | CAGACGATCTCTGAGAGTGTC<br>CAGACGATCTTTGAGAGTGTC | 19986 |
| bah52d09 | ACAGGGATTTTACAGACGATC<br>ACAGGGATTTCACAGACGATC | 19987 |
| bah52d09 | GGATCTGCTCTTTGTCTCTTG<br>GGATCTGCTCCTTGTCTCTTG | 19988 |
| bah52d09 | TCTGGGCACTTGGACTAGCT<br>TCTGGGCACGTGGACTAGCT | 19989 |
| bah52d09 | AGTTCAGGTGCAATTTTGGGT<br>AGTTCAGGTGTAATTTTGGGT | 19990 |

TABLE 25-11

| Clones | Haruna Nijo / H602 | SEQ ID NO: |
|---|---|---|
| BaGS26D18 | TCGTCAATTGTTTTCAGACAG<br>TCGTCAATTGCTTTCAGACAG | 19991 |
| BaGS26D18 | TGCTGAAATCATGCATTCCCC<br>TGCTGAAATCGTGCATTCCCC | 19992 |
| BaGS26D18 | CAGCGCCGCGATGTTCACTCG<br>CAGCGCCGCGGTGTTCACTCG | 19993 |
| BaGS26D18 | CAGACAGAGATCGCAGAATGA<br>CAGACAGAGACCGCAGAATGA | 19994 |
| baak33c22 | ATGAATAAGCGAAGTACGACA<br>ATGAATAAGCCAAGTACGACA | 19995 |
| baak33c22 | CATGGTTAAATACTCTGGTAC<br>CATGGTTAAACACTCTGGTAC | 19996 |
| baak33c22 | ATCTCAAAAGCGTCGTGTACC<br>ATCTCAAAAGGGTCGTGTACC | 19997 |
| baak11c22 | CAAGATAGTCCAAGATGCCAA<br>CAAGATAGTCAAAGATGCCAA | 19999 |
| baak11c22 | GCAGGAATCTATGGTGGCCTG<br>GCAGGAATCTGTGGTGGCCTG | 20000 |
| bags34l06 | TAAATCCAGTGGCAGAGATGG<br>TAAATCCAGTAGCAGAGATGG | 20001 |
| bags20p21 | AGCGATATATGTATGTCTTCA<br>AGCGATATATATATGTCTTCA | 20005 |
| bah52m01 | GTTCATATCATTTCCCTGTAC<br>GTTCATATCACTTCCCTGTAC | 20006 |
| basd15d07 | TATCTCTGGCGGAAGAGGTCT<br>TATCTCTGGCAGAAGAGGTCT | 20007 |
| basd15d07 | CCACTGGAGGAACATACTGAT<br>CCACTGGAGGGACATACTGAT | 20008 |
| BaAL36B07 | CAGATGCTGGGTTGTGCCAAC<br>CAGATGCTGGATTGTGCCAAC | 20011 |
| BaAL36B07 | AGACGACCCAGAAATTAACAA<br>AGACGACCCATAAATTAACAA | 20012 |
| kr67C0206 | AAGTTACTGAAAGTTAGTGTA<br>AAGTTACTGATAGTTAGTGTA | 20015 |
| kr67C0206 | GGCCACAATATGTTGGTCATT<br>GGCCACAATACGTTGGTCATT | 20016 |
| kr67C0206 | ACTTGTATCTAAAGCACTACG<br>ACTTGTATCTTAAGCACTACG | 20017 |
| kr67C0206 | GCCCGGCATAGTTAATTTTTT<br>GCCCGGCATAATTAATTTTTT | 20018 |
| bags15j20 | TGGCACCTGTAGGGAAAAGGA<br>TGGCACCTGTTGGGAAAAGGA | 20019 |
| bags15j20 | GTACAAAACAAGAATCTCCCT<br>GTACAAAACAGGAATCTCCCT | 20020 |
| BaH15E05 | CACAAGTAGTAGAAGTATTCA<br>CACAAGTAGTGGAAGTATTCA | 20021 |
| bah58k02 | TCAAATGCTCTGAGAGACTGA<br>TCAAATGCTCCGAGAGACTGA | 20022 |
| bah58k02 | TTTCACTTTCGTCTTCGCTTT<br>TTTCACTTTCCTCTTCGCTTT | 20023 |

TABLE 25-12

| Clones | Haruna Nijo / H602 | SEQ ID NO: |
|---|---|---|
| basd13d17 | ACCGTTTCTAGTTGCACGGGA<br>ACCGTTTCTATTTGCACGGGA | 20024 |
| basd13d17 | ATTAGGTTCTGACCGTAGGCT<br>ATTAGGTTCTCACCGTAGGCT | 20025 |
| basd13d17 | CAGAGATTTCAAGCAATAGA<br>CAGAGATTTCGAGCAATAGA | 20026 |
| basd13d17 | TTAACAAGCGTTGTGTCACCT<br>TTAACAAGCGCTGTGTCACCT | 20027 |
| basd13d17 | TAAAAACCTAAAAAGAGACAG<br>TAAAAACCTACAAAGAGACAG | 20028 |
| BaAK30F13 | GTTCATTTGTCGAGTAGACAT<br>GTTCATTTGTTGAGTAGACAT | 20030 |
| baal2n22 | CAGCCACAGTCCTTTGGATTA<br>CAGCCACAGTCCTTTGCATTA | 20033 |
| baal2n22 | AAAGACTGAATTATTGAGTTT<br>AAAGACTGAACTATTGAGTTT | 20034 |
| baal2n22 | AACTTAAACTATTACAAAGAC<br>AACTTAAACTTTTACAAAGAC | 20035 |
| baal2n22 | CTGTAGGCAACAAAACTGTAA<br>CTGTAGGCAAGAAAACTGTAA | 20036 |
| kr30c0705 | TGGGGTTATATGGCTTAGCGG<br>TGGGGTTATACGGCTTAGCGG | 20037 |
| BaSD19J21 | AACTTAAACTTTTACAAAGAC<br>AACTTAAACTATTACAAAGAC | 20038 |
| BaSD19J21 | AAAGACTGAACTATTGAGTTT<br>AAAGACTGAATTATTGAGTTT | 20039 |
| BaSD19J21 | CATGGTTTGTACCTATATTAC<br>CATGGTTTGTGCCTATATTAC | 20040 |
| BaSD19J21 | CAGCCACAGTTCTTTGGATTA<br>CAGCCACAGTCCTTTGGATTA | 20041 |
| BaSD19J21 | CTGTAGGCAAGAAAACTGTAA<br>CTGTAGGCAACAAAACTGTAA | 20042 |
| BaH34N22 | ACCGGAACTCGCTGCCGAATC<br>ACCGGAACTCACTGCCGAATC | 20043 |
| BaH34N22 | CTTCAGCTGCTGCTGCAGCGG<br>CTTCAGCTGCCGCTGCAGCGG | 20044 |
| BaGS1E22 | GTTTATCCAGCTGATGCGGAG<br>GTTTATCCAGTTGATGCGGAG | 20046 |
| baak34b17 | CTACAAGGGAGGCAGCCCAGG<br>CTACAAGGGAAGCAGCCCAGG | 20047 |
| baak34b17 | AAAATACAGTGCCGACCAAGA<br>AAAATACAGTCCCGACCAAGA | 20048 |
| baak34b17 | GAGCTAGCGCGGGCAAGACCA<br>GAGCTAGCGCTGGCAAGACCA | 20049 |
| kr32a0202 | CAAATGCTATGGCCTATGGCT<br>CAAATGCTATTGCCTATGGCT | 20051 |
| bags27h21 | TCCGACGAGGATGAGTTCAAC<br>TCCGACGAGGGTGAGTTCAAC | 20052 |
| bah62d17 | TATAGTTACCGTACTAATACT<br>TATAGTTACCATACTAATACT | 20053 |

TABLE 25-13

| Clones | Haruna Nijo H602 | SEQ ID NO: |
|---|---|---|
| bah62d17 | TTGCTTGGAAGTCCTTCATGA<br>TTGCTTGGAAATCCTTCATGA | 20054 |
| bah43e22 | CCAAGATCTGATGTTGATGCA<br>CCAAGATCTGGTGTTGATGCA | 20055 |
| BaAL30I23 | CGGGTACGGCAGCCCGGCGAC<br>CGGGTACGGCGGCCCGGCGAC | 20056 |
| baak34p06 | TCGGAGGTCATAATGATGTTC<br>TCGGAGGTCAGAATGATGTTC | 20059 |
| baak34p06 | CGCATTGCCTACACAGCATAG<br>CGCATTGCCTGCACAGCATAG | 20060 |
| baak34p06 | AGATGGTACAAGACACAGCAG<br>AGATGGTACAGGACACAGCAG | 20061 |
| bah63b08 | CGGGTTACAACAAAAGTGGCA<br>CGGGTACAACAAAAGTGGCA | 20062 |
| bast103f0812 | CGGGTTACAACAAAAGTGGCA<br>CGGGTTACAAGAAAAGTGGCA | 20063 |
| basd14m17 | CAGAGCCAGAAGCAGCAGCCG<br>CAGAGCCAGACGCAGCAGCCG | 20064 |
| basd14m17 | ATCCATATCCAACAATCAGAA<br>ATCCATATCCACAATCAGAA | 20065 |
| basd14m17 | AAAGAAGGCGCGATTGCGGAA<br>AAAGAAGGCGAGATTGCGGAA | 20066 |
| basd14m17 | TAGGCGACGGTGATGTCGAAC<br>TAGGCGACGGGGATGTCGAAC | 20067 |
| basd2j03 | TCGGCTCTGAACACCAAAGGT<br>TCGGCTCTGACCACCAAAGGT | 20068 |
| basd2j03 | AGCAGCAAACGTATAATTACC<br>AGCAGCAAACATATAATTACC | 20069 |
| baal32b23 | TGTCTCTCTCTGACTCCATCT<br>TGTCTCTCTCCGACTCCATCT | 20070 |
| bah44n03 | GCTTGTCACGAAGGTGCGGCT<br>GCTTGTCACGGAGGTGCGGCT | 20074 |
| bah44n03 | GCATCTTGGCGTCGTTGCAGA<br>GCATCTTGGCATCGTTGCAGA | 20075 |
| bags20h05 | GGGGGTTAGAGTAGAAGTAAT<br>GGGGGTTAGAATAGAAGTAAT | 20076 |
| bags20115 | GTACAACCGTTTCCACCGTAC<br>GTACAACCGTCTCCACCGTAC | 20077 |
| BaGS7E03 | GGTGGTGGTGTGATGTCCTTC<br>GGTGGTGGTGCGATGTCCTTC | 20078 |
| bast55e0709 | TCCTTATTTGCTTCTGTCCCC<br>TCCTTATTTGGTTCTGTCCCC | 20080 |
| baak38k04 | CTTTTGTGTTTACCTCGATCT<br>CTTTTGTGTTGACCTCGATCT | 20082 |
| baak38k04 | TGCCAATCATGGGGTATTGAT<br>TGCCAATCATAGGGTATTGAT | 20083 |
| bah42l12 | TCGGCGACCGTTGCATAGGTC<br>TCGGCGACCGCTGCATAGGTC | 20086 |
| bah42l12 | GCAGGCCAGAAAAGTGTAAAC<br>GCAGGCCAGAGAAGTGTAAAC | 20087 |

TABLE 25-14

| Clones | Haruna Nijo H602 | SEQ ID NO: |
|---|---|---|
| baet46c0905 | CTGCGCGAACACGTGAAGGAA<br>CTGCGCGAACGCGTGAAGGAA | 20089 |
| baet46c0905 | GTGGGAAAGGGAACTAGTTGC<br>GTGGGAAAGGAAACTAGTTGC | 20090 |
| bah26e10 | GCTTTCTGTCACCTGATGAAT<br>GCTTTCTGTCGCCTGATGAAT | 20092 |
| bah26e10 | GAGGTTCCCGGCATTTTTCAG<br>GAGGTTCCCGACATTTTTCAG | 20093 |
| bah32j04 | GCTCTCCATGTTGAGAACTCT<br>GCTCTCCATGCTGAGAACTCT | 20094 |
| bah32j04 | AGAGAGAGCCTCTTCGATTAC<br>AGAGAGAGCCGCTTCGATTAC | 20095 |
| bah32j04 | ACATGTACAACAGATTTACAT<br>ACATGTACAAGAGATTTACAT | 20096 |
| bah32j04 | TGAAGGAGGCACAAAATGTAC<br>TGAAGGAGGCCCAAAATGTAC | 20097 |
| bah32j04 | TATGGACATGGCTACAGAATT<br>TATGGACATGACTACAGAATT | 20098 |
| bah32j04 | TTATCTCTCTGCTCTATTG<br>TTATCTCTCTATGCTCTATTG | 20099 |
| bags20107 | AACCAACATATCGAAACCCTT<br>AACCAACATAGCGAAACCCTT | 20100 |
| bags20107 | GTGTTAAGACCGTCAGCAGCT<br>GTGTTAAGACTGTCAGCAGCT | 20101 |
| bags20107 | GAGCATGTTATACCTCTTTAT<br>GAGCATGTTAGACCTCTTTAT | 20102 |
| bags20107 | GCTGCAGCCTGTTCTTGAAGC<br>GCTGCAGCCTCTTCTTGAAGC | 20103 |
| bags20107 | GCTCTCCATGTTGAGAACTCT<br>GCTCTCCATGCTGAGAACTCT | 20104 |
| bags20107 | GATCAAACCGCGAACTCAATG<br>GATCAAACCGTGAACTCAATG | 20105 |
| bags20107 | CTCAATGACTGGAGCATGTTA<br>CTCAATGACTTGAGCATGTTA | 20106 |
| bags20107 | AGGAGGCCCATTGCAGAAGAT<br>AGGAGGCCCAATGCAGAAGAT | 20107 |
| kr18c0505 | ATTTGGCAGAGACGAAATGCG<br>ATTTGGCAGACACGAAATGCG | 20108 |
| kr18c0505 | TGGACCATACGTGATATCCAT<br>TGGACCATACTTGATATCCAT | 20109 |
| kr18c0505 | GCTTTTGGGGGGTCATCTAG<br>GCTTTTGGGGCGGTCATCTAG | 20110 |
| kr18c0505 | ACAAAAATCATCAGATAATGT<br>ACAAAAATCAGCAGATAATGT | 20111 |
| kr18c0505 | AAACACTATCGTTACGCCTAT<br>AAACACTATCATTACGCCTAT | 20112 |
| kr18c0505 | TGATGATTGATCAGGGCCTGA<br>TGATGATTGAACAGGGCCTGA | 20113 |
| basd11m24 | TGCAGAAACTGTGTTGCTAAA<br>TGCAGAAACTATGTTGCTAAA | 20114 |

TABLE 25-15

| Clones | Haruna Nijo H602 | SEQ ID NO: |
|---|---|---|
| basd1i15 | TTGTCTAGTGTTTGGGCTTGA<br>TTGTCTAGTGCTTGGGCTTGA | 20115 |
| basd1i15 | ACAAATCTACTTTCGCGAAGG<br>ACAAATCTACATTCGCGAAGG | 20116 |
| bah13i21 | TTGCAGGAAATACTGCAGAAC<br>TTGCAGGAAACACTGCAGAAC | 20119 |
| basd27o20 | CCTGTATGAACTTCGAAATGA<br>CCTGTATGAATTTCGAAATGA | 20120 |
| baak45l08 | TTATTCACTACCAACTTTGTA<br>TTATTCACTAGCAACTTTGTA | 20123 |
| baak45l08 | GGATGCCCGTTCCATGATCAA<br>GGATGCCCGTCCCATGATCAA | 20124 |
| baak45l08 | AGAATATCCAAGGACAAAGGT<br>AGAATATCCATGGACAAAGGT | 20125 |
| baak45l08 | TTGGCACAAGGGCAGCAGTAA<br>TTGGCACAAGAGCAGCAGTAA | 20126 |
| baak45l08 | AGGGCATTCAGTTTCGTTCCA<br>AGGGCATTCAATTTCGTTCCA | 20127 |
| baak45l08 | CTGCCAGCCCCCCGACGGTGA<br>CTGCCAGCCCTCCGACGGTGA | 20128 |
| baak45l08 | GCCAGCTCTCCACGCCGGACC<br>GCCAGCTCTCAACGCCGGACC | 20129 |
| baak45l08 | CCTCCCACAATTAAGCAGTGC<br>CCTCCCACAAATAAGCAGTGC | 20130 |
| BaAL36N04 | GCCAGAGAAATTTTTCCTCGA<br>GCCAGAGAAATTTTTCCTCGA | 20131 |
| baak41d17 | ACATGCATGGTCAATTTTACG<br>ACATGCATGGACAATTTTACG | 20132 |
| baak41d17 | GTGGACTTCTCCTTGGCGGCG<br>GTGGACTTCTTCTTGGCGGCG | 20133 |
| baak41d17 | TGGCCTCGCCGCCCATCTTTT<br>TGGCCTCGCCACCCATCTTTT | 20134 |
| baak41d17 | TCGGTGGCCGTCTTCTTCACG<br>TCGGTGGCCGGCTTCTTCACG | 20135 |
| baak41d17 | TTCACGGCCTCCGTCTTCTCG<br>TTCACGGCCTACGTCTTCTCG | 20136 |
| baak41d17 | TCTGCAGCGGTGTCCTGGACA<br>TCTGCAGCGGCGTCCTGGACA | 20137 |
| BaGS25M06 | CTAAACCAGGGCGCCTGAACA<br>CTAAACCAGGACGCCTGAACA | 20139 |
| BaGS25M06 | CGATGTAGACGTGGACGTTGA<br>CGATGTAGACATGGACGTTGA | 20140 |
| bah36f21 | ATGTCTCCGCTGGCGGTGCGT<br>ATGTCTCCGCCGGCGGTGCGT | 20141 |
| bah36f21 | CTTGCCATCCACGTCGCCGTC<br>CTTGCCATCCCCGTCGCCGTC | 20142 |
| baak13b12 | ATGCGGTCCAAACTCCAACCA<br>ATGCGGTCCACACTCCAACCA | 20143 |
| baak13b12 | TGTTCCTTCCGCTTGTTTGTT<br>TGTTCCTTCCTCTTGTTTGTT | 20144 |

TABLE 25-16

| Clones | Haruna Nijo H602 | SEQ ID NO: |
|---|---|---|
| bast63B0604 | GAGGAGCCAGCAGCAGCATCT<br>GAGGAGCCAGAAGCAGCATCT | 20145 |
| baak11n06 | AAACATGATCTTGATCCATGC<br>AAACATGATCCTGATCCATGC | 20146 |
| kr13f1012 | GTGTCTCGCTCGGTTCGTTCT<br>GTGTCTCGCTGGGTTCGTTCT | 20147 |
| kr13f1012 | TCCCTTCTTCCTTTTTTTTGT<br>TCCCTTCTTCGTTTTTTTTGT | 20148 |
| bags20k06 | GTCCTGGGATCTGAAGGAATC<br>GTCCTGGGATTTGAAGGAATC | 20149 |
| bags20k06 | CTTCCGTCGAGCAACCCAAAC<br>CTTCCGTCGAACAACCCAAAC | 20150 |
| bags20k06 | CAGCTTCATCAAAAGAATCGA<br>CAGCTTCATCAAAAGAATCGA | 20151 |
| baak15p20 | CTGATGAACATCTAAGATTTC<br>CTGATGAACACCTAAGATTTC | 20152 |
| BaH23 J08 | ACGGATTCTAGGCATGATCAA<br>ACGGATTCTAAGCATGATCAA | 20153 |
| BaH23 J08 | ATAGCTTACCACAATGGTCTC<br>ATAGCTTACCGCAATGGTCTC | 20154 |
| baet30b1004 | TGGACGACTAGGAATTATTGG<br>TGGACGACTAAGAATTATTGG | 20155 |
| bast133h0816 | CCGATTAACAGTGGCCCACAC<br>CCGATTAACACTGGCCCACAC | 20156 |
| baak42k19 | CTTTGGCGTTCCCTTTTCCGC<br>CTTTGGCGTTGCCTTTTCCGC | 20162 |
| bast60a1101 | GAACTTGCCTCCTGTCCTTTA<br>GAACTTGCCTACTGTCCTTTA | 20163 |
| bast60a1101 | TATGGCACCCATCACACCACA<br>TATGGCACCCCTCACACCACA | 20164 |
| bah52l06 | TCGGGCCCCACTCCCTCATGT<br>TCGGGCCCCAATCCCTCATGT | 20165 |
| bah52l06 | CTAAGTACCGTGTCCACCTCT<br>CTAAGTACGGCGTCCACCTCT | 20166 |
| bah23h10 | GAAGTGTAGCGTCAGGGTTGT<br>GAAGTGTAGCATCAGGGTTGT | 20167 |
| bah23h10 | GCAAAGAATAAGGGCCGCCTT<br>GCAAAGAATACGGGCCGCCTT | 20168 |
| bags15o23 | GATTTTAATTCAGATGATGAT<br>GATTTTAATTAAGATGATGAT | 20169 |
| bags15o23 | CCTTATCATCTTCCTGTACCA<br>CCTTATCATCATCCTGTACCA | 20170 |
| bags15o23 | TGATGAACCACTTGTTGATTT<br>TGATGAACCAGTTGTTGATTT | 20171 |
| bags15o23 | AGAGGTTGCACTCTTAACCGA<br>AGAGGTTGCAGTCTTAACCGA | 20172 |
| baak20e08 | CTATCCAAGAAGTTGAACATC<br>CTATCCAAGAGGTTGAACATC | 20173 |
| baak20e08 | CGCGGAGGCCAATGGTGTAGT<br>CGCGGAGGCCGATGGTGTAGT | 20174 |

TABLE 25-17

| Clones | Haruna Nijo H602 | SEQ ID NO: |
|---|---|---|
| baak20e08 | CCACCTCGTAGGGGATCTCCG<br>CCACCTCGTATGGGATCTCCG | 20175 |
| baak20e08 | AATCAACCCAAGGTGAAATTG<br>AATCAACCCAGGGTGAAATTG | 20176 |
| kr61a1202 | ATCTGAAATTGTGAGCATGAA<br>ATCTGAAATTATGAGCATGAA | 20177 |
| kr61a1202 | GTGTCCAAAACCGTGATGTTC<br>GTGTCCAAAAACGTGATGTTC | 20178 |
| bast03f0212 | CGGACGATATCAGCTAGCTAG<br>CGGACGATATGAGCTAGCTAG | 20179 |
| baak30o17 | TTAATCCTTCGTAGGCTCATT<br>TTAATCCTTCATAGGCTCATT | 20181 |
| baak30o17 | TTTTTCCTCCAATCCAGATGC<br>TTTTTCCTCCCATCCAGATGC | 20182 |
| baal2n04 | AGAGGACACCGCCGATAGCAA<br>AGAGGACACCACCGATAGCAA | 20186 |
| bags30n15 | CACCATCTTGCAGTAAATACA<br>CACCATCTTGAAGTAAATACA | 20188 |
| baal34d18 | TGTAGAAGGTTCTCCTGTCGT<br>TGTAGAAGGTGCTCCTGTCGT | 20189 |
| bags37i06 | TTCCCTGATGCAGTTCTTCAA<br>TTCCCTGATGTAGTTCTTCAA | 20191 |
| BaGS19N09 | ACTGGTAGACGAGGTCCATGC<br>ACTGGTAGACAAGGTCCATGC | 20192 |
| BaGS19N09 | ACCCGTCCACCAGCAGGGAGT<br>ACCCGTCCACGAGCAGGGAGT | 20193 |
| BaSD13H09 | CTCCGGATCCGCCGCGACGAA<br>CTCCGGATCCACCGCGACGAA | 20194 |
| BaSD13H09 | AACTCAAGCTCGCCTCTAACA<br>AACTCAAGCTTGCCTCTAACA | 20195 |
| baak28o08 | CAGGATAACTATCTGAACCCT<br>CAGGATAAGTGTCTGAACCCT | 20197 |
| BaH15K08 | CCGAGATTCGATGCCCAGGTA<br>CCGAGATTCGGTGCCCAGGTA | 20198 |
| bah28a11 | TCATACAAAACAAGAAAAAAC<br>TCATACAAAAGAAGAAAAAAC | 20201 |
| bah28a11 | ACACTTTTTCATCCTTGACTG<br>ACACTTTTTCGTCCTTGACTG | 20202 |
| basd25e01 | AGGTATTAAGATTAACTGCTG<br>AGGTATTAAGCTTAACTGCTG | 20203 |
| baet23F0111 | AACTCAATCAGGCCTTGTGCT<br>AACTCAATCAAGCCTTGTGCT | 20204 |
| baet23F0111 | AAATTGGATTCATGTACTAAC<br>AAATTGGATTTATGTACTAAC | 20205 |
| baet23F0111 | AATGCACCCTTTGTCCTGCAA<br>AATGCACCCTGTGTCCTGCAA | 20206 |
| basd11c04 | TCTAACGAGATCACAACAAGA<br>TCTAACGAGAGCACAACAAGA | 20208 |
| basd11c04 | TGTCGTTGCCAGCCACTTCTC<br>TGTCGTTGCCGGCCACTTCTC | 20209 |

TABLE 25-18

| Clones | Haruna Nijo H602 | SEQ ID NO: |
|---|---|---|
| bags22K17 | AAACACAGCTACTAAAATAAG<br>AAACACAGCTGCTAAAATAAG | 20210 |
| bags22k17 | TCTAATAATTGATTCGCTTCA<br>TCTAATAATTAATTCGCTTCA | 20211 |
| bags22a16 | AAAATATGCTCAAGAGTTCAA<br>AAAATATGCTTAAGAGTTCAA | 20212 |
| bags22a16 | CAAAGAGCAACAAAAATTCA<br>CAAAGAGCAGCAAAAATTCA | 20213 |
| bags22a16 | GAACATGATA-GAGGTATGTT<br>GAACATGATAAGAGGTATGTT | 20214<br>20215 |
| baak41l23 | ACCTAACTAATTCACACCAGC<br>ACCTAACTAAATCACACCAGC | 20219 |
| baak41l23 | GTAATCAACTGATTCCTTTGG<br>GTAATCAACTAATTCCTTTGG | 20220 |
| bastl26c1206 | ATGATGCCTTAATTGAGCTCA<br>ATGATGCCTATATTGAGCTCA | 20223 |
| bah27p20 | TGGTTTCTGACGCTTTCAGAA<br>TGGTTTCTGATGCTTTCAGAA | 20224 |
| bah27p20 | CGATCATAACGTGGACGGCGG<br>CGATCATAACATGGACGGCGG | 20225 |
| baal12d24 | TTCAAGTCCTTTCTCTTATAC<br>TTCAAGTCCTCTCTCTTATAC | 20226 |
| bastl41f0511 | TCGACCGTGGAAATCCCAACA<br>TCGACCGTGGGAATCCCAACA | 20227 |
| bastl41f0511 | CTAGGAGTAAGTCCCCACGTC<br>CTAGGAGTAACTCCCCACGTC | 20228 |

TABLE 26-1

| Clones | Haruna Nijo H602 | SEQ ID NO: |
|---|---|---|
| baal10j04 | AGGCAAACTCAGTCAGGGAAA<br>AGGCAAACTCGGTCAGGGAAA | 20230 |
| BaAK33J17 | CAACCCAACTTGATGATAATG<br>CAACCCAACTCGATGATAATG | 20231 |
| bast17h0515 | CCTACAAGTACTACAACTCAC<br>CCTACAAGTAGTACAACTCAC | 20233 |
| baak35a06 | TCACATGCTTTCGGTACGATT<br>TCACATGCTTCCGGTACGATT | 20234 |
| baak35a06 | ATACACAGTCCCCTGTAATAT<br>ATACACAGTCACCTGTAATAT | 20235 |
| baak18m22 | GGAAGTGTGCTTGGGCATTCG<br>GGAAGTGTGCCTGGGCATTCG | 20239 |
| baak18m22 | AAATCATGCACAAGAGGCGAT<br>AAATCATGCAGAAGAGGCGAT | 20240 |
| baak18m22 | CCCCATGCTCATGCAGGCATG<br>CCCCATGCTCTTGCAGGCATG | 20241 |
| baak18m22 | CGGAAGATGCAATGCCGACGC<br>CGGAAGATGCGATGCCGACGC | 20242 |
| bast26g0614 | TCACCAAGTTACCGTCTTCAG<br>TCACCAAGTTGCCGTCTTCAG | 20243 |

TABLE 26-1-continued

| Clones | Haruna Nijo H602 | SEQ ID NO: |
|---|---|---|
| basd22f13 | AATGCGGTATCGTCCGACCTC<br>AATGCGGTATTGTCCGACCTC | 20244 |
| basd22f13 | GTAGTGCAGAGGACAGTGATG<br>GTAGTGCAGATGACAGTGATG | 20245 |
| bah63l18 | ATTCTGTTTGACAGGATCTCA<br>ATTCTGTTTGTCAGGATCTCA | 20249 |
| bah63l18 | TCTCGGCCTCATCAAAGAAGA<br>TCTCGGCCTCGTCAAAGAAGA | 20250 |
| BaGS9H22 | TCAAGTCTGGTACCACTCTAT<br>TCAAGTCTGGAACCACTCTAT | 20251 |
| BaGS9H22 | ATGCAGCACAGACAACACGTT<br>ATGCAGCACAAACAACACGTT | 20252 |
| BaGS9H22 | GTACAACTCACGAGCTCTTGT<br>GTACAACTCAAGAGCTCTTGT | 20253 |
| BaGS9H22 | GAGCTCTTGTAGACGGTTTTC<br>GAGCTCTTGTCGACGGTTTTC | 20254 |
| BaGS9H22 | CGTTCCAAATGCGTGGTCCCA<br>CGTTCCAAATACGTGGTCCCA | 20255 |
| BaGS9H22 | ATATCGGCACTGCAAGGTGG<br>ATATCGGCATTGCAAGGTGG | 20256 |
| BaH17N17 | CCGGCACAAGTTCACATATCC<br>CCGGCACAAGCTCACATATCC | 20259 |
| BaH17N17 | CCGGATTTTCACGTCCGATTC<br>CCGGATTTTCGCGTCCGATTC | 20260 |
| bags34a05 | ACACGAGTCCTTTACAGAATA<br>ACACGAGTCCCTTACAGAATA | 20261 |
| bags34a05 | TCATACCAGTGATGCTTTTAT<br>TCATACCAGTCATGCTTTTAT | 20262 |
| bags1m23 | AAAAAGAGACGACGTGCACTT<br>AAAAAGAGACAACGTGCACTT | 20263 |

TABLE 26-2

| Clones | Haruna Nijo H602 | SEQ ID NO: |
|---|---|---|
| bags1m23 | TTTTGCCTTGACTATCTGGCT<br>TTTTGCCTTGGCTATCTGGCT | 20264 |
| BaH50B05 | ACATTTCAGAATTGTGTCACT<br>ACATTTCAGAGTTGTGTCACT | 20265 |
| BaH50B05 | TGACTTCCTATCTTGTGAAAT<br>TGACTTCCTACCTTGTGAAAT | 20266 |
| BaH50B05 | CCAAGTTCTCCTACTCTTCTC<br>CCAAGTTCTCTTACTCTTCTC | 20267 |
| BaH50B05 | AGGTGCAGTTTTACCTAACAT<br>AGGTGCAGTTCTACCTAACAT | 20268 |
| BaH50B05 | TATTCGCTGCACTCGTTGGTC<br>TATTCGCTGCCCTCGTTGGTC | 20269 |
| bags1h11 | TGGCGGCCTCAACCATGTTGG<br>TGGCGGCCTCGACCATGTTGG | 20270 |
| bags1h11 | GACCGCAGTCAGGGTTCACCC<br>GACCGCAGTCGGGGTTCACCC | 20271 |

TABLE 26-2-continued

| Clones | Haruna Nijo H602 | SEQ ID NO: |
|---|---|---|
| bah47e01 | TGCAGGGGTGCTTCACAGTGC<br>TGCAGGGGTGGTTCACAGTGC | 20274 |
| bast52E0109 | TGACGCTTGATAGCTCATCAT<br>TGACGCTTGACAGCTCATCAT | 20275 |
| bags1o08 | AGGACCCATGGGTGATGCATT<br>AGGACCCATGTGTGATGCATT | 20276 |
| bags1o08 | TGAAGACTAGACTGACAGCAG<br>TGAAGACTAGGCTGACAGCAG | 20277 |
| baak32l14 | CTAGCACTCAAGTTCCGAGGA<br>CTAGCACTCAGGTTCCGAGGA | 20279 |
| baak32l14 | CCTGCTACCGTGAAAGGGCCG<br>CCTGCTACCGCGAAAGGGCCG | 20280 |
| bah50o06 | CGCCCAGCCGATATGCAATCT<br>CGCCCAGCCGTTATGCAATCT | 20281 |
| bah50o06 | ATATGATCCACTTTTCATGAT<br>ATATGATCCATTTTTCATGAT | 20282 |
| bah50o06 | TCATGTATACCGGGAAGGAAG<br>TCATGTATACAGGGAAGGAAG | 20283 |
| bah50o06 | ACATGCATACATGTTATAAAT<br>ACATGCATACTTGTTATAAAT | 20284 |
| bah50o06 | GTATGTCGCAATTGATCTAAA<br>GTATGTCGCATTTGATCTAAA | 20285 |
| bah50o06 | CTCGTTATATTTGTACAGGTC<br>CTCGTTATATCTGTACAGGTC | 20286 |
| BaSD26I01 | TATTCCAGTAAAGTGATATTA<br>TATTCCAGTACAGTGATATTA | 20287 |
| BaSD26I01 | AGATTGCAGACGATTTCAAAT<br>AGATTGCAGATGATTTCAAAT | 20288 |
| BaSD26I01 | AATGTGACTACCATGTCAGAC<br>AATGTGACTAACATGTCAGAC | 20289 |
| bags1h24 | TGCTCAGCCAGCGCCAAGATC<br>TGCTCAGCCAACGCCAAGATC | 20290 |
| basd27g16 | GGCTGCTCCTGGTCTTAAGAA<br>GGCTGCTCCTAGTCTTAAGAA | 20291 |

TABLE 26-3

| Clones | Haruna Nijo H602 | SEQ ID NO: |
|---|---|---|
| basd27g16 | AAATGAAATAATTGGCTGCTC<br>AAATGAAATAGTTGGCTGCTC | 20292 |
| bags34c19 | TCGTAAGTGGCCGCAGAACGT<br>TCGTAAGTGGTCGCAGAACGT | 20294 |
| bags34c19 | ACAAGTGTTCGTGTTCTGGCT<br>ACAAGTGTTCATGTTCTGGCT | 20295 |
| bags34c19 | TACAGTGTGAAGCCTGCAGTC<br>TACAGTGTGAGGCCTGCAGTC | 20296 |
| bah20k17 | ACAAATTCAAGGTCTCCAGAA<br>ACAAATTCAACGTCTCCAGAA | 20297 |
| baak29c12 | TGAGATGAAATAACACACTTT<br>TGAGATGAAAGAACACACTTT | 20299 |

TABLE 26-3-continued

| Clones | Haruna Nijo H602 | SEQ ID NO: |
|---|---|---|
| baak29c12 | CTTTGAAGGAGGTTAGTTAAA<br>CTTTGAAGGAAGTTAGTTAAA | 20300 |
| baak29c12 | GCGATCTGCAGGAGCACCCTG<br>GCGATCTGCAAGAGCACCCTG | 20301 |
| baak29c12 | ACTGACCTGCCCACGGCTCCAA<br>ACTGACCTGCGACGGCTCCAA | 20302 |
| baal6a09 | GAATAAGAAACATTTCTTCC<br>GAATAAGAAAGCATTTCTTCC | 20304 |
| bah30p15 | GCCCTTCATCGGACCACACTT<br>GCCCTTCATCTGACCACACTT | 20306 |
| basd25d22 | CACAGCAGGGGTCCGGCCAAG<br>CACAGCAGGGTTCCGGCCAAG | 20308 |
| baak13n10 | AGAAAGGTGCGTACATAATTG<br>AGAAAGGTGCATACATAATTG | 20310 |
| bags18j21 | CCTTGTGACCGTCATACATCG<br>CCTTGTGACCTTCATACATCG | 20311 |
| bags18j21 | AGGTCACAATAGGTTGATCAA<br>AGGTCACAATGGGTTGATCAA | 20312 |
| bags33j02 | GATAAGATACATGACGACTGT<br>GATAAGATACGTGACGACTGT | 20313 |
| bags33j02 | AAAACAAACGTTCGGATGAAT<br>AAAACAAACGGTCGGATGAAT | 20314 |
| bags37f05 | GAGATGTCATCGACCGTGCAT<br>GAGATGTCATTGACCGTGCAT | 20316 |
| bags37f05 | AACACCCCGCGCGCCTTTTCGA<br>AACACCCCGTGCCTTTTCGA | 20317 |
| bags37f05 | ATTGCGATGCGTAACGGGATA<br>ATTGCGATGCATAACGGGATA | 20318 |
| BaAL17L15 | CAGTCCGAGCCGCCCCCGCCG<br>CAGTCCGAGCTGCCCCCGCCG | 20319 |
| bags20h12 | TGCTAGAATCATGTATATGGC<br>TGCTAGAATCCTGTATATGGC | 20320 |
| bags20h12 | CACTGTAAATGTTCAGCCTAT<br>CACTGTAAATTTTCAGCCTAT | 20321 |
| bags20h12 | ATCTGAAAAAGGTGATGATT<br>ATCTGAAAAAGGGTGATGATT | 20322 |
| kr65a0802 | TGTTCTTGTACTCGGCAATGG<br>TGTTCTTGTAATCGGCAATGG | 20323 |

TABLE 26-4

| Clones | Haruna Nijo H602 | SEQ ID NO: |
|---|---|---|
| kr65a0802 | CGTCGTGGTCCTTCTACCGCG<br>CGTCGTGGTCGTTCTACCGCG | 20324 |
| basd22j16 | CTATAAGCATCGTCAAGTGAA<br>CTATAAGCATTGTCAAGTGAA | 20325 |
| bah39n18 | GCAGACACTGTGGCACCAGAC<br>GCAGACACTGGGGCACCAGAC | 20326 |
| bah39n18 | GAACGTGTCGGGAAACCTCGA<br>GAACGTGTCGTGAAACCTCGA | 20327 |

TABLE 26-4-continued

| Clones | Haruna Nijo H602 | SEQ ID NO: |
|---|---|---|
| bags20d19 | CTATAATGTGAAGGTACATCC<br>CTATAATGTGGAGGTACATCC | 20328 |
| bags20d19 | GCATGGTATCGCCCGTATGCC<br>GCATGGTATCACCCGTATGCC | 20329 |
| bags20d19 | ACTTGCGGAGAACTGCCGATC<br>ACTTGCGGAGGACTGCCGATC | 20330 |
| bags20d19 | TCGATTTTTAGATTGCTATAA<br>TCGATTTTTACATTGCTATAA | 20331 |
| bags20d19 | GATAGGTGAAGCACTGCATGG<br>GATAGGTGAAACACTGCATGG | 20332 |
| bags20d19 | TCACTGCTCTCCAGATGAAAC<br>TCACTGCTCTGCAGATGAAAC | 20333 |
| bags20d19 | GAAACTGCCAACACAAAGAT<br>GAAACTGCCAGCACAAAGAT | 20334 |
| bags20d19 | CAAAGATTGTTTGCTTATTT<br>CAAAGATTGATTGCTTATTT | 20335 |
| bags34h19 | AAGTCCTAACCAACCAGCAAT<br>AAGTCCTAACAAACCAGCAAT | 20336 |
| bags34h19 | CATACCAAATCAAATGTTACA<br>CATACCAAATTAAATGTTACA | 20337 |
| bags34h19 | TTCATATCCACGACCCCATTA<br>TTCATATCCATGACCCCATTA | 20338 |
| baak42n10 | ATTACCAGTAAATAAATTTCT<br>ATTACCAGTAGATAAATTTCT | 20339 |
| baak42n10 | GAAAGCACTTTCCATCTAACT<br>CAAAGCACTTCCCATCTAACT | 20340 |
| basd24f03 | TCACCATGGGGTTTGATTCCA<br>TCACCATGGGATTTGATTCCA | 20341 |
| BaGS23N21 | GAAATATATATAGAACAGAGG<br>GAAATATATAAAGAACAGAGG | 20342 |
| BaGS23N21 | TCCAAACAGTCCGATGCCAAA<br>TCCAAACAGTTCGATGCCAAA | 20343 |
| BaGS23N21 | CTTCAGAGCATCAATGCCTCT<br>CTTCAGAGCAGCAATGCCTCT | 20344 |
| BaGS23N21 | GCTCCCAACAATTCTAAATTC<br>GCTCCCAACAGTTCTAAATTC | 20345 |
| BaGS23N21 | TATAAGTCTTTTAAGAGATTC<br>TATAAGTCTTCTAAGAGATTC | 20346 |
| B9GS23N21 | TCTCTTAGTAGAATCTCTAGA<br>TCTCTTAGTAAAATCTCTAGA | 20347 |
| BaAK45E04 | CATTCAACGAGAGCGAAGCCA<br>CATTCAACGAAAGCGAAGCCA | 20348 |

TABLE 26-5

| Clones | Haruna Nijo H602 | SEQ ID NO: |
|---|---|---|
| bags5n23 | CCTTGGGCACCGACGCCGTCA<br>CCTTGGGCACAGACGCCGTCA | 20349 |
| bast52h1216 | CAACAGTTGTGACAAAAGAGA<br>CAACAGTTGTAACAAAAGAGA | 20350 |

TABLE 26-5-continued

| Clones | Haruna Nijo H602 | SEQ ID NO: |
|---|---|---|
| bags22f23 | TGTGTCCTTCACAAAGGAGAT<br>TGTGTCCTTCCCAAAGGAGAT | 20351 |
| bags22f23 | TCCTGTGGTTTCATACAGGCA<br>TCCTGTGGTTCCATACAGGCA | 20352 |
| bags22f23 | TATGCTAGTTCTCTCGATTGC<br>TATGCTAGTTTTCTCGATTGC | 20353 |
| BaH38E02 | ACAGAGCCGGCGGACAGAAAC<br>ACAGAGCCGGGGGACAGAAAC | 20354 |
| BaH38E02 | GATGTTCTTGTTACTCCGACG<br>GATGTTCTTGCTACTCCGACG | 20355 |
| BaH50O07 | TTCTTAAGTTTATATACATCT<br>TTCTTAAGTTAATATACATCT | 20356 |
| BaH50O07 | AAGAGGTGTCTGTTGGCAATG<br>AAGAGGTGTCCGTTGGCAATG | 20357 |
| BaH50O07 | CGAGATTGAATGAAAGTAATG<br>CGAGATTGAACGAAAGTAATG | 20358 |
| BaH50O07 | GATCAGTCTTTATTTCTATTG<br>GATCAGTCTTCATTTCTATTG | 20359 |
| kr07c1006 | GTTCATCCTTGCTTACATTAC<br>GTTCATCCTTACTTACATTAC | 20360 |
| baak26a02 | GGCAAGTTATCATAAATAATA<br>GGCAAGTTATGATAAATAATA | 20361 |
| baak2j22 | CGATGGAAACAAGCTCGCCAT<br>CGATGGAAACCAGCTCGCCAT | 20362 |
| baak2j22 | AGAACAAGGAGGCTGAGCGCT<br>AGAACAAGGAAGCTGAGCGCT | 20363 |
| bah45h23 | AAGGTTTACGTTATGCTATGC<br>AAGGTTTACGGTATGCTATGC | 20364 |
| bah45h23 | ATTGACCTTGTTCTTCTTCAG<br>ATTGACCTTGGTCTTCTTCAG | 20365 |
| bah45h23 | CTGTGCAGATAATGACTTGGC<br>CTGTGCAGATTATGACTTGGC | 20366 |
| baak46m16 | AACTATGCACACAACATATAA<br>AACTATGCACCCAACATATAA | 20367 |
| baak46m16 | TTTATTCTATAAGGCTAGATG<br>TTTATTCTATCAGGCTAGATG | 20368 |
| baak46m16 | AACAGCAGCACAACTAATCAC<br>AACAGCAGCAAAACTAATCAC | 20369 |
| bah55m23 | TCTTCTTCTTTGCCTCTCCTC<br>TCTTCTTCTTCGCCTCTCCTC | 20370 |
| bah59c05 | ACAGGTCGCTTGCGGCCCCGT<br>ACAGGTCGCTCGCGGCCCCGA | 20371 |
| basd11l17 | TGAACTTGGCATAGATGTCAG<br>TGAACTTGGCGTAGATGTCAG | 20372 |
| bah19e08 | GTCGCCGGAGTGGGAAATGCA<br>GTCGCCGGAGAGGGAAATGCA | 20373 |

TABLE 26-6

| Clones | Haruna Nijo H602 | SEQ ID NO: |
|---|---|---|
| bah19e08 | CGCTGGAGCCAAAAACGGGCT<br>CGCTGGAGCCGAAAACGGGCT | 20374 |
| BaAK21N24 | CACATAGTGAACTGAACTCTC<br>CACATAGTGAGCTGAACTCTC | 20375 |
| BaAK21N24 | AGGTGGTGGTGTCCTAAATTC<br>AGGTGGTGGTATCCTAAATTC | 20376 |
| BaAK21N24 | GAAATAGAGCATACATGCAGA<br>GAAATAGAGCTTACATGCAGA | 20377 |
| bah50e09 | AATTATTTATCTACGAGAGAT<br>AATTATTTATTTACGAGAGAT | 20378 |
| baak17p18 | TCTCCATTTCCCATCACAACC<br>TCTCCATTTCTCATCACAACC | 20379 |
| baak17p18 | AAGCAATCATTACCATGATAA<br>AAGCAATCATGACCATGATAA | 20380 |
| baal7a04 | TCTGTCACGCAGCCAAGGCAC<br>TCTGTCACGCGGCCAAGGCAC | 20381 |
| bast47b0303 | GATGACCATTCCAAACTTCTC<br>GATGACCATTGCAAACTTCTC | 20382 |
| bah28o17 | TCTGAAGCTCGATCTTCCCG<br>TCTGAAGCTCAATCTTCCCG | 20383 |
| bah37k03 | ATCTCTCTCAGTTTTCCTCCA<br>ATCTCTCTCAATTTTCCTCCA | 20384 |
| bah37k03 | TGTTTGCCGGTTCAGCTTTGT<br>TGTTTGCCGGGTCAGCTTTGT | 20385 |
| bastl38A0501 | CAGCCAAAGCACAGCTCACCA<br>CAGCCAAAGCGCAGCTCACCA | 20386 |
| bags23c03 | GTATACAACTATAAGCACGCA<br>GTATACAACTTTAAGCACGCA | 20387 |
| basd13j01 | GTTTTCTGACGGTAGTTGATG<br>GTTTTCTGACAGTAGTTGATG | 20388 |
| basd13j01 | CATGGTTATCTCTGTAGTCGC<br>CATGGTTATCCCTGTAGTCGC | 20389 |
| bags21c02 | GTATTGAGCAGAGAGAGGTGG<br>GTATTGAGCACAGAGAGGTGG | 20390 |
| bags21c02 | GCATCATGGCAACCATAGAAA<br>GCATCATGGCGACCATAGAAA | 20391 |
| bags6k10 | ATATAGATGTGTATGCATGTA<br>ATATAGATGTATATGCATGTA | 20394 |
| bags9k18 | TCATATGGCAGCTCTGTGAGG<br>TCATATGGCAACTCTGTGAGG | 20395 |
| bags9k18 | TTTCCTCATCACACACGACGT<br>TTTCCTCATCGCACACGACGT | 20396 |
| bags9k18 | TGCATACCGAAGGTGGAAGCT<br>TGCATAGCGACGGTGGAAGCT | 20397 |
| baal18c19 | AAAGGGTAC-GTTTGATGTA<br>AAAGGGTACCGTTTGATGTA | 20398<br>20399 |
| baal18c19 | AGGATCTTGGNTATAACCTCT<br>AGGATCTTGGTTATAACCTCT | 20400 |
| baal18c19 | GTGCAATGCA-TTTCTACAAA<br>GTGCAATGCAATTTCTACAAA | 20401<br>20402 |

TABLE 26-7

| Clones | Haruna Nijo H602 | SEQ ID NO: |
|---|---|---|
| baak27p14 | AATATATATATGTTATTAGTC<br>AATATATATACGTTATTAGTC | 20403 |
| baak27p14 | AGCATATATTCGAAAGATGAC<br>AGCATATATTTGAAAGATGAC | 20404 |
| baak27p14 | CTTGCTTAGGNGGCATCTATG<br>CTTGCTTAGGTGGCATCTATG | 20405 |
| baak27p14 | GATAGTCTAAAAGATGCATGA<br>GATAGTCTAANAGATGCATGA | 20406 |
| bags30n21 | ACTGGAAATCGACAATGATAT<br>ACTGGAAATCCACAATGATAT | 20407 |
| bah55p23 | TGTTTACATCATAGATTCAGT<br>TGTTTACATCGTAGATTCAGT | 20408 |
| bah55p23 | AGGCTAGCGCAGCTGGAGGCA<br>AGGCTAGCGCGGCTGGAGGCA | 20409 |
| bah54p22 | ACCCAGAACCGAACCAAAACT<br>ACCCAGAACCAAACCAAAACT | 20410 |
| bah54p22 | GTCCAGTACCGTACTCTTCAA<br>GTCCAGTACCATACTCTTCAA | 20411 |
| bags34f05 | AGTGATGCCTCCTGAGACGCA<br>AGTGATGCCTACTGAGACGCA | 20412 |
| bags34f05 | CGCCTACGTCAGGCAGGCCTA<br>CGCCTACGTCGGGCAGGCCTA | 20413 |
| bah14a24 | ACGAAATGAGCCGCCACAGAA<br>ACGAAATGAGACGCCACAGAA | 20416 |
| bah50j11 | ATATTTTCCACTATGTGTTAT<br>ATATTTTCCAATATGTGTTAT | 20417 |
| basd22l21 | GAGGCGGGATTTTGATGTCAA<br>GAGGCGGGATGTTGATGTCAA | 20424 |
| basd22l21 | TATTTCCAAGCGTCCTTAGTT<br>TATTTCCAAGTGTCCTTAGTT | 20425 |
| kr27e0909 | TAACTTGTGAGTCGAGCCATT<br>TAACTAGTGACTCGAGCCATT | 20426 |
| bastl41H0216 | TGGCTTTATCAACTTTCTCGC<br>TGGCTTTATCGACTTTCTCGC | 20427 |
| baak36o17 | TGCTCTTGCAGAAGTGTGGGG<br>TGCTCTTGCANAAGTGTGGGG | 20428 |
| BaH31P15 | AAACAGAATTAAAGGACACAC<br>AAACAGAATTGAAGGACACAC | 20429 |
| bags9h03 | ACAAAGTCCGTCGCAGAGCTT<br>ACAAAGTCCGCCGCAGAGCTT | 20431 |
| basd26d07 | TCAGTGAGCTTTTTATGCCTT<br>TCAGTGAGCTGTTTATGCCTT | 20442 |
| bah21h17 | TAACTGGGATCCGTTTAGTTT<br>TAACTGGGATTCGTTTAGTTT | 20444 |
| bags5d21 | GCTGATGAAAAATAGACAGTA<br>GCTGATGAAAGATAGACAGTA | 20445 |
| baak34d14 | GATTCGTTCTGCTGAACTCGT<br>GATTCGTTCTCCTCAACTCGT | 20446 |
| baak18a16 | GTCTGCACACAACTTACAAAG<br>GTCTGCACACGACTTACAAAG | 20447 |

TABLE 26-8

| Clones | Haruna Nijo H602 | SEQ ID NO: |
|---|---|---|
| baak18a16 | TTCACCTTGAGTTCTTCGAAC<br>TTCACCTTGAATTCTTCGAAC | 20448 |
| bags4b01 | CATTTCTACGCCGCCTTGTTA<br>CATTTCTACGTCGCCTTGTTA | 20449 |
| bags4b01 | TGTTATGTGGCGAAATAGATG<br>TGTTATGTGGTGAAATAGATG | 20450 |
| bags38c19 | AGTTAAATTTCTGTGCACAGG<br>AGTTAAATTTTTGTGCACAGG | 20451 |
| bags38c19 | CGCTGTGGGATCAGTTAAATT<br>CGCTGTGGGAGCAGTTAAATT | 20452 |
| bags38c19 | GCCAAGAGTGACACTCGACAA<br>GCCAAGAGTGGCACTCGACAA | 20453 |
| bags38c19 | GCTATATTGGTGCTGACTATC<br>GCTATATTGGGGCTGACTATC | 20454 |
| kr42d0208 | CAAAGTAAGCGGCTGAATATT<br>CAAAGTAAGCCGCTGAATATT | 20456 |
| BaAK35N11 | CCCATGACCGATACGACTGGG<br>CCCATGACCGGTACGACTGGG | 20460 |
| bags26n10 | CCACCTATGAGTCGAATCTTC<br>CCACCTATGAATCGAATCTTC | 20461 |
| bags37n02 | GCCATAACCTTTATTATGGAC<br>GCCATAACCTCTATTATGGAC | 20462 |
| bags37n02 | CAGAAGAAGCGGTGGTTTCTC<br>CAGAAGAAGCAGTGGTTTCTC | 20463 |
| bags37n02 | CTATAGCATATTAGCCAGACC<br>CTATAGCATAGTAGCCAGACC | 20464 |
| baak26l11 | TATACCTGTGCTAGATGTGTG<br>TATACCTGTGGTAGATGTGTG | 20465 |
| BaH57C19 | CAACTACCTTCCTGTCAAGCC<br>CAACTACCTTTCTGTCAAGCC | 20466 |
| bags7a01 | GGCGCCTCCCGCTGCACCTCG<br>GGCGCCTCCCACTGCACCTCG | 20467 |
| bah19l15 | CACATGAAGCTGTGGGCACGT<br>CACATGAAGCCGTGGGCACGT | 20468 |
| baal4o02 | TATTCTTTCAACCTTACATCT<br>TATTCTTTCAGCCTTACATCT | 20469 |
| baal4o02 | AGCACCGCACACCAATGTTAC<br>AGCACCGCACGCCAATGTTAC | 20470 |
| baal4o02 | CAAGGTAGCTCTCAGTGCTGG<br>CAAGGTAGCTTTCAGTGCTGG | 20471 |
| baal4o02 | ATTAAGCTGATAGGTCTGACT<br>ATTAAGCTGAAAGGTCTGACT | 20472 |
| bah58a12 | TGGTAGAGACGAATCACATCG<br>TGGTAGAGACAAATCACATCG | 20473 |
| bah58a12 | TGGTAAATTCGTCAAGATTCA<br>TGGTAAATTCATCAAGATTCA | 20474 |
| bah58a12 | TCTGAGAAAGTCCGTCATCTT<br>TCTGAGAAAGCCCGTCATCTT | 20475 |
| bah58a12 | AAGTGTCGAAGCTGTCTTCCC<br>AAGTGTCGAATCTGTCTTCCC | 20476 |

TABLE 26-9

| Clones | Haruna Nijo / H602 | SEQ ID NO: |
|---|---|---|
| bah11b08 | CCGTTTGTACCTGTGGTGCAA<br>CCGTTTGTACTTGTGGTGCAA | 20477 |
| bah11b08 | TCTTGTATAAGCAATGGGCTA<br>TCTTGTATAAACAATGGGCTA | 20478 |
| bah11b08 | GTCTCGCCATTATGTGCAGTT<br>GTCTCGCCATGATGTGCAGTT | 20479 |
| bah11b08 | ATCCTCATGATTTCTTCATAG<br>ATCCTCATGAATTCTTCATAG | 20480 |
| bags14m15 | ACTGCATGCAAGTACATCATG<br>ACTGCATGCATGTACATCATG | 20481 |
| bags14m15 | CGACGTTACGTTGTAGAACTG<br>CGACGTTACGGTGTAGAACTG | 20482 |
| bags14m15 | CAACCTCTGAAATGGGTCCTG<br>CAACCTCTGACATGGGTCCTG | 20483 |
| bags14m15 | TTCAAACCGGGAACCTTGAAA<br>TTCAAACCGGAAACCTTGAAA | 20484 |
| bast104b1103 | GCGTTCCCAGTCACGAGTTTC<br>GCGTTCCCAGCCACGAGTTTC | 20486 |
| bags13g08 | CCAAATGCTTGATATGAGCTT<br>CCAAATGCTTCATATGAGCTT | 20487 |
| bags13g08 | ATGCCGATCCAAAAGGGACAC<br>ATGCCGATCCGAAAGGGACAC | 20488 |
| bags13g08 | AAAGGGACACCAAGCAGGCAA<br>AAAGGGACACGAAGCAGGCAA | 20489 |
| basd27p03 | GTGGAGGAACTTACAACCTGG<br>GTGGAGGAACCTACAACCTGG | 20490 |
| basd27p03 | AGAAATACCCATTTCTGGCAA<br>AGAAATACCCGTTTCTGGCAA | 20491 |
| basd27p03 | CTGCACGCTAGGTGGAGGAAC<br>CTGCACGCTAAGTGGAGGAAC | 20492 |
| bast38D0707 | TTTAGGGGATCGGTTAGAGTT<br>TTTAGGGGATTGGTTAGAGTT | 20493 |
| bast38D0707 | CACCGTATATGCTGGTATTTC<br>CACCGTATATCCTGGTATTTC | 20494 |
| baal19k05 | TGAATCAACTGCAAATCTGAG<br>TGAATGAACTCCAAATCTGAG | 20496 |
| baal19k05 | TGTTGCAGGCAAAGTAAACCT<br>TGTTGCAGGCGAAGTAAACCT | 20497 |
| baal19k05 | CATGGTGCCACAAACAAGTAT<br>CATGGTGCCATAAACAAGTAT | 20498 |
| baal19k05 | TTACACGAAGTATAGCTTCAT<br>TTACACGAAGAATAGCTTCAT | 20499 |
| baal19k05 | TGAAGCAAGTATGAGATTGTC<br>TGAAGCAAGTTTGAGATTGTC | 20500 |
| BaH19C21 | CACAATGATGTGATCTGCTAA<br>CACAATGATGCGATCTGCTAA | 20501 |
| bah49g10 | GTCTAGAGTGGAGAAATACCA<br>GTGTAGAGTGAAGAAATACCA | 20502 |
| bah49g10 | CCGTAAGCCATACTTGCAAAT<br>CCGTAAGCCAAACTTGCAAAT | 20503 |

TABLE 26-10

| Clones | Haruna Nijo / H602 | SEQ ID NO: |
|---|---|---|
| bah49g10 | GCTTGAATTTGAGGAGAGCAG<br>GCTTGAATTTAAGGAGAGCAG | 20504 |
| bah49g10 | AAGCAAGCCGTTAACACAAT<br>AAGCAAGCCGGTAACACAAT | 20505 |
| bah49g10 | TCGTGAGATCGCTGGATCTCT<br>TCGTGAGATCCCTGGATCTCT | 20506 |
| bah49g10 | CATCTTGCAATGTGCGTGCCC<br>CATCTTGCAACGTGCGTGCCC | 20507 |
| bags23g18 | AGAGCCTTGCGCAGTGCCTCC<br>AGAGCCTTGCACAGTGCCTCC | 20509 |
| bags23g18 | TTGTAATGATTTACAATTTTG<br>TTGTAATGATGTACAATTTTG | 20510 |
| bags23g18 | TTTTGCACATCTGATTGCATC<br>TTTTGCACATTTGATTGCATC | 20511 |
| bags22o22 | TGCACTATACAGTAAAAGCCA<br>TGCACTATACGGTAAAAGCCA | 20512 |
| bags22o22 | GTGTACAACTACTCCCATCAT<br>GTGTACAACTGCTCCCATCAT | 20513 |
| bags22o22 | AACACACATTGTTTTATTCGA<br>AACACACATTTTTTTATTCGA | 20514 |
| bags22o22 | ACTTCTTAGAGGGAATGTCTT<br>ACTTCTTAGAAGGAATGTCTT | 20515 |
| baal20a03 | CTGGTCGCAAGCGGCGCTATA<br>CTGGTCGCAAACGGCGCTATA | 20516 |
| baal20a03 | GTGTTGGCACAGGCAGCGGCA<br>GTGTTGGCACCGGCAGCGGCA | 20517 |
| bags5e24 | GAAATGTTTTCGTCACTATT<br>GAAATGTTTTCCGTCACTATT | 20518 |
| bags5e24 | GTAGGCCAGCAGCTGCTTCTG<br>GTAGGCCAGCGGCTGCTTCTG | 20519 |
| bags5e24 | CCTGTTTGTAAGATAACTAGG<br>CCTGTTTGTAGGATAACTAGG | 20520 |
| bags5f11 | TACCTGGCTTAATGATCTCAG<br>TACCTGGCTTCATGATCTCAG | 20521 |
| bags5f11 | TGCCCTCGTCGGCGTTAATCA<br>TGCCCTCGTCAGCGTTAATCA | 20522 |
| bags5f11 | TGCTGTCCGTCACCCCCAAA<br>TGCTGTCCGCCACCCCCAAA | 20523 |
| BaAK33B10 | GAAAAAAGAATATGGCAGCC<br>GAAAAAAGAGTATGGCAGCC | 20524 |
| BaAK33B10 | GCAATCTTACAAACAAAATCA<br>GCAATCTTACTAACAAAATCA | 20525 |
| BaAK33B10 | AGAAATAGGTACTTCGATTAT<br>AGAAATAGGTCCTTCGATTAT | 20526 |
| BaAK33B10 | GATGTATGAAGAACCTTGGTA<br>GATGTATGAAAAACCTTGGTA | 20527 |
| BaAK33B10 | GTACGGACTATAACGTTGCGC<br>GTACGGACTAAAACGTTGCGC | 20528 |
| BaAK33B10 | GCTTCTAGTTCTGTTGGTGAG<br>GCTTCTAGTTTTGTTGGTGAG | 20529 |

TABLE 26-11

| Clones | Haruna Nijo H602 | SEQ ID NO: |
|---|---|---|
| BaAK33B10 | GTCAATATGATAGAAATAGGT<br>GTCAATATGAGAGCAATAGGT | 20530 |
| BaAK33B10 | AGGCATGCCACACTGGAGTAT<br>AGGCATGCCAAACTGGAGTAT | 20531 |
| baal39j02 | AGAGAGCATGGACAGGCATCG<br>AGAGAGCATGAACAGGCATCG | 20537 |
| BaSD27H14 | ATGTCCGCGGTGTCGTCCAGG<br>ATGTCCGCGGGGTCGTCCAGG | 20538 |
| BaSD27H14 | CGAAGACCTTTGCCTCAGGGT<br>CGAAGACCTTCGCCTCAGGGT | 20539 |
| bah50m01 | GGATGGACTACCTCAACCCGG<br>GGATGGACTATCTCAACCCGG | 20540 |
| BaSD24E13 | GGGGATCTTTCACCACAAACT<br>GGGGATCTTTTACCACAAACT | 20541 |
| bah28k24 | CATAGACGATTCAATATTAGA<br>CATAGACGATACAATATTAGA | 20546 |
| bah28k24 | ACACAACACCCGAGTGCACAC<br>ACACAACACCTGAGTGCACAC | 20547 |
| bah47c11 | GACAGTTGTTTCATTAGAATT<br>GACAGTTGTTCCATTAGAATT | 20548 |
| bah47c11 | TTAGGGCAGACAGTATGGTTG<br>TTAGGGCAGAAAGTATGGTTG | 20549 |
| basd26m15 | GGCATGCCACGATCCACATAT<br>GGCATGCCACAATCCACATAT | 20550 |
| basd26m15 | CTTAATAATAAGGCATGCATC<br>CTTAATAATACGGCATGCATC | 20551 |
| bah60o02 | CAAAAATGTTTGAGCTCCGTC<br>CAAAAATGTTGGAGCTCCGTC | 20552 |
| bah60o02 | CGTCAGCGATTAGGATTTCAT<br>CGTCAGCGATAAGGATTTCAT | 20553 |
| bah60o02 | GTACTGTATATTGTCACCGTA<br>GTACTGTATACTGTCACCGTA | 20554 |
| bah50g06 | GGGGGGATTTGTGGICCTGATG<br>GGGGGGATTTCTGGCCTGATG | 20555 |
| bast15g0913 | AGTACATCAGCAGCTAAAGCA<br>AGTACATCAGTAGCTAAAGCA | 20556 |
| baal10n23 | GACAGAAATGGTCGAACCTGT<br>GACAGAAATGATCGAACCTGT | 20557 |
| baal10n23 | TGACAAAGCATACAGCACTCC<br>TGACAAAGCAAACAGCACTCC | 20558 |
| baal10n23 | TATCACAGCCGAAATGAGCCC<br>TATCACAGCCAAAATGAGCCC | 20559 |
| bags20c12 | TATCAGACTTCTAATTTCTAC<br>TATCAGACTTTTAATTTCTAC | 20560 |
| basd16f13 | CCCGGGCGTCGGGGACTATCT<br>CCCGGGCGTCCGGGACTATCT | 20561 |
| bags22p08 | TGGCATTAGATGAGAAAAGA<br>TGGCATTAGACGAGAAAAGA | 20564 |
| BaH23N06 | AGATGGAGGCCAGCAGCACGG<br>AGATGGAGGCTAGCAGCACGG | 20565 |

TABLE 26-12

| Clones | Haruna Nijo H602 | SEQ ID NO: |
|---|---|---|
| bags29c08 | AATGAAGCCGACTCAAGCACT<br>AATGAAGCCGGCTCAAGCACT | 20566 |
| bags29c08 | ATCAGCGCCCCTTCTTCTACC<br>ATCAGCGCCCTTTCTTCTACC | 20567 |
| bags11o23 | GGTCAACTAGCTTCGTGTTCC<br>GGTCAACTAGGTTCGTGTTCC | 20568 |
| baal18j13 | ACATTGCTTCTTTACCCATGA<br>ACATTGCTTCCTTACCCATGA | 20571 |
| baal18j13 | ACCTCTCTCAGGCCCAAGCTC<br>ACCTCTCTCAAGCCCAAGCTC | 20572 |
| baal18j13 | TAAGTACTCCCTCCATCCCAA<br>TAAGTACTCCATCCATCCCAA | 20573 |
| baal18j13 | TAAAGGGTTATTTCCATTGAC<br>TAAAGGGTTAATTCCATTGAC | 20574 |
| baal18ji3 | ATGAAGGCCAGCAACGGGCAA<br>ATGAAGGCCAACAACGGGCAA | 20575 |
| baal18j13 | TTAAGTGACTCAACTTTGTAC<br>TTAAGTGACTGAACTTTGTAC | 20576 |
| bah15m02 | ACTTCTTCACAATGCAGTTCC<br>ACTTCTTCACGATGCAGTTCC | 20577 |
| kr68b1103 | CCCTTTCGTTTTGACTTCCCT<br>CCCTTTCGTTATGACTTCCCT | 20580 |
| kr68b1103 | GAGCAAGGTATGTGTTTCCAC<br>GAGCAAGGTACGTGTTTCCAC | 20581 |
| bags15b10 | ACACTATACTCTGCAATCTGA<br>ACACTATACTTTGCAATCTGA | 20583 |
| bags20h21 | GAGCAATTCAGAGACCACAGA<br>GAGCAATTCAAAGACCACAGA | 20584 |
| BaAK29K06 | GCTGGGTGCAGGGAGTGATGA<br>GCTGGGTGCATGGAGTGATGA | 20585 |
| BaAK29K06 | TGTAGATAGCATGGACATGAG<br>TGTAGATAGCCTGGACATGAG | 20586 |
| BaAK29K06 | TTGTGGTTATGGAGATGGTGG<br>TTGTGGTTATAGAGATGGTGG | 20587 |
| BaAK29K06 | ATGACATGAAGAGGAGCAATT<br>ATGACATGAATAGGAGCAATT | 20588 |
| BaAK29K06 | CTAGGAAAATAAATGGGAAC<br>CTAGGAAAATGAATGGGAAC | 20589 |
| bah56j14 | CTTCATGCCTGTGACATCTTT<br>CTTCATGCCTATGACATCTTT | 20591 |
| bah56j14 | TTGCCATCCAGCCTGCAGGGT<br>TTGCCATCCATCCTGCAGGGT | 20592 |
| bah56j14 | CTGCAGCTGTCTTGTCCTGTT<br>CTGCAGCTGTTTTGTCCTGTT | 20593 |
| bags3j24 | CGTGGGGGTCAGCCGGCATGA<br>CGTGGGGGTCGGCCGGCATGA | 20595 |
| bags38m08 | AGACTTTACTTTGGTAGTAAT<br>AGACTTACTCTGGTAGTAAT | 20596 |
| bags35g06 | GTCTCTCCATCAACCTCAATG<br>GTCTCTCCATTAACCTCAATG | 20598 |

TABLE 26-13

| Clones | Haruna Nijo H602 | SEQ ID NO: |
|---|---|---|
| bags35g06 | GATCCCAGGCATGGAAGTTGT<br>GATCCCAGGCTTGGAAGTTGT | 20599 |
| bags37b01 | GAACTGCCTCTGAGCTCTTTA<br>GAACTGCCTCAGAGCTCTTTA | 20600 |
| bags37b01 | GGTCGCCGTCATCAGGTGTTG<br>GGTCGCCGTCGTCAGGTGTTG | 20601 |
| BaAL19F02 | CCAAGCAACAGTTATCTCCAC<br>CCAAGCAACATTTATCTCCAC | 20602 |
| BaAL19F02 | TCAAAACCTTCCTGACTTATG<br>TCAAAACCTTTCTGACTTATG | 20603 |
| BaAL19F02 | TGCTGAATTTGCTTGGAAAGA<br>TGCTGAATTTACTTGGAAAGA | 20604 |
| BaAL19F02 | TTTACAGATAGAACTTGCCTC<br>TTTACAGATACAACTTGCCTC | 20605 |
| BaAL19F02 | CTAGCCTTCCTCCTGATTTTA<br>CTAGCCTTCCACCTGATTTTA | 20606 |
| baal4d09 | ATTGTACCAAATTGGGTAAGT<br>ATTGTACCAAGTTGGGTAAGT | 20607 |
| bags27f15 | CCAGCAGTTACATATGACATG<br>CCAGCAGTTATATATGACATG | 20610 |
| bags27f15 | ATCATGCTAGCCATTTTGGGC<br>ATCATGCTAGTCATTTTGGGC | 20611 |
| bags10k14 | ACCACAAAATGGATTTATGTT<br>ACCACAAAATTGATTTATGTT | 20612 |
| bags10k14 | AGTTTGATAGTTCACTGGCTA<br>AGTTTGATAGATCACTGGCTA | 20613 |
| baak38n21 | CGATAGTGGACGGCCGGAAGA<br>CGATAGTGGATGGCCGGAAGA | 20615 |
| baak38n21 | ACATTGTCAATCTCCAGGCCT<br>ACATTGTCAACCTCCAGGCCT | 20616 |
| baak38n21 | TTCAAGTTGCAAAGCAAGCCG<br>TTCAAGTTGCGAAGCAAGCCG | 20617 |
| baak38n21 | TCCAGCCAGGAAAAACACCGTT<br>TCCAGCCAGGGAAAACACCGTT | 20618 |
| baale38n21 | ACTTATTCATTGTGGATACGT<br>ACTTATTCATCGTGGATACGT | 20619 |
| baak30e05 | GGTCTGAATTGTGGGCAGGCA<br>GGTCTGAATT-TGGGCAGGCA | 20620<br>20621 |
| bastl04a0101 | TACGACGACGGGCAGCCTTGG<br>TACGACGACGCGCAGCCTTGG | 20622 |
| baak28p18 | ATAGGCTTTTCTCCTGCCCAA<br>ATAGGCTTTTGTCCTGCCCAA | 20623 |
| BaGS34E01 | AAGACGGGCAAAACAAGAGGT<br>AAGACGGGCAGAACAAGAGGT | 20624 |
| BaH54H04 | AGTCTTGATATGATGAAACTT<br>AGTCTTGATACGATGAAACTT | 20625 |
| bah13o19 | TTGGTATTAGGGTTTCAAAAA<br>TTGGTATTAGAGTTTCAAAAA | 20626 |
| baht3o19 | AAATTCCCCAGTGGGAAAACA<br>AAATTCCCCAATGGGAAAACA | 20627 |

TABLE 26-14

| Clones | Haruna Nijo H602 | SEQ ID NO: |
|---|---|---|
| BaSD27A15 | AGCAACTCCAGCATAGCGTTT<br>AGCAACTCCAACATAGCGTTT | 20631 |
| BaSD27A15 | CTAATATAATCTGGTGCGCAG<br>CTAATATAATTTGGTGCGCAG | 20632 |
| BaSD27A15 | AATGCCCTCGCCTTCCAGCCC<br>AATGCCCTCGGCTTCCAGCCC | 20633 |
| BaSD27A15 | TGCTGTCCAGGAGCGTCTCCT<br>TGCTGTCCAGTAGCGTCTCCT | 20634 |
| BaSD27A15 | CCATCCTGCAAAATTCCTGTC<br>CCATCCTGCAGAATTCCTGTC | 20635 |
| BaSD27A15 | CGGTAATAATTGATGCTGTCC<br>CGGTAATAATCGATGCTGTCC | 20636 |
| BaSD27A15 | GCGTGGTAGGCGAGTTCTGAT<br>GCGTGGTAGGAGAGTTCTGAT | 20637 |
| bags9n02 | AGCACATACAGACCCCTCGGA<br>AGCACATACATACCCCTCGGA | 20639 |
| bastl30A0202 | CTGAGTGCAATAAACATAACA<br>CTGAGTGCAAGAAACATAACA | 20642 |
| bastl30A0202 | TGGAAGAAAATACAACAAAAT<br>TGGAAGAAAAAACAACAAAAT | 20643 |
| bastl30A0202 | TGGACGAACGTAACTGCGGCG<br>TGGACGAACGCAACTGCGGCG | 20644 |
| bags22k12 | CACTTTGGACCCTAAATGCCC<br>CACTTTGGACACTAAATGCCC | 20646 |
| bags22k12 | ACATTAATACGATGATCAGCT<br>ACATTAATACTATGATCAGCT | 20647 |
| bags22k12 | CGAAATCACAGGATAGATGAA<br>CGAAATCACATGATAGATGAA | 20640 |
| baak13g12 | GGACGGGTACATCTTCCTCAG<br>GGACGGGTACTTCTTCCTCAG | 20649 |
| baak13g12 | CGGCGGCTCCGAACACGGAGC<br>CGGCGGCTCCAAACACGGAGC | 20650 |
| baak13g12 | CGACGCGGCCGCGTCGATGGT<br>CGACGCGGCCACGTCGATGGT | 20651 |
| bags17j17 | AGGTCTTTGCATCACGCCTGG<br>AGGTCTTTGC-TCACGCCTGG | 20654<br>20655 |
| bags17j17 | CGTCTTTGTAGAAGGCACAGC<br>CGTCTTTGTA-AAGGCACAGC | 20656<br>20657 |
| baal12j15 | TACTAACTTCTTACATGGCAA<br>TACTAACTTCCTACATGGCAA | 20658 |
| baal12j15 | ATGGCAATCTCCAAGCAGTGT<br>ATGGCAATCTTCAAGCAGTGT | 20659 |
| baal12j15 | AAAGGGGCGGCGGGTTGACA<br>AAAGGGGCGGACGGGTTGACA | 20660 |
| bah34j11 | CTTCTCTCCGAAGGGCGTCAA<br>CTTCTCTCCGGAGGGCGTCAA | 20662 |
| bah34j11 | CTGATGATGTCTTGGCAAGGA<br>CTGATGATGTTTTGGCAAGGA | 20663 |
| BaGS30I11 | GGAGTGCCTCTGGTACCTCGT<br>GGAGTGCCTCCGGTACCTCGT | 20664 |

TABLE 26-15

| Clones | Haruna Nijo H602 | SEQ ID NO: |
|---|---|---|
| BaGS30I11 | CCATCCTCCTCTTCGTGGCT<br>CCATCCTCCTATTCGTGGCT | 20665 |
| BaGS30I11 | TCTACCGAGAGGAATGGATCG<br>TCTACCGAGACGAATGGATCG | 20666 |
| baal18m24 | CTGCAGCCCCCTGCCTNCAGA<br>CTGCAGCCCC-TGCCTNCAGA | 20668<br>20669 |
| baal18m24 | TGCTCCAGCGGCTTGACCACC<br>TGCTCCAGCGNCTTGACCACC | 20670 |
| baal18m24 | TTGAGCTTGGCCACCTCGATG<br>TTGAGCTTGGGCACCTCGATG | 20671 |
| baak15l06 | TGCGGGAGGCACGCGTGAGGA<br>TGCGGGAGGCGCGCGTGAGGA | 20672 |
| baak15l06 | CATTATTCTTATCATCAAATC<br>CATTATTCTTTTCATCAAATC | 20673 |
| bald18o14 | GATGCTTCTCTCCTGGCTGTA<br>GATGCTTCTCACCTGGCTGTA | 20674 |
| bald18o14 | ATGGGTTGGCAAGCAATCTTT<br>ATGGGTTGGCGAGCAATCTTT | 20675 |
| bags24p22 | GCATTTGGTGGCATTGAGCTG<br>GCATTTGGTGACATTGAGCTG | 20676 |
| bags24p22 | GCACTCCTATGACAGCACACA<br>GCACTCCTATCACAGCACACA | 20677 |
| bags24p22 | GGAGAAGAACAACAAAAAGCA<br>GGAGAAGAACGACAAAAAGCA | 20678 |
| baal37a09 | TGTTGCTGTTAGTTTCAGAGC<br>TGTTGCTGTTGGTTTCAGAGC | 20679 |
| bags5l01 | TTTAGGTCAACAATCATCTAA<br>TTTAGGTCAATAATCATCTAA | 20680 |
| bags5l01 | TCTGCTTTTCGAAGAGATGGT<br>TCTGCTTTTCAAAGAGATGGT | 20681 |
| BaAK12P03 | GGCATGCGACGTCACTCCCGT<br>GGCATGCGACATCACTCCCGT | 20682 |
| BaAK12P03 | CCACCAGCTGCTTTCCGACGT<br>CCACCAGCTGTTTTCCGACGT | 20683 |
| baak21 f10 | CGGAAAATGCAGGANCNAGGA<br>CGGAAAATGCNGGANCNAGGA | 20684 |
| bastl30e0410 | ATGGAAATTCTCCCACATCTT<br>ATGGAAATTCGCCCACATCTT | 20685 |
| kr25c0206 | CAATGGCGAAGACTCTGCCAT<br>CAATGGCGAAAACTCTGCCAT | 20686 |
| kr25c0206 | AAAAAGCTGATAAAGCGCCAG<br>AAAAAGCTGACAAAGCGCCAG | 20687 |
| bah54n06 | TTTCCCAAAAGAAACGCCAAA<br>TTTCCCAAAACAAACGCCAAA | 20690 |
| bast22F0311 | ATGAAATGACCTGACCAGCTA<br>ATGAAATGACGTGACCAGCTA | 20692 |
| bast22F0311 | ACTGCAATCGATAGTACTACA<br>ACTGCAATCGGTAGTACTACA | 20693 |
| bast22F0311 | TCGGAGGCTCATCAGATCAGA<br>TCGGAGGCTCGTCAGATCAGA | 20694 |

TABLE 26-16

| Clones | Haruna Nijo H602 | SEQ ID NO: |
|---|---|---|
| basd1 m04 | CGCATCTTCCACACGGCGGAA<br>CGCATCTTCCGCACGGCGGAA | 20695 |
| basd1 m04 | AGTAGAGTGCAAAGTCCTCGC<br>AGTAGAGTGCCAAGTCCTCGC | 20696 |
| basd1 m04 | TTTCTTACTCCTATGTCGGTG<br>TTTCTTACTCATATGTCGGTG | 20697 |
| baak41 d01 | GATAGTTACT-TCTGTTATAG<br>GATAGTTACTGTCTGTTATAG | 20699<br>20700 |
| baak41 d01 | TCTTANGAGCAAATATCTTCA<br>TCTTANGAGCNAATATCTTCA | 20701 |
| baak41 d01 | TTTGGCTATGGTCCACTCCAT<br>TTTGGCTATGATCCACTCCAT | 20702 |
| baak13j10 | TGTTATACACGCGACAAAGAA<br>TGTTATACACGCGACAAAGAA | 20704 |
| baak44h11 | AACTGTAATCGGAGAGATGCA<br>AACTGTAATCAGAGAGATGCA | 20705 |
| baal19j09 | GAAAGTCAGANGAGACCATCA<br>GAAAGTCAGAGGAGACCATCA | 20706 |
| baal19j09 | GGTTCTTGGCAGACTCCGGAC<br>GGTTCTTGGC-GACTCCGGAC | 20707<br>20708 |
| baet37C1105 | ATGCTTGTTATTGAAGCTAGA<br>ATGCTTGTTACTGAAGCTAGA | 20709 |
| baet37C1105 | CCTCCCTGTCGACCGGCATGT<br>CCTCCCTGTCTACCGGCATGT | 20710 |
| basd23f10 | AAAGGAACTGCTACGGCGTCA<br>AAAGGAACTGTTACGGCGTCA | 20712 |
| basd23f10 | TCCAGTATGGTCGGTACTTGG<br>TCCAGTATGGGCGGTACTTGG | 20713 |
| bah41 p07 | TGAGAACCTCGACGATCTCGC<br>TGAGAACCTCAACGATCTCGC | 20714 |
| bah41 p07 | CCACAGAGGCTACCTCGGTCT<br>CCACAGAGGCCACCTCGGTCT | 20715 |
| baak1g13 | TACACTCTAAAGATGTCTACT<br>TACACTCTAAGGATGTCTACT | 20716 |
| baak1g13 | CCGCAATTGAGATAGGGCTCC<br>CCGCAATTGAAATAGGGCTCC | 20717 |
| baak1g13 | ATAAATGTGCACTAGGAAATT<br>ATAAATGTGCGCTAGGAAATT | 20718 |
| baak1g13 | TGCGACTCGGTTCCTATGGTG<br>TGCGACTCGGCTCCTATGGTG | 20719 |
| baak1g13 | AGTTATGTGACAAGAAAAGGA<br>AGTTATGTGAGAAGAAAAGGA | 20720 |
| baak1g13 | AGTGCTCACAACAACTCTCCG<br>AGTGCTCACATCAACTCTCCG | 20721 |
| bags22l14 | GCTCACTCTCACGCCAAGCT<br>GCTCACTCTCGCGCCAAGCT | 20723 |
| bags22l14 | TCAAGAAGCAAAGCGGAAGTA<br>TCAAGAAGCAGAGCGGAAGTA | 20724 |
| bags22l14 | TCTTCTTCCCGGGGACGTGGA<br>TCTTCTTCCCAGGGACGTGGA | 20725 |

TABLE 26-17

| Clones | Haruna Nijo H602 | SEQ ID NO: |
|---|---|---|
| bags22114 | ATGAACAGCATACTCATCACA<br>ATGAACAGCA<u>A</u>ACTCATCACA | 20726 |
| bast26E1210 | AGCTCCTGCC<u>A</u>CATTATTGCC<br>AGCTCCTGCC<u>G</u>CATTATTGCC | 20727 |
| baet25f0911 | ACTTGCCGGGG<u>A</u>CGAAGTTGG<br>ACTTGCCGGGG<u>A</u>ACGAAGTTGG | 20728 |
| baet25f0911 | TGGTGGCGAA<u>G</u>GCCCAGGCGT<br>TGGTGGCGAA<u>A</u>GCCCAGGCGT | 20729 |
| BaAK32N13 | TCACATGCAA<u>C</u>ATCTATCAGT<br>TCACATGCAA<u>A</u>ATCTATCAGT | 20730 |
| BaAK32N13 | ACTTGCCGGG<u>G</u>ACGAAGTTGG<br>ACTTGCCGGG<u>A</u>ACGAAGTTGG | 20731 |
| BaAK32N13 | TGGTGGCGAA<u>G</u>GCCCAGGCGT<br>TGGTGGCGAA<u>A</u>GCCCAGGCGT | 20732 |
| BaAK32N13 | CGAAGAAGCC<u>A</u>AACATGGAGA<br>CGAAGAAGCC<u>G</u>AACATGGAGA | 20733 |
| bags31p01 | AGCCTCCGAA<u>G</u>CCGTAGAGGG<br>AGCCTCCGAA<u>T</u>CCGTAGAGGG | 20734 |
| bags31p01 | TGAGCACGCC<u>C</u>CGGGTCTCCT<br>TGAGCACGCC<u>G</u>CGGGTCTCCT | 20735 |
| bags31p01 | CGTCCATGGC<u>G</u>GTGACGGTCT<br>CGTCCATGGC<u>T</u>GTGACGGTCT | 20736 |
| bags31p01 | GGCGCTTGGC<u>G</u>CCGCCCTTGC<br>GGCGCTTGGC<u>A</u>CCGCCCTTGC | 20737 |
| baak30m11 | CTACGCCTA<u>C</u>TAATGTTCCAT<br>CTACGCCTA<u>C</u>CAATGTTCCAT | 20738 |
| baak30m11 | TGTTCCATCC<u>A</u>TTCATTCTTG<br>TGTTCCATCC<u>G</u>TTCATTCTTG | 20739 |
| baak30m11 | GTACAATTGT<u>T</u>TGGATCAGTG<br>GTACAATTGT<u>G</u>TGGATCAGTG | 20740 |
| bast146f1012 | TGCAGCCCAA<u>T</u>GTTTGGCATC<br>TGCAGCCCAA<u>G</u>GTTTGGCATC | 20741 |
| bast146f1012 | ACACTCATCA<u>C</u>CCCTACCGACA<br>ACACTCATCA<u>C</u>AACCTACCGACA | 20742 |
| bags3e06 | TCCCAAAGAA<u>G</u>AAGAGGGCCT<br>TCCCAAAGAA<u>A</u>AAGAGGGCCT | 20743 |
| bags3e06 | ATATGACACA<u>T</u>TAGGCATCAC<br>ATATGACACA<u>C</u>TAGGCATCAC | 20744 |
| baak46o19 | CAATGCTCAC<u>T</u>TTATCTATGT<br>CAATGCTCAC<u>C</u>TTATCTATGT | 20749 |
| baak46o19 | GCAGCTGCAG<u>C</u>AAGCCATCTT<br>GCAGCTGCAG-AAGCCATCTT | 20750<br>20751 |
| baak46o19 | GTACCCTTTT<u>N</u>CATATGTTGG<br>GTACCCTTTT<u>C</u>CATATGTTGG | 20752 |
| basd3c19 | ACGACAATGG<u>C</u>AACCAACTTT<br>ACGACAATGG<u>G</u>AACCAACTTT | 20753 |
| basd3c19 | GAATCAATGG<u>G</u>AACCAACTTT<br>GAATCAATGG<u>T</u>AACCAACTTT | 20754 |
| bags30f01 | CATCACCATC<u>G</u>TCACTCCCTG<br>CATCACCATC<u>A</u>TCACTCCCTG | 20755 |

TABLE 26-18

| Clones | Haruna Nijo H602 | SEQ ID NO: |
|---|---|---|
| bags30f01 | CCTCAGGGTCGTCGTCCTCAT<br>CCTCAGGGTC<u>A</u>TCGTCCTCAT | 20756 |
| bags32d08 | CAACAGGGGC<u>C</u>TGATCCCCAC<br>CAACAGGGGC<u>A</u>TGATCCCCAC | 20758 |
| bags32d08 | ATCATCGGT<u>T</u>TGTCATAAACT<br>ATCATCGGT<u>T</u>CGTCATAAACT | 20759 |
| BaAK23M23 | GCACGCCACA<u>C</u>AGTCCATATG<br>GCACGCCACA<u>G</u>AGTCCATATG | 20760 |
| BaAK23M23 | GGCTCATCAC<u>A</u>CACAGGATAC<br>GGCTCATCAC<u>G</u>CACAGGATAC | 20761 |
| bah21a16 | GGTGCTCCTC<u>T</u>GACCACCACG<br>GGTGCTCCTC<u>C</u>GACCACCACG | 20762 |
| baal3m08 | GGCTCATCACACACAGGATAC<br>GGCTCATCACGCACAGGATAC | 20763 |
| BaAK21I09 | TATTTGAATC<u>G</u>CAAACAAACA<br>TATTTGAATC<u>A</u>CAAACAAACA | 20764 |
| baet33a0301 | GCCGGCATGA<u>G</u>AAGCTTCCCC<br>GCCGGCATGA<u>A</u>AAGCTTCCCC | 20765 |
| baet33a0301 | TATTGAAATTCTAAAAATGTG<br>TATTGAAATT<u>T</u>TAAAAATGTG | 20766 |
| baet33a0301 | CCGCTTATT<u>T</u>ATTTTTTCTCC<br>CCGCTTATT<u>T</u>TTTTTTTCTCC | 20767 |
| baet33a0301 | ACACACAAAC<u>G</u>AGTGCCGGTT<br>ACACACAAAC<u>A</u>AGTGCCGGTT | 20768 |
| baet33a0301 | TGGCCATGAC<u>G</u>ATGTTATCGG<br>TGGCCATGAC<u>A</u>ATGTTATCGG | 20769 |
| baet33a0301 | TCAGTCTTCAGAGCGCGGCTT<br>TCAGTCTTCA<u>A</u>AGCGCGGCTT | 20770 |
| baet33a0301 | TCTCCTCCAC<u>G</u>AACTTGTCCA<br>TCTCCTCCAC<u>A</u>AACTTGTCCA | 20771 |
| baak24k02 | TCAAATGATT<u>T</u>CTAAACTAAC<br>TCAAATGATT<u>C</u>CTAAACTAAC | 20772 |
| baak24k02 | TGCCATGCTC<u>G</u>CTGAACAGCT<br>TGCCATGCTC<u>A</u>CTGAACAGCT | 20773 |
| bast75d1208 | GTGTGGCAGC<u>A</u>GCACTGGAGG<br>GTGTGGCAGC<u>G</u>GCACTGGAGG | 20775 |
| bag34f06 | ACATTATGGT<u>G</u>TGCCGGCAAC<br>ACATTATGGT<u>A</u>TGCCGGCAAC | 20776 |
| bags34f06 | GTGTGGCAGCGGCACTGGAGG<br>GTGTGGCAGCAGCACTGGAGG | 20777 |
| bags6f09 | CACCGTGCCT<u>C</u>ATTGTACACT<br>CACCGTGCCT<u>G</u>ATTGTACACT | 20778 |
| bags6f09 | AGGGCCTCTA<u>T</u>TATGGCATCT<br>AGGGCCTCTA<u>C</u>TATGGCATCT | 20779 |
| bags6f09 | ACAGAAAAGA<u>C</u>AATCAGCCTT<br>ACAGAAAAGA<u>T</u>AATCAGCCTT | 20780 |
| bags6f09 | TCTTCTCTCA<u>A</u>AGAACTGCCA<br>TCTTCTCTCA<u>G</u>AGAACTGCCA | 20781 |
| bags6f09 | TCTGATAGCT<u>T</u>AAAAAATGTA<br>TCTGATAGCT<u>G</u>AAAAAATGTA | 20782 |

TABLE 26-19

| Clones | Haruna Nijo H602 | SEQ ID NO: |
|---|---|---|
| bags6f09 | TCAAAGACATCGAGCCTTGTT<br>TCAAAGACATAGAGCCTTGTT | 20783 |
| bags7b10 | GAGATTCTTGTGATCCCCTCT<br>GAGATTCTTGCGATCCCCTCT | 20784 |
| bags7b10 | TGATTAAACAAAATATCAGTA<br>TGATTAAACAGAATATCAGTA | 20785 |
| bags7b10 | AAAGTTTCCATAATAACAACA<br>AAAGTTTCCACAATAACAACA | 20786 |
| bags7b10 | TCTACAAAGTTCACTATCCAT<br>TCTACAAAGTCCACTATCCAT | 20787 |
| bags7b10 | GTGGCTAATCCCTAATCCTGC<br>GTGGCTAATCACTAATCCTGC | 20788 |
| bags37e01 | AGCTCTGGGGTGCAGATTTCC<br>AGCTCTGGGGCGCAGATTTCC | 20791 |
| bags37e01 | GTCATTCATCTTCTCTTTTGA<br>GTCATTCATCCTCTCTTTTGA | 20792 |
| BaGS24M06 | GTTTGCCGACCATACCTCTTG<br>GTTTGCCGACAATACCTCTTG | 20794 |
| BaGS24M06 | CGTCATCCTCATCATCGTCGG<br>CGTCATCCTCGTCATCGTCGG | 20795 |
| BaGS24M06 | ACCTTCTTGTGAACTGCTTCC<br>ACCTTCTTGTAAACTGCTTCC | 20796 |
| BaGS24M06 | GCTAACAACAGGGTTGAAACA<br>GCTAACAACAAGGTTGAAACA | 20797 |
| bags22m23 | AATGCCTAGCAATCAGAATCA<br>AATGCCTAGCCATCAGAATCA | 20798 |
| bags22m23 | TCTGCAAGAATTGTATTTCTA<br>TCTGCAAGAACTGTATTTCTA | 20799 |
| bags22m23 | TTAAGTTCCGTAAAAATGTAC<br>TTAAGTTCCGCAAAAATGTAC | 20800 |
| bags22m23 | TGGCTGGCGTTTGACATATCC<br>TGGCTGGCGTCTGACATATCC | 20801 |
| bags22 m23 | CCCATGAAAGCAGCTCCAGTC<br>CCCATGAAAGAAGCTCCAGTC | 20802 |
| basd18d18 | AGTAAATGCAGACTTCTGATA<br>AGTAAATGCAAACTTCTGATA | 20803 |
| basd18d18 | GCATTAAGCACACCTCTCCCG<br>GCATTAAGCAAACCTCTCCCG | 20804 |
| basd18d18 | GGATTAGCAACCGAACACGAT<br>GGATTAGCAAGCGAACACGAT | 20805 |
| bast106F0212 | CCAGATCATCGACTTCAGCGG<br>CCAGATCATCAACTTCAGCGG | 20806 |
| BaH49O16 | TACTAGTTTTGTATATAAAAC<br>TACTAGTTTTTTATATAAAAC | 20807 |
| BaH49O16 | ATATAAACGTTCACGTAGCA<br>ATATAAACGGTCACGTAGCA | 20808 |
| BaH49O16 | AGGTCATTGCGCGGCCCTTCG<br>AGGTCATTGCACGGCCCTTCG | 20809 |
| BaH38 N06 | TTGAGACGGAGGAAGTATTAC<br>TTGAGACGGATGAAGTATTAC | 20811 |

TABLE 26-20

| Clones | Haruna Nijo H602 | SEQ ID NO: |
|---|---|---|
| BaH38N06 | ACTTATATAGCACTCCCTCCG<br>ACTTATATAGTACTCCCTCCG | 20812 |
| bah56p16 | AACTGAAAACTCCAGCCTTCC<br>AACTGAAAACCCCAGCCTTCC | 20813 |
| basd13o13 | ACTGTGATGGCTCAGCAGCCT<br>ACTGTGATGGTTCAGCAGCCT | 20814 |
| bah34f11 | TCATACGACCCGACACCTAAA<br>TCATACGACCTGACACCTAAA | 20816 |
| bags37g04 | TTGCTCTTACAATCGTATTTA<br>TTGCTCTTACTATCGTATTTA | 20817 |
| bags37g04 | CGAGCTGCTTCGTCCAGTCGA<br>CGAGCTGCTTAGTCCAGTCGA | 20818 |
| baak43o03 | CGGGGATGATGTAGTCTTTAT<br>CGGGGATGATATAGTCTTTAT | 20820 |
| BaAL4J21 | GGCAATGCTGTTCTTTGTAGT<br>GGCAATGCTGCTCTTTGTAGT | 20821 |
| BaH51J22 | GCCCAGACGTCCCCCAACACG<br>GCCCAGACGTTCCCCAACACG | 20822 |
| BaH51J22 | TTTTATCTGGGGAAGGATAAA<br>TTTTATCTGGAGAAGGATAAA | 20823 |
| BaH51J22 | CTGAGCTGAAAGTGCAGCAGC<br>CTGAGCTGAAGGTGCAGCAGC | 20824 |
| BaH51J22 | GTTCCTTGGTAGTCAATCGTC<br>GTTCCTTGGTCGTCAATCGTC | 20825 |
| bah58l03 | TAGCACCAACGCGGCCATTCG<br>TAGCACCAACACGGCCATTCG | 20826 |
| BaGS21M18 | TCAGGTTGTCACCGAACGTCT<br>TCAGGTTGTCGCCGAACGTCT | 20827 |
| bags31k06 | AAAGATCTGGAGGCGAGGCTC<br>AAAGATCTGGGGGCGAGGCTC | 20828 |
| bags31k06 | TAGTATAGCCACACTACTGAC<br>TAGTATAGCCCCACTACTGAC | 20829 |
| bags31k06 | TGTCCCTTGCAAAGCAGGCTG<br>TGTCCCTTGCGAAGCAGGCTG | 20830 |
| bags31k06 | GGACACCACACAGAGTTAGAT<br>GGACACCACAGAGAGTTAGAT | 20831 |
| baal4o01*VRN 2(sh2) | CTCTCGCCTGCCGCCGCTGGG<br>CTCTCGCCTGTCGCCGCTGGG | 20832 |
| baal4o01*VRN 2(sh2) | ACACCAATTCAAAAGATGGTT<br>ACACCAATTCGAAAGATGGTT | 20833 |
| baal4o01*VRN 2(sh2) | CCATCCACAGTGGAAGCGCCG<br>CCATCCACAGGGGAAGCGCCG | 20834 |
| baal4o01*VRN 2(sh2) | ACTACTTTAGTAATCTAAACG<br>ACTACTTTAGCAATCTAAACG | 20835 |
| baal4o01*VRN 2(sh2) | CTGCGACAGGCGGAGCATCCC<br>CTGCGACAGGGGGAGCATCCC | 20836 |
| bah39o04 | CCGTGTAGATACCGTCGCGCT<br>CCGTGTAGATGCCGTCGCGCT | 20837 |
| bah39o04 | CCACGATCTGCCCCTCGGAGA<br>CCACGATCTGGCCCTCGGAGA | 20838 |

TABLE 26-21

| Clones | Haruna Nijo / H602 | SEQ ID NO: |
|---|---|---|
| bah39o04 | GTAGATCACATAAATTTTGTT<br>GTAGATCACACAAATTTTGTT | 20839 |
| bast14h0416 | CATCATGATACATGTCTTGGT<br>CATCATGATATATGTCTTGGT | 20841 |
| bast144H115 | GCCGGCCCGACGGAGCTCGTC<br>GCCGGCCCGATGGAGCTCGTC | 20843 |
| bags23f02 | CGCAGAAACGGCTCTAACAAC<br>CGCAGAAACGACTCTAACAAC | 20849 |
| bast140e1010 | GGTTCAGAACGGTGGAGGATT<br>GGTTCAGAACCGTGGAGGATT | 20850 |
| bah15e16 | CATGGTCAAACCTTTGTGCCC<br>CATGGTCAAAACTTTGTGCCC | 20856 |
| basd27o16 | TCGCTCACCCTGCGGAACATC<br>TCGCTCACCCGGCGGAACATC | 20858 |
| basd27o16 | TCCATCTCGTACATGCCCTCG<br>TCCATCTCGTCCATGCCCTCG | 20859 |
| basd27o16 | ACTCGGCGACAAGGTCGTTCA<br>ACTCGGCGACGAGGTCGTTCA | 20860 |
| bald 27o16 | GAGCGAGCGAATCCGTTGCC<br>GAGCGGAGCGCATCCGTTGCC | 20061 |
| basd27o16 | CATATAGCTGAACGGAGCGGA<br>CATATAGCTGCACGGAGCGGA | 20862 |
| kr66g0713 | TTTATGATCATGAATTTACAA<br>TTTATGATCACGAATTTACAA | 20863 |
| kr66g0713 | TATCTTGAAGGGTCCCAAATT<br>TATCTTGAAGTGTCCCAAATT | 20864 |
| baak46c17 | GAAGCCATGAGTTCATTCATT<br>GAAGCCATGATTTCATTCATT | 20865 |
| baak46c17 | AATACCTTGTCTACAGAGTAC<br>AATACCTTGTTTACAGAGTAC | 20866 |
| baet19C1206 | TACACAAACAGACACAAGGCT<br>TACACAAACAAACACAAGGCT | 20867 |
| BaGS26G20 | GCAATGAACAATGCCAGTGCC<br>GCAATGAACACTGCCAGTGCC | 20870 |
| BaGS26G20 | AGAGGATCTTTTCAGGCACAC<br>AGAGGATCTTCTCAGGCACAC | 20871 |
| bags28c14 | GGCCATCACACGATGAATGCC<br>GGCCATCACAGGATGAATGCC | 20872 |
| bags28c14 | GAATAAAAAGTCTCAGTCCAA<br>GAATAAAAAGGCTCAGTCCAA | 20873 |
| bags28c14 | TGCTCTCTCACTCGGGGTGAT<br>TGCTCTCTCAGTCGGGGTGAT | 20874 |
| kr61g1214 | AAGATTTCGTCGAATAGCCTG<br>AAGATTTCGTTGGATAGCCTG | 20875 |
| kr61g1214 | GATTTCGTCGAATAGCCTGAA<br>GATTTCGTTGGATAGCCTGAA | 20876 |
| bags9g08 | CAAATATATGTGATTGATGCA<br>CAAATATATGGGATTGATGCA | 20877 |
| bags9g08 | TGAAGATGCACATATTACTAA<br>TGAAGATGCAAATATTACTAA | 20878 |

TABLE 26-22

| Clones | Haruna Nijo / H602 | SEQ ID NO: |
|---|---|---|
| bags9g08 | GGGAAAGAGCGGCCAAAAGTT<br>GGGAAAGAGCAGCCAAAAGTT | 20879 |
| bags5p01 | CTGGAGATCAACATGAATGAT<br>CTGGAGATCAGCATGAATGAT | 20880 |
| bags5p01 | AGATATCTGTGTTCTTGACAT<br>AGATATCTGTATTCTTGACAT | 20881 |
| bags5p01 | AGTTTTTTCAAGAGCTGCGAC<br>AGTTTTTTCAGGAGCTGCGAC | 20882 |
| bags5p01 | TGGAAGTTCACATCAAGGACA<br>TGGAAGTTCAAATCAAGGACA | 20883 |
| baal4d04 | CGGGGAAAACAACCGTGAAGT<br>CGGGGAAAACCACCGTGAAGT | 20884 |
| baal4d04 | CACTGGTCCAGGCTCAGCGAG<br>CACTGGTCCAAGCTCAGCGAG | 20885 |
| baal4d04 | GCTCCATGTCCGTGTACTGCG<br>GCTCCATGTCTGTGTACTGCG | 20886 |
| baal4d04 | CAATGTCTATGTCGTAGGCCA<br>CAATGTCTATATCGTAGGCCA | 20887 |
| baal4d04 | GCTGCTGCTGCTGCCTCCGCA<br>GCTGCTGCTGTTGCCTCCGCA | 20888 |
| bah11e02 | CGGGGAAAACAACCGTGAAGT<br>CGGGGAAAACCACCGTGAAGT | |
| bah11e02 | AGAGGTCGTCGGCCTTCCGCT<br>AGAGGTCGTCAGCCTTCCGCT | 20891 |
| bah11e02 | CACTGGTCCAGGCTCAGCGAG<br>CACTGGTCCAAGCTCAGCGAG | 20892 |
| bah11e02 | TCAGTTTGAATATATACCAAA<br>TCAGTTTGAACATATACCAAA | 20893 |
| bast41f0311 | TGCTGTTGCTCTTGTTGGTGT<br>TGTTGTTGCTTTTGTTGGTGT | 20894 |
| bast41f0311 | GCTGTTGTTGCTGTTGCTCTT<br>GCTGTTGTTGTTGTTGCTCTT | 20895 |
| bast154d0307 | CAGACTAGCTCAAATGGTGAA<br>CAGACTAGCTGAAATGGTGAA | 20896 |
| kr33h0816 | GGTAAACTAAACGGGGCATAT<br>GGTAAACTAAGCGGGGCATAT | 20899 |
| kr33h0816 | TTGCCTTGCCGTGCTGTTAGA<br>TTGCCTTGCCTTGCTGTTAGA | 20900 |
| BaH38F16 | GCTCTCATGCTGNGACCTCAA<br>GCTCTCATGCGNNGACCTCAA | 20901 |
| BaGS21P09 | TAAATCAAGCAGACGAGGCTC<br>TAAATCAAGCGGACGAGGCTC | 20902 |
| BaGS21P09 | CGGCAGCCCAGATGTACTCAT<br>CGGCAGCCCACATGTACTCAT | 20903 |
| BaGS21P09 | ATCAGATTCAGGAACAGGTTG<br>ATCAGATTCATGAACAGGTTG | 20904 |
| basd21g02 | GGCGACGGTGACGGCGGTGAT<br>GGCGACGGTGGCGGCGGTGAT | 20909 |
| bah22m17 | TTGTTCATTACACATACTAAC<br>TTGTTCATTATACATACTAAC | 20910 |

TABLE 26-23

| Clones | Haruna Nijo H602 | SEQ ID NO: |
|---|---|---|
| bah22m17 | TCAAGAACCCAACCTGGAGAA<br>TCAAGAACCCGACCTGGAGAA | 20911 |
| bah22m17 | ATCATGCTGCGACGGTCAGCT<br>ATCATGCTGCAACGGTCAGCT | 20912 |
| bah22m17 | TGTTTCCGGTATCTCTGCTGC<br>TGTTTCCGGTGTCTCTGCTGC | 20913 |
| BaGS9H19 | ATTATCACTTTAGTGGATAGT<br>ATTATCACTTAAGTGGATAGT | 20914 |
| BaGS9H19 | ATAGTGAATGAATGCGCAAAG<br>ATAGTGAATGTATGCGCAAAG | 20915 |
| BaGS9H19 | TGAGTGAGTTACTGAGATAAA<br>TGAGTGAGTTGCTGAGATAAA | 20916 |
| bah26m24 | ATTTTGAATTGTTTAAAATAT<br>ATTTTGAATTATTTAAAATAT | 20917 |
| BaH56D01 | AGCCATATCCGTCTGCAGTCA<br>AGCCATATCCATCTGCAGTCA | 20918 |
| BaH56D01 | GCGTACCATACAGGCGAGGCG<br>GCGTACCATATAGGCGAGGCG | 20919 |
| BaH56D01 | GATAATAGCCACCAACAGGAG<br>GATAATAGCCGCCAACAGGAG | 20920 |
| BaH56D01 | GGAGGTACACATGCAAAACCT<br>GGAGGTACACGTGCAAAACCT | 20921 |
| BaH56D01 | CTACACGCTTCCGTGTCAGCG<br>CTACACGCTTTCGTGTCAGCG | 20922 |
| baal9m13 | GTACACCTATGCTACAAGGAC<br>GTACACCTATACTACAAGGAC | 20926 |
| baak21k16 | CCTCNACGGCGCCCATGAGCA<br>CCTCNACGGCACCCATGAGCA | 20927 |
| baak21k16 | CNGGGTCGTCNGCAAGNCCGA<br>CNGGGTCGTCGGCAAGNCCGA | 20928 |
| baak21k16 | CTGGGTATAGNGGGTCAACAA<br>CTGGGTATAGCGGGTCAACAA | 20929 |
| baak21k16 | GAGCTCAGCAGAATGCCTCNG<br>GAGCTCAGCA-AATGCCTCNG | 20930<br>20931 |
| baak21k16 | GTGGTCCTCCGGCAATGCGGT<br>GTGGTCCTCCAGCAATGCGGT | 20932 |
| bags19o14 | ACGGCATGCGGTCAGTGTCTC<br>ACGGCATGCGTTCAGTGTCTC | 20935 |
| bags19o14 | CCTTTGAGTTTGCCATACACT<br>CCTTTGAGTTGGCCATACACT | 20936 |
| baak35m03 | CTACGTATCTATCCTCGTACC<br>CTACGTATCTTTCCTCGTACC | 20937 |
| baak35m03 | TCAGCAGACAATGCGTGTACG<br>TCAGCAGACAGTGCGTGTACG | 20938 |
| baak35m03 | TGCCTCCTCTGGCGAGAGATC<br>TGCCTCCTCTTGCGAGAGATC | 20939 |
| baak35m03 | GTGCATTGTCACCCCGCCTTG<br>GTGCATTGTCACCCCGCCTTG | 20940 |
| baak35m03 | GCTACACTTTTTTGTTACAAA<br>GCTACACTTTGTTGTTACAAA | 20941 |

TABLE 26-24

| Clones | Haruna Nijo H602 | SEQ ID NO: |
|---|---|---|
| baak35m03 | TCCTTACTTAAACATAATGAA<br>TCCTTACTTAGACATAATGAA | 20942 |
| baak33 o23 | GATCATGGACGCAACATAAAC<br>GATCATGGACACAACATAAAC | 20943 |
| kr57F1012 | TACAACATGGTATCGTATCCT<br>TACAACATGGCATCGTATCCT | 20944 |
| bags22l16 | TTTAGCAGACCAAGTGAAGAG<br>TTTAGCAGACAAAGTGAAGAG | 20945 |
| bags22l16 | AAACATCGGCAGTCATGAACT<br>AAACATCGGCGGTCATGAACT | 20946 |
| baet43C0505 | TGTACGATGCATGTTAGAACG<br>TGTACGATGCGTGTTAGAACG | 20947 |
| bastl22E1010 | CCTTGGTCTTATTCGAATATA<br>CCTTGGTCTTCTTCGAATATA | 20949 |
| BaH53N24 | TACAGCAACCAAAGCTGGGCC<br>TACAGCAACCGAAGCTGGGCC | 20950 |
| baal8e24 | GGGGCTCTCATGGATGTCGGT<br>GGGGCTCTCACGGATGTCGGT | 20951 |
| baal8e24 | TCAGTTTCCACTAGAGGCCC<br>TCAGTTTCCCCTAGAGGCCC | 20952 |
| BaH62H21 | AGCTAGGAAGTAAATATGTGT<br>AGCTAGGAAGCAAATATGTGT | 20953 |
| BaH62H21 | GCCGGACCGGATGTGGAAGCC<br>GCCGGACCGGCTGTGGAAGCC | 20954 |
| bah42k01 | TGAAACTTAATTGAGGTAGAC<br>TGAAACTTAACTGAGGTAGAC | 20955 |
| bah42k01 | AGTAAATAAAACAGAATGCCT<br>AGTAAATAAATCAGAATGCCT | 20956 |
| bah42k01 | CATACTGCAGAGCCTATTTTA<br>CATACTGCAGGGCCTATTTTA | 20957 |
| basd26p09 | CCAGTCATCAACTATGTCTAT<br>CCAGTCATCA-CTATGTCTAT | 20958<br>20959 |
| basd26p09 | ATCTATCCACCACCCAGTCAT<br>ATCTATCCAC-ACCCAGTCAT | 20960<br>20961 |
| basd26p09 | GGTCCCGAGAATAGTGCGGAT<br>GGTCCCGAGA-TAGTGCGGAT | 20962<br>20963 |
| bags4p18 | CAGGGTGGCTGTGTCCAGCTT<br>CAGGGTGGCTATGTCCAGCTT | 20964 |
| bags4p18 | AATGAAGATCACTCACAAGAA<br>AATGAAGATCGCTCACAAGAA | 20965 |
| bags4p18 | AACTGAGAAGTATGTTGGTTT<br>AACTGAGAAGCATGTTGGTTT | 20966 |
| bast70d1107 | ACCGGAGAAGCAGCAGCTGCG<br>ACCGGAGAAGAAGCAGCTGCG | 20967 |
| bast70d1107 | CCACTTCACCATTCTAATTAA<br>CCACTTCACCCTTCTAATTAA | 20968 |
| bah26i23 | CCTCGTAATCACGGCTTTCTG<br>CCTCGTAATCGCGGCTTTCTG | 20969 |
| baal39g02 | TCCTTGCTCAGCCTGCCCTTG<br>TCCTTGCTCATCCTGCCCTTG | 20970 |

TABLE 26-25

| Clones | Haruna Nijo / H602 | SEQ ID NO: |
|---|---|---|
| baal39g02 | TTCTGGCCGGTGGTCTTGTCC<br>TTCTGGCCGGAGGTCTTGTCC | 20971 |
| baal39g02 | TTGTCGTTGGTGATGGTGATC<br>TTGTCGTTGGAGATGGTGATC | 20972 |
| baal39g02 | ACTTCTCTGCGTCCTGGACCA<br>ACTTCTCTGCATCCTGGACCA | 20973 |
| baal39g02 | TCATGTTGTAGGCGTAGTTCT<br>TCATGTTGTAAGCGTAGTTCT | 20974 |
| baal39g02 | GAGACGTTCAGGATACCGTTG<br>GAGACGTTCAAGATACCGTTG | 20975 |
| bags22c13 | TCCGTAGCTCGGGCAGGCCAA<br>TCCGTAGCTCAGGCAGGCCAA | 20977 |
| bags22c13 | TCTTATGGCAGAATAAAAATA<br>TCTTATGGCAAAATAAAAATA | 20978 |
| bags22c13 | GGCCAACCAATCTTTGAAGAT<br>GGCCAACCAACCTTTGAAGAT | 20979 |
| baal16h03 | GATCCTCTTCCGAGTTCTGCC<br>GATCCTCTTCTGAGTTCTGCC | 20981 |
| bags18o20 | AGATCTGGCCAAAGCCACCAC<br>AGATCTGGCCGAAGCCACCAC | 20984 |
| bags18o20 | CAACTCGTGATTCGTCAGAA<br>CAACTCGTGACTCTGTCAGAA | 20985 |
| bags19c02 | TTATGCCACACCACACGAATA<br>TTATGCCACATCACACGAATA | 20991 |
| bah52e20 | AGNACCCTAAGCTGATCTTGA<br>AGAACCCTAACCTGATCTTGA | 20992 |
| baal4n05 | TGTCCTCAAA-TCAGATAGAG<br>TGTCCTCAAAATCAGATAGAG | 20993<br>20994 |
| bags7p06 | GTCCTATCCAGCCAGATAAAA<br>GTCCTATCCAACCAGATAAAA | 20995 |
| bast70c0905 | AGATAGATTGCGGGGTTACAG<br>AGATAGATTGGGGGGTTACAG | 20996 |
| basd15j01 | TGTACAAAGTAGGGGAGATGA<br>TGTACAAAGTGGGGGAGATGA | 20997 |
| basd15j01 | TGACCGCCACGATGTACTTGG<br>TGACCGCCACAATGTACTTGG | 20998 |
| BaH56H18 | AACAGAATCAGAAGTTCAGAG<br>AACAGAATCAAAAGTTCAGAG | 20999 |
| BaGS4N04 | GTTTGCAGCCATAGTCCATTC<br>GTTTGCAGCCGTAGTCCATTC | 21000 |
| bags31o13 | TTGTGCAAAGGAAGGACAACT<br>TTGTGCAAAGCAAGGACAACT | 21001 |
| bags31o13 | ACTAGCGGGTTGCTACACCGG<br>ACTAGCGGGTCGCTACACCGG | 21002 |
| bags31o13 | GCTAACTATATCATACAAGAG<br>GCTAACTATAGCATACAAGAG | 21003 |
| bags31o13 | CCGACGTCGTCGGCGGAGGA<br>CCGACGTCGTTGGCGGAGGA | 21004 |
| bags7h14 | TTGTTCATTACTTAATTGTTA<br>TTGTTCATTAGTTAATTGTTA | 21006 |

TABLE 26-26

| Clones | Haruna Nijo / H602 | SEQ ID NO: |
|---|---|---|
| bags7h14 | CCACGGCCGGAAGTGGCCGAT<br>CCACGGCCGGCAGTGGCCGAT | 21007 |
| bags7h14 | ACTGTGGGACGATGCCCTCCT<br>ACTGTGGGACAATGCCCTCCT | 21008 |
| bags7h14 | ATTGAGGGGAAAACGATCCG<br>ATTGAGGGGGAAAACGATCCG | 21009 |
| bags7h14 | GTATGGCCGCGCCACTCGACG<br>GTATGGCCGCCCCACTCGACG | 21010 |
| bags5n14 | CACACTGGGGAAAGGCCTGGC<br>CACACTGGGGGAAGGCCTGGC | 21011 |
| bags5n14 | CCGTCACAAGCGTCGCAGACT<br>CCGTCACAAGAGTCGCAGACT | 21012 |
| bast132h0816 | CGCACCCAGAGCGAGATGCC<br>CGCACCCAGATGCGAGATGCC | 21013 |
| bast132h0816 | GTGCTGCCACTCAAGGCTAGC<br>GTGCTGCCACCCAAGGCTAGC | 21014 |
| bast132h0816 | GCCAGCAAAGGTTAGATACAT<br>GCCAGCAAAGATTAGATACAT | 21015 |
| baak31p06 | AAACAGAGGCTGATTTTTGT<br>AAACAGAGGC-GATTTTTGT | 21016<br>21017 |
| baak31p06 | TTGGTAAGACGTGCTGCTTAT<br>TTGGTAAGACATGCTGCTTAT | 21018 |
| baak44j08 | TGATGGTATTGTTGCTCCCCG<br>TGATGGTATTATTGCTCCCCG | 21021 |
| baak44j08 | TGTGGAAGCTTCCGGATACAT<br>TGTGGAAGCTCCCGGATACAT | 21022 |
| baak18g16 | CTGATATCCGGCTCAGCTCGT<br>CTGATATCCGACTCAGCTCGT | 21023 |
| baak18g16 | TGAACATCGGGGATGCCTGCT<br>TGAACATCGGTGATGCCTGCT | 21024 |
| baak18g16 | CGCGCCGCTAGACGCGAAGCA<br>CGCGCCGCTACACGCGAAGCA | 21025 |
| baak18g16 | CCTTGGAGCACCTTTGAAGCC<br>CCTTGGAGCATCTTTGAAGCC | 21026 |
| baak11a11 | GCCCACCAAGTAATTGTGAGC<br>GCCCACCAAGCAATTGTGAGC | 21027 |
| baal9n02 | ACTCCAGAGGGGCTCGCCCTT<br>ACTCCAGAGGTGCTCGCCCTT | 21029 |
| baal9n02 | GCGAGAAAGAAAAGGTGTTTC<br>GCGAGAAAGACAAGGTGTTTC | 21030 |
| baal9n02 | GCGGGCTCAGGGAACGCGTCC<br>GCGGGCTCAGTGAACGCGTCC | 21031 |
| baal9n02 | ATGAGCTACGTGCGGGCTGGC<br>ATGAGCTACGGGCGGGCTGGC | 21032 |
| baal9n02 | ACTCCGGGGAGACATGGAATA<br>ACTCCGGGGAAACATGGAATA | 21033 |
| bags20f08 | AGGAAACAGCGAGCTCAGGCT<br>AGGAAACAGCAAGCTCAGGCT | 21034 |
| bags20f08 | AATACTAAACGACACAAAGA<br>AATACTAAATGACACAAAGA | 21035 |

TABLE 26-27

| Clones | Haruna Nijo H602 | SEQ ID NO: |
|---|---|---|
| bags20f08 | GGAATATGCAATAACATATAC<br>GGAATATGCAGTAACATATAC | 21036 |
| bags9c24 | ACAGCAGTTGCATCAGTGGAT<br>ACAGCAGTTGGATCAGTGGAT | 21037 |
| BaGS22O02 | TGTCCTTCTCCGCCAGCACAG<br>TGTCCTTCTCTGCCAGCACAG | 21038 |
| BaGS22O02 | CCAGCACGCCGAAGAAGATGG<br>CCAGCACGCCAAAGAAGATGG | 21039 |
| BaGS22O02 | CGCCGGGACCTTCCTCTCTCA<br>CGCCGGGACCATCCTCTCTCA | 21040 |
| bah41b17 | AGGTCATGAATGTAATCACAG<br>AGGTCATGAACGTAATCACAG | 21042 |
| bah41b17 | TAGTCTCTGCAGGCCTGATGT<br>TAGTCTCTGCGGGCCTGATGT | 21043 |
| bah63m11 | AAATAGACGGCTGAAATTAAT<br>AAATAGACGGGTGAAATTAAT | 21044 |
| bags28p07 | TTTTTCATGCTCCATGCCCTT<br>TTTTTCATGCACCATGCCCTT | 21045 |
| bags28p07 | CTTTCAATCATACGACTGACT<br>CTTTCAATCACACGACTGACT | 21046 |
| bast03d0408 | AAGCAGATTCCTTCATTAGCC<br>AAGCAGATTCTTTCATTAGCC | 21049 |
| baal17g06 | CAAACTGGTTTCCGAAGAGCC<br>CAAACTGGTTCCCGAAGAGCC | 21050 |
| baal17g06 | AGACCCTTGCCACGCCGCCGG<br>AGACCCTTGCGACGCCGCCGG | 21051 |
| baal17g06 | ACAGTACAACTTATTATCCAC<br>ACAGTACAACGTATTATCCAC | 21052 |
| baal17g06 | ACACAAATACCTACTAGTACA<br>ACACAAATACATACTAGTACA | 21053 |
| bags4p17 | GCATCCGTTGTTGGAGTCGCA<br>GCATCCGTTGCTGGAGTCGCA | 21055 |
| bags4p17 | GGCGGCCGCCCCCGTACCAGC<br>GGCGGCCGCCTCCGTACCAGC | 21056 |
| bags4p17 | ATCATCTTCCAGCACCGGCGG<br>ATCATCTTCCCGCACCGGCGG | 21057 |
| bags4p17 | CTGCTCGCTGCTGATGCGGAT<br>CTGCTCGCTGGTGATGCGGAT | 21058 |
| bags4p17 | GTGTTGAGCCCGAGAGCCTTC<br>GTGTTGAGCCTGAGAGCCTTC | 21059 |
| bags4p17 | CGGGGACCTCGCCGATGTCGG<br>CGGGGACCTCCCCGATGTCGG | 21060 |
| bags4p17 | GTCCACGATGTTGTCCTTGCA<br>GTCCACGATGCTGTCCTTGCA | 21061 |
| baal31o21 | AGGGGTAGGAGAAAATGATGC<br>AGGGGTAGGAAAAAATGATGC | 21062 |
| baal31o21 | CCATGCCACAGGAGATAGACA<br>CCATGCCACAAGAGATAGACA | 21063 |
| baal31o21 | GGTGGTCCGCAGTGGCTGGCT<br>GGTGGTCCGCGGTGGCTGGCT | 21064 |

TABLE 26-28

| Clones | Haruna Nijo H602 | SEQ ID NO: |
|---|---|---|
| bags4d11 | TCTTCTTCCCAAATTTCAGCA<br>TCTTCTTCCCGAATTTCAGCA | 21068 |
| basd13n18 | AGATAATCAATAAACAAAGTG<br>AGATAATCAACAAACAAAGTG | 21067 |
| basd0a08 | AGACCCTTGCGACGCCGCCGG<br>AGACCCTTGCCACGCCGCCGG | 21068 |
| basd0a08 | ACAGTACAACGTATTATCCAC<br>ACAGTACAACTTATTATCCAC | 21069 |
| basd0a08 | CAAACTGGTTCCCGAAGAGCC<br>CAAACTGGTTTCCGAAGAGCC | 21070 |
| basd0a08 | ACACAAATACGTACTAGTACA<br>ACACAAATACCTACTAGTACA | 21071 |
| bags32p24 | CTTAAACATACGCATCATATG<br>CTTAAACATATGCATCATATG | 21072 |
| kr06h0315 | ACCANACTCTCCTGAGCAGAC<br>ACCAGACTCTGCTGAGCAGAC | 21074 |
| baal26b09 | GACCGAGACCGTGTCCGTGTC<br>GACCGAGACCATGTCCGTGTC | 21075 |
| kr32c1105 | TATACACATACGAGTAGGATT<br>TATACACATAGGAGTAGGATT | 21076 |
| kr32c1105 | TTGTGGTTGTCGTTGTAGGTA<br>TTGTGGTTGTGGTTGTAGGTA | 21077 |
| kr32c1105 | ACTTTCTTTCTTTCTTTCTTT<br>ACTTTCTTTCCTTCTTTCTTT | 21078 |
| bah53b15 | ATTGCCAGAGGCAGAAATGCA<br>ATTGCCAGAGACAGAAATGCA | 21079 |
| bags13h04 | CAAGCCCTGCGTCAACGACAA<br>CAAGCCCTGCATCAACGACAA | 21080 |
| baal15i11 | AACCACCCTGAAAGAAAACTC<br>AACCACCCTGGAAGAAAACTO | 21081 |

TABLE 27-1

| Clones | Haruna Nijo H602 | SEQ ID NO: |
|---|---|---|
| BaH30E11 | TTCTTGGCCTCGGATTCGGAC<br>TTCTTGGCCTTGGATTCGGAC | 21084 |
| BaH30E11 | GGAATAATCCCCCTCATAACA<br>GGAATAATCCACCTCATAACA | 21085 |
| BaH59J05 | ATTACAGTTTTTTCGTCTACG<br>ATTACAGTTTCTTCGTCTACG | 21086 |
| BaH59J05 | AAAACATGGGAACTACATATA<br>AAAACATGGGCACTACATATA | 21087 |
| BaAL39O22 | AGTTGCGGCAGCGGCAATATG<br>AGTTGCGGCATCGGCAATATG | 21088 |
| BaAL39O22 | AACAGGCGTTTTCTGGTTAGT<br>AACAGGCGTTGTCTGGTTAGT | 21089 |
| BaAL39O22 | ATTCCAGACAAACATTTTTAT<br>ATTCCAGACACACATTTTTAT | 21090 |
| BaAL39O22 | GCCGGGAATACAACCATCAG<br>GCCGGGAATGCAACCATCAG | 21091 |

TABLE 27-1-continued

| Clones | Haruna Nijo H602 | SEQ ID NO: |
|---|---|---|
| baal16i24 | ATCCATCATGGCAGCTCATAC<br>ATCCATCATGCCAGCTCATAC | 21092 |
| baak43j24 | GCCAGTTGATCCCTGCCAACA<br>GCCAGTTGATGCCTGCCAACA | 21097 |
| baak43j24 | CCACACTGAAATTCATACCTC<br>CCACACTGAATTTCATACCTC | 21098 |
| bags3m02 | GCGCAGCACCACCGGACCCGA<br>GCGCAGCACCGCCGGACCCGA | 21109 |
| bags3m02 | CTTCTCTCTCTTCCCTTCCTT<br>CTTCTCTCTCCTCCCTTCCTT | 21110 |
| baal36l08 | ACCTACCACCAATCGCAAAGC<br>ACCTACCACCCATCGCAAAGC | 21111 |
| baal36l08 | CAGCTCTTCGCCATCAAGCAC<br>CAGCTCTTCGGCATCAAGCAC | 21112 |
| baet19e0309 | TTACAGTGACCCGGGCGCCGG<br>TTACAGTGACACGGGCGCCGG | 21113 |
| bast48d0307 | CCATGTAGGCGCCCGGTCTCC<br>CCATGTAGGCACCCGGTCTCC | 21114 |
| kr55D0707 | GGTTGACCGGCGCTGGTGGAA<br>GGTTGACCGGTGCTGGTGGAA | 21115 |
| kr55D0707 | CTGCCAGCGCCGACGCCACGG<br>CTGCCAGCGCAGACGCCACGG | 21116 |
| BaGS24F04 | TAACTAACCACAAGACTGCTC<br>TAACTAACCAAAAGACTGCTC | 21119 |
| BaGS24F04 | GGCGACTTGGTCTCCTTCTCG<br>GGCGACTTGGCCTCCTTCTCG | 21120 |
| bags26p07 | TCTCCCGGGAGGTGATGGTGG<br>TCTCCCGGGACGTGATGGTGG | 21122 |
| bags26p07 | CGTGCTTGGCGAGCTCGCCGG<br>CGTGCTTGGCCAGCTCGCCGG | 21123 |
| bags12f11 | TGGCCTTCCCGTCCAGCGGT<br>TGGCCTTCCCATCCAGCGGT | 21124 |
| bags20o14 | CTAAAGAACAGAATTATTCAC<br>CTAAAGAACAAAATTATTCAC | 21127 |

TABLE 27-2

| Clones | Haruna Nijo H602 | SEQ ID NO: |
|---|---|---|
| bags20o14 | CATGGAAAGAGATATGCATAT<br>CATGGAAAGAAATATGCATAT | 21128 |
| bags20o14 | AAATGGGGTTGTTAATGACGG<br>AAATGGGGTTCTTAATGACGG | 21129 |
| bags20o14 | AAAACTATCATGGGCACTGAC<br>AAAACTATCAGGGGCACTGAC | 21130 |
| bags20o14 | GCACTGACCAGCTTGCTTGAC<br>GCACTGACCATCTTGCTTGAC | 21131 |
| bags20o14 | TCTGTGGAAGCTGGTCTTCAC<br>TCTGTGGAAGTTGGTCTTCAC | 21132 |
| baak36d08 | GGAAGACGGCAGGGTGGAATG<br>GGAAGACGGCGGGGTGGAATG | 21133 |

TABLE 27-2-continued

| Clones | Haruna Nijo H602 | SEQ ID NO: |
|---|---|---|
| baak36d08 | TGGCGGTTGGAGGCAACCAGT<br>TGGCGGTTGGGGGCAACCAGT | 21134 |
| bast75h0616 | ATATATTTTCCAAGCAAGAGG<br>ATATATTTTCAAAGCAAGAGG | 21135 |
| bast75h0616 | TGGCGGTTGGGGGCAACCAGT<br>TGGCGGTTGGAGGCAACCAGT | 21136 |
| basd16g17 | CTAGCCGCCTTGCAGCCCCAC<br>CTAGCCGCCTCGCAGCCCCAC | 21137 |
| BaH21K13 | AACAAATTTCCGTACACAACA<br>AACAAATTTCTGTACACAACA | 21143 |
| BaH21K13 | AAGAGAGGAGACAACAAATTT<br>AAGAGAGGAGGCAACAAATTT | 21144 |
| baak14j02 | ACAGCCTTACATCGGGGAACT<br>ACAGCCTTACGTCGGGGAACT | 21145 |
| baak14j02 | TGAAGCCGACGGTTCTGTCCA<br>TGAAGCCGACCGTTCTGTCCA | 21146 |
| bah22c08 | CCACTCCCATGGTTAAATGTA<br>CCACTCCCATAGTTAAATGTA | 21147 |
| bah22c08 | TTCTGTGTTAAAGCTTCTTAC<br>TTCTGTGTTACAGCTTCTTAC | 21148 |
| bah22c08 | AAATGTAATACGAAATAATGA<br>AAATGTAATATGAAATAATGA | 21149 |
| bah22c08 | CCACATACCCTATCCAGAACA<br>CCACATACCCGATCCAGAACA | 21150 |
| bah22c08 | CTTATAAAAGGAAAACTCATA<br>CTTATAAAAGAAAAACTCATA | 21151 |
| bah22c08 | TCACCTTGATCTCAAGAATGT<br>TCACCTTGATTTCAAGAATGT | 21152 |
| bah22c08 | ATATCATTCGTGGGCACAAAA<br>ATATCATTCGCGGGCACAAAA | 21153 |
| bah12n12 | TGGGCGTCTTGAAGTACAAAT<br>TGGGCGTCTTAAAGTACAAAT | 21157 |
| baak32l04 | ATTCATAACAGGAGCATCCTT<br>ATTCATAACAAGAGCATCCTT | 21161 |
| baak32l04 | CATGCTGGGC-GGGAAGGCCC<br>CATGCTGGGCAGGGAAGGCCC | 21162<br>21163 |
| baak32l04 | CCCTCCGCGTCGCCACCGGGG<br>CCCTCCGCGTTGCCACCGGGG | 21164 |

TABLE 27-3

| Clones | Haruna Nijo H602 | SEQ ID NO: |
|---|---|---|
| baak32l04 | TCTGCCCTTCGCCGTAGCCAA<br>TCTGCCCTTCTCCGTAGCCAA | 21165 |
| BaAL7C19 | GTACCTTGGATATGGTGAGGG<br>GTACCTTGGAGATGGTGAGGG | 21167 |
| BaAL7C19 | GGAGTAGTAGATAGACAAGAT<br>GGAGTAGTAGGTAGACAAGAT | 21168 |
| BaAK23F04 | CTCCATCGCTTGCTTCGAGCC<br>CTCCATCGCTCGCTTCGAGCC | 21169 |

TABLE 27-3-continued

| Clones | Haruna Nijo H602 | SEQ ID NO: |
|---|---|---|
| basd0g08 | ATATATCTCCGAGCACCCCTT<br>ATATATCTCCAAGCACCCCTT | 21171 |
| basd0g08 | GAACTGTACAGTACTCCTGGT<br>GAACTGTACATTACTCCTGGT | 21172 |
| basd0g08 | GTTGCCCGTCCCAGGAGAAGC<br>GTTGCCCGTCTCAGGAGAAGC | 21173 |
| basd0g08 | TCAATATGGATTTGCCCTGTG<br>TCAATATGGACTTGCCCTGTG | 21174 |
| baal21b21 | CGACGACGACTACGACGGGCG<br>CGACGACGACGACGACGGGCG | 21176 |
| baal21b21 | GACCGACGACGCGACAGGGGA<br>GACCGACGACACGACAGGGGA | 21177 |
| baal21b21 | CTTGGAGCAGGTGCCGCTGCG<br>CTTGGAGCAGATGCCGCTGCG | 21178 |
| bags30e05 | ACTGTGTACTACATTGTTTCT<br>ACTGTGTACTGCATTGTTTCT | 21179 |
| bags30e05 | CTTGCACACTGCAAAGAACTG<br>CTTGCACACTACAAAGAACTG | 21180 |
| bags30e05 | AGCCATTACTGTAAACTCACC<br>AGCCATTACTTTAAACTCACC | 21181 |
| bags30e05 | GTCGAACAAGACTGGGCCGTC<br>GTCGAACAAGGCTGGGCCGTC | 21182 |
| bags30e05 | ACTTCCCTCCGGTAAGATAAA<br>ACTTCCCTCCCGTAAGATAAA | 21183 |
| bags30e05 | CATGGATGAGAACTTGCACAC<br>CATGGATGAGGACTTGCACAC | 21184 |
| bals30e05 | GGCAAATGTGTCTGACAGCCA<br>GGCAAATGTGCCTGACAGCCA | 21185 |
| baak13g04 | CACTGACACCGTCCGATCCAG<br>CACTGACACCCTCCGATCCAG | 21186 |
| bags9a04 | GCCCTTCCTTGTGGCCCATCC<br>GCCCTTCCTTATGGCCCATCC | 21187 |
| bags9a04 | AGTTCCTGTTCGTCGTTGATA<br>AGTTCCTGTTTGTCGTTGATA | 21188 |
| bags9a04 | TCCCCAATCATAAGGATGTGG<br>TCCCCAATCAGAAGGATGTGG | 21189 |
| bags9a04 | TCGCTCCTCTGAACTAGCAAC<br>TCGCTCCTCTAAACTAGCAAC | 21190 |
| bags9a04 | CTGCTAAGCATCAACAAATAA<br>CTGCTAAGCAGCAACAAATAA | 21191 |
| baak23m11 | GGCGAGCACTCGTCCTCTTCA<br>GGCGAGCACTAGTCCTCTTCA | 21193 |

TABLE 27-4

| Clones | Haruna Nijo H602 | SEQ ID NO: |
|---|---|---|
| baak41p21 | TGGAGGAGACCGTGTCAGCAA<br>TGGAGGAGACGGTGTCAGCAA | 21194 |
| baak41p21 | TGTAGATCTCATCAATAAGAG<br>TGTAGATCTCGTCAATAAGAG | 21195 |

TABLE 27-4-continued

| Clones | Haruna Nijo H602 | SEQ ID NO: |
|---|---|---|
| baak26j14 | GGAGTCCCCGACGCAATCTTT<br>GGAGTCCCCGCCGCAATCTTT | 21199 |
| baak26j14 | GTCACCTGTCGGTCACTCTGT<br>GTCACCTGTCAGTCACTCTGT | 21200 |
| BaAK37E04 | CGAAGAATGAAGGGGGGAAAA<br>CGAAGAATGATGGGGGGAAAA | 21204 |
| BaAK37E04 | GTGTTCATCTTAAAACAACAC<br>GTGTTCATCTAAAAACAACAC | 21205 |
| BaAK37E04 | CCTTCCTATGACTTCTCGGAT<br>CCTTCCTATGGCTTCTCGGAT | 21206 |
| bast131A0901 | TAGAAACCAACTGGCGAGTTT<br>TAGAAACCAATTGGCGAGTTT | 21210 |
| bah48o03 | CGCAGCAGTCTGCTATCGCGC<br>CGCAGCAGTCGGCTATCGCGC | 21211 |
| bah48o03 | TCGCGCCGTAAGCCTCGGTGC<br>TCGCGCCGTAGGCCTCGGTGC | 21212 |
| bah48o03 | GATCAGTAAGCAGGAAGAAGC<br>GATCAGTAAGTAGGAAGAAGC | 21213 |
| bah20k22 | TATAGGGAACACATTTTCCGT<br>TATAGGGAACGCATTTTCCGT | 21214 |
| bah47a17 | TGCCTCACCATGTGACCAGCC<br>TGCCTCACCAGGTGACCAGCC | 21217 |
| BaH56C11 | TGTCATCCTTTTCATCCTCCT<br>TGTCATCCTTCTCATCCTCCT | 21218 |
| basd15e10 | TGAGCACAACCTGGCATGCCC<br>TGAGCACAACTTGGCATGCCC | 21219 |
| BaH18C17 | GAAGTGTTGTCAACTTCAAAG<br>GAAGTGTTGTAAACTTCAAAG | 21220 |
| BaH18C17 | TTACACCTTTTACCGTCTGAG<br>TTACACCTTTCACCGTCTGAG | 21221 |
| BaH18C17 | CAGCATCTCCTGATGGACAGA<br>CAGCATCTCCAGATGGACAGA | 21222 |
| BaGS20G24 | AAGAATCAGTATATTAGGTGG<br>AAGAATCAGTCTATTAGGTGG | 21223 |
| BaGS20G24 | ATAAAGACCTGGGAAACAAAG<br>ATAAAGACCTAGGAAACAAAG | 21224 |
| bah52h21 | AGCCTCGGGCGTTGCACATGC<br>AGCCTCGGGCATTGCACATGC | 21227 |
| bah52h21 | GGAGGGCCTACCCCGGCCGTG<br>GGAGGGCCTATCCCGGCCGTG | 21228 |
| bah52h21 | AACCACGCTGGCGCTGGAGGG<br>AACCACGCTGACGCTGGAGGG | 21229 |
| bah52h21 | GACGCCACACTATACTGTGTG<br>GACGCCACACGATACTGTGTG | 21230 |
| bah52h21 | GCGGGGGCGGATAGCTGGACC<br>GCGGGGGCGGGTAGCTGGACC | 21231 |

TABLE 27-5

| Clones | Haruna Nijo H602 | SEQ ID NO: |
|---|---|---|
| basd18c12 | ACATCTGGGGGAGCCAAACAG<br>ACATCTGGGGCAGCCAAACAG | 21233 |
| basd18c12 | TCGGCGTTTCATTCGCGTAG<br>TCGGCGTTTCGTTCGCGTAG | 21234 |
| baak23k07 | CAGCTTGACGGCATCAGGCAG<br>CAGCTTGACGACATCAGGCAG | 21235 |
| baak23k07 | AAAAATACACCAGCAGATCTG<br>AAAAATACACAAGCAGATCTG | 21236 |
| BaSD15O17 | ACATCTGACGAGAACAACACA<br>ACATCTGACGGGAACAACACA | 21237 |
| bags16j16 | TAGTACTCTATAGGATTTGAG<br>TAGTACTCTACAGGATTTGAG | 21238 |
| bags16j16 | ATTAGCAGGGTTATCAAATTG<br>ATTAGCAGGGCTATCAAATTG | 21239 |
| bags16j16 | ATAAAGAGAAATTCCTCCAGA<br>ATAAAGAGAATTTCCTCCAGA | 21240 |
| BaGS4N23 | TCGGCAGGTCGTAGTTGATGA<br>TCGGCAGGTCATAGTTGATGA | 21243 |
| basd13i08 | ACTCACTACTGCTGCTCTGCG<br>ACTCACTACTGCTGCTCTGCG | 21246 |
| basd17p01 | ACTCACTACTGCTGCTCTGCG<br>ACTCACTACTACTGCTCTGCG | 21247 |
| baak13d19 | TTACAAGTCAGAGAGAAAATG<br>TTACAAGTCAAAGAGAAAATG | 21248 |
| baak13d19 | ATAGTGTTAAGCATTAACACA<br>ATAGTGTTAAACATTAACACA | 21249 |
| baal3h14 | CACACAAAAGGGGAACCTAGG<br>CACACAAAAGAGGAACCTAGG | 21250 |
| baal3h14 | ATGCAACTAAGATATTGTCAG<br>ATGCAACTAAAATATTGTCAG | 21251 |
| bags33j18 | GCGGTTGCAATGCTCCACGTG<br>GCGGTTGCAACGCTCCACGTG | 21252 |
| baak21n07 | AGCACCTACACTGATCAGTGT<br>AGCACCTACATTGATCAGTGT | 21254 |
| bah53f05 | CATGTATCCAGTTCCATGCTG<br>CATGTATCCACTTCCATGCTG | 21256 |
| bah53f05 | CAAACTATTAGCAAACCTGCA<br>CAAACTATTACCAAACCTGCA | 21257 |
| baak12d02 | CATCGTTCGAGGCAATGACAC<br>CATCGTTCGACGCAATGACAC | 21258 |
| baet01F1212 | CGAACCCGAGCGGGTTGAAGA<br>CGAACCCGAGTGGGTTGAAGA | 21259 |
| bags11h12 | TATGATAGCAAATTGCTTGTA<br>TATGATAGCATATTGCTTGTA | 21260 |
| bags11h12 | GCAACTAGTCTTCTTTATGAT<br>GCAACTAGTCCTCTTTATGAT | 21261 |
| bags11h12 | AATGCTCAGAATTTCCGTAAG<br>AATGCTCAGATTTTCCGTAAG | 21262 |
| bags11h12 | GGCTAGGCCTTGAAGCGCTTG<br>GGCTAGGCCTCGAAGCGCTTG | 21263 |

TABLE 27-6

| Clones | Haruna Nijo H602 | SEQ ID NO: |
|---|---|---|
| baak17l11 | AATGCCACGGTTACTCATTGA<br>AATGCCACGGATACTCATTGA | 21264 |
| baak17l11 | GCCTGGAAAACGCAGTTTTCC<br>GCCTGGAAAAGGCAGTTTTCC | 21265 |
| basd20e17 | GGAGCCAGCGACCGGGAGAGC<br>GGAGCCAGCGGCCGGGAGAGC | 21266 |
| bags30o05 | TTGGAGGAACCTGCGGGTCGA<br>TTGGAGGAACTTGCGGGTCGA | 21267 |
| bags30o05 | AAAGATCGCACGCCACACCAT<br>AAAGATCGCATGCCACACCAT | 21268 |
| bah29p24 | TCTCATACCCTGAACCGTCTT<br>TCTCATACCCCGAACCGTCTT | 21269 |
| kr68d0208 | ATCACTAGTAATGTACATGTT<br>ATCACTAGTAGTGTACATGTT | 21270 |
| bags37l11 | CAGCCATCAACGCAACAAGTG<br>CAGCCATCAATGCAACAAGTG | 21272 |
| bags37l11 | TCATACAGTAGTGTTTTCAAG<br>TCATACAGTAATGTTTTCAAG | 21273 |
| bags37l11 | AACTTCATATGATCGCAAGGT<br>AACTTCATATAATCGCAAGGT | 21274 |
| BaH58I23 | AAAGCAAAGCATTCTTTGAAG<br>AAAGCAAAGCGTTCTTTGAAG | 21275 |
| bags39l04 | GGTCATCCTCGGGGTCTGTCC<br>GGTCATCCTCAGGGTCTGTCC | 21276 |
| bags39l04 | TTCCTCACAATCAGCGCTATG<br>TTCCTCACAAACAGCGCTATG | 21277 |
| bags39l04 | CTTTCCGCTGCAAGGCGGACA<br>CTTTCCGCTGAAAGGCGGACA | 21278 |
| bags39l04 | ATTGAACAGATCGAGTAGAGT<br>ATTGAACAGACCGAGTAGAGT | 21279 |
| bah60p09 | TACACACCAGTGGTCTGAAGA<br>TACACACCAGCGGTCTGAAGA | 21283 |
| bah60p09 | GTTGCCAGAAGATCACAATAA<br>GTTGCCAGAAAATCACAATAA | 21284 |
| bah60p09 | TACCTAGGGGCAGCTTGTTGA<br>TACCTAGGGGTAGCTTGTTGA | 21285 |
| bah22o14 | AGAAGTCTGCGGCAAACCTCA<br>AGAAGTCTGCAGCAAACCTCA | 21289 |
| bah22o14 | GATATTCTTGCGGTTATCTTC<br>GATATTCTTGTGGTTATCTTC | 21290 |
| bah22o14 | TCACGCTGTTTAGGGTAGGCT<br>TCACGCTGTTCAGGGTAGGCT | 21291 |
| bah14l20 | TATATAGTACNCCCTCTGTTC<br>TATATAGTACTCCCTCTGTTC | 21292 |
| bah42p22 | TCCGAAGTGGTTGGCCTTTCA<br>TCCGAAGTGGCTGGCCTTTCA | 21293 |
| bah42p22 | CTTATGCCCAGATTAAAATAC<br>CTTATGCCCACATTAAAATAC | 21294 |
| baak21g03 | CACGTACCCCGTCCTCTTGCT<br>CACGTACCCCATCCTCTTGCT | 21295 |

315

TABLE 27-7

| Clones | Haruna Nijo / H602 | SEQ ID NO: |
|---|---|---|
| baak21g03 | GAATTTTTCAGGTTATATATG<br>GAATTTTTCAAGTTATATATG | 21296 |
| baak21g03 | GCGTGCAGATCATTGAATGTG<br>GCGTGCAGATAATTGAATGTG | 21297 |
| baak21g03 | ATTTAGCACACGATGAAGGGT<br>ATTTAGCACATGATGAAGGGT | 21298 |
| baal35d24 | CTCTCCCGCTGGATAGCGCGC<br>CTCTCCCGCTAGATAGCGCGC | 21299 |
| baal35d24 | AAGAGAGCTGTGGTCATCACG<br>AAGAGAGCTGCGGTCATCACG | 21300 |
| baak45h14 | GGGGACAAGTGGGGTGAGTTT<br>GGGGACAAGTCGGGTGAGTTT | 21301 |
| baak45h14 | GGACCCTGGGTGGGGCTTTG<br>GGACCCTGGCTGGGGCTTTG | 21302 |
| baak45h14 | GCTTTGGGGGCTCCCCTTTCC<br>GCTTTGGGGGGTCCCCTTTCC | 21303 |
| baak45h14 | TTTTTTTTGTCCAAAGGATTT<br>TTTTTTTTGTACAAAGGATTT | 21304 |
| BaAK31P07 | AAACATGACACACCATATATG<br>AAACATGACATACCATATATG | 21305 |
| BaAK31P07 | AAAAATATACTATCACAAATC<br>AAAAATATACAATCACAAATC | 21306 |
| BaAK31P07 | AATCCACAGGTTTTATCTTCG<br>AATCCACAGGGTTTATCTTCG | 21307 |
| bags28o05 | CTTTGTGCACGAGGGCATTAA<br>CTTTGTGCACAAGGGCATTAA | 21308 |
| bah36c06 | CAAGACGCCCGGTCCGGCCAG<br>CAAGACGCCCAGTCCGGCCAG | 21309 |
| bags37h24 | AACTGTCATCGTCAGTCTCAT<br>AACTGTCATCATCAGTCTCAT | 21310 |
| bast65b0303 | AGCAGCAGCAGCAACAACAAC<br>AGCAGCAGCAACAACAACAAC | 21311 |
| BaGS39K23 | ATCTGCGCGCCCGGCCTTTTG<br>ATCTGCGCGCGCGGCCTTTTG | 21312 |
| BaGS39K23 | AAGAACTGACAGAGGACACGA<br>AAGAACTGACGGAGGACACGA | 21313 |
| bah51a22 | TACCCAGTTGCTTCGATGTTT<br>TACCCAGTTGGTTCGATGTTT | 21314 |
| BaH57F12 | CTGCAGGTTGACGGTGCTGGT<br>CTGCAGGTTGTCGGTGCTGGT | 21315 |
| BaH57F12 | TCATCTGAAGGTTCAGTTCCG<br>TCATCTGAAGCTTCAGTTCCG | 21316 |
| BaH57F12 | ATTGTGTGGCGAAACCATCCG<br>ATTGTGTGGCAAAACCATCCG | 21317 |
| basd14o12 | TTATCTACATACCTAGATTTG<br>TTATCTACATCCCTAGATTTG | 21318 |
| basd14o12 | CACCTTTGCATTGGCTCACCA<br>CACCTTTGCAGTGGCTCACCA | 21319 |
| BaAL40N06 | ATCTCCAAACGAACAGCCTCT<br>ATCTCCAAACAAACAGCCTCT | 21321 |

316

TABLE 27-8

| Clones | Haruna Nijo / H602 | SEQ ID NO: |
|---|---|---|
| BaAL40N06 | ACTTGTTTGACAGATTAACTA<br>ACTTGTTTGATAGATTAACTA | 21322 |
| bah11b14 | TTAAAACTAGATAACTGAAAT<br>TTAAAACTAGGTAACTGAAAT | 21323 |
| bah15j14 | AGCACTCCTG-ACTAAAAAGT<br>AGCACTCCTGCACTAAAAAGT | 21324<br>21325 |
| basd21l07 | CAGCAGCTGGCTGTACACCTC<br>CAGCAGCTGGTTGTACACCTC | 21330 |
| bah42d07 | AGAGGTGAAGGACACCGGACG<br>AGAGGTGAAGAACACCGGACG | 21331 |
| bah42d07 | AGCTACCACAGAAGTCCTTTC<br>AGCTACCACAAAAGTCCTTTC | 21332 |
| bah42d07 | CCCATGTCTGGACAACAAAAG<br>CCCATGTCTGCACAACAAAAG | 21333 |
| BaAK24L01 | CTTGCTTAGAGGGACCGATGT<br>CTTGCTTAGATGGACCGATGT | 21334 |
| BaAK24L01 | ATCGAGCTGTGGGCGACGAGG<br>ATCGAGCTGTAGGCGACGAGG | 21335 |
| bags23k24 | TCTTGATGTCGGTCAGTGAAA<br>TCTTGATGTCAGTCAGTGAAA | 21336 |
| BaAL11H22 | TGATGACATCATGCTCCTCTC<br>TGATGACATCGTGCTCCTCTC | 21337 |
| baal6m22 | CAGATGTACACATGGAATGGA<br>CAGATGTACATATGGAATGGA | 21339 |
| basd20p03 | CCCATTTACGAGGGAAGTTCA<br>CCCATTTACGGGGAAGTTCA | 21340 |
| kr59H0416 | CACATGACATAAAATCGCTAA<br>CACATGACATGAAATCGCTAA | 21341 |
| bah19b13 | TACAACATCCGAAGCAGCCAC<br>TACAACATCCAAGGCAGCCAC | 21342 |
| bah19b13 | CAACATCCGAAGCAGCCACAT<br>CAACATCCAAGGCAGCCACAT | 21343 |
| BaGS14A02 | AATGTAAACCGCAGGCTGCTT<br>AATGTAAACCACAGGCTGCTT | 21344 |
| bah61o16 | TATAAGTCCCGTGACACTGCA<br>TATAAGTCCCATGACACTGCA | 21345 |
| bah34p05 | TAATGCATCAGCTACACACTT<br>TAATGCATCAACTACACACTT | 21346 |
| bah24n07 | CCACGAGCACGAAAAGTAGCG<br>CCACGAGCACAAAAAGTAGCG | 21348 |
| bah54b04 | TGCGGCTTCTGCGCCTCCTCA<br>TGCGGCTTCTACGCCTCCTCA | 21349 |
| bah54b04 | GCTTGCTATTCCGAAGTCACT<br>GCTTGCTATTACGAAGTCACT | 21350 |
| bah54b04 | AATAATGACTGCAGACAAAAT<br>AATAATGACTACAGACAAAAT | 21351 |
| baal11h20 | ATGACTCTGGTCCATATTTGT<br>ATGACTCTGGCCCATATTTGT | 21352 |
| basd20m23 | CGTATGTAGATATCTAGTGAA<br>CGTATGTAGACATCTAGTGAA | 21354 |

TABLE 27-9

| Clones | Haruna Nijo / H602 | SEQ ID NO: |
|---|---|---|
| basd20m23 | AGTATAGATTTATTCATTTTG<br>AGTATAGATTCATTCATTTTG | 21355 |
| basd20m23 | ATATAAGTCTCTCTAGAGGTT<br>ATATAAGTCTTTCTAGAGGTT | 21356 |
| basd20m23 | AGGACCTGCTCTTGTTGAACG<br>AGGACCTGCTTTTGTTGAACG | 21357 |
| baal15d09 | GGTTGATCTCCGCTTGGCTTC<br>GGTTGATCTCTGCTTGGCTTC | 21358 |
| baak39n20 | TGACATCCTCGAACCCTGCCT<br>TGACATCCTCAAACCCTGCCT | 21359 |
| bah43n16 | AACTCCTCTTCCTCGGATACG<br>AACTCCTCTTTCTCGGATACG | 21361 |
| basd22c03 | TGTATGTAAGCAGCTTGTTCC<br>TGTATGTAAGTAGCTTGTTCC | 21363 |
| kr47F0511 | CATAACATCAATGATAAACGA<br>CATAACATCAGTGATAAACGA | 21364 |
| kr47F0511 | AGCTTCTTGTCCCCTCCTCCT<br>AGCTTCTTGTTCCCTCCTCCT | 21365 |
| bast77a0402 | ATCATCTAACCCATATAACCA<br>ATCATCTAACGCATATAACCA | 21366 |
| bah58f04 | CACTCTCCTCGAGATTAAATA<br>CACTCTCCTCAAGATTAAATA | 21367 |
| kr39G1113 | GTGTTTTTGGATATGATCTGA<br>GTGTTTTTGGGTATGATCTGA | 21368 |
| baak30109 | TGCCCATCATGATTCATCAGA<br>TGCCCATCATCATTCATCAGA | 21369 |
| baak1c16 | TCCGCAAAAAACACACTATA<br>TCCGCAAAAACACACTATA | 21370 |
| BaAK12F18 | AATTCTTAGCCATGAATACAA<br>AATTCTTAGCAATGAATACAA | 21371 |
| BaAK12F18 | CCTTGGGGTCAATGCCGTCGA<br>CCTTGGGGTCCATGCCGTCGA | 21372 |
| BaAK12F18 | GGTGCAGCCAAGCTGACGCAG<br>GGTGCAGCCACGCTGACGCAG | 21373 |
| BaAK12F18 | TCTTAAGCGGAGATCTCAACC<br>TCTTAAGCGGGGATCTCAACC | 21374 |
| BaAK12F18 | TATAAGTCACACCATCCCTAA<br>TATAAGTCACGCCATCCCTAA | 21375 |
| BaAK12F18 | GGGCTAGCATGAGCATACAAT<br>GGGCTAGCATAAGCATACAAT | 21376 |
| basd20e05 | ATTCAGAGAGGGAGATGCAGT<br>ATTCAGAGAGAGAGATGCAGT | 21377 |
| basd20e05 | AGCAGAAATATCATCAACTGG<br>AGCAGAAATACCATCAACTGG | 21378 |
| basd20e05 | TTAGCGTCATCGTGTTCCCTT<br>TTAGCGTCATAGTGTTCCCTT | 21379 |
| baal17d05 | TATCACAACTCGATATTCCAT<br>TATCACAACTGGATATTCCAT | 21382 |
| baal17d05 | CATGTATACTCTCTGCATGCA<br>CATGTATACTTTCTGCATGCA | 21383 |

TABLE 27-10

| Clones | Haruna Nijo / H602 | SEQ ID NO: |
|---|---|---|
| baal17d05 | AAGACTGACTCACTTAGAAAA<br>AAGACTGACTGACTTAGAAAA | 21384 |
| bast70d0107 | TAATAATGTTCAACTTCAATA<br>TAATAATGTTGAACTTCAATA | 21385 |
| baak46g03 | TGGCAAACACAGATTATAAC<br>TGGCAAACACGGATTATAAC | 21386 |
| bah63m17 | TGAGCAGTTACACTAAAGAGA<br>TGAGCAGTTATACTAAAGAGA | 21387 |
| bah63m17 | TCTCACGTGGACTGAGATAAC<br>TCTCACGTGGGCTGAGATAAC | 21388 |
| bah15l15 | AGACAACCACGTGAGAGCAGC<br>AGACAACCACATGAGAGCAGC | 21389 |
| bah15l15 | TGATCCCGTTCGCGTCGAGGT<br>TGATCCCGTTGGCGTCGAGGT | 21390 |
| bags19n01 | GCAAAATTCACGATTTTAAGA<br>GCAAAATTCAGGATTTTAAGA | 21391 |
| bags19n01 | AAGAGAAAAACATTACAAGCT<br>AAGAGAAAAAGATTACAAGCT | 21392 |
| bags19n01 | CGTAGTACAAAAGTATCAAGA<br>CGTAGTACAACAGTATCAAGA | 21393 |
| baak32p07 | AACAATGACAGCTTTGGCTGG<br>AACAATGACACCTTTGGCTGG | 21394 |
| baak32p07 | CAGAAAATGGCTTTATTGATT<br>CAGAAAATGGATTTATTGATT | 21395 |
| bags14l13 | AAATGAGTAGCGACATGCCAG<br>AAATGAGTAGGGACATGCCAG | 21396 |
| bags14l13 | TAAGAAGGCAAATAACTGGTA<br>TAAGAAGGCAGATAACTGGTA | 21397 |
| bags14l13 | TACCCGCGGTTGCAAGCTCCT<br>TACCCGCGGTCGCAAGCTCCT | 21398 |
| bags14l13 | GACAGAAAGATGTTCATGGTT<br>GACAGAAAGACGTTCATGGTT | 21399 |
| bags37o24 | ACACAAAACAGAGCAAATGTG<br>ACACAAAACAAAGCAAATGTG | 21400 |
| bags37o24 | TTAAGTTCTAGCTGATTGAAA<br>TTAAGTTCTATCTGATTGAAA | 21401 |
| bags37o24 | CGGACATGTAGCTGTATCAAC<br>CGGACATGTAACTGTATCAAC | 21402 |
| baal27m03 | AAACAGGGGANAGGGACAACC<br>AAACAGGGGAGAGGGACAACC | 21406 |
| baal27m03 | CTTTCACCGTCTGAGGGCATG<br>CTTTCACCGTTTGAGGGCATG | 21407 |
| baal27m03 | GCTCAGCTGCNAGGAAAATAA<br>GCTCAGCTGCAAGGAAAATAA | 21408 |
| baal27m03 | GGGCATCAGCNGATCGAGCTA<br>GGGCATCAGCCGATCGAGCTA | 21409 |
| baal27m03 | TCATATCACTGATTGGGAAC<br>TCATATCACTTATTGGGAAC | 21410 |
| BaAK1C18 | ACTATGCACTGGTATATAACT<br>ACTATGCACTAGTATATAACT | 21411 |

TABLE 27-11

| Clones | Haruna Nijo H602 | SEQ ID NO: |
|---|---|---|
| BaAK1C18 | GCGACCCTTGTTGGGGGCAAC<br>GCGACCCTTGCTGGGGGCAAC | 21412 |
| bah52b11 | TCTATGGAAA-TACATGGAAG<br>TCTATGGAAAATACATGGAAG | 21416<br>21417 |
| bah27f05 | CGAGATGTACGCTCTGCCGAC<br>CGAGATGTACCCTCTGCCGAC | 21419 |
| bah59c10 | ACGAGAAACTAAATGAAATC<br>ACGAGAAACCAAATGAAATC | 21420 |
| basd14e01 | CCTCGCCGTAGGCCGCGATGT<br>CCTCGCCGTAAGCCGCGATGT | 21421 |
| basd14e01 | TGATGTCGGCCGTCTCGTGCT<br>TGATGTCGGCTGTCTCGTGCT | 21422 |
| basd14e01 | CACACGGCGATCGGAGCTTCA<br>CACACGGCGACCGGAGCTTCA | 21423 |
| bags38j06 | GTTTCCTCTACTGTAACGGAT<br>GTTTCCTCTAGTGTAACGGAT | 21424 |
| bags38j06 | AATAGATTGTGTGAATTTGTG<br>AATAGATTGTTTGAATTTGTG | 21425 |
| basd18e06 | CCTCTTTATTCTCATCTCCTC<br>CCTCTTTATTTTCATCTCCTC | 21429 |
| basd18e06 | TGGTGTTGACAGCGAGCTTGA<br>TGGTGTTGACGGCGAGCTTGA | 21430 |
| basd18e06 | AGTAGAGCCGTCGGAACTCAA<br>AGTAGAGCCGGCGGAACTCAA | 21431 |
| baak16e08 | AAGGGGAAGGTTCACGTGCAG<br>AAGGGGAAGGCTCACGTGCAG | 21432 |
| basd2o16 | TCAAAACAAACAAGCTCCGTC<br>TCAAAACAAAGAAGCTCCGTC | 21433 |
| basd2o16 | GGACAGGGTAGAAGGGTAGAG<br>GGACAGGGTACAAGGGTAGAG | 21434 |
| basd2o16 | TTGAAGGGGATCTGCTTCTTG<br>TTGAAGGGGAACTGCTTCTTG | 21435 |
| basd2o16 | CTTGAAACGGATCCGGAACAG<br>CTTGAAACGGTTCCGGAACAG | 21436 |
| bags18h01 | GAAACAGATTGTTAAAAGATT<br>GAAACAGATTTTTAAAAGATT | 21437 |
| bags18h01 | CGATTTAGTATTTCCCTGGT<br>CGATTTAGTAATTCCCTGGT | 21438 |
| bags18h01 | ACACACAAAACAGAAAACAAC<br>ACACACAAAAAAGAAAACAAC | 21439 |
| bags4l20 | GGAAATTTTACCTGCCTCGAT<br>GGAAATTTTATCTGCCTCGAT | 21441 |
| bah30j08 | TTATTGTCTGTTTGTCACATG<br>TTATTGTCTGCTTGTCACATG | 21450 |
| bah30j08 | GGATTTCTGTCCTCATGAAAG<br>GGATTTCTGTGCTCATGAAAG | 21451 |
| bah30j08 | AGGGAACATTGGAATCAGCCA<br>AGGGAACATTAGAATCAGCCA | 21452 |
| bah30j08 | TGAATTAACCATACGGCTAAT<br>TGAATTAACCGTACGGCTAAT | 21453 |

TABLE 27-12

| Clones | Haruna Niio H602 | SEQ ID NO.: |
|---|---|---|
| bah30j08 | GCATTCTCGGTCACCGCCTTG<br>GCATTCTCGGGCACCGCCTTG | 21454 |
| bah30j08 | GCTTCGCTGCGTCTGAATTAA<br>GCTTCGCTGCCTCTGAATTAA | 21455 |
| bast22G0313 | TTCTAGTTACAGGTCTTCAGC<br>TTCTAGTTACGGGTCTTCAGC | 21456 |
| bags33n21 | CACCTGCGCTCTAACATCCTT<br>CACCTGCGCTGTAACATCCTT | 21458 |
| bags33n21 | AAACAAGTAATTGATACAGTC<br>AAACAAGTAACTGATACAGTC | 21459 |
| bags33n21 | CAAACTTTCCAGGGGGGCAAA<br>CAAACTTTCCCGGGGGGCAAA | 21460 |
| baak33c11 | ATCTATTCCTTCAAATTTTGA<br>ATCTATTCCTTCAAATTTTGA | 21461 |
| baak33c11 | TCCATCACTCGGAGCATATTC<br>TCCATCACTCCGAGCATATTC | 21462 |
| BaH36P06 | CATCTCCGGCAGTCTCAACAG<br>CATCTCCGGCCGTCTCAACAG | 21464 |
| BaH36P06 | GATATGAATCGGGAGTTGTTG<br>GATATGAATCAGGAGTTGTTG | 21465 |
| BaH36P06 | TGTTTCTTTTCGATTAAATCA<br>TGTTTCTTTTTGATTAAATCA | 21466 |
| BaH36P06 | GTACCATCCGGGCAAGAATCG<br>GTACCATCCGAGCAAGAATCG | 21467 |
| baet25H0115 | TCTCAGCGGCTCCATGGTGTG<br>TCTCAGCGGCCCCATGGTGTG | 21468 |
| bald12l01 | CGCTTCACAGACGCAAAACAC<br>CGCTTCACAGGCGCAAAACAC | 21469 |
| basd12l01 | TGCCCGACGCTTCCAAGATCT<br>TGCCCGACGCATCCAAGATCT | 21470 |
| BaAK29I15 | CCGTGCCGACGTGTGCTTGCT<br>CCGTGCCGACATGTGCTTGCT | 21474 |
| BaAK29I15 | TCCGGTGTGTCCGTGCTGCCC<br>TCCGGTGTGTACGTGCTGCCC | 21475 |
| bast62B0404 | GGCGGGTACAGACAAGCAACC<br>GGCGGGTACATACAAGCAACC | 21476 |
| bast62B0404 | ATCTCCATCTTATTATTCTGC<br>ATCTCCATCTCATTATTCTGC | 21477 |
| bast62B0404 | AAGTTTCAAGTAGCTGCCGCT<br>AAGTTTCAAGCAGCTGCCGCT | 21478 |
| baak18i01 | AAGAAATGATACCCAAATTGA<br>AAGAAATGATCCCCAAATTGA | 21479 |
| baak18i01 | AATGATTAGGCGGCTATCAGG<br>AATGATTAGGGGGCTATCAGG | 21480 |
| bah25l03 | CTGCGAGCTCAACCGATGATT<br>CTGCGAGCTCGACCGATGATT | 21482 |
| bah25l03 | TGTGAGCCTCGCTGCCTTTAC<br>TGTGAGCCTCACTGCCTTTAC | 21483 |
| bah25l03 | AAACCAAAGAAGCGGCACAC<br>AAACCAAAGCAGCGGCACAC | 21484 |

TABLE 27-13

| Clones | Haruna Niio H602 | SEQ ID NO: |
|---|---|---|
| bah25l03 | TTGATCAATAGTAGAAACTCA<br>TTGATCAATACTAGAAACTCA | 21485 |
| bah25l03 | AACATGTATATGAAAGATCA<br>AACATGTATACGAAAGATCA | 21486 |
| bah25l03 | ATGATTACAAGAAGATCGGAG<br>ATGATTACAAAAAGATCGGAG | 21487 |
| bah25l03 | TCGCATGATCGTTAAGAATGA<br>TCGCATGATCATTAAGAATGA | 21488 |
| baa1n11 | GCAAGCCCTTGCAATACCGTA<br>GCAAGCCCTTTCAATACCGTA | 21489 |
| baak16l07 | TTCCTTATGGGCAGTGAGCAG<br>TACGTTATGGACAGTGAGCAG | 21490 |
| baal13c18 | TTACTTTGCATCGTTGATGAC<br>TTACTTTGCACCGTTGATGAC | 21494 |
| baal13c18 | GAGCGCTGGTGTTAGACGA<br>GAGCGCTGGTATTGTAGACGA | 21495 |
| baal13c18 | GAACAAATGACAGAATTTTC<br>GAACAAATGAAAGAATTTTC | 21496 |

TABLE 27-13-continued

| Clones | Haruna Niio H602 | SEQ ID NO: |
|---|---|---|
| baal13c18 | CATGCACATTGTAGCTACGTA CATGCACATTATAGCTACGTA | 21497 |
| baal13c18 | TGACGGCCCATATAAGAAGCC TGACGGCCCAGATAAGAAGCC | 21498 |
| baal13c18 | TGAGTCCACTGTCAGTGAAAA TGAGTCCACTTTCAGTGAAAA | 21499 |
| baak29k23 | ACCTCCTTTTGAAATTCATAT ACCTCCTTTTCAAATTCATAT | 21500 |
| baak29k23 | GAGCGCTGGTGTTGTAGACGA GAGCGCTGGTGTATTGTAGACGA | 21501 |
| baak29k23 | CATGCACATTGTAGCTACGTA CATGCACATTATAGCTACGTA | 21502 |
| bags7d17 | CATGGTGTCAGCTTTAATATA CATGGTGTCAGCTTTAATATA | 21503 |
| bags7d17 | GCAAGCTTGTTAGGTTAAACT GCAAGCTTGTCAGGTTAAACT | 21504 |
| bags7d17 | ACTTGTACAAAGGCAAGCTTG ACTTGTACAAAGGGCAAGCTTG | 21505 |
| bags7d17 | CTTTAATATACGCTCGAAGCA CTTTAATATATGCTCGAAGCA | 21506 |
| bags7d17 | CTATCATCTCGGAAATGTTTG CTATCATCTCAGAAATGTTTG | 21507 |
| bags7d17 | TTGCCTGTGAAGTCTATCTTG TTGCCTGTGAAGTCTATCTTG | 21508 |
| bags7d17 | CTAATCTGCAGCTCTGCTTTG CTAATCTGCAGCTCTGCTTTG | 21509 |
| bags7d17 | GAAATGTTTGCTGGCAGCATG GAAATGTTTGGCTGGCAGCATG | 21510 |
| baal9c20 | CACACAAAATCTCACGATGTC CACACAAAATTTCACGATGTC | 21511 |
| baal9c20 | GTATGGGGCAAGGAGGGAAGA GTATGGGGCATGGAGGGAAGA | 21512 |

TABLE 27-14

| Clones | Haruna Niio H602 | SEQ ID NO: |
|---|---|---|
| baal9c20 | TGTTACCGTGATTTCTCATCT TGTTACCGTGGTTTCTCATCT | 21513 |
| bags20j08 | TGTTTGTATCATTACTTGTAG TGTTTGTATCCTTACTTGTAG | 21514 |
| bags20l05 | TAACGAGTCATCCACCGACGG TAACGAGTCAGCCACCGACGG | 21515 |
| bags20l05 | TTGTAAGTTCGACAGGTTACT TTGTAAGTTCCACAGGTTACT | 21516 |
| bags20l05 | CCAGTACAAACGGGAAGTTAG CCAGTACAAAAGGGAAGTTAG | 21517 |
| bags20l05 | CACCTGATGCGACAGGATGCT CACCTGATGCAACAGGATGCT | 21518 |
| baal15j23 | AAGTCATCAGTTGCTTACCAG AAGTCATCAGATGCTTACCAG | 21520 |
| baal15j23 | CATAACATTTGATTTGAACAA CATAACATTTTATTTGAACAA | 21521 |
| baal15j23 | TGTGTGTGTGTGCGCGCTTGG TGTGTGTGTGCGCGCGCTTGG | 21522 |
| baal15j23 | CGTATTGGATTTGGTCAGAGT CGTATTGGATGTGGTCAGAGT | 21523 |
| baal15j23 | TAACATGAGAAAGGATATATT TAACATGAGAGAGGATATATT | 21524 |
| BaGS37E11 | GACGGTCACCAAGGGGAAACT GACGGTCACCAGGGGGAAACT | 21528 |
| bah50l14 | GCTCCTGGCCCGTTCGCTGCA GCTCCTGGCCCTGTTCGCTGCA | 21529 |
| BaSD27E20 | GCTCCATGGCAGTGTTCACGT GCTCCATGGCCGTGTTCACGT | 21530 |
| BaSD27E20 | CGGCGTTGTCGAGGGTATTGC CGGCGTTGTCAAGGGTATTGC | 21531 |
| basd17f18 | TATATATACCGTAGTTTGTAA TATATATACCATAGTTTGTAA | 21532 |
| basd17f18 | ATCCCTAAAAAGGGATAATTT ATCCCTAAAATGGGATAATTT | 21533 |
| basd17f18 | CACCGCCGCTGTTCCCCGCAG CACCGCCGCTGTTCCCCGCAG | 21534 |

TABLE 27-14-continued

| Clones | Haruna Niio H602 | SEQ ID NO: |
|---|---|---|
| basd17f18 | GAAATACTCAGAAATAAACCA GAAATACTCAAAAATAAACCA | 21535 |
| basd17f18 | GAGATTGTGTTGACAGAAATA GAGATTGTGTCGACAGAAATA | 21536 |
| basd17f18 | AACAGGTGACTAATGAGATTG AACAGGTGACCAATGAGATTG | 21537 |
| BaSD12L12 | CCGACCATGTTGATAATGANN CCGACCATGTGNATAATGANN | 21538 |
| baal32m04 | TGTTACCGTAGATGTTACCTC TGTTACCGTAAATGTTACCTC | 21539 |
| baal32m04 | TTCACTTGGGAAGACATCTC TTCACTTGGGGAAGACATCTC | 21540 |
| baal32m04 | AGGAGTTGATCATCTGTCAGG AGGAGTTGATGATCTGTCAGG | 21541 |

TABLE 27-15

| Clones | Haruna Niio H602 | SEQ ID NO: |
|---|---|---|
| baal32m04 | CTGCGTGCCAGATCCTGCTCT CTGCGTGCCAGATCCTGCTCT | 21542 |
| baal32m04 | CTGCTCTAGTAATAACAGGGT CTGCTCTAGTCATAACAGGGT | 21543 |
| BaAK24G10 | ATGCTTAACACAAGTCATATC ATGCTTAACATAAGTCATATC | 21547 |
| bah50f16 | ATCTCACTGTCATATATCTTT ATCTCACTGTTATATATCTTT | 21549 |
| bah50f16 | CAACAAAGCAAATTGCCTGTG CAACAAAGCATATTGCCTGTG | 21550 |
| bah50f16 | CCTTCGGCCTACTAGGTATAT CCTTCGGCCTGCTAGGTATAT | 21551 |
| bah50f16 | AGCTTGGTGCGCCAAAATCCC AGCTTGGTGCACCAAAATCCC | 21552 |
| basd17d11 | ACCACCTCAAGAGAACGCGCA ACCACCTCAATAGAACGCGCA | 21553 |
| basd17d11 | ATGCTTGAGAATTGTAACCGT ATGCTTGAGACTTGTAACCGT | 21554 |
| bah37p24 | GCATTGGTAGTCAAATGTCAT GCATTGGTAGCCAAATGTCAT | 21555 |
| bah37p24 | AGCAGAGCAGCTTACGGAAGA AGCAGAGCAGATTACGGAAGA | 21556 |
| baet45C1105 | CAGGATGGACGGTGAAACATA CAGGATGGACTGTGAAACATA | 21557 |
| baet45C1105 | AGAAAAAGAAGAACTTTCAGA AGAAAAAGAAAAACTTTCAGA | 21558 |
| baet45C1105 | ATTATCTGTACGTACATAACG ATTATCTGTATGTACATAACG | 21559 |
| baet45C1105 | GAAACCGAAGGGCGGCTAGTC GAAACCGAAGTGCGGCTAGTC | 21560 |
| baet45C1105 | ATTTGTCCTCAGGGTTCATCT ATTGTCCTCGGGGTTCATCT | 21561 |
| bah47l21 | TTGCCTTGAAGGCAAACCTTG TTGCCTTGAATGCAAACCTTG | 21562 |
| bah47l21 | CATTCTCTTCGTGCGAAACTA CATTCTCTTCATGCGAAACTA | 21563 |
| bah47l21 | TCCACCCGTCGGTCCTTTGCT TCCACCCGTCTGTCCTTTGCT | 21564 |
| bah47l21 | ACACCTCGCCATCGTCGCCGC ACACCTCGCCGTCGTCGCCGC | 21565 |
| baak14b08 | TGTGACATGATAGCTCACCTC TGTGACATGAGAGCTCACCTC | 21569 |
| baak14b08 | CACAATCTGCGTCATACAGAA CACAATCTGCATCATACAGAA | 21570 |
| baak14b08 | AGCCTTTTGTATTTCATAGAA AGCCTTTTGTGTTTCATAGAA | 21571 |
| baak14b08 | GAGAGTAGAAGAGAGAGAGCA GAGAGTAGAAAAGAGAGAGCA | 21572 |
| bah54n10 | CCGTGGCGTAACGGCACCTTT CCGTGGCGTAGCGGCACCTTT | 21573 |

TABLE 27-16

| Clones | Haruna Niio H602 | SEQ ID NO: |
|---|---|---|
| bah54n10 | CAGTTTGGTTACGAAAGGTAA<br>CAGTTTGGTTTCGAAAGGTAA | 21574 |
| bags34p08 | CGCGGTTGCCATGCAACATGT<br>CGCGGTTGCCGTGCAACATGT | 21576 |
| bags34p08 | ACCGGCCAGAAAAAAAATCCC<br>ACCGGCCAGGGAAAAAATCCC | 21577 |
| baal1e06 | ATCATCACCTCGTAGCAGGAT<br>ATCATCACCTTGTAGCAGGAT | 21578 |
| baal1e06 | GAGCACAGGCCAGANAATTAC<br>GAGCACAGGCNAGANAATTAC | 21579 |
| baak14k12 | GCATCCGCTGAGGCTGGTCA<br>GCATCCGCTGGGGCTGGTCA | 21581 |
| baak14k12 | GCACCCTTGTTATCGTCCAAC<br>GCACCCTTGTCATCGTCCAAC | 21582 |
| baal6a21 | ACCCGATCGGAAGCGGCGCCA<br>ACCCGATCGGCAGCGGCGCCA | 21588 |
| baal29l09 | CCACTGCCAAATTTCAAGAAG<br>CCACTGCCAAGTTTCAAGAAG | 21593 |
| baal29l09 | TAAGAAGACTTCATCCACAGT<br>TAAGAAGACTGCATCCACAGT | 21591 |
| bastl47C0606 | ATTTCTGAATTCCTCTTCCTC<br>ATTTCTGAATGCCTCTTCCTC | 21592 |
| kr66d1107 | TAATTTCAATGTCACATCCAG<br>TAATTTCAATTTCACATCCAG | 21593 |
| bah50m03 | TGGGCGTGGTGGGCAACCCGT<br>TGGGCGTGGTCGGCAACCCGT | 21594 |
| basd27k17 | GTGAGCGATAGGCATGAGCAT<br>GTGAGCGATATGCATGAGCAT | 21595 |
| basd27k17 | AGGATCACCCGGGCTTTCCTC<br>AGGATCACCCCGGCTTTCCTC | 21596 |
| basd27k17 | ACCTCCATGTCTGACCTGACA<br>ACCTCCATGTGTGACCTGACA | 21597 |

TABLE 28-1

| Clones | Haruna Niio H602 | SEQ ID NO: |
|---|---|---|
| basd2p19 | ATAGCAGCAGGATCACTTCAC<br>ATAGCAGCAG-ATCACTTCAC | 21598<br>21599 |
| bags6f02 | CTGAGACTGCGGGCGACACAC<br>CTGAGACTGCAGGCGACACAC | 21601 |
| bags6f02 | CGACACACGCGACAAGAACAG<br>CGACACACGCAACAAGAACAG | 21602 |
| bags6f02 | GGGTCCGCCGCCGCAGCCCCC<br>GGGTCCGCCGTCGCAGCCCCC | 21603 |
| bags6f02 | CACGCCCACCGGGCTCTGCAG<br>CACGCCCACCAGGCTCTGCAG | 21604 |
| baak39j07 | CGTCCATGGATACAGAACATG<br>CGTCCATGGACACAGAACATG | 21605 |
| BaAK1L23 | AANATGTGATTCCTATANNNN<br>AANATGTGAT-CCTATANNNN | 21606<br>21607 |
| BaAK1L23 | CCACTCTTGANCACATCTTCA<br>CCACTCTTGAGCACATCTTCA | 21608 |
| BaAK1L23 | TCTTGATGACAATCATGTGTT<br>TCTTGATGACGATCATGTGTT | 21609 |
| baak17e10 | CCAGCATGATGTTGATGGAGG<br>CCAGCATGATATTGATGGAGG | 21610 |
| baak17e10 | TTTGGTGTAAGAAGGAAGAAA<br>TTTGGTGTAACAAGGAAGAAA | 21611 |
| baak17e10 | TGCAGGTGCCGCCCAGCATGA<br>TGCAGGTGCCTCCCAGCATGA | 21612 |
| bah50h08 | TGCTGGTTCCCGGGATCGAGC<br>TGCTGGTTCCGGGGATCGAGC | 21613 |
| bah50h08 | CTCCGTGCGGCGGCTGGTCAG<br>CTCCGTGCGGTGGCTGGTCAG | 21614 |
| baall7e10 | TCATGCTCGTTTACGAGTATC<br>TCATGCTCGTCTACGAGTATC | 21615 |
| basd17c05 | ATTTCATTTACAAAAACATAC<br>ATTTCATTTATAAAAACATAC | 21616 |
| basd17c05 | ACCTCTGTACCATAATATAAG<br>ACCTCTGTACCATAATATAAG | 21617 |
| basd17c05 | AAAGAACACAGACAAAAAACC<br>AAAGAACACATACAAAAAACC | 21618 |

TABLE 28-1-continued

| Clones | Haruna Niio H602 | SEQ ID NO: |
|---|---|---|
| basd17c05 | GAAGCATTGATTCAAAGCCTG<br>GAAGCATTGAATCAAAGCCTG | 21619 |
| basd17c05 | AGGCGTGTCACAGAGAAGCAT<br>AGGCGTGTCATAGAGAAGCAT | 21620 |
| bags14p02 | CCCCCGCCGCGGCATAGATGG<br>CCCCCGCCGCTGCATAGATGG | 21621 |
| bags14p02 | TTGTTGAACAGGTAGACCCCC<br>TTGTTGAACAAGTAGACCCCC | 21622 |
| bastl42H0115 | TTGTTCATCCCATCACATCCC<br>TTGTTCATCCAATCACATCCC | 21623 |
| bastl42H0115 | CCGACATCATATTATTTATCT<br>CCGACATCATGTTATTTATCT | 21624 |
| baak19c08 | TTGTTGTAAGTGATCAGTCTA<br>TTGTTGTAAGCGATCAGTCTA | 21625 |

TABLE 28-2

| Clones | Haruna Niio H602 | SEQ ID NO: |
|---|---|---|
| baak19c08 | CGCCCATCACGAAGCTCTGCA<br>CGCCCATCACAAAGCTCTGCA | 21626 |
| bastl40h1115 | GCTCACCGCCGTGACGAAAAC<br>GCTCACCGCCATGACGAAAAC | 21627 |
| bastl40h1115 | CTTGAAATGCGTAGATTTGTG<br>CTTGAAATGCATAGATTTGTG | 21628 |
| BaAK21P12 | GGATCGCCCCGCCCTCTGGAA<br>GGATCGCCCCACCCTCTGGAA | 21632 |
| bast79C0406 | AATCAAACTCCAGAGAAGGAA<br>AATCAAACTCAAGAGAAGGAA | 21635 |
| bah45m08 | TAGGCGGCGATGCTGCAACAT<br>TAGGCGGCGACGCTGCAACAT | 21636 |
| kr28a0301 | CTATTCAGTCCCTCCTACAA<br>CTATTCAGTCACCTCCTACAA | 21637 |
| kr28a0301 | TTTGGTTCTGCCTTTGTTTA<br>TTTGGTTCTCACCTTTGTTTA | 21638 |
| kr28a0301 | CCAGTTTTAGCTTCTCATGTG<br>CCACTTTTAGGTTCTCATGTG | 21639 |
| kr28a0301 | CTCCCCTGTCGGTGGATTATA<br>CTCCCCTGTCAGTGGATTATA | 21640 |
| kr28a0301 | TTGTGTTGTTATGTTAGGATT<br>TTGTGTTGTTGTGTTAGGATT | 21641 |
| kr28a0301 | GGCATGTTTTGAATGTGAAAA<br>GGCATGTTTTCAATGTGAAAA | 21642 |
| baak21l22 | AACAGCTAAGCGTATTTGGGC<br>AACAGCTAAGGGTATTTGGGC | 21646 |
| baak21l22 | TTTCAGAAGCGGATTGAAACT<br>TTTCAGAAGCAGATTGAAACT | 21647 |
| baak21l22 | CTTTAGAAGAGCTACCTCACC<br>CTTTAGAAGAACTACCTCACC | 21648 |
| baak21l22 | TTCAGGCACAGACATCAGGTA<br>TTCAGGCACAAACATCAGGTA | 21649 |
| basd15h01 | GGTTGATGGCGACCCACAGCA<br>GGTTGATGGCAACCCACAGCA | 21650 |
| basd15h01 | GGCCCTTGGCGAACGGGTACA<br>GGCCCTTGGCCAACGGGTACA | 21651 |
| basd15h01 | AGTTCTGGGATGGCGGGTTGA<br>AGTTCTGGGACGGCGGGTTGA | 21652 |
| basd15h01 | CGGCGAACTCATCGTTTTCGT<br>CGGCGAACTCGTCGTTTTCGT | 21653 |
| bah19o11 | CAGCAGACAAGATGGGGAAG<br>CAGCAGACAATATGGGGAAG | 21654 |
| bah19o11 | TGACGAGGGGAGCGGGCTCAG<br>TGACGAGGGCAGCGGGCTCAG | 21655 |
| bah19o11 | ATCATCATCACCATCAATCTC<br>ATCATCATCATCATCAATCTC | 21656 |
| bags39l05 | ACTGCGAGGATCTTAGCAGTA<br>ACTGCGAGGACTTAGCAGTA | 21658 |
| bags39l05 | CTGATAGATAGGGAGTTTACC<br>CTGATAGATATGGAGTTTACC | 21659 |

TABLE 28-3

| Clones | Haruna Niio H602 | SEQ ID NO: |
|---|---|---|
| bags39l05 | CAAGCAAACAGCCAATGGTCA CAAGCAAACAACCAATGGTCA | 21660 |
| bags39l05 | AGCAGAAAAACAATGTTTAAT AGCAGAAAAATAATGTTTAAT | 21661 |
| BaH58P03 | TTGTTGTTGTCCACGGAAGAA TTGTTGTTGTACACGGAAGAA | 21663 |
| BaH58P03 | ATCAAGATTGTTAGCAGGACG ATCAAGATTGGTAGCAGGACG | 21664 |
| BaH58P03 | ACCACTTGAAATATCTTACTT ACCACTTGAAGTATCTTACTT | 21665 |
| BaAL4O04 | TTATTGTGGTTGGGGTGGTGG TTATTGTGGTCGGGGTGGTGG | 21667 |
| BaAL4O04 | GATGGATGGCGGAAGGGCGGG GATGGATGGCAGAAGGGCGGG | 21668 |
| BaAL4O04 | CACAACACAAACGATGAAAGA CACAACACAAGCGATGAAAGA | 21669 |
| baak14c23 | AGTAGGCCATACTGGCTGGCG AGTAGGCCATGCTGGCTGGCG | 21671 |
| baak14c23 | TCCAGTTTGCGAAGGACGGCT TCCAGTTTGCCAAGGACGGCT | 21672 |
| kr61A1101 | CTATAAACACAAACAAGACTC CTATAAACACGAACAAGACTC | 21673 |
| kr61A1101 | TCGCAAATATAAGAAAGAAGC TCGCAAATATTAGAAAGAAGC | 21674 |
| BaH42J17 | GATGGATGGCGGAAGGGCGGG GATGGATGGCAGAAGGGCGGG | 21675 |
| BaH42J17 | TTATTGTGGTTGGGGTGGTGG TTATTGTGGTGGGGTGGTGG | 21676 |
| BaH42J17 | CGAGCTTCCTGTGGAGGAGAG CGAGCTTCCTTTGGAGGAGAG | 21677 |
| bah58h08 | TGTTGGACAGGAAATCGTACG TGTTGGACAGCAAATCGTACG | 21678 |
| bah58h08 | GTACGTGACAGCTGACAAGAC GTACGTGACAACTGACAAGAC | 21679 |
| bast78a0202 | GCGCTCTCCCGGAGCTCCAGC GCGCTCTCCCAGAGCTCCAGC | 21680 |
| BaSD18O16 | TGCTTCTGCATATATGTCTTA TGCTTCTGCACATATGTCTTA | 21682 |
| baak22j11 | GCTCACATCAGTGACCGCCGC GCTCACATCAATGACCGCCGC | 21683 |
| baak22j11 | GTGGAGGCGGTGCTCCATGGC GTGGAGGCGGGGCTCCATGGC | 21684 |
| baak22j11 | CCGCCTCCGTCTTCTCGGCCA CCGCCTCCGTTTTCTCGGCCA | 21685 |
| baak22j11 | CCCGCTCGTGCGCCAGCTCAC CCCGCTCGTGAGCCAGCTCAC | 21686 |
| baak20k04 | GGCTCGCAATGCCCAGGTACC GGCTCCCAATTCCCAGGTACC | 21687 |
| baak20k04 | ATCAAGCCGGACAGCAGCCAG ATCAAGCCGGCCAGCAGCCAG | 21688 |

TABLE 28-4

| Clones | Haruna Niio H602 | SEQ ID NO: |
|---|---|---|
| bags29l11 | CCTCCTCTTCATCATCATCAA CCTCCTCTTCATCATCATCAA | 21689 |
| bags29l11 | TAAACAAAAATCAAAAGGGTA TAAACAAAAACAAAAGGGTA | 21690 |
| baak14o13 | ACAGATCAGGTAAGGCATTT ACAGATCAGGTTAAGGCATTT | 21691 |
| baak14o13 | CAATTTACAACCTTCCAAAGA CAATTTACAACATCTTCCAAAGA | 21692 |
| baak14o13 | GGGGCATGACCAATATGAACA GGGGCATGACTAATATGAACA | 21693 |
| bags28k04 | CAGCGTGCGGTATGCCACATC CAGCGTGCGGGATGCCACATC | 21696 |
| bags28k04 | CATCCTTTTATGTTGATTCAT CATCCTTTTACGTTGATTCAT | 21697 |
| bags28k04 | TGCTTGCCCAGCAGCAGCGCC TGCTTGCCCAACAGCAGCGCC | 21698 |
| BaGS37M03 | AAAATAGCTCACACCAGTGATT AAAATAGCTCATACCAGTGATT | 21701 |

TABLE 28-4-continued

| Clones | Haruna Niio H602 | SEQ ID NO: |
|---|---|---|
| bags18c14 | CATGGTTTGCCATGTTAGATA CATGGTTTGCTATGTTAGATA | 21702 |
| bast23G0214 | TAATTTGCAAATCCCAAGTGA TAATTTGCAAGTCCCAAGTGA | 21703 |
| bast23G0214 | GGGTGACGACGCGTGAAAAAC GGGTGACGACTCGTGAAAAAC | 21704 |
| bast23G0214 | ACACATGCATGCGCATCCTGG ACACATGCATACGCATCCTGG | 21705 |
| bah47p02 | TCATCTGGGCGCCTCTATGCC TCATCTGGGCACCTCTATGCC | 21706 |
| bah47p02 | CAACTTCTACTTACATACTTG CAACTTCTACGTACATACTTG | 21707 |
| kr66h0216 | AAAAAAAAAAAAAAAAAAAAAA AAAAAAAAAACAAAAAAAAAA | 21712 |
| kr66h0216 | TTTTACAACTCGCAACACAAT TTTTACAACTGGCAACACAAT | 21713 |
| BaG323D15 | ACCCACAAATCCTCCAATTA ACCCACAAAAGCCTCCAATTA | 21714 |
| BaGS23D15 | GCGTTTAGAGTATTTACACCA GCGTTTAGAGCATTTACACCA | 21715 |
| BaG323D15 | ACAAATGTAAGCAAAAACCAG ACAAATGTAATCAAAAACCAG | 21716 |
| baal22c17 | ACATTGTTTAITGTGACAAAT ACATTGTTTAATGTGACAAAT | 21717 |
| baal22c17 | ACCCACAAAAGCCTCCAATTA ACCCACAAAATCCTCCAATTA | 21718 |
| bags34l17 | ATGTAACTCTACATGGCAAAG ATGTAACTCTGCATGGCAAAG | 21720 |
| bags34l17 | GGTTGACTAATAGAACTCCAG GGTTGACTAACAGAACTCCAG | 21721 |
| bags34l17 | CTAATGCTACCTTAAGTCCCA CTAATGCTACATTAAGTCCCA | 21722 |

TABLE 28-5

| Clones | Haruna Niio H602 | SEQ ID NO: |
|---|---|---|
| bags34l17 | CCAGAGATTACCAGCCAAATT CCAGAGATTAGCAGCCAAATT | 21723 |
| bags34l17 | TTAAGTCCCATGTAAGCCCTT TTAAGTCCCAGGTAAGCCCTT | 21724 |
| bah14j16 | GCAGAGAGCAGAAATAGGTGC GCAGAGAGCAAAAATAGGTGC | 21726 |
| BaAK21B17 | TCCTTTTGATACCGAGGTCGG TCCTTTTGATGCCGAGGTCGG | 21727 |
| baak21m13 | TGGCTCTATGAAGGAATCTTC TGGCTCTATGTAGGAATCTTC | 21729 |
| baak21m13 | ATTTAGATGAGTCGACTATAC ATTTAGATGAATCGACTATAC | 21730 |
| baak21m13 | CATTCCTCATGTACCATTTAG CATTCCTCATATACCATTTAG | 21731 |
| baak21m13 | AAAATAATTCTGTACTTCTGG AAAATAATTCAGTACTTCTGG | 21732 |
| baak21m13 | GTTTACCTGGTGCGGCCCTT GTTTACCTGTTGCGGCCCTT | 21733 |
| baak21m13 | ATGAGTTTAGGGCGTCGAGCT ATGAGTTTAGTGCGTCGAGCT | 21734 |
| baak21m13 | TAAGGAAAAATTCGCACTTG TAAGGAAAATTTCGCACTTG | 21735 |
| BaH38E01 | TGGTCACCTTGACACATGTCTG TGGTCACCTTACACATGTCTG | 21736 |
| bast03G0313 | GATCGCAAGACGCGAACTGCT GATCGCAAGATGCGAACTGCT | 21737 |
| bast03G0313 | GCGCTACAGAGACAGCCGGCG GCGCTACAGATACAGCCGGCG | 21738 |
| basd18g06 | TCGCTCTAGGACTAGGACTAG TCGCTCTAGGTCTAGGACTAG | 21739 |
| basd18g06 | ACTAGGACAGGATGGCCGGGT ACTAGGACAGAATGGCCGGGT | 21740 |
| baak40i22 | AGGTTGGTACAAAATTTTGAA AGGTTGGTACGAAATTTTGAA | 21741 |
| baak40i22 | CTGTGTTGGGGGATATACATG CTGTGTTGGGTGATATACATG | 21742 |

TABLE 28-5-continued

| Clones | Haruna Niio H602 | SEQ ID NO: |
|---|---|---|
| baal2n12 | CGACGACGACGATGAGGTTTT<br>CGACGACGACAATGAGGTTTT | 21743 |
| baal2n12 | ATGCATGCACGGACTGAGGTG<br>ATGCATGCACAGACTGAGGTG | 21744 |
| baal2n12 | ATAATAATAACATAATGATAA<br>ATAATAATAATATAATGATAA | 21745 |
| BaSD3C24 | CGCGATGTCACAATCTCGTCA<br>CGCGATGTCATAATCTCGTCA | 21746 |
| baak46m07 | ACAAAACTGGAATTAGAATGT<br>ACAAAACTGGGATTAGAATGT | 21747 |
| baak46m07 | CTAGACCGCTGATCTCAGTTT<br>CTAGACCGCTCATCTCAGTTT | 21748 |
| baak46m07 | TCTTCTGTTCCATGACCGCCT<br>TCTTCTGTTCAATGACCGCCT | 21749 |

TABLE 28-6

| Clones | Haruna Niio H602 | SEQ ID NO: |
|---|---|---|
| baak46m07 | TGGAGAAGCCTGTTCACTATG<br>TGGAGAAGCCAGTTCACTATG | 21750 |
| BaGS17N04 | TTCTTAAGAAGGTAGTCGGTG<br>TTCTTAAGAATGTAGTCGGTG | 21751 |
| BaGS17N04 | CTCTACCAATGCCTAGGGGCC<br>CTCTACCAATACCTAGGGGCC | 21752 |
| BaGS17N04 | GACATTCCGATGGAACTAGCC<br>GACATTCCGAGGGAACTAGCC | 21753 |
| bags12d09 | TAGGTACATCTATACGCAACT<br>TAGGTACATCGATACGCAACT | 21754 |
| basd20c08 | GGAACCGCCCGTCCGAGGAGT<br>GGAACCGCCCATCCGAGGAGT | 21755 |
| basd20c08 | GACACCGTCCAGGTGCCACGC<br>GACACCGTCCGGGTGCCACGC | 21756 |
| basd20c08 | GTCCCACACCTGGCAGGTCTT<br>GTCCCACACCGGGCAGGTCTT | 21757 |
| baak15p03 | GACGAGGTGAGGGCTACTGGT<br>GACGAGGTGATGGCTACTGGT | 21759 |
| baak15p03 | TACTGGTCAGGGTCTGAACTC<br>TACTGGTCATCGTCTGAACTC | 21760 |
| baal18g11 | GTCCATTGGACTTCGATTGAA<br>GTCCATTGGATTTCGATTGAA | 21761 |
| baak40g02 | GTTTCAGGAAATTCTACAGTT<br>GTTTCAGGAAGTTCTACAGTT | 21764 |
| BaH26B16 | CGAAGATGATTGCCGCACATC<br>CGAAGATGATCGCCGCACATC | 21765 |
| baal5n08 | TCGGGACATAGCTGGTGGCGG<br>TCGGGACATATCTGGTGGCGG | 21766 |
| baal5n08 | TTTTTACAGGGGACTTGCTTC<br>TTTTTACAGGTGACTTGCTTC | 21767 |
| bags9c08 | CATCTGCAAGTATAAAGACAA<br>CATCTGCAAGCATAAAGACAA | 21768 |
| bags9c08 | ATAAAGACAACGGTCAGTCAA<br>ATAAAGACAATGGTCAGTCAA | 21769 |
| basd1j22 | ATGCACACTGGATGAAGGATG<br>ATGCACACTGCATGAAGGATG | 21772 |
| basd1j22 | AGGTAAATAGGGTGTGCGAGT<br>AGGTAAATAGAGTGTGCGAGT | 21773 |
| basd1j22 | TTGAAACCAGTGAGTGTGTTT<br>TTGAAACCAGGGAGTGTGTTT | 21774 |
| basd1j22 | AGCTAAGGGCAGTCTACTTCT<br>AGCTAAGGGCGGTCTACTTCT | 21775 |
| BaH23N03 | ACTTTTATTACGGAATTGAGA<br>ACTTTTATTATGGAATTGAGA | 21776 |
| bast46d0808 | ATGCTCAGATGATGAGCATTT<br>ATGCTCAGATCATGAGCATTT | 21777 |
| bast22a0802 | TCTTGTGCCTTCCACCTCGCC<br>TCTTGTGCCTCCACCTCGCC | 21778 |
| bast34d0808 | TCTACACACACAAAAAATACT<br>TCTACACACAAAAAAAATACT | 21779 |

TABLE 28-7

| Clones | Haruna Niio H602 | SEQ ID NO: |
|---|---|---|
| bast48e0509 | ATGACACAGACGGATTCAACA<br>ATGACACAGATGGATTCAACA | 21780 |
| bast48e0509 | AGTTGGATAATGTGTTCATGA<br>AGTTGGATAACGTGTTCATGA | 21781 |
| bast26f1012 | AGAAAGAATGGACACATGTAT<br>AGAAAGAATGGACACATGTAT | 21782 |
| baal30e07 | TCTCCATTACGAGCTTCATGT<br>TCTCCATTACCAGCTTCATGT | 21783 |
| baal30e07 | CCTCTTCACTAGGATCTCCAC<br>CCTCTTCACTGGGATCTCCAC | 21784 |
| baal30e07 | TAGTCTTCATGGCCTCTGACT<br>TAGTCTTCATAGCCTCTGACT | 21785 |
| baal30e07 | TATTTAAGCACTCATGTGATC<br>TATTTAAGCAGTCATGTGATC | 21786 |
| bags18i05 | TGGTTTGCTCATGCAATTCTA<br>TGGTTTGCTCGTGCAATTCTA | 21787 |
| bags8o06 | CGATCACTCGTCCTTTGGTTA<br>CGATCACTCGCCCTTTGGTTA | 21793 |
| baak46e14 | ACCTGCACGGAAGATGCGCCG<br>ACCTGCACGGCAGATGCGCCG | 21794 |
| baak46e14 | TAGCGGCGTCGTCACGTGATC<br>TAGCGGCGTCATCACGTGATC | 21795 |
| baak46e14 | GTGTAAGCAACTTACTGTTAT<br>GTGTAAGCAAGTTACTGTTAT | 21796 |
| baak46e14 | CAGGACATAGTCCCTCATGAG<br>CAGGACATAGGCCCTCATGAG | 21797 |
| BaGS38N08 | TCTGTAAAACCAACATCAGGT<br>TCTGTAAAACTAACATCAGGT | 21798 |
| BaH49P17 | TAGGATCCTGCGTGTAGAAGG<br>TAGGATCCTGTGTGTAGAAGG | 21799 |
| BaH49P17 | GGGGTATCTGCCTGCGGCCAT<br>GGGGTATCTGTCTGCGGCCAT | 21800 |
| bags21d11 | GTAAGAAAGAAGATTGTCACT<br>GTAAGAAAGAGGATTGTCACT | 21805 |
| bags21d11 | TTTTATTTCCTGCTTTGTAAG<br>TTTTATTTCCCGCTTTGTAAG | 21806 |
| kr39H0816 | TCGTGCAGGCCTGAACAGGTG<br>TCGTGCAGGCTTGAACAGGTG | 21807 |
| kr39H0816 | GTCTCGTCTCCCCCATCCTGC<br>GTCTCGTCTCCCCCATCCTGC | 21808 |
| kr39H0816 | CCCTGGACTAGTGAGGAAGAC<br>CCCTGGACTACTGAGGAAGAC | 21809 |
| kr67d0208 | CAAATTCAGCATAAGGCGGTA<br>CAAATTCAGCGTAAGGCGGTA | 21814 |
| baak1h16 | TTCGTGTAGTAGCGAGATGTG<br>TTCGTGTAGTGGCGAGATGTG | 21815 |
| BaH26F10 | GACGCTTAGCCTCTCTCTCCG<br>GACGCTTAGCTTCTCTCTCCG | 21816 |
| bags14n02 | AGTCAACCGAGACGCACACAA<br>AGTCAACCGAAACGCACACAA | 21817 |

TABLE 28-8

| Clones | Haruna Niio H602 | SEQ ID NO: |
|---|---|---|
| bah36f01 | CAGTTCCTCTAGAACAGAGCT<br>CAGTTCCTCTGGAACAGAGCT | 21818 |
| bah36f01 | CGGGTGTAGTTGCACCAGCCG<br>CGGGTGTAGTGGCACCAGCCG | 21819 |
| bast79d1107 | ATGTTCATGCGTCTCTCTATA<br>ATGTTCATGCATCTCTCTATA | 21820 |
| bast79d1107 | TCTATATACAGACTAAATGTC<br>TCTATATACAAACTAAATGTC | 21821 |
| bast79d1107 | ACTTGAAAAAGAAAATGTGAT<br>ACTTGAAAAAAAAAATGTGAT | 21822 |
| bast79d1107 | CTTACCTCCAGACCGCAGTCA<br>CTTACCTCCATACCGCAGTCA | 21823 |
| bast79d1107 | GTACAAAGTCTGAATGTTCAT<br>GTACAAAGTCCGAATGTTCAT | 21824 |
| BaGS26O20 | CAACAGATCAAGCTTTCGTAG<br>CAACAGATCATGCTTTCGTAG | 21825 |
| BaGS26O20 | GCGCAGCTGAGAAATGACATT<br>GCGCAGCTGACAAATGACATT | 21826 |

TABLE 28-8-continued

| Clones | Haruna Niio H602 | SEQ ID NO: |
|---|---|---|
| BaGS26O20 | AAGCTCAACCCATAGCCTTCTT AAGCTCAACCCTAGCCTTCTT | 21827 |
| BaGS26O20 | GGGCTTCATACCATCAAGCTC GGGCTTCATAACATCAAGCTC | 21828 |
| BaGS26O20 | CCAACATCAAAGTGTGGTTCG CCAACATCAAGGTGTGGTTCG | 21829 |
| BaGS26O20 | CATCGAGGCAAACTTCTTAAA CATCGAGGCAGACTTCTTAAA | 21830 |
| bags22h11 | TATTTCAACATGCAGTGCAAC TATTTCAACACGCAGTGCAAC | 21832 |
| bags22h11 | GAAATATTACCAATAGCACAC GAAATATTACGAATAGCACAC | 21833 |
| baet19D0608 | CGGCTAGGCCGAGTGGGTCAA CGGCTAGGCCAAGTGGGTCAA | 21834 |
| bags23a14 | TCGCTCCCACATCTGAAGTTC TCGCTCCCACGTCTGAAGTTC | 21835 |
| bags23a14 | CAGGTGCTGGTTCAGTGCTCA CAGGTGCTGGGTCAGTGCTCA | 21836 |
| bags37c09 | CATCGTCAAAGTTATTAAACA CATCGTCAAAATTATTAAACA | 21837 |
| bags37c09 | AAAAGTGAGTGACAAGATTTC AAAAGTGAGTTACAAGATTTC | 21838 |
| bags20a01 | TGATTGGGCGTTTCAAGTGGG TGATTGGGCGCTTCAAGTGGG | 21839 |
| bags20a01 | CATCAAATATGGTCTGATCAG CATCAAATATTGTCTGATCAG | 21840 |
| bags20a01 | GCCGGTAGGCAATGTGCTGGA GCCGGTAGGCGATGTGCTGGA | 21841 |
| bags20a01 | GGCATACCGCGGACGACCGGC GGCATACCGCTGACGACCGGC | 21842 |
| bags20a01 | AGAAAAGGACGCGGCATACCG AGAAAAGGACGCGGCATACCG | 21843 |

TABLE 28-9

| Clones | Haruna Niio H602 | SEQ ID NO: |
|---|---|---|
| bah53m11 | GCGCGTCGCAGACGAACTCCC GCGCGTCGCATACGAACTCCC | 21844 |
| bah53m11 | CGAAGAAGTTGGTCTTGCCCT CGAAGAAGTTTGTCTTGCCCT | 21845 |
| bah53m11 | ATCACTCCGTCTAACTGTCAC ATCACTCCGTGTAACTGTCAC | 21846 |
| bags26l01 | GACTCAAGACGCAGATAAATT GACTCAAGACACAGATAAATT | 21847 |
| bags26l01 | TTATTGACGGGCAAGCGAAGC TTATTGACGGCCAAGCGAAGC | 21848 |
| bags21p23 | AACACACCTTGCACATTCATT AACACACCTTCCACATTCATT | 21849 |
| baak24b01 | ACTTACAGCGCCTACAGAATG ACTTACAGCGGCTACAGAATG | 21850 |
| bast156C0105 | TTAATCTGGAGTTTTTGAAGG TTAATCTGGATTTTTTGAAGG | 21852 |
| bast156C0105 | CTGATTACAACGCACCAATTA CTGATTACAAGGCACCAATTA | 21853 |
| bags28d11 | TCGGGCATCACCAGTCACAGC TCGGGCATCAACAGTCACAGC | 21855 |
| bags28d11 | AAACCTGATATCCAAATGAGG AAACCTGATAGCCAAATGAGG | 21856 |
| bags28d11 | AGAAGAAATCGAGTCGTCTTG AGAAGAAATCAAGTCGTCTTG | 21857 |
| baak11d12 | AGAGTTTTACGAGATACCCAT AGAGTTTTACAAGATACCCAT | 21858 |
| BaH42A07 | CAACTCTACAGTTTTTTGTA CAACTCTACATTTTTTTGTA | 21859 |
| BaH42A07 | ACCTAACAGTTGGCGCCAACG ACCTAACAGTGGGCGCCAACG | 21860 |
| bah60f18 | CTACCATCCATCCAACAATAT CTACCATCCATCCAACAATAT | 21863 |
| bah60f18 | TCATTGATCAACTCCTTCACC TCATTGATCAGCTCCTTCACC | 21864 |
| bah60f18 | TAGCACAATCAATTACCACAT TAGCACAATCTATTACCACAT | 21865 |

TABLE 28-9-continued

| Clones | Haruna Niio H602 | SEQ ID NO: |
|---|---|---|
| bah60f18 | AATATTTTCCGCACTTTTAAG AATATTTTCCACACTTTTAAG | 21866 |
| baal2n10 | GTCAATAGAT-CACGGCGTGG GTCAATAGATACACGGCGTGG | 21867 |
| baal2n10 | TGTGGGAGGATGCGTCTTCCT TGTGGGAGGACGCGTCTTCCT | 21869 |
| baak32c23 | CTGGACCATCGATAGACCATA CTGGACCATCAATAGACCATA | 21876 |
| baak32c23 | GAATTTCTCACAGCATACGGT GAATTTCTCAAAGCATACGGT | 21877 |
| baak32c23 | ATGCAGCGTCCGAGGGGTTGG ATGCAGCGTCGGAGGGGTTGG | 21878 |
| baak32c23 | AATTGTAGTCTCAGAGATGTG AATTGTAGTCCCAGAGATGTG | 21879 |

TABLE 28-10

| Clones | Haruna Niio H602 | SEQ ID NO: |
|---|---|---|
| baal9e06 | ACCATCTATAGAGTTTCCTTA ACCATCTATATAGTTTCCTTA | 21880 |
| baal9e06 | TACTTATGCGCGCGTAGATTA TACTTATGCGAGCGTAGATTA | 21881 |
| bast147E0309 | CCCAAAGCCGTCGCTCTGGCA CCCAAAGCCGCCGCTCTGGCA | 21883 |
| bast147E0309 | CAACCGAAGCAGACACCCTAC CAACCGAAGCTGACACCCTAC | 21884 |
| bast147E0309 | ATCTCCGAAGCCGTCACTTCG ATCTCCGAAGTCGTCACTTCG | 21885 |
| bast147E0309 | CCCTGCTGTCTAAGCAACCGA CCCTGCTGTCCAAGCAACCGA | 21886 |
| baak30o08 | GGGTCAGAAGAAGCATTCATA GGGTCAGAAGGAGCATTCATA | 21887 |
| baet44C0606 | TGACCATGACGTCCTGCTTCA TGACCATGACATCCTGCTTCA | 21888 |
| baet44C0606 | CCTTGAGGAGGAACGGCTTGA CCTTGAGGAGAAACGGCTTGA | 21889 |
| baet44C0606 | TGTCCTTGAGCGTCGTCTCCT TGTCCTTGAGAGTCGTCTCCT | 21890 |
| bags39g18 | GCTGATCGCATGTTTTGCGGT GCTGATCGCACGTTTTGCGGT | 21891 |
| bags38m06 | AGCATGTATCGATGCAGCACA AGCATGTATCAATGCAGCACA | 21893 |
| bags38m06 | CATGGTGGTTTACACTTAGAT CATGGTGGTTCACACTTAGAT | 21894 |
| bags38m06 | TATGAAACATAGGATATACAT TATGAAACATGGGATATACAT | 21895 |
| bags38m06 | AGAGAATGTCTTAGTGACCAG AGAGAATGTCATAGTGACCAG | 21896 |
| bags3i04 | TCGAATCTGCCATCCGTAATC TCGAATCTGCAATCCGTAATC | 21897 |
| bags3i04 | TTCAAAAAATTATGTCCACGT TTCAAAAAATCATGTCCACGT | 21898 |
| bags3i04 | ACATGGAATGATACCCTCCAT ACATGGAATGTTACCCTCCAT | 21899 |
| baal1a11 | TTTCAACATCGCTTACCTCCC TTTCAACATCACTTACCTCCC | 21900 |
| basd2m23 | CTCACAAACAGTTTGCACAAA CTCACAAACAATTTGCACAAA | 21901 |
| basd12k23 | ACATGAACCTTGCATTGCACA ACATGAACCTCGCATTGCACA | 21905 |
| basd12k23 | GTCTGGAGCTACCGGTTGCTG GTCTGGAGCTCCCGGTTGCTG | 21906 |
| basd12k23 | ATTCATAGCAGCTTGAAGATT ATTCATAGCAACTTGAAGATT | 21907 |
| bast22c0105 | AAAAAACTTCGCTTCCAAAAG AAAAAACTTCCCTTCCAAAAG | 21908 |
| bast22c0105 | ACCTCCTTAGTGCCACCACGA ACCTCCTTAGGGCCACCACGA | 21909 |

TABLE 28-11

| Clones | Haruna Niio H602 | SEQ ID NO: |
|---|---|---|
| BaGS38H20 | AGTGCAACTGCACATAAAAAT AGTGCAACTGTACATAAAAAT | 21910 |
| BaGS38H20 | TATACATTCCTTACAATGTGT TATACATTCCATACAATGTGT | 21911 |
| bah61p21 | GCTATGCTTGCAACACAACGC GCTATGCTTGTACACAACGC | 21912 |
| basd11h13 | AGGGTGAAAATAAAGGTCAAG AGGGTGAAAACAAAGGTCAAG | 21913 |
| basd11h13 | ACTGAAAATGCTGCAGGGTGA ACTGAAAATGTTGCAGGGTGA | 21914 |
| basd11h13 | ATATTTGCCGGTCCTTCGCTC ATATTTGCCGCTCCTTCGCTC | 21915 |
| basd11h13 | GTTGCCATCACCCTGACTGTG GTTGCCATCAGCCTGACTGTG | 21916 |
| basd11h13 | GTCATAGATGCTGAATGTCAA GTCATAGATGTTGAATGTCAA | 21917 |
| baal0f04 | GGGCAGCAGCAATGCCACCTT GGGCAGCAGCGATGCCACCTT | 21918 |
| baal0f04 | ATGTACAGCACAAACGTGAAT ATGTACAGCAAAAACGTGAAT | 21919 |
| baal0f04 | TGGAAAAATCACAACATCGCA TGGAAAAATCGCAACATCGCA | 21920 |
| baal0f04 | CACCTTCTTTCGTAGCAACTG CACCTTCTTTTGTAGCAACTG | 21921 |
| kr18e0810 | CATTTTTTGCGATAAATTGCA CATTTTTTGCAATAAATTGCA | 21922 |
| bags24f02 | TTATGAATTAATAATGAATAG TTATGAATTAGTAATGAATAG | 21924 |
| bags24f02 | CCTAGAAATCTTCATGTTTTC CCTAGAAATCGTCATGTTTTC | 21925 |
| bags24f02 | GTGTGGTCTACAATAGAAAAT GTGTGGTCTAGAATAGAAAAT | 21926 |
| baal19m12 | CAAGGTACGTNACATGAGAAT CAAGGTACGTGACATGAGAAT | 21927 |
| baal19m12 | GAATGATGGCNATGAATGACG GAATGATGGCAATGAATGACG | 21928 |
| baak2e06 | AACTTTTTTCTTAATCAATTA AACTTTTTTCGTAATCAATTA | 21929 |
| baak2e06 | ATTTCTGTAAGTAACTAATCC ATTTCTGTAAATAACTAATCC | 21930 |
| baak12l16 | AATCATAATCATTGCTATAAC AATCATAATCGTTGCTATAAC | 21932 |
| baak29d01 | TGTCACAGACATGCGGATCTT TGTCACAGACGTGCGGATCTT | 21933 |
| baak19n06 | TAGTGATATCAGTGTGCATAT TAGTGATATCTGTGTGCATAT | 21934 |
| baak19n06 | CATCCCTCCTCCCAATCATAT CATCCCTCCTCCCAATCATAT | 21935 |
| baak4i02 | CCACCACCTCCATCAGCTTAC CCACCACCTCAATCAGCTTAC | 21936 |

TABLE 28-12

| Clones | Huruna Niio H602 | SEQ ID NO: |
|---|---|---|
| bah49k10 | CACCAAATCAGTATCATTCAC CACCAAATCACTATCATTCAC | 21937 |
| bah49k10 | AAAGACCCAAGGGCAGATCA AAAGACCCAAGGGGCAGATCA | 21938 |
| baal2o03 | TCCGCGTCCAATGGCTCAACC TCCGCGTCCAGTGGCTCAACC | 21939 |
| baak28g14 | CATTCTCAGTGAATGCCCAGC CATTCTCAGTAAATGCCCAGC | 21940 |
| baak28g14 | ACTTGACGCATAGATAAAACA ACTTGACGCAAAGATAAAACA | 21941 |
| baak28g14 | AGAAAGATGAGCAGCCACTGG AGAAAGATGAACAGCCACTGG | 21942 |
| baak28g14 | ACTGGTTCATAAAAAGGCTAC ACTGGTTCATTAAAAGGCTAC | 21943 |
| baak28g14 | AATCGAGGATGTGAATCACAA AATCGAGGATGTGAATCACAA | 21944 |
| bags16e11 | TCTGGAGAGAAGAAAGCGGGG TTGGAGAGATGAAAGCGGGG | 21946 |

TABLE 28-12-continued

| Clones | Huruna Niio H602 | SEQ ID NO: |
|---|---|---|
| bags16e11 | ACTGCGCACTAAATCGAAATA ACTGCGCACTTAATCGAAATA | 21947 |
| bags16e11 | CCGTAGGGCTAAATAAACCT CCGTAGGGCTGAAATAAACCT | 21948 |
| bags23g13 | CCGCCGTGAGGGACAGCTTCT CCGCCGTGAGAGACAGCTTCT | 21949 |
| bags23g13 | TATCCTGCAATGTCGCGTGCA TATCCTGCAACGTCGCGTGCA | 21950 |
| bags23g13 | GTATGTGACATTAGTTCTCGA GTATGTGACAGTAGTTCTCGA | 21951 |
| bags23g13 | TTTCGGGCGGACACGATGACT TTTCGGGCGGTCACGATGACT | 21952 |
| basd23c05 | GCACAGACTCAAGACCTCTGA GCACAGACTCCAGACCTCTGA | 21953 |
| basd23c05 | TGACCCCATCCAGAAAATGGG TGACCCCATCTAGAAAATGGG | 21954 |
| basd23c05 | GCAGAATTTGTTGAATATGTT GCAGAATTTGCTGAATATGTT | 21955 |
| bah19f17 | GAGGAGAATTGAACAGAGAAT GAGGAGAATTAAACAGAGAAT | 21956 |
| bah19f17 | TGCTGTAAATTATCTACTCCA TGCTGTAAATCATCTACTCCA | 21957 |
| bags26g17 | GGTCAAATTTTCCCACCTACG GGTCAAATTTGCCCACCTACG | 21963 |
| bags26g17 | TGTATTTTGTGAGGGGGTTTC TGTATTTTGTAAGGGGGTTTC | 21964 |
| baal6j16 | GCTGAGAAAGGAAACAGTTTC GCTGAGAAAGAAAACAGTTTC | 21965 |
| bags29b09 | TATCATAATTGGGGCTTGCAT TATCATAATTTGGGCTTGCAT | 21966 |
| bags29b09 | TAGTGTCGCAGTAGATGCTGC TAGTGTCGCACTAGATGCTGC | 21967 |

TABLE 28-13

| Clones | Haruna Niio H602 | SEQ ID NO: |
|---|---|---|
| bags29b09 | ATCCAAGTATAAGAGCCACCA ATCCAAGTATGAGAGCCACCA | 21968 |
| baal20e03 | GGGATATCAGACTCTGAATCA GGGATATCAGTCTCTGAATCA | 21969 |
| bags9123 | CAAATATACTGATACACATAG CAAATATACTTATACACATAG | 21970 |
| bags9123 | ATAGTCAAGAAAAACTTTCAT ATAGTCAAGAGAAACTTTCAT | 21971 |
| bags9123 | CAGAATAACACATTAGTGAAA CAGAATAACAAATTAGTGAAA | 21972 |
| bah32e22 | GGATGGTTACCTCTCATCACT GGATGGTTACGTCTCATCGCT | 21973 |
| bah32e22 | ACCTCTCATCACTCCCAATTT ACGTCTCATCGCTCCCAATTT | 21974 |
| baak17o14 | CGACTGTTCAATGTTACTAGT CGACTGTTCAGTGTTACTAGT | 21975 |
| baak17o14 | GATACCTGACGTCAGCCTTGG GATACCTGACATCAGCCTTGG | 21976 |
| BaH42O04 | GAACAGGCTCGCCTCCTTTCC GAACAGGCTCACCTCCTTTCC | 21981 |
| bast74F0111 | CAAGGAAGGAAACCCTAGATA CAAGGAAGGAGACCCTAGATA | 21982 |
| BaSD21F13 | GTTCAGGGCCGGCCCAGCAGA GTTCAGGGCAGCCCAGCAGA | 21983 |
| baal29l08 | CTTTGGTCCGTGAGTTTGCTC CTTTGGTCCGCGAGTTTGCTC | 21986 |
| baak21a04 | TTTGAGCATAGCTAACAGTGA TTTGAGCATATCTAACAGTGA | 21988 |
| baak21a04 | GGGGAGGTCCGGCGCACCCTC GGGGAGGTCCAGCGCACCCTC | 21989 |
| bags37f18 | TATACTGTTACTGACACTGAG TATACTGTTAATGACACTGAG | 21990 |
| baal12h12 | ATCATGGAGATACTGCAAGGT ATCATGGAGAAACTGCAAGGT | 21991 |
| BaAK26F12 | TGAGACCTCGTGCAGCGCCCT TGAGACCTCGGGCAGCGCCCT | 21994 |

TABLE 28-13-continued

| Clones | Haruna Niio H602 | SEQ ID NO: |
|---|---|---|
| bags12b05 | CGGAGAGGTCATGGTCAGGCT<br>CGGAGAGGTCGTGGTCAGGCT | 21995 |
| bags12b05 | TCAGCTGAGAAAAACCCTGC<br>TCAGCTGAGAGAAAACCCTGC | 21996 |
| baal12h24 | TGATTGACACACATCTGATCA<br>TGATTGACACGCATCTGATCA | 21997 |
| baal12h24 | TAGGTGATATATTCCTTTTGG<br>TAGGTGATATCTTCCTTTTGG | 21998 |
| baal35j16 | TGTCGGCTGCGCGGCAGCCCG<br>TGTCGGCTGCACGGCAGCCCG | 21999 |
| bags37c07 | CGAAGTTGTAATTGCTCTTGG<br>CGAAGTTGTAGTTGCTCTTGG | 22000 |
| bags37c07 | AGACTGAGATTTCTGGAGAGC<br>AGACTGAGATATCTGGAGAGC | 22001 |

TABLE 28-14

| Clones | Haruna Niio H602 | SEQ ID NO: |
|---|---|---|
| baak45d23 | GTGATGGACCCGAGGGCGACA<br>GTGATGGACCAGAGGGCGACA | 22002 |
| bah42g09 | GGGGGGGGGGGGAGGGGGGGGG<br>GGGGGGGGGGGGAGGGGGGGGG | 22003 |
| bah42g09 | GGCAAGTTCTTAGGAGCAAAG<br>GGCAAGTTCTCAGGAGCAAAG | 22004 |
| bah42g09 | ACATCGAGTCGTCAGGAATCC<br>ACATCGAGTCATCAGGAATCC | 22005 |
| baal40p01 | TTCCGGGCTGACGTCTGGACG<br>TTCCGGGCTGTCGTCTGGACG | 22006 |
| baal40p01 | ATGCCTTGAGAGATATATATA<br>ATGCCTTGAGGGATATATATA | 22007 |
| baal40p01 | ACAGTGAATAGCCCGATCGTG<br>ACAGTGAATATCCCGATCGTG | 22008 |
| baal40p01 | ATTAATCAGAACATCGAGTGG<br>ATTAATCAGACCATCGAGTGG | 22009 |
| baal40p01 | TAAGCAATCAGTGAAATAAAG<br>TAAGCAATCAATGAAATAAAG | 22010 |
| baal40p01 | TTTAACATACTGATAATTTA<br>TTTAACCATATTGATAATTTA | 22011 |
| baal40p01 | CACTTGAAATGATTCAATGAT<br>CACTTGAAATAATTCAATGAT | 22012 |
| baal40p01 | ATAAAATAGCTGGTGGTTAAT<br>ATAAAATAGCAGGTGGTTAAT | 22013 |
| baal40p01 | GCTCCTCTCCCAACACGCCAT<br>GCTCCTCTCCAAACACGCCAT | 22014 |
| baal40p01 | CCATTTCCCACAGGAATAGAT<br>CCATTTCCCATAGGAATAGAT | 22015 |
| baal40p01 | TGGCCCAGACCATAGCGAGGG<br>TGGCCCAGACAATAGCGAGGG | 22016 |
| baal40p01 | TCTCACATGGATGCTGTCTTT<br>TCTCACATGGCTGCTGICTIT | 22017 |
| kr61a0901 | GTCTATAATCGTTTTTGATGT<br>GTCTATAATCTTTTTTGATGT | 22018 |
| kr61a0901 | TTTATTTTACCAAGTAACAAT<br>TTTATTTTACGAAGTAACAAT | 22019 |
| kr61a0901 | TATTAATATAGACCTCTATAA<br>TATTAATATAAACCTCTATAA | 22020 |
| kr61a0901 | CAGTTAGTAATCACGCCTGCA<br>CAGTTAGTAACCACGCCTGCA | 22021 |
| bah44b17 | AAGACAGTGCGTCACTCACTG<br>AAGACAGTGC-TCACTCACTG | 22027<br>22028 |
| basd2k11 | ATATTGAGTCTGAGGTAACAA<br>GAATTGAGTC-GAGGTAACAA | 22029<br>22030 |
| bags23e20 | TGAAATCCTCCTCTTGCATTT<br>TGAAATCCTCGTCTTGCATTT | 22032 |
| bags33i10 | AACCAAGAAACATTATTAGTG<br>AACCAAGAAATATTATTAGTG | 22033 |
| bags35k06 | GAGAAGGAGGTTTGCTGATGG<br>GAGAAGGAGGGTTGCTGATGG | 22034 |

TABLE 28-15

| Clones | Haruna Niio H602 | SEQ ID NO: |
|---|---|---|
| bags35k06 | CTAAGGAAAAACATACCTAGT<br>CTAAGGAAAAGCATACCTAGT | 22035 |
| BaGS22M17 | AACCACACAA-CGAAGGGCTA<br>TACCACACAAGCGAAGGGCTA | 22037<br>22038 |
| baak21j24 | GAGAACAAACGAGCAGACAGG<br>GAGAACAAACAAGCAGACAGG | 22039 |
| baal16o08 | TCAGTTCATCGCTAGCATAGA<br>TCAGTTCATCACTAGCATAGA | 22042 |
| baal16o08 | CCTTTGTCACAGCAACCGGGT<br>CCTTTGTCACGGCAACCGGGT | 22043 |
| baal27n7 | TGGTGTTCACGGGCGCGCTGG<br>TGGTGTTCACCGGCGCGCTGG | 22044 |
| baal27n7 | CGATCTCCTCTAGCTTGGAGA<br>CGATCTCCTCCAGCTTGGAGA | 22045 |
| baal27n7 | TAACCTGCCCGGCGATCTCCT<br>TAACCTGCCCCGCGATCTCCT | 22046 |
| baet31B1103 | GCCTCCTGCAGTTGAGCCTGA<br>GCCTCCTGCAATTGAGCCTGA | 22047 |
| baet31B1103 | CTGACCAGCGCGTCCTGCGAC<br>CTGACCAGCGAGTCCTGCGAC | 22048 |
| BaGS24K08 | CAATAGGAAAACAGTAGGAAG<br>CAATAGGAAAGCAGTAGGAAG | 22051 |
| BaGS24K08 | TCACTGAGGTTGGAGTGGAT<br>TCACTGGAGGATGGAGTGGAT | 22052 |
| bah16c17 | TCGTGCTTATCACATCAACCT<br>TCGTGCTTATTACATCAACCT | 22053 |
| bah16c17 | ACATCAACCTAGTATCGTGTG<br>ACATCAACCTCGTATCGTGTG | 22054 |
| bah16c17 | ACGGGAGATGATGGGATTCAC<br>ACGGGAGATGCTGGGATTCAC | 22055 |
| bags28l21 | CTACTCCTACACCAGTGCCTC<br>CTACTCCTACGCCAGTGCCTC | 22056 |
| bags28l21 | GCCTGTTAGCATTAGGCATGA<br>GCCTGTTAGCGTTAGGCATGA | 22057 |
| bags28l21 | CAAGTTGGGCAGCGGAGAGGC<br>CAAGTTGGGCTGCGGAGAGGC | 22058 |
| bags28l21 | AGATTTACTTGGGACGCTTGC<br>AGATTACTTTGGGACGCTTGC | 22059 |
| bah31m22 | TGGATCATCAATTTCATCACA<br>TGGATCATCAGTTTCATCACA | 22060 |
| bah31m22 | CGGGGTCTTGTTCGGGGATGT<br>CGGGGTCTTGCTCGGGGATGT | 22061 |
| bah31m22 | GTAGAGCTCTTGCTGGAAGGA<br>GTAGAGCTCTAGCTGGAAGGA | 22062 |
| bah31m22 | GTCTACATGCAAAGAACCCTG<br>GTCTACATGCGAAGAACCCTG | 22063 |
| baal30c17 | GTTAACTGTGGCACGCGTCTG<br>GTTAACTGTGACACGCGTCTG | 22064 |
| baak37n01 | GTCGATCTCCTGCATACGGTT<br>GTCGATCTCCCGCATACGGTT | 22066 |

TABLE 28-16

| Clones | Haruna Niio H602 | SEQ ID NO: |
|---|---|---|
| BaGS24O11 | GAAAGTATGCAACAGGAGGAT<br>GAAAGTATGCCACAGGAGGAT | 22067 |
| BaGS24O11 | TGCCAGCTAAGAAAATAACT<br>TGCCAGCTAATAAAAATAACT | 22068 |
| BaGS24O11 | AGGCAGAAAATGTGAATTGTA<br>AGGCAGAAAACGTGAATTGTA | 22069 |
| bah50i23 | ATTCCAAGTTCGCACCACACA<br>ATTCCAAGTTTGCACCACACA | 22073 |
| bah50i23 | AGGTAGCAGAAAAGAGGTGAT<br>AGGTAGCAGATAAGAGGTGAT | 22074 |
| bah50i23 | GCTTGCATGCTAATGCCATCG<br>GCTTGCATGCCAATGCCATCG | 22075 |
| bah50i23 | TTTGGAGAACCATGAGATTAA<br>TTTGGAGAACTATGAGATTAA | 22076 |
| BaH56D06 | TTTCCACTTGGGCACTTCTCG<br>TTTCCACTTGAGCACTTCTCG | 22077 |
| BaAK39M05 | GCTGTGAATGAGTTTCCAGCT<br>GCTGTGAATGTGTTTCCAGCT | 22078 |

TABLE 28-16-continued

| Clones | Haruna Niio H602 | SEQ ID NO: |
|---|---|---|
| BaAK39M05 | TCCATCTGACCATGAGTTCCC TCCATCTGACCATGAGTTCCC | 22079 |
| bah11m16 | TATATATACCGTGCTTGCTAT TATATATACCATGCTTGCTAT | 22080 |
| bah49d03 | ACCCGAAGCATCGGTCGCATA ACCCGAAGCAACGGTCGCATA | 22081 |
| bah49d03 | CCACCTCAAAGATGAATGACT CCACCTCAAAAATGAATGACT | 22082 |
| bah49d03 | TTCCCCTGATTTCTGCGATCG TTCCCCTGATGTCTGCGATCG | 22083 |
| bah49d03 | ATGAATGACTGGGTGGGATCA ATGAATGACTTGGTGGGATCA | 22084 |
| bah49d03 | ACGTAGAACAGCGAATGACCA ACGTAGAACATCGAATGACCA | 22085 |
| bah49d03 | GCAACCCGGTGCTTCAAGTCC GCAACCCGGTACTTCAAGTCC | 22086 |
| bah62l23 | ATTTGCCTATGCAAGAAAGAT ATTTGCCTATACAAGAAAGAT | 22087 |
| bah62l23 | CCACAATTGCGAATTTGCCTA CCACAATTGCGAATTTGCCTA | 22088 |
| BaAK38J13 | TACTGACTGCGATGTACCGTC TACTGACTGCGATGTACCGTC | 22089 |
| BaAK38J13 | AACAGGTTACGTTCAAGTTAC AACAGGTTACATTCAAGTTAC | 22090 |
| BaAK38J13 | GCCAGATGCTTTGTAGGATTC GCCAGATGCTGTGTAGGATTC | 22091 |
| BaH37N04 | GAGATAATGTAAACGCTAGAA GAGATAATGTAAACGCTAGAA | 22092 |
| BaH37N04 | TGTGACCCAGTAAGAAGGGGC TGTGACCCAGAAAGAAGGGGC | 22093 |
| BaH37N04 | ATTGTTGCATGAGTAAAAAGA ATTGTTGCATTAGTAAAAAGA | 22094 |

TABLE 28-17

| Clones: | Haruna Niio H602 | SEQ ID NO: |
|---|---|---|
| BaH37N04 | GTACAACAGCGAAAAGTTAAC GTACAACAGCAAAAAGTTAAC | 22095 |
| basd27c06 | GCCGAGGCGCCTGTGCCGTGC GCCGAGGCGCGTGTGCCGTGC | 22096 |
| bah39g10 | TGGAGAATGTTCAAGACACCG TGGAGAATGTACAAGACACCG | 22097 |
| bah39g10 | GATACGAAAAAGACGAGAATG GATACGAAAAGGACGAGAATG | 22098 |
| bags20a13 | TGTCTCCAATTGTCTTCTCTA TGTCTCCGATGGTCTTCTCTA | 22099 |
| bags20a13 | GATAAACGTACTTGCATTTAT GATAAACATAGTTGCATTTAT | 22100 |
| bags20a13 | CACTGTCTCCAATTGTCTTCT CACTGTCTCCGATGGTCTTCT | 22101 |
| bags20a13 | AAAGATAAACGTACTTGCATT AAAGATAAACATAGTTGCATT | 22102 |
| BaH27L15 | CCGTTTCCTCGGAGATCGCAT CCGTTTCCTCAGAGATCGCAT | 22104 |
| bah59f07 | CCAGACTCAGCGTCCCTACTG CCAGACTCAGTGTCCCTACTG | 22105 |
| bah59f07 | TGGACAGCAACCCCAGACTCA TGGACAGCAAGCCCAGACTCA | 22106 |
| bags9l05 | ATACAGAGAAACAAATGATAT ATACAGAGAAGCAAATGATAT | 22107 |
| bags9l05 | GCCTCAGCAGGAGCTCCACCT GCCTCAGCAGCAGCTCCACCT | 22108 |
| bags9l05 | CACCAGCAGCAGCACCACCAC CACCAGCAGCGGCACCACCAC | 22109 |
| bags9l05 | CACCACCACCAATCGGACCAG CACCACCACCGATCGGACCAG | 22110 |
| bags9l05 | CCACCTGCTCAAGTTTCAGA CCACCTGCATCAAGTTTCAGA | 22111 |
| bags9l05 | GTAATGGTCCATTAGTTCAGC GTAATGGTCCCTTAGTTCAGC | 22112 |
| bah53j21 | TTTCAAGCACCCTCTTGTTCA TTTCAAGCACGCTCTTGTTCA | 22116 |

TABLE 28-17-continued

| Clones: | Haruna Niio H602 | SEQ ID NO: |
|---|---|---|
| bah53j21 | AATGTATGCCGAAATTTGATT AATGTATGCCAAAATTTGATT | 22117 |
| bah53j21 | CCGCAGCAGAAATGATGAGCT CCGCAGCAGAGATGATGAGCT | 22118 |
| bah21f16 | GATTCATAGGAATAGGAAAAA GATTCATAGGTATAGGAAAAA | 22119 |
| bah21f16 | TAAAACATAAGAACAAGAAA TAAAACATAGGAACAAGAAA | 22120 |
| baet39E0309 | TGCTTCAGGCTGATCGGTCGG TGCTTCAGGCAGATCGGTCGG | 22121 |
| baet39E0309 | TTCGTTCTCCAACGGCGGATG TTCGTTCTCCAACGGCGGATG | 22122 |
| bags5l04 | TCACATACCCGGCACCGGGAA TCACATACCCAGCACCGGGAA | 22123 |

TABLE 28-18

| Clones | Haruna Niio H602 | SEQ ID NO: |
|---|---|---|
| bags5l04 | TCCGCCATTTTGTTCGAATGC TCCGCCATTTGGTTCGAATGC | 22124 |
| bags5l04 | AGCACCCGCATCATTTAGCAG AGCACCCGCAGCATTTAGCAG | 22125 |
| bags7g10 | TGTAGGTTTCCGCCTCATCAG TGTAGGTTTCTGCCTCATCAG | 22126 |
| bags7g10 | AACAATACACAACCCTATTIG AACAATACACGACCCTATTTG | 22127 |
| bags9d22 | ATATGTTCTCGACAGCCCGC- ATATGTTCTCGACAGCCCGCA | 22128 22129 |
| bah18j14 | GGAAAAAATTGCTTGTCAAAT GGAAAAAATTTCTTGTCAAAT | 22132 |
| bah18j14 | TTCCCAACATAATTGCAATGT TTCCCAACATGATTGCAATGT | 22133 |
| bags37k14 | GACCGAATGATAGATCTCATA GACCGAATGAGAGATCTCATA | 22134 |
| bags37k14 | GCATTGATTTAATCTATGTTA GCATTGATTTGATCTATGTTA | 22135 |
| bah42k03 | CATAGCCCGATGCCACGACAT CATAGCCCGACGCCACGACAT | 22136 |
| bah42k03 | TAAAGGGCAGGGGAAAATATC TAAAGGGCAGGGAAAATATC | 22137 |
| bags12i02 | CGACTCTATGGGCAGCCACCG CGACTCTATGAGCAGCCACCG | 22139 |
| bags12i02 | CCACGTAAGGCAAATCTCCTG CCACGTAAGGGAAATCTCCIG | 22140 |
| bags12i02 | CAGACAGCAGCTCTTAGTCGA CAGACAGCAGTTCTTAGTCGA | 22141 |
| bags12i02 | CACTATACAGATTGTAAAACC CACTATACAGTTTGTAAAACC | 22142 |
| bags12i02 | ATGACGCCATAATATAAATCA ATGACGCCATTATATAAATCA | 22143 |
| baet25b0604 | GCGCTTGCTCGATGGAGGATG GCGCTTGCTCAATGGAGGATG | 22145 |
| baet25b0604 | TGCAGTAGTTATAGATCATGT TGCAGTAGTTGTAGATCATGT | 22146 |
| baak46e21 | ACTAATCTACGAATATTTGCC ACTAATCTACGAATATTTGCC | 22147 |
| baak46e21 | GCATTCTGTGGCCTAACTAAA GCATTCTGTGCCCTAACTAAA | 22148 |
| bags37j12 | ATGGAGGGTTTGTTGGAGGCT ATGGAGGGTTCGTTGGAGGCT | 22149 |
| bags37j12 | CATACACACTGCTTCATGCAT CATACACACTTCTTCATGCAT | 22150 |
| bags37j12 | ATACGGCATGCGATTAAACAG ATACGGCATGTGATTAAACAG | 22151 |
| baak30b08 | AAACAGTGTGCCCATCAGGCA AAACAGTGTGTCCATCAGGCA | 22153 |
| baak20o12 | ATGCATCTAGGTTCTAGATAC ATGCATCTAGATTCTAGATAC | 22155 — |

TABLE 28-19

| Clones | Haruna Niio H602 | SEQ ID NO: |
|---|---|---|
| baak20o12 | GCCTGATCGTCCTGGAGCGTC<br>GCCTGATCGTGCTGGAGCGTC | 22156 |
| baak20o12 | CCACGCTCCCGATGAAGAAGA<br>CCACGCTCCCCATGAAGAAGA | 22157 |
| baak20o12 | TAGATGCTAGCCATGCATCTA<br>TAGATGCTAGTCATGCATCTA | 22158 |
| basd14k23 | CTGCTCATGCTGAGAAGGCTG<br>CTGCTCATGCCGAGAAGGCTG | 22159 |
| BaAK23L05 | GCTTACCAGCGAAGATCAGGC<br>GCTTACCAGCAAAGATCAGGC | 22160 |
| BaAK23L05 | CCACCTCCAAGGTGATGGTCT<br>CCACCTCCAAGGTGATGGTCT | 22161 |
| BaAK23L05 | CACCACGAAGGCGGAGGACAA<br>CACCACGAAGGCAGGAGGACAA | 22162 |
| BaAK23L05 | TCGCCTTCACGTTGTCAATGG<br>TCGCCTTCACATTGTCAATGG | 22163 |
| bags33o01 | TGTGCTTGGATTTCAAGTTCA<br>TGTGCTTGGACTTCAAGTTCA | 22165 |
| bags33o01 | GGTATATATGCGAGTGTGCAA<br>GGTATATATGTGAGTGTGCAA | 22166 |
| bah24d24 | ACCCAATGGCGGGCAGTTTGG<br>ACCCAATGGCAGGCAGTTTGG | 22168 |
| bah24d24 | TGCAGGGAATTCTCAGCAAGG<br>TGCAGGGAATTCCTCAGCAAGG | 22169 |
| bags12f09 | CCACTCGTAGTAGCGTGTGTT<br>CCACTCGTAGCAGCGTGTGTT | 22170 |
| baak33h23 | ACGATCATATGGCACTTATAT<br>ACGATCATATTGCACTTATAT | 22171 |
| baak33h23 | TTTTACAAGCAACATAAGGAA<br>TTTTACAAGCGACATAAGGAA | 22172 |
| baak33h23 | CTTGTTCACAGGAAGTCTACT<br>CTTGTTCACACGAAGTCTACT | 22173 |
| bah47p03 | TTTTTAGGACACTCATAGCCT<br>TTTTTAGGACGCTCATAGCCT | 22174 |
| bah47p03 | AAAATCAGAAGGAGAATTTGA<br>AAAATCAGAAAGAGAATTTGA | 22175 |
| bah47p03 | CTGACTAATCTTCCGGGGTAG<br>CTGACTAATCGTCCGGGGTAG | 22176 |
| basd14f09 | GCTTACCAGCAAAGATCAGGC<br>GCTTACCAGCGAAGATCAGGC | 22177 |
| BaSD22F10 | GCAAAGATTAGGCGCTGCTGG<br>GCAAAGATTAAGCGCTGCTGG | 22179 |
| BaSD22F10 | TCAACCTCCAGTGTGATGGTC<br>TCAACCTCCAATGTGATGGTC | 22180 |
| BaSD22F10 | GCTGGTCCGGGGGGATGCCCT<br>GCTGGTCCGGAGGGATGCCCT | 22181 |
| BaSD22F10 | TGGTCTTGCCGGTGAGAGTCT<br>TGGTCTTGCCGGTGAGAGTCT | 22182 |
| BaSD22F10 | GCTTACCAGCAAAGATCAGGC<br>GCTTACCAGCGAAGAT-CAGGC_ | 22183 |

TABLE 28-20

| Clones | Haruna Niio H602 | SEQ ID NO: |
|---|---|---|
| bags27o20 | GTTGATCTAAAGGCAGATCCA<br>GTTGATCTAAGGGCAGATCCA | 22186 |
| bags27o20 | GGTCGTCTGACGAGGACTGT<br>GGTCGTCTGATGGAGGACTGT | 22187 |
| bags27o20 | CTCTTTTCGGGTTCATCGCCAG<br>CTCTTTTCGGGGTCATCGCCAG | 22188 |
| baak31o10 | AATCAGCACTCAACTGACCTT<br>AATCAGCACTGAACTGACCTT | 22189 |
| baak31o10 | GAAATCGTGAGGCCTAACGCC<br>GAAATCGTGAGGCCTAACGCC | 22190 |
| bags10f16 | CAAAGGACTCAATGACGGGGA<br>CAAAGGACTCGATGACGGGGA | 22191 |
| bags10f16 | TGCTTGAGAATCCAAAGGACT<br>TGCTTGAGAACCCAAAGGACT | 22192 |
| BaGS9H02 | GTCGGCAACCGCATTTCCCTT<br>GTCGGCAACCACATTTCCCTT | 22194 |
| kr66C0705 | GTGTGCACATCGTCTGATCAG<br>GTGTGCACATTGTCTGATCAG | 22197 |

TABLE 28-20-continued

| Clones | Haruna Niio H602 | SEQ ID NO: |
|---|---|---|
| kr66C0705 | CTTTTGGGAATGTTAACTGAT<br>CTTTTGGGAACGTTAACTGAT | 22198 |
| kr66C0705 | GGTGATCCGAACGTGTGAATA<br>GGTGATCCGAGCGTGTGAATA | 22199 |
| kr66C0705 | CTTTGATCTGGGCAGTAGTCG<br>CTTTGATCTGTGCAGTAGTCG | 22200 |
| BaGS33M05 | CCATGCCCTCCCCTGTGTACC<br>CCATGCCCTCGCCTGTGTACC | 22201 |
| BaGS33M05 | CTATCACCACGTGACAGCACC<br>CTATCACCACCTCACAGCACC | 22202 |
| baal24b02 | CCTAGAGCATAATATGCGGGT<br>CCTAGAGCATGATATGCGGGT | 22208 |
| baal24b02 | CTCCATGCCTAAACCAGCAAC<br>CTCCATGCCTGAACCAGCAAC | 22209 |
| bags34f08 | CAGATATATCTTTGCCAAATC<br>CAGATATATCATTGCCAAATC | 22210 |
| bags34f08 | CAGTGTTTCAAACTATTGTTA<br>CAGTGTTTCAGACTATTGTTA | 22211 |
| bags34f08 | GGCTTATTTTGATCTGCCACA<br>GGCTTATTTTCATCTGCCACA | 22212 |
| bast36D1208 | GCCGTCGCTACCCAAGCTCCC<br>GCCGTCGCTATCCAAGCTCCC | 22213 |
| kr25b1103 | ACTGCCCACCGGTCGTCCCCA<br>ACTGCCCACCAGTCGTCCCCA | 22214 |
| kr25b1103 | AGGGCTGCGGCCCCTACTGCC<br>AGGGCTGCGGTCCCTACTGCC | 22215 |
| kr25b1103 | GATCAACACGCTGAAGCTGGG<br>GATCAACACGTTGAAGCTGGG | 22216 |
| baal19g05 | ACACCAGCTGGCTGACTGACT<br>ACACCAGCTGACTGACTGACT | 22217 |
| baal19g05 | TCTACATACAGTTCGCTAACC<br>TCTACATACAATTCGCTAACC | 22218 |

TABLE 28-21

| Clones | Haruna Niio H602 | SEQ ID NO: |
|---|---|---|
| baal19g05 | GATGCCCGTCGGAGTCAGGCG<br>GATGCCCGTCAGAGTCAGGCG | 22219 |
| baal19g05 | TTCGCTAACCGCAAGAACAAG<br>TTCGCTAACCACAAGAACAAG | 22220 |
| bags19c10 | ACGCAAAAAAAGAGTAATAA<br>ACGCAAAAAGAGAGTAATAA | 22222 |
| bags19c10 | TACAACAGTGTATAAGAAGGC<br>TACAACAGTGCATAAGAAGGC | 22223 |
| bags19c10 | TTCTTCTTAGGGGCTAAATGA<br>TTCTTCTTAGCGGCTAAATGA | 22224 |
| bags19c10 | ACTTTAAGCATATGTGCTTAG<br>ACTTTAAGCAGATGTGCTTAG | 22225 |
| bags19c10 | TGCAAGCCATCATAGATCTAT<br>TGCAAGCCATTATAGATCTAT | 22226 |
| bags29k01 | CTCATAAAGTTGACATTCAGG<br>CTCATAAAGTGGACATTCAGG | 22227 |
| bags29k01 | AAGCTTAAGAAAGACAAACTC<br>AAGCTTAAGACAGACAAACTC | 22228 |
| bags29k01 | CTCCTCATCAATCCCAATGGC<br>CTCCTCATCAGTCCCAATGGC | 22229 |
| bags29k01 | CAGGAGATGTTACAAACAAAT<br>CAGGAGATGTGACAAACAAAT | 22230 |
| bags29k01 | TCATCGTCCCGAAGAATCGATC<br>TCATCGTCCCAAGAATCGATC | 22231 |
| bags29k01 | ACTTGCCGGCAGAGTATCAGG<br>ACTTGCCGGCGGAGTATCAGG | 22232 |
| bags29k01 | TGAGTGCTTCTTTCTCAGGCT<br>TGAGTGCTTCCTTCTCAGGCT | 22233 |
| bags29k01 | GGCTAACATCGACACTGAAAG<br>GGCTAACATCTACACTGAAAG | 22234 |
| bags29k01 | TGAAAGGCCCAACAAGTGTGA<br>TGAAAGGCCCGACAAGTGTGA | 22235 |
| bags29k01 | AAACAAATCAACCTACATTTC<br>AAACAAATCATCCTACATTTC | 22236 |
| bastl54G0414 | TATCTAGAAGACCAGAACATA<br>TATCTAGAAGGCCAGAACATA | 22237 |

TABLE 28-21-continued

| Clones | Haruna Niio H602 | SEQ ID NO: |
|---|---|---|
| bast15400414 | CTACTCCTTCGGACATTCCCC<br>CTACTCCTTCCGACATTCCCC | 22238 |
| bags34b15 | AGCCCCTTGT-CAGACCGCTG<br>AGCCCCTTGTACAGACCGCTG | 22240<br>22241 |
| bah31l17 | AAAATAATAAGAGGAACCCAC<br>AAAATAATAAAAGGAACCCAC | 22244 |
| bah31l17 | TTGATCAAATAAGGCCAAAAT<br>TTGATCAAATGAGGCCAAAAT | 22245 |
| bah31l17 | AGTCAAACTGATTGCACATTT<br>AGTCAAACTGGTTGCACATTT | 22246 |
| bah31l17 | ATCAAAACAGTATAGAACTT<br>ATCAAAACATTATAGAACTT | 22247 |
| bah31l17 | AGGATGCCACAGCCTTTTGTA<br>AGGATGCCACGGCCTTTTGTA | 22248 |

TABLE 28-22

| Clones | Haruna Niio H602 | SEQ ID NO: |
|---|---|---|
| baak32a05 | GACCATGCACAATCTCTTCCA<br>GACCATGCACTATCTCTTCCA | 22249 |
| baak32a05 | TCCCCTCCTTTCCCACAGTCA<br>TCCCCTCCTTGCCCACAGTCA | 22250 |
| bags30n22 | CACCTAATGTAGATGGAGCCA<br>CACCTAATGTTGATGGAGCCA | 22251 |
| bags30n22 | CACTGGCATTTTGCCATGGT<br>CACTGGCATTTTTGCCATGGT | 22252 |
| bags30n22 | ACTCTTATCGTCAGTAGCTGA<br>ACTCTTATCGGCAGTAGCTGA | 22253 |
| BaH27L17 | AGCCCTCGACGCCGATGATGT<br>AGCCCTCGACTCCGATGATGT | 22258 |
| BaH27L17 | TCGAGCAATCGAGCGCGATGA<br>TCGAGCAATCAAGCGCGATGA | 22259 |
| BaH27L17 | TTCTGTTTGCGGGTGTGTTGA<br>TTCTGTTTGCTGGTGTGTTGA | 22260 |
| BaH27L17 | GCAACTCTATGCCCCAACGAA<br>GCAACTCTATTCCCCAACGAA | 22261 |
| basd17e11 | ATATGGTCTCGAAGAGTTCCT<br>ATATGGTCTCAAAGAGTTCCT | 22262 |
| basd17e11 | TGTATTAAGAAGTGCATGCTA<br>TGTATTAAGAGGTGCATGCTA | 22263 |
| basd17e11 | GGTACTCCTGGCCACTGTTTA<br>GGTACTCCTGTCCACTGTTTA | 22264 |
| basd17e11 | ACTTCGGTCGGTGICCTGCAA<br>ACTTCGGTCGCTGTCCTGCAA | 22265 |
| basd17e11 | TGTCCTGCAACCCCAAAGGAC<br>TGTCCTGCAAACCCAAAGGAC | 22266 |
| bags15i06 | TCGAACTCCTCTGGTCGCTAG<br>TCGAACTCCTITGGTCGCTAG | 22267 |
| bags15i06 | ACTGCAGGACAAGCTGCTTCA<br>ACTGCAGGACGAGCTGCTTCA | 22268 |
| bags15i06 | CTGCTCCTGGTACTGCAGGAC<br>CTGCTCCTGGGACTGCAGGAC | 22269 |
| bags15i06 | AGTAGATTTTCAGTTCAGAT<br>AGTAGATTTTGCAGTTCAGAT | 22270 |
| bags15i06 | CAGCGCGTAGTTGTTGATCTG<br>CAGCGCGTAGGTGTTGATCTG | 22271 |
| bags15i06 | CGCCCTATCCCACGGCCAACA<br>CGCCCTATCCGACGGCCAACA | 22272 |
| bags15i06 | ACTCTCAATCACCAAGGGCCA<br>ACTCTCAATCTCCAAGGGCCA | 22273 |
| baak36f09 | CGATGGCGGCTCCGTAGTGCG<br>CGATGGCGGCGCCGTAGTGCG | 22274 |
| baak36f09 | CGGGCACGCGTGTGAGGTAGA<br>CGGGCACGCGGGTGAGGTAGA | 22275 |
| bast57a0101 | TTCTCCATTACAAACCTATTA<br>TTCTCCATTAIAAAACCTATTA | 22276 |
| basd13b15 | GGTGAGGCTCGCGTCTTCGCT<br>GGTGAGGCTCACGTCTTCGCT | 22278 |

TABLE 28-23

| Clones | Haruna Niio H602 | SEQ ID NO: |
|---|---|---|
| basd13b15 | TCAGCTGCGCGTTGTCGATGA<br>TCAGCTGCGCATTGTCGATGA | 22279 |
| bags9d11 | ACAATCATCAGATATGAGTGG<br>ACAATCATCATATATGAGTGG | 22280 |
| bags9d11 | GGGCCCATAGTTAACCCAACT<br>GGGCCCATAGGTAACCCAACT | 22281 |
| bags9d11 | CTAAGTTGTTGTATAGGCATC<br>CTAAGTTGTTGTATAGGCATC | 22282 |
| bags9d11 | TAACCCAACTTCTTGGGGGAA<br>TAACCCAACTCCTTGGGGGAA | 22283 |
| bags9d11 | TGTTCCATATTTGATCGATGA<br>TGTTCCATATCTGATCGATGA | 22284 |
| bags9d11 | GTTTTGCCGCGCGATATAGTG<br>GTTTTGCCGCACGATATAGTG | 22285 |
| bags9d11 | GTAATAAATTGAATGCTCTTC<br>GTAATAAATTAAATGCTCTTC | 22286 |
| bags9d11 | TGTCTTAATTGTTAGTCTTCA<br>TGTCTTAATTATTAGTCTTCA | 22287 |
| bags9d11 | AAACTAAAACTTACCTGTGGG<br>AAACTAAAACATACCTGTGGG | 22288 |
| bags9d11 | ATTTCAGCCTGTTAAAAAACC<br>ATTTCAGCCTATTAAAAAACC | 22289 |
| kr30f1212 | TTCGACAAGAGAGCCACAAAC<br>TTCGACAAGAAAGCCACAAAC | 22290 |
| bast145b0903 | CAGTCCAACACTTCTTTCTAA<br>CAGTCCAACACTTTCTTTCTAA | 22291 |
| BaGS32I12 | CCTTGGCCGCCGCAGATGCGT<br>CCTTGGCCGCTGCAGATGCGT | 22292 |
| BaGS32I12 | CACAGCCATCGTATGGCATGT<br>CACAGCCATCITATGGCATGT | 22293 |
| BaGS32I12 | CCGAGCAAACTACATTTTGCT<br>CCGAGCAAACCACATTTTGCT | 22294 |
| baak27p06 | AGTGACAATGCCATGCTTTTG<br>AGTGACAATGTCATGCTTTTG | 22296 |
| baak27p06 | CAAGAAAAATTTCCTAAAAGG<br>CAAGAAAAATGTCCTAAAAGG | 22297 |
| baak27p06 | CAAGTACCTCAGTAAAATCAT<br>CAAGTACCTCGGTAAAATCAT | 22298 |
| baak27p06 | CATCACCAAGCAGGGGGTTCC<br>CATCACCAAGTAGGGGATTCC | 22299 |
| baak27p06 | CTGGGTCTCAAAAGTGACAAT<br>CTGGGTCTCAGAAGTGACAAT | 22300 |
| bags21m21 | TCCCCTGGAAAACCTCGCCGC<br>TCCCCTGGAAAGACCTCGCCGC | 22301 |
| basd16e11 | TAGGTTCATACATTCACGTAT<br>TAGGTTCATACATTCACGTAT | 22304 |
| basd16e11 | TGCTCGCGCACCTCTCCACCA<br>TGCTCGCGCATCTCTCCACCA | 22305 |
| basd16e11 | TCAAAGAACACAGGAAGGATG<br>TCAAAGAACAGAGGAAGGATG | 22306 |

TABLE 28-24

| Clones | Haruna Niio H602 | SEQ ID NO: |
|---|---|---|
| basd16e11 | CAGTCTCTATTCTTTGATCCA<br>CAGTCTCTATGCTTTGATCCA | 22307 |
| baak21n09 | ATCCATAACTTTTGGCCACCC<br>ATCCATAACTGTTGGCCACCC | 22308 |
| baak21n09 | CCACTTCCTCATCCGCATTTG<br>CCACTTCCTCGTCCGCATTTG | 22309 |
| baak21n09 | CTTGCAAGCTATCGAACTGGC<br>CTTGCAAGCTGICGAACTGGC | 22310 |
| baak1g17 | ACATGAAACAAACTCAGACCT<br>ACATGAAACAGACTCAGACCT | 22311 |
| baak1g17 | AACAGAGCACTGTTCGTTTCA<br>AACAGAGCACCGTTCGTTTCA | 22312 |
| baak1g17 | GTGGTTTTTTCCGCTACTTCA<br>GTGGTTTTTTGCGCTACTTCA | 22313 |
| baal35f12 | AGCTTATTATGCTCATGTTCA<br>AGCTTATTATTCTCATGTTCA | 22315 |
| baal35f12 | AGTTGGATACNAGAGACACTA<br>AGTTGGATACAAGAGACAGTA | 22316 |

TABLE 28-24-continued

| Clones | Haruna Niio H602 | SEQ ID NO: |
|---|---|---|
| baa135f12 | GACCACCTCTGCATGATAGAG GACCACCTCTACATGATAGAG | 22317 |
| bah29b02 | ACTTCTTGCCATCAGTGCTTG ACTTCTTGCCGTCAGTGCTTG | 22320 |
| bah29b02 | TTAAGCCAAGTTCAGTACTGG TTAAGCCAAGGTCAGTACTGG | 22321 |
| bah29b02 | ATCTGCTGACTGATTCACCAA ATCTGCTGACCGATTCACCAA | 22322 |
| bah29b02 | AGCATACCAAAATTTTTAGGT AGCATACCAAGATTTTTAGGT | 22323 |
| kr61C0305 | CCGGGCAAAAGCATGTTGTTT CCGGGCAAAAACATGTTGTTT | 22325 |
| kr61C0305 | ATAATATGCAAGAACACTTGT ATAATATGCAGGAACACTTGT | 22326 |
| kr61C0305 | CCTTTGATATATCTGCATGCA CCTTTGATATGTCTGCATGCA | 22327 |
| BaH23B08 | ACAATCCAAGGCACCTTCATA ACAATCCAAGACACCTTCATA | 22328 |
| bah51g17 | CAAATCAATTACACAAATAGT CAAATCAATTACACAAATAGT | 22330 |
| bah51g17 | TAGAGAGCTGCAACGCCACAT TAGAGAGCTGAAACGCCACAT | 22331 |
| bah51g17 | CATGTTAAAATTTGTAGGGAA CATGTTAAAACTTGTAGGGAA | 22332 |
| basd22e19 | TGCCGGGCGCTTAGCAGCAGC TGCCGGGCGCATAGCAGCAGC | 22333 |
| basd22e19 | CTTGCATATTGTGTCGGAGCC CTTGCATATTATGTCGGAGCC | 22334 |
| basd22e19 | TATTAGTCCATAAGACAATAC TATTAGTCCACAAGACAATAC | 22335 |
| basd22e19 | TAATATGATTAAAGTTTTGAG TAATATGATTGAAGTTTTGAG | 22336 |

TABLE 28-25

| Clones | Haruna Niio H602 | SEQ ID NO: |
|---|---|---|
| basd22e19 | GAGAATATAAAATGTATGTTT GAGAATATAAGATGTATGTTT | 22337 |
| basd22e19 | CCATTTCTTCAATCTTAGCAA CCATTTCTTCCATCTTAGCAA | 22338 |
| basd22e19 | TAGCAGTGCAGGCATATCATT TAGCAGTGCAGGCATATCATT | 22339 |
| basd22e19 | ATTGTAGGTACACATTAACAT ATTGTAGGTAAACATTAACAT | 22340 |
| basd22e19 | CATTCAACAACTTATTGTAGG CATTCAACAATTTATTGTAGG | 22341 |
| basd22e19 | TTTTGCATGGAAAGAGAATAT TTTTGCATGGGAAGAGAATAT | 22342 |

As described above, a gene polymorphism detection instrument according to the present invention is realized with a support immobilized thereon polynucleotides that comprise part of the base sequences of amplified DNA fragments that have polymorphism between different varieties. The amplified DNA fragments with polymorphism are not limited to those shown in Table 8-1 through Table 14-9, as long as they are DNA fragments that have polymorphism between different varieties and that have been amplified, using the genomic DNA of Triticeae species as a template, with a primer set that comprises a combination of two primers arbitrarily selected from (i) primers that have been designed based on the base sequence of SEQ ID NO: n (where n is an odd number), and (ii) primers that have been designed based on the base sequence of SEQ ID NO: (n+1), from among the base sequences of SEQ ID NO: 1 through 5780. In the case of SNP, part of amplified DNA fragments is a polynucleotide that comprises the base sequence of a region including a SNP base. In fragment length polymorphism, part of amplified DNA fragments is a polynucleotide that includes, or does not include, the base sequence of a region, if specified, causing a fragment length difference (a base sequence portion that is present in one of the varieties but not in the other). A polynucleotide that includes such base sequence portion, and a polynucleotide that does not include such base sequence portion may be used together.

In the case where a gene polymorphism detection instrument according to the present invention is used for detection of single nucleotide polymorphism (SNP), the polynucleotide immobilized on the support is preferably a synthetic oligonucleotide. Many SNP detecting arrays currently available use synthetic oligonucleotides, and these techniques can be used for the present invention. The polynucleotide immobilized on the support may have any number of bases as long as it can detect gene expression. For example, in the case where only one synthetic oligonucleotide is immobilized in each region, an oligonucleotide with at least 50 bases is considered to be sufficient for detection of gene expression. When more than one synthetic nucleotide is immobilized in each region as in the Affymetrix system, an oligonucleotide with about 25 bases is sufficient.

[Gene Polymorphism Detection Instrument with the Polynucleotides Immobilized in Regions that are Arranged in the Chromosomal Order]

As described above, the chromosomal order of polynucleotides on barley chromosomes (1H, 2H, 3H, 4H, 5H, 6H, or 7H) (distance from the short arm end of each chromosome) has been specified in clones that have the base sequences of SEQ ID NO: n (where n is an odd number) and SEQ ID NO: n+1 from among the base sequences of SEQ ID NO: 1 through SEQ ID NO: 5780. Thus, if the polynucleotides comprising part of the DNA fragments amplified with the primers that have been designed based on the respective base sequences were placed, for example, according to the order of the polynucleotides, as represented in Table 1-1 through Table 7-9, having the reference base sequences of the primers, it would be possible to place the polynucleotides according to the order in which these polynucleotides are arranged from the short arm end of 1H chromosome to the long arm end of 7H chromosome, i.e., chromosomal order. For clones that have the same order from the short arm end, the order by which these clones are placed is not particularly limited. Once the precise order of these clones were specified by a future study, these clones will be able to be placed accordingly. Note that, the reference point (origin) on the chromosome is not just limited to the short arm end of 1H chromosome. Any position on a chromosome can be used as a reference point. If the polynucleotides immobilized on the support have overlapping portions, one closest to the 5' end is placed first. When there is more than one polynucleotide having the same 5' end position, these polynucleotides are placed contiguously in any order relative to one another.

With the polynucleotides immobilized on a support in the order they are arranged on the chromosomes, the value of a gene polymorphism detection instrument according to the present invention can be greatly improved in crossbreeding of Triticeae species. More specifically, by using a gene polymorphism detection instrument according to the present invention for comprehensive investigation of gene polymorphism of Triticeae species, the genotype of a target gene of breeding can be determined. Further, the location and extent of recombination on chromosomes can be checked to see if unnecessary recombination has occurred. That is, the genotypes of the parents are directly inherited as the haplotype in portions of the chromosomes where no recombination has occurred. As a result, the genotype of a trait conferred to the selected individuals can be easily determined, with the result that the efficiency of breeding is improved.

[Gene Polymorphism Detection Instrument with the Polynucleotides Immobilized in Regions appended with Chromosomal Order Information]

The regions in which the polynucleotides are immobilized (spots) may be appended with information indicative of the order in which the polynucleotides are arranged on barley chromosomes. The spots may be arranged in any way as long as they are appended with the order information. With the order information added to the spots, the data obtained from the spots can be rearranged in the chromosomal order even when the spots are randomly placed on a support. In this way, a gene detection instrument according to the present invention can improve the efficiency of breeding. Note that, the order information added to the spots can follow the foregoing criteria used to place the polynucleotides.

Adding order information enables the spots to be arranged in an arbitrary order in a gene polymorphism detection instrument of an array type, in which more than one polynucleotide is immobilized on a support such as a membrane or a glass slide. Further, the chromosomal order information of individual polynucleotides can also be added in a gene polymorphism detection instrument that employs a collection of beads (bead array) in which the polynucleotide is immobilized on each bead serving as a support.

[Examples of a Gene Polymorphism Detection Instrument according to the Present Invention]

Various conventional techniques that are designed for detection of gene polymorphism, particularly single nucleotide polymorphism (SNP) can be suitably used for a gene polymorphism detection instrument according to the present invention.

A representative example of such conventional techniques is GeneChip array for DNA analysis (Affymetrix). In this array, total genomic DNA is excised with restriction enzyme, and adapters that recognize cohesive ends of 4 bases are ligated. The adapters can be ligated to all fragments of any size generated by the restriction enzyme treatment. From these fragments, fragments of 250 to 1000 bp are selectively amplified by PCR and hybridized with an array that has been designed to cause a match or mismatch with SNP portions. Many other conventional SNP detecting arrays have been commercially marketed, which are also applicable to a gene polymorphism detection instrument according to the present invention. The present invention can also employ the techniques disclosed in Non-Patent Publications 1 and 2.

Alternatively, an array system can be realized with use of Gene Silicon of TOYO KOHAN. Gene Silicon is a multipurpose chip made of a DLC (diamond like carbon)-coated semiconductor silicon substrate with an activated ester-bearing carboxyl group introduced on the surface. With the activated ester-bearing carboxyl group, Gene Silicon can immobilize DNA or proteins on the substrate.

For example, a plurality of primer sets is designed that serves as genetic markers for distinguishing barley variety A and barley variety B, and that can cause amplification in only one of the varieties when PCR is performed with the genomic DNA of these two varieties as templates. Specifically, the primers are preferably designed based on polymorphic sites of the both varieties.

One of the primers from each primer set is placed and immobilized on Gene Silicon in the chromosomal order. The array is then hybridized with genomic DNA prepared from the hybrid of a cross between variety A and variety B, and PCR reaction is performed in a reaction solution containing Cydye-dNTP.

The presence or absence of amplification in each spot can easily be confirmed by observing fluorescence emitted by the incorporation of Cydye-dNTP. Specifically, whether the genomic DNA that resides in portions of chromosomes where the genetic markers (amplified fragments) are mapped originates in which of the parents (variety A or variety B) is confirmed according to the presence or absence of amplification. In this way, locations of recombination can be found easily.

(3) Polypeptide-Interacting Substance Detection Instrument According to the Present Invention A polypeptide-interacting substance detection instrument according to the present invention is an instrument for detecting substances that interact with proteins encoded by genes that reside in the genomes of Triticeae species, or substances that interact with polypeptides that constitutes part of the proteins. The organisms to which a polypeptide-interacting substance detection instrument of the invention is applicable may be any Triticeae species, among which barley, wheat, and rye are preferable. As will be described later, a polypeptide-interacting substance detection instrument according to the present invention includes a support on which polypeptides encoded by polynucleotides that constitute part of DNA of barley chromosomes (1H, 2H, 3H, 4H, 5H, 6H, and 7H chromosomes) are immobilized. The polypeptides immobilized on the support may solely be polypeptides encoded by polynucleotides constituting part of barley chromosomal DNA, or other polypeptides may additionally be immobilized on the support. Such additional polypeptides are not particularly limited. For example, the additional polypeptides may be those encoded by polynucleotides with the base sequences originating in non-barley organisms, or those with arbitrary amino acid sequences that have been artificially synthesized.

In the case where the polypeptides are immobilized in more than one region of the support, the polypeptides immobilized in these regions may have non-overlapping amino acid sequences or partially overlapping amino acid sequences. Alternatively, polypeptides of the same amino acid sequence may be immobilized in these different regions of the support. In the case where the polypeptides have overlapping base sequences, the polypeptides may have partially overlapping amino acid sequences, or the amino acid sequence of one of the polypeptides may be a partial sequence of the other polypeptide.

Further, the polypeptide immobilized in each region is not necessarily required to be of the same kind. More than one kind of polypeptide may be immobilized in each region.

The support is not particularly limited as long as it can immobilize polypeptides, and it may have any shape and may be made of any material. Examples of a support material generally include: inorganic materials such as glass and silicon wafer; natural polymers such as paper; synthetic polymers such as nitrocellulose and nylon; and gels using synthetic polymers or natural polymers. The shape of the support is not particularly limited as long as it provides enough area to support the polypeptides. Generally, those with a two-dimensional plane, for example, such as a substrate with little or no flexibility, a flexible membrane, or a flexible substrate with intermediate flexibility can be preferably used. The thickness of the substrate or membrane is not particularly limited either, and it can be suitably set according to the material or use of the substrate or membrane. Various types of beads may be used as supports.

[Polypeptides Immobilized on a Support of the Polypeptide-Interacting Substance Detection Instrument]

In a polypeptide-interacting substance detection instrument according to the present invention, at least one polypeptide encoded by the following polynucleotides (a) or (b) is immobilized on a support.

(a) Polynucleotides with base sequences constituting part of barley chromosomal DNA, or variants thereof with the substitution, deletion, insertion, and/or addition of one or more bases.

(b) Polynucleotides with a combination of base sequences constituting part of barley chromosomal DNA, or variants thereof with the substitution, deletion, insertion, and/or addition of one or more bases.

As used herein, a polynucleotide with a base sequence constituting part of barley chromosomal DNA is not particularly limited as long as it is a polynucleotide with a base sequence constituting part of the entire base sequences of chromosomal DNA of barley 1H, 2H, 3H, 4H, 5H, 6H, and 7H chromosomes, and including a protein-coding region. Further, a polynucleotide with a combination of base sequences constituting part of barley chromosomal DNA refers to a polynucleotide in which a base sequence constituting part of the entire base sequences of chromosomal DNA of barley 1H, 2H, 3H, 4H, 5H, 6H, and 7H chromosomes is joined to non-continuous base sequences constituting other parts of these chromosomes, and in which a protein-coding region is contained. For example, base sequences from two different parts of the chromosomes may constitute the polynucleotide, or three or more base sequences may join together to form the polynucleotide. Specifically, for example, cDNA with a plurality of exons from a protein-coding gene on barley chromosomal DNA can be regarded as a polynucleotide with a combination of base sequences constituting part of barley chromosomal DNA. However, the polynucleotide is not just limited to this specific example.

A variant with the substitution, deletion, insertion, and/or addition of one or more bases in the polynucleotide with a base sequence, or a combination of base sequences, constituting part of barley chromosomal DNA may be a polynucleotide that has been mutated on purpose, or a polynucleotide that exists in nature. For example, think of a base sequence of chromosomal DNA in a specific variety of barley. Comparing this base sequence with those of other varieties, no sequence is completely identical. Rather, these sequences are variants with the substitution, deletion, insertion, and/or addition of one or more bases. The polypeptide encoded by a polynucleotide with such variant base sequence may have the same amino acid sequence as the polypeptide encoded by a polynucleotide with a non-variant base sequence. Further, the polypeptides encoded by the polynucleotides with variant and non-variant base sequences may differ from each other with the substitution of some of the amino acids, or most of or all of the amino acid sequences may be different between these polypeptides.

Polynucleotides that encode polypeptides immobilized on a support of a polypeptide-interacting substance detection instrument according to the present invention are preferably polynucleotides with the base sequences of SEQ ID NO: 1 through 5780, or variants with the substitution, deletion, insertion, and/or addition of one or more bases in the polynucleotides with the base sequences of SEQ ID NO: 1 through 5780. (Such polynucleotides and variants will be referred to as polynucleotides or the like with the base sequences of SEQ ID NO: 1 through 5780.)

The base sequences of SEQ ID NO: 1 through 5780 are base sequences of the barley EST (expressed sequence tag) independently developed by the inventors. The inventors have previously confirmed that a polynucleotide with the base sequences of SEQ ID NO: 1 through 770, a polynucleotide with the base sequences of SEQ ID NO: 771 through 1754, a polynucleotide with the base sequences of SEQ ID NO: 1755 through 2642, a polynucleotide with the base sequences of SEQ ID NO: 2643 through 3324, a polynucleotide with the base sequences of SEQ ID NO: 3325 through 4320, a polynucleotide with the base sequences of SEQ ID NO: 4321 through 4962, and a polynucleotide with the base sequences of SEQ ID NO: 4963 through 5780 are mapped on 1H, 2H, 3H, 4H, 5H, 6H, and 7H chromosomes, respectively.

It follows from this that the base sequences of SEQ ID NO: 1 through 5780 are partial sequences of barley cDNA. Thus, if polynucleotides with the base sequences of SEQ ID NO: 1 through 5780 contained protein-coding regions, polypeptides encoded by these polynucleotides can be immobilized on the support. Further, variants with the substitution, deletion, insertion, and/or addition of one or more bases in the base sequences of SEQ ID NO: 1 through 5780 constitute variant base sequences of barley cDNA. Thus, if these polynucleotides with variant base sequences contained protein-coding regions, polypeptides encoded by these polynucleotides can be immobilized on the support. The polynucleotides with variant base sequences may be polynucleotides that have been mutated on purpose, or polynucleotides that exist in nature.

Polynucleotides that encode polypeptides immobilized on a support of a polypeptide-interacting substance detection instrument according to the present invention may be a part of the polynucleotides or the like with the base sequences of SEQ ID NO: 1 through 5780. Since the base sequence of such partial polynucleotide is a partial base sequence of barley cDNA, a polypeptide encoded by such partial polynucleotide can be immobilized on the support if the partial polynucleotide contains a protein-coding region.

Further, polynucleotides that encode polypeptides immobilized on a support of a polypeptide-interacting substance detection instrument according to the present invention may be polynucleotides whose partial sequence comprises all of or part of the base sequences of SEQ ID NO: 1 through 5780. The remaining base sequences of the polynucleotides are not limited. For example, since the base sequences of SEQ ID NO: 1 through 5780 are partial sequences of barley cDNA, these base sequences do not have the sequences on either end as originally found in the full length cDNA. Thus, a polynucleotide whose partial sequence comprises all of or part of the base sequences of SEQ ID NO: 1 through 5780, and which additionally includes the cDNA sequences on the both ends or one end as originally found in the full length cDNA can be regarded as a polynucleotide whose partial sequence comprises all of or part of the base sequences of SEQ ID NO: 1 through 5780. Further, vectors such as plasmids and BACs (bacterial artificial chromosomes) that have incorporated all of or part of the polynucleotides or the like with the base sequences of SEQ ID NO: 1 through 5780, and polynucleotides in which the partial sequence is ligated to arbitrary base sequences can also be regarded as polynucleotides whose partial sequence comprises all of or part of the base sequences of SEQ ID NO: 1 through 5780. Such polynucleotides at least include all of or part of the polynucleotides or the like with the base sequences of SEQ ID NO: 1 through 5780, i.e., part of barley cDNA. Therefore, polypeptides encoded by such polynucleotides can be immobilized on the support if the polynucleotides contain a protein-encoding region.

Further, polynucleotides that encode polypeptides immobilized on a support of a polypeptide-interacting substance detection instrument according to the present invention may be polynucleotides or the like whose partial sequences comprise all of or part of the base sequence, or a variant thereof, of SEQ ID NO: n (where n is an odd number), and all of or part of the base sequence, or a variant thereof, of SEQ ID NO: n+1, from among the base sequences of SEQ ID NO: 1 through 5780. As described above, the base sequences of SEQ ID NO: 1 through 5780 are EST sequences of barley, and comprise sequences that can be read by sequencing the cloned cDNA from the both ends only once. In other words, the base sequences of SEQ ID NO: n (where n is an odd number) and SEQ ID NO: n+1 among the base sequences of SEQ ID NO: 1 through 5780 are base sequences that are read from the both ends of the cDNA of the same clone. As such, these base sequences can realize a full length cDNA base sequence, which corresponds to all of or part of the full length cDNA. Thus, polynucleotides or the like whose partial sequences comprise all of or part of the base sequence, or a variant thereof, of SEQ ID NO: n (where n is an odd number), and all of or part of the base sequence, or a variant thereof, of SEQ ID NO: n+1, from among the base sequences of SEQ ID NO: 1 through 5780 can be regarded as polynucleotides with full length cDNA that comprises the base sequences of SEQ ID NO: n (where n is an odd number) and SEQ ID NO: n+1, or polynucleotides that comprise part of the full length cDNA. Further, the polynucleotides may be polynucleotides in which vector sequences or arbitrary base sequences for example are ligated to the both ends or one end of the full length cDNA or a polynucleotide that comprises part of the full length cDNA. Further, the polynucleotides may be variants that have a base substitution or other mutations in sequences other than the base sequences of SEQ ID NO: 1 through 5780, i.e., a middle section of the total cDNA unspecified by SEQ ID NO: n (where n is an odd number) and SEQ ID NO: n+1. Such polynucleotides include the full length or part of barley cDNA, enabling polypeptides encoded by the polynucleotides to be immobilized on the support. In particular, when the polynucleotides are full length cDNA or include full length cDNA, the entire proteins encoded by the genes located on the barley chromosomes can be immobilized on the support.

[Peptide-Interacting Substance Detection Instrument with the Polypeptides Immobilized in Regions that are Arranged in the Chromosomal Order]

As described above, the chromosomal order of polynucleotides on barley chromosomes (1H, 2H, 3H, 4H, 5H, 6H, or 7H) (distance from the short arm end of chromosome) has been specified in clones that have the base sequences of SEQ ID NO: n (where n is an odd number) and SEQ ID NO: n+1 from among the base sequences of SEQ ID NO: 1 through SEQ ID NO: 5780. Thus, if the polypeptides encoded by the polynucleotides with the base sequences of SEQ ID NO: 1 through SEQ ID NO: 5780 were placed according to the order, as represented in Table 1-1 through Table 7-9, of the polynucleotides encoding the polypeptides, it would be possible to place the polypeptides according to the order from the short arm end of 1H chromosome to the long arm end of 7H chromosome, i.e., chromosomal order. For clones that have the same order from the short arm end, the order by which these clones are placed is not particularly limited. Once the precise order of these clones were specified by a future study, these clones will be able to be placed accordingly. Note that, the reference point (origin) on the chromosome is not just limited to the short arm end of 1H chromosome. Any position on a chromosome can be used as a reference point.

With the polypeptides immobilized on a support in the order they are arranged on the chromosomes, the location and extent of recombination on chromosomes can be checked for genes from which the expressed proteins originate. That is, the genotypes of the parents are directly inherited as the haplotype in portions of the chromosomes where no recombination has occurred. As a result, the genotype of a trait conferred to the selected individuals can be easily determined, with the result that the efficiency of breeding is improved.

[Polypeptide-Interacting Substance Detection Instrument with the Polypeptides Immobilized in Regions Appended with Chromosomal Order Information]

The regions in which the polypeptides are immobilized (spots) may be appended with information indicative of the order in which the polynucleotides encoding the polypeptides are arranged on barley chromosomes. The spots may be arranged in any way as long as they are appended with the order information. With the order information added to the spots, the data obtained from the spots can be rearranged in the chromosomal order even when the spots are randomly placed on a support. Note that, the order information added to the spots can follow the foregoing criteria used to place the polypeptides.

Adding order information enables the spots to be arranged in an arbitrary order in a polypeptide-interacting substance detection instrument of an array type, in which more than one polypeptide is immobilized on a support such as a membrane or a glass slide. Further, the chromosomal order information of individual polypeptides can also be added in a polypeptide-interacting substance detection instrument that employs a collection of beads (bead array) in which the polypeptide is immobilized on each bead serving as a support.

[Examples of a Polypeptide-Interacting Substance Detection Instrument According to the Present Invention]

Various conventional techniques that are designed for detection of protein (polypeptide)-interacting substances can suitably be used in a polypeptide-interacting substance detecting instrument according to the present invention.

For example, a biological chip, one kind of protein chip, has been commercially available from Ciphergen Biosystems, Inc. This biological chip has an activated group such as carbonyl diimidazole or epoxy on a surface of a substrate (support), allowing a user to freely immobilize target proteins or antibodies. This technique is therefore applicable to a polypeptide-interacting substance according to the present invention. Since the activated group such as carbonyl diimidazole or epoxy can immobilize antibodies or polynucleotides, the biological chip can be used for the fabrication of other detection instruments of the present invention.

(4) Polypeptide Detection Instrument according to the Present Invention

A polypeptide detection instrument according to the present invention is an instrument for detecting proteins encoded by genes that reside in the genomes of Triticeae species, or polypeptides that constitutes part of the proteins. The organisms to which a polypeptide detection instrument of the invention is applicable may be any Triticeae species, among which barley, wheat, and rye are preferable. As will be described later, a polypeptide detection instrument according to the present invention includes a support on which polypeptides encoded by polynucleotides that constitute part of DNA of barley chromosomes (1H, 2H, 3H, 4H, 5H, 6H, and 7H chromosomes) are immobilized. The polypeptides immobilized on the support may solely be antibodies against the polypeptides encoded by polynucleotides constituting part of barley chromosomal DNA, or other antibodies may additionally be immobilized on the support. Such additional antibodies are not particularly limited. For example, antibodies encoded by polynucleotides with the base sequences originating in non-barley organisms may be immobilized.

As used herein, the term "antibodies" refers to immunoglobulins that can recognize and bind to specific antigens. However, the term does not necessarily mean antibody molecules as a whole, but also refers to part of antibody molecules including antigen binding sites.

It is preferable that the support include a plurality of immobilizing regions, and that different kinds of antibodies be immobilized in these regions. Further, the antibodies immobilized in each region are not necessarily required to be of the same kind. More than one kind of antibodies may be immobilized in each region.

The support is not particularly limited as long as it can immobilize antibodies, i.e., proteins, and it may have any shape and may be made of any material. Examples of a support material generally include: inorganic materials such as glass and silicon wafer; natural polymers such as paper; synthetic polymers such as nitrocellulose and nylon; and gels using synthetic polymers or natural polymers. The shape of the support is not particularly limited as long as it provides enough area to support the polynucleotides. Generally, those with a two-dimensional plane, for example, such as a substrate with little or no flexibility, a flexible membrane, or a flexible substrate with intermediate flexibility can be preferably used. The thickness of the substrate or membrane is not particularly limited either, and it can be suitably set according to the material or use of the substrate or membrane. Various types of beads may be used as supports.

[Antibodies Immobilized on a Support of the Polypeptide Detection Instrument]

In a polypeptide detection instrument according to the present invention, at least one antibody against a polypeptide encoded by a polynucleotide selected from the following polynucleotides (a) or (b) is immobilized on a support.

(a) Polynucleotides with base sequences constituting part of barley chromosomal DNA, or variants thereof with the substitution, deletion, insertion, and/or addition of one or more bases.

(b) Polynucleotides with a combination of base sequences constituting part of barley chromosomal DNA, or variants thereof with the substitution, deletion, insertion, and/or addition of one or more bases.

As used herein, a polynucleotide with a base sequence constituting part of barley chromosomal DNA is not particularly limited as long as it is a polynucleotide that has a base sequence constituting part of the entire base sequences of chromosomal DNA of barley 1H, 2H, 3H, 4H, 5H, 6H, and 7H chromosomes, and that includes a protein-coding region. Further, a polynucleotide with a combination of base sequences constituting part of barley chromosomal DNA refers to a polynucleotide in which a base sequence constituting part of the entire base sequences of chromosomal DNA of barley 1H, 2H, 3H, 4H, 5H, 6H, and 7H chromosomes is joined to non-continuous base sequences constituting other parts of these chromosomes, and in which a protein-coding region is contained. For example, base sequences from two different parts of the chromosomes may constitute the polynucleotide, or three or more base sequences may join together to form the polynucleotide. Specifically, for example, cDNA with a plurality of exons from a protein-coding gene on barley chromosomal DNA can be regarded as a polynucleotide with a combination of base sequences constituting part of barley chromosomal DNA. However, the polynucleotide is not just limited to this specific example.

A variant with the substitution, deletion, insertion, and/or addition of one or more bases in the polynucleotide with a base sequence, or a combination of base sequences, constituting part of barley chromosomal DNA may be a polynucleotide that has been mutated on purpose, or a polynucleotide that exists in nature. For example, think of a base sequence of chromosomal DNA in a specific variety of barley. Comparing this base sequence with those of other varieties, no sequence is completely identical. Rather, these sequences are variants with the substitution, deletion, insertion, and/or addition of one or more bases. The polypeptide encoded by a polynucleotide with such variant base sequence may have the same amino acid sequence as the polypeptide encoded by a polynucleotide with a non-variant base sequence. Further, the polypeptides encoded by the polynucleotides with variant and non-variant base sequences may differ from each other with the substitution of some of the amino acids, or most of or all of the amino acid sequences may be different between these polypeptides.

Polynucleotides that encode polypeptides used for production of antibodies immobilized on a support of a polypeptide detection instrument according to the present invention are preferably polynucleotides with the base sequences of SEQ ID NO: 1 through 5780, or variants with the substitution, deletion, insertion, and/or addition of one or more bases in the polynucleotides with the base sequences of SEQ ID NO: 1 through 5780. (Such polynucleotides and variants will be referred to as polynucleotides or the like with the base sequences of SEQ ID NO: 1 through 5780.)

The base sequences of SEQ ID NO: 1 through 5780 are base sequences of the barley EST (expressed sequence tag) independently developed by the inventors. The inventors have previously confirmed that a polynucleotide with the base sequences of SEQ ID NO: 1 through 770, a polynucleotide with the base sequences of SEQ ID NO: 771 through 1754, a polynucleotide with the base sequences of SEQ ID NO: 1755 through 2642, a polynucleotide with the base sequences of SEQ ID NO: 2643 through 3324, a polynucleotide with the base sequences of SEQ ID NO: 3325 through 4320, a polynucleotide with the base sequences of SEQ ID NO: 4321 through 4962, and a polynucleotide with the base sequences of SEQ ID NO: 4963 through 5780 are mapped on 1H, 2H, 3H, 4H, 5H, 6H, and 7H chromosomes, respectively.

It follows from this that the base sequences of SEQ ID NO: 1 through 5780 are partial sequences of barley cDNA. Thus, if polynucleotides with the base sequences of SEQ ID NO: 1 through 5780 contained protein-coding regions, antibodies against polypeptides encoded by these polynucleotides can be immobilized on the support. Further, variants with the substitution, deletion, insertion, and/or addition of one or more bases in the base sequences of SEQ ID NO: 1 through 5780 constitute variant base sequences of barley cDNA. Thus, if these polynucleotides with variant base sequences contained protein-coding regions, antibodies against polypeptides encoded by these polynucleotides can be immobilized on the support. The polynucleotides with variant base sequences may be polynucleotides that have been mutated on purpose, or polynucleotides that exist in nature.

Polynucleotides that encode polypeptides used for production of antibodies immobilized on a support of a polypeptide detection instrument according to the present invention may be part of the polynucleotides or the like with the base sequences of SEQ ID NO: 1 through 5780. Since the base sequence of such partial polynucleotide is a partial base sequence of barley cDNA, antibodies against polypeptides encoded by such partial polynucleotides can be immobilized on the support if the partial polynucleotides contained a protein-coding region.

Further, a polynucleotide that encodes a polypeptide used for production of an antibody immobilized on a support of a polypeptide detection instrument according to the present invention may be a polynucleotide whose partial sequence comprises all of or part of the base sequences of SEQ ID NO: 1 through 5780. The remaining base sequences of the polynucleotide are not limited. For example, since the base sequences of SEQ ID NO: 1 through 5780 are partial sequences of barley cDNA, these base sequences do not have the sequences on either end as originally found in the full length cDNA. Thus, a polynucleotide whose partial sequence comprises all of or part of the base sequences of SEQ ID NO: 1 through 5780, and which additionally includes the cDNA sequences on the both ends or one end as originally found in the full length cDNA can be regarded as a polynucleotide whose partial sequence comprises all of or part of the base sequences of SEQ ID NO: 1 through 5780. Further, vectors such as plasmids and BACs (bacterial artificial chromosomes) that have incorporated all of or part of the polynucleotide or the like with the base sequences of SEQ ID NO: 1 through 5780, and polynucleotides in which the partial sequence is ligated to arbitrary base sequences can also be regarded as polynucleotides whose partial sequence comprises all of or part of the base sequences of SEQ ID NO: 1 through 5780. Such polynucleotides at least include all of or part of the polynucleotide or the like with the base sequences of SEQ ID NO: 1 through 5780, i.e., part of barley cDNA. Therefore, antibodies against polypeptides encoded by such polynucleotides can be immobilized on the support if the polynucleotides contained a protein-encoding region.

Further, polynucleotides that encode polypeptides used for production of antibodies immobilized on a support of a polypeptide detection instrument according to the present invention may be polynucleotides or the like whose partial sequences comprise all of or part of the base sequence, or a variant thereof, of SEQ ID NO: n (where n is an odd number), and all of or part of the base sequence, or a variant thereof, of SEQ ID NO: n+1, from among the base sequences of SEQ ID NO: 1 through 5780. As described above, the base sequences of SEQ ID NO: 1 through 5780 are EST sequences of barley, and comprise sequences that can be read by sequencing the cloned cDNA from the both ends only once. In other words, the base sequences of SEQ ID NO: n (where n is an odd number) and SEQ ID NO: n+1 among the base sequences of SEQ ID NO: 1 through 5780 are base sequences that are read from the both ends of the cDNA of the same clone. As such, these base sequences can realize a full length cDNA base sequence, which corresponds to all of or part of the full length cDNA. Thus, polynucleotides or the like whose partial sequences comprise all of or part of the base sequence, or a variant thereof, of SEQ ID NO: n (where n is an odd number), and all of or part of the base sequence, or a variant thereof, of SEQ ID NO: n+1, from among the base sequences of SEQ ID NO: 1 through 5780 can be regarded as polynucleotides with full length cDNA that comprises the base sequences of SEQ ID NO: n (where n is an odd number) and SEQ ID NO: n+1, or polynucleotides that comprise part of the full length cDNA. Further, the polynucleotides may be polynucleotides in which vector sequences or arbitrary base sequences for example are ligated to the both ends or one end of the full length cDNA or polynucleotides that comprise part of the full length cDNA. Further, the polynucleotides may be variants that have a base substitution or other mutations in sequences other than the base sequences of SEQ ID NO: 1 through 5780, i.e., a middle section of the total cDNA unspecified by SEQ ID NO: n (where n is an odd number) and SEQ ID NO: n+1. Such polynucleotides include the full length or part of barley cDNA, and therefore antibodies against polypeptides encoded by the polynucleotides can be produced. In particular, when the polynucleotides are full length cDNA or include full length cDNA, antibodies against the entire proteins encoded by the genes located on the barley chromosomes can be produced.

[Peptide Detection Instrument with the Antibodies Immobilized in Regions that are Arranged in the Chromosomal Order of the Polynucleotides Encoding Polypeptides Used for Production of the Antibodies]

As described above, the chromosomal order of polynucleotides on barley chromosomes (1H, 2H, 3H, 4H, 5H, 6H, or 7H) (distance from the short arm end of chromosome) has been specified in clones that have the base sequences of SEQ ID NO: n (where n is an odd number) and SEQ ID NO: n+1 from among the base sequences of SEQ ID NO: 1 through SEQ ID NO: 5780. Thus, if antibodies against the polypeptides encoded by the polynucleotides with the base sequences of SEQ ID NO: 1 through SEQ ID NO: 5780 were placed according to the order, as represented in Table 1-1 through Table 7-9, of the polynucleotides encoding the polypeptides, it would be possible to place the polypeptides according to the order from the short arm end of 1H chromosome to the long arm end of 7H chromosome, i.e., chromosomal order. For clones that have the same order from the short arm end, the order by which these clones are placed is not particularly limited. Once the precise order of these clones were specified by a future study, these clones will be able to be placed accordingly. Note that, the reference point (origin) on the chromosome is not just limited to the short arm end of 1H chromosome. Any position on a chromosome can be used as a reference point.

With the antibodies immobilized on a support in the order the polynucleotides encoding the polypeptides used for production of the antibodies are arranged on the chromosomes, the location and extent of recombination on chromosomes can be checked for genes from which the expressed proteins originate. That is, the genotypes of the parents are directly inherited as the haplotype in portions of the chromosomes where no recombination has occurred. As a result, the genotype of a trait conferred to the selected individuals can be easily determined, with the result that the efficiency of breeding is improved.

[Polypeptide Detection Instrument with the Antibodies Immobilized in Regions appended with Chromosomal Order Information of the Polynucleotides Encoding Polypeptides Used for Production of the Antibodies]

The regions in which the antibodies are immobilized (spots) may be appended with information indicative of the order in which the polynucleotides encoding the polypeptides used for production of the antibodies are arranged on barley chromosomes. The spots may be arranged in any way as long as they are appended with the order information. With the order information added to the spots, the data obtained from the spots can be rearranged in the chromosomal order even when the spots are randomly placed on a support. Note that, the order information added to the spots can follow the foregoing criteria used to place the antibodies.

Adding order information enables the spots to be arranged in an arbitrary order in a polypeptide detection instrument of an array type, in which more than one antibody is immobilized on a support such as a membrane or a glass slide. Further, the chromosomal order information of individual antibodies can also be added in a polypeptide detection instrument that employs a collection of beads (bead array) in which the antibody is immobilized on each bead serving as a support.

[Examples of a Polypeptide Detection Instrument according to the Present Invention]

Various conventional techniques that are designed for detection of protein (polypeptide) using antibodies can suitably be used in a polypeptide detecting instrument according to the present invention.

As an example of a peptide detection instrument according to the present invention, the following describes an antibody array of a bead type. The substance immobilized on the beads serving as supports is not limited to antibody. Other polypeptides or polynucleotides may be immobilized as well. As such, a gene detection instrument, a gene polymorphism detection instrument, and a polypeptide-interacting substance detection instrument according to the present invention can also be realized as bead arrays.

In an antibody array of a bead type, it is preferable that one kind of antibody be immobilized on each bead, and that each bead be appended with barley chromosomal order information of polynucleotides encoding polypeptides used for production of the antibodies. For example, by using each well of a micro titer plate as a small vessel, a plurality of beads with identification code (information of the immobilized antibodies, position information on the chromosomes, etc.) is placed in each well. By reading the identification code, information regarding identity of the immobilized antibodies can be specified. With use of a two-wavelength laser beam, 100 kinds of beads can be quantified. Further, since the technique allows for detection in a liquid phase, it is particularly effective in efficiently quantifying proteins. A representative example is Luminex, which is a fluorescent micro beads array system manufactured by HitachiSoft.

(5) Use of a Detection Instrument according to the Present Invention

Use of a detection instrument according to the present invention is not particularly limited. For example, the detection instrument can be suitably used to identify chromosome fragments including a target trait (identification of genotype), from hybrids obtained by crossing Triticeae species. Further, the detection instrument can be suitably used to screen for a variety with a target trait, from hybrids obtained by crossing Triticeae species for variety improvement. For these purposes, it is preferable that the polynucleotides or other substances immobilized on the support such as an array be arranged in the chromosomal order.

In conventional arrays, the polynucleotides or other substances immobilized on the support are randomly arranged. This enables the expression level or other profiles of the immobilized polynucleotides etc. to be individually analyzed. In hybrids, individual genes are inherited in units of blocks, from a point of cross over to the next point of cross over, on the chromosomes. Therefore, for the genotype identification or selection in variety improvement, etc., it is necessary to determine the location and extent of recombination and the presence or absence of unnecessary recombination, in addition to finding individual traits. Thus, conventional arrays with randomly arranged DNA fragments cannot be used efficiently for the screening in variety improvement, etc.

On the other hand, in a detection instrument of the present invention, the polynucleotides or other substances immobilized on the support are arranged in the chromosomal order. Thus, with a detection instrument of the present invention, the locations of recombination on the chromosomes can be found, if any, with a single round of testing. This allows for accurate selection of individuals with desirable traits from a segregating population of hybrid individuals. Further, with a detection instrument according to the present invention, chromosomal recombinations in the hybrid generation can easily be estimated. This allows a group of genes to be introduced in units of blocks, or genes in the blocks to be modified.

Further, with a detection instrument according to the present invention, the recombination patterns, i.e., the location and type of recombination on the chromosomes can be accurately grasped. Thus, by identifying conserved regions of chromosomes where recombination frequency is small in the population of hybrids or natural population, recombination can be efficiently promoted only in these regions of the chromosomes.

Figure 2:
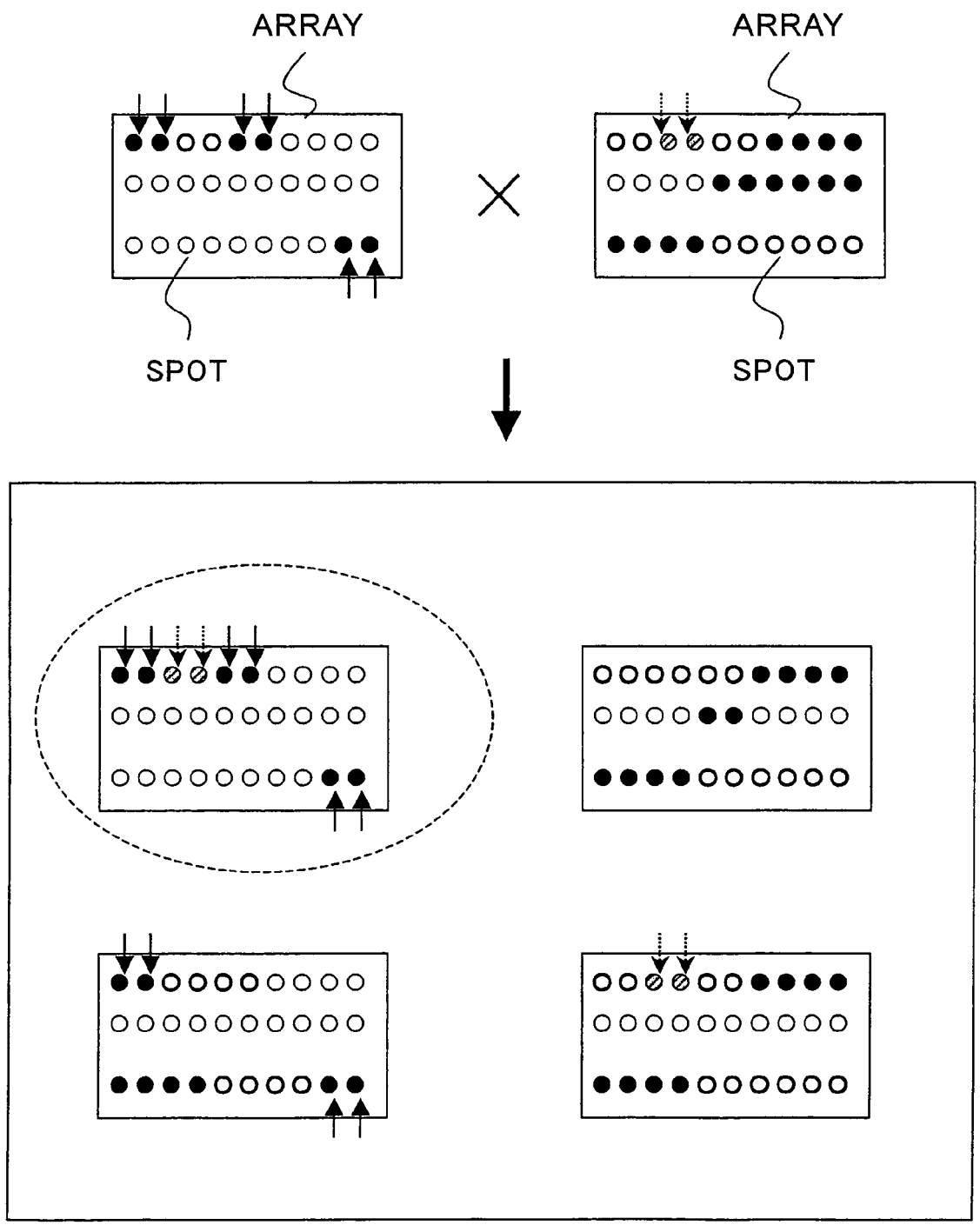
FIG. 2 is a schematic view illustrating expression of genes conferring certain characteristics in a segregating population obtained from a cross between varieties that showed the gene expression represented in FIGS. 1(a) and 1(b), and in specific varieties selected from the segregating population.

Referring to FIG. 1 and FIG. 2, the following briefly describes an example of a method by which target traits are screened for using a detection instrument according to the present invention. For example, a DNA micro array was used in which polynucleotides with partial base sequences of chromosomal DNA of barley were placed and immobilized on a support in the chromosomal order. In the DNA micro array, solid spots X in FIG. 1($a$) indicate that genes that confer brewing characteristics are expressed, and hatched spots Y in FIG. 1($b$) indicates expression of genes that confer disease-resistance.

In the DNA micro array, the spots are arranged in a chromosomal order, and therefore the positions of spots X and Y are fixed. For example, in FIG. 1($a$), the spots X are fixed at the first, second, fifth, and sixth positions of the first row, and at the ninth and tenth positions of the bottom row. The spots Y are fixed at the third and fourth positions of the first row, as shown in FIG. 1($b$).

It is assumed here that segregating populations as represented by four micro arrays in the bottom of FIG. 2 were obtained from a cross between a variety expressing the brewing genes as indicated by spots X (corresponding to the upper left DNA micro array in FIG. 2) and a variety expressing the disease-resistant genes as indicated by spots Y (corresponding to the upper right DNA micro array in FIG. 2), for example. From the result of analysis using these DNA micro arrays, varieties expressing both the brewing genes and disease-resistant genes can be screened for from the segregating populations (variety corresponding to the upper left DNA micro array circled by a dotted line in the lower portion of FIG. 2).

Further, whether the chromosome fragments have derived from which parent can easily be determined also for other regions of the genome. Thus, a backcross, for example, between a hybrid and the variety shown in FIG. 1($a$) easily allows for selection and development of varieties having all of the expressed spots as illustrated in FIG. 1($a$), i.e., the first, second, fifth, and sixth spots of the first row, and the ninth and tenth spots of the bottom row, as well as the third and fourth spots of the first row as shown in FIG. 1($b$).

In using a detection instrument according to the present invention for genotyping (whether chromosome sites originated from which parent) or detection of traits (quantitative and qualitative) linked to the genetic markers, the accuracy of data can be improved by increasing the density of the genetic markers with increased numbers of polynucleotides, polypeptides, or antibodies immobilized on a support of a detection instrument according to the present invention.

The density of polynucleotides, polypeptides, or antibodies (a distance between adjacent polynucleotides etc.) immobilized on the support is preferably no greater than 30 cM, more preferably no greater than 15 cM, or particularly preferably no greater than 10 cM, in order to confirm linkage between two adjacent markers.

For the entire barley genome, the number of polynucleotides, polypeptides, or antibodies immobilized on the support is preferably no less than 50, more preferably no less than 100, and particularly preferably no less than 150. When performing genotyping for a Mendelian segregating population of barley with a resolution as high as 1 cM, the number of polynucleotides, polypeptides, or antibodies immobilized on the support is preferably no less than 1500.

Example

With the polynucleotides immobilized on a support of a detection instrument according to the present invention, assessment was made as to whether the genotype of each parent occurs in which part of 1H chromosome in 5 lines of hybrids (DHHS1, DHHS2, DHHS3, DHHS4, and DHHS5) obtained from a cross between malting barley (Haruna Nijo), and wild type barley (H602). That is, locations of recombination were determined.

[Genetic Markers]

Nine genetic markers mapped on 1H chromosome of barley were used. Clones: bah47d23, baa119i12, bah45i3, bags30g20, BaGS13F08, baet45e0410, bah16m01, BaH56B06, and BaH39L18.

[Primers]

Table. 29 below shows the primers used in this experiment.

A, a purine, G, was selected (and vice versa), and when the base in the original sequence was C, a pyrimidine, T, was selected (and vice versa).

For the designing of forward primers, the base sequences in the vicinity of the SNPs of the SNP markers, shown in Tables 22-1 through 22-20, mapped on 1H chromosome were used. Specifically, the forward primers (SEQ ID NO: 22343 (Haruna Nijo) and SEQ ID NO: 22344 (H602)) for bah47d23 had the base sequence of SEQ ID NO: 17380. The forward primers (SEQ ID NO: 22345 (Haruna Nijo) and SEQ ID NO: 22346 (H602)) for baa119i12 had the base sequence of SEQ ID NO: 17419. The forward primers (SEQ ID NO: 22347 (Haruna Nijo) and SEQ ID NO: 22348 (H602)) for bah45i13 had the base sequence of SEQ ID NO: 17556. The forward primers (SEQ ID NO: 22349 (Haruna Nijo) and SEQ ID NO: 22350 (H602)) for bags30g20 had the base sequence of SEQ ID NO: 17669. The forward primers (SEQ ID NO: 22351 (Haruna Nijo) and SEQ ID NO: 22352 (H602)) for BaGS13F08 had the base sequence of SEQ ID NO: 17723. The forward primers (SEQ ID NO: 22353 (Haruna Nijo) and SEQ ID NO: 22354 (H602)) for baet45e0410 had the base sequence of SEQ ID NO: 17742. The forward primers (SEQ

TABLE 29

| Clones | Forward Primer Haruna Nijo<br>Forward Primer H602 | SEQ ID<br>NO: | Reverse Primer | SEQ ID<br>NO: |
|---|---|---|---|---|
| bah47d23 | AGATGGAGGGGCCCTGTGCAT<br>TAGATGGAGGGGCCCTGTGTAT | 22343<br>22344 | CTGTGGGAAAGCCTACATCC | 5880 |
| baa119i12 | TCAGAGAGGTGAATCTGGGTCAA<br>TTCAGAGAGGTGAATCTGGGTTAA | 22345<br>22346 | GAACTGAGGCGTGCACATAA | 6012 |
| bah45i13 | CCATGACCAGCAAAAGCAGTCC<br>CCATGACCAGCAAAAGCAGCCC | 22347<br>22348 | GCAAATCAGTTGCTGGAACA | 6340 |
| bags30g20 | GGACTACGTACGGACTGAAATAG<br>GGACTACGTACGGACTGAAACAG | 22349<br>22350 | GGTTCCATTCCTGCAGATGT | 6632 |
| BaGS13F08 | TCACAAGGTAACCAAAACAATTCGA<br>ATCACAAGGTAACCAAACAATTTGA | 22351<br>22352 | CTCAGGCAATGCATCAAATG | 6760 |
| baet45E0410 | CCGGACTTGACAAGCGGTAATTG<br>CGGACTTGACAAGCGGTAAGTG | 22353<br>22354 | CGGCTCTCCATAGACTGCTC | 6800 |
| bah16m01 | CATGGGGGAGGTTTTGGCTCTTT<br>ATGGGGGAGGTTTTGGCTCGTT | 22355<br>22356 | AAGACCTCACTCCAAAGCGA | 6904 |
| BaH56B06 | CTTTTTGGTCCTCAGTCCTCATTG<br>TTTTTGGTCCTCAGTCCTCACTG | 22357<br>22358 | AGATCCGCTACTGCTTGGAA | 7064 |
| BaH39L18 | GCTTCTAGACGCAGACAAGCTG<br>AGCTTCTAGACGCAGACAAGTTG | 22359<br>22360 | GTATGCTTGCAGGAAGGCTC | 7316 |

As the reverse primers, the primers used to find polymorphism in 1H chromosomes, shown in Tables 8-1 through 8-8, were used. Specifically, bah47d23, baa119i12, bah45i13, bags30g20, BaGS13F08, baet45e0410, bah16m01, BaH56B06, and BaH39L18 are primers with the base sequences of SEQ ID NO: 5880, SEQ ID NO: 6012, SEQ ID NO: 6340, SEQ ID NO: 6632, SEQ ID NO: 6760, SEQ ID NO: 6800, SEQ ID NO: 6904, SEQ ID NO: 7064, and SEQ ID NO: 7316, respectively.

The forward primers were designed based on SNP-containing portions of the base sequences. Specifically, the third base from the 3' end of the primer sequence was designated as a base characterizing "Haruna Nijo" or "H602". For the first and second bases on the 3' end, the same kind of base but different from one found in the original base sequence was used. Specifically, when the base in the original sequence was ID NO: 22355 (Haruna Nijo) and SEQ ID NO: 22356 (H602)) for bah16m01 had the base sequence of SEQ ID NO: 17785. The forward primers (SEQ ID NO: 22357 (Haruna Nijo) and SEQ ID NO: 22358 (H602)) for BaH56B06 had the base sequence of SEQ ID NO: 17860. The forward primers (SEQ ID NO: 22359 (Haruna Nijo) and SEQ ID NO: 22360 (H602)) for BaH39L18 had the base sequence of SEQ ID NO: 17958.

[PCR Reaction]

From each of the 5 lines of barley hybrids, genomic DNA was prepared and used as a template. Table 30 shows the composition of the PCR reaction solution. The reaction was performed under the following conditions.
94° C. for 2 minutes
Start of 5 cycles consisting of:
  94° C. for 30 seconds;
  65° C. for 30 seconds (−1° C./cycle); and 72° C. for 1 minute
Start of 30 cycles consisting of:
  94° C. for 30 seconds;
  60° C. for 30 seconds; and
  72° C. for 1 minute
72° C. for 7 minutes
End of Reaction

TABLE 30

Composition of PCR reaction solution

| | (×1) |
|---|---|
| mQH$_2$O | 6.86 |
| 10X Blend Taq buffer | 1.00 |
| dNTPs (2.0 mM) | 1.00 |
| Primer fwd. (50 μM) | 0.02 |
| Primer rev. (50 μM) | 0.02 |
| Blend Taq (2.5 U/μl) | 0.10 |
| DNA (10 ng/μl) | 1.00 |
| Total (μl) | 10.00 |

[Result]

Figure 3:
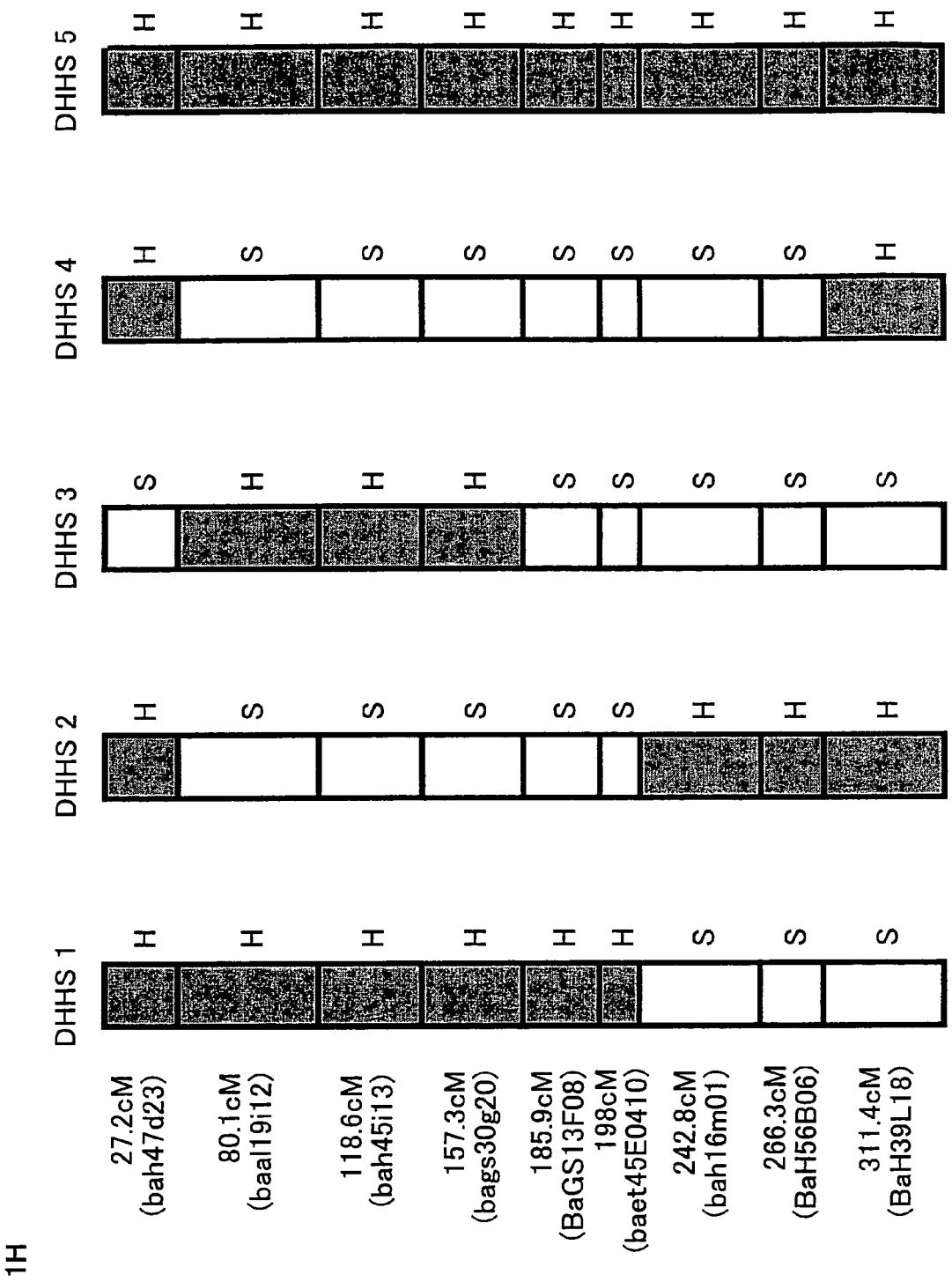
FIG. 3 is a view showing a result of analysis on genotypes (recombination sites) of barley hybrids that were subjected to PCR in which polynucleotides immobilized on a support of a gene polymorphism detection instrument according to the present invention were used as primers, and genomic DNA of the barley hybrids was used as a template.

FIG. 3 shows the result. In FIG. 3, regions indicated by "H" (black) are regions originating in Haruna Nijo, and regions indicated by "S" (blank) are regions originating in H602. As can be seen in FIG. 3, in DHHS1, bah47d23 through BaGS13F08 were amplified by the forward primers based on the base sequences of Haruna Nijo, and baet45e0410 through BaH39L18 were amplified by the forward primers based on the base sequence of H602. In other words, in DHHS1, there were recombinations between the genetic markers based on BaGS13F08 and the genetic markers based on baet45e0410.

Similarly, in DHHS2, two recombinations were observed: one between bah47d23 and baa119i12, and one between BaGS13F08 and baet45e0410. In DHHS3, two recombinations were observed: one between bah47d23 and baa119i12, and one between bags30g20 and BaGS13F08. In DHHS4, two recombinations were observed: one between bah47d23 and baa119i12, and one between BaH56B06 and BaH39L18.

In DHHS5, all clones had the genotype of H602, suggesting that the entire 1H chromosome of these individuals is very likely to be of the H602 origin.

The polynucleotides used in this Example were not immobilized on a support. However, the forward primers and reverse primers used in this Example may be immobilized, for example, on the Gene Silicon in the chromosomal order, so as to fabricate a detection instrument according to the present invention. It should be apparent to a person ordinary skill in the art that the result obtained in this Example can also be obtained with such a detection instrument.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

A detection instrument according to the present invention uses polynucleotides that can be used as genetic markers mapped on barley chromosomes. The detection instrument can be used to quickly and comprehensively detect gene expression, gene polymorphism, proteins (polypeptides), and protein (polypeptide)-interacting substances in Triticeae species. This greatly improves the efficiency of screening and breeding of Triticeae species. If the detection instrument were able to grow useful Triticeae species of various characteristics in a short time period, it would be possible to offer a solution to food problems.

Taken together, a detection instrument according to the present invention can be suitably used for breeding of Triticeae species, and is applicable to a wide range of agricultural fields. A detection instrument of the present invention can also be used for the basic research in agriculture and other fields of biology.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07977087B2). An electronic copy of the "Sequence Listing" will also be available from the USPTO upon request and payment of the fee set forth in 37 CFR 1.19(b)(3).

The invention claimed is:

1. A gene detection instrument for detecting expression or polymorphism of genes existing in a genome of Triticeae species, said gene detection instrument comprising a support on which are immobilized at least 50 polynucleotides selected from the group consisting of:
(a) polynucleotides with partial base sequences of chromosomal DNA of barley and
(b) polynucleotides in which a base sequence constituting part of entire base sequences of chromosomal DNA of barley is joined to non-continuous base sequences constituting other parts of the entire base sequences of chromosomal DNA of barley wherein the polynucleotide immobilized on the support comprises;
at least one kind of polynucleotide is selected from the group consisting of:
(1) polynucleotides with the base sequences of SEQ ID NO: 1 through 5780;
(2) a polynucleotide whose partial sequence comprises all of any one of the polynucleotides set forth in (1); and
(3) a polynucleotide whose partial sequence comprises: all of a base sequence of SEQ ID NO: n (where n is an odd number), or in the polynucleotides set forth in (1), and all of a base sequence of SEQ ID NO: n+1, or in the polynucleotides set forth in (1);

the polynucleotides being mapped on barley chromosomes for an entire genome of barley, and the polynucleotides being mapped on the support at an average density of no greater than 30 cM;

regions on the support in which said at least 50 polynucleotides are respectively immobilized being arranged in the same order as a chromosomal order of said at least 50 polynucleotides immobilized on the support, or information indicative of a chromosomal order of said at least 50 polynucleotides immobilized on the support being appended to regions on the support in which said at least 50 polynucleotides are respectively immobilized.

2. A gene detection instrument as set forth in claim 1, wherein the polynucleotide immobilized on the support comprises cDNA.

* * * * *